(12) United States Patent
Lagiakos et al.

(10) Patent No.: US 12,365,655 B2
(45) Date of Patent: Jul. 22, 2025

(54) COMPOUNDS

(71) Applicant: CTXT PTY LTD, Melbourne (AU)

(72) Inventors: H. Rachel Lagiakos, Parkville (AU); Richard Charles Foitzik, Parkville (AU); Catherine Fae Hemley, Melbourne (AU); Michelle Ang Camerino, Parkville (AU); Paul Anthony Stupple, Parkville (AU); Ylva Elisabet Bergman Bozikis, Parkville (AU); Scott Raymond Walker, Parkville (AU)

(73) Assignee: CTXT PTY LTD, Melbourne (AU)

( * ) Notice: Subject to any disclaimer, the term of this patent is extended or adjusted under 35 U.S.C. 154(b) by 0 days.

(21) Appl. No.: 17/392,356

(22) Filed: Aug. 3, 2021

(65) Prior Publication Data

US 2022/0153710 A1 May 19, 2022

Related U.S. Application Data

(63) Continuation of application No. 16/446,868, filed on Jun. 20, 2019, now abandoned.

(30) Foreign Application Priority Data

Jun. 20, 2018 (GB) .................................. 1810092

(51) Int. Cl.
| C07D 261/20 | (2006.01) |
| C07D 413/10 | (2006.01) |
| C07D 413/12 | (2006.01) |
| C07D 417/12 | (2006.01) |

(52) U.S. Cl.
CPC ......... C07D 261/20 (2013.01); C07D 413/10 (2013.01); C07D 413/12 (2013.01); C07D 417/12 (2013.01)

(58) Field of Classification Search
CPC .......................... C07D 261/20; C07D 413/10
See application file for complete search history.

(56) References Cited

U.S. PATENT DOCUMENTS

| 2,358,031 | A | 9/1944 | Roblin et al. |
| 2,525,321 | A | 10/1950 | Hultquist et al. |
| 3,064,003 | A | 11/1962 | Satzinger et al. |
| 3,332,942 | A | 7/1967 | Breivogel et al. |
| 3,951,967 | A | 4/1976 | Novello |
| 3,960,854 | A | 6/1976 | Novello |
| 4,172,896 | A | 10/1979 | Uno et al. |
| 4,251,664 | A | 2/1981 | Spitzner |
| 6,248,767 | B1 | 6/2001 | Blok et al. |
| 9,493,429 | B2 | 11/2016 | Chen et al. |
| 11,492,346 | B2 | 11/2022 | Bozikis et al. |
| 2006/0025415 | A1 | 2/2006 | Gonzalez et al. |
| 2006/0128706 | A1 | 6/2006 | Bruncko et al. |
| 2006/0258657 | A1 | 11/2006 | Bruncko et al. |
| 2007/0015787 | A1 | 1/2007 | Bruncko et al. |
| 2007/0072860 | A1 | 3/2007 | Bruncko et al. |
| 2009/0042945 | A1 | 2/2009 | Frank et al. |
| 2009/0163545 | A1 | 6/2009 | Goldfarb |
| 2012/0208811 | A1 | 8/2012 | Taka et al. |
| 2013/0022629 | A1 | 1/2013 | Sharpe et al. |
| 2015/0183802 | A1 | 7/2015 | Chen et al. |
| 2016/0009667 | A1 | 1/2016 | Chen et al. |
| 2016/0376289 | A1 | 12/2016 | Okuyama et al. |
| 2020/0039945 | A1 | 2/2020 | Lagiakos et al. |
| 2020/0399258 | A1 | 12/2020 | Bozikis et al. |

FOREIGN PATENT DOCUMENTS

| BE | 617370 A | 11/1962 |
| CA | 2121724 A1 | 10/1994 |
| CN | 101747325 A | 6/2010 |
| CN | 101845043 A | 9/2010 |
| CN | 107098846 A | 8/2017 |
| DE | 1102745 B | 3/1961 |
| EP | 181018 A2 | 5/1986 |
| EP | 371438 A2 | 6/1990 |
| EP | 0558258 A1 | 9/1993 |
| EP | 0569193 A1 | 11/1993 |
| FR | 2690160 A1 | 10/1993 |
| GB | 689281 A | 3/1953 |
| JP | 29002834 B | 5/1927 |
| JP | 36003685 B | 4/1936 |
| JP | 36019566 B | 10/1936 |
| JP | 3901229 B | 2/1939 |
| JP | 49008255 B | 2/1974 |
| JP | 5452075 A | 4/1979 |

(Continued)

OTHER PUBLICATIONS

Neidlein & J. Tauber, Pharmazeutische Zentralhalle, 1968, 107(6), 430-432.
Pachhamia J. Indian Chem. Soc., 1988, 65(5), 357-361.
Pattan et al., Asian Journal of Research in Chemistry, 2009, 2(2), 123-126.
Pattan et al., Iranian Journal of Pharmaceutical Sciences, 2009, 5(4), 225-230.
Persa et al., Cancer Letters, 2015 368(2), 252-261 doi:10.1016/j.canlet.2015.03.003.

(Continued)

*Primary Examiner* — Kamal A Saeed
(74) *Attorney, Agent, or Firm* — Banner & Witcoff, Ltd.

(57) ABSTRACT

A compound of formula (I), or a pharmaceutical salt thereof:

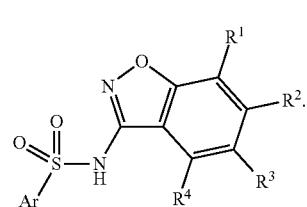

(I)

14 Claims, No Drawings
Specification includes a Sequence Listing.

(56) References Cited

FOREIGN PATENT DOCUMENTS

| | | | |
|---|---|---|---|
| JP | 03-258771 | A | 11/1991 |
| JP | 63238006 | A | 10/1998 |
| JP | 2003292485 | A | 10/2003 |
| PL | 220630 | B1 | 11/2015 |
| WO | 199321171 | A1 | 10/1993 |
| WO | 199427979 | A1 | 12/1994 |
| WO | 199631492 | A1 | 10/1996 |
| WO | 199739000 | A1 | 10/1997 |
| WO | 199813366 | A1 | 4/1998 |
| WO | 199821186 | A1 | 5/1998 |
| WO | 199849162 | A1 | 11/1998 |
| WO | 2001019798 | A2 | 3/2001 |
| WO | 200149289 | A1 | 7/2001 |
| WO | 200164642 | A2 | 9/2001 |
| WO | 200164643 | A2 | 9/2001 |
| WO | 2003042700 | A2 | 5/2003 |
| WO | 2003044000 | A1 | 5/2003 |
| WO | 2004085385 | A2 | 10/2004 |
| WO | 2004103980 | A1 | 12/2004 |
| WO | 2004113310 | A1 | 12/2004 |
| WO | 2005009967 | A2 | 2/2005 |
| WO | 2005013914 | A2 | 2/2005 |
| WO | 2006044405 | A1 | 4/2006 |
| WO | 2006116614 | A1 | 11/2006 |
| WO | 2006116615 | A1 | 11/2006 |
| WO | 2006122799 | A1 | 11/2006 |
| WO | 2006124744 | A1 | 11/2006 |
| WO | 2007039174 | A2 | 4/2007 |
| WO | 2007039175 | A1 | 4/2007 |
| WO | 2007057093 | A1 | 5/2007 |
| WO | 2007075895 | A2 | 7/2007 |
| WO | 2008022286 | A2 | 2/2008 |
| WO | 2008063668 | A1 | 5/2008 |
| WO | 2008064116 | A2 | 5/2008 |
| WO | 2008089307 | A2 | 7/2008 |
| WO | 2009012242 | A2 | 1/2009 |
| WO | 2009058348 | A1 | 5/2009 |
| WO | 2009080223 | A1 | 7/2009 |
| WO | 201019788 | A1 | 2/2010 |
| WO | 2010046780 | A2 | 4/2010 |
| WO | 2010121963 | A1 | 10/2010 |
| WO | 2011017561 | A1 | 2/2011 |
| WO | 2011082400 | A2 | 7/2011 |
| WO | 2011085575 | A1 | 7/2011 |
| WO | 2011137089 | A1 | 11/2011 |
| WO | 2011156610 | A2 | 12/2011 |
| WO | 20120007868 | A2 | 1/2012 |
| WO | 2012080729 | A2 | 6/2012 |
| WO | 2012088438 | A1 | 6/2012 |
| WO | 2012129562 | A2 | 9/2012 |
| WO | 2014144545 | A2 | 9/2014 |
| WO | 2015112465 | A1 | 7/2015 |
| WO | 2016135582 | A1 | 9/2016 |
| WO | 2016198507 | A1 | 12/2016 |
| WO | 2017002120 | A1 | 1/2017 |
| WO | 2017098421 | A1 | 6/2017 |
| WO | 2018081167 | A1 | 5/2018 |
| WO | 2018102419 | A1 | 6/2018 |
| WO | 2018226976 | A1 | 12/2018 |
| WO | 2019243491 | A1 | 12/2019 |
| WO | 2020254946 | A1 | 12/2020 |

OTHER PUBLICATIONS

Polozov et al., Tetrahedron Letters, 2010, 51(4), 575-578.
Potkin et al., Russian Journal of Organic Chemistry, 2009, 45(6), 879-883.
Rosenthal et al., Bioorganic & Medicinal Chemistry Letters, 2013, 23(20), 5660-5666.
Savastre et al., Bulletin of University of Agricultural Sciences and Veterinary Medicine Cluj-Napoca, Veterinary Medicine, 2013, 70(1), 134-139.
U.S. Appl. No. 16/446,868 amendment filed Jan. 5, 2021.
U.S. Appl. No. 16/902,515 pending claims filed Jun. 16, 2020.
Sheikh et al., Blood, 2015, 125(12), 1910-21 doi:10.1182/blood-2014-08-594655.
Shi et al., Nature Biotech, 2015, 33, 661-667 doi:10.1038/nbt.3235.
Singh et al., International Journal of Chemical Sciences, 2012, 10(3), 1487-1492.
Smaine et al., Bioorganic & Medicinal Chemistry Letters, 2008, 18(24), 6332-6335.
Spillane et al., Journal of Agricultural and Food Chemistry (2009), 57(12), 5486-5493.
Stachel, Chemische Berichte, 1963, 96, 1088-97.
Stein et al., Journal of Medicinal Chemistry, 1995, 38, 1344-1354.
Stern et al., Crit. Rev. Oncol. Hematol., 2005, 54, 11-29 doi:10.1016/j.critrevonc.2004.10.011.
Su et al., Int. J. Mol. Sci., 2016, 17, 1-18 doi:10.3390/ijms17101594.
Sugai et al., Chemical & Pharmaceutical Bulletin, 1984, 32(2), 530-7.
Suyama et al., Heterocycles, 2003, 60(1), 121-129.
Tait et al., Bollettino chimico Farmaceutico, 1990, 129(9), 273-275.
Tan et al., Yingyong Huaxue, 2016, 33(9), 1067-1072.
Tao, H et al., Lung Cancer, 2012, 75, 95-101 doi:10.1016/j.lungcan.2011.06.002.
Thomas et al., Development, 2000, 127, 2537-2548 PMID:10821753.
Thomas et al., Genes Dev, 2006, 20(9), 1175.
Turner-Ivey et al., Neoplasia, 2014, 16(8): 644-655 doi:10.1016/j.neo.2014.07.007.
Valerio et al., Cancer Research, 2017, 77(7), 1753-62 doi:10.1158/0008-5472.CAN-16-2374.
Vikani et al., Journal of the Indian Chemical Society, 1990, 67(10), 859-61.
Vizmanos et al., Genes Chromosomes Cancer, 2003, 36(4), 402-405 doi:10.1002/gcc.10174.
Voss et al., BioEssays, 2009, 31(10), 1050-1061 doi:10.1002/bies.200900051.
Wang et al. EBioMedicine, 2016, 13, 99-112 doi:10.1016/j.ebiom.2016.10.018.
Wang et al., Gaodeng Xuexiao Huaxue Xuebao, 1987, 8(2), 133-6.
Wang et al., Oncogene, 2017, 36, 3048-3058 doi:10.1038/onc.2016.458.
Wells et al., Journal of Medicinal Chemistry, 2001, 44(21), 3488-3503.
Xiao et al., Cell reports, 2014, 7, 1471-1480 doi :10.1016/j.celrep.2014.04.021.
Xiao-Jian et al., Frontiers in Oncology, 2015, 5, 108.
Yan et al., Breast Cancer Research, 2011, 13, R47 doi:10.1186/bcr2869.
Yoshida et al., Yakugaku Zasshi 1954, 74, 948-50.
Young et al., Blood Res 2016 51(3), 152-154 doi:10.5045/br.2016.51.3.152.
Zack et al., Nature Genetics 2013 45, 1134-1140 doi:10.1038/ng.2760.
Zhang et al., Mini. Rev. Med. Chem., 2017, 17, 1-8 doi:10.2174/1389557516666160923125031.
Bruncko et al., database CAPLUS Acc. No. 2007:359148, CAS SciFinder abstract of US 2007/0072860 A1 (Mar. 29, 2007).
Dekker et al., Drug, Discov. Today, 2014, 19, 654-660 doi:10.1016/j.drudis.2013.11.012.
Dhuban et al., Sci. Immunol., 2017, 2, 9297 doi:10.1126/sciimmunol.aai9297.
Doyon et al., Mol. Cell., 2006, 21, 51-64 doi :10.1016/j.molcel.2005.12.007.
Duong et al., Cancer Res., 2013, 73, 5556-5568 doi:10.1158/0008-5472.CAN-13-0013.
Dzhemukhadze et al., Fenol'nye Soedineniya i Ikh Biologicheskie Funktsii, Materialy Vsesoyuznogo Simpoziuma po Fenol'nym Soedineniyam 1968, 196-202.
Fairley et al., Synlett, 2013, 24(5), 570-574.
Falk et al., J. Biomolecular Screening 16(10): 2011 DOI:10.1177/1087057111421631.
Fan et al., Oncogene, 2015, 1-12.
Fernandes et al., Journal of the Institution of Chemists (India), 1991, 63(3), 83-4.

(56) References Cited

OTHER PUBLICATIONS

Fujita et al., Yakugaku Zasshi, 1964, 84(11), 1061-7.
Geng et al.. Nature Immunology, 2 017, (online) doi:10.1038/ni. 3748.
Ghizzoni et al., Eur. J. Med. Chem., 2012, 47, 337-344 doi:10.1016/j.ejmech.2011.11.001.
Gil et al., J. Proteomics, 2017, 150, 297-309 doi :10.1016/j.jprot. 2016.10.003.
Giri et al., Journal of the Indian Chemical Society, 1964, 41(4), 295-8.
Gobert et al., Cancer Research, 2009, 69, 2000-2009 doi:10.1158/0008-5472.CAN-08-2360.
Grashey et al., Chemiker-Zeitung 1976, 100(11), 497-8.
Grashey et al., Chemiker-Zeitung, 1973, 97(11), 623.
Grashey et al., Tetrahedron Letters, 1972, (29), 2943-6.
Hangan et al., Farmacia, 2012, 60(6), 932-938.
Hangan et al., Journal of Chemical Sciences (Bedin, Germany), 2016, 128(5), 815-824.
Hangan et al., Russian Journal of Coordination Chemistry, 2015, 41(6), 395-404.
Hassan et al., Journal of Chemical Technology and Biotechnology, 1982, 32(2), 416-20.
Hategan et al., Bioorganic & Medicinal Chemistry Letters, 2009, 19(23), 6797-6800.
Hirsch et al., J. Mol. Biol., 2017, 429(13), 1958-1977.
Hitchin et al., Med. Chem. Commun., 2013, 4, 1513-1522.
Holbert et al., J. Biol. Chem., 2007, 282, 36603-36613 doi:10.1074/jbc.M705812200.
Hultquist et al., Journal of the American Chemical Society, 1951, 73, 2558-66.
Iizuka et al, Cancer Sci., 2013, 104, 1647-1655 doi:10.1111/cas. 12303.
Iizuka et al., Mol. Cell. Biol., 2006, 26, 1098-1108 doi :10.1128/MCB.26.3.1098-1108.2006.
International Preliminary Report on Patentability for PCT/EP2019/066337, dated Dec. 22, 2020.
International Search Report and Written Opinion for PCT/IB2020/055589, dated Jul. 9, 2020.
Joshi et al., Immunity 2015, 43, 579-590 doi:10.1016/j.immuni. 2015.08.006.
Judes et al., Epigenomics, 2015, 7(8), 1351-1363.
Keil et al., ChemMedChem, 2011, 6(4), 633-653.
King et al., Journal of Biological Chemistry, 2009, 284(14), 9059-9065.
Klosa, Archiv der Pharmazie und Berichte der Deutschen Pharmazeutischen Gesellschaft, 1954, 287, 12-14.
Kurihara et al., Yakugaku Zasshi, 1965, 85(10), 920-5.
Kuznetsov et al., Izvestiya Akademii Nauk SSSR, Seriya Khimicheskaya 1976, (2), 319-22.
Lalezar et al., Journal of Heterocyclic Chemistry, 1966, 3(3), 336-7.
Lazaris et al., Khimiya Geterotsiklicheskikh Soedinenii, 1973, (10), 1345-50.
Lee, Archives of Pharmacal Research, 2004, 27(3), 305-313.
Li et al., PNAS, 2007, 104, 4571-4576 doi:10.1073/pnas. 0700298104.
Liu, Workman and Vignali, The FEBS journal, 2016, 283, 2731-2748.
Malev, Metody Polucheniya Khimicheskikh Reaktivov i Preparatov 1964, No. 8, 44-8.
Melero et al. Nature Reviews Cancer, 2015, 15, 457-472 doi:10.1038/nrc3973.
Meng et al., Zhongguo Yaowu Huaxue Zazhi, 1996, 6(4), 257-261.
Merson et al., J. Neurosci., 2006, 26, 11359-11370 doi :10.1523/JNEUROSCI.2247-6.2006.
Miller, A.M. et al. J. Immunol., 2006, 177, 7398-7405 doi:10.4049/jimmunol.177.10.7398.
Mochona et al., Bioorg. & Med. Chem. Lett., 2016, 26(12), 2847-2851.

Neidlein & Hausmann, Zeitschrift fur Naturforschung, Teil B. Chemie, Biochemie, Biophysik, Biologie und wervandte Gebeite, 1966, 21(9), 898.
Aggarwal and Calvi, Nature, 2004, 430, 372-376 doi:10.1038/nature02694.
Aiello et al., Ricerca Scientifica, Parte 2: Rendiconti, Sezione B: Biologica, 1964, 4(4), 575-80.
Avvakumov et al., Oncogene, 2007, 26, 5395-5407 doi:10.1038/sj.onc.1210608.
Baell et al., Nature, doi://10.1038/s41 586-018-0387-5, 2018.
Berge et al., J. Pharm. Sci., 1977, 66, 1-19 doi:10.1002/jps. 2600660104.
Borrow et al., Nat. Genet., 1996, 14, 33-41 doi:10.1038/ng0996-33.
Brown et al., Biocehmical Society Transactions, 2016, 44(4), 979-986.
CAS Registry No. 1032507-60-0, 2094317-93-6, 891027-49-9, and 891028-05-0.
CAS Registry No. 1032507-60-0, entered STN Jul. 3, 2008.
CAS Registry No. 1207646-75-0, entered STN Mar. 2, 2010.
CAS Registry No. 1207661-17-3, entered STN Mar. 2, 2010.
CAS Registry No. 1808493-75-5, entered STN Sep. 29, 2015.
CAS registry No. 1808522-80-6, entered STN Sep. 29, 2015.
CAS registry No. 1808570-72-0, entered STN Sep. 29, 2015.
CAS Registry No. 1808779-04-5, entered STN Sep. 29, 2015.
CAS registry No. 1808779-26-1, entered STN Sep. 29, 2015.
CAS registry No. 2094188-03-9, entered STN May 2, 2017.
CAS registry No. 2094235-06-8, entered STN May 2, 2017.
CAS Registry No. 2094317-93-6, entered STN May 2, 2017.
CAS Registry No. 2094373-00-7, entered STN May 2, 2017.
CAS Registry No. 2094434-10-7, entered STN May 2, 2017.
CAS Registry No. 2094666-45-0, entered STN May 2, 2017.
CAS Registry No. 2094857-16-4, entered STN May 3, 2017.
CAS registry No. 2094888-54-5, entered STN May 3, 2017.
CAS registry No. 2138109-21-2, entered STN Nov. 2, 2017.
CAS registry No. 2138573-90-5, entered STN Nov. 6, 2017.
CAS Registry No. 2178688-56-5, entered STN Feb. 22, 2018.
CAS Registry No. 2189108-08-3, entered STN Mar. 12, 2018.
CAS Registry No. 2224022-18-6, entered STN May 20, 2018.
CAS Registry No. 2224161-16-8, entered STN May 20, 2018.
CAS Registry No. 891026-69-0, entered STN Jul. 9, 2006.
CAS Registry No. 891026-77-0, entered STN Jul. 9, 2006.
CAS registry No. 891027-33-1, entered STN Jul. 9, 2006.
CAS Registry No. 891027-11-1, entered STN Jul. 9, 2006.
CAS Registry No. 891027-19-9, entered STN Jul. 9, 2006.
CAS Registry No. 891027-57-9, entered STN Jul. 9, 2006.
CAS Registry No. 891027-65-9, entered STN Jul. 9, 2006.
CAS Registry No. 891027-73-9, entered STN Jul. 9, 2006.
CAS Registry No. 891027-89-7, entered STN Jul. 9, 2006.
CAS registry No. 891027-97-7, entered STN Jul. 9, 2006.
CAS Registry No. 891028-05-0, entered STN Jul. 9, 2006.
CAS Registry No. 891028-12-9, entered STN Jul. 9, 2006.
CAS Registry No. 891028-89-0, entered STN Jul. 9, 2006.
CAS registry No. 892699-07-9, entered STN Jul. 14, 2006.
CAS Registry No. 892699-21-7, entered STN Jul. 14, 2006.
CAS registry No. 892699-30-8, entered STN Jul. 14, 2006.
CAS Registry No. 892699-39-7, entered STN Jul. 14, 2006.
CAS registry No. 892699-67-1, entered STN Jul. 14, 2006.
Chavan et al., Indian Journal of Heterocyclic Chemistry, 2007, 17(1), 45-48.
Czudor et al., Bioorganic & Med. Chem. Let., 2018, vol. 28, p. 769-773.
Bruncko et al., "N-Acyl arenesulfonamides as apoptosis promoters and their preparation, pharmaceutical compositions and use in the treatment of diseases," database CAPLUS Acc. No. 2007:359148, CAS SciFinder abstract of US 2007/0072860 A1 (Mar. 29, 2007).
International Search Report and Written Opinion for PCT/EP2018/073431 dated Dec. 3, 2018, 9 pages.
Lagiakos et al., U.S. Appl. No. 16/902,515 Notice of Allowance dated Feb. 15, 2022.
Lagiakos et al., U.S. Appl. No. 16/902,515 Notice of Allowance dated May 23, 2022.
Lagiakos et al., U.S. Appl. No. 16/902,515 Notice of Allowance dated Sep. 7, 2022.

(56) References Cited

OTHER PUBLICATIONS

Lagiakos et al., U.S. Appl. No. 16/902,515 Request to Correct Inventorship filed Sep. 7, 2022.
Lagiakos et al., U.S. Appl. No. 16/902,515 Specification, claims, abstract filed Jun. 16, 2020.
Lagiakos et al., U.S. Appl. No. 16/902,515 Submission Under Rule 114 filed Aug. 23, 2022.
Lagiakos et al., U.S. Appl. No. 16/902,515 Submission Under Rule 114 with substitute specification filed May 14, 2022.
Lagiakos et al., U.S. Appl. No. 16/902,515 Updated Filing Receipt and Acceptance of Request to Correct Inventorship dated Sep. 12, 2022.
Lagiakos et al., U.S. Appl. No. 16/902,515, Nonfinal Office Action dated Oct. 1, 2021.
Lagiakos et al., U.S. Appl. No. 16/902,515, Response filed Dec. 30, 2021.
Lagiakos et al., U.S. Appl. No. 17/946,101, Preliminary Amendment with Substitute Specification filed Feb. 6, 2023.
Lagiakos et al., U.S. Appl. No. 17/946,101, Specification, claims, abstract filed Sep. 16, 2022.
Bozikis, U.S. Appl. No. 17/946,101, Non-Final Office Action dated Aug. 24, 2023, 12 pp.
Database CA [Online] Chemical Abstracts Service, Columbus, Ohio, US, compound with RN 1800260-63-2, retrieved from STN, entered Jul. 24, 2015.

SEQUENCE LISTING

```
<160> NUMBER OF SEQ ID NOS: 4

<210> SEQ ID NO 1
<211> LENGTH: 480
<212> TYPE: PRT
<213> ORGANISM: Artificial Sequence
<220> FEATURE:
<223> OTHER INFORMATION: Human KAT5 isoform

<400> SEQUENCE: 1

Met Gly His His His His His His Gly Thr Glu Asn Leu Tyr Phe Gln
1               5                   10                  15

Gly Ser Ala Glu Val Gly Glu Ile Ile Glu Gly Cys Arg Leu Pro Val
            20                  25                  30

Leu Arg Arg Asn Gln Asp Asn Glu Asp Glu Trp Pro Leu Ala Glu Ile
        35                  40                  45

Leu Ser Val Lys Asp Ile Ser Gly Arg Lys Leu Phe Tyr Val His Tyr
    50                  55                  60

Ile Asp Phe Asn Lys Arg Leu Asp Glu Trp Val Thr His Glu Arg Leu
65                  70                  75                  80

Asp Leu Lys Lys Ile Gln Phe Pro Lys Lys Glu Ala Lys Thr Pro Thr
                85                  90                  95

Lys Asn Gly Leu Pro Gly Ser Arg Pro Gly Ser Pro Glu Arg Glu Val
            100                 105                 110

Lys Arg Lys Val Glu Val Val Ser Pro Ala Thr Pro Val Pro Ser Glu
        115                 120                 125

Thr Ala Pro Ala Ser Val Phe Pro Gln Asn Gly Ala Ala Arg Arg Ala
    130                 135                 140

Val Ala Ala Gln Pro Gly Arg Lys Arg Lys Ser Asn Cys Leu Gly Thr
145                 150                 155                 160

Asp Glu Asp Ser Gln Asp Ser Ser Asp Gly Ile Pro Ser Ala Pro Arg
                165                 170                 175

Met Thr Gly Ser Leu Val Ser Asp Arg Ser His Asp Asp Ile Val Thr
            180                 185                 190

Arg Met Lys Asn Ile Glu Cys Ile Glu Leu Gly Arg His Arg Leu Lys
        195                 200                 205

Pro Trp Tyr Phe Ser Pro Tyr Pro Gln Glu Leu Thr Thr Leu Pro Val
    210                 215                 220
```

```
Leu Tyr Leu Cys Glu Phe Cys Leu Lys Tyr Gly Arg Ser Leu Lys Cys
225                 230                 235                 240

Leu Gln Arg His Leu Thr Lys Cys Asp Leu Arg His Pro Pro Gly Asn
            245                 250                 255

Glu Ile Tyr Arg Lys Gly Thr Ile Ser Phe Phe Glu Ile Asp Gly Arg
            260                 265                 270

Lys Asn Lys Ser Tyr Ser Gln Asn Leu Cys Leu Leu Ala Lys Cys Phe
            275                 280                 285

Leu Asp His Lys Thr Leu Tyr Tyr Asp Thr Asp Pro Phe Leu Phe Tyr
            290                 295                 300

Val Met Thr Glu Tyr Asp Cys Lys Gly Phe His Ile Val Gly Tyr Phe
305                 310                 315                 320

Ser Lys Glu Lys Glu Ser Thr Glu Asp Tyr Asn Val Ala Cys Ile Leu
            325                 330                 335

Thr Leu Pro Pro Tyr Gln Arg Arg Gly Tyr Gly Lys Leu Leu Ile Glu
            340                 345                 350

Phe Ser Tyr Glu Leu Ser Lys Val Glu Gly Lys Thr Gly Thr Pro Glu
            355                 360                 365

Lys Pro Leu Ser Asp Leu Gly Leu Leu Ser Tyr Arg Ser Tyr Trp Ser
            370                 375                 380

Gln Thr Ile Leu Glu Ile Leu Met Gly Leu Lys Ser Glu Ser Gly Glu
385                 390                 395                 400

Arg Pro Gln Ile Thr Ile Asn Glu Ile Ser Glu Ile Thr Ser Ile Lys
            405                 410                 415

Lys Glu Asp Val Ile Ser Thr Leu Gln Tyr Leu Asn Leu Ile Asn Tyr
            420                 425                 430

Tyr Lys Gly Gln Tyr Ile Leu Thr Leu Ser Glu Asp Ile Val Asp Gly
            435                 440                 445

His Glu Arg Ala Met Leu Lys Arg Leu Leu Arg Ile Asp Ser Lys Cys
            450                 455                 460

Leu His Phe Thr Pro Lys Asp Trp Ser Lys Arg Gly Lys Trp Ala Ser
465                 470                 475                 480

<210> SEQ ID NO 2
<211> LENGTH: 791
<212> TYPE: PRT
<213> ORGANISM: Artificial Sequence
<220> FEATURE:
<223> OTHER INFORMATION: Human KAT6A isoform

<400> SEQUENCE: 2

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
            35                  40                  45

Ile Asp Arg Lys Ser Gly Asp Phe Asp Thr Phe Arg Arg Trp Leu Val
            50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
            85                  90                  95

Ile Glu Ser Val Thr Phe Asp Arg Ile Thr Thr Gln Thr Ala Lys Gln
            100                 105                 110
```

```
Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
                180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
                260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
        290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
                340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
                420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
        450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Thr
                485                 490                 495

Ser Gly Ser Gly His His His His His Ser Ala Gly Glu Asn Leu
                500                 505                 510

Tyr Phe Gln Gly Ala Met Gly Arg Cys Pro Ser Val Ile Glu Phe Gly
        515                 520                 525
```

-continued

Lys Tyr Glu Ile His Thr Trp Tyr Ser Ser Pro Tyr Pro Gln Glu Tyr
    530                 535                 540

Ser Arg Leu Pro Lys Leu Tyr Leu Cys Glu Phe Cys Leu Lys Tyr Met
545                 550                 555                 560

Lys Ser Arg Thr Ile Leu Gln Gln His Met Lys Lys Cys Gly Trp Phe
                565                 570                 575

His Pro Pro Val Asn Glu Ile Tyr Arg Lys Asn Asn Ile Ser Val Phe
            580                 585                 590

Glu Val Asp Gly Asn Val Ser Thr Ile Tyr Cys Gln Asn Leu Cys Leu
        595                 600                 605

Leu Ala Lys Leu Phe Leu Asp His Lys Thr Leu Tyr Tyr Asp Val Glu
    610                 615                 620

Pro Phe Leu Phe Tyr Val Leu Thr Gln Asn Asp Val Lys Gly Cys His
625                 630                 635                 640

Leu Val Gly Tyr Phe Ser Lys Glu Lys His Cys Gln Gln Lys Tyr Asn
                645                 650                 655

Val Ser Cys Ile Met Ile Leu Pro Gln Tyr Gln Arg Lys Gly Tyr Gly
            660                 665                 670

Arg Phe Leu Ile Asp Phe Ser Tyr Leu Leu Ser Lys Arg Glu Gly Gln
        675                 680                 685

Ala Gly Ser Pro Glu Lys Pro Leu Ser Asp Leu Gly Arg Leu Ser Tyr
    690                 695                 700

Met Ala Tyr Trp Lys Ser Val Ile Leu Glu Cys Leu Tyr His Gln Asn
705                 710                 715                 720

Asp Lys Gln Ile Ser Ile Lys Lys Leu Ser Lys Leu Thr Gly Ile Cys
                725                 730                 735

Pro Gln Asp Ile Thr Ser Thr Leu His His Leu Arg Met Leu Asp Phe
            740                 745                 750

Arg Ser Asp Gln Phe Val Ile Ile Arg Arg Glu Lys Leu Ile Gln Asp
        755                 760                 765

His Met Ala Lys Leu Gln Leu Asn Leu Arg Pro Val Asp Val Asp Pro
    770                 775                 780

Glu Cys Leu Arg Trp Thr Pro
785                 790

<210> SEQ ID NO 3
<211> LENGTH: 307
<212> TYPE: PRT
<213> ORGANISM: Artificial Sequence
<220> FEATURE:
<223> OTHER INFORMATION: Human KAT7 isoform

<400> SEQUENCE: 3

Met Gly His His His His His Gly Thr Glu Asn Leu Tyr Phe Gln
1               5                   10                  15

Gly Ser Arg Leu Gln Gly Gln Ile Thr Glu Gly Ser Asn Met Ile Lys
                20                  25                  30

Thr Ile Ala Phe Gly Arg Tyr Glu Leu Asp Thr Trp Tyr His Ser Pro
            35                  40                  45

Tyr Pro Glu Glu Tyr Ala Arg Leu Gly Arg Leu Tyr Met Cys Glu Phe
        50                  55                  60

Cys Leu Lys Tyr Met Lys Ser Gln Thr Ile Leu Arg Arg His Met Ala
65                  70                  75                  80

Lys Cys Val Trp Lys His Pro Pro Gly Asp Glu Ile Tyr Arg Lys Gly
                85                  90                  95

```
Ser Ile Ser Val Phe Glu Val Asp Gly Lys Lys Asn Lys Ile Tyr Cys
            100                 105                 110

Gln Asn Leu Cys Leu Leu Ala Lys Leu Phe Leu Asp His Lys Thr Leu
        115                 120                 125

Tyr Tyr Asp Val Glu Pro Phe Leu Phe Tyr Val Met Thr Glu Ala Asp
    130                 135                 140

Asn Thr Gly Cys His Leu Ile Gly Tyr Phe Ser Lys Glu Lys Asn Ser
145                 150                 155                 160

Phe Leu Asn Tyr Asn Val Ser Cys Ile Leu Thr Met Pro Gln Tyr Met
                165                 170                 175

Arg Gln Gly Tyr Gly Lys Met Leu Ile Asp Phe Ser Tyr Leu Leu Ser
            180                 185                 190

Lys Val Glu Glu Lys Val Gly Ser Pro Glu Arg Pro Leu Ser Asp Leu
        195                 200                 205

Gly Leu Ile Ser Tyr Arg Ser Tyr Trp Lys Glu Val Leu Leu Arg Tyr
    210                 215                 220

Leu His Asn Phe Gln Gly Lys Glu Ile Ser Ile Lys Glu Ile Ser Gln
225                 230                 235                 240

Glu Thr Ala Val Asn Pro Val Asp Ile Val Ser Thr Leu Gln Ala Leu
                245                 250                 255

Gln Met Leu Lys Tyr Trp Lys Gly Lys His Leu Val Leu Lys Arg Gln
            260                 265                 270

Asp Leu Ile Asp Glu Trp Ile Ala Lys Glu Ala Lys Arg Ser Asn Ser
    275                 280                 285

Asn Lys Thr Met Asp Pro Ser Cys Leu Lys Trp Thr Pro Pro Lys Gly
290                 295                 300

Thr Ala Ser
305

<210> SEQ ID NO 4
<211> LENGTH: 296
<212> TYPE: PRT
<213> ORGANISM: Artificial Sequence
<220> FEATURE:
<223> OTHER INFORMATION: Human KAT8 isoform

<400> SEQUENCE: 4

Met Ser Tyr Tyr His His His His His His Asp Tyr Asp Ile Pro Thr
1               5                   10                  15

Thr Glu Asn Leu Tyr Phe Gln Gly Ala Lys Tyr Val Asp Lys Ile His
            20                  25                  30

Ile Gly Asn Tyr Glu Ile Asp Ala Trp Tyr Phe Ser Pro Phe Pro Glu
        35                  40                  45

Asp Tyr Gly Lys Gln Pro Lys Leu Trp Leu Cys Glu Tyr Cys Leu Lys
    50                  55                  60

Tyr Met Lys Tyr Glu Lys Ser Tyr Arg Phe His Leu Gly Gln Cys Gln
65                  70                  75                  80

Trp Arg Gln Pro Pro Gly Lys Glu Ile Tyr Arg Lys Ser Asn Ile Ser
                85                  90                  95

Val Tyr Glu Val Asp Gly Lys Asp His Lys Ile Tyr Cys Gln Asn Leu
            100                 105                 110

Cys Leu Leu Ala Lys Leu Phe Leu Asp His Lys Thr Leu Tyr Phe Asp
        115                 120                 125

Val Glu Pro Phe Val Phe Tyr Ile Leu Thr Glu Val Asp Arg Gln Gly
    130                 135                 140
```

```
Ala His Ile Val Gly Tyr Phe Ser Lys Glu Lys Glu Ser Pro Asp Gly
145                 150                 155                 160

Asn Asn Val Ala Cys Ile Leu Thr Leu Pro Pro Tyr Gln Arg Arg Gly
                165                 170                 175

Tyr Gly Lys Phe Leu Ile Ala Phe Ser Tyr Glu Leu Ser Lys Leu Glu
            180                 185                 190

Ser Thr Val Gly Ser Pro Glu Lys Pro Leu Ser Asp Leu Gly Lys Leu
        195                 200                 205

Ser Tyr Arg Ser Tyr Trp Ser Trp Val Leu Leu Glu Ile Leu Arg Asp
        210                 215                 220

Phe Arg Gly Thr Leu Ser Ile Lys Asp Leu Ser Gln Met Thr Ser Ile
225                 230                 235                 240

Thr Gln Asn Asp Ile Ile Ser Thr Leu Gln Ser Leu Asn Met Val Lys
                245                 250                 255

Tyr Trp Lys Gly Gln His Val Ile Cys Val Thr Pro Lys Leu Val Glu
            260                 265                 270

Glu His Leu Lys Ser Ala Gln Tyr Lys Lys Pro Pro Ile Thr Val Asp
        275                 280                 285

Ser Val Cys Leu Lys Trp Ala Pro
    290                 295
```

COMPOUNDS

CROSS-REFERENCE TO RELATED APPLICATION

This application is a continuation of Ser. No. 16/446,868 filed on Jun. 20, 2019, which claims the benefit of GB Patent Application No. 1810092.5 filed Jul. 20, 2018, which is incorporated by reference herein in its entirety.

This application incorporates by reference the contents of a 16.2 kb text file created on Oct. 16, 2019 and named "16446868sequencelisting.txt," which is the sequence listing for this application.

FIELD OF THE INVENTION

The present invention relates to compounds which act as Lysine Acetyl Transferase (KAT) inhibitors of the MYST family.

BACKGROUND TO THE INVENTION

The MYST family is the largest family of KATs and is named after the founding members in yeast and mammals: MOZ, Ybf2/Sas3, Sas2 and TIP60 (Dekker 2014). MYST proteins mediate many biological functions including gene regulation, DNA repair, cell-cycle regulation and development (Avvakumov 2007; Voss 2009). The KAT proteins of the MYST family play key roles in post-translational modification of histones and thus have a profound effect on chromatin structure in the eukaryotic nucleus (Avvakumov 2007). The family currently comprises five mammalian KATs: TIP60 (KAT5; HTATIP; MIM 601409), MOZ (KAT6A; MIM 601408; MYST3), MORF (KAT6b; QKF; MYST4), HBO (KAT8; HBO1; MYST2) and MOF (KAT8; MYST1) (Voss 2009). These five members of the MYST family are present in humans and malfunction of MYST proteins is known to be associated with cancer (Avvakumov 2007). The most frequently used names for members of the MYST family are:

| Common name | MYST name | Systematic name |
| --- | --- | --- |
| MOF | MYST1 | KAT8 |
| HBO | MYST2 | KAT7 |
| MOZ | MYST3 | KAT6A |
| MORF | MYST4 | KAT6B |
| TIP60 | | KAT5 |

MYST Functional Domains

MYST proteins function in multisubunit protein complexes including adaptors such as ING proteins that mediate DNA binding (Avvakumov 2007). For instance, TIP60 is affiliated to the NuA4 multiprotein complex (which embraces more than 16 members) (Zhang 2017). However, there have also been some reports of a helix-turn-helix DNA-binding motif within the structure of the MOZ protein itself (Holbert 2007), which suggests the capacity to bind directly to DNA.

The acetyltransferase activity of MYST proteins is effected by the MYST domain (the catalytic domain). The MYST domain contains an acetyl-coenzyme A binding motif, which is structurally conserved with other HATs, and an unusual $C_2HC$-type zinc finger (Voss 2009). The highly conserved MYST domain, including the acetyl-CoA binding motif and zinc finger, is considered to be the defining feature of this family of enzymes (Avvakumov 2007).

Role of MYST Proteins

Acetylation of histone residues is generally associated with transcriptional activation. However, in some instances, transcriptional repression has also been attributed to MYST proteins (Voss 2009). The individual members of the MYST family are known to participate in a broad range of important biochemical interactions:

HBO1 positively regulates initiation of DNA replication (Avvakumov 2007; Aggarwal 2004; Doyon 2006; Iizuka 2006) via acetylation of histone substrates, which presumably leads to a more accessible chromatin conformation (Avvakumov 2007, Iizuka 2006). HBO1 is also known to play a role in the pathogenesis of breast cancer by promoting an enrichment of cancer stem-like cells (Duong 2013) and by destabilising the estrogen receptor α (ERα) through ubiquinitiation, which proceeds via the histone-acetylating activity of HBO1 (Iizuka 2013). HBO1 has also been implicated in Acute myeloid leukaemia (AML) (Shi 2015).

TIP60 (KAT5) is the most studied member of the MYST family. TIP60 plays an important role not only in the regulation of transcription but also in the process of DNA damage repair, particularly in DNA double-strand breaks (DSB) (Gil 2017). TIP60 can acetylate p53, ATM and c-Myc. TIP60 and MOF specifically acetylate lysine 120 (K120) of p53 upon DNA damage (Avvakumov 2007). TIP60 has also been implicated in being important for regulatory T-cell (Treg) biology. FOXP3 is the master regulator in the development and function of Tregs and it has been shown that acetylation of FOXP3 by TIP60 is essential for FOXP3 activity (Li 2007, Xiao 2014). Underscoring this, conditional TIP60 deletion in mice leads to a scurfy-like fatal autoimmune disease, mimicking a phenotype seen in FOXP3 knock out mice (Xiao 2014). In cancer, Treg cells can facilitate tumour progression by suppressing adaptive immunity against the tumour.

MOF ("males absent on the first") was originally identified as one of the components of the dosage compensation in *Drosophila*, and was classified as a member of the MYST family based on functional studies and sequence analysis (Su 2016). The human ortholog exhibits significant similarity to drosophila MOF; containing an acetyl-CoA-binding site, a chromodomain (which binds histones) and a $C_2HC$-type zinc finger (Su 2016). MOF is a key enzyme for acetylating histone H4K16, and MOF-containing complexes are implicated in various essential cell functions with links to cancer (Su 2016). Besides the global reduction of histone acetylation, depletion of MOF in mammalian cells can result in abnormal gene transcription, particularly causing abnormal expression of certain tumor suppressor genes or oncogenes, suggesting a critical role of MOF in tumorigenesis (Su 2016). For example, KAT activity of MOF has been shown to be required to sustain MLL-AF9 leukemia and may be important for multiple AML subtypes (Valerio 2017).

KAT6B (Querkopf) was first identified in a mutation screen for genes regulating the balance between proliferation and differentiation during embryonic development (Thomas 2000). Mice homozygous for the KAT6B mutant allele have severe defects in cerebral cortex development resulting from a severe reduction in both proliferation and differentiation of specifically the cortical progenitor population during embryonic development. KAT6B is required for the maintenance of the adult neural stem cell population and is part of a system regulating differentiation of stem cells into neurons (Merson 2006). KAT6B is also mutated in rare forms of leukaemia (Vizmanos 2003).

The MOZ locus ranks as the 12th most commonly amplified region across all cancer types (Zack 2013). MOZ is within the 8p11-p12 amplicon, which is seen at frequencies around 10-15% in various cancers, especially breast and ovarian (Turner-/vey 2014). MOZ was first identified as a fusion partner of the CREB-binding protein (CBP) during examination of a specific chromosomal translocation in acute myeloid leukaemia (AML) (Avvakumov 2007; Borrow 1996). MOZ KAT activity is necessary for promoting the expression of MEIS1 and HOXa9, proteins that are typically seen overexpressed in some lymphomas and leukaemias. Increased survival of MOZ$_{+/-}$ heterozygote mice in the Ep-Myc transgenic model of B-cell lymphoma is seen, where loss of a single MOZ allele leads to a biologically relevant reduction in Meis1 and Hoxa9 levels in pre-B-cells (Sheikh 2015).

Inhibitors of some MYSTs are known. For example, the following Anacardic acid derivative is reported (Ghizzoni 2012) as inhibiting TIP60 (IC$_{50}$=74 µM) and MOF (IC$_{50}$=47 µM):

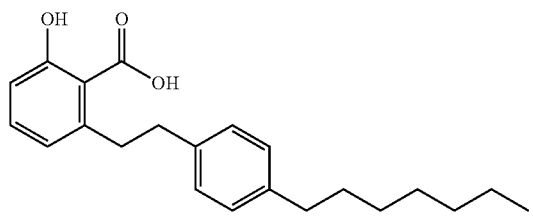 [SMILES: CCCCCCCc1ccc(CCc2cccc(O)c2C(=O)O)cc1]

Other known inhibitors include (Zhang 2017):

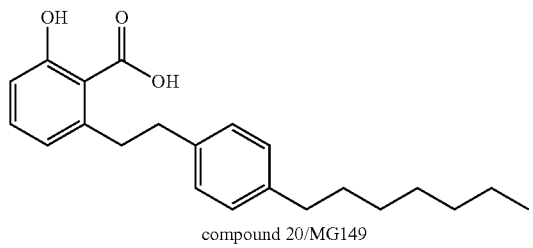

compound 20/MG149

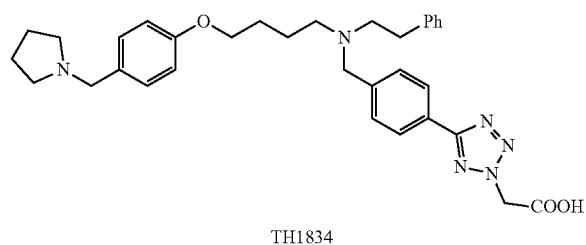

TH1834

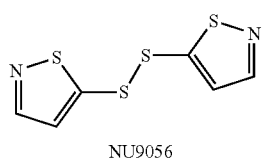

NU9056

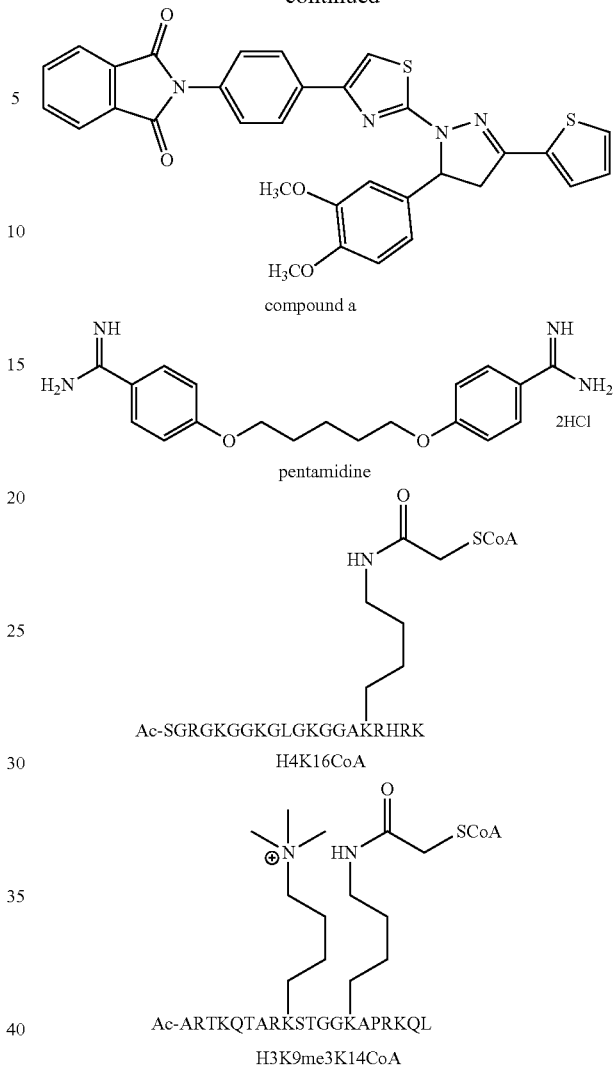

compound a pentamidine

Ac-SGRGKGGKGLGKGGAKRHRK
H4K16CoA

Ac-ARTKQTARKSTGGKAPRKQL
H3K9me3K14CoA

In light of the established role of KATs in general, and MYSTs in particular, in diseases such as cancer, a need exists for new inhibitors of these proteins.

DISCLOSURE OF THE INVENTION

The present invention provides compounds which inhibit the activity of one or more KATs of the MYST family, i.e., TIP60, KAT6B, MOZ, HBO1 and MOF.

A first aspect of the present invention provides a compound of formula (I), or a pharmaceutically acceptable salt thereof, for use in a method of therapy:

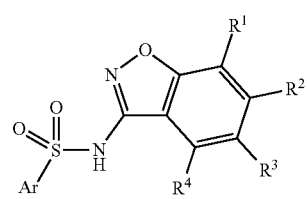

(I)

wherein:

R$^1$, R$^2$, R$^3$ and R$^4$ are independently selected from:
  (i) H;
  (ii) C$_{1-3}$ alkyl, optionally substituted by:
    hydroxy,
    C$_{1-2}$ alkoxy, optionally substituted by one or more fluoro groups,
    NH$_2$,
    phenyl,
    C$_{5-6}$ heteroaryl,
    C$_{1-4}$ alkyl carbamoyl,
    acylamido, or
    one or more fluoro groups;
  (iii) C$_{1-3}$ alkoxy, optionally substituted by C$_{3-6}$ cycloalkyl or by one or more fluoro groups;
  (iv) C$_{3-6}$ cycloalkyl;
  (v) halo;
  (vi) COR$^C$, where R$^C$ is selected from NR$^{N1}$R$^{N2}$, where R$^{N1}$ and R$^{N2}$ are independently selected from H and methyl;
  (vii) cyano, NH$_2$, or NO$_2$; and
  (viii) phenyl or C$_{5-6}$ heteroaryl, optionally substituted by methyl, cyano, hydroxy or methoxy;

Ar is a phenyl, napthyl, or C$_{5-10}$ heteroaryl group, which groups are optionally substituted by one or more groups selected from:
  (i) C$_{1-4}$ alkyl, optionally substituted by hydroxy, C$_{1-2}$ alkoxy, NH$_2$, C$_{1-4}$alkyl carbamoyl, or by one or more fluoro groups;
  (ii) C$_{3-6}$ cycloalkyl;
  (iii) hydroxy; cyano; NR$^{N3}$R$^{N4}$, where R$^{N3}$ and R$^{N4}$ are independently selected from H and methyl; or acylamido;
  (iv) halo;
  (v) C$_{1-3}$ alkoxy, optionally substituted by hydroxy, C(O)NH$_2$, C$_{3-6}$ cycloalkyl, phenyl, C$_{5-6}$ heteroaryl, or by one or more fluoro groups;
  (vi) phenoxy, optionally substituted by fluoro;
  (vii) phenyl, or C$_{5-6}$ heteroaryl
  (viii) SF$_5$ or SO$_2$CH$_3$;
  (ix) —(CH$_2$)$_n$—Y—, where Y is O or CH$_2$, and n is 2 or 3; or
  (x) C$_{1-4}$ alkyl ester.

A first aspect also provides a pharmaceutical composition comprising a compound of formula (I), or a pharmaceutically acceptable salt thereof, as defined and a pharmaceutically acceptable excipient.

A second aspect of the present invention provides a method of treatment of cancer, comprising administering to a patient in need of treatment, a compound, or a pharmaceutically acceptable salt thereof, as defined in the first aspect of the invention or a pharmaceutical composition of the first aspect of the invention. The second aspect of the present invention also provides the use of a compound, or a pharmaceutically acceptable salt thereof, as defined in the first aspect of the invention in the manufacture of a medicament for treating cancer, and a compound, or a pharmaceutically acceptable salt thereof, as defined in the first aspect of the invention or pharmaceutical composition thereof for use in the treatment of cancer.

As described below, the compound as defined in the first aspect may be administered simultaneously or sequentially with radiotherapy and/or chemotherapy in the treatment of cancer.

A third aspect of the invention provides a compound of formula (I), or a pharmaceutically acceptable salt thereof:

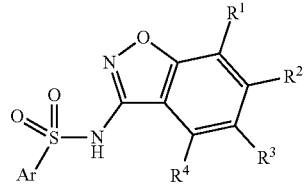

(I)

wherein:

R$^1$, R$^2$, R$^3$ and R$^4$ are independently selected from:
  (i) H;
  (ii) C$_{1-3}$ alkyl, optionally substituted by:
    hydroxy,
    C$_{1-2}$ alkoxy, optionally substituted by one or more fluoro groups,
    NH$_2$,
    phenyl,
    C$_{5-6}$ heteroaryl,
    C$_{1-4}$ alkyl carbamoyl,
    acylamido, or
    one or more fluoro groups;
  (iii) C$_{1-3}$ alkoxy, optionally substituted by C$_{3-6}$ cycloalkyl or by one or more fluoro groups;
  (iv) C$_{3-6}$ cycloalkyl;
  (v) halo;
  (vi) COR$^C$, where R$^C$ is selected from NR$^{N1}$R$^{N2}$, where R$^{N1}$ and R$^{N2}$ are independently selected from H and methyl;
  (vii) cyano, NH$_2$, or NO$_2$; and
  (viii) phenyl or C$_{5-6}$ heteroaryl, optionally substituted by methyl, cyano, hydroxy or methoxy;

Ar is a phenyl, napthyl, or C$_{5-10}$ heteroaryl group, which groups are optionally substituted by one or more groups selected from:
  (i) C$_{1-4}$ alkyl, optionally substituted by hydroxy, C$_{1-2}$ alkoxy, NH$_2$, C$_{1-4}$alkyl carbamoyl, or by one or more fluoro groups;
  (ii) C$_{3-6}$ cycloalkyl;
  (iii) hydroxy; cyano; NR$^{N3}$R$^{N4}$, where R$^{N3}$ and R$^{N4}$ are independently selected from H and methyl; or acylamido;
  (iv) halo;
  (v) C$_{1-3}$ alkoxy, optionally substituted by hydroxy, C(O)NH$_2$, C$_{3-6}$ cycloalkyl, phenyl, C$_{5-6}$ heteroaryl, or by one or more fluoro groups;
  (vi) phenoxy, optionally substituted by fluoro;
  (vii) phenyl or C$_{5-6}$ heteroaryl;
  (viii) SF$_5$ or SO$_2$CH$_3$;
  (ix) —(CH$_2$)$_n$—Y—, where Y is O or CH$_2$, and n is 2 or 3; or
  (x) C$_{1-4}$ alkyl ester;

with the proviso that:
(a) at least one of R$^1$, R$^2$, R$^3$ and R$^4$ is not H, and optionally that R$^3$ is not CF$_3$; or
(b) R$^4$ is OMe; or
(c) R$^4$ is Cl, and either R$^1$, R$^2$ and R$^3$ are H, or R$^2$ is C$_{1-3}$ alkyl or bromo, and R$^1$ and R$^3$ are H; or
(d) R$^3$ is C$_{1-3}$ alkyl and R$^1$, R$^2$ and R$^4$ are H.

A fourth aspect of the present invention provides the synthesis of compounds as defined in the first or third aspects of the invention, as described below.

Definitions

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. The phrase "optionally substituted" as used herein, pertains to a parent group which may be unsubstituted or which may be substituted.

$C_{5-12}$ heteroaryl: The term "$C_{5-12}$ heteroaryl" as used herein, pertains to a monovalent moiety obtained by removing a hydrogen atom from an aromatic structure having from 5 to 12 rings atoms, of which from 1 to 3 are ring heteroatoms. The term 'aromatic structure' is used to denote a single ring or fused ring systems having aromatic properties, and the term 'ring heteroatom' refers to a nitrogen, oxygen or sulphur atom.

In this context, the prefixes (e.g. $C_{5-12}$, $C_{5-6}$, etc.) denote the number of atoms making up the aromatic structure, or range of number of atoms making up the aromatic structure, whether carbon atoms or heteroatoms.

Examples of $C_{5-12}$ heteroaryl structures include, but are not limited to, those derived from:
$N_1$: pyrrole (azole) ($C_5$), pyridine (azine) ($C_6$); pyridone ($C_6$); indole ($C_9$); quinoline ($C_{10}$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_1S_1$: thiazole ($C_5$), isothiazole ($C_5$);
$N_2S_1$: thiadiazole ($C_5$)
$N_2$: imidazole (1,3-diazole) ($C^5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$); benzimidazole ($C_9$)
$N_3$: triazole ($C_5$), triazine ($C_6$).

Halo: The term "halo" as used herein, refers to a group selected from fluoro, chloro, bromo and iodo.

Cyano: The term "cyano" as used herein, refers to a group —C≡N.

Hydroxy: the term "hydroxyl" as used herein, refers to a group —OH.

Phenyl: the term "phenyl" as used herein, pertains to a monovalent moiety obtained by removing a hydrogen atom from a single aromatic ring structure having 6 carbon ring atoms (—$C_6H_5$).

Phenoxy: the term "phenoxy" as used herein, pertains to a monovalent moiety obtained by removing a hydrogen atom from the oxygen atom of phenol (—O—$C_6H_5$). $C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, methyl ($C_1$), ethyl ($C_2$), propyl ($C_3$), and butyl ($C_4$).

Examples of saturated linear alkyl groups include, but are not limited to, methyl ($C_1$), ethyl ($C_2$), n-propyl ($C_3$), and n-butyl ($C_4$).

Examples of saturated branched alkyl groups include iso-propyl ($C_3$), iso-butyl ($C_4$), sec-butyl ($C_4$) and tert-butyl ($C_4$).

$C_{3-6}$ cycloalkyl: The term "$C_{3-6}$ cycloalkyl" as used herein, pertains to a monovalent moiety obtained by removing a hydrogen atom from a carbon atom of a saturated cyclic hydrocarbon compound having from 3 to 6 carbon atoms. Examples of $C_{3-6}$ cycloalkyl groups include, but are not limited to, cyclopropyl ($C_3$), cyclobutyl ($C_4$), cyclopentyl ($C_5$) and cyclonexyl ($C_6$).

$C_{1-4}$ alkoxy: The term "$C_{1-4}$ alkoxy" as used herein, pertains to a monovalent moiety obtained by removing a hydrogen atom from an oxygen atom of a saturated alcohol compound having from 1 to 4 carbon atoms. It can be represented as —O—$C_{1-4}$ alkyl. Examples of $C_{1-4}$ alkoxy groups include, but are not limited to, methoxy ($C_1$), ethoxy ($C_2$), propyloxy ($C_3$), and butyloxy ($C_4$).

$C_{1-4}$ alkyl carbamoyl: —NHC(═O)OR wherein R is a $C_{1-4}$ alkyl group as defined above. Examples of $C_{1-4}$ alkyl carbamoyl include, but are not limited to, —N(H)C(═O)OCH$_3$, —N(H)C(═O)OCH$_2$CH$_3$, and —N(H)C(═O)OC(CH$_3$)$_3$.

Acylamido: —NR(C═O)R' wherein R and R' are independently selected from H and $C_{1-4}$ alkyl as defined above. R and R' may also be —(CH$_2$)$_n$—, where n is 3 or 4. Examples of an acylamido group include, but are not limited to, —N(H)C(═O)CF$_3$, N(H)C(═O)Me, and:

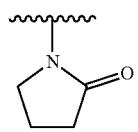 [SMILES: *N1CCCC1=O]

$C_{1-4}$ alkyl ester: The term "$C_{1-4}$ alkyl ester" as used herein, pertains to a monovalent moiety obtained by removing a hydrogen atom from an oxygen atom of a saturated carboxylic acid compound having from 1 to 5 carbon atoms. It can be represented as —O—C(O)—$C_{1-4}$ alkyl. Examples of $C_{1-4}$ alkyl ester groups include, but are not limited to, acetoxy (—O—C(O)—CH$_3$), propanoyloxy (—O—C(O)—CH$_2$CH$_3$), butanoyloxy (—O—C(O)—CH$_2$CH$_2$CH$_3$) and pentanoyloxy (—O—C(O)—CH$_2$CH$_2$CH$_2$CH$_3$).

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge 1977. For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

In the present invention, the carbon atom to which $R^1$ and Cy are bound may be a stereochemical centre, i.e. when $R^1$ is not H and $R^1$ and Cy are different. The compounds of the present invention may be a racemic mixture, or may be in enantiomeric excess or substantially enantiomerically pure.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

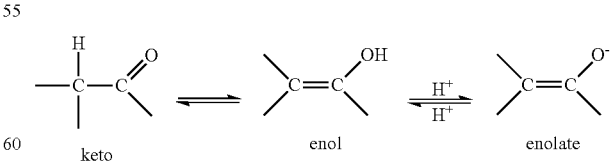

keto  enol  enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Inhibition

The compounds of the present invention inhibit the activity of one or more KATs of the MYST family, i.e., TIP60, KAT6B, MOZ, HBO1 and MOF.

The inhibitory activity of the compounds of the invention is likely to vary between the KATs of the MYST family.

The compounds of the present invention may selectively inhibit the activity of one or more KATs of the MYST family over other KATs of the MYST family, i.e. the inhibitory activity of the compound may be higher for one or more of the KATs of the MYST family over one or more of the other KATs of the MYST family.

Compounds of the present invention may (selectively) inhibit the activity of a single KAT of the MYST family. Thus, compounds of the present invention may inhibit the activity of TIP60, MORF, MOZ, HBO1 or MOF.

Compounds of the present invention may inhibit the activity of two KATs of the MYST family, for example MOZ and MORF.

Compounds of the present invention may inhibit the activity of three KATs of the MYST family, for example MOZ, MORF and HO1.

Compounds of the present invention may inhibit the activity of four KATs of the MYST family, for example MOZ, MORF, HBO1 and TIP60.

Compounds of the present invention may inhibit the activity of all five KATs of the MYST family, thus the compounds may inhibit the activity of TIP60, MORF, MOZ, HBO1 and MOF.

Compounds of the present invention may, in particular, inhibit the activity of MOZ and/or KAT6B and/or HBO1 and/or TIP60.

Therapeutic Indications

Compounds disclosed herein may provide a therapeutic benefit in a number of disorders, in particular, in the treatment or prevention of cancers.

Cancer

Inhibitors of post-translational lysine acetylation mediated by KATs of the MYST family are considered to be promising anti-neoplastic agents and therefore may be useful therapeutic agents, e.g. for use in the treatment of cancer. Such agents may also be useful as therapeutic agents for the treatment of cancers which exhibit overexpression of MYST proteins.

A "cancer" may be any form of cancer. In particular, a cancer can comprise any one or more of the following: leukemia, acute lymphocytic leukemia (ALL), acute myeloid leukemia (AML), chronic lymphocytic leukemia (CLL), chronic myeloid leukemia (CML), non-Hodgkin® lymphoma, Hodgkin® disease, prostate cancer, lung cancer, melanoma, breast cancer, colon and rectal cancer, colon cancer, squamous cell carcinoma and gastric cancer.

Alternatively, the cancer may comprise adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi® sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom s macroglobulinemia and/or Wilms☐tumor.

Cancers may be of a particular type. Examples of types of cancer include lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, sarcoma (e.g. angiosarcoma, chrondrosarcoma, osteosarcoma).

The cancer may be a MYST overexpressing cancer. The cancer may over-express MYST protein relative to non-cancerous tissue. In some cases, the cancer overproduces MYST mRNA relative to non-cancerous tissue. The over-expressed MYST protein or MYST mRNA may be any one KATs of the MYST family, i.e. any one of TIP60, KAT6B, MOZ, HBO1 and MOF. In some embodiments, the cancer may overexpress more than one KATs of the MYST family, e.g. two or more selected from the group consisting of TIP60, KAT6B, MOZ, HBO1 and MOF. The cancer may be a cancer that evades immune recognition, e.g. via tumor-associated Treg cells.

Alternatively or additionally, the cancer may be a bromodomain overexpressing cancer: The cancer cell may overexpress one or more bromodomain-containing proteins (herein referred to as "bromodomain proteins") relative to non-cancerous tissue. It may overproduce one or more bromodomain mRNA as compared to non-cancerous tissue. In some cases, the level of bromodomain protein and/or mRNA in the cell is at a level approximately equivalent to that of a non-cancerous cell. The cancer may overexpress one or more bromodomain proteins selected from the group consisting of; a bromodomain protein (namely BRD2, BRD3, BRD4, BRD7, BRD8, BRD9 and BRDT), TAF1/TAF1L, TFIID, SMARC2 (also called BRM) and SMARC4 (also called BRG1). For example, some colon cancers overexpress BRD8. Some acute myeloid leukemia cells overexpress BRD4.

Treg Cells as a Cancer Target

Treg cells are immunosuppressive cells, which act to prevent autoimmunity in the healthy mammalian immune system. However, some cancers act to upregulate Treg activity to evade the host immune system. Infiltration of Tregs in many tumour types correlates with poor patient prognoses and Treg cell depletion in tumour models demonstrates increased anti-tumour immune responses (Melero 2015). Tumour-associated Treg suppression of the host immune system has been reported in lung (Joshi 2015), (Tso 2012), breast (Gobert 2009; Yan 2011), prostate (Miller 2006) & pancreatic (Wang X 2016) cancers. FOXP3 is considered to be the master regulator of Treg differentiation, development and function of Treg cells.

Several studies have demonstrated that acetylation of FOXP3 plays a critical role in the stability of the FOXP3 protein and in regulating its ability to access DNA; and FOXP3 acetylation is mediated by KATs (Dhuban 2017). Decreases in TIP60-mediated FOXP3 acetylation has been shown to attenuate Treg development, suggesting a further mechanism by which the inhibition of the acetylating activity of MYST proteins could be used to intervene in diseases such as cancer.

Combination Therapies

The agents described herein may be useful in combination with other anti-cancer therapies. They may act synergistically with chemo- or radiotherapy, and/or with targeted therapies, including but not limited to FGFR1 inhibitors and therapies targeting nuclear hormone receptors. For example, the agents described herein may be useful in combination with bromodomain targeted drugs including BET inhibitors. BET inhibitors reversibly bind the bromodomains of the BET proteins BRD2, BRD3, BRD4 and BRDT.

Inhibition of KAT proteins of the MYST family, to reduce the extent of lysine acetylation of histones (and other nuclear proteins described herein) will likely sensitize tumour cells to chemo- and radiotherapy by attenuating the process of DNA damage repair, e.g. the repair of DNA double-strand breaks (DSB), thus increasing the frequency of chemo- and radiotherapy induced cancer cell death. Therefore, it is likely that inhibition of KAT proteins of the MYST family would synergize well with low dose chemo- or radiotherapy.

Thus, in some cases, a MYST protein antagonist disclosed herein may be administered in conjunction with a radiotherapeutic or chemotherapeutic regime. It may be administered simultaneously or sequentially with radio and/or chemotherapy. Suitable chemotherapeutic agents and radiotherapy protocols will be readily appreciable to the skilled person. In particular, the compound described herein may be combined with low dose chemo or radio therapy. Appropriate dosages for "low dose" chemo or radio therapy will be readily appreciable to the skilled practitioner.

In particular, where the compounds of the present application are used to abrogate Treg suppression, these may be combined with immune checkpoint inhibitors (Melero 2015, Wang L 2016). Furthermore, where compounds of the present invention which abrogate Treg suppression may be used in combination with radiotherapy, to reduce the depletion of Treg function in tumours (Persa 2015, Jeong 2016)

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern 2005; such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus. In one preferred embodiment, the subject/patient is a human.

General Synthesis Methods

The compounds of the invention can be prepared by employing the following general methods and using procedures described in detail for the examples. The reaction conditions referred to are illustrative and non-limiting, for example one skilled in the art may use a diverse range of synthetic methods to synthesise the desired compounds such as but not limited to methods described in literature (for example but not limited to March's Advanced Organic Chemistry: Reactions, Mechanisms, and Structure, 7th Edition or Larock's Comprehensive Organic Transformations: Comprehensive Organic Transformations: A Guide to Functional Group Preparations).

Compounds of formula (I), as described above, can be prepared by synthetic strategies outlined below, wherein the definitions above apply.

General Synthesis 1

Scheme 1A illustrates the formation of a sulfonamide bond to form compounds with the structure I by coupling a relevant sulfonyl chloride compound of structure G2 with a primary or secondary amine such as benzisoxazole amine G3

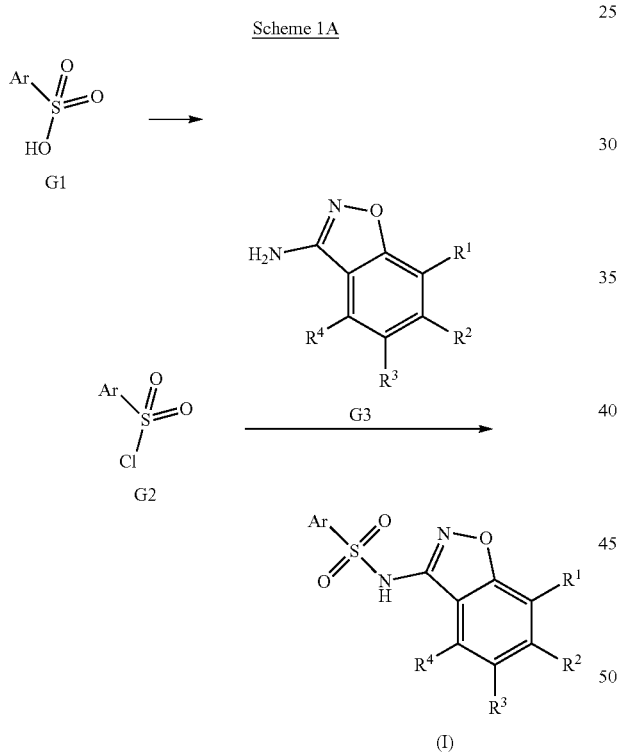

Methods to form such sulfonamides will be apparent to those skilled in the art, but include for example the use of a suitable base such as but not limited to pyridine, LiHMDS, n-BuLi or NaH and the use of activated forms of the sulfonic acid such as the corresponding sulfonyl halide. Formation of sulfonyl chlorides of structure G2 from the corresponding acids of structure G1 can be achieved by for example use of thionyl chloride or cyanuric chloride.

Alternatively, the activated form of a sulfonic acid such as but not limited to a pentafluorophenyl sulfonate ester or trichlorophenyl sulfonate ester with the structure G5 can be coupled with the relevant primary or secondary amine, such as benzisoxazole amine G3 (Scheme 1B).

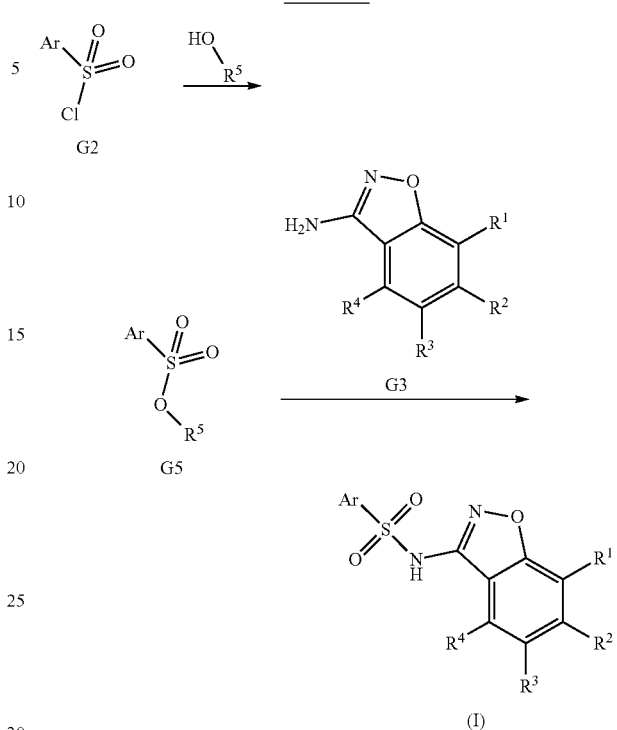

Formation of the sulfonate ester in G5 from the corresponding sulfonyl chloride G2 and relevant phenol ($R^5$ may be for example pentaflurorphenyl or trichlorophenyl) can be achieved using a suitable base such as but not limited to pyridine or triethylamine. Methods to form the sulfonamides in I will be apparent to those skilled in the art, but include for example the use of a suitable base such as but not limited to LiHMDS.

General Synthesis 2

Scheme 2A illustrates the formation of a sulfonyl chloride such as G2, as a substituent which is part of Ar.

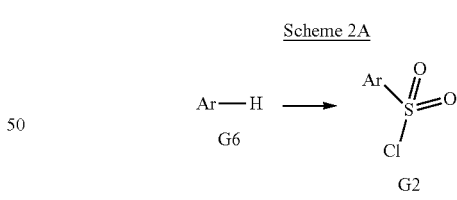

This can be achieved by reacting a relevant aryl compound with the structure G6 with for example but not limited to chlorosulfonic acid. Alternatively, the aryl compound G6 may be sequentially treated with a base, such as but not limited to n-BuLi, and sulphur dioxide to furnish the lithium arylsulfinate which is further oxidised by for example sulfuryl chloride to give the desired sulfonyl chloride in G2. The product G2 may be isolated by methods know to those skilled in the art or may be formed in situ and used immediately in subsequent step.

In addition, the sulfonyl chloride in G2 may be formed from an aryl thiol in structure G8 illustrated.

Scheme 2B

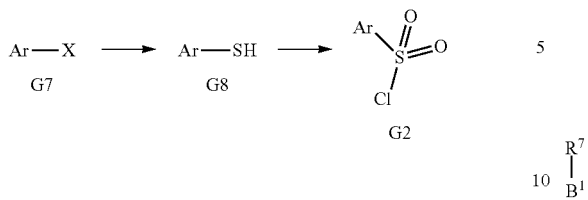

Methods to form G2 include for example the use of a suitable oxidant such as but not limited to hydrogen peroxide and potassium nitrate in the presence of a chloride source such as but not limited to chlorotrimethylsilane or thionyl chloride. A thiol of structure G8 may be synthesised from a compound of structure G7 where (X) may be a halogen by methods known to those skilled in the art, including but not limited to nucleophilic displacement in the presence or absence of a transition metal. Alternatively, sulfonation of an aryl compound such as G6 may give the corresponding sulfonic acid of structure G1. This can be achieved by any suitable reagent known to those skilled in the art, for example sulphur trioxide or sulfuric acid.

Scheme 2C

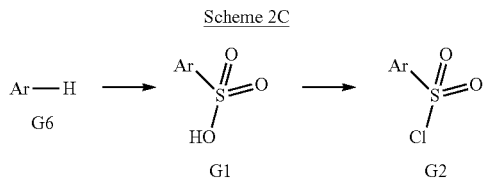

The sulfonic acid G1 may be converted to the sulfonyl chloride G2 by methods outlined in General Synthesis 1, Scheme 1A.

General Synthesis 3

Scheme 3A illustrates the formation of a benzisoxazole amine such as G3 from an aryl nitrile with an ortho substituent X, such as structure G9. The group (X) may be, but is not limited to, a halogen such as a chloro or a fluoro group and is chosen to be suitable for the reaction employed.

Scheme 3A

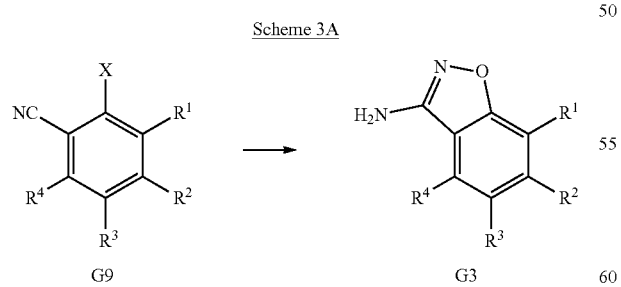

For example, the starting material G9 may be reacted with an oxime such as but not limited to acetone oxime or with for example acetohydroxamic acid, in the presence of a suitable base such as but not limited to potassium tert-butoxide, to form the benzisoxazole amine G3.

General Synthesis 4

Scheme 4A

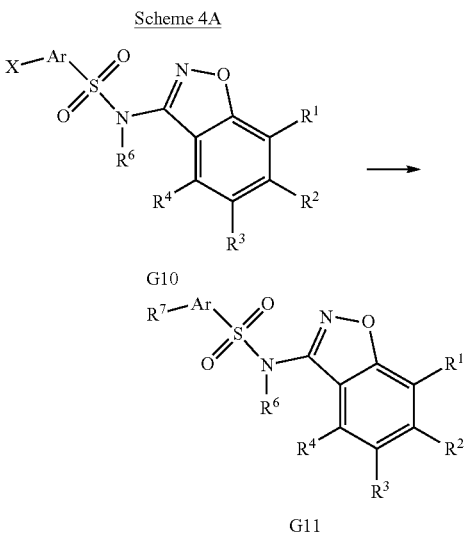

Scheme 4A illustrates the addition of an $R^7$ group to a compound of structure G10 (where $R^6$ represents H or a suitable protecting group including but not limited to 2,4-dimethoxybenzyl (DMB); methods for the removal of said protecting groups will be known to those skilled in the art (for example Greene's Protective Groups in Organic Synthesis, 4th Edition)), as a substituent which is part of Ar. This can be achieved using any suitable coupling reaction known to the person skilled in the art, for example Suzuki coupling. The groups $R^7B^1$ and X are chosen to be suitable for the coupling reaction employed. For example, in the case of a Suzuki coupling reaction, (X) may be a halogen, triflate or other suitable group and $B^1$ represents a suitable boron compound including but not limited to a boronic acid or boronate ester.

Examples of $B^1$ that can be used in the Suzuki coupling include, but are not limited to, those shown below.

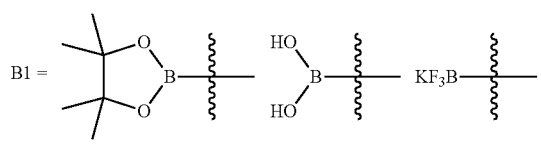

The types of $R^7B^1$ compounds that can be used in the Suzuki coupling include, but are not limited to, those shown below.

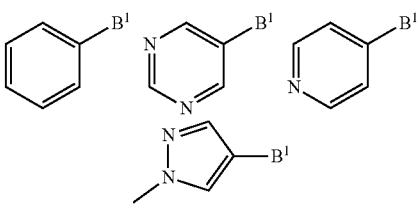

In addition to scheme 4A, the position of the (X) and ($B^1$) can be reversed as shown below in scheme 4B, to give the same final compound G11. Similarly to Scheme 2A, the groups denoted by $R^7X$ and $B^1$ are chosen to be suitable for the coupling reaction employed. For example, in the case of a Suzuki coupling reaction (X) may be a halogen, triflate or other suitable group and $B^1$ represents a suitable boron compound including, but not limited to, a boronic acid or boronate ester.

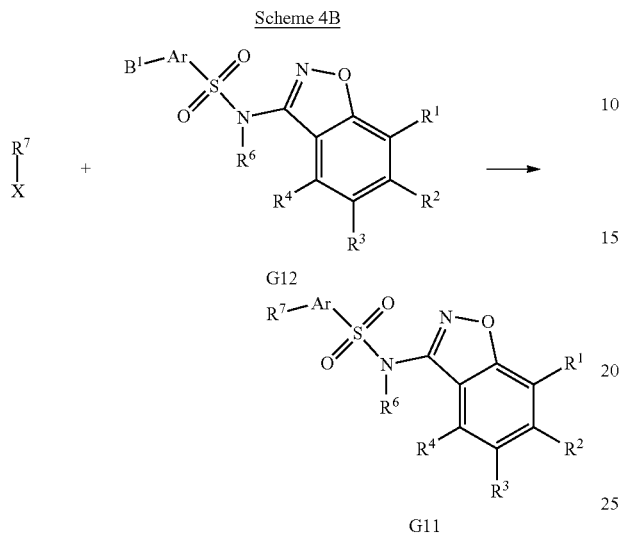

A variety of coupling reactions may be used to introduce the $R^7$ group other than Suzuki coupling, such as for example transition metal catalysed coupling reactions or for example tin (Stille type reaction) and zinc (Negishi type reaction) compounds. In addition, a Chan-Lam type coupling may be used when the group (X) is for example, but not limited to, a phenol (O—H) or primary or secondary amine (R'R"N—H).

The transitions described in Scheme 4A and 4B may also be carried out with substituent $R^1$, $R^2$, $R^3$ or $R^4$ on the benzisoxazole moiety in structure G13, represented by Scheme 4C below.

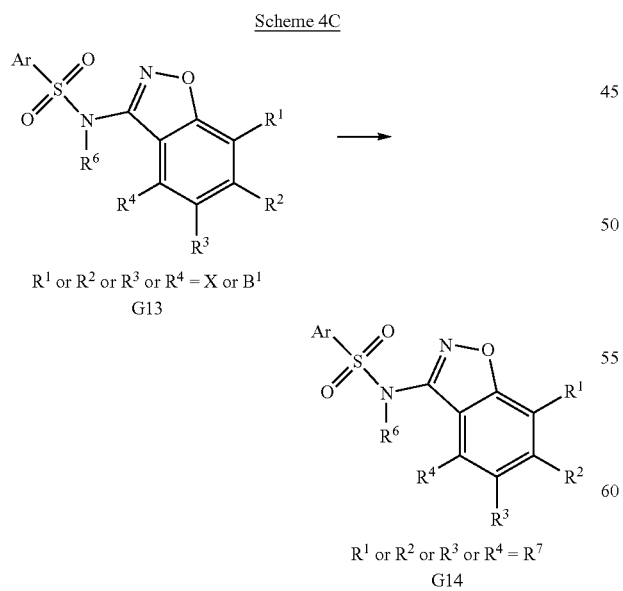

In addition, substituent $R^7$ may be introduced prior to sulfonamide and benzisoxazole formation on the nitrile precursor G9 (when $R^1$ or $R^2$ or $R^3$ or $R^4$=X or $B^1$) in General Synthesis 3, Scheme 3D.

General Synthesis 5

Scheme 5A illustrates the addition of a nitrogen linked $R^8$ group, as a substituent which is part of Ar or on the benzisoxazole moiety to give a compound of structure G16. This can be achieved using any suitable coupling reaction known to the person skilled in the art, for example, by SnAr displacement or Buchwald coupling. The group denoted by (X) may be, but not limited to, a halogen and is chosen to be suitable for the coupling reaction employed.

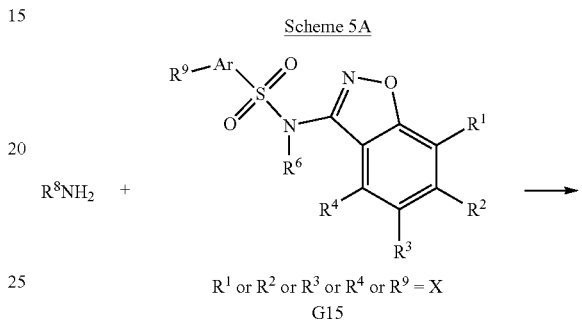

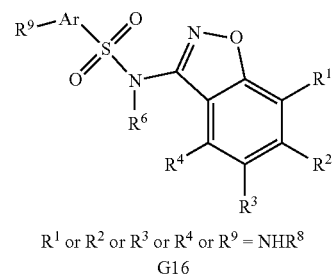

Alternatively, to synthesise ether linked compounds, a similar strategy can be employed as shown in Scheme 5B. This can be achieved using any suitable coupling reaction known to a person skilled in the art, for example, by a SnAr or Ullman-type coupling to give compounds with structure G17.

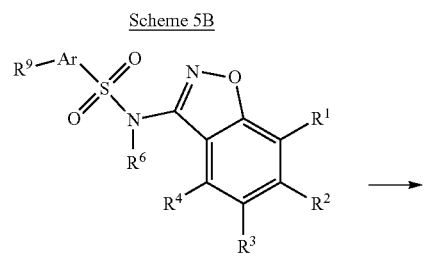

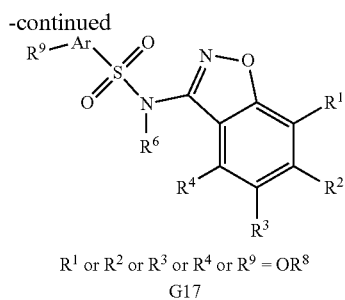

R¹ or R² or R³ or R⁴ or R⁹ = OR⁸
G17

Both the above couplings may also be reversed, such that the group added is R⁸—X.

In addition, substituent OR⁸ or NHR⁸ may be introduced prior to sulfonamide and benzisoxazole formation on the nitrile precursor G9 (when R¹ or R² or R³ or R⁴=X) in General Synthesis 3, Scheme 3D.
General Synthesis 6 the amide to form the amine or dehydration of the amide to form the nitrile. Methods to perform such transformation will be known to those skilled in the art.

In addition, an amide CONR¹⁰R¹¹ may be introduced prior to sulfonamide and benzisoxazole formation on the nitrile precursor G9 (when R¹ or R² or R³ or R⁴=CO$_2$R¹², R¹²=Alk or H) in General Synthesis 3, Scheme 3D.
General Synthesis 7

Conversion of (X) in structure G20 in Scheme 7A into an ester in structure G18 (R¹²=Alkyl, such as methyl or ethyl) will be apparent to those skilled in the art, but include for example a carbonylation reaction which can be achieved by the use of carbon monoxide in the presence of an transition metal catalyst such as but not limited to PdCl$_2$dppf.DCM; and an alcoholic solvent such as but not limited to methanol or ethanol. Formation of the carboxylic acid in structure G18 (R=H) can be achieved by for example hydrolysis with a base such as an alkali metal hydroxide or an acid for example aqueous hydrochloric acid.

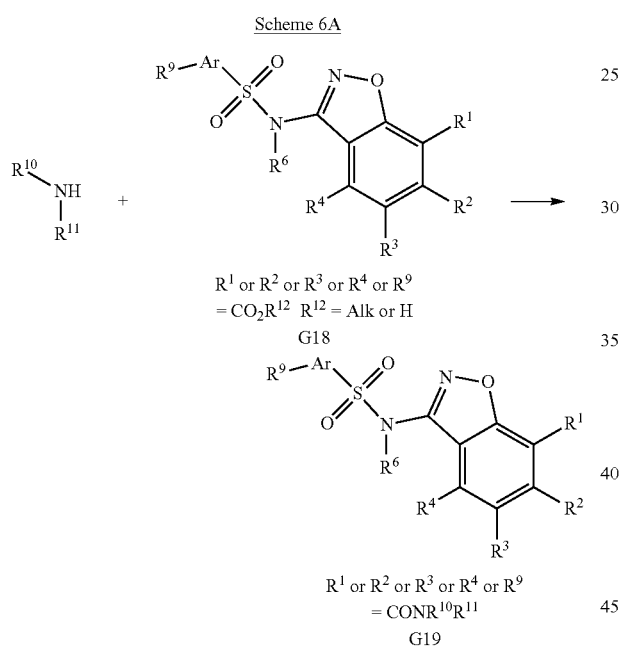

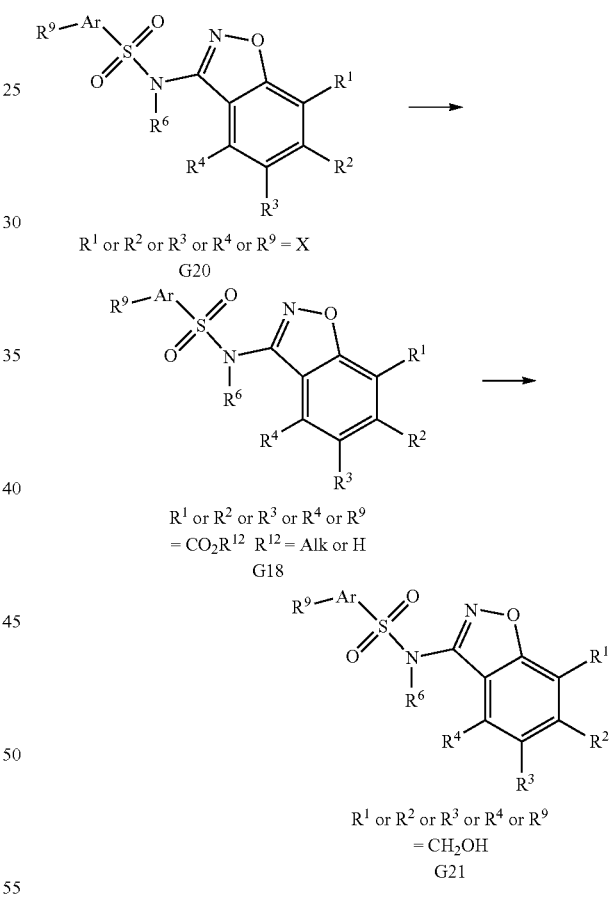

Scheme 6A illustrates the addition of an amine (HNR¹⁰R¹¹) to form the corresponding amide, as a substituent which is a part of Ar or on the benzisoxazole moiety to give a compound of structure G19. This can be achieved by coupling a relevant carboxylic acid with a primary amine or a secondary amine NHR¹⁰R¹¹. Methods to form such amides will be apparent to those skilled in the art, but include for example the use of reagents such as HATU, HBTU, T3P and EDCI/HOBt, and the use of activated forms of the carboxylic acid such as the corresponding acyl halide, mixed anhydride or N-hydroxysuccinimide ester. Amide G19 may also be synthesised directly from the ester compound (when R¹²=Alk, such as but not limited to methyl or ethyl). Formation of the carboxylic acid (when R¹²=H) from the corresponding ester can be achieved by for example hydrolysis with a base such as an alkali metal hydroxide or an acid for example aqueous hydrochloric acid.

From the amide compound G19, further transformations may be carried out, such as but not limited to, reduction of The ester or acid G18 in Scheme 7A may be reduced to the hydroxyl compound such as structure G21. Methods for such transformation will be known to those skilled in the art but include for example the use of reducing agents such as lithium aluminium hydride (for the ester and carboxylic acid) and borane (for the carboxylic acid).

From the hydroxyl compound G21, further transformations may be carried out, such as but not limited to, Mitsunobu or nucleophilc substitution reactions. Methods to perform such transformation will be known to those skilled in the art.

In addition, an ester group may be introduced prior to sulfonamide and benzisoxazole formation on the nitrile precursor G9 (when $R^1$ or $R^2$ or $R^3$ or $R^4$=X) in General Synthesis 3, Scheme 3D.

General Synthesis 8

Scheme 8A illustrates the reduction of a nitro group in structure G22 to form the corresponding amine in structure G23, as a substituent which is part of the Ar or on the benzisoxazole moiety.

Scheme 8A

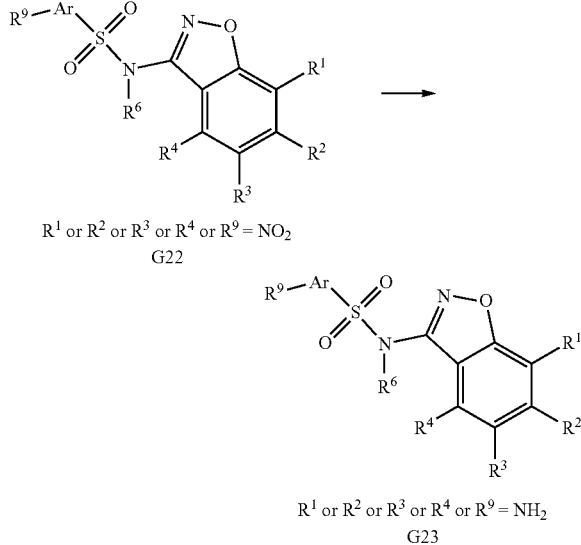

$R^1$ or $R^2$ or $R^3$ or $R^4$ or $R^9$ = $NO_2$
G22

$R^1$ or $R^2$ or $R^3$ or $R^4$ or $R^9$ = $NH_2$
G23

Reduction of the nitro group to the primary amine G23 will be apparent to those skilled in the art and include but are not limited to using reducing conditions such as a transition metal (Fe, In, Zn) in the presence of HCl, hydrogenation in the presence of a transition metal or transition metal catalyst.

From the amine compound G23, further transformations may be carried out, such as but not limited to amide bond formation. Methods to perform such transformation will be similar to those described in General Synthesis 6.

In addition, an amine group may be introduced prior to sulfonamide and benzisoxazole formation on the nitrile precursor G9 (when $R^1$ or $R^2$ or $R^3$ or $R^4$=$NO_2$) in General Synthesis 3, Scheme 3D.

General Synthesis 9

Scheme 9A illustrates the introduction of a nitrile group in structure G25, as a substituent which is part or the Ar or on the benzisoxazole moiety.

Scheme 9A

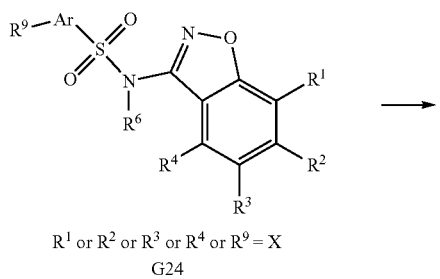

$R^1$ or $R^2$ or $R^3$ or $R^4$ or $R^9$ = X
G24

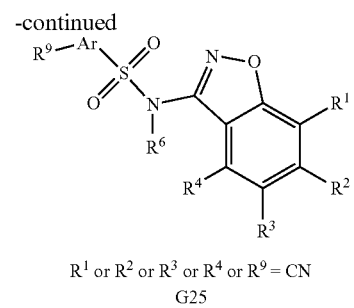

$R^1$ or $R^2$ or $R^3$ or $R^4$ or $R^9$ = CN
G25

The method for such transformation will be apparent to those skilled in the art and include but are not limited to SnAr displacement, or a transition metal catalysed coupling with a suitable cyanide reagent. The group denoted by (X) in structure G24 may be, but not limited to, a halogen, triflate or mesylate and is chosen to be suitable for the reaction employed.

Further Preferences

The following preferences may apply to all aspects of the invention as described above, or may relate to a single aspect. The preferences may be combined together in any combination.

$R^1$, $R^2$, $R^3$ and $R^4$

In some embodiments, at least one of $R^1$, $R^2$, $R^3$ and $R^4$ may be H. In some of these embodiments, one of $R^1$, $R^2$, $R^3$ and $R^4$ are H. In other of these embodiments, two of $R^1$, $R^2$, $R^3$ and $R^4$ are H. In other of these embodiments, three of $R^1$, $R^2$, $R^3$ and $R^4$ are H.

In some embodiments, at least one of $R^1$, $R^2$, $R^3$ and $R^4$ is not H.

In some embodiments, at least one of $R^1$, $R^2$, $R^3$ and $R^4$ may be $C_{1-3}$ alkyl, optionally substituted by:

hydroxy,
$C_{1-2}$ alkoxy, optionally substituted by one or more fluoro groups
$NH_2$,
phenyl,
$C_{5-6}$ heteroaryl,
$C_{1-4}$ alkyl carbamoyl,
acylamido, or
one or more fluoro groups.

In these embodiments, at least one of $R^1$, $R^2$, $R^3$ and $R^4$ may be $C_{1-3}$ alkyl. Further, in these embodiments, the $C_{1-3}$ alkyl group may be methyl, ethyl or propyl. These groups may be unsubstituted. These groups may be substituted by one or more fluoro groups, and may be perfluorinated, e.g. $CF_3$, $C_2F_5$. These groups may be substituted by one, two, three, four or five fluoro groups. In some embodiment, these groups may be substituted by one; one or two; or one, two or three fluoro groups.

If the alkyl group is substituted, the substituent may be selected from:

(i) hydroxy; or
(ii) unsubstituted $C_{1-2}$ alkoxy, i.e. methoxy, ethoxy; or $C_{1-2}$ alkoxy substituted by one or more fluoro groups, e.g. —$OCH_2F$, —$OCH_2CF_3$; or
(iii) $NH_2$; or
(iv) phenyl; or
(v) $C_{5-6}$ heteroaryl, e.g. N-pyrazolyl; or
(vi) $C_{1-4}$alkyl carbamoyl, e.g. NHC(O)Me; or
(vii) acylamido, e.g. $NHCO_2Me$.

In some embodiments, at least one of $R^1$, $R^2$, $R^3$ and $R^4$ may be $C_{1-3}$ alkoxy, optionally substituted by $C_{3-6}$ cycloalkyl or by one of more fluoro groups. In these embodiments, the $C_{1-3}$ alkoxy group may be methoxy, ethoxy or propyloxy. These groups may be unsubstituted. These groups may be substituted by one or more fluoro groups, and may be perfluorinated, e.g. $OCF_3$, $OC_2F_5$. These groups may be substituted by one, two, three, four or five fluoro groups. In some embodiment, these groups may be substituted by one; one or two; or one, two or three fluoro groups. The alkoxy group may be substituted by $C_{3-6}$ cycloalkyl, e.g. cyclopropyl. Thus the overall group may be $OCH_2$(cyclopropyl).

In some embodiments, at least one of $R^1$, $R^2$, $R^3$ and $R^4$ may be $C_{3-6}$ cycloalkyl. In these embodiments, the $C_{3-6}$ cycloalkyl group may be cyclopropyl, cyclobutyl, cyclopentyl or cyclohexyl. In particular, the $C_{3-6}$ cycloalkyl group may be cyclopropyl.

In some embodiments, at least one of $R^1$, $R^2$, $R^3$ and $R^4$ may be halo. In these embodiments, the halo group may be fluoro, chloro, bromo or iodo.

In some embodiments, at least one of $R^1$, $R^2$, $R^3$ and $R^4$ may be $COR^C$, where $R^C$ is selected from $NR^{N1}R^{N2}$, where $R^{N1}$ and $R^{N2}$ are independently selected from H and methyl. In these embodiments, the group may be selected from $C(O)NH_2$, $C(O)NHCH_3$ and $C(O)N(CH_3)_2$.

In some embodiments, at least one of $R^1$, $R^2$, $R^3$ and $R^4$ may be cyano, $NH_2$, $NO_2$. In some of these embodiments at least one of $R^1$, $R^2$, $R^3$ and $R^4$ may be cyano. In others of these embodiments at least one of $R^1$, $R^2$, $R^3$ and $R^4$ may be $NH_2$. In others of these embodiments at least one of $R^1$, $R^2$, $R^3$ and $R^4$ may be $NO_2$.

In some embodiments, at least one of $R^1$, $R^2$, $R^3$ and $R^4$ may be phenyl or $C_{5-6}$ heteroaryl, which groups are optionally substituted by methyl, cyano, hydroxy or methoxy. In some of these embodiments at least one of $R^1$, $R^2$, $R^3$ and $R^4$ may be phenyl. In others of these embodiments at least one of $R^1$, $R^2$, $R^3$ and $R^4$ may be $C_{5-6}$ heteroaryl, for example oxazolyl, pyrazolyl, triazolyl, pyridyl and pyrimidinyl. The phenyl or $C_{5-6}$ heteroaryl group may be unsubstituted. In certain embodiments, the phenyl group may be substituted by methyl, cyano or methoxy. In certain embodiments, the $C_{5-6}$ heteroaryl group may be substituted by one or more methyl groups, such that the overall group is, for example, dimethylpyrazolyl or N-methylpyrazolyl.

In some embodiments, $R^4$ is methoxy.

In some embodiments, $R^4$ is methoxy, $R^2$ is $CH_2OCH_3$ or $CH_2OCH_2CH_3$ and $R^1$ and $R^3$ are H.

In some embodiments, $R^4$ is methoxy, $R^2$ is phenyl, optionally substituted by methyl or methoxy, and $R^1$ and $R^3$ are H.

In some embodiments, $R^4$ is methoxy, $R^2$ is $C_{5-6}$ heteroaryl, optionally substituted by methyl.

In some embodiments, $R^4$ is methoxy and $R^1$, $R^2$ and $R^3$ are H.

In some embodiments, $R^4$ is chloro, $R^2$ is $C_{1-3}$ alkyl or bromo, and $R^1$ and $R^3$ are H.

In some embodiments, $R^4$ is chloro and $R^1$, $R^2$ and $R^4$ are H.

In some embodiments, $R^3$ is $C_{1-3}$ alkyl and $R^1$, $R^2$ and $R^4$ are H.

Ar

Ar is selected from phenyl, napthyl and $C_{5-10}$ heteroaryl groups, which may be unsubstituted or substituted.

In some embodiments, Ar is phenyl.

In some embodiments, Ar is napthyl.

In some embodiments, Ar is a $C_{5-10}$ heteroaryl group. The $C_{5-10}$ heteroaryl group may be selected from: quinolinyl, benzothiazolyl, quinoxalinyl, benzooxadiazolyl, benzothiadiazolyl, benzofuran and benzotriazolyl. In certain of these embodiments, Ar is quinolinyl or benzothiazolyl.

In some embodiments, Ar is the group:

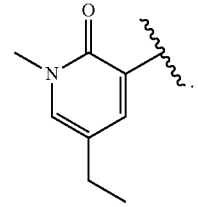 [SMILES: *c1cc(CC)cn(C)c1=O]

In some embodiments, a substituent for Ar is $C_{1-4}$ alkyl, optionally substituted by hydroxy, $C_{1-2}$ alkoxy, $NH_2$, $C_{1-4}$alkyl carbamoyl, or by one or more fluoro groups. In these embodiments, the $C_{1-4}$ alkyl group may be methyl, ethyl, propyl or butyl. These groups may be unsubstituted. These groups may be substituted by one or more fluoro groups, and may be perfluorinated, e.g. $CF_3$, $C_2F_5$. If the alkyl group is substituted, the substituent may be selected from:

(i) hydroxy; or (ii) $C_{1-2}$ alkoxy, i.e. methoxy, ethoxy; or (iii) $NH_2$; or (iv) $C_{1-4}$alkyl carbamoyl, e.g. $NHC(O)CH_3$.

In some embodiments, a substituent for Ar is $C_{3-6}$ cycloalkyl. In these embodiments, the $C_{3-6}$ cycloalkyl group may be cyclopropyl, cyclobutyl, cyclopentyl or cyclohexyl. In particular, the $C_{3-6}$ cycloalkyl group may be cyclohexyl.

In some embodiments, a substituent for Ar is hydroxy; cyano; $NR^{N3}R^{N4}$, where $R^{N3}$ and $R^{N4}$ are independently selected from H and methyl; or acylamido. In some of these embodiments, the substituent may be hydroxy. In other of these embodiments, the substituent may be cyano. In other of these embodiments, the substituent may be $NR^{N3}R^{N4}$, where $R^{N3}$ and $R^{N4}$ are independently selected from H and methyl—thus the substituent may be $NH_2$, $NHCH_3$ or $N(CH_3)_2$. In other of these embodiments, the substituent may be acylamido, such as $NHCO_2CH_3$.

In some embodiments, a substituent for Ar is halo. In these embodiments, the halo group may be fluoro, chloro, bromo or iodo.

In some embodiments, a substituent for Ar is $C_{1-3}$ alkoxy, optionally substituted by hydroxy, $C(O)NH_2$, $C_{3-6}$ cycloalkyl, phenyl, $C_{5-6}$ heteroaryl, or by one of more fluoro groups. In these embodiments, the $C_{1-3}$ alkoxy group may be methoxy, ethoxy or propyloxy. These groups may be unsubstituted. These groups may be substituted by one or more fluoro groups, and may be perfluorinated, e.g. $OCF_3$, $OC_2F_5$. The alkoxy group may be substituted by hydroxyl, such that the overall group is, for example, $OC_2H_4OH$. The alkoxy group may be substituted by $C(O)NH_2$, such that the overall group is, for example, $OCH_2C(O)NH_2$. The alkoxy group may be substituted by $C_{3-6}$ cycloalkyl, e.g. cyclopropyl, such that overall group may be, for example, $OCH_2$(cyclopropyl). The alkoxy group may be substituted by phenyl, such that the overall group is, for example, benzyloxy. The alkoxy group may be substituted by $C_{5-6}$ heteroaryl, e.g. pyridyl, pyrazolyl, such that the overall group is, for example, $OCH_2$(N-methylpyrazolyl) or $OCH_2$(methoxypyridyl).

In some embodiments, a substituent for Ar is phenoxy, optionally substituted by fluoro. In some of these embodiments the substituent may be phenoxy. In others of these embodiments, the substituent may be $OC_6H_4F$.

In some embodiments, a substituent for Ar is phenyl or C$_{5-6}$ heteroaryl. In some of these embodiments, the substituent is phenyl. In others of these embodiments, the substituent may be C$_{5-6}$ heteroaryl, such as oxazolyl or N-pyrazolyl.

In some embodiments, a substituent for Ar is SF$_5$ or SO$_2$CH$_3$. In some of these embodiments, the substituent is SF$_5$. In others of these embodiments, the substituent is SO$_2$Me.

In some embodiments, a substituent for Ar is —(CH$_2$)$_n$—Y—, where Y is O or CH$_2$, and n is 2 or 3. This substituent is particularly relevant when Ar is phenyl, and forms a partially unsaturated fused ring with the phenyl. Thus, Ar can be tetralinyl (i.e. fused cyclohexane), indanyl (i.e. fused cyclopentane), chromanyl (i.e. fused tetrahydopyran) or dihydrobenzofuranyl.

In some embodiments, a substituted for Ar is C$_{1-4}$ alkyl ester. In some of these embodiments, the substituent is C(O)OCH$_3$. In others of these embodiments, the substituent is C(O)OC(CH$_3$)$_3$.

Certain embodiments of Ar may be represented by the formula (Ar-1):

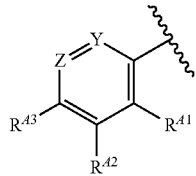

(Ar-1)

where Y is either N or C—R$^{44}$, and Z is either N or C—R$^{45}$; and
R$^{41}$, R$^{42}$, R$^{43}$, R$^{44}$ (if present) and R$^{45}$ (if present) are independently selected from H and the optional substituents for Ar.

In some embodiments, R$^{42}$ is ethyl.

In some embodiments, R$^{43}$ is selected from cycloalkyl; phenoxy; phenyl; C$_{5-6}$ heteroaryl; SF$_5$; and SO$_2$CH$_3$.

In some embodiments, Ar is 5-ethyl-2-methoxyphenyl.
In some embodiments, Ar is 5-CF$_3$-2-methoxyphenyl.
In some embodiments, Ar is 2,6-dimethoxyphenyl.
In some embodiments, Ar is quinolinyl. These compounds may show selective activity against HBO1.

In some embodiments, R$^4$ is methoxy, R$^2$ is selected from CH$_2$O CH$_3$, CH$_2$O CH$_2$CH$_3$ and optionally substituted phenyl, and Ar is 2,6-dimethoxybenzene. These compounds may show particular activity against MOZ and MORF. Compounds where R$^2$ is selected from CH$_2$OCH$_3$ and CH$_2$OCH$_2$CH$_3$ may show selective activity against MOZ and MORF.

In some embodiments, for compounds where R$^1$, R$^2$, R$^3$ and R$^4$ are H, then Ar is not 4-aminophenyl.

In some embodiments, for compounds where R$^1$, R$^2$, R$^3$ and R$^4$ are H, then Ar is not 2,4,6-trimethylphenyl.

In some embodiments, for compounds where R$^1$, R$^2$ and R$^4$ are H, and R$^3$ is CF$_3$, then Ar is not 2-(difluromethoxy)phenyl.

In some embodiments, for compounds where R$^1$, R$^2$, R$^3$ and R$^4$ are H, then Ar is not 4-fluoro-3-methyl-phenyl.

In some embodiments, for compounds where R$^1$, R$^2$ and R$^3$ are H, and R$^4$ is methoxy, then Ar is not unsubstituted napthyl.

Compounds of particular interest include those of the examples.

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), N-propyl (nPr), isopropyl (iPr), N-butyl (nBu), tert-butyl (tBu), phenyl (Ph), benzyl (Bn), methoxy (MeO), ethoxy (EtO), trimethylsilyl (TMS), and acetyl (Ac).

For convenience, many chemical compounds are represented using well known abbreviations, including but not limited to, methanol (MeOH), deuterated methanol (methanol-d$_4$) ethanol (EtOH), isopropanol (i-PrOH), ethyl acetate (EtOAc), acetic acid (AcOH), acetonitrile (MeCN or ACN), dichloromethane (methylene chloride, DCM), trifluoroacetic acid (TFA), N,N-dimethylformamide (DMF), tetrahydrofuran (THF), dimethylsulfoxide (DMSO), N-methyl-2-pyrrolidone (NMP), deuterated acetone (acetone-d$_6$), deuterated chloroform (CDCl), deuterated dimethylsulfoxide (DMSO-d$_6$), 1,1$_8$ bis(diphenylphosphino)ferrocene (dppf), triethylamine (Et$_3$N or TEA), N,N-diisopropylethylamine (DIPEA or DIEA), 1,1$_8$ bis(diphenylphosphino)ferrocene dichloropalladium (II) (PdCl$_2$(dppf)), trans-dichlorobis (triphenylphosphine)palladium(II) (PdCl$_2$(PPh$_3$)$_2$), tris (dibenzylideneacetone) dipalladium(0) (Pd$_2$(dba)$_3$), tetrakis (triphenylphosphine)palladium(0) (Pd(PPh$_3$)$_4$), 2,4-dimethoxybenzyl (DMB), petroleum ether (Pet. ether), lithium bis(trimethylsilyl)amide (LHMDS or LiHMDS), potassium bis(trimethylsilyl)amide (KHMDS), sodium bis (trimethylsilyl)amide (NaHMDS), n-butyllithium (n-BuLi), N-bromosuccinimide (NBS), N-chlorosuccinimide (NCS), pyridinium p-toluenesulfonate (PPTS), azobisisobutyronitrile (AIBN), tetramethylethylenediamine (TMEDA), tert-butyldimethylsilyl chloride (TBSCl), tetra-n-butylammonium fluoride (TBAF), and diisopropyl azodicarboxylate (DIAD).

In addition, TLC refers to thin layer chromatography.

Other abbreviations: retention time (rt or R$_t$), minute(s) (min), hour(s) (h), room temperature (RT), concentrated (conc.), atmosphere (atm), aqueous (aq.), saturated (sat.), eq. (equivalent(s)).

General Experimental Details

Unless otherwise stated the following generalisations apply. $^1$H NMR spectra were recorded on a Bruker Ultrashield Plus (400 MHz) or a Bruker AVANCE III (400 MHz). The multiplicity of a signal is designated by the following abbreviations: s, singlet; d, doublet; t, triplet; q, quartet; p, pentet; dd, doublet of doublets; dt, doublet of triplets; tt, triplet of triplets; br, broad; m, multiplet. All observed coupling constants, J, are reported in Hertz (Hz). Exchangeble protons are not always observed.

LCMS data was generated using either an Agilent 6100 Series Single Quad (LCMS-A), an Agilent 1260 Infinity Series UPLC/MS (LCMS-B), an Agilent 1200 (LCMS-C and LCMS-D), a Waters 2695 alliance (LCMS-E), an Agilent 6120 Single Quad (LCMS-F) or mass-directed HPLC-MS. Chlorine isotopes are reported as $^3$Cl, Bromine isotopes are reported as either $^{79}$Br or $^{81}$Br or both $^{79}$Br/$^{81}$Br.

LCMS Method A (LCMS-A):
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler Detector: 1200 Series G1314B Variable Wavelength Detector
LC Conditions:
Reverse Phase HPLC analysis
Column: Luna C8 (2) 5 μm 50×4.6 mm 100 Å
Column temperature: 30° C.
Injection Volume: 5 μL
Solvent A: Water 0.1% Formic Acid
Solvent B: MeCN 0.1% Formic Acid
Gradient: 5-100% solvent B over 10 min
Detection: 254 nm or 214 nm
Ms Conditions:
Ion Source: Quadrupole
Ion Mode: Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min
LCMS Method B (LCMS-B):
Instrument: Agilent 1260 Infinity Series UPLC/MS
Pump: 1260 Infinity G1312B Binary pump
Autosampler: 1260 Infinity G1367E 1260 HiP ALS
Detector: 1290 Infinity G4212A 1290 DAD
LC Conditions:
Reverse Phase HPLC analysis
Column: Poroshell 120 EC-C18 2.7 μm 50×3.0 mm
Column temperature: 35° C.
Injection Volume: 1 μL
Solvent A: Water 0.1% Formic Acid
Solvent B: MeCN 0.1% Formic Acid
Gradient: 5-100% solvent B over 3.8 min
Detection: monitored at 254 nm and 214 nm
MS Conditions:
Ion Source: Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min
LCMS Method C (LCMS-C):
LC model: Agilent 1200
(Pump type: Binary Pump, Detector type: DAD)
MS model: Agilent G6110A Quadrupole
LC Conditions:
Column: Xbridge-C18, 2.5 μm, 2.1×30 mm
Column temperature: 30° C.
Acquisition of wavelength: 214 nm, 254 nm
Mobile phase: A: 0.07% HCOOH aqueous solution, B: MeOH
MS Conditions:
MS: Ion source: ES+ (or ES−) MS range: 50-900 m/z
Fragmentor: 60 Drying gas flow: 10 L/min
Nebulizer pressure: 35 psi Drying gas temperature: 350° C.
Vcap: 3.5 kV Gradient Table:

| Flow (mL/min) | T (min) | A (%) | B (%) |
|---|---|---|---|
| 0.5 | 0.0 | 70 | 30 |
| 0.5 | 0.2 | 70 | 30 |
| 0.5 | 1.8 | 5 | 95 |
| 0.5 | 2.4 | 5 | 95 |
| 0.5 | 2.6 | 70 | 30 |
| 0.5 | 3.5 | 70 | 30 |

Sample Preparation:
The sample was dissolved in methanol, the concentration about 0.11-1 mg/mL, then filtered through syringe filter with 0.22 μm. (Injection volume: 1-10 μL)
LCMS Method D (LCMS-D):
LC model: Agilent 1200
(Pump type: Binary Pump, Detector type: DAD)
MS model: Agilent G6110A Quadrupole
LCMS Conditions:
LC: Column: Xbridge-C18, 2.5 μm, 2.1×30 mm
Column temperature: 30° C.
Acquisition of wavelength: 214 nm, 254 nm
Mobile phase: A: 0.07% HCOOH aqueous solution, B: MeOH
MS Conditions:
MS: Ion source: ES+(or ES−) MS range: 50-900 m/z
Fragmentor: 60 Drying gas flow: 10 L/min
Nebulizer pressure: 35 psi Drying gas temperature: 350° C.
Vcap: 3.5 kV Gradient Table:

| Flow (mL/min) | T (min) | A (%) | B (%) |
|---|---|---|---|
| 0.5 | 0.0 | 70 | 30 |
| 0.5 | 0.3 | 70 | 30 |
| 0.5 | 0.6 | 50 | 50 |
| 0.5 | 0.9 | 40 | 60 |
| 0.5 | 1.2 | 30 | 70 |
| 0.5 | 3.2 | 5 | 95 |
| 0.5 | 3.5 | 5 | 95 |
| 0.5 | 4.0 | 70 | 30 |
| 0.5 | 5.0 | 70 | 30 |

Sample Preparation:
The sample was dissolved in methanol, the concentration about 0.11-1 mg/mL, then filtered through the syringe filter with 0.22 μm. (Injection volume: 1-10 μL)
LCMS Method E (LCMS-E):
Equipment Information:
LC model: Waters 2695 alliance
(Pumptype: Quaternary Pump, Detector: 2996 Photodiode Array Detector)
MS model: Micromass ZQ
LC Conditions:
LC: Column: Xbridge-C18, 3.5 μm, 2.1×50 mm
Column temperature: 30° C.
Acquisition of wavelength: 214 nm, 254 nm
Mobile phase: A: 0.07% HCOOH aqueous solution, B: MeOH
MS Conditions:
MS: Ion source: ES+(or ES−) MS range: 50-900 m/z
Capillary: 3 kV Cone: 3 V Extractor: 3 V
Drying gas flow: 600 L/hr Cone: 50 L/hr
Desolvation temperature: 300° C.
Source temperature: 100° C.

Gradient Table:

| Flow (mL/min) | T (min) | A (%) | B (%) |
|---|---|---|---|
| 0.3 | 0.0 | 80 | 20 |
| 0.3 | 0.5 | 80 | 20 |
| 0.3 | 0.8 | 50 | 50 |
| 0.3 | 1.2 | 35 | 65 |
| 0.3 | 2.0 | 20 | 80 |
| 0.3 | 4.0 | 5 | 95 |
| 0.3 | 5.0 | 5 | 95 |
| 0.3 | 5.8 | 15 | 85 |
| 0.3 | 6.2 | 80 | 20 |
| 0.3 | 8.0 | 80 | 20 |

Sample Preparation:
The sample was dissolved in methanol, the concentration about 0.11-1 mg/mL, then filtered through the syringe filter with 0.22 µm. (Injection volume: 1-10 µL)
LCMS Method F (LCMS-F)
Instrument: Agilent 6120 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC Conditions:
Reverse Phase HPLC analysis
Column: Luna C8 (2) 5 µm 50×4.6 mm 100 Å
Column temperature: 30° C.
Injection Volume: 1-10 µL
Solvent A: Water 0.1% Formic Acid
Solvent B: MeCN 0.1% Formic Acid
Gradient: 0-95% solvent B over 10 min
Detection: 254 nm or 214 nm
MS Conditions:
Ion Source: Quadrupole
Ion Mode: Multimode-ES & APCI
Drying gas temp: 250° C.
Vaporizer temperature: 200° C.
Capillary voltage (V): 4000 (positive)
Capillary voltage (V): 4000 (negative)
Scan Range: 100-1000
Step size: 0.1 sec
Acquisition time: 10 min
Preparative Mass-Directed HPLC
Instrument:
Waters ZQ 3100-Mass Detector
Waters 2545-Pump
Waters SFO System Fluidics Organizer
Waters 2996 Diode Array Detector
Waters 2767 Sample Manager
LC Conditions:
Reverse Phase HPLC analysis
Column: XBridge TM C18 5 µm 19×50 mm
Injection Volume 500 µL
Solvent A: Water 0.1% Formic Acid
Solvent B: Acetonitrile 0.1% Formic Acid
Gradient: 25-100% B over 10 min
Flow rate: 19 mL/min
Detection: 100-600 nm
MS Conditions:
Ion Source: Single-quadrupole
Ion Mode: ES positive
Source Temp: 150° C.
Desolvation Temp: 350° C.
Detection: Ion counting
Capillary (KV)-3.00
Cone (V): 30
Extractor (V):3
RF Lens (V): 0.1
Scan Range: 100-1000 Amu
Scan Time: 0.5 sec
Acquisition time: 10 min
Gas Flow
Desolvation L/hour-650
Cone L/hour-100
Preparative HPLC (Prep. HPLC):
Instrument type: Varian 940-LC series;
Pump type: Quaternary Pump;
Detector type: Diode Array Detector
HPLC Conditions:
Waters Sunfire prep C18 OBD, 5 µm 19×100 mm column, eluting with a gradient of MeOH in water with 0.07% TFA at a flow rate of 15 mL/min. Acquisition wavelength 214 nm, 254 nm.

Analytical thin-layer chromatography was performed on Merck silica gel 60 F254 aluminium-backed plates which were visualised using fluorescence quenching under UV light or a basic $KMnO_4$ dip or Ninhydrin dip.

Preparative thin-layer chromatography (preparative TLC or prep. TLC) was performed using Tklst (China), grand grade: (HPTLC): 8±2 µm>80%; (TLC): 10-40 µm. Type: GF254. Compounds were visualised by UV (254 nm).

Column chromatography was performed using a Biotage Isolera purification system using either Grace or RediSep® silica cartridges or with Tklst (China), grand grade, 100-200 meshes silica gel.

Microwave irradiation was achieved using a CEM Explorer SP Microwave Reactor. Where necessary, anhydrous solvents were purchased from Sigma-Aldrich or dried using conventional methods.

Unless stated otherwise, acidification was done with concentrated or aqueous solution of HCl.
Additional Cartridges Used are as Follows:
Phase Separator:
Manufacturer: Biotage
Product: ISOLUTE® Phase Separator (3 mL unless otherwise stated)
Si-Amine Cartridges:
Manufacturer: Biotage
Product: Isolute® NH2, 1 g/6 mL
Or
Manufacturer: Silicycle
Product: Si-amine 500 mg or 1 g
Synthesis of Intermediates i) 6-(Methoxymethyl)-5-methylbenzo[d]isoxazol-3-amine I4

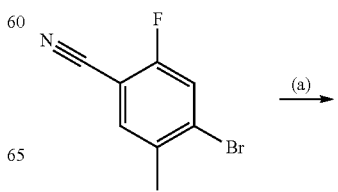

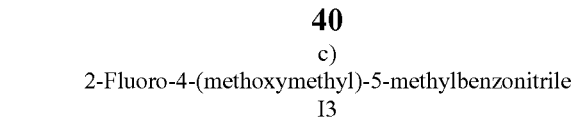

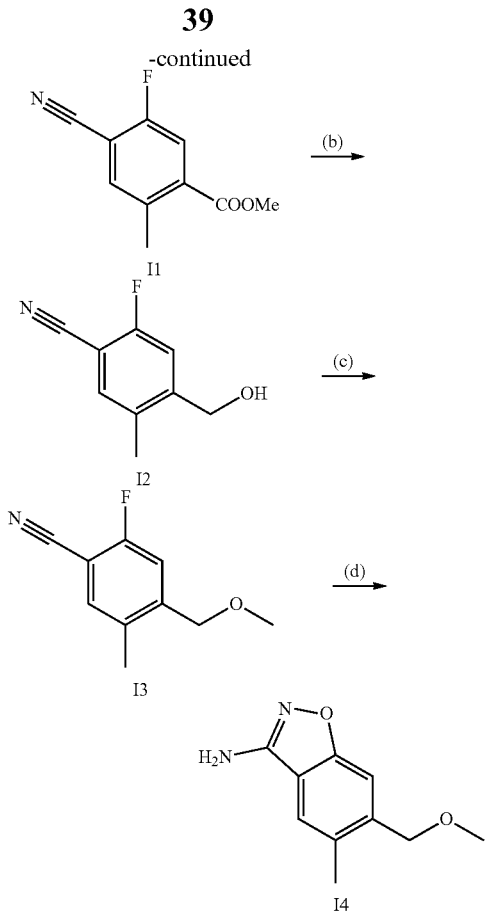

a) Methyl 4-cyano-5-fluoro-2-methylbenzoate I1

A mixture of 4-bromo-2-fluoro-5-methylbenzonitrile (3.5 g, 16.4 mmol), Pd(dppf)Cl$_2$.DCM (668 mg, 0.82 mmol) and Et$_3$N (5.0 g, 49.1 mmol) in MeOH (80 mL) was heated at 100° C. under a CO atmosphere (0.2 MPa) overnight. Additional Pd(dppf)Cl$_2$.DCM (340 mg, 0.4 mmol) was added and heating was continued under a CO atmosphere (0.2 MPa) overnight. The catalyst was removed by filtration, washed with MeOH and the filtrate was concentrated under reduced pressure. The residue was purified by column chromatography (Pet. ether/EtOAc=20/1 to 10/1 to 5/1) to give the title compound (2.4 g, 74%) as a yellow solid. LCMS-D: R$_t$ 2.48 min; m/z 216.1 [M+Na]$^+$.

b) 2-Fluoro-4-(hydroxymethyl)-5-methylbenzonitrile I2

To a solution of methyl 4-cyano-5-fluoro-2-methylbenzoate I1 (2.4 g, 12.4 mmol) in anhydrous THF (20 mL) at RT under N$_2$ was added LiBH$_4$ (2.0 M solution in THF, 12.4 mL, 24.8 mmol) dropwise and the mixture was heated at reflux for 2 h. The reaction was quenched with water (80 mL) and the mixture was extracted with EtOAc (90 mL×3). The combined organic extracts were washed with water (100 mL×3), brine, dried over anhydrous Na$_2$SO$_4$, filtered and concentrated under reduced pressure. The residue was purified by column chromatography (Pet. ether/EtOAc=20/1 to 10/1 to 5/1) to give the title compound (1.6 g, 79%) as a yellow solid. LCMS-D: R$_t$ 1.43 min; m/z 166.1 [M+H]$^+$, 188.1 [M+Na]$^+$.

c) 2-Fluoro-4-(methoxymethyl)-5-methylbenzonitrile I3

To a solution of 2-fluoro-4-(hydroxymethyl)-5-methylbenzonitrile I2 (800 mg, 8.8 mmol) and iodomethane (3.4 g, 24.2 mmol) in DMF (12 mL) at 0° C. was added NaH (60% w/w dispersion in oil, 379 mg, 9.7 mmol) and the mixture was stirred at 0° C. for 30 min. Water was added and the mixture was extracted with EtOAc (50 mL×3). The combined organic extracts were washed with brine, dried over anhydrous Na$_2$SO$_4$, filtered and concentrated under reduced pressure. The residue was purified by column chromatography (Pet. ether/EtOAc=20/1 to 10/1 to 5/1) to give the title compound (660 mg, 76%) as a yellow solid. LCMS-D: R$_t$ 2.44 min; m/z 180.1 [M+H]$^+$, 202.1.1 [M+Na]$^+$.

d) 6-(Methoxymethyl)-5-methylbenzo[d]isoxazol-3-amine I4

To a solution of acetohydroxamic acid (792 mg, 10.6 mmol) in anhydrous DMF (20 mL) at 0° C. was added potassium tert-butoxide (1.2 g, 10.6 mmol) and the mixture was stirred at RT for 2 h. 2-Fluoro-4-(methoxymethyl)-5-methylbenzonitrile I3 (630 mg, 3.5 mmol) was then added and the mixture was heated at 60° C. overnight. Water was added and the mixture was extracted with EtOAc (80 mL×3). The combined organic extracts were washed with brine, dried over anhydrous Na$_2$SO$_4$, filtered and concentrated under reduced pressure. The residue was purified by column chromatography (DCM/MeOH=20/1 to 10/1) to give the title compound (1.0 g, 77%) as a yellow solid. LCMS-D: R$_t$ 1.75 min; m/z 193.1 [M+H]$^+$.

ii) 4-Methoxy-6-(methoxymethyl)benzo[d]isoxazol-3-amine I9

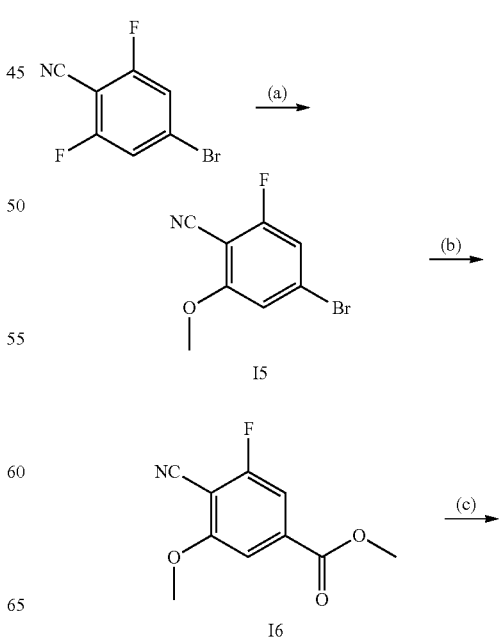

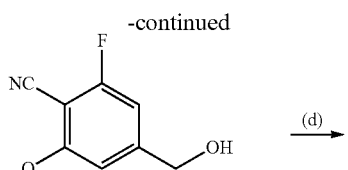

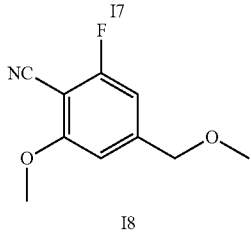

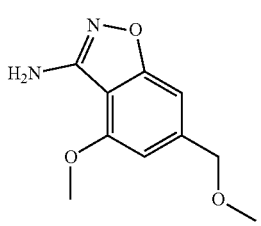

a) 4-Bromo-2-fluoro-6-methoxybenzonitrile I5

To a solution of 4-bromo-2,6-difluorobenzonitrile (6.0 g, 27.5 mmol) in THF (100 mL) was added sodium methanolate (1.5 g, 55.0 mmol) and the mixture was stirred at RT for 48 h. Water was added and the mixture was extracted with EtOAc (150 mL×3). The combined organic extracts were washed with brine, dried over anhydrous Na₂SO₄, filtered and concentrated under reduced pressure. The residue was purified by column chromatography (Pet. ether/EtOAc=300/1 to 200/1) to give the title compound (4.3 g, 68%) as a white solid. LCMS-D: $R_t$ 2.53 min; m/z 251.8/253.8 [M+Na]⁺.

b) Methyl 4-cyano-3-fluoro-5-methoxybenzoate I6

A mixture of 4-bromo-2-fluoro-6-methoxybenzonitrile I5 (4.3 g, 18.7 mmol), Pd(dppf)Cl₂.DCM (768 mg, 0.94 mmol) and Et₃N (5.7 g, 56.1 mmol) in MeOH (50 mL) was heated at 100° C. under a CO atmosphere (0.2 MPa) overnight. The catalyst was removed by filtration, washed with MeOH and the filtrate was concentrated under reduced pressure. The residue was purified by column chromatography (Pet. ether/EtOAc=200/1 to 50/1) to give the title compound (2.9 g, 74%) as a white solid. LCMS-D: $R_t$ 2.41 min; m/z 210.0 [M+H]⁺, 232.0 [M+Na]⁺.

c) 2-Fluoro-4-(hydroxymethyl)-6-methoxybenzonitrile I7

To a solution of LiBH₄ (2.0 M solution in THF, 13.9 mL, 27.8 mmol) in anhydrous THF (60 mL) at RT under N₂ was added a solution of methyl 4-cyano-3-fluoro-5-methoxybenzoate I1 (2.9 g, 13.9 mmol) in anhydrous THF (10 mL) dropwise and the mixture was heated at reflux for 1 h. The reaction was quenched with 1 M aq. HCl and extracted with EtOAc (100 mL×3). The combined organic extracts were washed with water (100 mL×3), brine, dried over anhydrous Na₂SO₄, filtered and concentrated to give the title compound (2.5 g, 100%) as a white solid. LCMS-D: $R_t$ 2.31 min; m/z 182.1 [M+H]⁺, 204.1 [M+Na]⁺.

d) 2-Fluoro-6-methoxy-4-(methoxymethyl)benzonitrile I8

To a solution of 2-fluoro-4-(hydroxymethyl)-6-methoxybenzonitrile I7 (2.7 g, 14.9 mmol) and iodomethane (10.6 g, 74.5 mmol) in DMF (100 mL) at 0° C. was added NaH (60% w/w dispersion in oil, 1.2 g, 29.8 mmol) in small portions and the mixture was stirred at RT for 30 min. Water was added and the mixture was extracted with EtOAc (100 mL×3). The combined organic extracts were washed with brine, dried over anhydrous Na₂SO₄, filtered and concentrated under reduced pressure. The residue was purified by column chromatography (Pet. ether/EtOAc=100/1 to 5/1) to give the title compound (2.2 g, 76%) as a yellow solid. LCMS-D: $R_t$ 2.22 min; m/z 218.0 [M+Na]⁺.

e) 4-Methoxy-6-(methoxymethyl)benzo[d]isoxazol-3-amine I9

To a solution of acetohydroxamic acid (2.3 g, 30.8 mmol) in anhydrous DMF (1500 mL) at RT was added potassium tert-butoxide (3.5 g, 30.8 mmol) and the mixture was stirred at RT for 1 h. 2-Fluoro-6-methoxy-4-(methoxymethyl)benzonitrile I8 (2.0 g, 10.3 mmol) was then added and stirring was continued at RT overnight. Water was added and the mixture was extracted with EtOAc. The combined organic extracts were dried over anhydrous Na₂SO₄, filtered and concentrated under reduced pressure. The residue was purified by column chromatography (DCM/MeOH=20/1 to 10/1 to 3/1) to give the title compound (580 mg, 27%) as a yellow solid. ¹H NMR (400 MHz, DMSO-d₆) δ 6.92 (d, J=0.8 Hz, 1H), 6.65 (s, 1H), 5.91 (s, 2H), 4.48 (s, 2H), 3.90 (s, 3H), 3.32 (s, 3H, obscured by water peak). LCMS-D: $R_t$ 1.33 min; m/z 209.0 [M+H]⁺.

iii) 4-Nitrobenzo[d]isoxazol-3-amine I10

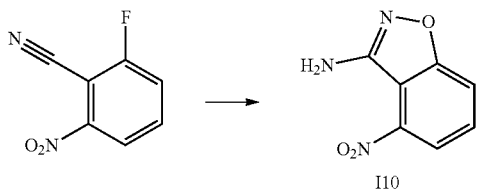 [SMILES: N#Cc1c(F)cccc1[N+](=O)[O-] ; "I10" ; Nc1noc2cccc([N+](=O)[O-])c12]

To a solution of 2-fluoro-6-nitrobenzonitrile (1.0 g, 6.17 mmol) in DMF/H₂O (32 mL/32 mL) was added acetohydroxamic acid (2.78 g, 37.0 mmol) and K₂CO₃ (10.23 g, 74.0 mmol) and the mixture was heated at 70° C. for 19 h. Water (200 mL) was added and the mixture was extracted with EtOAc (100 mL×3). The combined organic extracts were washed with water, brine, dried over anhydrous Na₂SO₄, filtered and concentrated under reduced pressure. The residue was purified by column chromatography (Pet. ether/EtOAc=30/1 to 1/1) to give the title compound (380 mg, 35%) as a yellow solid. LCMS-D: $R_t$ 2.82 min; m/z 180.1 [M+H]⁺.

iv) 4-Methoxy-6-(1-methoxyethyl)benzo[d]isoxazol-3-amine I15

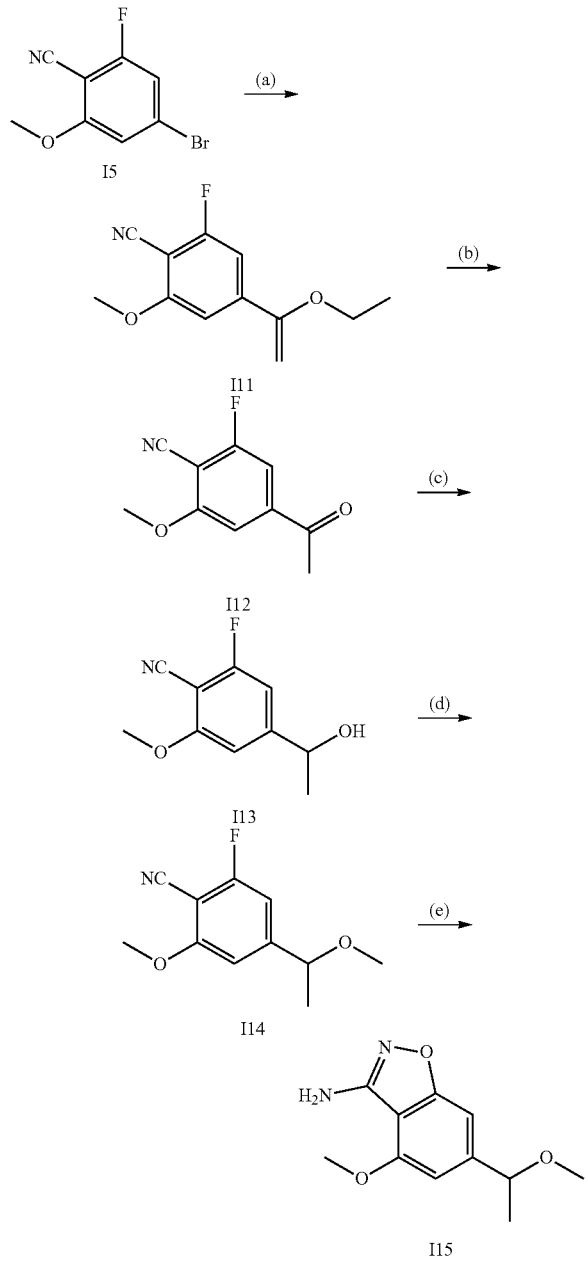

a)
4-(1-Ethoxyvinyl)-2-fluoro-6-methoxybenzonitrile I11

To a solution of 4-bromo-2-fluoro-6-methoxybenzonitrile I5 (2.0 g, 8.7 mmol) in THF (40 mL) was added tributyl(1-ethoxyvinyl)stannane (3.4 g, 9.6 mmol), Pd(PPh$_3$)$_4$ (201 mg, 0.174 mmol) and LiCl (1.15 g, 27.0 mmol) and the mixture was heated at reflux under N$_2$ for 48 h. The mixture was diluted with EtOAc and washed consecutively with water, 5% aqueous ammonium hydroxide solution and brine. The organic layer was dried over anhydrous Na$_2$SO$_4$, filtered and concentrated under reduced pressure. The residue was purified by column chromatography (Pet. ether/EtOAc=200/1) to give the title compound (1.6 g, 84%) as a light yellow solid. LCMS-C: R$_t$ 2.41 min; m/z 222.0 [M+H]$^+$.

b) 4-Acetyl-2-fluoro-6-methoxybenzonitrile I12

To a solution of 4-(1-ethoxyvinyl)-2-fluoro-6-methoxybenzonitrile I11 (1.0 g, 4.5 mmol) in THF (10 mL) was added 2 M aq. HCl (6.0 mL) and the mixture was stirred at RT for 3 h. The mixture was diluted with diethyl ether and washed with a saturated aqueous NaHCO$_3$ solution and water. The organic layer was dried over anhydrous Na$_2$SO$_4$, filtered and concentrated under reduced pressure to give the title compound (710 mg, 81%) as a white solid. LCMS-C: R$_t$ 1.42 min; m/z 194.0 [M+H]$^+$.

c)
2-Fluoro-4-(1-hydroxyethyl)-6-methoxybenzonitrile I13

To a solution of 4-acetyl-2-fluoro-6-methoxybenzonitrile I12 (700 mg, 3.6 mmol) in THF (30 mL) was added sodium borohydride (206 mg, 5.4 mmol) and the mixture was stirred at RT overnight. Water was added and the mixture was extracted with EtOAc (30 mL×3). The combined organic extracts were dried over anhydrous Na$_2$SO$_4$, filtered and concentrated under reduced pressure to give the title compound (675 mg, 95%) as a colorless oil. LCMS-C: R$_t$ 0.98 min; m/z 196.0 [M+H]$^+$.

d)
2-Fluoro-6-methoxy-4-(1-methoxyethyl)benzonitrile I14

To a solution of 2-fluoro-4-(1-hydroxyethyl)-6-methoxybenzonitrile I13 (670 mg, 3.4 mmol) and iodomethane (1.5 g, 10.3 mmol) in DMF (20 mL) at 0° C. was added NaH (60% w/w dispersion in oil, 274 mg, 6.8 mmol) in small portions and the mixture was stirred at 0° C. for 2 h. Water was added and the mixture was extracted with EtOAc (40 mL×3). The combined organic extracts were dried over anhydrous Na$_2$SO$_4$, filtered and concentrated under reduced pressure to give the title compound (650 mg, 90%) as a light yellow solid. LCMS-C: R$_t$ 1.95 min; m/z 210.0 [M+H]$^+$.

e) 4-Methoxy-6-(1-methoxyethyl)benzo[d]isoxazol-3-amine I15

To a solution of acetohydroxamic acid (698 mg, 9.3 mmol) in anhydrous DMF (20 mL) at 0° C. was added potassium tert-butoxide (1.04 g, 9.3 mmol) and the mixture was stirred at RT for 1 h. A solution of 2-fluoro-6-methoxy-4-(1-methoxyethyl)benzonitrile I14 (650 mg, 3.1 mmol) in anhydrous DMF (10 mL) was then added dropwise and the mixture was stirred at RT overnight. Water was added and the mixture was extracted with EtOAc (50 mL×3). The combined organic extracts were dried over anhydrous Na$_2$SO$_4$, filtered and concentrated under reduced pressure. The residue was purified by column chromatography (DCM/MeOH=300/1 to 200/1) to give the title compound (130 mg, 19%) as a yellow solid. $^1$H NMR (400 MHz, DMSO-d$_6$) δ 6.90 (s, 1H), 6.64 (s, 1H), 5.92 (s, 2H), 4.39 (q, J=6.4 Hz, 1H), 3.90 (s, 3H), 3.15 (s, 3H), 1.36 (d, J=6.4 Hz, 3H). LCMS-C: R$_t$ 0.73 min; m/z 223.0 [M+H]$^+$.

v) 4-Methoxy-6-phenylbenzo[d]isoxazol-3-amine I17

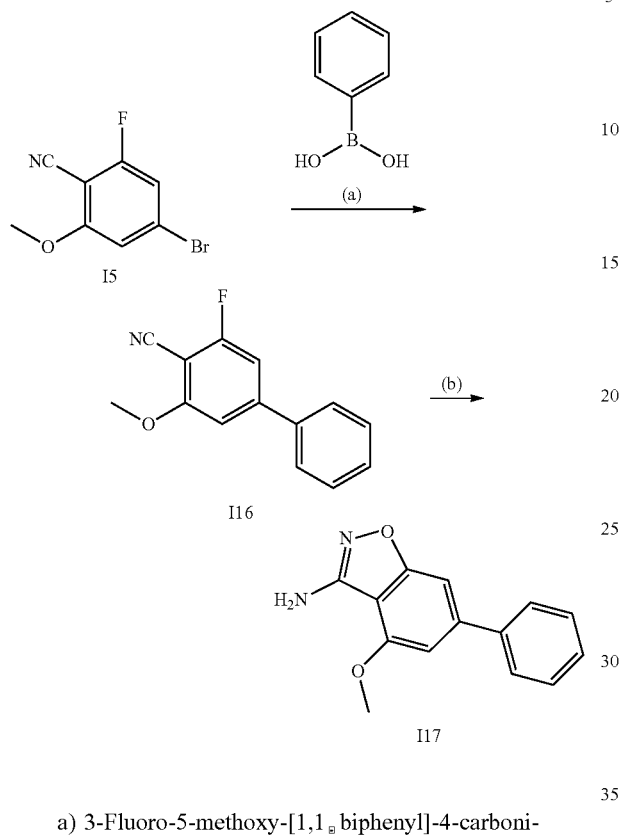

a) 3-Fluoro-5-methoxy-[1,1ᴮ biphenyl]-4-carbonitrile I16

To a solution of 4-bromo-2-fluoro-6-methoxybenzonitrile I5 (6.0 g, 26.1 mmol) and phenylboronic acid (6.36 g, 52.2 mmol) in 1,4-dioxane (200 mL) and water (50 mL) under N₂ was added Pd(PPh₃)₄ (2.99 g, 2.66 mmol) and Na₂CO₃ (8.29 g, 78.2 mmol) and the mixture was heated at 100° C. overnight. Water was added and the mixture was extracted with EtOAc. The combined organic extracts were washed with brine, dried over anhydrous Na₂SO₄, filtered and concentrated under reduced pressure. The residue was purified by column chromatography (Pet. ether/EtOAc=100/1 to 50/1) to give the title compound (5.45 g, 93%) as a yellow solid. LCMS-C: $R_t$ 2.48 min; m/z 228.0 [M+H]⁺.

b) 4-Methoxy-6-phenylbenzo[d]isoxazol-3-amine I17

To a solution of acetohydroxamic acid (8.15 g, 23.98 mmol) in anhydrous DMF (200 mL) at 0° C. was added potassium tert-butoxide (5.5 g, 24.0 mmol) and the mixture was stirred at RT for 1 h. 3-Fluoro-5-methoxy-[1,1ᴮ biphenyl]-4-carbonitrile I16 (5.45 g, 7.99 mmol) was then added and the mixture was heated at 60° C. for 4 h. Water was added and the mixture was extracted with EtOAc. The combined organic extracts were washed with brine, dried over anhydrous Na₂SO₄, filtered and concentrated under reduced pressure. The residue was purified by column chromatography (Pet. ether/EtOAc=10/1 to 8/1 to 6/1) to give the title compound (2.2 g, 38%) as a yellow solid. ¹H NMR (400 MHz, DMSO-d₆) δ 7.79-7.74 (m, 2H), 7.52-7.46 (m, 2H), 7.45-7.39 (m, 1H), 7.26 (d, J=1.1 Hz, 1H), 6.95 (s, 1H), 5.97 (s, 2H), 4.00 (s, 3H). LCMS-C: $R_t$ 2.15 min; m/z 241.0 [M+H]⁺ vi) 3-(3-Amino-4-methoxybenzo[d]isoxazol-6-yl) phenol I19

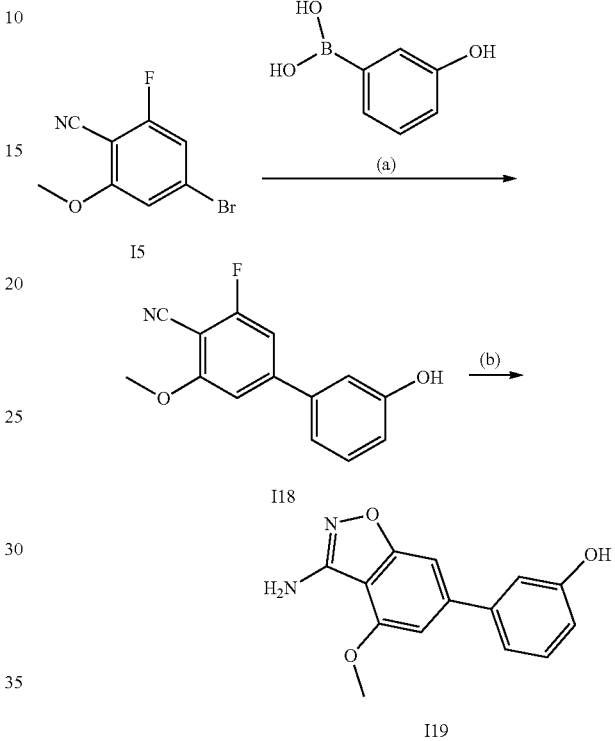

a) 3-Fluoro-3ᴱ hydroxy-5-methoxy-[1, 1ᴮ biphenyl]-4-carbonitrile I18

To a solution of 4-bromo-2-fluoro-6-methoxybenzonitrile I5 (650 mg, 2.8 mmol) and (3-hydroxyphenyl)boronic acid (1.2 g, 5.6 mmol) in 1,4-dioxane (40 mL) and water (10 mL) under N₂ was added Pd(PPh₃)₄ (327 mg, 0.28 mmol) and Na₂CO₃ (899 mg, 8.5 mmol) and the mixture was heated at 100° C. overnight. Water was added and the mixture was extracted with EtOAc. The combined organic extracts were washed with brine, dried over anhydrous Na₂SO₄, filtered and concentrated under reduced pressure. The residue was purified by column chromatography (Pet. ether/EtOAc=3/1) to give the title compound (687 mg, 94%) as a yellow solid. LCMS-C: $R_t$ 2.07 min; m/z 244.0 [M+H]⁺.

b) 3-(3-Amino-4-methoxybenzo[d]isoxazol-6-yl) phenol I19

To a solution of acetohydroxamic acid (636 mg, 8.5 mmol) in anhydrous DMF (60 mL) at 0° C. was added potassium tert-butoxide (952 mg, 8.5 mmol) and the mixture was stirred at RT for 1 h. 3-Fluoro-3ᴱ hydroxy-5-methoxy-[1,1ᴮ biphenyl]-4-carbonitrile I18 (687 mg, 2.8 mmol) was then added and the mixture was heated at 60° C. for 4 h. Water was added and the mixture was extracted with EtOAc. The combined organic extracts were washed with brine, dried over anhydrous Na₂SO₄, filtered and concentrated under reduced pressure. The residue was purified by column chromatography (Pet. ether/EtOAc=1/1) to give the title compound (282 mg, 39%) as a yellow solid. LCMS-C: $R_t$ 2.3 min; m/z 257.0 [M+H]$^+$.

vii) 6-(Ethoxymethyl)-4-methoxybenzo[d]isoxazol-3-amine I21

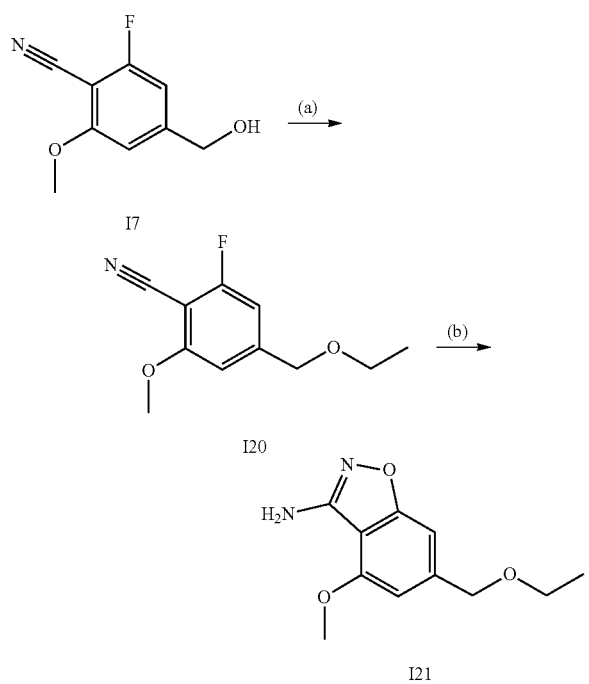

a) 4-(Ethoxymethyl)-2-fluoro-6-methoxybenzonitrile I20

To a solution of 2-fluoro-4-(hydroxymethyl)-6-methoxybenzonitrile I7 (1.15 g, 6.4 mmol) and iodoethane (5.0 g, 31.7 mmol) in DMF (40 mL) at 0° C. was added NaH (60% w/w dispersion in oil, 508 mg, 12.7 mmol) in small portions and the mixture was stirred at RT for 30 min. Water was added and the mixture was extracted with EtOAc (100 mL×3). The combined organic extracts were washed with brine, dried over anhydrous Na$_2$SO$_4$, filtered and concentrated under reduced pressure. The residue was purified by column chromatography (Pet. ether/EtOAc=2/1) to give the title compound (1.0 g, 79%) as a yellow solid. LCMS-C: $R_t$ 2.15 min; m/z 210.0 [M+H]$^+$.

b) 6-(Ethoxymethyl)-4-methoxybenzo[d]isoxazol-3-amine I21

To a solution of acetohydroxamic acid (1.1 g, 14.3 mmol) in anhydrous DMF (50 mL) at RT was added potassium tert-butoxide (1.6 g, 14.3 mmol) and the mixture was stirred at RT for 1 h. 4-(Ethoxymethyl)-2-fluoro-6-methoxybenzonitrile I20 (1.0 g, 4.8 mmol) was then added and the mixture was stirred at RT overnight. Water was added and the mixture was extracted with EtOAc. The organic extracts were dried over anhydrous Na$_2$SO$_4$, filtered and concentrated under reduced pressure. The residue was purified by column chromatography (DCM/MeOH=20/1 to 10/1 to 3/1) to give the title compound (650 mg, 61%) as a yellow oil. $^1$H NMR (400 MHz, DMSO-d$_6$) δ 6.92 (s, 1H), 6.65 (s, 1H), 5.91 (s, 2H), 4.53 (s, 2H), 3.89 (s, 3H), 3.51 (q, J=7.0 Hz, 2H), 1.17 (t, J=7.0 Hz, 3H). LCMS-C: $R_t$ 0.82 min; m/z 223.0 [M+H]$^+$.

viii) 6-Bromo-4-methoxybenzo[d]isoxazol-3-amine I22

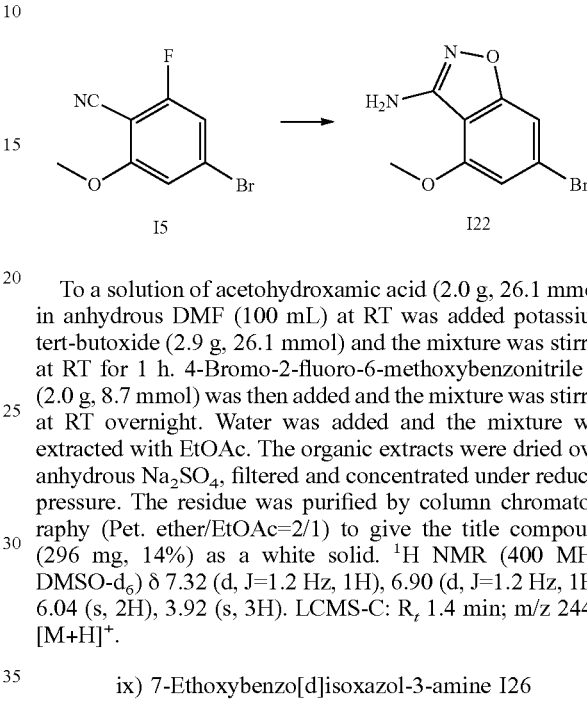

To a solution of acetohydroxamic acid (2.0 g, 26.1 mmol) in anhydrous DMF (100 mL) at RT was added potassium tert-butoxide (2.9 g, 26.1 mmol) and the mixture was stirred at RT for 1 h. 4-Bromo-2-fluoro-6-methoxybenzonitrile I5 (2.0 g, 8.7 mmol) was then added and the mixture was stirred at RT overnight. Water was added and the mixture was extracted with EtOAc. The organic extracts were dried over anhydrous Na$_2$SO$_4$, filtered and concentrated under reduced pressure. The residue was purified by column chromatography (Pet. ether/EtOAc=2/1) to give the title compound (296 mg, 14%) as a white solid. $^1$H NMR (400 MHz, DMSO-d$_6$) δ 7.32 (d, J=1.2 Hz, 1H), 6.90 (d, J=1.2 Hz, 1H), 6.04 (s, 2H), 3.92 (s, 3H). LCMS-C: $R_t$ 1.4 min; m/z 244.0 [M+H]$^+$.

ix) 7-Ethoxybenzo[d]isoxazol-3-amine I26

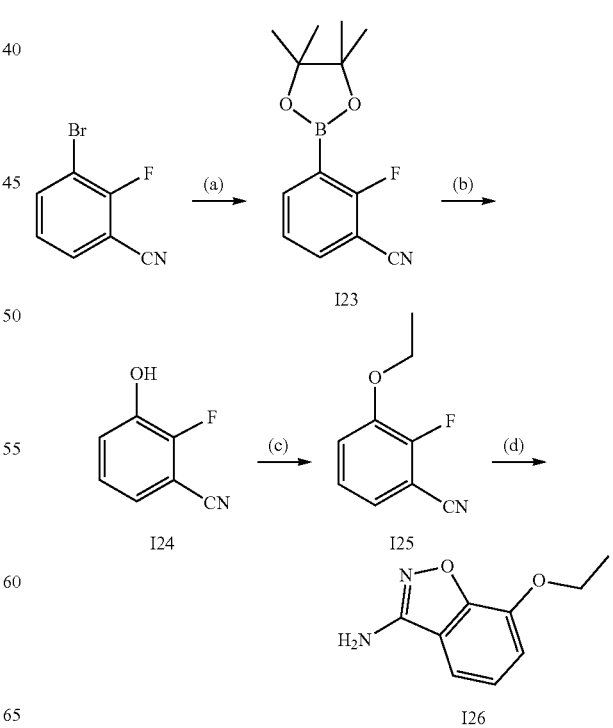

a) 2-Fluoro-3-(4,4,5,5-tetramethyl-1,3,2-dioxaborolan-2-yl)benzonitrile I23

A mixture of 3-bromo-2-fluorobenzonitrile (3.0 g, 15.0 mmol), 4,4,4',4',5,5,5',5'-octamethyl-2,2'-bi(1,3,2-dioxaborolane) (11.4 g, 45 mmol), potassium acetate (5.9 g, 60.0 mmol) and Pd(dppf)Cl$_2$ (2.2 g, 3.0 mmol) in DMSO (45 mL) and 1,4-dioxane (15 mL) was heated at 105° C. under N$_2$ for 3 h. The mixture was diluted with EtOAc (30 mL) and washed with water (30 mL×3). The organic layer was dried over anhydrous Na$_2$SO$_4$, filtered, concentrated under reduced pressure and the residue was purified by column chromatography (Pet. ether/EtOAc=20/1) to give the title compound (3.9 g, >100%) as a white solid, which was used directly in the next step.

b) 2-Fluoro-3-hydroxybenzonitrile I24

To a solution of 2-fluoro-3-(4,4,5,5-tetramethyl-1,3,2-dioxaborolan-2-yl)benzonitrile I23 (1.9 g, 7.6 mol) in AcOH (19 mL) under N$_2$ was added H$_2$O$_2$ (30% aqueous solution, 1.9 mL) dropwise and the mixture was stirred at RT for 2 h then poured into a mixture of EtOAc and excess aqueous Na$_2$SO$_3$. The layers were then separated and the organic layer was washed with water, brine, dried over anhydrous Na$_2$SO$_4$, filtered, concentrated under reduced pressure to give the title compound (650 mg, 62%) as an off-white waxy solid. LCMS-D: R$_t$ 0.93 min; m/z 138.1 [M+H]$^+$.

c) 3-Ethoxy-2-fluorobenzonitrile I25

To a solution of 2-fluoro-3-hydroxybenzonitrile I24 (360 mg, 2.6 mmol) in DMF (30 mL) was added Cs$_2$CO$_3$ (4.3 g, 13.1 mmol) and iodoethane (1.0 g, 6.6 mmol) and the mixture was stirred at RT overnight. The mixture was diluted with EtOAc (80 mL) and washed with water (50 mL×3). The organic layer was dried over anhydrous Na$_2$SO$_4$, filtered, concentrated under reduced pressure to give the title compound (220 mg, 51%) as a yellow solid. LCMS-D: R$_t$ 2.31 min; m/z 166.1 [M+H]$^+$.

d) 7-Ethoxybenzo[d]isoxazol-3-amine I26

To a solution of acetohydroxamic acid (300 mg, 4.0 mmol) in DMF (15 mL) at 0° C. under N$_2$ was added potassium tert-butoxide (450 mg, 4.0 mmol) and the mixture was heated at 30° C. for 1 h. A solution of 3-ethoxy-2-fluorobenzonitrile I25 (220 mg, 1.3 mmol) in DMF (10 mL) was added and the mixture was heated at 30° C. overnight. EtOAc (80 mL) was added and the mixture was washed with water (50 mL×3). The organic layer was dried over anhydrous Na$_2$SO$_4$, filtered, concentrated under reduced pressure to give the title compound (170 mg, 70%) as a yellow solid. LCMS-D: R$_t$ 1.68 min; m/z 179.1 [M+H]$^+$.

x) 7-(Cyclopropylmethoxy)benzo[d]isoxazol-3-amine I28

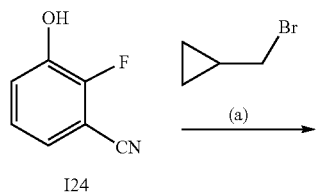

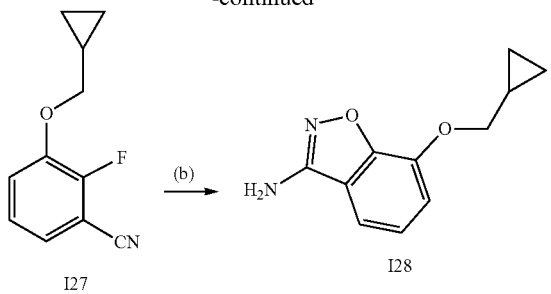

a) 3-(Cyclopropylmethoxy)-2-fluorobenzonitrile I27

To a solution of 2-fluoro-3-hydroxybenzonitrile I24 (360 mg, 2.6 mmol) in DMF (30 mL) was added Cs$_2$CO$_3$ (4.3 g, 13.1 mmol), KI (87 mg, 0.5 mmol) and (bromomethyl)cyclopropane (880 mg, 6.6 mmol) and the mixture was stirred at RT overnight. EtOAc (80 mL) was added and the mixture was washed with water (50 mL×3). The organic layer was dried over anhydrous Na$_2$SO$_4$, filtered, concentrated under reduced pressure to give the title compound (150 mg, 30%) as a red solid. LCMS-D: R$_t$ 2.54 min; m/z 192.1 [M+H]$^+$.

b) 7-(Cyclopropylmethoxy)benzo[d]isoxazol-3-amine I28

Prepared from 3-(cyclopropylmethoxy)-2-fluorobenzonitrile I27 according to the procedure described for 7-ethoxybenzo[d]isoxazol-3-amine I26, step d. LCMS-D: R$_t$ 2.23 min; m/z 205.1 [M+H]$^+$.

xi) 6-Ethoxybenzo[d]isoxazol-3-amine I32

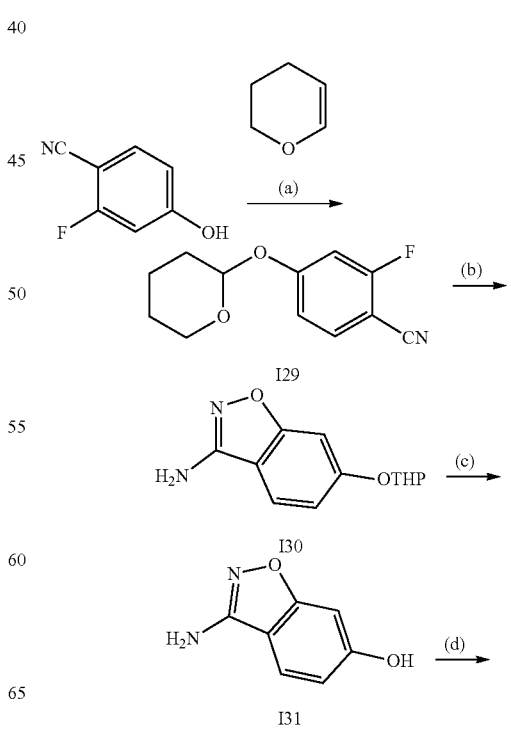

-continued

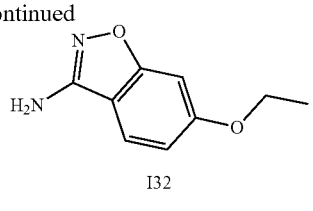

I32 a) 2-Fluoro-4-((tetrahydro-2H-pyran-2-yl)oxy)benzonitrile I29

To a solution of 2-fluoro-4-hydroxybenzonitrile (20 g, 145.9 mmol) and PPTS (733 mg, 2.9 mmol) in DCM (500 mL) under $N_2$ was added 3,4-dihydro-2H-pyran (24.5 g, 292 mmol) and the mixture was stirred at RT overnight. The solvent was removed under reduced pressure and the residue was purified by column chromatography (Pet. ether/EtOAc=100/0 to 100/2) to give the title compound (27 g, 83%) as a white solid, which was used directly in the next step.

b) 6-((Tetrahydro-2H-pyran-2-yl)oxy)benzo[d]isoxazol-3-amine I30

To a solution of acetohydroxamic acid (13.7 g, 182.3 mmol) in DMF (60 mL) at 0° C. under $N_2$ was added potassium tert-butoxide (20.4 g, 182.3 mmol) and the mixture was stirred at RT for 1 h. 2-Fluoro-4-((tetrahydro-2H-pyran-2-yl)oxy)benzonitrile I29 (13.4 g, 60.8 mmol) was then added and the mixture was stirred at RT overnight. EtOAc (500 mL) was added and the mixture was washed with water (100 mL×5). The organic layer was dried over anhydrous $Na_2SO_4$, filtered and concentrated under reduced pressure. The residue was purified by column chromatography (Pet. ether/EtOAc=100/1 to 5/1) to give the title compound (12.1 g, 85%) as a white solid. LCMS-D: $R_t$ 2.31 min; m/z 235.1 $[M+H]^+$.

c) 3-Aminobenzo[d]isoxazol-6-ol I31

To a solution of 6-((tetrahydro-2H-pyran-2-yl)oxy)benzo[d]isoxazol-3-amine I30 (3.5 g, 15 mmol) in THF (50 mL) was added 2 M aq. HCl (20 mL) and the mixture was stirred at RT for 3 h. The mixture was diluted with EtOAc (300 mL) and washed with water (×2). The organic layer was dried over anhydrous $Na_2SO_4$, filtered, concentrated under reduced pressure to give the title compound (2.1 g, 94%) as a white solid, which was used directly in the next step.

d) 6-Ethoxybenzo[d]isoxazol-3-amine I32

A mixture of 3-aminobenzo[d]isoxazol-6-ol I31 (300 mg, 2 mmol), $Cs_2CO_3$ (2.0 g, 6 mmol), KI (66 mg, 0.4 mmol) and bromoethane (436 mg, 4 mmol) in DMF (30 mL) was heated at 50° C. under $N_2$ overnight. The mixture was diluted with EtOAc (300 mL) and washed with water (100 mL×5). The organic layer was dried over anhydrous $Na_2SO_4$ and concentrated under reduced pressure. The residue was purified by column chromatography (Pet. ether/EtOAc=100/1 to 5/1) to give the title compound (270 mg, 76%) as a white solid. LCMS-D: $R_t$ 0.37 min; m/z 179.0 $[M+H]^+$.

xii) 6-(Cyclopropylmethoxy)benzo[d]isoxazol-3-amine I33

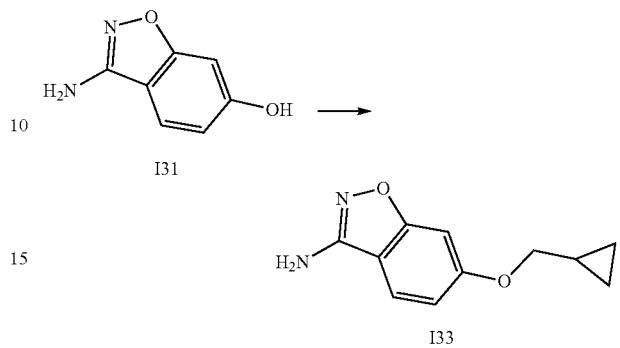

Prepared from 3-aminobenzo[d]isoxazol-6-ol I31 according to the procedure described for 6-ethoxybenzo[d]isoxazol-3-amine I32, step d (395 mg, 97%). LCMS-D: $R_t$ 2.27 min; m/z 205.1 $[M+H]^+$.

xiii) 6-(1H-1,2,3-Triazol-1-yl)benzo[d]isoxazol-3-amine I36

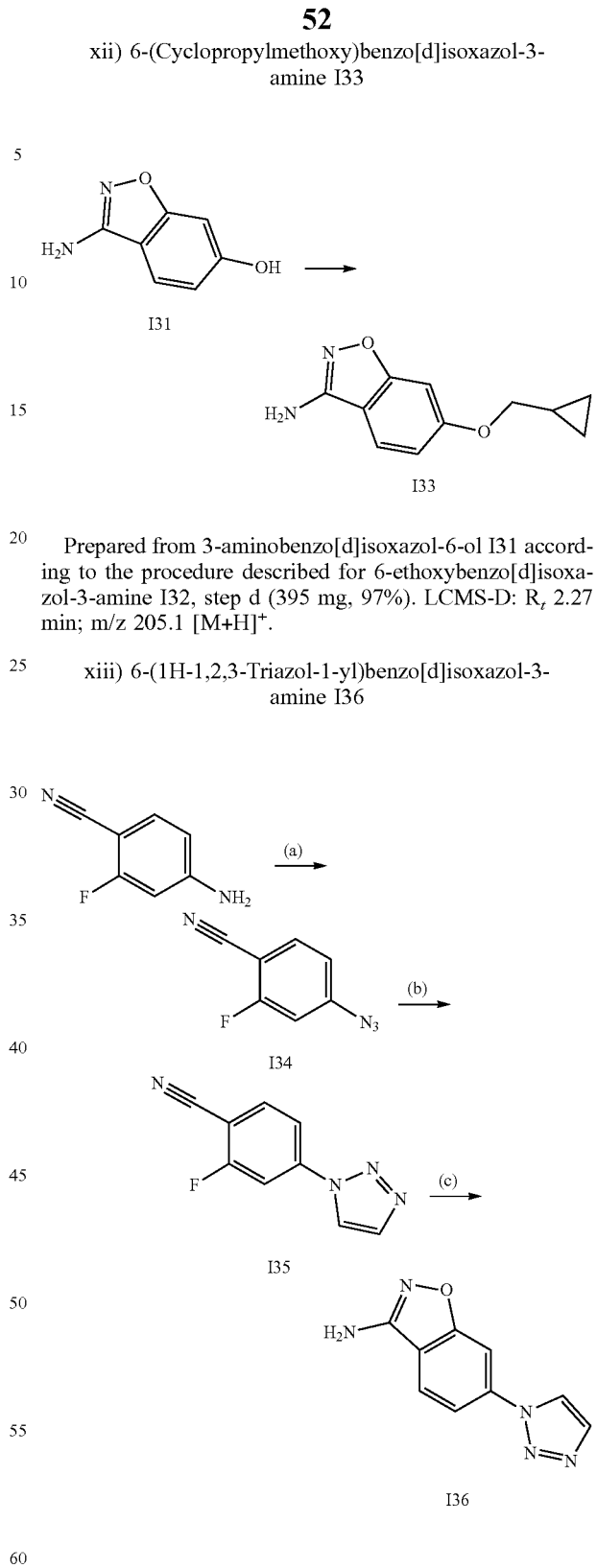

a) 4-Azido-2-fluorobenzonitrile I34

A mixture of 4-amino-2-fluorobenzonitrile (2.0 g, 14.7 mmol) in water (4 mL), ACN (32 mL), and concentrated HCl (10 mL) was stirred at RT under $N_2$ overnight. $NaNO_2$ (2.0 g, 29.4 mmol) was then added portion-wise and stirring was continued at RT for 2 h. The mixture was cooled to 0°

C., NaN₃ (1.9 g, 29.4 mmol) was added portion-wise and stirring was continued at RT for 2 h. Water (50 mL) was added and most of the organic solvent was removed under reduced pressure. The remaining aqueous mixture was then extracted with DCM (50 mL×4) and the combined organic extracts were washed with water, brine, dried over anhydrous Na₂SO₄, filtered and concentrated under reduced pressure. The residue was purified by column chromatography (Pet. ether/EtOAc=100/0 to 20/1) to give the title compound (1.5 g, 62%) as a yellow solid, which was used directly in the next step.

b) 2-Fluoro-4-(1H-1,2,3-triazol-1-yl)benzonitrile I35

A mixture of 4-azido-2-fluorobenzonitrile I34 (500 mg, 3.1 mmol), ethynyltrimethylsilane (454 mg, 4.6 mmol) and CuI (704 mg, 3.7 mmol) in THF (50 mL) was heated at 50° C. under N₂ for 24 h. Additional ethynyltrimethylsilane (454 mg, 4.6 mmol) was added and the mixture was heated at 50° C. for a further 24 h, then concentrated under reduced pressure. The residue was purified by column chromatography (Pet. ether/EtOAc=100/1 to 10/1) to give 2-fluoro-4-(5-(trimethylsilyl)-1H-1,2,3-triazol-1-yl)benzonitrile (410 mg), which was dissolved in a 1 M solution of TBAF in THF (50 mL) and heated at 45° C. under N₂ overnight. The solvent was removed under reduced pressure and the residue was purified by column chromatography (Pet. ether/EtOAc=50/1 to 2/1) to give the title compound (200 mg, 34%) as a white solid, which was used directly in the next step.

c) 6-(1H-1,2,3-Triazol-1-yl)benzo[d]isoxazol-3-amine I36

To a solution of acetohydroxamic acid (239 mg, 3.16 mmol) in DMF (25 mL) at 0° C. under N₂ was added potassium tert-butoxide (357 mg, 3.18 mmol) and the mixture was stirred at RT for 2 h. A solution of 2-fluoro-4-(1H-1,2,3-triazol-1-yl)benzonitrile I35 (200 mg, 1.06 mmol) in DMF (15 mL) was then added and stirring was continued at RT overnight. EtOAc (100 mL) was added and the mixture was washed with water (× 5). The organic layer was dried over anhydrous Na₂SO₄, filtered and concentrated under reduced pressure. The residue was purified by column chromatography (Pet. ether/EtOAc=100/1 to 2/1) to give the title compound (150 mg, 70%) as a white solid. LCMS-D: $R_t$ 0.47 min; m/z 202.1 [M+H]⁺.

xiv) 6-(Pyrimidin-2-yl)benzo[d]isoxazol-3-amine I39

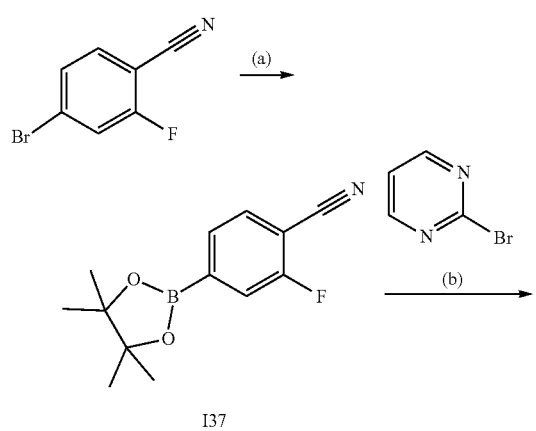

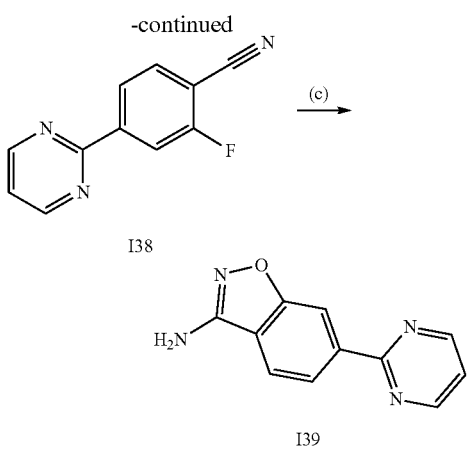

a) 2-Fluoro-4-(4,4,5,5-tetramethyl-1,3,2-dioxaborolan-2-yl)benzonitrile I37

A mixture of 4-bromo-2-fluorobenzonitrile (1.0 g, 5.0 mmol), 4,4,4',4',5,5,5',5'-octamethyl-2,2'-bi(1,3,2-dioxaborolane) (1.3 g, 5.0 mmol), potassium acetate (5.9 g, 20.0 mmol) and Pd(dppf)Cl₂ (2.0 g, 1.0 mmol) in DMSO (50 mL) and 1,4-dioxane (10 mL) was heated at 105° C. under N₂ for 3 h. The mixture was diluted with EtOAc (200 mL) and washed with water (100 mL×3). The organic layer was dried over anhydrous Na₂SO₄, filtered, concentrated under reduced pressure and the residue was purified by column chromatography (Pet. ether/EtOAc=100/0 to 50/1) to give the title compound (1.1 g, 89%) as a white solid, which was used directly in the next step.

b) 2-Fluoro-4-(pyrimidin-2-yl)benzonitrile I38

To a solution of 2-fluoro-4-(4,4,5,5-tetramethyl-1,3,2-dioxaborolan-2-yl)benzonitrile I37 (464 mg, 2 mmol) and 2-bromopyrimidine (736 mg, 4 mmol) in water (40 mL), toluene (40 mL) and i-PrOH (10 mL) under N₂ was added Pd(dppf)Cl₂ (146 mg, 0.2 mmol) and K₃PO₄.3H₂O (1.33 g, 5.0 mmol) and the mixture was heated at 85° C. for 4 h. The mixture was diluted with EtOAc (200 mL) and washed with water (50 mL). The organic layer was dried over anhydrous Na₂SO₄, filtered, concentrated under reduced pressure and the residue was purified by column chromatography (Pet. ether/EtOAc=50/1 to 2/1) to give the title compound (270 mg, 68%) as a white solid. LCMS-D: $R_t$ 2.38 min; m/z 200.1 [M+H]⁺.

c) 6-(Pyrimidin-2-yl)benzo[d]isoxazol-3-amine I39

To a solution of acetohydroxamic acid (306 mg, 4.07 mmol) in DMF (20 mL) at 0° C. under N₂ was added potassium tert-butoxide (457 mg, 4.07 mmol) and the mixture was heated at 30° C. for 1 h. A solution of 2-fluoro-4-(pyrimidin-2-yl)benzonitrile I38 (270 mg, 1.36 mmol) in DMF (10 mL) was then added and heating was continued at 30° C. overnight. The mixture was diluted with EtOAc (100 mL) and washed with water (50 mL×3). The organic layer was dried over anhydrous Na₂SO₄, filtered, concentrated under reduced pressure and the residue was purified by column chromatography (Pet. ether/EtOAc=50/1 to 2/1) to give the title compound (200 mg, 69%) as a white solid. LCMS-D: $R_t$ 0.38 min; m/z 213.1 [M+H]⁺, 235.1 [M+Na]⁺.

xv) 5-Bromobenzo[d]isoxazol-3-amine I40

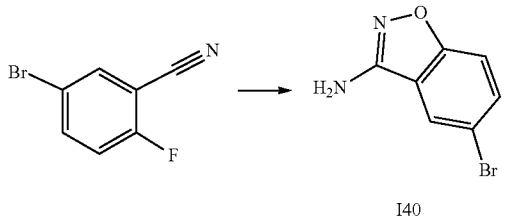

I40

To a solution of acetohydroxamic acid (23.7 g, 0.315 mol) in DMF (800 mL) at 0° C. under N₂ was added t-BuOK (35.4 g, 0.315 mol) and the mixture was stirred at 15° C. for 2 h. 5-Bromo-2-fluorobenzonitrile (21.0 g, 0.105 mol) was then added and the mixture was stirred at RT overnight. The mixture was diluted with EtOAc (1.5 L) and washed with water (400 mL×4). The organic layer was washed with brine, dried over anhydrous Na₂SO₄, filtered, concentrated under reduced pressure. The residue was purified by column chromatography (Pet. ether/EtOAc=50/1 to 3/1) to give the title compound (19 g, 86%) as a white solid. LCMS-D: R$_t$ 2.13 min; m/z 212.9/214.9 [M+H]⁺.

xvi) 4-Bromobenzo[d]isoxazol-3-amine I41

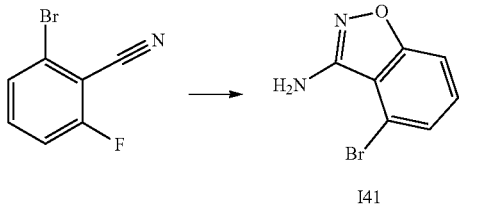

I41

To a solution of acetohydroxamic acid (11.25 g, 0.15 mol) in DMF (220 mL) at 0° C. under N₂ was added t-BuOK (16.8 g, 0.15 mol) and the mixture was stirred at 25° C. for 1 h. A solution of 2-bromo-6-fluorobenzonitrile (10.0 g, 0.05 mol) in DMF (80 mL) was then added dropwise and stirring was continued at 25° C. overnight. The mixture was diluted with water (200 mL) and extracted with EtOAc (400 mL). The organic extract was washed with water (400 mL×3), dried over anhydrous Na₂SO₄, filtered and concentrated under reduced pressure to give the title compound (7.0 g, 66%) as a light red solid. LCMS-D: R$_t$ 2.05 min; m/z 212.9/214.9 [M+H]⁺.

xvii) 4-(Trifluoromethyl)benzo[d]isoxazol-3-amine I42

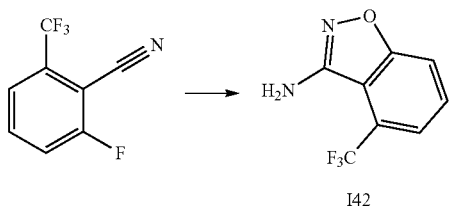

I42

To a solution of acetohydroxamic acid (2.25 g, 30 mmol) in DMF (80 mL) at 0° C. under N₂ was added t-BuOK (3.37 g, 30 mmol) and the mixture was heated at 30° C. for 1 h. A solution of 2-fluoro-6-(trifluoromethyl)benzonitrile (1.89 g, 10 mmol) in DMF (20 mL) was then added and heating was continued at 30° C. overnight. The mixture was partitioned between EtOAc (300 mL) and water (100 mL), the layers were separated and the organic layer was washed with water (100 mL×3), brine, dried over anhydrous Na₂SO₄, filtered and concentrated under reduced pressure. The residue was purified by column chromatography (Pet. ether/EtOAc=50/1 to 1/1) to give the title compound (1.3 g, 64%) as a white solid LCMS-D: R$_t$ 2.19 min; m/z 203.0 [M+H]⁺.

xviii) 5-Bromo-4-chlorobenzo[d]isoxazol-3-amine I44

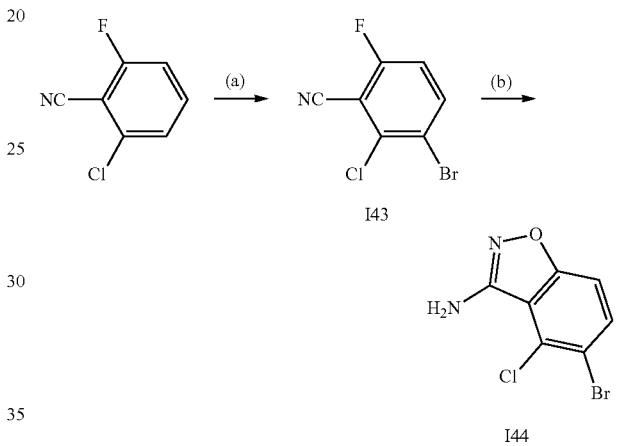

I44 a) 3-Bromo-2-chloro-6-fluorobenzonitrile I43

To a solution of 2-chloro-6-fluorobenzonitrile (1.0 g, 6.4 mmol) in trifluoromethanesulfonic acid (10 mL) at 0° C. under N₂ was added NBS (1.1 g, 6.4 mmol) and the mixture was stirred at RT overnight. The mixture was poured onto ice and extracted with EtOAc (30 mL×2). The combined organic extracts were dried over anhydrous Na₂SO₄, filtered and concentrated under reduced pressure. The residue was purified by column chromatography (Pet. ether/EtOAc=200/1 to 100/1) to give the title compound (705 mg, 47%) as a white solid, which was used directly in the next step.

b) 5-Bromo-4-chlorobenzo[d]isoxazol-3-amine I44

To a solution of acetohydroxamic acid (5.1 g, 67.8 mmol) in DMF (150 mL) at 0° C. under N₂ was added t-BuOK (7.6 g, 6.4 mmol) and the mixture was stirred at RT for 2 h. 3-Bromo-2-chloro-6-fluorobenzonitrile I43 (5.3 g, 22.6 mmol) was then added and the mixture was stirred at RT overnight. The mixture was diluted with EtOAc (500 mL) and washed with water (×3), brine, dried over anhydrous Na₂SO₄, filtered and concentrated under reduced pressure. The residue was purified by column chromatography (Pet. ether/EtOAc=50/1 to 2/1) to give the title compound (3.1 g, 52%) as a white solid, which was used directly in the next step.

xix) 5-Bromo-4-methoxybenzo[d]isoxazol-3-amine I48

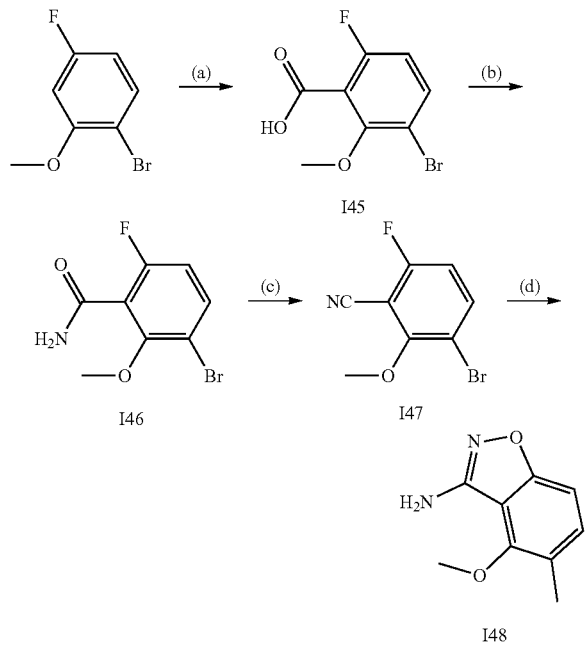

a) 3-Bromo-6-fluoro-2-methoxybenzoic acid I45

To a solution of diisopropylamine (5.4 g, 53.7 mmol) in THF (150 mL) at −78° C. under $N_2$ was added n-BuLi (2.5 M solution in hexanes, 23.4 mL, 58.5 mmol) dropwise and the mixture was stirred at −78° C. for 1 h. The resulting mixture was added dropwise to a solution of 1-bromo-4-fluoro-2-methoxybenzene (10.0 g, 48.8 mmol) in THF (50 mL) at −78° C. and stirring was continued for 90 min. $CO_2$ was bubbled through the mixture for 20 min with stirring at −78° C., then allowed to warm to RT and stirred for 15 min. The reaction mixture was adjusted to pH=1 with HCl and the mixture was diluted with water and extracted with DCM (500 mL). The combined organic extracts were washed with brine, dried over anhydrous $Na_2SO_4$, filtered and concentrated under reduced pressure. The residue was purified by column chromatography (DCM/MeOH=100/1 to 30/1) to give the title compound (8.0 g, 66%) as a colorless oil. LCMS-D: $R_t$ 2.12 min; m/z 248.9/250.9 [M+H]$^+$.

b) 3-Bromo-6-fluoro-2-methoxybenzamide I46

A mixture of 3-bromo-6-fluoro-2-methoxybenzoic acid I45 (8.0 g, 32.1 mmol) and $SOCl_2$ (30 mL) was heated at 85° C. for 3 h. The mixture was concentrated under reduced pressure and the residue was dissolved in DCM (5 mL) and added to conc. $NH_4OH$ (20 mL) at 0° C. dropwise. The mixture was allowed to warm to RT, stirred for 20 min then extracted with DCM (50 mL×3). The combined organic extracts were washed with water, brine, dried over anhydrous $Na_2SO_4$, filtered and concentrated under reduced pressure. The residue was purified by column chromatography (Pet. ether/EtOAc=50/1 to 1/1) to give the title compound (6.8 g, 80%) as a white solid. LCMS-E: $R_t$ 2.24 min; m/z 247.8/249.8 [M+H]$^+$ c) 3-Bromo-6-fluoro-2-methoxybenzonitrile I47

A mixture of 3-bromo-6-fluoro-2-methoxybenzamide I46 (6.8 g, 25.6 mmol) and $SOCl_2$ (30 mL) was heated at 80° C. overnight, then concentrated under reduced pressure. The residue was partitioned between water and EtOAc, the phases were separated and the organic layer was washed with water, brine, dried over anhydrous $Na_2SO_4$, filtered and concentrated under reduced pressure. The residue was purified by column chromatography (Pet. ether/EtOAc=100/1 to 20/1) to give the title compound (3.5 g, 55%) as a colorless oil, which was used directly in the next step.

d) 5-Bromo-4-methoxybenzo[d]isoxazol-3-amine I48

To a solution of acetohydroxamic acid (3.4 g, 45.7 mmol) in DMF (150 mL) at 0° C. under $N_2$ was added t-BuOK (5.1 g, 45.7 mmol) and the mixture was stirred at RT for 90 min. A solution of 3-bromo-6-fluoro-2-methoxybenzonitrile I47 (3.5 g, 15.2 mmol) in DMF (30 mL) was then added and the mixture was heated at 70° C. overnight. The mixture was diluted with EtOAc (1000 mL) and washed with water (×3), brine, dried over anhydrous $Na_2SO_4$, filtered and concentrated under reduced pressure. The residue was purified by column chromatography (Pet. ether/EtOAc=50/1 to 3/1) to give the title compound (3.2 g, 86%) as a white solid. LCMS-D: $R_t$ 2.24 min; m/z 243.0/244.9 [M+H]$^+$.

xx) 4-(Methoxymethyl)benzo[d]isoxazol-3-amine I51

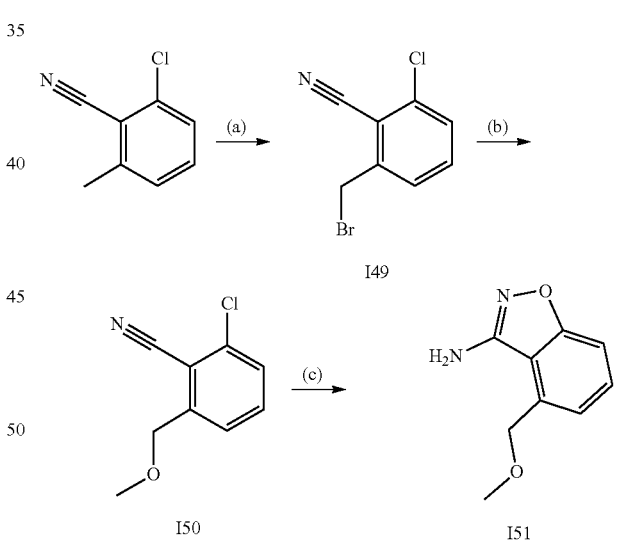

a) 2-(Bromomethyl)-6-chlorobenzonitrile I49

A mixture of 2-chloro-6-methylbenzonitrile (2.0 g, 13.2 mmol), NBS (2.5 g, 13.8 mmol) and AIBN (660 mg, 4.0 mmol) in $CCl_4$ (60 mL) was heated at 85° C. under $N_2$ overnight. The mixture was concentrated under reduced pressure and the residue was purified by column chromatography (Pet. ether/EtOAc=100/1 to 50/1) to give the title compound (1.7 g, 37%) as a white solid, which was used directly in the next step.

b) 2-Chloro-6-(methoxymethyl)benzonitrile I50

Sodium metal (115 mg, 4.8 mmol) was dissolved in MeOH (5 mL) and THF (5 mL) and the mixture was stirred at RT for 20 min. 2-(Bromomethyl)-6-chlorobenzonitrile I49 (560 mg, 2.4 mmol) was then added and the mixture was stirred at RT for 5 h. The solvent was removed under reduced pressure and the residue was purified by column chromatography (Pet. ether/EtOAc=50/1) to give the title compound (340 mg, 77%) as a colorless oil. $^1$H NMR (400 MHz, DMSO-$d_6$) δ 7.75-7.70 (m, 3H), 4.82 (s, 2H), 3.35 (s, 3H).

c) 4-(Methoxymethyl)benzo[d]isoxazol-3-amine I51

To a solution of acetohydroxamic acid (422 mg, 5.6 mmol) in DMF (25 mL) at −78° C. under $N_2$ was added t-BuOK (630 mg, 5.6 mmol) and the mixture was stirred at 0° C. for 1 h. 2-Chloro-6-(methoxymethyl)benzonitrile I50 (340 mg, 1.9 mmol) was then added and the mixture was stirred at RT overnight, then heated at 85° C. overnight. The mixture was diluted with water (70 mL) and extracted with EtOAc (100 mL×2). The combined organic extracts were washed with water (200 mL×3), dried over $Na_2SO_4$, filtered and concentrated under reduced pressure. The residue was purified by column chromatography (Pet. ether/EtOA=5/1 to 3/1) to give the title compound (105 mg, 31%) as a light yellow oil. LCMS-D: $R_t$ 1.57 min; m/z 179.1 [M+H]$^+$.

xxi) 4-Ethoxybenzo[d]isoxazol-3-amine I53

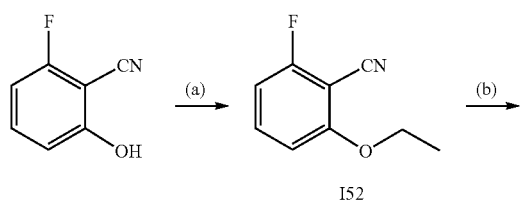

a) 2-Ethoxy-6-fluorobenzonitrile I52

A mixture of 2-fluoro-6-hydroxybenzonitrile (2.0 g, 14.6 mmol), $K_2CO_3$ (6.04 g, 43.8 mmol) and bromoethane (2.38 g, 21.9 mmol) in DMF (4 mL) was stirred at RT under $N_2$ overnight. The mixture was diluted with EtOAc (300 mL), washed with water (100 mL×5), brine, dried over $Na_2SO_4$, filtered and concentrated under reduced pressure. The residue was purified by column chromatography (Pet. ether/EtOAc=100/1 to 5/1) to give the title compound (1.6 g, 67%) as a white solid. LCMS-E: $R_t$ 5.24 min; m/z 166.1 [M+H]$^+$.

b) 4-Ethoxybenzo[d]isoxazol-3-amine I53

To a solution of acetohydroxamic acid (2.18 g, 29 mmol) in DMF (40 mL) at 0° C. under $N_2$ was added t-BuOK (3.26 g, 29 mmol) and the mixture was stirred at RT for 1 h. 2-Ethoxy-6-fluorobenzonitrile I52 (1.6 g, 9.7 mmol) was then added and the mixture was stirred at RT overnight. The mixture was diluted with DCM (80 mL), washed with water (60 mL×4), dried over $Na_2SO_4$, filtered and concentrated under reduced pressure. The residue was purified by column chromatography (Pet. ether/EtOAc=5/1) to give the title compound (240 mg, 15%) as a white solid. LCMS-E: $R_t$ 5.05 min; m/z 179.0 [M+H]$^+$.

xxii) 5-Methoxybenzo[d]isoxazol-3-amine I54

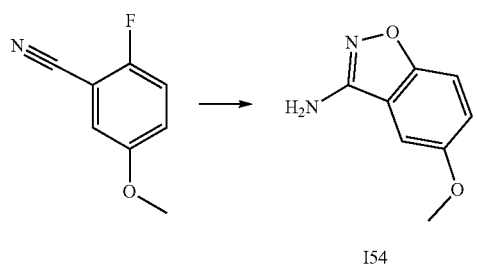

To a solution of acetohydroxamic acid (1.49 mg, 19.8 mmol) in DMF (35 mL) at 0° C. under $N_2$ was added t-BuOK (2.23 mg, 19.8 mmol) and the mixture was heated at 30° C. for 1 h. A solution of 2-fluoro-5-methoxybenzonitrile (1.0 g, 6.6 mmol) in DMF (5 mL) was then added and the mixture was heated at 30° C. overnight. The mixture was diluted with water (70 mL) and extracted with EtOAc (100 mL×3). The combined organic extracts were washed with water (200 mL×3) then dried over anhydrous $Na_2SO_4$, filtered and concentrated under reduced pressure to give the title compound (110 mg, 11%) as a yellow solid, which was used directly in the next step.

xxiii) 5-Ethoxybenzo[d]isoxazol-3-amine I57

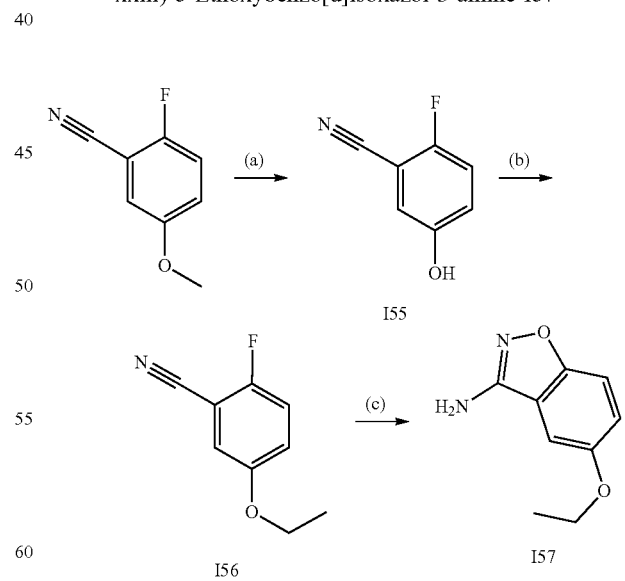

a) 2-Fluoro-5-hydroxybenzonitrile I55

A mixture of 2-fluoro-5-methoxybenzonitrile (1.7 g, 1.2 mmol) and pyridine.HCl (17 g) was heated at 80° C. under N₂ for 5 h, then diluted with DCM (40 mL) and washed with 2 M aq. HCl (8 mL) and water (2×40 mL). The organic layer was extracted with an aqueous K₂CO₃ solution (50 mL×2) and the combined aqueous extracts were washed with DCM (70 mL×2), then adjusted to pH 3-4 with 2 M aq. HCl and extracted with DCM (80 mL×3). The combined organic extracts were dried over anhydrous Na₂SO₄, filtered and concentrated under reduced pressure to give the title compound (430 mg, 28%) as an off-white solid, which was used directly in the next step.

b) 5-Ethoxy-2-fluorobenzonitrile I56

To a solution of 2-fluoro-5-hydroxybenzonitrile I55 (430 mg, 3.1 mmol) in DMF (15 mL) was added K₂CO₃ (1.3 g, 9.4 mmol) and the mixture was stirred at RT under N₂ for 30 min. Bromoethane (512 mg, 4.7 mmol) was then added and stirring was continued at RT overnight. The mixture was diluted with water (70 mL) and extracted with EtOAc (100 mL×2). The combined organic extracts were washed with water (200 mL×3), dried over anhydrous Na₂SO₄, filtered and concentrated under reduced pressure. The residue was purified by silica gel chromatography (Pet. ether/EtOAc=30/1 to 20/1) to give the title compound (480 mg, 92%) as a white solid. LCMS-D: R$_t$ 2.44 min; m/z 166.0 [M+H]⁺ 188.0 [M+Na]⁺.

c) 5-Ethoxybenzo[d]isoxazol-3-amine I57

To a solution of acetohydroxamic acid (645 mg, 8.7 mmol) in DMF (35 mL) at 0° C. under N₂ was added t-BuOK (978 mg, 8.7 mmol) and the mixture was heated at 30° C. for 1 h. A solution of 5-ethoxy-2-fluorobenzonitrile I56 (480 mg, 2.9 mmol) in DMF (5 mL) was then added and the mixture was heated at 30° C. overnight. The mixture was diluted with water (60 mL) and extracted with EtOAc (80 mL×2). The combined organic extracts were washed with water (150 mL×2), dried over anhydrous Na₂SO₄, filtered and concentrated under reduced pressure to give the title compound (400 mg, 77%) as a light yellow solid. LCMS-D: R$_t$ 2.02 min; m/z 179.1 [M+H]⁺.

xxiv) 6-(3,5-Dimethyl-1H-pyrazol-1-yl)benzo[d]isoxazol-3-amine I59

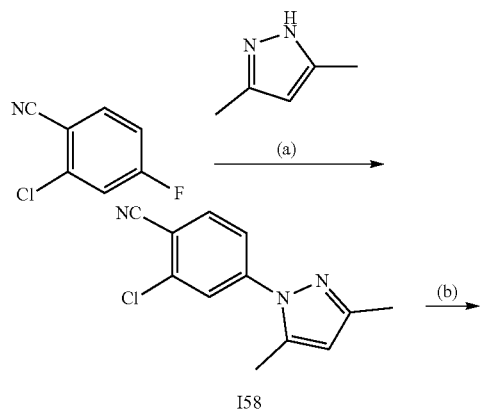

-continued

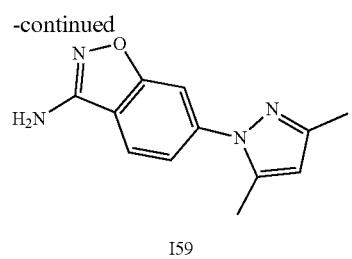

I59 a) 2-Chloro-4-(3,5-dimethyl-1H-pyrazol-1-yl)benzonitrile I58

A mixture of 3,5-dimethyl-1H-pyrazole (5 g, 0.052 mol), NaH (60% dispersion in oil, 2.6 g, 0.065 mol) in DMF (50 mL) was stirred at RT for 1 h. A solution of 2-chloro-4-fluorobenzonitrile (6.74 g, 0.043 mol) in DMF (50 mL) was then added and stirring was continued at RT for 1 h. The reaction was quenched with water and the mixture was extracted with EtOAc. The organic extract was concentrated under reduced pressure to give the title compound (11.0 g, 92%) as a yellow solid. LCMS-D: R$_t$ 2.58 min; m/z 232.1 [M+H]⁺.

b) 6-(3,5-Dimethyl-1H-pyrazol-1-yl)benzo[d]isoxazol-3-amine I59

To a solution of acetohydroxamic acid (972 mg, 12.9 mmol) in DMF (20 mL) at 0° C. under N₂ was added t-BuOK (1.45 g, 12.9 mmol) and the mixture was heated at 30° C. for 1 h. 2-Chloro-4-(3,5-dimethyl-1H-pyrazol-1-yl)benzonitrile I58 (1 g, 4.3 mmol) was then added and the mixture was heated at 60° C. for 5 h. The mixture was diluted with water and extracted with EtOAc. The organic extract was dried over anhydrous Na₂SO₄, filtered and concentrated under reduced pressure. The residue was purified by preparative TLC (MeOH/DCM=1/20) to give the title compound (150 mg, 15%) as a white solid. LCMS-D: R$_t$ 2.22 min; m/z 229.1 [M+H]⁺.

xxv) 5-Methylbenzo[d]isoxazol-3-amine I60

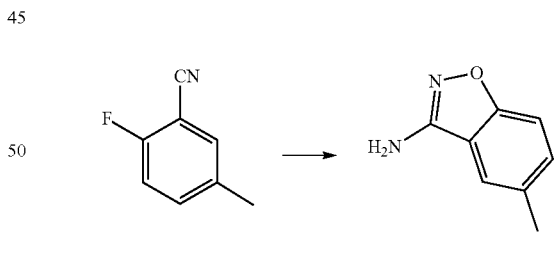

I60

To a solution of acetohydroxamic acid (8.33 g, 0.11 mol) in DMF (200 mL) was added t-BuOK (12.5 g, 0.11 mol) and the mixture was stirred at RT for 1 hour. 2-Fluoro-5-methylbenzonitrile (5 g, 0.37 mol) was then added and the mixture was heated at 60° C. overnight. The mixture was diluted with water and extracted with EtOAc. The organic extract was concentrated under reduced pressure and the residue was purified by a silica gel chromatography (DCM/MeOH=200/1 to 50/1) to give the title compound (3.0 g, 55%) as a white solid. LCMS-D: R$_t$ 1.75 min, m/z 149.0 [M+H]⁺.

xxvi) 6-(Methoxymethyl)benzo[d]isoxazol-3-amine I62

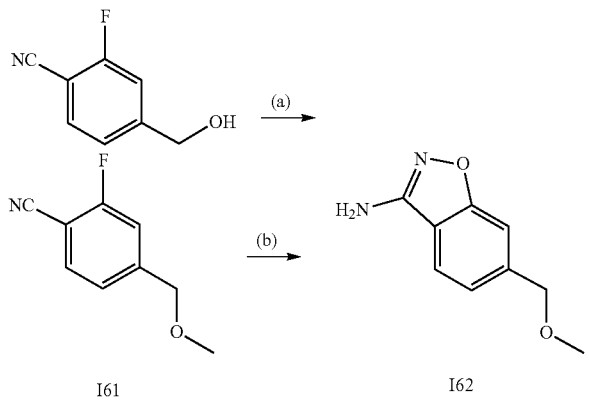

a) 2-Fluoro-4-(methoxymethyl)benzonitrile I61

A mixture of MeI (2.0 g, 13.2 mmol) and NaH (60% suspension in oil, 790 mg, 19.8 mmol) in THF (50 mL) was stirred at 0° C. for 10 min, then 2-fluoro-4-(hydroxymethyl)benzonitrile (2.0 g, 13.2 mmol) was added and the mixture was stirred at RT for 2 h. The reaction was quenched with water and the mixture was extracted with EtOAc. The organic extract was concentrated under reduced pressure and the residue was purified by silica gel chromatography (Pet. ether/EtOAc=100/1 to 20/1) to give the title compound (1.7 g, 78%) as a white solid. LCMS-D: $R_t$ 2.01 min; m/z 166.0 [M+H]$^+$ 187.9 [M+Na]$^+$.

b) 6-(Methoxymethyl)benzo[d]isoxazol-3-amine I62

To a solution of acetohydroxamic acid (1.5 g, 9.1 mmol) in DMF (50 mL) was added t-BuOK (3.06 g, 27.2 mmol) and the mixture was stirred at RT for 1 h. 2-Fluoro-4-(methoxymethyl)benzonitrile I61 (1.5 g, 9.1 mmol) was then added and the mixture was heated at 40° C. overnight. The mixture was diluted with water and extracted with EtOAc. The organic extract was concentrated under reduced pressure and the residue was purified by silica gel chromatography (Pet. ether/EtOAc=100/1 to 10/1) to give the title compound (1 g, 62%) as a yellow solid. LCMS-D: $R_t$ 0.95 min, m/z 179.0 [M+H]$^+$.

xxvii) 5-(Trifluoromethoxy)benzo[d]isoxazol-3-amine I63

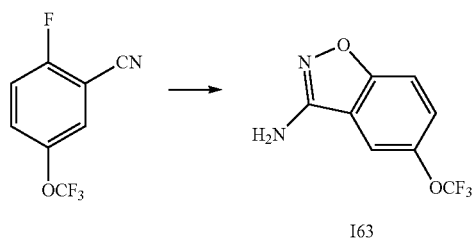 [SMILES: "I63" ; N#Cc1cc(OC(F)(F)F)ccc1F ; Nc1noc2ccc(OC(F)(F)F)cc12]

To a solution of acetohydroxamic acid (2.2 g, 0.029 mol) in DMF (50 mL) was added t-BuOK (3.28 g, 0.029 mol) and the mixture was stirred RT for 1 hour. 2-Fluoro-5-(trifluoromethoxy)benzonitrile (2 g, 9.75 mmol) was then added and the mixture was heated at 60° C. overnight. The mixture was diluted with water and extracted with EtOAc. The organic extract was concentrated under reduced pressure to give the title compound (1.6 g, 75%) as a yellow solid. LCMS-D: $R_t$ 2.43 min; m/z 219.0 [M+H]$^+$.

xxviii) 5-Methyl-6-(oxazol-2-yl)benzo[d]isoxazol-3-amine I65

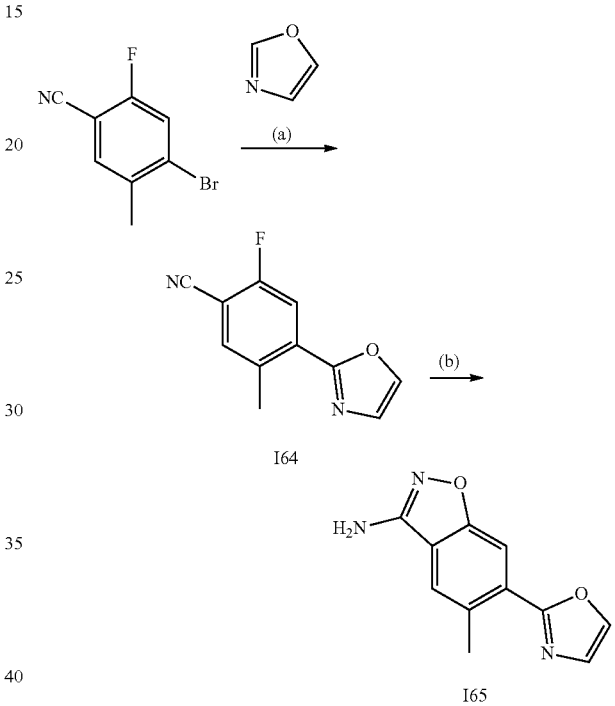

a) 2-Fluoro-5-methyl-4-(oxazol-2-yl)benzonitrile I64

To a solution of oxazole (90 mg, 1.31 mmol) in THF (10 mL) at −70° C. under N$_2$ was added n-BuLi (2.5 M solution in hexane, 1.1 mL, 2.66 mmol) and the mixture was stirred for 10 min. Solid ZnCl$_2$ (380 mg, 2.79 mmol) was added and the mixture was allowed to warm to RT. 4-Bromo-2-fluoro-5-methylbenzonitrile (200 mg, 0.93 mmol) was added and the mixture was heated at 60° C. overnight. The solvent was removed under reduced pressure and the residue was purified by silica gel chromatography (Pet. ether/EtOAc 10/1) to give the title compound (50 mg, 27%) as a white solid. LCMS-D: $R_t$ 2.51 min; m/z 203.0 [M+H]$^+$.

b) 5-Methyl-6-(oxazol-2-yl)benzo[d]isoxazol-3-amine I65

To a solution of acetohydroxamic acid (189 mg, 2.52 mmol) in DMF (10 mL) at 0° C. under N$_2$ was added t-BuOK (377 mg, 3.26 mmol) and the mixture was stirred at 0° C. for 1 h. 2-Fluoro-5-methyl-4-(oxazol-2-yl)benzonitrile I64 (170 mg, 0.84 mmol) was then added and the mixture was heated at 50° C. overnight. The mixture was diluted with water and extracted with EtOAc. The organic extract was dried over anhydrous $Na_2SO_4$, filtered and concentrated under reduced pressure. The residue was purified by preparative TLC (DCM/MeOH=10/1) to give the title compound (90 mg, 50%) as a white solid. LCMS-D: $R_t$ 2.10 min; m/z 216.0 $[M+H]^+$.

xxix) 7-Bromobenzo[d]isoxazol-3-amine I66

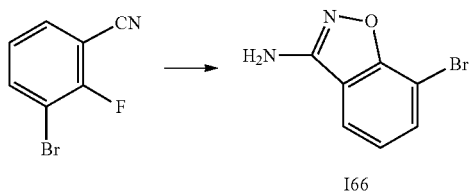 [SMILES: "I66" ; N#Cc1cccc(Br)c1F ; Nc1noc2c(Br)cccc12]

To a solution of acetohydroxamic acid (3.75 g, 0.05 mol) in DMF (60 mL) at 0° C. was added t-BuOK (5.6 g, 0.05 mol) and the mixture was stirred at RT for 1 h. A solution of 3-bromo-2-fluorobenzonitrile (5.0 g, 0.025 mol) in DMF (90 mL) was then added dropwise and stirred was continued at RT overnight. The mixture was diluted with DCM (300 mL), washed with water (250 mL×4), brine, dried over anhydrous $Na_2SO_4$, filtered and concentrated under reduced pressure to give the title compound (4.0 g, 63%) as a white solid. LCMS-D: $R_t$ 2.09 min, m/z 213.0/215.0 $[M+H]^+$.

xxx) 7-(Pyrimidin-2-yl)benzo[d]isoxazol-3-amine I68

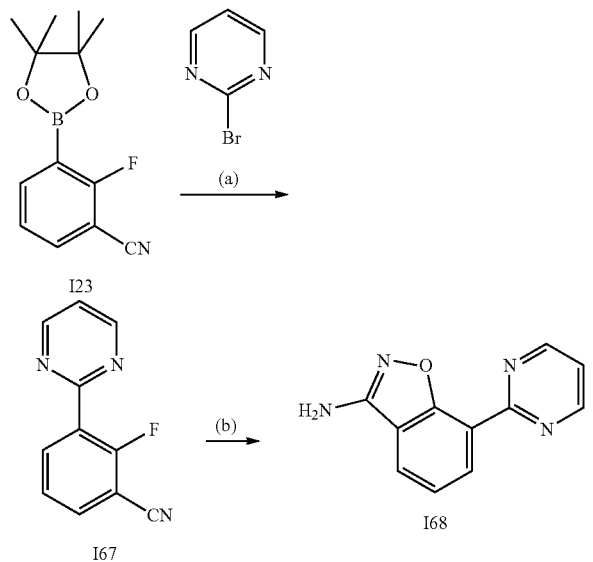

a) 2-Fluoro-3-(pyrimidin-2-yl)benzonitrile I67

A mixture of 2-fluoro-3-(4,4,5,5-tetramethyl-1,3,2-dioxaborolan-2-yl)benzonitrile I23 (1.5 g, 6.1 mmol), 2-bromopyrimidine (1.9 g, 12.0 mmol), Pd(dppf)Cl$_2$ (1.3 g, 1.8 mmol) and K$_3$PO$_4$ (6.5 g, 24.2 mmol) in water (60 mL), toluene (60 mL) and i-PrOH (15 mL) was heated at 85° C. under N$_2$ for 4 h. The mixture was diluted with EtOAc (50 mL) and washed with water (80 mL×3). The organic layer was dried over anhydrous $Na_2SO_4$, filtered, concentrated under reduced pressure and the residue was purified by column chromatography (Pet. ether/EtOAc=4/1) to give the title compound (450 mg, 38%) as a light yellow solid. LCMS-E: $R_t$ 4.82 min; m/z 199.9 $[M+H]^+$.

b) 7-(Pyrimidin-2-yl)benzo[d]isoxazol-3-amine I68

To a solution of acetohydroxamic acid (243 mg, 3.2 mmol) in DMF (15 mL) at 0° C. under N$_2$ was added t-BuOK (363 mg, 3.2 mmol) and the mixture was stirred for 1 h. A solution of 2-fluoro-3-(pyrimidin-2-yl)benzonitrile I67 (400 mg, 1.6 mmol) in DMF (5 mL) was then added dropwise and the mixture was stirred at RT overnight. The mixture was diluted with EtOAc (80 mL) and washed with water (60 mL×3). The organic layer was dried over anhydrous $Na_2SO_4$, filtered and concentrated under reduced pressure to give the title compound (230 mg, 67%) as a yellow solid. LCMS-D: $R_t$ 0.80 min. m/z 213.1 $[M+H]^+$.

xxxi) 6-(1H-Pyrazol-1-yl)benzo[d]isoxazol-3-amine I70

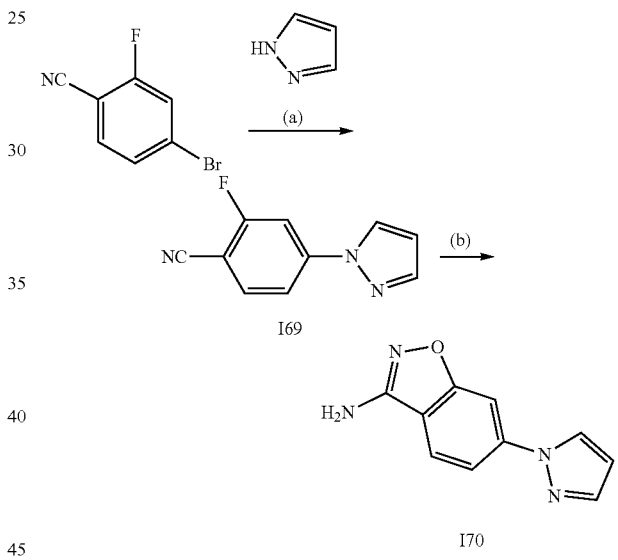

a) 2-Fluoro-4-(1H-pyrazol-1-yl)benzonitrile I69

A mixture of 4-bromo-2-fluorobenzonitrile (400 mg, 2.0 mmol), 1H-pyrazole (177 mg, 2.6 mmol), CuI (381 mg, 2.0 mmol), K$_3$PO$_4$ (849 mg, 4.0 mmol) and (1S,2S)—N$^1$,N$^2$-dimethylcyclohexane-1,2-diamine (28 mg, 0.2 mmol) in DMF (20 mL) was heated at 100° C. in a microwave for 1 h. The mixture was partitioned between EtOAc (200 mL) and water (100 mL), the layers were separated and the organic layer was washed with water (×3), brine, dried over anhydrous $Na_2SO_4$, filtered and concentrated under reduced pressure. The residue was purified by column chromatography (Pet. ether/EtOAc=100/1 to 20/1) to give the title compound (120 mg, 32%) as a white solid. LCMS-D: $R_t$ 2.20 min, m/z 188.1 $[M+H]^+$.

b) 6-(1H-Pyrazol-1-yl)benzo[d]isoxazol-3-amine I70

To a solution of acetohydroxamic acid (215 mg, 2.9 mmol) in DMF (25 mL) at 0° C. was added t-BuOK (322 mg, 2.9 mmol) and the mixture was heated 30° C. for 2 h. 2-Fluoro-4-(1H-pyrazol-1-yl)benzonitrile I69 (120 mg, 0.64 mmol) was then added and the mixture was heated at 30° C. overnight. The mixture was partitioned between EtOAc (100 mL) and water (50 mL), the layers were separated and the organic layer was washed with water (×3), brine, dried over anhydrous Na$_2$SO$_4$, filtered and concentrated under reduced pressure. The residue was purified by column chromatography (Pet. ether/EtOAc=50/1 to 2/1) to give the title compound (72 mg, 57%) as a white solid, which was used directly in the next step.

xxxii) 6-(2H-1,2,3-Triazol-2-yl)benzo[d]isoxazol-3-amine I72

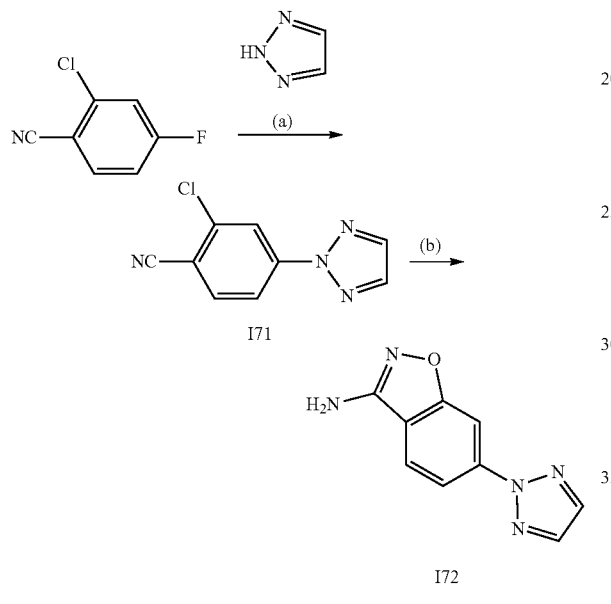

a) 2-Chloro-4-(2H-1,2,3-triazol-2-yl)benzonitrile I71

A mixture of 2H-1,2,3-triazole (553 mg, 8.0 mmol) and NaH (60% dispersion in oil, 192 mg, 4.8 mmol) in DMF (20 mL) was stirred at 0° C. for 30 min, then a solution of 2-chloro-4-fluorobenzonitrile (622 mg, 4.0 mmol) in DMF (10 mL) was added. The mixture was stirred at 0° C. for 2 h then allowed to warm to RT and stirred for 2 h. The mixture was partitioned between EtOAc (300 mL) and water (100 mL), the layers were separated and the organic layer was washed with water (×3), brine, dried over anhydrous Na$_2$SO$_4$, filtered and concentrated under reduced pressure. The residue was purified by column chromatography (Pet. ether/EtOAc=100/1 to 20/1) to give the title compound (200 mg, 24%) as a white solid. $^1$H NMR (400 MHz, DMSO-d$_6$) δ 8.31-8.28 (m, 3H), 8.19-8.14 (m 2H).

b) 6-(2H-1,2,3-Triazol-2-yl)benzo[d]isoxazol-3-amine I72

To a solution of acetohydroxamic acid (221 mg, 2.9 mmol) in DMF (25 mL) at 0° C. was added t-BuOK (330 mg, 2.9 mmol) and the mixture was heated at 30° C. for 2 h. 2-Chloro-4-(2H-1,2,3-triazol-2-yl)benzonitrile I71 (200 mg, 0.98 mmol) was then added and the mixture was heated at 30° C. overnight. The mixture was partitioned between EtOAc (100 mL) and water (50 mL), the layers were separated and the organic layer was washed with water (×3), brine, dried over anhydrous Na$_2$SO$_4$, filtered and concentrated under reduced pressure. The residue was purified by column chromatography (Pet. ether/EtOAc=50/1 to 2/1) to give the title compound (90 mg, 46%) as a white solid. LCMS-D: R$_t$ 1.93 min, m/z 202.1 [M+H]$^+$.

xxxiii) 6-(Pyridin-2-yl)benzo[d]isoxazol-3-amine I74

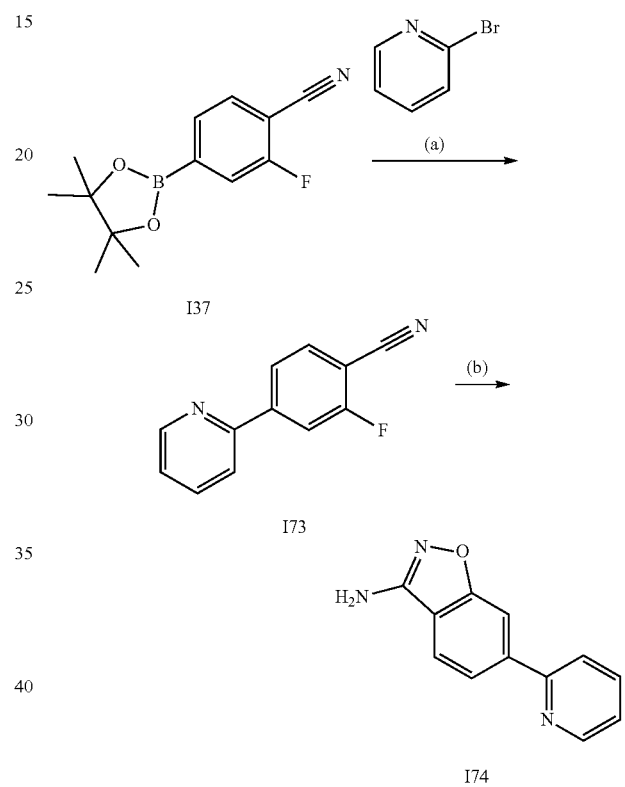

a) 2-Fluoro-4-(pyridin-2-yl)benzonitrile I73

A mixture of 2-fluoro-4-(4,4,5,5-tetramethyl-1,3,2-dioxaborolan-2-yl)benzonitrile I37 (494 mg, 2.0 mmol), 2-bromopyridine (948 mg, 6.0 mmol), Pd(dppf)Cl$_2$ (293 mg, 0.4 mmol) and K$_3$PO$_4$·3H$_2$O (2.66 g, 10.0 mmol) in H$_2$O (40 mL), toluene (40 mL) and i-PrOH (10 mL) was heated at 85° C. under N$_2$ for 4 h. The mixture was partitioned between EtOAc (200 mL) and water (30 mL), the layers were separated and the organic layer was washed with water, brine, dried over anhydrous Na$_2$SO$_4$, filtered and concentrated under reduced pressure. The residue was purified by column chromatography (Pet. ether/EtOAc=30/1 to 10/1) to give the title compound (190 mg, 48%) as a white solid. LCMS-D: R$_t$ 2.32 min, m/z 199.1 [M+H]$^+$.

b) 6-(Pyridin-2-yl)benzo[d]isoxazol-3-amine I74

To a solution of acetohydroxamic acid (216 mg, 2.88 mmol) in DMF (50 mL) at 0° C. was added t-BuOK (323 mg, 2.88 mmol) and the mixture was stirred at RT for 1 h.

A solution of 2-fluoro-4-(pyridin-2-yl)benzonitrile I73 (190 mg, 0.96 mmol) in DMF (10 mL) was then added and the mixture was stirred at RT overnight. The mixture was partitioned between EtOAc (200 mL) and water (50 mL), the layers were separated and the organic layer was washed with water (50 mL×3), brine, dried over anhydrous Na$_2$SO$_4$, filtered and concentrated under reduced pressure. The residue was purified by column chromatography (DCM/MeOH=100/0 to 100/1) to give the title compound (105 mg, 52%) as a white solid. LCMS-D: R$_t$ 0.83 min, m/z 212.1 [M+H]$^+$.

xxxiv) 6-Bromobenzo[d]isoxazol-3-amine I75

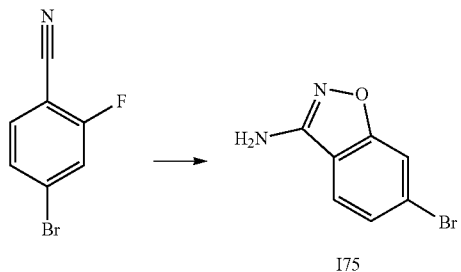 [SMILES: "I75" ; N#Cc1ccc(Br)cc1F ; Nc1noc2cc(Br)ccc12]

To a solution of acetohydroxamic acid (13.7 g, 182 mmol) in DMF (60 mL) at 0° C. was added t-BuOK (20.5 g, 182 mmol) and the mixture was stirred at 0° C. for 1 h. A solution of 4-bromo-2-fluorobenzonitrile (12.2 g, 60.8 mmol) in DMF (30 mL) was then added and the mixture was stirred at RT overnight. The mixture was partitioned between EtOAc (500 mL) and water (200 mL), the layers were separated and the organic layer was washed with water (×2), brine, dried over anhydrous Na$_2$SO$_4$, filtered and concentrated under reduced pressure. The residue was purified by column chromatography (Pet. ether/EtOAc=100/1 to 30/1) to give the title compound (8.1 g, 63%) as a white solid. LCMS-D: R$_t$ 2.34 min; m/z 213.0/215.0 [M+H]$^+$.

xxxv) 4-Methoxy-6-(pyridin-2-yl)benzo[d]isoxazol-3-amine I77

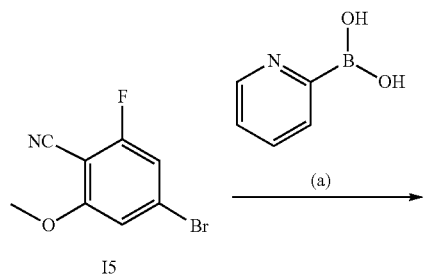

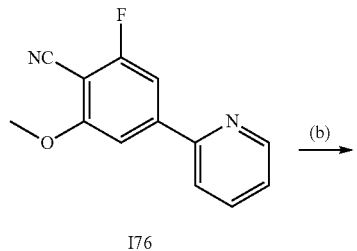

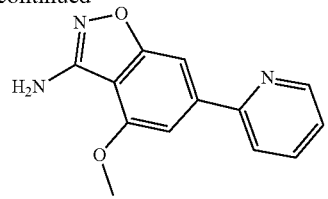

a) 2-Fluoro-6-methoxy-4-(pyridin-2-yl)benzonitrile I76

A mixture of 4-bromo-2-fluoro-6-methoxybenzonitrile I5 (244 mg, 1.06 mmol), pyridin-2-ylboronic acid (195 mg, 1.59 mmol), CuCl (105 mg, 1.06 mmol), Pd(OAc)$_2$ (24 mg, 0.106 mmol), XPhos (100 mg, 0.212 mmol) and Cs$_2$CO$_3$ (1.38 g, 4.24 mmol) in DMF (10.6 mL) was heated under a nitrogen atmosphere in a 20 mL sealed tube at 100° C. for 16 h. The reaction was repeated a further three times on the same scale and the four reactions were quenched with a saturated aqueous NH$_4$Cl, combined and extracted with EtOAc (80 mL×3). The combined organic extracts were washed with water, dried over anhydrous Na$_2$SO$_4$, filtered and concentrated under reduced pressure. The residue was purified by column chromatography (Pet. ether/EtOAc=10/1 to 5/1) to give the title compound (190 mg, 20%) as a yellow solid. LCMS-C: R$_t$ 2.13 min; m/z 229.0 [M+H]$^+$.

b) 4-Methoxy-6-(pyridin-2-yl)benzo[d]isoxazol-3-amine I77

To a solution of acetohydroxamic acid (178 mg, 2.37 mmol) in anhydrous DMF (20 mL) at 0° C. was added potassium tert-butoxide (266 mg, 2.37 mmol) and the mixture was stirred at 0° C. for 1 h. 2-Fluoro-6-methoxy-4-(pyridin-2-yl)benzonitrile I76 (180 mg, 0.79 mmol) was then added and the mixture was heated at 40° C. overnight. Water was added and the mixture was extracted with EtOAc. The combined organic extracts were dried over anhydrous Na$_2$SO$_4$, filtered and concentrated under reduced pressure. The residue was purified by column chromatography (DCM/MeOH=200/1 to 100/1 to 60/1) to give the title compound (70 mg, 37%) as a yellow solid. LCMS-C: R$_t$ 0.52 min; m/z 242.0 [M+H]$^+$. $^1$H NMR (400 MHz, DMSO-d$_6$) δ 8.73-8.68 (m, 1H), 8.14-8.09 (m, 1H), 7.95-7.88 (m, 1H), 7.70 (d, J=1.0 Hz, 1H), 7.46 (s, 1H), 7.44-7.38 (m, 1H), 6.01 (s, 2H), 4.01 (s, 3H).

xxxvi) 4-Methoxy-7-phenylbenzo[d]isoxazol-3-amine I80

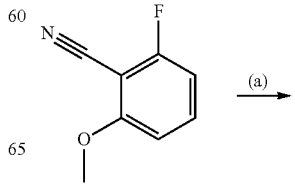

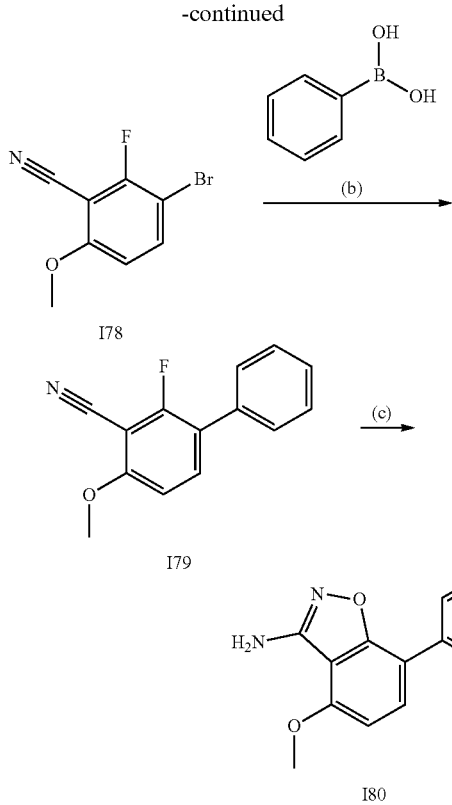

a) 3-Bromo-2-fluoro-6-methoxybenzonitrile I78

A solution of Br$_2$ (507 mg, 3.2 mmol) in CCl$_4$ (4.0 mL) was added to a solution of 2-fluoro-6-methoxybenzonitrile (480 mg, 3.2 mmol) and Fe (8.0 mg, 0.1 mmol) in CCl$_4$ (4.0 mL) at −10° C. over a period of 30 min and the mixture was then allowed to warm to RT and stirred overnight. The mixture was partitioned between water and EtOAc, the layers were separated and the organic layer was washed with a saturated aqueous Na$_2$SO$_3$ solution (×2), brine, dried over anhydrous Na$_2$SO$_4$, filtered and concentrated to give the title compound (580 mg, 80%) as a white solid. LCMS-C: R$_t$ 2.12 min; m/z 229.9 [M+H]$^+$.

b) 2-Fluoro-4-methoxy-[1,1$_B$ biphenyl]-3-carbonitrile I79

To a solution of 3-bromo-2-fluoro-6-methoxybenzonitrile I78 (600 mg, 2.6 mmol), phenylboronic acid (636 mg, 5.2 mmol) and Na$_2$CO$_3$ (829 mg, 7.8 mmol) in 1,4-dioxane (40 mL) and water (10 mL) under N$_2$ was added Pd(PPh$_3$)$_4$ (300 mg, 0.26 mmol) and the mixture was heated at 100° C. overnight. The mixture was partitioned between water and EtOAc, the layers were separated and the organic layer was washed with water, brine, dried over anhydrous Na$_2$SO$_4$, filtered and concentrated under reduced pressure. The residue was purified by column chromatography (Pet. ether/EtOAc=10/1 to 3/1) to give the title compound (538 mg, 90%) as a white solid. LCMS-C: R$_t$ 2.43 min; m/z 228.0 [M+H]$^+$.

c) 4-Methoxy-7-phenylbenzo[d]isoxazol-3-amine I80

To a solution of acetohydroxamic acid (533 mg, 7.11 mmol) in anhydrous DMF (30 mL) at RT was added potassium tert-butoxide (797 mg, 7.11 mmol) and the mixture was stirred at RT for 1 h. 2-Fluoro-4-methoxy-[1,1$_E$ biphenyl]-3-carbonitrile I79 (538 mg, 2.37 mmol) was then added and the mixture was heated at 60° C. overnight. Water was added and the mixture was extracted with EtOAc (30 mL×3). The combined organic extracts were dried over anhydrous Na$_2$SO$_4$, filtered and concentrated under reduced pressure. The residue was purified by column chromatography (Pet. ether/EtOAc=10/1 to 5/1) to give the title compound (413 mg, 72%) as an orange solid. LCMS-C: R$_t$ 1.33 min; m/z 209.0 [M+H]$^+$. $^1$H NMR (400 MHz, CDCl$_3$) δ 7.84-7.79 (m, 2H), 7.61 (d, J=8.1 Hz, 1H), 7.46 (t, J=7.7 Hz, 2H), 7.38-7.32 (m, 1H), 6.67 (d, J=8.2 Hz, 1H), 4.00 (s, 3H).

xxxvii) 4-Methoxy-7-(1-methyl-1H-pyrazol-4-yl)benzo[d]isoxazol-3-amine I82

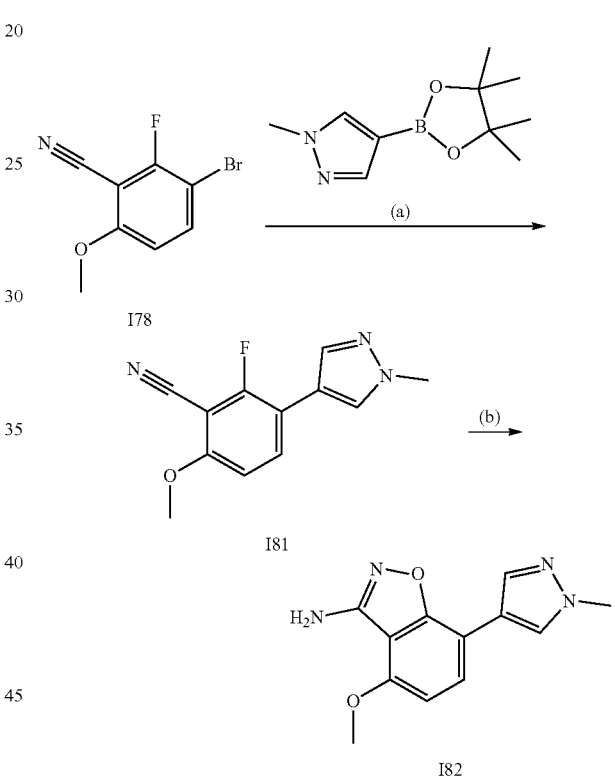

a) 2-Fluoro-6-methoxy-3-(1-methyl-1H-pyrazol-4-yl)benzonitrile I81

To a solution of 3-bromo-2-fluoro-6-methoxybenzonitrile I78 (720 mg, 3.31 mmol), 1-methyl-4-(4,4,5,5-tetramethyl-1,3,2-dioxaborolan-2-yl)-1H-pyrazole (1.30 g, 6.26 mmol) and Na$_2$CO$_3$ (995 mg, 9.39 mmol) in 1,4-dioxane (50 mL) and water (10 mL) under N$_2$ was added Pd(PPh$_3$)$_4$ (358 mg, 0.30 mmol) and the mixture was heated at 100° C. overnight. Water was added and the mixture was extracted with EtOAc. The combined organic extracts were washed with brine, dried over anhydrous Na$_2$SO$_4$, filtered and concentrated under reduced pressure. The residue was purified by column chromatography (DCM/MeOH=100/1) to give the title compound (485 mg, 63%) as a white solid. LCMS-C: R$_t$ 1.26 min; m/z 232.0 [M+H]$^+$.

b) 4-Methoxy-7-(1-methyl-1H-pyrazol-4-yl)benzo[d]isoxazol-3-amine I82

To a solution of acetohydroxamic acid (474 mg, 6.24 mmol) in anhydrous DMF (20 mL) at RT was added potassium tert-butoxide (700 mg, 6.24 mmol) and the mixture was stirred at RT for 1 h. 2-Fluoro-6-methoxy-3-(1-methyl-1H-pyrazol-4-yl)benzonitrile I81 (485 mg, 2.04 mmol) was then added and the mixture was heated at 60° C. overnight. Water was added and the mixture was extracted with EtOAc (30 mL×3). The combined organic extracts were dried over anhydrous Na$_2$SO$_4$, filtered and concentrated under reduced pressure. The residue was purified by column chromatography (DCM/MeOH=50/1) to give the title compound (225 mg, 45%) as a yellow solid. LCMS-C: R$_t$ 0.46 min; m/z 245.0 [M+H]$^+$. $^1$H NMR (400 MHz, DMSO-d$_6$) δ 8.19 (s, 1H), 7.95 (s, 1H), 7.69 (d, J=8.2 Hz, 1H), 6.74 (d, J=8.2 Hz, 1H), 6.00 (s, 2H), 3.91 (s, 3H), 3.90 (s, 3H).

xxxviii) 5-Chloro-4-methoxy-6-(methoxymethyl)benzo[d]isoxazol-3-amine I83

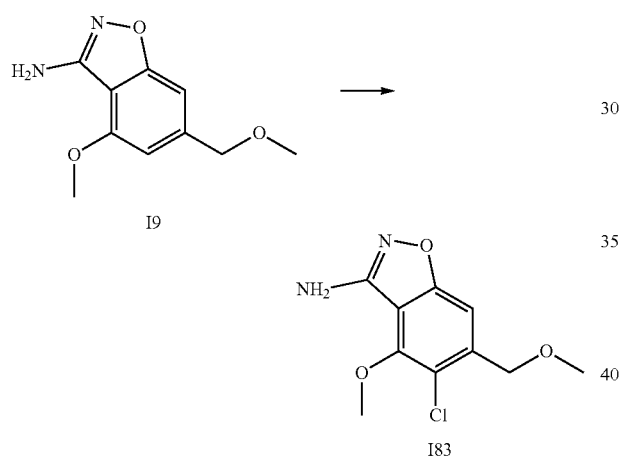

To a solution of 4-methoxy-6-(methoxymethyl)benzo[d]isoxazol-3-amine I9 (300 mg, 1.4 mmol) in DMF (10 mL) was added NCS (192 mg, 1.4 mmol) and the mixture was heated at 50° C. for 2 h. The mixture was diluted with EtOAc (100 mL) and washed with H$_2$O (40 mL×3). The organic layer was dried over anhydrous Na$_2$SO$_4$, filtered and concentrated under reduced pressure. The residue was purified by column chromatography (Pet. ether/EtOAc=7/1 to 5/1) to give the title compound (190 mg, 54%) as a white solid. LCMS-C: R$_t$ 1.21 min; m/z 242.9 [M+H]$^+$. $^1$H NMR (400 MHz, DMSO-d$_6$) δ 7.32 (s, 1H), 6.19 (s, 2H), 4.55 (s, 2H), 3.93 (s, 3H), 3.41 (s, 3H).

xxxix) 4-Methoxy-6-(oxazol-2-yl)benzo[d]isoxazol-3-amine I86 a) 2-(Tributylstannyl)oxazole I84

To a solution of oxazole (500 mg, 7.25 mmol) in THF (15 mL) at −78° C. under N$_2$ was added n-BuLi (2.5 M solution in hexanes, 2.9 mL, 7.32 mmol) dropwise and the mixture was stirred at −78° C. for 30 min. Tributylchlorostannane (1.96 mL, 7.25 mmol) was then added and the mixture was allowed to warm to RT and stirred for 1 h. The solvent was removed under reduced pressure and residue was taken up in hexanes (50 mL). The resulting precipitate was removed by filtration and the filtrate was concentrated under reduced pressure to give the title compound (2.0 g, 77%) as colorless oil. $^1$H NMR (400 MHz, DMSO-d$_6$) δ 8.20 (s, 1H), 7.20 (s, 1H), 1.59-1.49 (m, 6H), 1.31-1.26 (m, 6H), 1.16-1.10 (m, 6H), 0.83 (t, J=7.3 Hz, 9H).

b) 2-Fluoro-6-methoxy-4-(oxazol-2-yl)benzonitrile I85

To a solution of 4-bromo-2-fluoro-6-methoxybenzonitrile I5 (305 mg, 1.33 mmol) in 1,4-dioxane (25 mL) was added 2-(tributylstannyl)oxazole 184 (1.43 g, 3.98 mmol) and Pd(PPh$_3$)$_4$ (154 mg, 0.133 mmol) and the mixture was heated at 90° C. overnight. The mixture was diluted with water and extracted with EtOAc. The combined organic extracts were washed with water, brine, dried over anhydrous Na$_2$SO$_4$, filtered and concentrated. The residue was purified by column chromatography (Pet. ether/EtOAc=8/1) to give the title compound (370 mg, 96%) as a white solid. LCMS-C: R$_t$ 1.86 min; m/z 218.9 [M+H]$^+$.

c) 4-Methoxy-6-(oxazol-2-yl)benzo[d]isoxazol-3-amine I86

To a solution of acetohydroxamic acid (382 mg, 5.09 mmol) in DMF (25 mL) at 0° C. was added potassium tert-butoxide (570 mg, 5.09 mmol) and the mixture was stirred at RT for 1 h. 2-Fluoro-6-methoxy-4-(oxazol-2-yl)benzonitrile I85 (370 mg, 1.7 mmol) was then added and the mixture was heated at 60° C. for 2 h. The mixture was diluted with EtOAc and washed with water, brine, dried over anhydrous $Na_2SO_4$, filtered and concentrated to give the title compound (100 mg, 26%) as a yellow solid. LCMS-C: $R_t$ 0.57 min; m/z 232.0 $[M+H]^+$. $^1$H NMR (400 MHz, DMSO-$d_6$) δ 8.29 (s, 1H), 7.56 (s, 1H), 7.47-7.42 (m, 1H), 7.27 (s, 1H), 6.09 (s, 2H), 4.00 (s, 3H).

xl) 6-(Oxazol-2-yl)benzo[d]isoxazol-3-amine I90

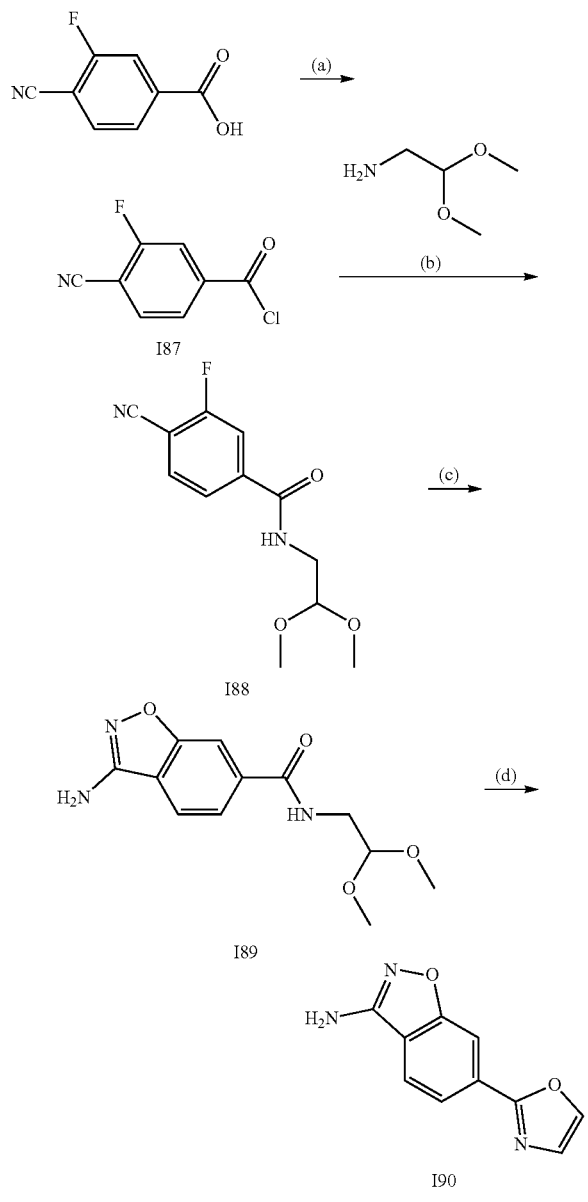

a) 4-Cyano-3-fluorobenzoyl chloride I87

To a solution of 4-cyano-3-fluorobenzoic acid (1.0 g, 6.1 mmol) in DCM (20 mL) at 0° C. was added DMF (0.1 mL) and oxalyl chloride (1.86 g, 12.1 mmol) dropwise and the mixture was stirred at RT overnight. The solvent was removed under reduced pressure to give the title compound (1.2 g) as a white solid, which was used directly in the next step without further purification.

b) 4-Cyano-N-(2,2-dimethoxyethyl)-3-fluorobenzamide I88

To a solution of 4-cyano-3-fluorobenzoyl chloride I87 (1.1 g, 6.06 mmol) and $Et_3N$ (1.84 g, 18 mmol) in DCM (20 mL) at 0° C. was added 2,2-dimethoxyethanamine (955 mg, 9.1 mmol) and the mixture was stirred for 2 h. The mixture was poured into water and extracted with EtOAc. The organic extract was washed with water and brine, dried over anhydrous $Na_2SO_4$, filtered and concentrated under reduced pressure. The residue was purified by column chromatography (Pet. ether/EtOAc=1/1, v/v) to give the title compound (1.2 g, 78%) as a white solid. LCMS-D: $R_t$ 1.55 min, m/z 274.9 $[M+Na]^+$.

c) 3-Amino-N-(2,2-dimethoxyethyl)benzo[d]isoxazole-6-carboxamide I89

To a solution of acetohydroxamic acid (448 mg, 5.95 mmol) in DMF (30 mL) at 0° C. was added t-BuOK (889 mg, 7.92 mmol) portion-wise and the mixture was stirred for 1 h. 4-Cyano-N-(2,2-dimethoxyethyl)-3-fluorobenzamide I88 (500 mg, 1.98 mmol) was then added and the mixture was heated at 40° C. overnight. The mixture was poured into water and extracted with EtOAc. The organic layer was washed with water and brine, dried over anhydrous $Na_2SO_4$, filtered and concentrated under reduced pressure. The residue was purified by column chromatography (Pet. ether/EtOAc=1/1, v/v) to give the title compound (380 mg, 72%) as a yellow solid. LCMS-D: $R_t$ 0.59 min, m/z 287.9 $[M+Na]^+$.

d) 6-(Oxazol-2-yl)benzo[d]isoxazol-3-amine I90

A mixture of 3-amino-N-(2,2-dimethoxyethyl)benzo[d]isoxazole-6-carboxamide I89 (240 mg, 0.9 mmol) and $P_2O_5$ (193 mg, 1.36 mmol) in methanesulfonic acid (10 mL) was heated at 150° C. under microwave irradiation for 30 min. The mixture was poured into water, made basic with aqueous KOH and extracted with EtOAc. The organic extract was washed with brine, dried over anhydrous $Na_2SO_4$, filtered and concentrated under reduced pressure. The residue was purified by prep. TLC (DCM/MeOH=10/1, v/v) to give the title compound (50 mg, 28%) as a solid. LCMS-D: $R_t$ 1.57 min, m/z 201.9 $[M+H]^+$.

xli) 5-Ethyl-1-methyl-2-oxo-1,2-dihydropyridine-3-sulfonyl chloride I94

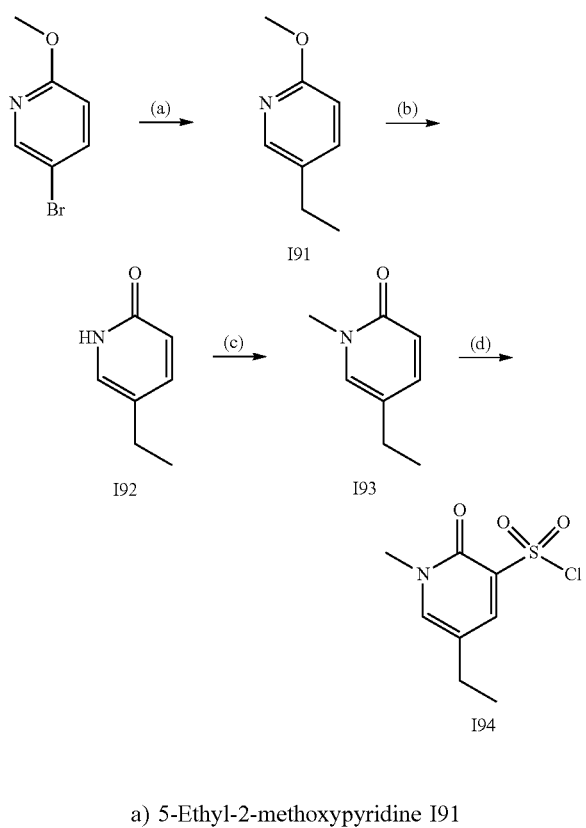

a) 5-Ethyl-2-methoxypyridine I91

To a solution of 5-bromo-2-methoxypyridine (10.2 g, 54.25 mmol) in THF (200 mL) at −78° C. under N$_2$ was added n-BuLi (2.5 M solution in hexane, 24.0 mL, 60.0 mmol) dropwise and the mixture was stirred at −78° C. for 1.5 h. Iodoethane (12.7 g, 81.4 mmol) was then added dropwise and the mixture was stirred at −78° C. for 20 min, then warmed to RT and stirred for 30 min. The reaction was quenched with water (5 mL) and the solvent was removed under reduced pressure. The residue was dissolved in DCM, washed with water, brine, dried over anhydrous Na$_2$SO$_4$, filtered and concentrated under reduced pressure. The residue was purified by column chromatography (Pet. ether/EtOAc=100/1 to 5/1) to give the title compound (2.8 g, 38%) as a colorless oil. LCMS-D: R$_t$ 1.80 min; m/z 138.1 [M+H]$^+$.

b) 5-Ethylpyridin-2(1H)-one I92

A solution of 5-ethyl-2-methoxypyridine I91 (1.6 g, 11.66 mmol) in conc. HCl (30 mL) was heated at 100° C. overnight. The mixture was concentrated under reduced pressure and the residue was purified by column chromatography (DCM/MeOH=20/1) to give the title compound (800 mg, 56%) as a white solid, which was used directly in the next step.

c) 5-Ethyl-1-methylpyridin-2(1H)-one I93

A mixture of 5-ethylpyridin-2(1H)-one I92 (800 mg, 6.5 mmol), K$_2$CO$_3$ (1.8 g, 13 mmol) and iodomethane (1.85 g, 13 mmol) in MeOH (20 mL) was heated at 50° C. under N$_2$ overnight. The solvent was removed under reduced pressure and the residue was dissolved in DCM (100 mL), washed with water, brine, dried over anhydrous Na$_2$SO$_4$, filtered and concentrated under reduced pressure. The residue was purified by column chromatography (DCM/MeOH=40/1) to give the title compound (500 mg, 56%) as a colorless oil. LCMS-D: R$_t$ 0.68 min; m/z 138.1 [M+H]$^+$.

d) 5-Ethyl-1-methyl-2-oxo-1,2-dihydropyridine-3-sulfonyl chloride I94

A mixture of chlorosulfonic acid (6 mL) and 5-ethyl-1-methylpyridin-2(1H)-one I93 (0.6 g, 4.37 mmol) was heated at 150° C. under N$_2$ for 3 h, then allowed to cool to RT and poured onto ice (100 g). The mixture was extracted with DCM (50 mL×3) and the combined organic extracts were washed twice with ice-cold water, dried over anhydrous Na$_2$SO$_4$, filtered and concentrated under reduced pressure. The residue was purified by column chromatography (DCM/MeOH=100/1 to 20/1) to give the title compound (200 mg, 12%) as a yellow solid. $^1$H NMR (400 MHz, DMSO-d$_6$) δ 7.87-7.84 (m, 1H), 7.71 (s, 1H), 3.47 (s, 3H), 2.39 (q, J=7.6 Hz, 2H), 1.09 (t, J=7.5 Hz, 3H). LCMS-D: R$_t$ 1.58 min; m/z 236.0 [M+H]$^+$.

xlii) 5-Bromo-2,3-dihydrobenzofuran-7-sulfonyl chloride I95

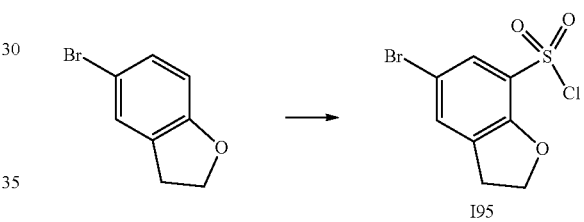

5-Bromo-2,3-dihydrobenzofuran (2.0 g, 10 mmol) was added slowly to chlorosulfonic acid (6 mL) at −5° C. and the mixture was stirred at −5° C. for 30 min. The mixture was poured into ice-cold water (100 mL) and extracted with EtOAc (180 mL×2). The combined organic extracts were washed with water (250 mL×3), dried over anhydrous Na$_2$SO$_4$, filtered and concentrated under reduced pressure. The residue was purified by column chromatography (Pet. ether/EtOAc=15/1) to give the title compound (1.45 g, 48%) as a white solid. $^1$H NMR (400 MHz, CDCl$_3$) δ 7.80-7.76 (m, 1H), 7.63-7.58 (m, 1H), 4.91 (m, 2H), 3.35 (m, 2H). LCMS-D: R$_t$ 2.74 min; m/z 318.8/320.8 [M+Na]$^+$.

xliii) 4,6-Dimethoxy-2,3-dihydro-1H-indene-5-sulfonyl chloride I98

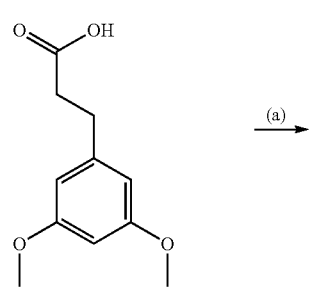

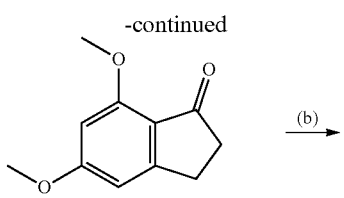

I96

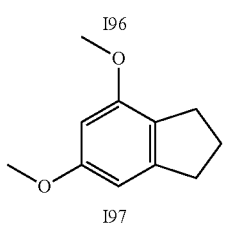

I97

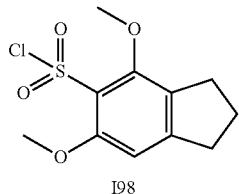

I98 a) 5,7-Dimethoxy-2,3-dihydro-1H-inden-1-one I96

A mixture of 3-(3,5-dimethoxyphenyl)propanoic acid (5 g, 23.8 mmol) and methanesulfonic acid (24 mL) was heated at 90° C. for 10 min then allowed to cool to RT and poured into water. The mixture was adjusted to pH 9 with 10 M aq. KOH and extracted with EtOAc (×5). The combined organic extracts were washed with water, brine, dried over anhydrous $Na_2SO_4$, filtered and concentrated under reduced pressure to give the title compound (3.5 g, 76%) as a white solid. LCMS-D: $R_t$ 1.76 min; m/z 193.1 $[M+H]^+$.

b) 4,6-Dimethoxy-2,3-dihydro-1H-indene I97

A mixture of 5,7-dimethoxy-2,3-dihydro-1H-inden-1-one I96 (3.0 g, 15.6 mmol) and triethylsilane (7.3 g, 62.4 mmol) in TFA (20 mL) was stirred at RT under $N_2$ for 11 h. The mixture was concentrated under reduced pressure and the residue was purified by column chromatography (Pet. ether/EtOAc=20/1) to give the title compound (2.0 g, 72%) as a white solid. $^1$H NMR (400 MHz, $CDCl_3$) δ 6.42 (s, 1H), 6.29 (d, J=2.0 Hz, 1H), 3.81 (s, 3H), 3.80 (s, 3H), 2.89 (t, J=7.5 Hz, 2H), 2.80 (t, J=7.3 Hz, 2H), 2.13-2.02 (m, 2H).

c) 4,6-Dimethoxy-2,3-dihydro-1H-indene-5-sulfonyl chloride I98

To a solution of 4,6-dimethoxy-2,3-dihydro-1H-indene I97 (1 g, 5.6 mmol) and TMEDA (0.72 g, 6.17 mmol) in n-hexane (20 mL) at −70° C. was added n-BuLi (2.5 M in hexane, 2.5 mL, 6.17 mmol) dropwise and the mixture was allowed to warm to 0° C. and stirred for 2 h. The mixture was then re-cooled to −65° C., bubbled with $SO_2$ gas for 20 min, then allowed to warm slowly to 10° C. The resulting precipitate was collected by filtration and washed with dry diethyl ether. The solid was suspended in n-hexane (20 mL), cooled to 0° C. and $SO_2Cl_2$ (0.83 g, 6.2 mmol) was added dropwise. The mixture was stirred at 0° C. under $N_2$ for 1 h, then filtered. The filter cake was dissolved in diethyl ether and washed with water, brine, dried over anhydrous $Na_2SO_4$, filtered and concentrated under reduced pressure to give the title compound (550 mg, 35%) as a white solid. $^1$H NMR (400 MHz, $CDCl_3$) δ 6.72 (s, 1H), 3.95 (s, 3H), 3.94 (s, 3H), 2.96 (q, J=7.6 Hz, 4H), 2.18-2.08 (m, 2H).

xliv) 2-Methoxy-5-phenoxybenzenesulfonyl chloride I100

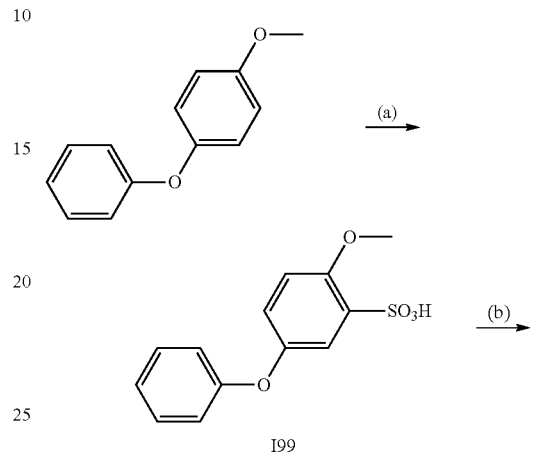

a) 2-Methoxy-5-phenoxybenzenesulfonic acid I99

To a solution of 1-methoxy-4-phenoxybenzene (2 g, 10 mmol) in DCM (15 mL) at 0° C. was added a solution of chlorosulfonic acid (0.35 mL) in DCM (10 mL) dropwise and the mixture was stirred at 0° C. for 15 min. The mixture was poured slowly into ice-cold water (100 mL) and then concentrated under reduced pressure. The residue was rinsed with DCM (100 mL×2) and dried to give the title compound (560 mg, 40%) as an off-white solid. LCMS-D: $R_t$ 0.62 min; m/z 281.0 $[M+H]^+$.

b) 2-Methoxy-5-phenoxybenzenesulfonyl chloride I100

A mixture of 2-methoxy-5-phenoxybenzenesulfonic acid I99 (250 mg, 0.9 mmol) and $PCl_5$ (284 mg, 1.3 mmol) in $POCl_3$ (3 mL) was heated at 90° C. under $N_2$ for 1 h. The mixture was then added slowly to ice-cold water (20 mL) and extracted with DCM (15 mL×2). The combined organic extracts were washed with brine, dried over anhydrous $Na_2SO_4$, filtered and concentrated under reduced pressure to give the title compound (51 mg, 18%) as a yellow oil. LCMS-D: $R_t$ 2.72 min; m/z 295.0 $[M-Cl+OCH_3]^+$, 317.0 $[M-Cl+OCH_3+Na]^+$.

xlv) 2,6-Dimethoxy-3-(trifluoromethyl)benzenesulfonyl chloride I102 xlvi) 3-Ethyl-2,6-dimethoxybenzenesulfonyl chloride I106

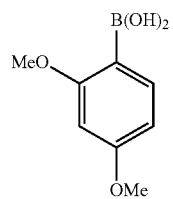 (a) 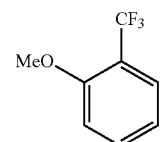 (b)

I101

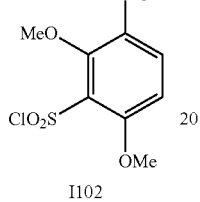

I102

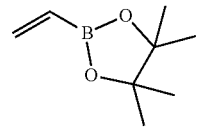

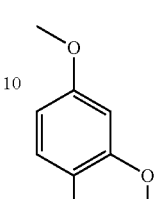 (a) 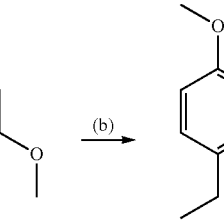

I103    (b)    I104    (c)

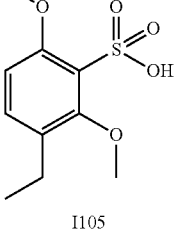 (d) 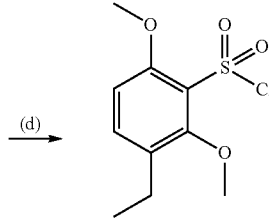

I105      I106 a) 2,4-Dimethoxy-1-(trifluoromethyl)benzene I101

To a mixture of (2,4-dimethoxyphenyl)boronic acid (3.0 g, 16.5 mmol), CF$_3$SO$_2$Na (18.0 g, 115.4 mmol), Cu(OAc)$_2$ (748 mg, 4.1 mmol), imidazole (281 mg, 4.1 mmol), 2,4,6-collidine (3.0 g, 33.0 mmol) and NH$_4$Cl (11.3 g, 206.0 mmol) in water (16.5 mL) and DCM (100 mL) at 0° C. was added t-BuOOH (3.6 mL, 4.1 mmol) dropwise and the mixture was stirred at RT for 16 h. The layers were then separated and the aqueous layer was extracted with DCM. The combined organic layers were dried over anhydrous Na$_2$SO$_4$, filtered and concentrated under reduced pressure. The residue was purified by column chromatography (Pet. ether) to give the title compound (900 mg, 27%) as an oil. $^1$H NMR (400 MHz, CDCl$_3$) δ 7.42-7.36 (m, 1H), 6.45-6.37 (m, 2H), 3.79 (s, 3H), 3.76 (s, 3H).

b) 2,6-Dimethoxy-3-(trifluoromethyl)benzenesulfonyl chloride I102

To a solution of 2,4-dimethoxy-1-(trifluoromethyl)benzene I101 (1.5 g, 7.3 mmol) and TMEDA (0.93 g, 8.0 mmol) in n-hexane (30 mL) at −78° C. under N$_2$ was added n-BuLi (2.5 M in hexane, 3.2 mL, 8.0 mmol) dropwise and the mixture was stirred at 0° C. for 1 h. SO$_2$ gas was then bubbled through the mixture at −78° C. for 20 minutes and then allowed to warm to 0° C. and stirred for 1 h. The resulting precipitate was collected by filtration and washed with hexane. The filter cake was suspended in n-hexane (30 mL), cooled to 0° C. and SO$_2$Cl$_2$ (1.1 g, 8.0 mmol) was added dropwise. The mixture was stirred at 0° C. for 1 h and the solids were collected by filtration and washed with cold n-hexane. The filter cake was dissolved in ether and washed with water. The aqueous phase was extracted with ether and the combined organic layers were dried over anhydrous Na$_2$SO$_4$, filtered and concentrated under reduced pressure. The residue was purified by column chromatography (Pet. ether/EtOAc=5/1) to give the title compound (1.5 g, 68%) as a yellow solid. $^1$H NMR (400 MHz, CDCl$_3$) δ 7.90-7.84 (m, 1H), 6.98-6.92 (m, 1H), 4.09 (s, 3H), 4.04 (s, 3H).

a) 2,4-Dimethoxy-1-vinylbenzene I103

A suspension of 1-bromo-2,4-dimethoxybenzene (4.0 g, 18.4 mmol), 4,4,5,5-tetramethyl-2-vinyl-1,3,2-dioxaborolane (3.4 g, 22.1 mmol), Pd(dppf)Cl$_2$.DCM (753 mg, 0.92 mmol) and K$_2$CO$_3$ (7.6 g, 55.2 mmol) in 1,4-dioxane (40 mL) and water (10 mL) was heated at 90° C. under N$_2$ overnight. The mixture was filtered through a pad of Celite and rinsed with EtOAc. The filtrate was diluted with water and extracted with EtOAc (60 mL×3). The combined organic extracts were washed with brine, dried over anhydrous Na$_2$SO$_4$, filtered and concentrated under reduced pressure. The residue was purified by column chromatography (Pet. ether) to give the title compound (2.6 g, 86%) as a yellow oil. LCMS-D: R$_t$ 2.28 min; m/z 165.0 [M+H]$^+$.

b) Ethyl-2,4-dimethoxybenzene I104

To a solution of 2,4-dimethoxy-1-vinylbenzene I103 (2.6 g, 15.8 mmol) in EtOAc (50 mL) was added 10% Pd/C (300 mg) and the mixture was stirred at RT under a H$_2$ atmosphere overnight. The catalyst was removed by filtration through Celite and rinsed with EtOAc. The filtrate was concentrated under reduced pressure to give the title compound (2.0 g, 83%) as a yellow oil. LCMS-D: R$_t$ 2.39 min; m/z 167.1 [M+H]$^+$.

c) 3-Ethyl-2,6-dimethoxybenzenesulfonic acid I105

Prepared from ethyl-2,4-dimethoxybenzene I104 according to the procedure described for 2,6-dimethoxybenzenesulfonyl chloride I111. The product obtained was found to be mostly 3-ethyl-2,6-dimethoxybenzenesulfonic acid. LCMS-D: R$_t$ 2.36 min; m/z 247.0 [M+H]$^+$.

d) 3-Ethyl-2,6-dimethoxybenzenesulfonyl chloride I106

A mixture of 3-ethyl-2,6-dimethoxybenzenesulfonic acid I105 (300 mg, 1.22 mmol) and thionyl chloride (6 mL) was heated at 95° C. for 3 h then concentrated under reduced pressure to give the title compound (322 mg, 100%) as a brown oil, which was used directly in the next step.

xlvii) 7-Methoxyquinoline-8-sulfonyl chloride I107

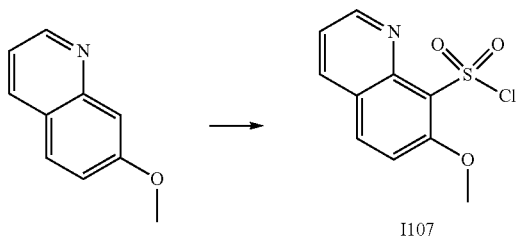 [SMILES: "I107" ; COc1ccc2cccnc2c1 ; COc1ccc2cccnc2c1S(=O)(=O)Cl]

Chlorosulfonic acid (1.8 g, 15.7 mmol) was added dropwise to 7-methoxyquinoline (500 mg, 3.14 mmol) at 0° C. and the mixture was heated at 100° C. for 1 h. The mixture allowed to cool to RT, poured onto ice and then neutralised with a saturated aqueous NaHCO$_3$ solution. The mixture was extracted with EtOAc (30 mL×3) and the combined organic extracts were washed with brine, dried over anhydrous Na$_2$SO$_4$, filtered and concentrated under reduced pressure to give the title compound (280 mg, 34%) as a yellow solid. LCMS-D: R$_t$ 0.27 min; m/z 239.9 [M-C$_1$+H$_2$O]$^+$ xlviii) 6-Methoxy-2,3-dihydro-1H-indene-5-sulfonyl chloride I108

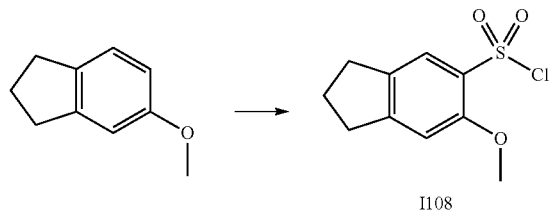

To a solution of 5-methoxy-2,3-dihydro-1H-indene (3.1 g, 20.9 mmol) in DCM (40 mL) at −5° C. under N$_2$ was added chlorosulfonic acid (6.5 g, 62.8 mmol) dropwise and the mixture was stirred at −5° C. for 40 min. The reaction was quenched with ice water (20 mL) and the mixture was extracted with EtOAc (30 mL×2). The combined organic extracts were washed with water (50 mL×3), dried over anhydrous Na$_2$SO$_4$, filtered and concentrated under reduced pressure. The residue was purified by column chromatography (Pet. ether/EtOAc=20/1) to give the title compound (3.1 g, 60%) as a white solid, which was used directly in the next step. $^1$H NMR (400 MHz, CDCl$_3$) δ 7.77 (d, J=1.1 Hz, 1H), 6.98 (s, 1H), 4.02 (s, 3H), 2.99 (t, J=7.5 Hz, 2H), 2.91 (t, J=7.4 Hz, 2H), 2.19-2.10 (m, 2H).

xlix) 3-Methoxy-5,6,7,8-tetrahydronaphthalene-2-sulfonyl chloride I109

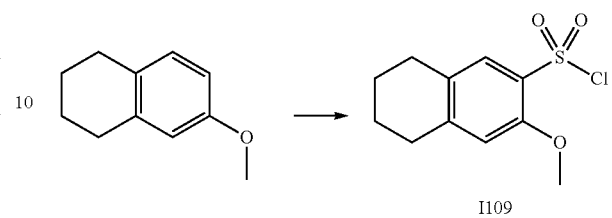

Prepared from 6-methoxy-1,2,3,4-tetrahydronaphthalene and chlorosulfonic according to the procedure described for 6-methoxy-2,3-dihydro-1H-indene-5-sulfonyl chloride I108 and used directly in the next step without purification.

l) 4-Bromo-2-methoxybenzenesulfonyl chloride I110

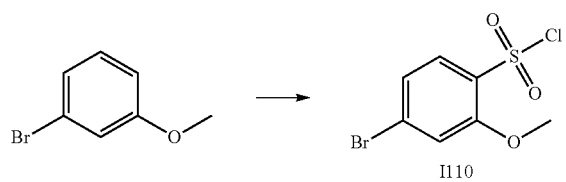

1-Bromo-3-methoxybenzene (15.0 g, 80 mmol) was added slowly to chlorosulfonic acid (16 mL) at −5° C. and the mixture was stirred at −5° C. for 5 min. The mixture was poured into ice-cold water (50 mL) and extracted with EtOAc (80 mL×2). The combined organic extracts were washed with water (150 mL×3), dried over anhydrous Na$_2$SO$_4$, filtered and concentrated under reduced pressure. The residue was purified by column chromatography (Pet. ether/EtOAc=50/1) to give the title compound (2.6 g, 17%) as yellow solid, which was used directly in the next step.

li) 2,6-Dimethoxybenzenesulfonyl chloride I111

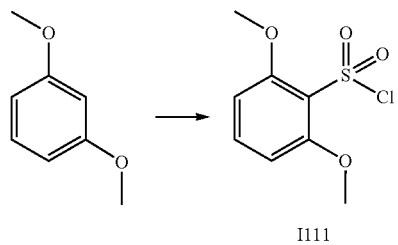

To a solution of 1,3-dimethoxybenzene (5.0 g, 36 mmol) and TMEDA (4.6 g, 39.8 mmol) in n-hexane (100 mL) at 0° C. under N$_2$ was added n-BuLi (2.5 M solution in hexanes, 16.0 mL, 39.8 mmol) dropwise while keeping the internal reaction temperature below 5° C. The mixture was stirred at 0° C. for 20 min then cooled to −78° C. and bubbled with SO$_2$ gas for 20 min. The mixture was then allowed to warm slowly to 10° C. and the resulting precipitate was collected by filtration and washed with dry diethyl ether. The solid was suspended in n-hexane (100 mL), cooled to 0° C. and a solution of SO₂Cl₂ (4.9 g, 36 mmol) in n-hexane (20 mL) was added dropwise while keeping the internal temperature below 3° C. The mixture was then stirred at 0° C. for 1 h and the solids were collected by filtration and washed with cold n-hexane. The solids were then partitioned between diethyl ether and water, the layers were separated and the aqueous layer was further extracted with diethyl ether. The combined organic extracts were dried over anhydrous Na₂SO₄, filtered and concentrated under reduced pressure to give the title compound (4.0 g, 47%) as a white solid. 1H NMR (400 MHz, CDCl₃) δ 7.54 (t, J=8.4 Hz, 1H), 6.66 (d, J=8.4 Hz, 2H), 3.97 (s, 6H).

lii) 5-Ethyl-2-methoxybenzenesulfonyl chloride I112

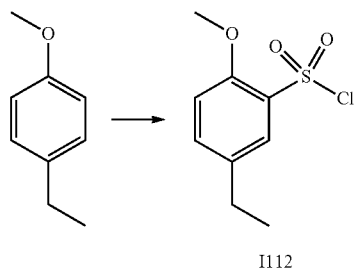

I112

1-Ethyl-4-methoxybenzene (5.0 g, 37 mmol) was added dropwise to chlorosulfonic acid (20 mL) at 0° C. and the mixture was stirred at RT for 2 h then poured onto ice and extracted with EtOAc (50 mL×3). The combined organic extracts were dried over anhydrous Na₂SO₄, filtered and concentrated under reduced pressure. The residue was purified by column chromatography (Pet. ether/EtOAc=100/1 to 30/1) to give the title compound (4.6 g, 53%) as a white solid. LCMS-D: $R_t$ 2.70 min; m/z 256.9 [M+Na]⁺.

liii) 2,4-Dimethoxy-[1,1ᴇbiphenyl]-3-sulfonyl chloride I114

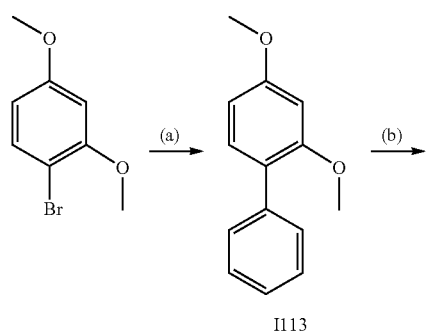

I113

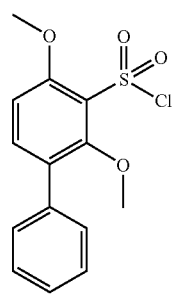

I114 a) 2,4-Dimethoxy-1,1ᴇbiphenyl I113

A suspension of 1-bromo-2,4-dimethoxybenzene (5.0 g, 23.0 mmol), phenylboronic acid (3.4 g, 27.6 mmol), Pd(PPh₃)₄ (1.3 g, 1.15 mmol) and potassium carbonate (7.3 g, 69.0 mmol) in 1,4-dioxane (30 mL) and water (6 mL) was heated at 90° C. under N₂ for 16 h. The mixture was filtered through a pad of Celite and washed with EtOAc. The filtrate was diluted with water and extracted with EtOAc (30 mL×3). The combined organic extracts were dried over Na₂SO₄, filtered and concentrated under reduced pressure. The residue was purified by column chromatography (Pet. ether/EtOAc=100/1 to 10/1) to give the title compound (2.8 g, 57%) as a yellow oil. LCMS-D: $R_t$ 2.46 min; m/z 215.0 [M+H]⁺.

b) 2,4-Dimethoxy-[1,1ᴇbiphenyl]-3-sulfonyl chloride I114

To a solution of 2,4-dimethoxy-1,1ᴇbiphenyl I113 (1.0 g, 4.70 mmol) and TMEDA (601 mg, 5.20 mmol) in n-hexane (40 mL) at 0° C. under N₂ was added n-BuLi (2.5 M solution in hexanes, 2.1 mL, 5.20 mmol) dropwise while keeping the internal reaction temperature below 5° C. The mixture was stirred at 0° C. for 20 min then cooled to −70° C. and bubbled with SO₂ gas for 20 min. The mixture was then allowed to warm slowly to 10° C. and the resulting precipitate was collected by filtration and washed with dry diethyl ether. The solid was suspended in n-hexane (40 mL), cooled to 0° C. and a solution of SO₂Cl₂ (634 mg, 4.7 mmol) in n-hexane (5 mL) was added dropwise while keeping the internal temperature below 3° C. The mixture was then stirred at 0° C. for 1 h and the solids were collected by filtration and washed with cold n-hexane. The solids were then partitioned between diethyl ether and water, the layers were separated and the aqueous layer was further extracted with diethyl ether. The combined organic extracts were dried over Na₂SO₄, filtered and concentrated under reduced pressure to give the title compound (590 mg, 40%) as a white solid. ¹H NMR (400 MHz, DMSO-d₆) δ 7.48-7.35 (m, 4H), 7.34-7.21 (m, 2H), 6.87 (m, 1H), 3.76 (s, 3H), 3.29 (s, 3H).

liv) 3,5-Dimethoxy-[1,1ᴇbiphenyl]-4-sulfonyl chloride I116

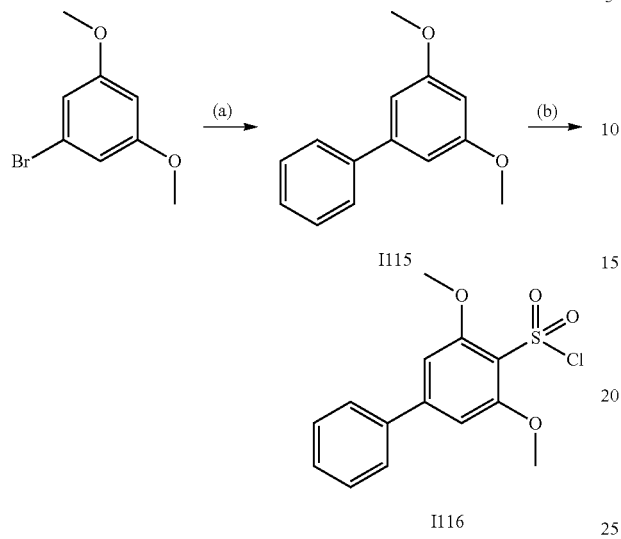

a) 3,5-Dimethoxy-1,1ᴇbiphenyl I115

A suspension of 1-bromo-3,5-dimethoxybenzene (5.0 g, 23.0 mmol), phenylboronic acid (2.8 g, 23.0 mmol), Pd(dppf)Cl$_2$ (0.57 g, 0.69 mmol) and potassium carbonate (4.8 g, 34.6 mmol) in 1,4-dioxane (80 mL) and water (20 mL) was heated at 90° C. under N$_2$ for 4 h. The mixture was diluted with water, extracted with EtOAc and the combined organic extracts were dried over Na$_2$SO$_4$, filtered and concentrated under reduced pressure. The residue was purified by column chromatography (Pet. ether/EtOAc=500/1 to 200/1 to 100/1) to give the title compound (5.2 g, 100%) as a white solid. LCMS-C: R$_t$ 2.47 min; m/z 215.0 [M+H]$^+$.

b) 3,5-Dimethoxy-[1,1ᴇbiphenyl]-4-sulfonyl chloride I116

Prepared from 3,5-dimethoxy-1,1ᴇbiphenyl I115 according to the procedure described for 2,4-dimethoxy-[1,1ᴇbiphenyl]-3-sulfonyl chloride I114. $^1$H NMR (400 MHz, CDCl$_3$) δ 7.62-7.55 (m, 2H), 7.54-7.44 (m, 3H), 6.81 (s, 2H), 4.04 (s, 6H).

lv) 4-Methoxy-6-((2,2,2-trifluoroethoxy)methyl) benzo[d]isoxazol-3-amine I118

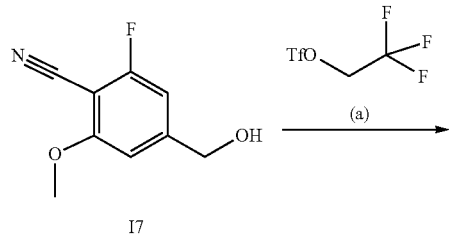

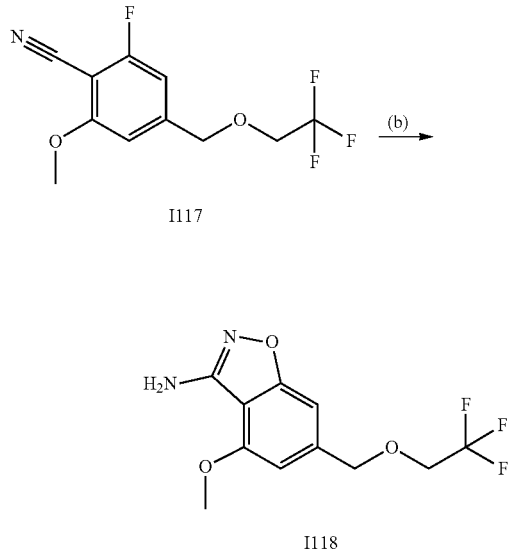

a) 2-Fluoro-6-methoxy-4-((2,2,2-trifluoroethoxy) methyl)benzonitrile I117

To a solution of 2-fluoro-4-(hydroxymethyl)-6-methoxybenzonitrile I7 (500 mg, 2.76 mmol) in dry THF (50 mL) at 0° C. under N$_2$ was added NaH (60% w/w dispersion in oil, 331 mg, 8.28 mmol) followed by 2,2,2-trifluoroethyl trifluoromethanesulfonate (1.9 g, 8.28 mmol) and the mixture was stirred at 0° C. for 1 h, then allowed to warm to RT and stirred overnight. The mixture was diluted with water and extracted with EtOAc. The organic extract was washed with brine, dried over Na$_2$SO$_4$, filtered and concentrated under reduced pressure. The reaction was repeated two times using 2-fluoro-4-(hydroxymethyl)-6-methoxybenzonitrile I7 (100 mg, 0.55 mmol) and the three batches were combined and purified by column chromatography (Pet. ether/EtOAc=5/1 to 2/1) to give the title compound (577 mg, 57%) as a white solid. LCMS-C: R$_t$ 2.43 min; m/z 263.9 [M+H]$^+$.

b) 4-Methoxy-6-((2,2,2-trifluoroethoxy)methyl) benzo[d]isoxazol-3-amine I118

A suspension of acetohydroxamic acid (86 mg, 1.14 mmol) and t-BuOK (128 mg, 1.14 mmol) in anhydrous DMF (10 mL) was stirred at RT for 1 h. 2-Fluoro-6-methoxy-4-((2,2,2-trifluoroethoxy)methyl)benzonitrile I117 (100 mg, 0.38 mmol) was then added and the mixture was stirred at RT overnight. The mixture was diluted with water and extracted with EtOAc. The organic extract was washed with brine, dried over Na$_2$SO$_4$, filtered and concentrated under reduced pressure. The reaction was scaled up accordingly using 2-fluoro-6-methoxy-4-((2,2,2-trifluoroethoxy)methyl)benzonitrile I117 (400 mg, 1.52 mmol) and the two batches were combined and purified by column chromatography (Pet. ether/EtOAc=20/1 to 5/1) to give the title product (350 mg, 67%) as a yellow solid. LCMS-C: R$_t$ 2.08 min; m/z 277.0 [M+H]$^+$. $^1$H NMR (400 MHz, DMSO-d$_6$) δ 6.96 (s, 1H), 6.68 (s, 1H), 5.94 (s, 2H), 4.74 (s, 2H), 4.13 (q, J=9.4 Hz, 2H), 3.90 (s, 3H).

lvi) 6-(Difluoromethoxy)-4-methoxybenzo[d]isoxazol-3-amine I121

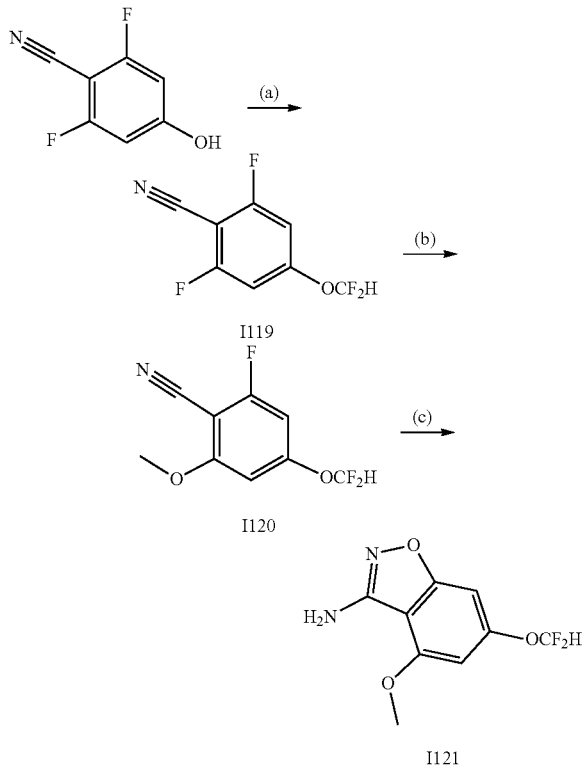

a) 4-(Difluoromethoxy)-2,6-difluorobenzonitrile I119

To a suspension of KOH (22.0 g, 392 mmol) in acetonitrile (30 mL) and water (30 mL) at −20° C. was added 2,6-difluoro-4-hydroxybenzonitrile (3.1 g, 20.0 mmol) portion-wise followed by diethyl (bromodifluoromethyl)phosphonate (10.0 g, 37.4 mmol) and the mixture was stirred at RT overnight. Water was added and the mixture was extracted with EtOAc (50 mL×3). The combined organic extracts were washed with brine, dried over $Na_2SO_4$, filtered and concentrated under reduced pressure to give the title compound (4.0 g, 97%) as a colorless oil. LCMS-C: $R_t$ 2.11 min; m/z 205.9 $[M+H]^+$.

b) 4-(Difluoromethoxy)-2-fluoro-6-methoxybenzonitrile I120

To a solution of 4-(difluoromethoxy)-2,6-difluorobenzonitrile I119 (2.52 g, 12.3 mmol) in dry THF (30 mL) was added NaOMe (1.32 g, 24.57 mmol) portion-wise and the mixture was warmed at 40° C. overnight. Water was added and the mixture was extracted with EtOAc (30 mL×3). The combined organic extracts were washed with brine, dried over $Na_2SO_4$, filtered and concentrated under reduced pressure. The residue was purified by column chromatography (Pet. ether/EtOAc=10/1 to 5/1) to give the title compound (663 mg, 25%) as a white solid. LCMS-C: $R_t$ 2.11 min; m/z 217.9 $[M+H]^+$.

c) 6-(Difluoromethoxy)-4-methoxybenzo[d]isoxazol-3-amine I121

A suspension of acetohydroxamic acid (680 mg, 9.15 mmol) and t-BuOK (1.03 g, 9.15 mmol) in anhydrous DMF (50 mL) was stirred at RT for 1 h. 5-(Difluoromethoxy)-1-fluoro-2-isocyano-3-methoxybenzene I120 (663 mg, 3.05 mmol) was then added and the mixture was stirred at RT overnight. The mixture was diluted with water and extracted with EtOAc (30 mL×3). The combined organic extracts were washed with brine, dried over $Na_2SO_4$, filtered and concentrated under reduced pressure. The residue was purified by column chromatography (Pet. ether/EtOAc=10/1 to 8/1) to give the title compound (186 mg, 26%) as light orange solid. LCMS-C: $R_t$ 1.14 min; m/z 231.0 $[M+H]^+$.

lviii) 5-Methyl-6-(pyridin-2-yl)benzo[d]isoxazol-3-amine I124

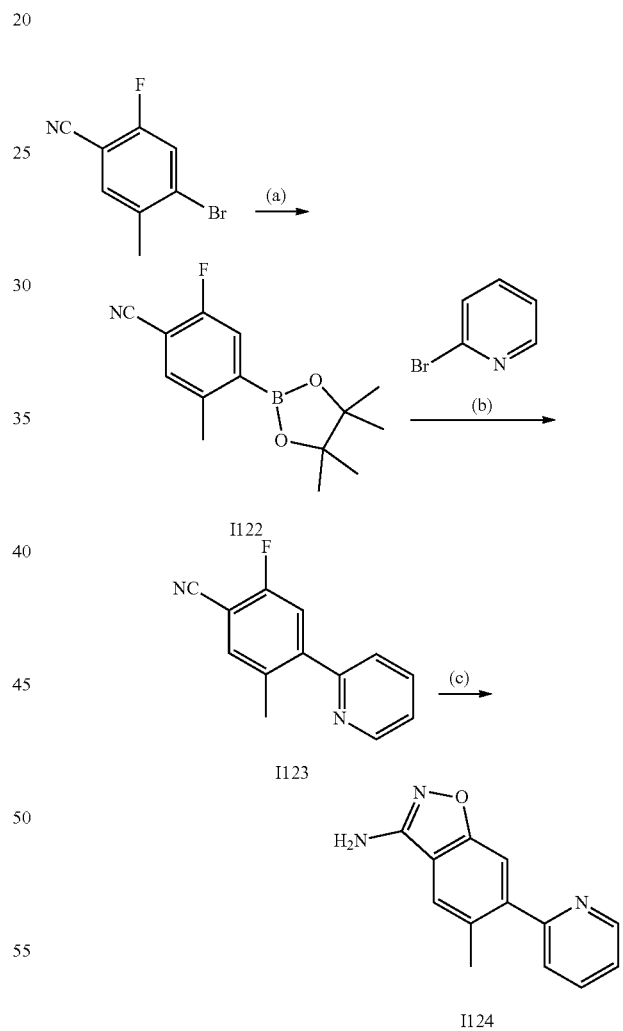

a) 2-Fluoro-5-methyl-4-(4,4,5,5-tetramethyl-1,3,2-dioxaborolan-2-yl)benzonitrile I122

A mixture of 4-bromo-2-fluoro-5-methylbenzonitrile (500 mg, 2.34 mmol), 4,4,4′,4′,5,5,5′,5′-octamethyl-2,2′-bi(1,3,2-dioxaborolane) (1.78 g, 2.34 mmol), potassium acetate (918 mg, 9.36 mmol) and $Pd(dppf)Cl_2$ (188 mg, 0.23 mmol)

in 1,4-dioxane (20 mL) was heated at reflux under $N_2$ for 3 h. The mixture was diluted with water, extracted with EtOAc (300 mL) and the organic layer was washed with water (50 mL×3), dried over $Na_2SO_4$, filtered and concentrated under reduced pressure to give the title compound (1.56 g, 88%), which was used in the next step without further purification. LCMS-C: $R_t$ 2.75 min; m/z 262.0 $[M+H]^+$.

b) 2-Fluoro-5-methyl-4-(pyridin-2-yl)benzonitrile I123

To a solution of 2-fluoro-5-methyl-4-(4,4,5,5-tetramethyl-1,3,2-dioxaborolan-2-yl)benzonitrile I122 (1.32 g, 5.1 mmol) and 2-bromopyridine (1.69 g, 7.65 mmol) in 1,4-dioxane (50 mL) and water (10 mL) under $N_2$ was added $Pd(PPh_3)_4$ (589 mg, 0.5 mmol) and $Na_2CO_3$ (2.16 g, 20.4 mmol) and the mixture was heated at 100° C. for 3 h. Water was added and the mixture was extracted with EtOAc. The combined organic extracts were washed with brine, dried over anhydrous $Na_2SO_4$, filtered and concentrated under reduced pressure. The residue was purified by column chromatography (Pet. ether/EtOAc=8/1 to 3/1) to give the title compound (440 mg, 88%) as a red solid. LCMS-C: $R_t$ 1.09 min; m/z 213.0 $[M+H]^+$.

c) 5-Methyl-6-(pyridin-2-yl)benzo[d]isoxazol-3-amine I124

A suspension of acetohydroxamic acid (255 mg, 3.39 mmol) and t-BuOK (381 mg, 3.39 mmol) in anhydrous DMF (30 mL) was stirred at 0° C. for 1 h. 2-Fluoro-5-methyl-4-(pyridin-2-yl)benzonitrile I123 (240 mg, 1.13 mmol) was then added and the mixture was allowed to warm to RT and stirred overnight. Water was added and the mixture was extracted with EtOAc (50 mL×3). The combined organic extracts were washed with brine, dried over $Na_2SO_4$, filtered and concentrated under reduced pressure. The residue was purified by column chromatography (Pet. ether/EtOAc=8/1 to 3/1) to give the title compound (180 mg, 73%) as a white solid. LCMS-C: $R_t$ 0.50 min; m/z 226.0 $[M+H]^+$.

lix) 7-Bromo-5-methylbenzo[d]isoxazol-3-amine I129

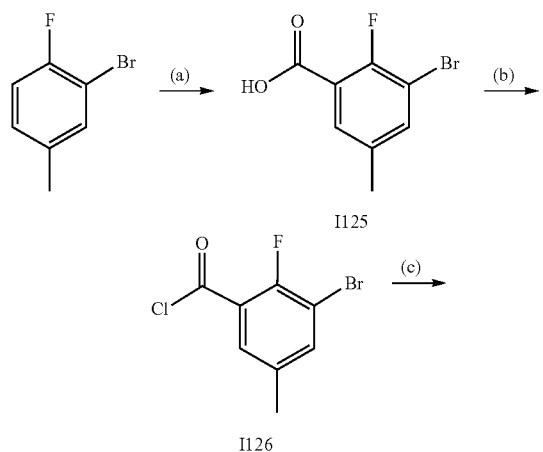

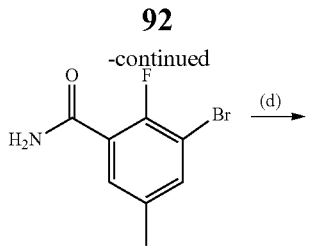

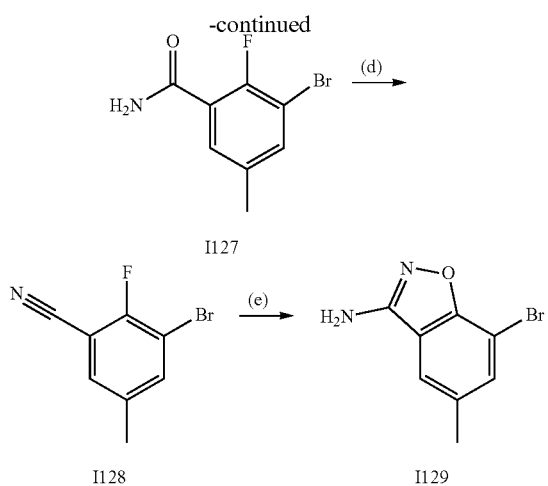

a) 3-Bromo-2-fluoro-5-methylbenzoic acid I125

To a solution of 2-bromo-1-fluoro-4-methylbenzene (10.0 g, 53 mmol) and diisopropylamine (5.9 g, 58 mmol) in anhydrous THF (200 mL) at −78° C. under $N_2$ was added n-BuLi (2.5 M solution in hexanes, 25.6 mL, 64.0 mmol) dropwise and the mixture stirred at −78° C. for 1 h. Excess solid $CO_2$ (dry ice) was added and stirring was continued at −78° C. for 3 h. The mixture was diluted with water (500 mL) and extracted with EtOAc (500 mL). The organic layer was washed with brine, dried over $Na_2SO_4$, filtered and concentrated under reduced pressure to give the title compound (12.3 g, 100%) as a brown solid, which was used in the next step without further purification. LCMS-C: $R_t$ 2.03 min; m/z 232.8 $[M+H]^+$.

b) 3-Bromo-2-fluoro-5-methylbenzoyl chloride I126

To a solution of 3-bromo-2-fluoro-5-methylbenzoic acid I125 (12.3 g, 53 mmol) and DMF (4 drops) in DCM (100 mL) at RT under $N_2$ was added oxalyl chloride (13.0 g, 106 mmol) dropwise and the mixture was stirred for 2 h. The mixture was concentrated under reduced pressure to give the title compound (14.0 g, 100%) as a brown solid, which was used in the next step without further purification.

c) 3-Bromo-2-fluoro-5-methylbenzamide I127

A solution of 3-bromo-2-fluoro-5-methylbenzoyl chloride I126 (14.0 g, 53 mmol) in DCM (100 mL) was added dropwise to a 30% aqueous ammonium hydroxide solution (100 mL) and the mixture was stirred for 2 h. The mixture was diluted with EtOAc (200 mL), washed with water (200 mL×3), brine and the organic layer was dried over $Na_2SO_4$, filtered and concentrated under reduced pressure to give the title compound (12.0 g, 97%) as a brown solid, which was used in the next step without further purification. LCMS-C: $R_t$ 1.01 min; m/z 231.9 $[M+H]^+$.

d) 3-bromo-2-fluoro-5-methylbenzonitrile I128

A solution of 3-bromo-2-fluoro-5-methylbenzamide I127 (10.0 g, 43.0 mmol) and thionyl chloride (15.4 g, 129 mmol) in DMF (100 mL) was heated at 100° C. for 3 h. The mixture was diluted with EtOAc (200 mL) and washed with water (400 mL×5), brine and the organic layer was dried over Na$_2$SO$_4$, filtered and concentrated under reduced pressure to give the title compound (5.0 g, 54%) as a brown solid, which was used in the next step without further purification. LCMS-C: R$_t$ 2.50 min; m/z 213.9 [M+H]$^+$.

e) 7-Bromo-5-methylbenzo[d]isoxazol-3-amine I129

A suspension of acetohydroxamic acid (5.27 g, 70.2 mmol) and t-BuOK (7.88 g, 70.2 mmol) in anhydrous DMF (200 mL) was stirred at 0° C. for 1 h. 3-Bromo-2-fluoro-5-methylbenzonitrile I128 (5.0 g, 23.4 mmol) was then added and the mixture was allowed to warm to RT and stirred overnight. The mixture was diluted with EtOAc (300 mL), washed with water (600 mL×4), brine and the organic layer was dried over Na$_2$SO$_4$, filtered and concentrated under reduced pressure. The residue was purified by column chromatography (Pet. ether/EtOAc=10/1) to give the title compound (2.8 g, 52%) as a yellow solid. LCMS-C: R$_t$ 0.50 min; m/z 226.9 [M+H]$^+$.

SYNTHESIS OF EXAMPLES

Examples 1-45 (Table A)

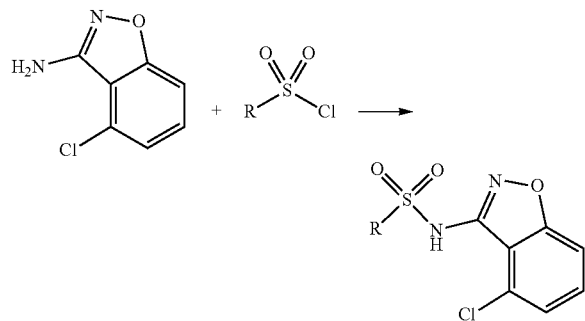

Method AA

LiHMDS (1 M in THF, 445 μL, 0.445 mmol) was added to a solution of 4-chlorobenzo[d]isoxazol-3-amine (50 mg, 0.297 mmol) in THF (3 mL) and stirred at room temperature for 10 minutes. The sulfonyl chloride (0.445 mmol) was added and the reaction was stirred for 16 hours at room temperature. The volatiles were reduced to approximately 1 mL before DCM (3 mL) and water (3 mL) were added and the mixture was stirred for 10 minutes. The mixture was passed through a phase separator, the organic fraction was then loaded onto a 1 g Si-amine cartridge (Biotage) and the cartridge was washed with MeOH (6 mL), the product was then eluted with a HCl solution (2 M, 1:1 methanol:1,4-dioxane 6 mL). The HCl washings were then evaporated in vacuo to yield the desired product.

Method AB

LiHMDS (1 M in THF, 445 μL, 0.445 mmol) was added to a solution of 4-chlorobenzo[d]isoxazol-3-amine (50 mg, 0.297 mmol) in THF (3 mL) and stirred at room temperature for 10 minutes. The sulfonyl chloride (0.445 mmol) was added and the reaction was stirred for 16 hours at room temperature. The volatiles were reduced to approximately 1 mL before DCM (3 mL) and water (3 mL) were added and the mixture was stirred for 10 minutes. The mixture was passed through a phase separator, the organic fraction was then loaded onto a 1 g Si-amine cartridge (Biotage) and the cartridge was washed with MeOH (6 mL), the product was then eluted with a HCl solution (2 M, 1:1 methanol:1,4-dioxane 6 mL). The HCl washings were then evaporated in vacuo to yield the crude product which was loaded onto silica gel and purified by silica gel column chromatography (Biotage Isolera, SiO$_2$ cartridge, 0-100% EtOAc in petroleum benzine 40-60° C.) to yield the desired product.

Method AC

LiHMDS (1 M in THF, 445 μL, 0.445 mmol) was added to a solution of 4-chlorobenzo[d]isoxazol-3-amine (50 mg, 0.297 mmol) in THF (3 mL) and stirred at room temperature for 10 minutes. The sulfonyl chloride (0.445 mmol) was added and the reaction stirred for 16 hours at room temperature. The volatiles were reduced to approximately 1 mL before DCM (3 mL) and water (3 mL) were added and the mixture was stirred for 10 minutes. The mixture was passed through a phase separator, the organic fraction was then loaded onto a 1 g Si-amine cartridge (Biotage) and the cartridge was washed with MeOH (10 mL), the product was then eluted with a methanolic HCl solution (~1.25 M, 10 mL). The HCl washings were then evaporated in vacuo to yield the desired product.

Method AD

A solution of 4-chlorobenzo[d]isoxazol-3-amine (50 mg, 0.298 mmol) and the sulfonyl chloride (2 eq., 0.595 mmol) in pyridine (1.5 mL) was irradiated in the microwave for 2 hours at 100° C. Upon cooling, the reaction mixture was loaded onto silica gel and purified using silica gel column chromatography (Biotage Isolera, 24 g SiO$_2$ cartridge, 0-100% EtOAc in petroleum benzine 40-60° C.) to yield the desired product.

Method E

A suspension of the sulfonyl chloride (2 eq., 1.19 mmol) and 4-chlorobenzo[d]isoxazol-3-amine (100 mg, 0.593 mmol) in pyridine (1.5 mL) was irradiated in the microwave for 2 hours at 100° C. Upon cooling, the mixture was loaded onto silica gel and purified using silica gel column chromatography (Biotage Isolera, 24 g SiO$_2$ cartridge, 0-100% EtOAc in petroleum benzine 40-60° C. then 0-40% MeOH in EtOAc) to yield the desired product.

Method AF

A suspension of the sulfonyl chloride (2 eq., 1.19 mmol) and 4-chlorobenzo[d]isoxazol-3-amine (100 mg, 0.593 mmol) in pyridine (1 mL) was irradiated in the microwave for 1 hour at 80° C. Upon cooling, the mixture was loaded onto silica gel and purified using silica gel column chromatography (Biotage Isolera, 24 g SiO$_2$ cartridge, 0-100% EtOAc in petroleum benzine 40-60° C.) to yield the desired product.

TABLE A

| | Structure | Name | Analytical data | Method |
|---|---|---|---|---|
| 1 | 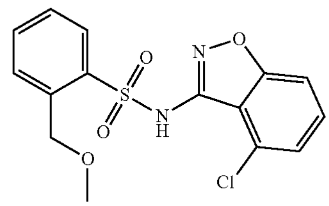 [SMILES: COCc1ccccc1S(=O)(=O)Nc1noc2cccc(Cl)c12] | N-(4-chlorobenzo[d]isoxazol-3-yl)-2-(methoxymethyl)benzenesulfonamide | LCMS-A: rt 6.538 min, m/z 352.1 [M − H]− | Method AB |
| 2 | 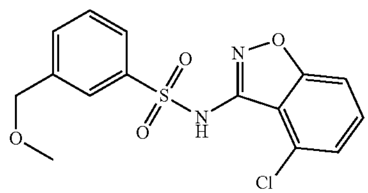 [SMILES: COCc1cccc(S(=O)(=O)Nc2noc3cccc(Cl)c23)c1] | N-(4-chlorobenzo[d]isoxazol-3-yl)-3-(methoxymethyl)benzenesulfonamide | LCMS-A: rt 6.374 min, m/z 353.1 [M + H]+ | Method AA |
| 3 | 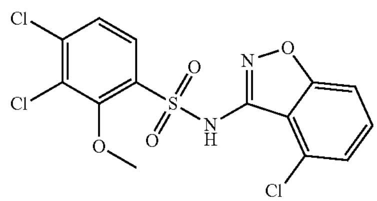 [SMILES: COc1c(S(=O)(=O)Nc2noc3cccc(Cl)c23)ccc(Cl)c1Cl] | 3,4-dichloro-N-(4-chlorobenzo[d]isoxazol-3-yl)-2-methoxybenzenesulfonamide | LCMS-A: rt 6.751 min, m/z 409.0 [M + H]+ | Method AA |
| 4 | 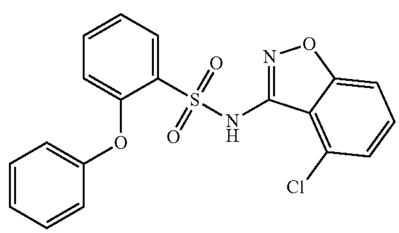 [SMILES: O=S(=O)(Nc1noc2cccc(Cl)c12)c1ccccc1Oc1ccccc1] | N-(4-chlorobenzo[d]isoxazol-3-yl)-2-phenoxybenzenesulfonamide | LCMS-A: rt 6.745 min, m/z 401.1 [M + H]+ | Method AA |
| 5 | 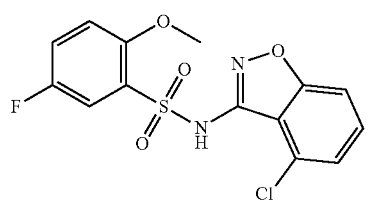 [SMILES: COc1ccc(F)cc1S(=O)(=O)Nc1noc2cccc(Cl)c12] | N-(4-chlorobenzo[d]isoxazol-3-yl)-5-fluoro-2-methoxybenzenesulfonamide | LCMS-A: rt 6.360 min, m/z 357.1 [M + H]+ | Method AA |
| 6 | 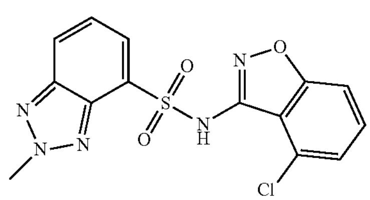 [SMILES: Cn1nc2cccc(S(=O)(=O)Nc3noc4cccc(Cl)c34)c2n1] | N-(4-chlorobenzo[d]isoxazol-3-yl)-2-methyl-2H-benzo[d][1,2,3]triazole-4-sulfonamide | LCMS-A: rt 6.200 min, m/z 364.1 [M + H]+ | Method AA |
| 7 | 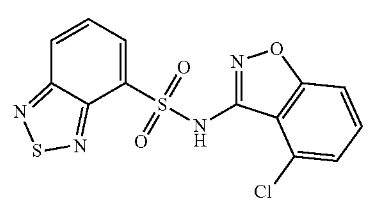 | N-(4-chlorobenzo[d]isoxazol-3-yl)benzo[c][1,2,5]thiadiazole-4-sulfonamide | LCMS-A: rt 6.346 min, m/z 367.0 [M + H]+ | Method AA |

TABLE A-continued

| | Structure | Name | Analytical data | Method |
|---|---|---|---|---|
| 8 | 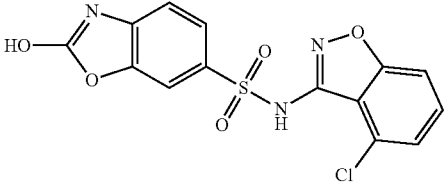 [SMILES: O=S(=O)(Nc1noc2cccc(Cl)c12)c1ccc2nc(O)oc2c1] | N-(4-chlorobenzo[d]isoxazol-3-yl)-2-hydroxybenzo[d]oxazole-6-sulfonamide | LCMS-A: rt 5.856 min, m/z 364.0 [M − H]⁻ | Method AA |
| 9 | 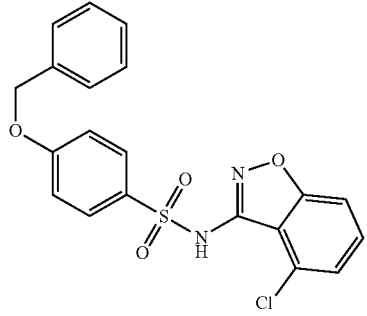 [SMILES: O=S(=O)(Nc1noc2cccc(Cl)c12)c1ccc(OCc2ccccc2)cc1] | 4-(benzyloxy)-N-(4-chlorobenzo[d]isoxazol-3-yl)benzenesulfonamide | LCMS-A: rt 6.764 min, m/z 415.1 [M + H]⁺ | Method AA |
| 10 | 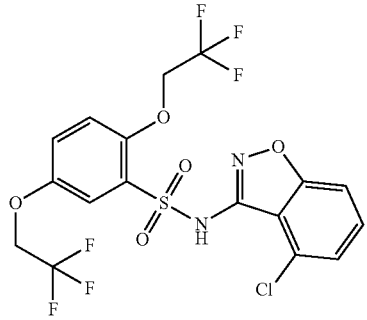 [SMILES: O=S(=O)(Nc1noc2cccc(Cl)c12)c1cc(OCC(F)(F)F)ccc1OCC(F)(F)F] | N-(4-chlorobenzo[d]isoxazol-3-yl)-2,5-bis(2,2,2-trifluoroethoxy)benzenesulfonamide | LCMS-A: rt 6.785 min, m/z 505.0 [M + H]⁺ | Method AA |
| 11 | 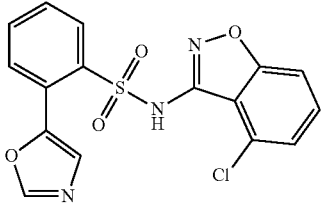 [SMILES: O=S(=O)(Nc1noc2cccc(Cl)c12)c1ccccc1-c1cnco1] | N-(4-chlorobenzo[d]isoxazol-3-yl)-2-(oxazol-5-yl)benzenesulfonamide | LCMS-A: rt 6.322 min, m/z 376.1 [M + H]⁺ | Method AA |
| 12 | 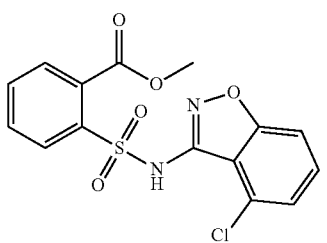 [SMILES: COC(=O)c1ccccc1S(=O)(=O)Nc1noc2cccc(Cl)c12] | methyl 2-(N-(4-chlorobenzo[d]isoxazol-3-yl)sulfamoyl)benzoate | LCMS-A: rt 6.484 min, m/z 367.1 [M + H]⁺ | Method AA |

TABLE A-continued

| | Structure | Name | Analytical data | Method |
|---|---|---|---|---|
| 13 | 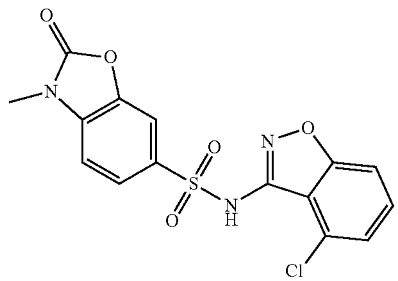 [SMILES: Cn1c(=O)oc2cc(S(=O)(=O)Nc3noc4cccc(Cl)c34)ccc21] | N-(4-chlorobenzo[d]isoxazol-3-yl)-3-methyl-2-oxo-2,3-dihydrobenzo[d]oxazole-6-sulfonamide | LCMS-A: rt 6.103 min, m/z 378.0 [M − H]⁻ | Method AA |
| 14 | 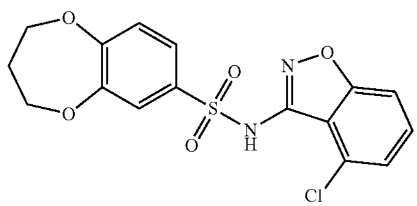 [SMILES: O=S(=O)(Nc1noc2cccc(Cl)c12)c1ccc2c(c1)OCCCO2] | N-(4-chlorobenzo[d]isoxazol-3-yl)-3,4-dihydro-2H-benzo[b][1,4]dioxepine-7-sulfonamide | LCMS-A: rt 6.362 min, m/z 381.1 [M + H]⁺ | Method AA |
| 15 | 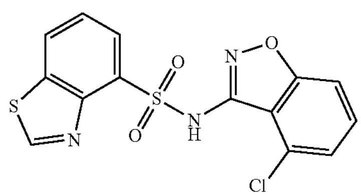 [SMILES: O=S(=O)(Nc1noc2cccc(Cl)c12)c1cccc2scnc12] | N-(4-chlorobenzo[d]isoxazol-3-yl)benzo[d]thiazole-4-sulfonamide | LCMS-A: rt 6.212 min, m/z 366.0 [M + H]⁺ | Method AA |
| 16 | 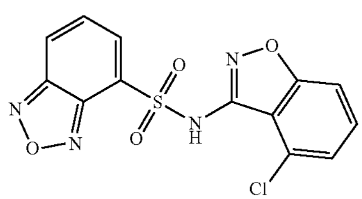 [SMILES: O=S(=O)(Nc1noc2cccc(Cl)c12)c1cccc2nonc12] | N-(4-chlorobenzo[d]isoxazol-3-yl)benzo[c][1,2,5]oxadiazole-4-sulfonamide | LCMS-A: rt 6.973 min, m/z 351.0 [M + H]⁺ | Method AA |
| 17 | 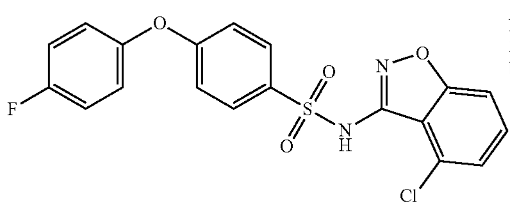 [SMILES: O=S(=O)(Nc1noc2cccc(Cl)c12)c1ccc(Oc2ccc(F)cc2)cc1] | N-(4-chlorobenzo[d]isoxazol-3-yl)-4-(4-fluorophenoxy)benzenesulfonamide | LCMS-A: rt 6.781 min, m/z 419.1 [M + H]⁺ | Method AA |
| 18 | 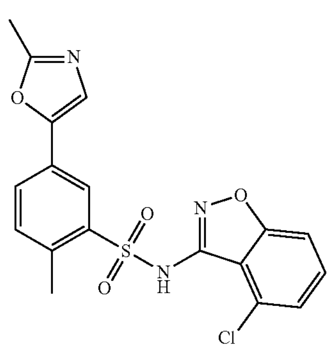 [SMILES: Cc1ncc(-c2ccc(C)c(S(=O)(=O)Nc3noc4cccc(Cl)c34)c2)o1] | N-(4-chlorobenzo[d]isoxazol-3-yl)-2-methyl-5-(2-methyloxazol-5-yl)benzenesulfonamide | LCMS-A: rt 6.410 min, m/z 404.1 [M + H]⁺ | Method AA |

TABLE A-continued

| | Structure | Name | Analytical data | Method |
|---|---|---|---|---|
| 19 | 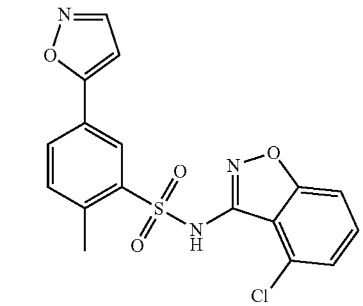 [SMILES: Cc1ccc(-c2ccno2)cc1S(=O)(=O)Nc1noc2cccc(Cl)c12] | N-(4-chlorobenzo[d]isoxazol-3-yl)-5-(isoxazol-5-yl)-2-methylbenzenesulfonamide | LCMS-A: rt 6.542 min, m/z 390.1 [M + H]$^+$ | Method AA |
| 20 | 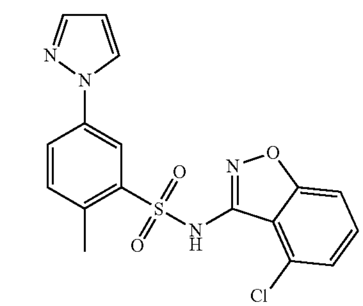 [SMILES: Cc1ccc(-n2cccn2)cc1S(=O)(=O)Nc1noc2cccc(Cl)c12] | N-(4-chlorobenzo[d]isoxazol-3-yl)-2-methyl-5-(1H-pyrazol-1-yl)benzenesulfonamide | LCMS-A: rt 6.493 min, m/z 389.1 [M + H]$^+$ | Method AA |
| 21 | 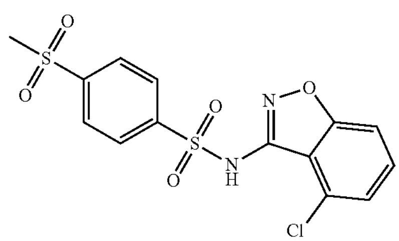 [SMILES: CS(=O)(=O)c1ccc(S(=O)(=O)Nc2noc3cccc(Cl)c23)cc1] | N-(4-chlorobenzo[d]isoxazol-3-yl)-4-(methylsulfonyl)benzenesulfonamide | LCMS-A: rt 6.317 min, m/z 385.0 [M − H]$^-$ | Method AA |
| 22 | 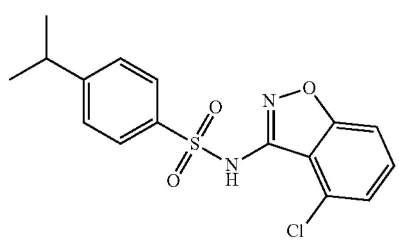 [SMILES: CC(C)c1ccc(S(=O)(=O)Nc2noc3cccc(Cl)c23)cc1] | N-(4-chlorobenzo[d]isoxazol-3-yl)-4-isopropylbenzenesulfonamide | LCMS-A: rt 6.745 min, m/z 351.1 [M + H]$^+$ | Method AA |
| 23 | 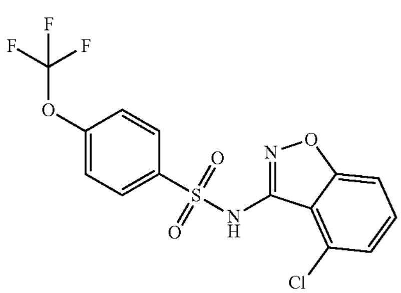 [SMILES: O=S(=O)(Nc1noc2cccc(Cl)c12)c1ccc(OC(F)(F)F)cc1] | N-(4-chlorobenzo[d]isoxazol-3-yl)-4-(trifluoromethoxy)benzenesulfonamide | LCMS-A: rt 6.763 min, m/z 391.0 [M − H]$^-$ | Method AA |

TABLE A-continued

| | Structure | Name | Analytical data | Method |
|---|---|---|---|---|
| 24 | 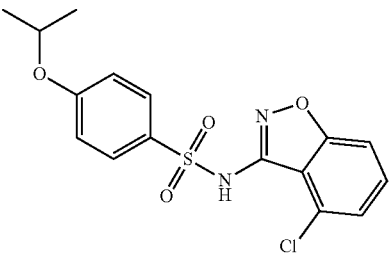 [SMILES: CC(C)Oc1ccc(S(=O)(=O)Nc2noc3cccc(Cl)c23)cc1] | N-(4-chlorobenzo[d]isoxazol-3-yl)-4-isopropoxybenzenesulfonamide | LCMS-A: rt 6.620 min, m/z 367.1 [M + H]$^+$ | Method AA |
| 25 | 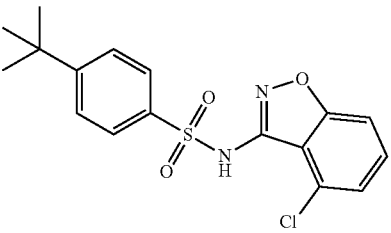 [SMILES: CC(C)(C)c1ccc(S(=O)(=O)Nc2noc3cccc(Cl)c23)cc1] | 4-(tert-butyl)-N-(4-chlorobenzo[d]isoxazol-3-yl)benzenesulfonamide | LCMS-A: rt 6.826 min, m/z 365.1 [M + H]$^+$ | Method AA |
| 26 | 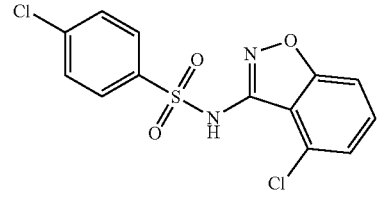 [SMILES: O=S(=O)(Nc1noc2cccc(Cl)c12)c1ccc(Cl)cc1] | 4-chloro-N-(4-chlorobenzo[d]isoxazol-3-yl)benzenesulfonamide | LCMS-A: rt 6.614 min, m/z 343.0, 345.0 [M + H]$^+$ | Method AA |
| 27 | 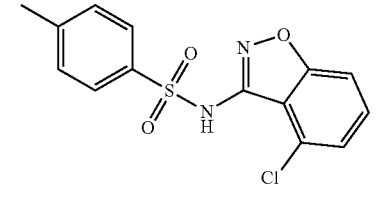 [SMILES: Cc1ccc(S(=O)(=O)Nc2noc3cccc(Cl)c23)cc1] | N-(4-chlorobenzo[d]isoxazol-3-yl)-4-methylbenzenesulfonamide | LCMS-A: rt 6.447 min, m/z 321.0 [M − H]$^-$ | Method AC |
| 28 | 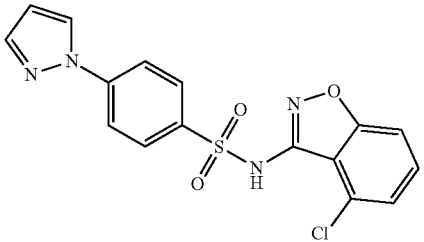 [SMILES: O=S(=O)(Nc1noc2cccc(Cl)c12)c1ccc(-n2cccn2)cc1] | N-(4-chlorobenzo[d]isoxazol-3-yl)-4-(1H-pyrazol-1-yl)benzenesulfonamide | LCMS-A: rt 6.321 min, m/z 375.1 [M + H]$^+$ | Method AC |
| 29 | 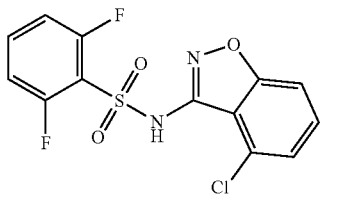 [SMILES: O=S(=O)(Nc1noc2cccc(Cl)c12)c1c(F)cccc1F] | N-(4-chlorobenzo[d]isoxazol-3-yl)-2,6-difluorobenzenesulfonamide | LCMS-A: rt 6.657 min, m/z 343.0 [M − H]$^-$ | Method AC |
| 30 | 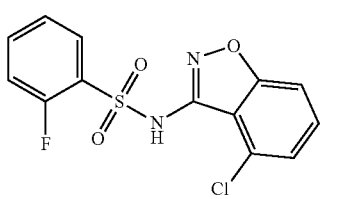 [SMILES: O=S(=O)(Nc1noc2cccc(Cl)c12)c1ccccc1F] | N-(4-chlorobenzo[d]isoxazol-3-yl)-2-fluorobenzenesulfonamide | LCMS-A: rt 6.389 min, m/z 327.0 [M + H]$^+$ | Method AC |

TABLE A-continued

| | Structure | Name | Analytical data | Method |
|---|---|---|---|---|
| 31 | 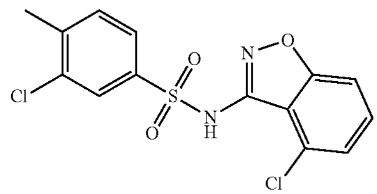 [SMILES: Cc1ccc(S(=O)(=O)Nc2noc3cccc(Cl)c23)cc1Cl] | 3-chloro-N-(4-chlorobenzo[d]isoxazol-3-yl)-4-methylbenzenesulfonamide | LCMS-A: rt 6.808 min, m/z 355.0, 357.0 [M − H]⁻ | Method AC |
| 32 | 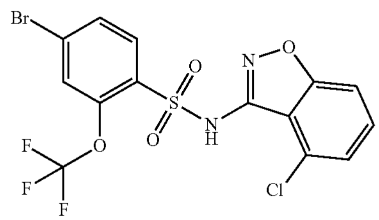 [SMILES: O=S(=O)(Nc1noc2cccc(Cl)c12)c1ccc(Br)cc1OC(F)(F)F] | 4-bromo-N-(4-chlorobenzo[d]isoxazol-3-yl)-2-(trifluoromethoxy)benzenesulfonamide | LCMS-A: rt 7.440 min, m/z 468.9, 470.9 [M − H]⁻ | Method AC |
| 33 | 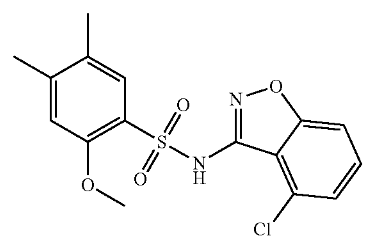 [SMILES: COc1cc(C)c(C)cc1S(=O)(=O)Nc1noc2cccc(Cl)c12] | N-(4-chlorobenzo[d]isoxazol-3-yl)-2-methoxy-4,5-dimethylbenzenesulfonamide | LCMS-A: rt 6.538 min, m/z 367.1 [M + H]⁺ | Method AC |
| 34 | 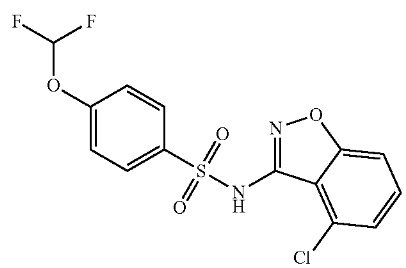 [SMILES: O=S(=O)(Nc1noc2cccc(Cl)c12)c1ccc(OC(F)F)cc1] | N-(4-chlorobenzo[d]isoxazol-3-yl)-4-(difluoromethoxy)benzenesulfonamide | LCMS-A: rt 6.487 min, m/z 373.0 [M − H]⁻ | Method AC |
| 35 | 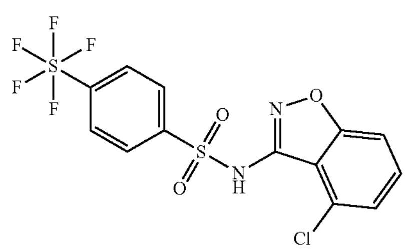 [SMILES: O=S(=O)(Nc1noc2cccc(Cl)c12)c1ccc(S(F)(F)(F)(F)F)cc1] | N-(4-chlorobenzo[d]isoxazol-3-yl)-4-(pentafluoro-$\lambda^6$-sulfanyl)benzenesulfonamide | LCMS-A: rt 7.021 min; m/z 435.0 [M + H]⁺ | Method AD |
| 36 | 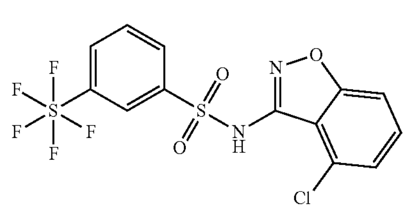 [SMILES: O=S(=O)(Nc1noc2cccc(Cl)c12)c1cccc(S(F)(F)(F)(F)F)c1] | N-(4-chlorobenzo[d]isoxazol-3-yl)-3-(pentafluoro-$\lambda^6$-sulfanyl)benzenesulfonamide | LCMS-A: rt 7.219 min; m/z 435.0 [M + H]⁺ | Method AD |

TABLE A-continued

| | Structure | Name | Analytical data | Method |
|---|---|---|---|---|
| 37 | 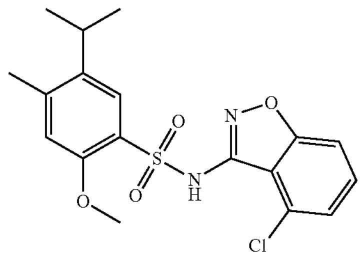 [SMILES: COc1cc(C)c(C(C)C)cc1S(=O)(=O)Nc1noc2cccc(Cl)c12] | N-(4-chlorobenzo[d]isoxazol-3-yl)-5-isopropyl-2-methoxy-4-methylbenzenesulfonamide | LCMS-A: rt 7.537 min; m/z 395.1 [M + H]+ | Method AD |
| 38 | 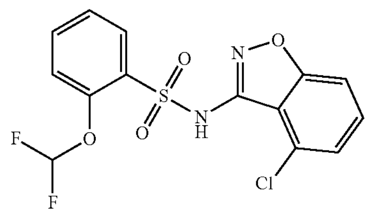 [SMILES: O=S(=O)(Nc1noc2cccc(Cl)c12)c1ccccc1OC(F)F] | N-(4-chlorobenzo[d]isoxazol-3-yl)-2-(difluoromethoxy)benzenesulfonamide | LCMS-A: rt 6.695 min; m/z 375.0 [M + H]+ | Method AD |
| 39 | 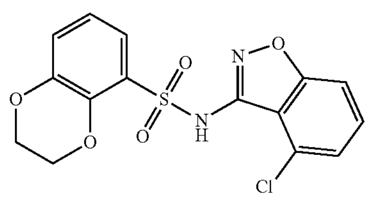 [SMILES: O=S(=O)(Nc1noc2cccc(Cl)c12)c1cccc2c1OCCO2] | N-(4-chlorobenzo[d]isoxazol-3-yl)-2,3-dihydrobenzo[b][1,4]dioxine-5-sulfonamide | LCMS-A: rt 6.620 min; m/z 367.0 [M + H]+ | Method AD |
| 40 | 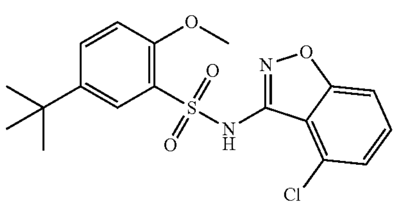 [SMILES: COc1ccc(C(C)(C)C)cc1S(=O)(=O)Nc1noc2cccc(Cl)c12] | 5-(tert-butyl)-N-(4-chlorobenzo[d]isoxazol-3-yl)-2-methoxybenzenesulfonamide | LCMS-B: rt 3.876 min, m/z 395.2 [M + H]+ | Method AD |
| 41 | 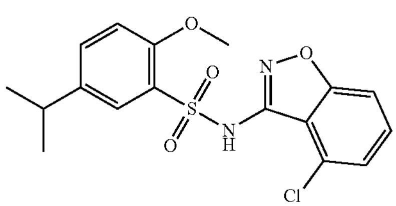 [SMILES: COc1ccc(C(C)C)cc1S(=O)(=O)Nc1noc2cccc(Cl)c12] | N-(4-chlorobenzo[d]isoxazol-3-yl)-5-isopropyl-2-methoxybenzenesulfonamide | LCMS-A: rt 6.684 min, m/z 381.1 [M + H]+ | Method AD |
| 42 | 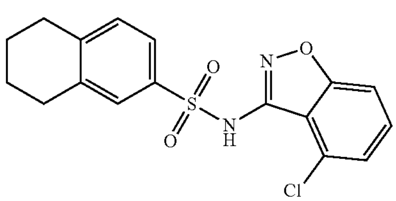 [SMILES: O=S(=O)(Nc1noc2cccc(Cl)c12)c1ccc2c(c1)CCCC2] | N-(4-chlorobenzo[d]isoxazol-3-yl)-5,6,7,8-tetrahydronaphthalene-2-sulfonamide | LCMS-B: rt 3.859 min, m/z 363.1 [M + H]+ | Method AD |

TABLE A-continued

| | Structure | Name | Analytical data | Method |
|---|---|---|---|---|
| 43 | 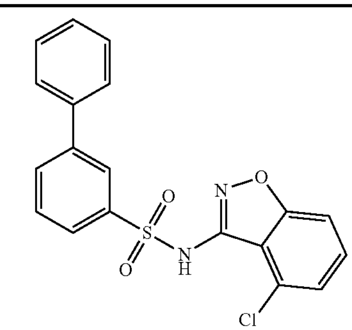 | N-(4-chlorobenzo[d]isoxazol-3-yl)-[1,1-biphenyl]-3-sulfonamide | LCMS-B: rt 3.823 min, m/z 385.1 [M + H]+ | Method AD |
| 44 | 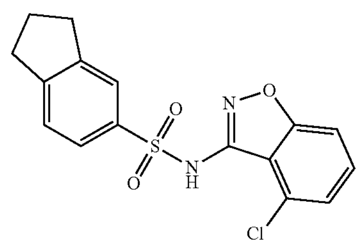 [SMILES: O=S(=O)(Nc1noc2cccc(Cl)c12)c1ccc2c(c1)CCC2] | N-(4-chlorobenzo[d]isoxazol-3-yl)-2,3-dihydro-1H-indene-5-sulfonamide | LCMS-B: rt 3.785 min, m/z 349.1 [M + H]+ | Method AE |
| 45 | 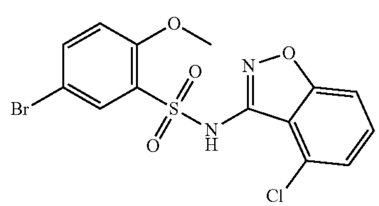 [SMILES: COc1ccc(Br)cc1S(=O)(=O)Nc1noc2cccc(Cl)c12] | 5-bromo-N-(4-chlorobenzo[d]isoxazol-3-yl)-2-methoxybenzenesulfonamide | LCMS-B: rt 3.752 min, m/z 417.0, 419.0 [M + H]+ | Method AF |

Examples 46-71 (Table D)

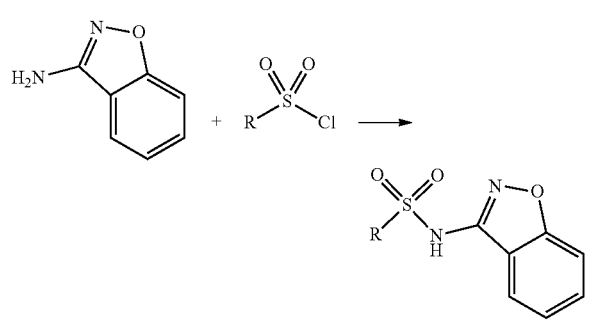

Method BA

A mixture of benzo[d]isoxazol-3-amine and a sulfonyl chloride in pyridine (1 mL) was stirred at room temperature for 16 hours. The reaction was concentrated and diluted with 5% aqueous HCl (1 mL) and sonicated for a minimum of 30 minutes. The resulting precipitate was collected by filtration or DCM extraction (2×1 mL) and purified using silica gel column chromatography (EtOAc/petroleum benzine 40-60° C. gradient) or preparative mass-directed HPLC to give the desired product. See Table B for reaction components and amounts used as well as purification conditions.

Method BB

A mixture of benzo[d]isoxazol-3-amine and a sulfonyl chloride in pyridine (0.5 mL) was stirred at room temperature for 64 hours. The reaction was concentrated and diluted with 5% aqueous HCl (1 mL) and sonicated for a minimum of 30 minutes. The resulting precipitate was collected by filtration and a portion of the crude material (50 mg or less) was purified by preparative mass-directed HPLC to give the desired product. See Table B for reaction components and amounts used.

Method BC

A mixture of benzo[d]isoxazol-3-amine and a sulfonyl chloride in pyridine (0.5 mL) was stirred at room temperature for 16 hours. The reaction was concentrated and diluted with 5% aqueous HCl (1 mL) and sonicated for a minimum of 30 minutes. The resulting precipitate was collected by filtration and a portion of the crude material (50 mg or less) was purified by mass directed preparative HPLC to give the desired product. See Table B for reaction components and amounts used.

TABLE B

| Product | Benzenesulfonyl chloride Structure and name | Mass (g) | Moles (mmol) | Benzo[d]isoxazol-3-amine Mass (g) | Moles (mmol) | Method/Work-up/Purification method |
|---|---|---|---|---|---|---|
| 46 | 2,5-dimethoxybenzenesulfonyl chloride | 0.143 | 0.602 | 0.030 | 0.23 | Method BA/Filtration/Column chromatography 0-45% gradient |
| 47 | 2-methoxy-5-methylbenzenesulfonyl chloride | 0.150 | 0.682 | 0.031 | 0.23 | Method BA/Filtration/Column chromatography 0-40% gradient |
| 48 | 5-(tert-butyl)-2-methoxybenzenesulfonyl chloride | 0.148 | 0.563 | 0.033 | 0.25 | Method BA/Filtration/Column chromatography 0-40% gradient |
| 49 | 5-isopropyl-2-methoxybenzenesulfonyl chloride | 0.140 | 0.561 | 0.031 | 0.23 | Method BA/Filtration/Column chromatography 0-40% gradient |
| 50 | methyl 3-(chlorosulfonyl)-4-methoxybenzoate | 0.142 | 0.535 | 0.030 | 0.22 | Method BA/Filtration/Column chromatography 0-100% gradient |
| 51 | 5-chloro-2-methoxy-4-methylbenzenesulfonyl chloride | 0.156 | 0.611 | 0.033 | 0.24 | Method BA/Filtration/Column chromatography 0-100% gradient |
| 52 | 3-ethylbenzenesulfonyl chloride | 0.036 | 0.180 | 0.028 | 0.21 | Method BA/DCM extraction/Column chromatography 0-50% gradient |

TABLE B-continued

| Product | Benzenesulfonyl chloride Structure and name | Mass (g) | Moles (mmol) | Benzo[d]isoxazol-3-amine Mass (g) | Moles (mmol) | Method/Work-up/Purification method |
|---|---|---|---|---|---|---|
| 53 | 4-ethylbenzenesulfonyl chloride | 0.074 | 0.360 | 0.032 | 0.24 | Method BA/DCM extraction/Column chromatography 0-50% gradient |
| 54 | 2-methoxy-5-(1H-pyrazol-1-yl) benzenesulfonyl chloride | 0.148 | 0.54 | 0.034 | 0.25 | Method BA/Filtration/Column chromatography 0-100% gradient |
| 55 | 5-(isoxazol-5-yl)-2-methoxybenzenesulfonyl chloride | 0.158 | 0.58 | 0.030 | 0.22 | Method BA/Filtration/Column chromatography 0-100% gradient |
| 56 | 2,5-diethylbenzenesulfonyl chloride | 0.063 | 0.27 | 0.030 | 0.22 | Method BA/DCM extraction/Column chromatography 0-100% gradient |
| 57 | 2-ethoxy-5-ethylbenzenesulfonyl chloride | 0.170 | 0.68 | 0.027 | 0.20 | Method BA/Filtration/Column chromatography 0-40% gradient. Triturated minimal acetone, product contained approx. 10% sulfonic acid by-product |
| 58 | 2-methoxybenzenesulfonyl chloride | 0.101 | 0.488 | 0.029 | 0.21 | Method BA/Filtration/mass-directed HPLC |

TABLE B-continued

| | Benzenesulfonyl chloride | | | Benzo[d]isoxazol-3-amine | | Method/Work- |
| --- | --- | --- | --- | --- | --- | --- |
| Product | Structure and name | Mass (g) | Moles (mmol) | Mass (g) | Moles (mmol) | up/Purification method |
| 59 | 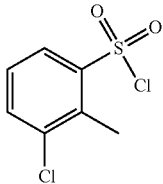<br>3-chloro-2-methylbenzenesulfonyl chloride | 0.105 | 0.466 | 0.033 | 0.25 | Method BB |
| 60 | 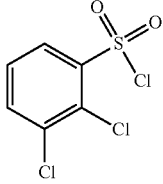 [SMILES: O=S(=O)(Cl)c1cccc(Cl)c1Cl]<br>2,3-dichlorobenzenesulfonyl chloride | 0.171 | 0.698 | 0.032 | 0.24 | Method BB |
| 61 | 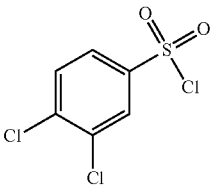 [SMILES: O=S(=O)(Cl)c1ccc(Cl)c(Cl)c1]<br>3,4-dichlorobenzenesulfonyl chloride | 0.100 | 0.640 | 0.032 | 0.24 | Method BB |
| 62 | 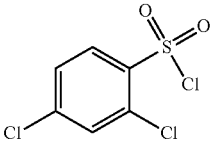 [SMILES: O=S(=O)(Cl)c1ccc(Cl)cc1Cl]<br>2,4-dichlorobenzenesulfonyl chloride | 0.170 | 0.694 | 0.031 | 0.23 | Method BB |
| 63 | 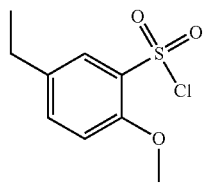<br>5-ethyl-2-methoxybenzenesulfonyl chloride | 0.107 | 0.454 | 0.033 | 0.25 | Method BC |
| 64 | 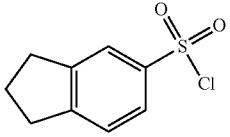 [SMILES: O=S(=O)(Cl)c1ccc2c(c1)CCC2]<br>2,3-dihydro-1H-indene-5-sulfonyl chloride | 0.120 | 0.553 | 0.029 | 0.22 | Method BC |

TABLE B-continued

| Product | Benzenesulfonyl chloride Structure and name | Mass (g) | Moles (mmol) | Benzo[d]isoxazol-3-amine Mass (g) | Moles (mmol) | Method/Work-up/Purification method |
|---|---|---|---|---|---|---|
| 65 | 5,6,7,8-tetrahydronaphthalene-2-sulfonyl chloride | 0.103 | 0.447 | 0.032 | 0.24 | Method BC |
| 66 | naphthalene-2-sulfonyl chloride | 0.111 | 0.490 | 0.030 | 0.23 | Method BC |
| 67 | 3-(5-methyl-1,3,4-oxediazol-2-yl)benzenesulfonyl chloride | 0.1025 | 0.396 | 0.033 | 0.25 | Method BC |
| 68 | 5-bromopyridine-2-sulfonyl chloride | 0.111 | 0.432 | 0.033 | 0.25 | Method BB |

Method CA

A mixture of benzo[d]isoxazol-3-amine and a sulfonyl chloride in pyridine (1 mL) was stirred at room temperature for 16 hours when a second portion of benzenesulfonyl chloride was added and stirred for an additional 64 hours. The reaction was concentrated and diluted with 5% aqueous HCl (1 mL) and sonicated for a minimum of 30 minutes. The resulting precipitate was collected by filtration and purified either by preparative mass-directed HPLC (up to 50 mg of crude material) or by silica gel column chromatography (0-40% EtOAc/petroleum benzine 40-60° C.) to give the desired product. See Table C for reaction components and amounts used as well as purification conditions.

TABLE C

| Product | Benzenesulfonyl chloride (added in 2 portions) Structure and name | Portion | Mass (g) | Moles (mmol) | Benzo[d]isoxazol-3-amine Mass (g) | Moles (mmol) | Method/Purification method |
|---|---|---|---|---|---|---|---|
| 69 | [1,1'-biphenyl]-4-sulfonyl chloride | $1^{st}$ $2^{nd}$ | 0.117 0.103 | 0.463 0.408 | 0.060 | 0.45 | Method CA/Mass-directed HPLC |

TABLE C-continued

| | Benzenesulfonyl chloride (added in 2 portions) | | | | Benzo[d] isoxazol-3-amine | | Method/ |
|---|---|---|---|---|---|---|---|
| Product | Structure and name | Portion | Mass (g) | Moles (mmol) | Mass (g) | Moles (mmol) | Purification method |
| 70 | [1,1'-biphenyl]-3-sulfonyl chloride | 1st 2nd | 0.092 0.088 | 0.36 0.35 | 0.052 | 0.39 | Method CA/column chromatography |
| 71 | 4-cyclohexylbenzenesulfonyl chloride | 1st 2nd | 0.103 0.101 | 0.398 0.390 | 0.065 | 0.48 | Method CA/column chromatography |

TABLE D

| | Structure | Name | Analytical |
|---|---|---|---|
| 46 | 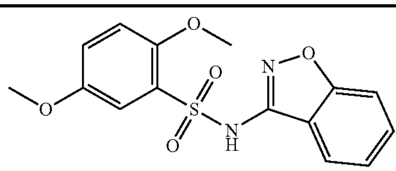 | N-(benzo[d]isoxazol-3-yl)-2,5-dimethoxybenzene-sulfonamide | LCMS-B: rt 3.560 min; m/z 335.1 [M + H]+; $^1$H NMR (400 MHz, acetone-$d_6$) δ 10.01 (br s, 1H), 8.14-8.06 (m, 1H), 7.64 (ddd, J = 8.3, 7.0, 1.2 Hz, 1H), 7.55 (dt, J = 8.5, 0.8 Hz, 1H), 7.43-7.36 (m, 2H), 7.17 (dd, J = 9.1, 2.9 Hz, 1H), 7.13 (d, J = 8.8 Hz, 1H), 3.82 (s, 3H), 3.77 (s, 3H) |
| 47 | 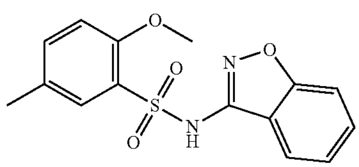 [SMILES: COc1ccc(C)cc1S(=O)(=O)Nc1noc2ccccc12] | N-(benzo[d]isoxazol-3-yl)-2-methoxy-5-methyl benzene sulfonamide | LCMS-B: rt 3.585 min; m/z 319.1 [M + H]+; $^1$H NMR (400 MHz, acetone-$d_6$) δ 9.94 (br s, 1H), 8.14-8.06 (m, 1H), 7.70-7.65 (m, 1H), 7.63 (ddd, J = 8.3, 7.0, 1.2 Hz, 1H), 7.54 (dt, J = 8.5, 0.8 Hz, 1H), 7.43-7.36 (m, 2H), 7.08 (d, J = 8.5 Hz, 1H), 3.84 (s, 3H), 2.28 (s, 3H). |
| 48 | 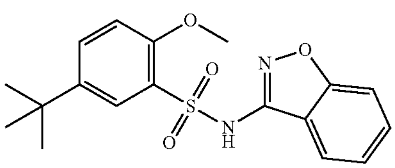 [SMILES: COc1ccc(C(C)(C)C)cc1S(=O)(=O)Nc1noc2ccccc12] | N-(benzo[d]isoxazol-3-yl)-5-(tert-butyl)-2-methoxy benzene sulfonamide | LCMS-B: rt 3.806 min; m/z 361.2 [M + H]+; $^1$H NMR (400 MHz, acetone-$d_6$) δ 10.00 (br s, 1H), 8.13-8.08 (m, 1H), 7.91 (d, J = 2.5 Hz, 1H), 7.66-7.60 (m, 2H), 7.55-7.51 (m, 1H), 7.38 (ddd, J = 8.0, 7.0, 0.9 Hz, 1H), 7.10 (d, J = 8.7 Hz, 1H), 3.83 (s, 3H), 1.26 (s, 9H) |
| 49 | 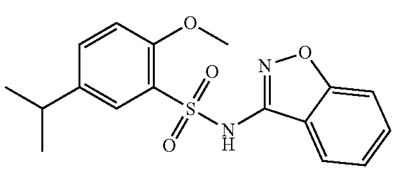 [SMILES: COc1ccc(C(C)C)cc1S(=O)(=O)Nc1noc2ccccc12] | N-(benzo[d]isoxazol-3-yl)-5-isopropyl-2-methoxy benzene sulfonamide | LCMS-B: rt 3.744 min; m/z 347.2 [M + H]+; $^1$H NMR (400 MHz, acetone-$d_6$) δ 9.97 (br s, 1H), 8.12-8.08 (m, 1H), 7.75 (d, J = 2.4 Hz, 1H), 7.63 (ddd, J = 8.4, 7.0, 1.2 Hz, 1H), 7.53 (dt, J = 8.5, 0.9 Hz, 1H), 7.48 (ddd, J = 8.5, 2.4, 0.6 Hz, 1H), 7.38 (ddd, J = 8.0, 7.0, 0.9 Hz, 1H), 7.10 (d, J = 8.6 Hz, 1H), 3.84 (s, 3H), 2.95-2.87 (m, 1H), 1.18 (d, J = 6.9 Hz, 6H) |
| 50 | 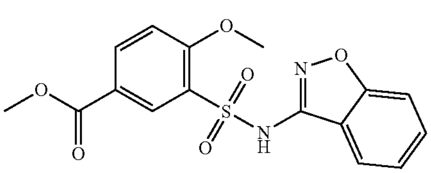 [SMILES: COC(=O)c1ccc(OC)c(S(=O)(=O)Nc2noc3ccccc23)c1] | methyl 3-(N-(benzo[d]isoxazol-3-yl)sulfamoyl)-4-methoxy benzoate | LCMS-A: rt 6.024 min; m/z 363.1 [M + H]+; $^1$H NMR (400 MHz, acetone-$d_6$) δ 10.24 (br s, 1H), 8.55 (d, J = 2.2 Hz, 1H), 8.24 (dd, J = 8.8, 2.2 Hz, 1H), 8.09 (dt, J = 8.1, 1.0 Hz, 1H), 7.66 (ddd, J = 8.4, 7.0, 1.2 Hz, 1H), 7.57 (dt, J = 8.5, 0.8 Hz, 1H), 7.42 (ddd, J = 8.0, 7.0, 0.9 Hz, 1H), 7.35 (d, J = 8.8 Hz, 1H), 4.00 (s, 3H), 3.89 (s, 3H) |

TABLE D-continued

| | Structure | Name | Analytical |
|---|---|---|---|
| 51 | 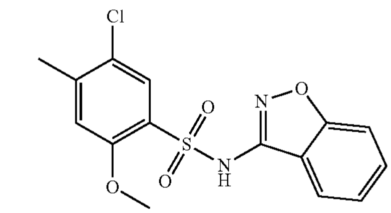 [SMILES: COc1cc(C)c(Cl)cc1S(=O)(=O)Nc1noc2ccccc12] | N-(benzo[d]isoxazol-3-yl)-5-chloro-2-methoxy-4-methylbenzenesulfonamide | LCMS-B: rt 3.738 min; m/z 353.1/355.1 [M + H]+; 1H NMR (400 MHz, acetone-$d_6$) δ 8.10-8.06 (m, 1H), 7.81 (s, 1H), 7.65 (ddd, J = 8.3, 7.0, 1.2 Hz, 1H), 7.58-7.54 (m, 1H), 7.43-7.37 (m, 1H), 7.21 (s, 1H), 3.87 (s, 3H), 2.38 (s, 3H) |
| 52 | 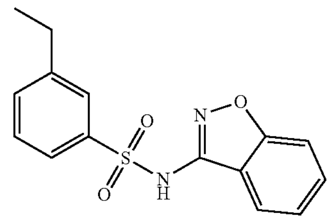 [SMILES: CCc1cccc(S(=O)(=O)Nc2noc3ccccc23)c1] | N-(benzo[d]isoxazol-3-yl)-3-ethylbenzenesulfonamide | LCMS-B: rt 3.707 min; m/z 303.2 [M + H]+; 1H NMR (400 MHz, acetone-$d_6$) δ 8.02-7.97 (m, 1H), 7.85-7.82 (m, 1H), 7.82-7.78 (m, 1H), 7.68-7.62 (m, 1H), 7.59-7.55 (m, 1H), 7.54-7.45 (m, 2H), 7.41-7.35 (m, 1H), 2.70 (q, J = 7.6 Hz, 2H)*, 1.19 (t, J = 7.6 Hz, 3H). * Partially overlapping with water peak |
| 53 | 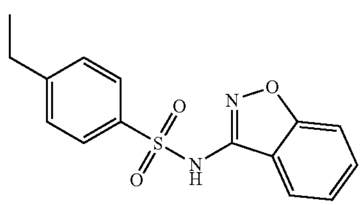 [SMILES: CCc1ccc(S(=O)(=O)Nc2noc3ccccc23)cc1] | N-(benzo[d]isoxazol-3-yl)-4-ethylbenzenesulfonamide | LCMS-B: rt 3.690 min; m/z 303.1 [M + H]+; 1H NMR (400 MHz, acetone-$d_6$) δ 8.03-7.98 (m, 1H), 7.93-7.89 (m, 2H), 7.65 (ddd, J = 8.2, 7.0, 1.1 Hz, 1H), 7.60-7.55 (m, 1H), 7.46-7.41 (m, 2H), 7.41-7.36 (m, 1H), 2.71 (q, J = 7.6 Hz, 2H)*, 1.21 (t, J = 7.6 Hz, 3H). * Partially overlapping with water peak |
| 54 | 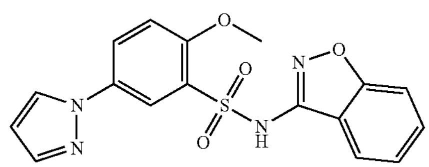 [SMILES: COc1ccc(-n2cccn2)cc1S(=O)(=O)Nc1noc2ccccc12] | N-(benzo[d]isoxazol-3-yl)-2-methoxy-5-(1H-pyrazol-1-yl)benzenesulfonamide | LCMS-B: rt 3.554 min; m/z 371.1 [M + H]+; 1H NMR (400 MHz, acetone-$d_6$) δ 8.36 (d, J = 2.8 Hz, 1H), 8.33-8.31 (m, 1H), 8.13-8.07 (m, 1H), 8.05 (dd, J = 9.0, 2.8 Hz, 1H), 7.68-7.61 (m, 2H), 7.56-7.52 (m, 1H), 7.40 (ddd, J = 8.0, 7.1, 0.8 Hz, 1H), 7.33 (d, J = 9.0 Hz, 1H), 6.49 (dd, J = 2.5, 1.7 Hz, 1H), 3.93 (s, 3H). |
| 55 | 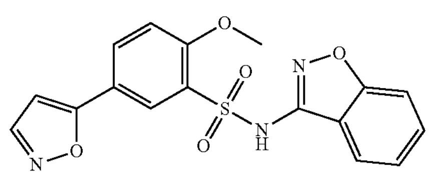 [SMILES: COc1ccc(-c2ccno2)cc1S(=O)(=O)Nc1noc2ccccc12] | N-(benzo[d]isoxazol-3-yl)-5-(isoxazol-5-yl)-2-methoxybenzenesulfonamide | LCMS-B: rt 3.516 min; m/z 372.1 [M + H]+; 1H NMR (400 MHz, acetone-$d_6$) δ 8.46 (d, J = 1.9 Hz, 1H), 8.36 (d, J = 2.3 Hz, 1H), 8.13-8.07 (m, 2H), 7.63 (ddd, J = 8.3, 7.1, 1.2 Hz, 1H), 7.56-7.52 (m, 1H), 7.43-7.36 (m, 2H), 6.90 (d, J = 1.9 Hz, 1H), 3.97 (s, 3H) |
| 56 | 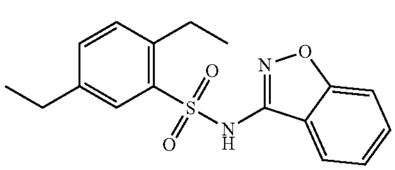 [SMILES: CCc1ccc(CC)c(S(=O)(=O)Nc2noc3ccccc23)c1] | N-(benzo[d]isoxazol-3-yl)-2,5-diethylbenzenesulfonamide | LCMS-B: rt 3.801 min; m/z 331.2 [M + H]+; 1H NMR (400 MHz, acetone-$d_6$) δ 8.01-7.97 (m, 1H), 7.95-7.92 (m, 1H), 7.66-7.61 (m, 1H), 7.57-7.52 (m, 1H), 7.45-7.41 (m, 1H), 7.40-7.34 (m, 2H), 3.10 (q, J = 7.5 Hz, 2H)*, 2.66 (q, J = 7.5 Hz, 2H)*, 1.22 (t, J = 7.5 Hz, 3H), 1.17 (t, J = 7.6 Hz, 3H). * Partially overlapping with water peak |
| 57 | 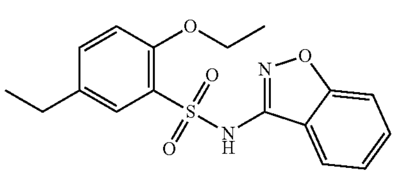 [SMILES: CCOc1ccc(CC)cc1S(=O)(=O)Nc1noc2ccccc12] | N-(benzo[d]isoxazol-3-yl)-2-ethoxy-5-ethylbenzenesulfonamide | LCMS-B: rt 3.763 min; m/z 347.2 [M + H]+; 1H NMR (400 MHz, acetone-$d_6$) δ 9.78 (br s, 1H), 8.13-8.08 (m, 1H), 7.74 (d, J = 2.3 Hz, 1H), 7.63 (ddd, J = 8.3, 7.0, 1.2 Hz, 1H), 7.56-7.52 (m, 1H), 7.44-7.41 (m, 1H), 7.38 (ddd, J = 8.0, 7.1, 0.8 Hz, 1H), 7.09 (d, J = 8.5 Hz, 1H), 4.16 (q, J = 7.0 Hz, 2H), 1.29 (t, J = 7.0 Hz, 3H), 1.16 (t, J = 7.6 Hz, 3H). NB approx. 10% sulfonic acid impurity |
| 58 | 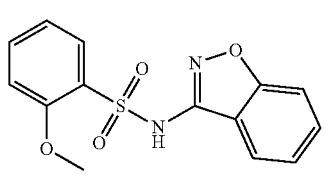 [SMILES: COc1ccccc1S(=O)(=O)Nc1noc2ccccc12] | N-(benzo[d]isoxazol-3-yl)-2-methoxybenzenesulfonamide | HPLC-MS: rt 5.11 min; m/z 305.2 [M + H]+; 1H NMR (400 MHz, acetone-$d_6$) δ 10.35-9.70 (br s, 1H), 8.12-8.08 (m, 1H), 7.90-7.86 (dd, J = 7.9, 1.7 Hz, 1H), 7.66-7.58 (m, 2H), 7.56-7.52 (m, 1H), 7.41-7.36 (ddd, J = 8.0, 7.0, 0.9 Hz, 1H), 7.21-7.17 (dd, J = 8.4, 0.8 Hz, 1H), 7.09-7.03 (m, 1H), 3.90-3.87 (s, 3H). |

TABLE D-continued

| | Structure | Name | Analytical |
|---|---|---|---|
| 59 | 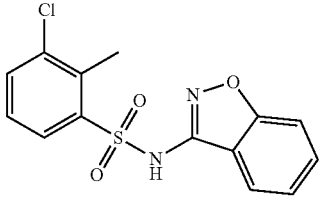 [SMILES: Cc1c(Cl)cccc1S(=O)(=O)Nc1noc2ccccc12] | N-(benzo[d]isoxazol-3-yl)-3-chloro-2-methylbenzene-sulfonamide | HPLC-MS: rt 6.38 min; m/z 323.22/325.17 [M + H]$^+$; $^1$H NMR (400 MHz, acetone-d$_6$) δ 11.10-10.01 (br s, 1H), 8.15-8.10 (dd, J = 8.0, 1.0 Hz, 1H), 8.02-7.97 (m, 1H), 7.74-7.69 (m, 1H), 7.68-7.62 (ddd, J = 8.3, 7.0, 1.2 Hz, 1H), 7.59-7.54 (m, 1H), 7.46-7.41 (m, 1H), 7.41-7.37 (ddd, J = 8.0, 7.0, 0.9 Hz, 1H), 2.77-2.74 (s, 3H) |
| 60 | 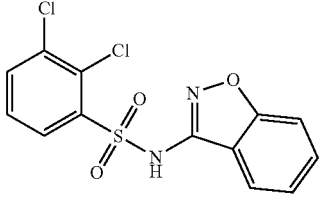 [SMILES: O=S(=O)(Nc1noc2ccccc12)c1cccc(Cl)c1Cl] | N-(benzo[d]isoxazol-3-yl)-2,3-dichlorobenzene-sulfonamide | HPLC-MS: rt 6.27 min; m/z 343.13/345.15/347.10 [M + H]$^+$; $^1$H NMR (400 MHz, acetone-d$_6$) δ 8.25-8.22 (dd, J = 8.0, 1.5 Hz, 1H), 8.06-8.02 (m, 1H), 7.93-7.90 (dd, J = 8.1, 1.5 Hz, 1H), 7.69-7.64 (ddd, J = 8.3, 7.0, 1.2 Hz, 1H), 7.64-7.59 (m, 1H), 7.59-7.55 (m, 1H), 7.44-7.38 (ddd, J = 8.0, 7.0, 0.9 Hz, 1H) |
| 61 | 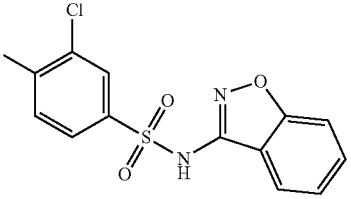 | N-(benzo[d]isoxazol-3-yl)-3,4-dichlorobenzene-sulfonamide | HPLC-MS: rt 6.62 min; m/z 343.13/345.15/347.10 [M + H]$^+$; $^1$H NMR (400 MHz, acetone-d$_6$) δ 8.19-8.17 (d, J = 2.1 Hz, 1H), 7.99-7.94 (m, 2H), 7.85-7.82 (d, J = 8.5 Hz, 1H), 7.70-7.65 (ddd, J = 8.2, 7.0, 1.2 Hz, 1H), 7.62-7.58 (m, 1H), 7.43-7.37 (ddd, J = 8.0, 7.0, 0.9 Hz, 1H) |
| 62 | 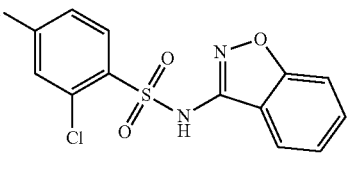 | N-(benzo[d]isoxazol-3-yl)-2,4-dichlorobenzene-sulfonamide | HPLC-MS: rt 6.42 min; m/z 343.13/345.15/347.16 [M + H]$^+$; $^1$H NMR (400 MHz, acetone-d$_6$) δ 8.26-8.22 (d, J = 8.6 Hz, 1H), 8.06-8.02 (m, 1H), 7.75-7.72 (d, J = 2.0 Hz, 1H), 7.70-7.63 (m, 2H), 7.60-7.56 (m, 1H), 7.44-7.38 (ddd, J = 8.0, 7.0, 0.9 Hz, 1H) |
| 63 | 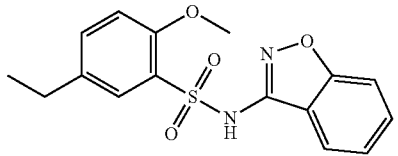 [SMILES: CCc1ccc(OC)c(S(=O)(=O)Nc2noc3ccccc23)c1] | N-(benzo[d]isoxazol-3-yl)-5-ethyl-2-methoxy benzene-sulfonamide | HPLC-MS: rt 5.39 min; m/z 333.2 [M + H]$^+$; $^1$H NMR (400 MHz, acetone-d$_6$) δ 10.19-9.73 (br s, 1H), 8.13-8.08 (ddd, J = 8.1, 1.0, 1.0 Hz, 1H), 7.73-7.69 (dd, J = 2.3 Hz, 1H), 7.66-7.60 (ddd, J = 8.3, 7.0, 1.2 Hz, 1H), 7.56-7.52 (ddd, J = 8.5, 0.8, 0.8 Hz, 1H), 7.47-7.42 (dd, J = 8.5, 2.3 Hz, 1H), 7.42-7.36 (ddd, J = 8.0, 7.0, 0.9 Hz, 1H), 7.13-7.07 (d, J = 8.5 Hz, 1H), 3.86-3.82 (s, 3H), 2.65-2.56 (q, J = 7.6 Hz, 2H), 1.18-1.12 (t, J = 7.6 Hz, 3H) |
| 64 | 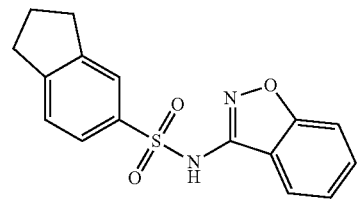 [SMILES: O=S(=O)(Nc1noc2ccccc12)c1ccc2c(c1)CCC2] | N-(benzo[d]isoxazol-3-yl)-2,3-dihydro-1H-indene-5-sulfonamide | HPLC-MS: rt 5.45 min; m/z 315.2 [M + H]$^+$; $^1$H NMR (400 MHz, acetone-d$_6$) δ 10.80-9.43 (br s, 1H), 8.04-7.99 (ddd, J = 8.1, 1.0, 1.0 Hz, 1H), 7.84-7.80 (m, 1H), 7.78-7.73 (m, 1H), 7.68-7.62 (ddd, J = 8.3, 7.0, 1.2 Hz, 1H), 7.60-7.54 (ddd, J = 8.5, 0.8, 0.8 Hz, 1H), 7.42-7.35 (m, 2H), 2.97-2.88 (t, J = 7.5 Hz, 4H), 2.12-2.05 (dd, J = 15.0, 7.6 Hz, 2H). |
| 65 | 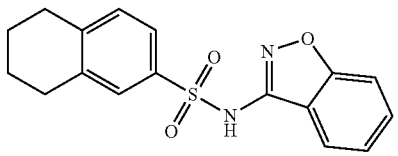 [SMILES: O=S(=O)(Nc1noc2ccccc12)c1ccc2c(c1)CCCC2] | N-(benzo[d]isoxazol-3-yl)-5,6,7,8-tetrahydro-naphthalene-2-sulfonamide | HPLC-MS: rt 5.57 min; m/z 329.5 [M + H]$^+$; $^1$H NMR (400 MHz, acetone-d$_6$) δ 10.44-9.90 (br s, 1H), 8.03-7.98 (ddd, J = 8.1, 1.1, 1.1 Hz, 1H), 7.69-7.63 (m, 3H), 7.60-7.55 (ddd, J = 8.5, 0.8, 0.8 Hz, 1H), 7.42-7.36 (ddd, J = 8.0, 7.0, 0.9 Hz, 1H), 7.25-7.20 (d, J = 8.3 Hz, 1H), 2.81-2.76 (m, 4H), 1.83-1.73 (m, 4H). |

TABLE D-continued

| | Structure | Name | Analytical |
|---|---|---|---|
| 66 | 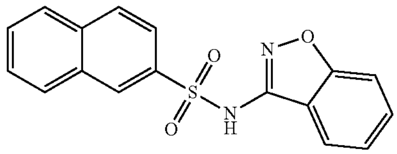 [SMILES: O=S(=O)(Nc1noc2ccccc12)c1ccc2ccccc2c1] | N-(benzo[d]isoxazol-3-yl)naphthalene-2-sulfonamide | HPLC-MS: rt 5.46 min; m/z 325.1 [M + H]+; 1H NMR (400 MHz, acetone-$d_6$) δ 11.03-9.58 (br s, 1H), 8.66-8.62 (m, 1 H), 8.15-8.11 (m, 1H), 8.11-8.08 (d, J = 8.9 Hz, 1H), 8.04-7.98 (m, 3H), 7.73-7.60 (m, 3H), 7.56-7.52 (ddd, J = 8.5, 0.8, 0.8 Hz, 1H), 7.41-7.35 (ddd, J = 8.0, 7.0, 0.9 Hz, 1H). |
| 67 | 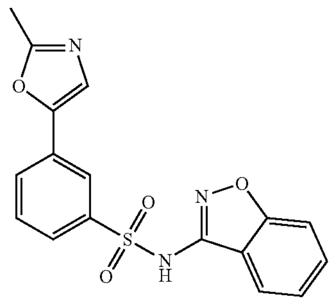 [SMILES: Cc1ncc(-c2cccc(S(=O)(=O)Nc3noc4ccccc34)c2)o1] | N-(benzo[d]isoxazol-3-yl)-3-(5-methyl-1,3,4-oxadiazol-2-yl)benzene sulfonamide | HPLC-MS: rt 5.00 min; m/z 357.7 [M + H]+; 1H NMR (400 MHz, acetone-$d_6$) δ 8.62-8.61 (dd, J = 1.6, 1.6 Hz, 1H), 8.29-8.26 (ddd, J = 7.8, 1.4, 1.4 Hz, 1H), 8.23-8.19 (ddd, J = 8.0, 1.8, 1.1 Hz, 1H), 7.99-7.96 (ddd, J = 8.1, 0.9, 0.9 Hz, 1H), 7.85-7.80 (dd, J = 7.9, 7.9 Hz, 1H), 7.67-7.63 (ddd, J = 8.3, 7.0, 1.2 Hz, 1H), 7.58-7.55 (m, 1H), 7.41-7.36 (ddd, J = 7.9, 7.0, 0.8 Hz, 1H), 2.63-2.60 (s, 3H). |
| 68 | 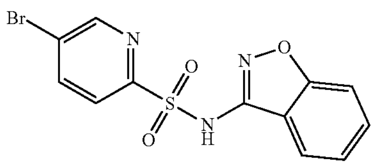 [SMILES: O=S(=O)(Nc1noc2ccccc12)c1ccc(Br)cn1] | N-(benzo[d]isoxazol--3-yl)-5-bromopyridine-2-sulfonamide | LCMS-B: rt 3.583 min; m/z 354/356 [M + H]+; 1H NMR (400 MHz, acetone-$d_6$) δ 11.19-10.23 (br s, 1H), 8.81-8.78 (dd, J = 2.3, 0.7 Hz, 1H), 8.38-8.34 (dd, J = 8.4, 2.3 Hz, 1H), 8.15-8.10 (dd, J = 8.4, 0.7 Hz, 1H), 8.06-8.01 (ddd, J = 8.1, 1.0, 1.0 Hz, 1H), 7.69-7.64 (ddd, J = 8.3, 7.0, 1.2 Hz, 1H), 7.59-7.56 (ddd, J = 8.5, 0.8, 0.8 Hz, 1H), 7.43-7.38 (ddd, J = 8.0, 7.0, 0.9 Hz, 1H). |
| 69 | 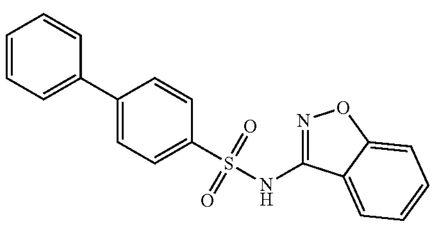 [SMILES: O=S(=O)(Nc1noc2ccccc12)c1ccc(-c2ccccc2)cc1] | N-(benzo[d]isoxazol-3-yl)-[1,1-biphenyl]-4-sulfonamide | HPLC-MS: rt 6.62 min; m/z 351.19 [M + H]+; 1H NMR (400 MHz, acetone-$d_6$) δ 8.11-8.06 (m, 2H), 8.04-8.00 (m, 2H), 7.90-7.85 (m, 2H), 7.76-7.68 (m, 2H), 7.66 (ddd, J = 8.3, 7.0, 1.2 Hz, 1H), 7.58 (dt, J = 8.5, 0.8 Hz, 1H), 7.53-7.47 (m, 2H), 7.46-7.37 (m, 2H). |
| 70 | 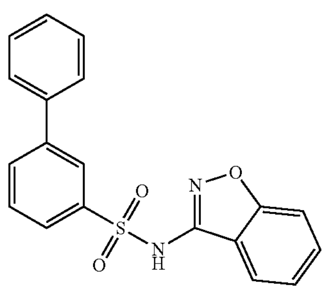 [SMILES: O=S(=O)(Nc1noc2ccccc12)c1cccc(-c2ccccc2)c1] | N-(benzo[d]isoxazol-3-yl)-[1,1-biphenyl]-3-sulfonamide | LCMS-B: rt 3.754 min; m/z 351.1 [M + H]+; 1H NMR (400 MHz, acetone-$d_6$) δ 8.29-8.26 (m, 1H), 8.03-8.00 (m, 1H), 7.97 (dddd, J = 9.0, 7.8, 1.8, 0.9 Hz, 2H), 7.72-7.63 (m, 4H), 7.58 (dt, J = 8.5, 0.8 Hz, 1H), 7.54-7.48 (m, 2H), 7.46-7.37 (m, 2H) |
| 71 | 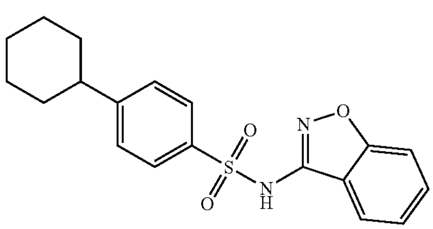 [SMILES: O=S(=O)(Nc1noc2ccccc12)c1ccc(C2CCCCC2)cc1] | N-(benzo[d]isoxazol-3-yl)-4-cyclohexyl benzene-sulfonamide | LCMS-B: rt 3.999 min m/z 357.1 [M + H]+; 1H NMR (400 MHz, acetone-$d_6$) δ 8.02-7.98 (m, 1H), 7.93-7.89 (m, 2H), 7.65 (ddd, J = 8.3, 7.0, 1.2 Hz, 1H), 7.59-7.55 (m, 1H), 7.47-7.43 (m, 2H), 7.38 (ddd, J = 8.0, 7.0, 0.9 Hz, 1H), 2.66-2.58 (m, 2H), 1.85-1.78 (m, 4H), 1.76-1.69 (m, 1H), 1.50-1.34 (m, 4H), 1.32-1.24 (m, 1H). |

Examples 72-88 (Table E)

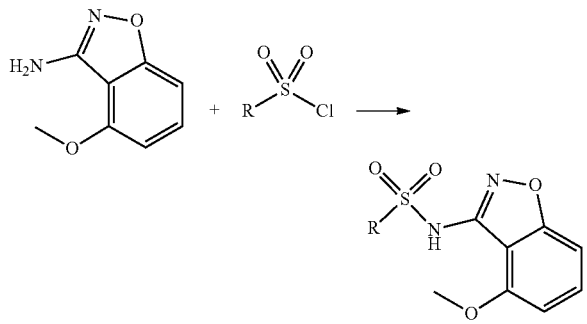

Method EA

NaH (60% in mineral oil, 49 mg, 1.22 mmol) was added to a solution of 4-methoxybenzo[d]isoxazol-3-amine (50 mg, 0.305 mmol) in THF (3.0 mL) and stirred at room temperature for 10 minutes. The sulfonyl chloride (1 eq., 0.305 mmol) was added and the reaction was stirred for 16 hours. The volatiles were reduced to approximately 1 mL before DCM (3 mL) and water (3 mL) were added and the mixture was stirred for 10 minutes. The mixture was passed through a phase separator, the organic fraction was then loaded onto a 1 g Si-amine cartridge (Biotage) and the cartridge was washed with MeOH (6 mL), the product was then eluted with a HCl solution (1.25 M in methanol, 6 mL). The HCl washings were evaporated in vacuo to yield the desired product.

Method EB

NaH (60% in mineral oil, 61 mg, 1.52 mmol) was added to a solution of 4-methoxybenzo[d]isoxazol-3-amine (50 mg, 0.305 mmol) in DMF (3.0 mL) and stirred at room temperature for 10 minutes. The sulfonyl chloride (1 eq., 0.305 mmol) was added and the reaction was stirred for 16 hours. The resultant mixture was loaded onto silica gel and purified by column chromatography (0-100% petroleum benzine 40-60° C. then 0-60% MeOH in EtOAc) to yield the desired product.

Method EC

NaH (60% in mineral oil, 22 mg, 0.914 mmol) was added to a solution of 4-methoxybenzo[d]isoxazol-3-amine (50 mg, 0.305 mmol) in DMF (5 mL) and stirred at room temperature for 10 minutes. The sulfonyl chloride (1 eq., 0.305 mmol) was added and the reaction was stirred for 16 hours. The resultant mixture was quenched with water (3 mL), stirred for 10 minutes at room temperature then loaded onto silica gel and purified by column chromatography (0-100% petroleum benzine 40-60° C. then 0-60% MeOH in EtOAc) to yield the desired product.

Method ED

NaH (60% in mineral oil, 5 or 10 eq.) was added to a solution of 4-methoxybenzo[d]isoxazol-3-amine (100 mg, 0.609 mmol) in THF (5.0 mL) and stirred at room temperature for 10 minutes. The sulfonyl chloride (1 eq., 0.609 mmol) was added and the reaction was stirred for 16 hours. The resultant mixture was loaded onto silica gel and purified by column chromatography (0-100% petroleum benzine 40-60° C. then 0-60% MeOH in EtOAc) to yield the desired product.

Method EF

NaH (60% in mineral oil, 122 mg, 3.05 mmol) was added to a solution of 4-methoxybenzo[d]isoxazol-3-amine (100 mg, 0.609 mmol) in THF (5.0 mL) and stirred at room temperature for 10 minutes. The sulfonyl chloride (1 eq., 0.609 mmol) was added and the reaction was stirred for 16 hours. The resultant mixture was loaded onto silica gel and purified by column chromatography (0-100% petroleum benzine 40-60° C. then 0-60% MeOH in EtOAc) and the isolated solid was sonicated in MeOH (1 mL) and collected by filtration to yield the desired product.

Method EG

NaH (60% in mineral oil, 122 mg, 3.05 mmol) was added to a solution of 4-methoxybenzo[d]isoxazol-3-amine (100 mg, 0.609 mmol) in THF (5.0 mL) and stirred at room temperature for 10 minutes. The sulfonyl chloride (1 eq., 0.609 mmol) was added and the reaction was stirred for 16 hours at room temperature. The volatiles were reduced to approximately 1 mL before DCM (3 mL) and water (3 mL) were cautiously added and stirred for 10 minutes. The mixture was passed through a phase separator, the organic fraction was then loaded onto a 1 g Si-amine cartridge (Biotage) and the cartridge was washed with MeOH (6 mL), the product was then eluted with a HCl solution (2 M, 1:1 methanol:1,4-dioxane, 6 mL). The HCl washings were then evaporated in vacuo to yield the desired product.

Method EH

A suspension of 4-methoxybenzo[d]isoxazol-3-amine (48 mg, 0.29 mmol) and NaH (60% in mineral oil, 0.117 mg, 2.93 mmol) in DMF (10 mL) was stirred at room temperature for 10 minutes before being cooled to −78° C. To this cooled mixture the sulfonyl chloride (1.5 eq., 0.439 mmol) was added and the mixture was stirred at −78° C. for 1 hour then warmed to room temperature and stirred for 16 hours. The reaction mixture was loaded onto silica gel and purified by column chromatography (Biotage Isolera, 24 g $SiO_2$ cartridge, 0-100% EtOAc in petroleum benzine 40-60° C. then 0-40% MeOH in EtOAc) to give a solid which was suspended in diethyl ether (25 mL) and sonicated for 5 minutes. The solid was collected by filtration and air dried to give the desired product.

Method EI

A mixture of 4-methoxybenzo[d]isoxazol-3-amine (0.035 g, 0.21 mmol) and a sulfonyl chloride (1.05 eq., 0.22 mmol) in pyridine (1 mL) was stirred at room temperature for 16 hours. The reaction was concentrated and diluted with 5% aqueous HCl (1 mL) and sonicated for a minimum of 30 minutes. Extraction with DCM (2×1 mL) and purification using silica gel column chromatography (0-100% EtOAc in petroleum benzine 40-60° C.) gave the desired product.

Method EJ

To a solution of 4-methoxybenzo[d]isoxazol-3-amine (1 eq.) in THF (3 mL) was added LiHMDS (1M in THF, 1.5 eq.). After 10 minutes of stirring, the sulfonyl chloride (1.5 eq.) was added and the reaction was left to stir for 17 hours, open to air. The THF was removed in vacuo, then DCM (3 mL) and water (3 mL) were added and stirred for 10 minutes. After separation of the layers, the organic fraction was loaded onto a 1 g Si-amine cartridge (Biotage). The cartridge was washed with MeOH (6 mL), then stripped with 1.25 M HCl in MeOH (6 mL). The HCl washings were then evaporated in vacuo to yield the desired product.

TABLE E

| | Structure and yield (where applicable) | Name | Analytical data | Method |
|---|---|---|---|---|
| 72 | 15 mg, 13% | 2-methoxy-N-(4-methoxybenzo[d]isoxazol-3-yl)-4,6-dimethylbenzene sulfonamide | LCMS-A: rt 6.474 min, m/z 363.1 [M + H]$^+$; $^1$H NMR (400 MHz, DMSO-d$_6$) δ 9.51-9.42 (s, 1H), 7.61-7.51 (t, J = 8.2 Hz, 1H), 7.19-7.10 (d, J = 8.4 Hz, 1H), 6.90-6.87 (s, 1H), 6.87-6.82 (d, J = 8.0 Hz, 1H), 6.80-6.74 (s, 1H), 3.99-3.93 (s, 3H), 3.84-3.78 (s, 3H), 2.58-2.54 (s, 3H), 2.31-2.25 (s, 3H). | Method EA |
| 73 | 10 mg, 8% | N-(4-methoxy benzo[d]isoxazol-3-yl)-3-methyl quinoline-8-sulfonamide | LCMS-A: rt 6.469 min, m/z = 370.1 [M + H]$^+$; $^1$H NMR (400 MHz, DMSO-d$_6$) δ = 8.94 (d, J = 2.1 Hz, 1H), 8.37 (dd, J = 7.3, 1.3 Hz, 1H), 8.33 (s, 1H), 8.25 (d, J = 8.0 Hz, 1H), 7.76 (t, J = 7.8 Hz, 1H), 7.50 (t, J = 8.2 Hz, 1H), 7.10 (d, J = 8.4 Hz, 1H), 6.79 (d, J = 8.1 Hz, 1H), 3.89 (s, 3H), 2.52 (s, 3H). | Method EB |
| 74 | 35 mg, 29% | 5-methoxy-N-(4-methoxybenzo[d]isoxazol-3-yl) quinoline-8-sulfonamide | LCMS-A: rt 6.461 min, m/z 386.1 [M + H]$^+$; $^1$H NMR (400 MHz, DMSO-d$_6$) δ 9.08 (dd, J = 4.3, 1.7 Hz, 1H), 8.62 (dd, J = 8.5, 1.7 Hz, 1H), 8.42 (d, J = 8.4 Hz, 1H), 7.67 (dd, J = 8.5, 4.3 Hz, 1H), 7.49 (t, J = 8.2 Hz, 1H), 7.22 (d, J = 8.5 Hz, 1H), 7.08 (d, J = 8.4 Hz, 1H), 6.78 (d, J = 8.0 Hz, 1H), 4.08 (s, 3H), 3.94 (s, 3H) | Method EC |
| 75 | 29 mg, 24% | 4-methoxy-N-(4-methoxybenzo[d]isoxazol-3-yl)quinoline-8-sulfonamide | LCMS-A: rt 6.253 min, m/z 386.1 [M + H]$^+$; $^1$H NMR (400 MHz, DMSO-d$_6$) δ 8.93 (d, J = 5.4 Hz, 1H), 8.52-8.37 (m, 2H), 7.75 (t, J = 7.8 Hz, 1H), 7.50 (t, J = 8.3 Hz, 1H), 7.22 (d, J = 5.3 Hz, 1H), 7.10 (d, J = 8.6 Hz, 1H), 6.80 (d, J = 8.1 Hz, 1H), 4.08 (s, 3H), 3.93 (s, 3H) | Method EC |
| 76 | 59 mg, 26% | 2,4-dimethoxy-N-(4-methoxybenzo[d]isoxazol-3-yl)benzene sulfonamide | LCMS-A: rt 6.188 min, m/z = 365.1 [M + H]$^+$; $^1$H NMR (400 MHz, DMSO-d$_6$) δ 9.76 (s, 1H), 7.80-7.73 (m, 1H), 7.55 (t, J = 8.2 Hz, 1H), 7.15 (d, J = 8.4 Hz, 1H), 6.84 (d, J = 8.0 Hz, 1H), 6.73-6.62 (m, 2H), 3.92 (s, 3H), 3.84 (s, 3H), 3.79 (s, 3H) | Method ED 10 eq. NaH used |
| 77 | 68 mg, 30% | N-(4-methoxy benzo[d]isoxazol-3-yl)-7-methyl quinoline-8-sulfonamide | LCMS-A: rt 6.419 min, m/z = 370.2 [M + H]$^+$ | Method EF |

TABLE E-continued

| | Structure and yield (where applicable) | Name | Analytical data | Method |
|---|---|---|---|---|
| 78 | 4 mg, 2% | N-(4-methoxy benzo[d]isoxazol-3-yl)-6-methyl quinoline-8-sulfonamide | LCMS-A: rt 6.332 min, m/z = 370.1 [M + H]$^+$ | Method ED 5 eq. NaH used |
| 79 | 15 mg, 7% | N-(4-methoxy benzo[d]isoxazol-3-yl)-4-methyl quinoline-8-sulfonamide | LCMS-A: rt 6.325 min, m/z = 370.1 [M + H]$^+$ | Method ED 5 eq. NaH used |
| 80 | 50 mg, 22% | N-(4-methoxy benzo[d]isoxazol-3-yl)-2-methyl quinoline-8-sulfonamide | LCMS-A: rt 6.349 min, m/z = 370.1 [M + H]$^+$ | Method ED 5 eq. NaH used |
| 81 | 38 mg, 18% | N-(4-methoxy benzo[d]isoxazol-3-yl)benzofuran-7-sulfonamide | LCMS-A: rt 6.225 min, m/z = 345.1 [M + H]$^+$ | Method EG |
| 82 | 44 mg, 20% | N-(4-methoxy benzo[d]isoxazol-3-yl)chromane-8-sulfonamide | LCMS-A: rt 6.282 min, m/z = 361.1 [M + H]$^+$ | Method EG |

TABLE E-continued

| | Structure and yield (where applicable) | Name | Analytical data | Method |
|---|---|---|---|---|
| 83 | 10 mg, 9% | N-(4-methoxy benzo[d]isoxazol-3-yl)quinoline-8-sulfonamide | LCMS-A: rt 6.198 min; m/z = 356.2 [M + H]+; 1H NMR (400 MHz, DMSO-d6) δ = 9.08 (dd, J = 4.3, 1.7 Hz, 1H), 8.57 (dd, J = 8.4, 1.6 Hz, 1H), 8.46 (dd, J = 7.4, 1.4 Hz, 1H), 8.36 (d, J = 8.0 Hz, 1H), 7.81 (t, J = 7.8 Hz, 1H), 7.73 (dd, J = 8.3, 4.3 Hz, 1H), 7.50 (t, J = 8.2 Hz, 1H), 7.10 (d, J = 8.4 Hz, 1H), 6.78 (d, J = 8.0 Hz, 1H), 3.88 (s, 3H) | Method EH |
| 84 | 9 mg, 12% | N-(4-methoxy benzo[d]isoxazol-3-yl)-5,6,7,8-tetrahydro-naphthalene-2-sulfonamide | LCMS-A: rt 6.955 min; m/z 359.1 [M + H]+; 1H NMR (400 MHz, acetone-d6) δ 7.81-7.76 (m, 2H), 7.55-7.49 (m, 1H), 7.23 (d, J = 7.7 Hz, 1H), 7.06 (d, J = 8.4 Hz, 1H), 6.79 (d, J = 8.0 Hz, 1H), 3.96 (s, 3H), 1.81-1.77 (m, 4H). NB: solvent obscuring aliphatic 2 × CH2 | Method EI |
| 85 | | 2,4,6-trimethoxy-N-(4-methoxy benzo[d]isoxazol-3-yl)benzene sulfonamide | LCMS-A: rt 6.095 min; m/z 395.1 [M + H]+ | Method EJ |
| 86 | | 2,6-dimethoxy-N-(4-methoxy benzo[d]isoxazol-3-yl)benzene sulfonamide | LCMS-A: rt 5.991 min; m/z 365.1 [M + H]+ | Method EJ |
| 87 | | 2-methoxy-N-(4-methoxybenzo[d]isoxazol-3-yl)-5-(trifluoromethyl)benzene-sulfonamide | LCMS-B: rt 3.379 min; m/z 403.0 [M + H]+ | Method EJ |
| 88 | | N-(4-methoxy benzo[d]isoxazol-3-yl)-2-(methoxy methyl)benzene-sulfonamide | LCMS-B: rt 3.344 min; m/z 349.1 [M + H]+ | Method EJ |

Examples 89-147 (Table F)

Method FA

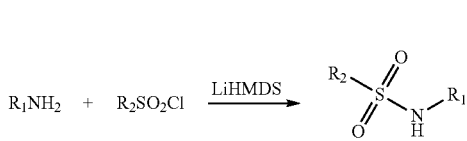

To a solution of the amine (0.5 mmol, 1.0 eq.) in anhydrous THF (10 mL) at −78° C. under $N_2$ was added LiHMDS (1 M solution in THF, 3 eq.) dropwise and the mixture was stirred at −78° C. for 30 min. A solution of the sulfonyl chloride (1.5 eq.) in anhydrous THF (2.0 mL) was then added dropwise and the mixture was allowed to warm to RT and stirred overnight. Water was added and the mixture was extracted with EtOAc. The combined organic extracts were washed with brine, dried over anhydrous $Na_2SO_4$, filtered and concentrated under reduced pressure. The residue was purified by column chromatography or prep. TLC to give the title compound. Variations to above conditions have been noted in Table F.

Method FB

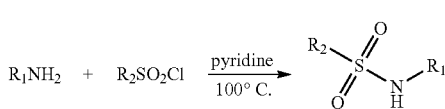

To a solution of the amine (0.3 mmol, 1.0 eq.) in pyridine (5 mL) under $N_2$ was added the sulfonyl chloride (2.0 eq.) and the mixture was heated at 100° C. overnight. The reaction was quenched with 1 M aq. HCl, water was then added and the mixture was extracted with EtOAc. The combined organic extracts were washed with brine, anhydrous $Na_2SO_4$, filtered and concentrated under reduced pressure. The residue was purified by column chromatography or prep. TLC to give the title compound. Variations to above conditions have been noted in Table F.

Method FC

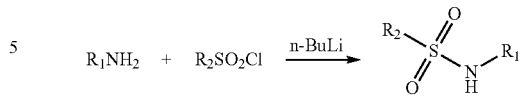

To a solution of the amine (0.5 mmol, 1.0 eq.) in anhydrous THF (10 mL) at −20° C. under $N_2$ was added n-BuLi (2.5 M in hexanes, 1.5 eq.) dropwise and the mixture was stirred at −20° C. for 1 h. A solution of the sulfonyl chloride (1.5 eq.) in anhydrous THF (2.0 mL) was then added dropwise and the mixture was allowed to warm to RT and stirred overnight. Water was added and the mixture was extracted with EtOAc. The combined organic extracts were washed with brine, dried over anhydrous $Na_2SO_4$, filtered and concentrated under reduced pressure. The residue was purified prep. TLC (DCM/MeOH=20/1) to give the title compound.

Method FD

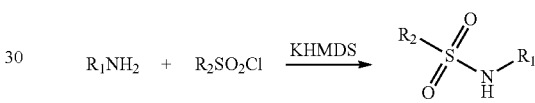

To a solution of the amine (0.5 mmol, 1.0 eq.) in anhydrous THF (10 mL) at −78° C. under $N_2$ was added KHMDS (1 M solution in THF, equivalents specified in Table F) dropwise and the mixture was stirred at −78° C. or 0° C. for 30 min to 1 h (specified in Table F). A solution of the sulfonyl chloride (equivalents specified in Table F) in anhydrous THF (2.0 mL) was then added dropwise and the mixture was allowed to warm to RT and stirred overnight. Water was added and the mixture was extracted with EtOAc. The combined organic extracts were washed with brine, dried over anhydrous $Na_2SO_4$, filtered and concentrated under reduced pressure. The residue was purified by column chromatography or prep. TLC to give the title compound.

TABLE F

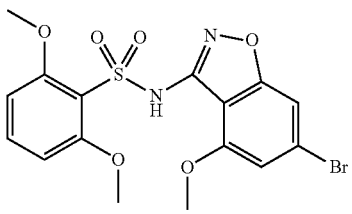 [SMILES: COc1cccc(OC)c1S(=O)(=O)Nc1noc2cc(Br)cc(OC)c12]

| | Name and structure | Analytical | Intermediates (if applicable) | Method | Notes |
|---|---|---|---|---|---|
| 89 | N-(6-Bromo-4-methoxybenzo[d]isoxazol-3-yl)-2,6-dimethoxybenzenesulfonamide | LCMS-C: $R_t$ 2.18 min, m/z 442.9 $[M + H]^+$; $^1H$ NMR (400 MHz, DMSO-$d_6$) δ 9.80 (s, 1H), 7.54-7.48 (m, 2H), 7.05 (s, 1H), 6.78 (d, J = 8.4 Hz, 2H), 3.92 (s, 3H), 3.76 (s, 6H). | 2,6-Dimethoxybenzenesulfonyl chloride I111 6-Bromo-4-methoxybenzo[d]isoxazol-3-amine I22 | FA | 4 eq. LiHMDS used. Prep. TLC (DCM/MeOH = 100/1) |

TABLE F-continued

| | Name and structure | Analytical | Intermediates (if applicable) | Method | Notes |
|---|---|---|---|---|---|
| 90 | 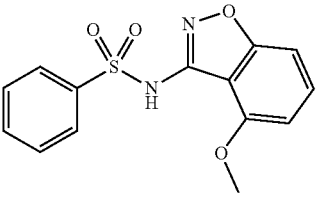 [SMILES: COc1cccc2onc(NS(=O)(=O)c3ccccc3)c12]<br>N-(4-Methoxybenzo[d]isoxazol-3-yl)benzenesulfonamide | LCMS-C: $R_t$ 1.97 min, m/z 304.9 [M + H]$^+$; $^1$H NMR (400 MHz, CDCl$_3$) δ 8.21 (d, J = 7.2 Hz, 2H), 7.82 (s, 1H), 7.61-7.54 (m, 3H), 7.43 (t, J = 8.0 Hz, 1H), 7.02 (d, J = 8.0 Hz, 1H), 6.59 (d, J = 7.6 Hz, 1H), 3.91 (s, 3H). | | FA | Stirred 2 h before adding sulfonyl chloride. Prep. TLC (DCM/ MeOH = 100/1) |
| 91 | 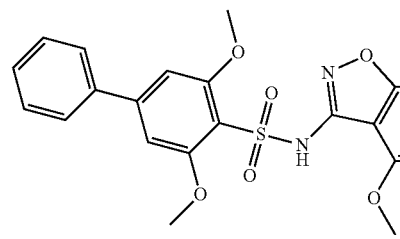<br>3,5-Dimethoxy-N-(4-methoxy-6-(methoxymethyl)benzo[d]isoxazol-3-yl)-[1,1-biphenyl]-4-sulfonamide | LCMS-C: $R_t$ 2.33 min, m/z 485.0 [M + H]$^+$; $^1$H NMR (400 MHz, CDCl$_3$) δ 8.26 (s, 1H), 7.52 (d, J = 6.8 Hz, 2H), 7.46-7.42 (m, 3H), 6.98 (s, 1H), 6.73 (s, 2H), 6.65 (s, 1H), 4.51 (s, 2H), 4.04 (s, 3H), 3.94 (s, 6H), 3.41 (s, 3H). | 3,5-Dimethoxy-[1,1-biphenyl]-4-sulfonyl chloride I116 4-Methoxy-6-(methoxymethyl)benzo[d]isoxazol-3-amine I9 | FA | 5 eq. LiHMDS used, stirred 2 h before adding sulfonyl chloride. Column chromatography (Pet. ether/ EtOAc = 2/1) |
| 92 | 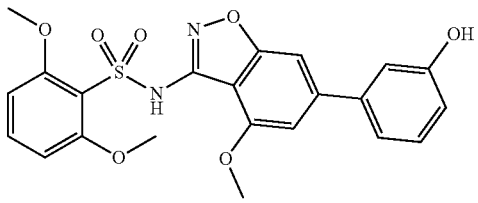 [SMILES: COc1cccc(OC)c1S(=O)(=O)Nc1noc2cc(-c3cccc(O)c3)cc(OC)c12]<br>N-(6-(3-Hydroxyphenyl)-4-methoxybenzo[d]isoxazol-3-yl)-2,6-dimethoxybenzenesulfonamide | LCMS-C: $R_t$ 2.19 min, m/z 457.0 [M + H]$^+$; $^1$H NMR (400 MHz, DMSO-d$_6$) δ 9.64 (s, 1H), 9.62 (s, 1H), 7.53 (t, J = 8.8 Hz, 1H), 7.35 (s, 1H), 7.30 (t, J = 8.0 Hz, 1H), 7.19 (d, J = 7.6 Hz, 1H), 7.12 (s, 1H), 7.01 (s, 1H), 6.85-6.78 (m, 3H), 4.01 (s, 3H), 3.79 (s, 6H). | 2,6-Dimethoxy benzenesulfonyl chloride I111 3-(3-Amino-4-methoxybenzo[d]isoxazol-6-yl)phenol I19 | FA | 8 eq. LiHMDS used, stirred 1 h before adding sulfonyl chloride. Prep. TLC (DCM/ MeOH = 30/1) |
| 93 | 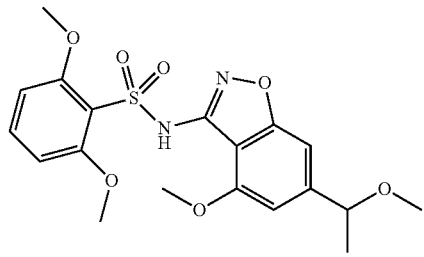 [SMILES: COc1cccc(OC)c1S(=O)(=O)Nc1noc2cc(C(C)OC)cc(OC)c12]<br>2,6-Dimethoxy-N-(4-methoxy-6-(1-methoxyethyl)benzo[d]isoxazol-3-yl)benzenesulfonamide | LCMS-C: $R_t$ 1.94 min, m/z 423.0 [M + H]$^+$; $^1$H NMR (400 MHz, DMSO-d$_6$) δ 9.56 (s, 1H), 7.51 (t, J = 8.4 Hz, 1H), 7.08 (s, 1H), 6.80 (d, J = 8.4 Hz, 2H), 6.78 (s, 1H), 4.45 (q, J = 6.4 Hz, 1H), 3.92 (s, 3H), 3.78 (s, 6H), 3.17 (s, 3H), 1.37 (d, J = 6.4 Hz, 3H). | 2,6-Dimethoxy benzenesulfonyl chloride I111 4-Methoxy-6-(1-methoxyethyl)benzo[d]isoxazol-3-amine I15 | FA | Stirred 2 h before adding sulfonyl chloride. Prep. TLC (DCM/ MeOH = 75/1) |

TABLE F-continued

| | Name and structure | Analytical | Intermediates (if applicable) | Method | Notes |
|---|---|---|---|---|---|
| 94 | 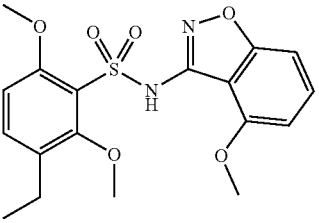 [SMILES: CCc1ccc(OC)c(S(=O)(=O)Nc2noc3cccc(OC)c23)c1OC]<br>3-Ethyl-2,6-dimethoxy-N-(4-methoxybenzo[d]isoxazol-3-yl)benzenesulfonamide | LCMS-C: $R_t$ 2.31 min, m/z 393.0 [M + H]$^+$; $^1$H NMR (400 MHz, DMSO-$d_6$) δ 9.57 (s, 1H), 7.57 (t, J = 8.0 Hz, 1H), 7.46 (d, J = 8.8 Hz, 1H), 7.16 (d, J = 8.8 Hz, 1H), 6.93 (d, J = 8.8 Hz, 1H), 6.85 (d, J = 8.0 Hz, 1H), 3.92 (s, 3H), 3.78 (s, 3H), 3.75 (s, 3H), 2.60 (q, J = 7.2 Hz, 2H), 1.15 (t, J = 7.2 Hz, 3H). | 3-Ethyl-2,6-dimethoxybenzenesulfonyl chloride I106 | FA | Stirred 3 h before adding sulfonyl chloride. Prep. TLC (DCM/MeOH = 75/1) |
| 95 | 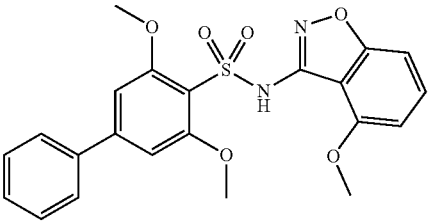 [SMILES: COc1cc(-c2ccccc2)cc(OC)c1S(=O)(=O)Nc1noc2cccc(OC)c12]<br>3,5-Dimethoxy-N-(4-methoxybenzo[d]isoxazol-3-yl)-[1,1-biphenyl]-4-sulfonamide | LCMS-C: $R_t$ 2.34 min, m/z 441.0 [M + H]$^+$; $^1$H NMR (400 MHz, DMSO-$d_6$) δ 9.60 (s, 1H), 7.79 (d, J = 6.8 Hz, 2H), 7.58-7.44 (m, 4H), 7.17 (d, J = 8.0 Hz, 1H), 6.99 (s, 2H), 6.87 (d, J = 7.6 Hz, 1H), 3.95 (s, 3H), 3.88 (s, 6H). | 3,5-Dimethoxy-[1,1-biphenyl]-4-sulfonyl chloride I116 | FA | 3.3 eq. LiHMDS used, stirred at −70° C. for 3 h before adding 1.8 eq. sulfonyl chloride. Purification: Precipitated from DCM with Pet. ether |
| 96 | 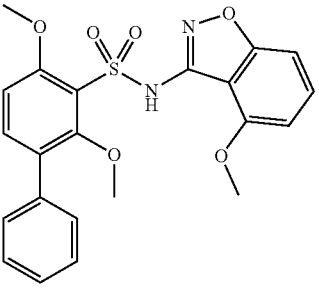 [SMILES: COc1ccc(-c2ccccc2)c(OC)c1S(=O)(=O)Nc1noc2cccc(OC)c12]<br>2,4-Dimethoxy-N-(4-methoxybenzo[d]isoxazol-3-yl)-[1,1-biphenyl]-3-sulfonamide | LCMS-C: $R_t$ 2.42 min, m/z 441.0 [M + H]$^+$; $^1$H NMR (400 MHz, DMSO-$d_6$) δ 9.84 (s, 1H), 7.59-7.54 (m, 2H), 7.48-7.42 (m, 4H), 7.39-7.35 (m, 1H), 7.18 (d, J = 8.0 Hz, 1H), 7.07 (d, J = 8.8 Hz, 1H), 6.87 (d, J = 8.0 Hz, 1H), 3.91 (s, 3H), 3.81 (s, 3H), 3.34 (s, 3H). | 2,4-Dimethoxy-[1,1-biphenyl]-3-sulfonyl chloride I114 | FA | 2 eq. LiHMDS used and stirred 3 h before adding sulfonyl chloride. Prep. TLC (DCM/MeOH = 50/1) |
| 97 | 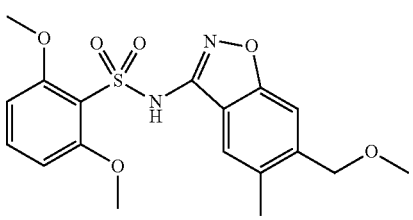 [SMILES: COCc1cc2onc(NS(=O)(=O)c3c(OC)cccc3OC)c2cc1C]<br>2,6-Dimethoxy-N-(6-(methoxymethyl)-5-methylbenzo[d]isoxazol-3-yl)benzenesulfonamide | LCMS-D: $R_t$ 2.38 min, m/z 393.1 [M + H]$^+$; $^1$H NMR (400 MHz, DMSO-$d_6$) δ 11.3 (s, 1H), 7.81 (s, 1H), 7.48-7.45 (m, 2H), 6.75-6.73 (m, 2H), 4.51 (s, 2H), 3.73 (s, 6H), 3.35 (s, 3H), 2.31 (s, 3H). | 2,6-Dimethoxy benzenesulfonyl chloride I111 6-(Methoxymethyl)-5-methylbenzo[d]isoxazol-3-amine I4 | FA | 2 eq. LiHMDS used, stirred 2.5 h before adding 3 eq. sulfonyl chloride. Purified by prep-HPLC |

TABLE F-continued

| | Name and structure | Analytical | Intermediates (if applicable) | Method | Notes |
|---|---|---|---|---|---|
| 98 | 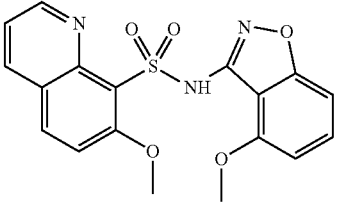 [SMILES: COc1ccc2cccnc2c1S(=O)(=O)Nc1noc2cccc(OC)c12]<br>7-Methoxy-N-(4-methoxybenzo[d]isoxazol-3-yl)quinoline-8-sulfonamide | LCMS-D: $R_t$ 1.79 min, m/z 385.8 [M + H]$^+$; $^1$H NMR (400 MHz, DMSO-$d_6$) δ 10.6 (s, 1H), 8.98 (dd, J = 4.4, 1.6 Hz, 1H), 8.46 (dd, J = 8.0, 1.6 Hz, 1H), 8.31 (d, J = 5.6 Hz, 1H), 7.55 (dd, J = 8.0, 4.0 Hz, 1H), 7.52 (d, J = 6.0 Hz, 1H), 7.50 (t, J = 8.0 Hz, 1H), 7.08 (d, J = 8.4 Hz, 1H), 6.81 (d, J = 8.0 Hz, 1H), 4.06 (s, 3H), 3.99 (s, 3H). | 7-Methoxy quinoline-8-sulfonyl chloride I107 | FA | LiHMDS added at −60° C. and stirred at 0° C. for 1 h before adding sulfonyl chloride. Prep. TLC (DCM/MeOH = 20/1) |
| 99 | 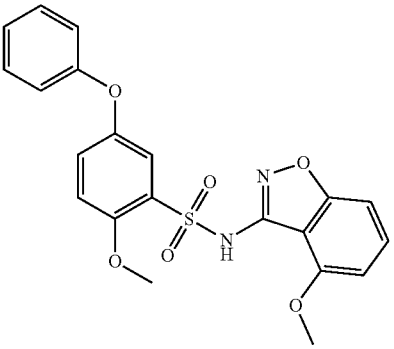 [SMILES: COc1ccc(Oc2ccccc2)cc1S(=O)(=O)Nc1noc2cccc(OC)c12]<br>2-Methoxy-N-(4-methoxybenzo[d]isoxazol-3-yl)-5-phenoxybenzenesulfonamide | LCMS-D: $R_t$ 2.91 min, m/z 427.1 [M + H]$^+$; $^1$H NMR (400 MHz, DMSO-$d_6$) δ 7.79 (d, J = 8.8 Hz, 2H), 7.56 (t, J = 8.4 Hz, 1H), 7.15-6.99 (m, 7H), 6.82 (d, J = 8.0 Hz, 1H), 3.90 (s, 3H), 3.76 (s, 3H). | 2-Methoxy-5-phenoxyben-zenesulfonyl chloride I100 | FA | 1.1 eq. LiHMDS and 1.05 eq. sulfonyl chloride used. Product not purified |
| 100 | 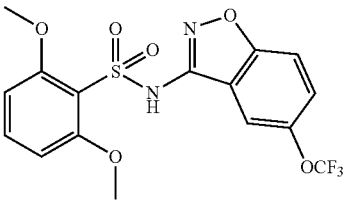 [SMILES: COc1cccc(OC)c1S(=O)(=O)Nc1noc2ccc(OC(F)(F)F)cc12]<br>2,6-Dimethoxy-N-(5-(trifluoromethoxy)benzo[d]isoxazol-3-yl)benzenesulfonamide | LCMS-D: $R_t$ 2.61 min, m/z 419.0 [M + H]$^+$; $^1$H NMR (400 MHz, methanol-$d_4$) δ 8.01 (d, J = 0.8 Hz, 1H), 7.59-7.42 (m, 3H), 6.71 (d, J = 8.8 Hz, 2H), 3.82 (s, 6H). | 2,6-Dimethoxy benzenesulfonyl chloride I111 5-(Trifluorometh-oxy)benzo[d]isoxazol-3-amine I63 | FA | Added LiHMDS at −60° C. and stirred at 0° C. for 1 h before adding sulfonyl chloride. Prep. TLC (Pet. ether/EtOAc = 5/1) |
| 101 | 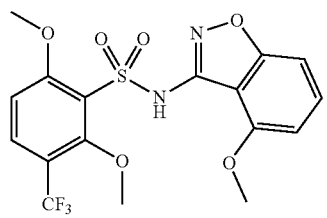 [SMILES: COc1ccc(C(F)(F)F)c(OC)c1S(=O)(=O)Nc1noc2cccc(OC)c12]<br>2,6-Dimethoxy-N-(4-methoxybenzo[d]isoxazol-3-yl)-3-(trifluoromethyl)benzenesulfonamide | LCMS-D: $R_t$ 2.64 min, m/z 433.1 [M + H]$^+$; $^1$H NMR (400 MHz, DMSO-$d_6$) δ 10.5 (s, 1H), 7.92 (d, J = 8.8 Hz, 1H), 7.59 (t, J = 8.0 Hz, 1H), 7.20-7.14 (m, 2H), 6.85 (d, J = 8.4 Hz, 1H), 3.87 (s, 6H), 3.85 (s, 3H). | 2,6-Dimethoxy-3-(trifluoro methyl)benzene-sulfonyl chloride I102 | FA | Added 2 eq. LiHMDS at 0° C. Prep. TLC (Pet. ether/EtOAc = 1/1) |

TABLE F-continued

| | Name and structure | Analytical | Intermediates (if applicable) | Method | Notes |
|---|---|---|---|---|---|
| 102 | 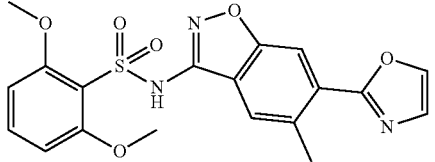 [SMILES: COc1cccc(OC)c1S(=O)(=O)Nc1noc2cc(-c3ncco3)c(C)cc12]<br>2,6-Dimethoxy-N-(5-methyl-6-(oxazol-2-yl)benzo[d]isoxazol-3-yl)benzenesulfonamide | LCMS-D: $R_t$ 2.42 min, m/z 415.9 [M + H]$^+$; $^1$H NMR (400 MHz, DMSO-$d_6$) δ 11.5 (s, 1H), 8.32 (s, 1H), 7.07 (t, J = 8.4 Hz, 2H), 7.50-7.30 (m, 2H), 6.76 (d, J = 8.4 Hz, 2H), 3.75 (s, 6H), 2.70 (s, 3H). | 2,6-Dimethoxy benzenesulfonyl chloride I111 5-Methyl-6-(oxazol-2-yl)benzo[d]isoxazol-3-amine I65 | FA | 1.5 eq. LiHMDS used. Prep. TLC (Pet. ether/ EtOAc = 1/2) |
| 103 | 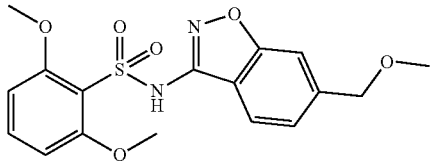 [SMILES: COCc1ccc2c(NS(=O)(=O)c3c(OC)cccc3OC)noc2c1]<br>2,6-Dimethoxy-N-(6-(methoxymethyl)benzo[d]isoxazol-3-yl)benzenesulfonamide | LCMS-D: $R_t$ 2.22 min, m/z 378.9 [M + H]$^+$; $^1$H NMR (400 MHz, DMSO-$d_6$) δ 11.4 (s, 1H), 8.04 (d, J = 8.4 Hz, 1H), 7.50-7.45 (m, 2H), 7.31 (d, J = 8.4 Hz, 1H), 6.75 (d, J = 8.8 Hz, 2H), 4.55 (s, 2H), 3.73 (s, 6H), 3.32 (s, 3H). | 2,6-Dimethoxy benzenesulfonyl chloride I111 6-(Methoxymethyl)benzo[d]isoxazol-3-amine I62 | FA | Added LiHMDS at −78° C. and stirred at 0° C. for 30 min before adding sulfonyl chloride. Prep. TLC (Pet. ether/ EtOAc = 2/1) |
| 104 | 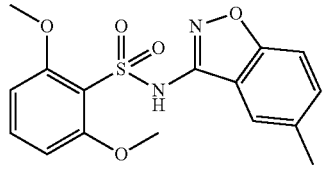 [SMILES: COc1cccc(OC)c1S(=O)(=O)Nc1noc2ccc(C)cc12]<br>2,6-Dimethoxy-N-(5-methylbenzo[d]isoxazol-3-yl)benzenesulfonamide | LCMS-D: $R_t$ 2.40 min, m/z 348.9 [M + H]$^+$; $^1$H NMR (400 MHz, DMSO-$d_6$) δ 11.3 (s, 1H), 7.83 (s, 1H), 7.49-7.44 (m, 3H), 6.75 (d, J = 8.4 Hz, 2H), 3.74 (s, 6H), 2.40 (s, 3H). | 2,6-Dimethoxy benzenesulfonyl chloride I111 5-Methyl benzo[d]isoxazol-3-amine I60 | FA | Added LiHMDS at −60° C. and stirred at 0° C. for 1 h before adding sulfonyl chloride. Prep. TLC (DCM/ MeOH = 20/1) |
| 105 | 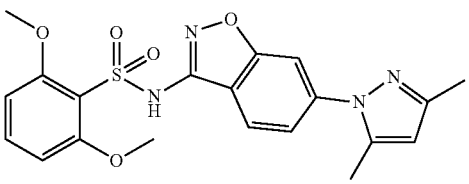 [SMILES: COc1cccc(OC)c1S(=O)(=O)Nc1noc2cc(-n3nc(C)cc3C)ccc12]<br>N-(6-(3,5-Dimethyl-1H-pyrazol-1-yl)benzo[d]isoxazol-3-yl)-2,6-dimethoxybenzenesulfonamide | LCMS-D: $R_t$ 2.44 min, m/z 429.1 [M + H]$^+$; $^1$H NMR (400 MHz, DMSO-$d_6$) δ 11.5 (s, 1H), 8.16 (d, J = 8.8 Hz, 1H), 7.74 (d, J = 1.6 Hz, 1H), 7.57 (dd, J = 8.8, 2.0 Hz, 1H), 7.48 (t, J = 8.8 Hz, 1H), 6.75 (d, J = 8.4 Hz, 2H), 6.13 (s, 1H), 3.75 (s, 6H), 2.36 (s, 3H), 2.19 (s, 3H). | 2,6-Dimethoxy benzenesulfonyl chloride I111 6-(3,5-Dimethyl-1H-pyrazol-1-yl)benzo[d]isoxazol-3-amine I59 | FC | |
| 106 | 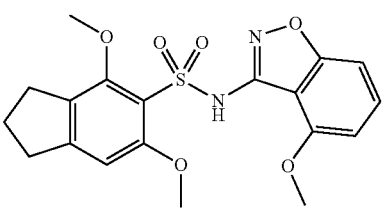 [SMILES: COc1cc2c(c(OC)c1S(=O)(=O)Nc1noc3cccc(OC)c13)CCC2]<br>4,6-Dimethoxy-N-(4-methoxybenzo[d]isoxazol-3-yl)-2,3-dihydro-1H-indene-5-sulfonamide | LCMS-D: $R_t$ 2.58 min, m/z 405.1 [M + H]$^+$; $^1$H NMR (400 MHz, DMSO-$d_6$) δ 9.40 (s, 1H), 7.58 (t, J = 8.0 Hz, 1H), 7.16 (d, J = 8.0 Hz, 1H), 6.86-6.84 (m, 2H), 3.96 (s, 3H), 3.80 (s, 3H), 3.75 (s, 3H), 2.88-2.84 (m, 4H), 2.02-1.99 (m, 2H). | 4,6-Dimethoxy-2,3-dihydro-1H-indene-5-sulfonyl chloride I98 | FA | Added 1.33 eq. LiHMDS at −78° C. and stirred at 0° C. for 1 h before adding 0.67 eq. sulfonyl chloride. Column chromatography (Pet. ether/ EtOAc = 1/1) |

TABLE F-continued

| | Name and structure | Analytical | Intermediates (if applicable) | Method | Notes |
|---|---|---|---|---|---|
| 107 | 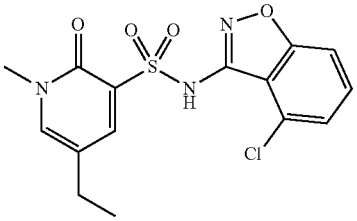 [SMILES: CCc1cc(S(=O)(=O)Nc2noc3cccc(Cl)c23)c(=O)n(C)c1]<br>N-(4-Chlorobenzo[d]isoxazol-3-yl)-5-ethyl-1-methyl-2-oxo-1,2-dihydropyridine-3-sulfonamide | LCMS-D: $R_t$ 2.34 min, m/z 368.0 [M + H]$^+$; $^1$H NMR (400 MHz, DMSO-$d_6$) δ 10.5 (s, 1H), 7.98 (s, 2H), 7.70-7.62 (m, 2H), 7.45 (d, J = 7.2 Hz, 1H), 3.50 (s, 3H), 2.46 (q, J = 7.2 Hz, 2H), 1.13 (t, J = 7.2 Hz, 3H). | 5-Ethyl-1-methyl-2-oxo-1,2-dihydropyridine-3-sulfonyl chloride I94 | FA | Added 2.1 eq. LiHMDS at −78° C. and stirred at 0° C. for 1 h before adding 2 eq. sulfonyl chloride. Column chromatography (DCM/MeOH = 50/1) |
| 108 | 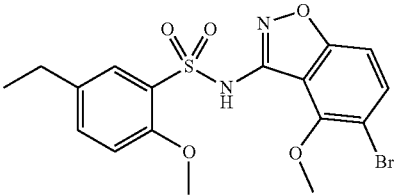 [SMILES: CCc1ccc(OC)c(S(=O)(=O)Nc2noc3ccc(Br)c(OC)c23)c1]<br>N-(5-Bromo-4-methoxybenzo[d]isoxazol-3-yl)-5-ethyl-2-methoxybenzenesulfonamide | LCMS-D: $R_t$ 2.82 min, m/z 441.0 [M + H]$^+$; $^1$H NMR (400 MHz, DMSO-$d_6$) δ 10.8 (s, 1H), 7.86 (d, J = 8.8 Hz, 1H), 7.62 (d, J = 1.2 Hz, 1H), 7.50-7.43 (m, 2H), 7.17 (d, J = 8.8 Hz, 1H), 3.91 (s, 3H), 3.79 (s, 3H), 2.64 (q, J = 7.6 Hz, 2H), 1.17 (t, J = 7.6 Hz, 3H). | 5-Ethyl-2-methoxybenzenesulfonyl chloride I112 5-Bromo-4-methoxybenzo[d]isoxazol-3-amine I48 | FD | Added 2 eq. KHMDS, stirred at 0° C. for 1 h before adding 2 eq. sulfonyl chloride. Column chromatography (Pet. ether/EtOAc = 50/1 to 3/1) |
| 109 | 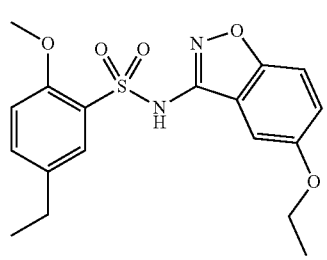 [SMILES: CCOc1ccc2onc(NS(=O)(=O)c3cc(CC)ccc3OC)c2c1]<br>N-(5-Ethoxybenzo[d]isoxazol-3-yl)-5-ethyl-2-methoxybenzenesulfonamide | LCMS-D: $R_t$ 2.78 min, m/z 377.1 [M + H]$^+$; $^1$H NMR (400 MHz, DMSO-$d_6$) δ 11.5 (s, 1H), 7.69 (d, J = 2.0 Hz, 1H), 7.50-7.44 (m, 3H), 7.20 (dd, J = 9.8, 2.4 Hz, 1H), 7.10 (d, J = 8.8 Hz, 1H), 4.06 (q, J = 7.4 Hz, 2H), 3.74 (s, 3H), 2.63 (q, J = 7.6 Hz, 2H), 1.38 (t, J = 6.8 Hz, 3H), 1.16 (t, J = 7.6 Hz, 3H). | 5-Ethyl-2-methoxybenzenesulfonyl chloride I112 5-Ethoxybenzo[d]isoxazol-3-amine I57 | FB | Column chromatography (Pet. ether/EtOAc = 4/1 to 3/1) |
| 110 | 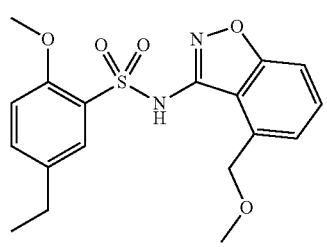 [SMILES: CCc1ccc(OC)c(S(=O)(=O)Nc2noc3cccc(COC)c23)c1]<br>5-Ethyl-2-methoxy-N-(4-(methoxymethyl)benzo[d]isoxazol-3-yl)benzenesulfonamide | LCMS-D: $R_t$ 2.66 min m/z 377.1 [M + H]$^+$; | 5-Ethyl-2-methoxybenzenesulfonyl chloride I112 4-(Methoxymethyl)benzo[d]isoxazol-3-amine I51 | FB | Prep. TLC (Pet. ether/EtOAc = 2/1) |

TABLE F-continued

| | Name and structure | Analytical | Intermediates (if applicable) | Method | Notes |
|---|---|---|---|---|---|
| 111 | 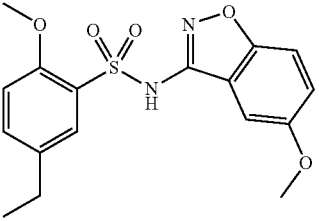 [SMILES: CCc1ccc(OC)c(S(=O)(=O)Nc2noc3ccc(OC)cc23)c1]<br>5-Ethyl-2-methoxy-N-(5-methoxybenzo[d]isoxazol-3-yl)benzenesulfonamide | LCMS-D: $R_t$ 2.65 min, m/z 363.1 [M + H]$^+$; $^1$H NMR (400 MHz, DMSO-$d_6$) δ 11.5 (s, 1H), 7.69 (d, J = 2.0 Hz, 1H), 7.52-7.44 (m, 3H), 7.23 (dd, J = 9.8, 2.4 Hz, 1H), 7.10 (d, J = 8.8 Hz, 1H), 3.79 (s, 3H), 3.75 (s, 3H), 2.63 (q, J = 7.6 Hz, 2H), 1.16 (t, J = 7.6 Hz, 3H). | 5-Ethyl-2-methoxybenzene-sulfonyl chloride I112 5-Methoxy benzo[d]isoxazol-3-amine I54 | FB | Prep. TLC |
| 112 | 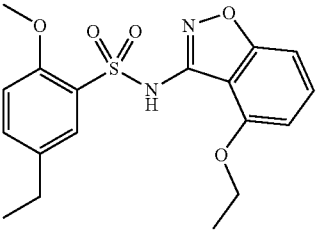 [SMILES: CCOc1cccc2onc(NS(=O)(=O)c3cc(CC)ccc3OC)c12]<br>N-(4-Ethoxybenzo[d]isoxazol-3-yl)-5-ethyl-2-methoxybenzenesulfonamide | LCMS-E: $R_t$ 5.57 min m/z 376.7 [M + H]$^+$; $^1$H NMR (400 MHz, DMSO-$d_6$) δ 9.68 (s, 1H), 7.67 (d, J = 2.0 Hz, 1H), 7.56-7.45 (m, 2H), 7.16-7.08 (m, 2H), 6.83 (d, J = 8.0 Hz, 1H), 4.19 (q, J = 7.2 Hz, 2H), 3.63 (s, 3H), 2.64 (q, J = 7.6 Hz, 2H), 1.31 (t, J = 7.4 Hz, 3H), 1.17 (t, J = 7.6 Hz, 3H). | 5-Ethyl-2-methoxybenzene-sulfonyl chloride I112 4-Ethoxy benzo[d]isoxazol-3-amine I53 | FA | Added 1.5 eq. LiHMDS at −78° C. and stirred at 0° C. for 1 h before adding 1.5 eq. sulfonyl chloride. Column chromatography (Pet. ether/ EtOAc = 3/1) |
| 113 | 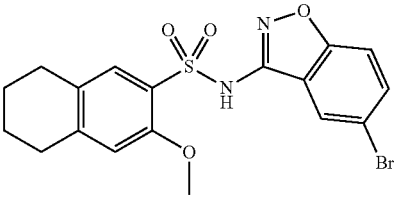 [SMILES: COc1cc2c(cc1S(=O)(=O)Nc1noc3ccc(Br)cc13)CCCC2]<br>N-(5-Bromobenzo[d]isoxazol-3-yl)-3-methoxy-5,6,7,8-tetrahydronaphthalene-2-sulfonamide | LCMS-D: $R_t$ 3.07 min, m/z 437.0 [M + H]$^+$; $^1$H NMR (400 MHz, DMSO-$d_6$) δ 11.6 (s, 1H), 8.25 (s, 1H), 7.78 (dd, J = 8.8, 2.0 Hz, 1H), 7.62-7.56 (m, 2H), 6.85 (s, 1H), 3.69 (s, 3H), 2.73-2.69 (m, 4H), 1.71 (m, 4H). | 3-Methoxy-5,6,7,8-tetrahydro-naphthalene-2-sulfonyl chloride I109 5-Bromo benzo[d]isoxazol-3-amine I40 | FA | Added 2 eq. LiHMDS at −78° C. and stirred at 0° C. for 1 h before adding 2 eq. sulfonyl chloride. Column chromatography (DCM/ MeOH = 200/1 to 100/1) |
| 114 | 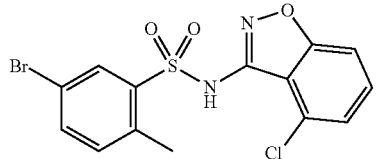 [SMILES: Cc1ccc(Br)cc1S(=O)(=O)Nc1noc2cccc(Cl)c12]<br>5-Bromo-N-(4-chlorobenzo[d]isoxazol-3-yl)-2-methylbenzenesulfonamide | LCMS-D: $R_t$ 2.82 min, m/z 401.0 [M + H]$^+$; $^1$H NMR (400 MHz, DMSO-$d_6$) δ 8.02 (d, J = 2.0 Hz, 1H), 7.73-7.76 (m, 3H), 7.43-7.35 (m, 2H), 2.49 (s, 3H). | | FA | Added 1 eq. LiHMDS at −78° C. and stirred at 0° C. for 1 h before adding 0.67 eq. sulfonyl chloride. Column chromatography (Pet. ether/ EtOAc = 6/1) |

TABLE F-continued

| | Name and structure | Analytical | Intermediates (if applicable) | Method | Notes |
|---|---|---|---|---|---|
| 115 | Methyl 4-chloro-2-(N-(4-chlorobenzo[d]isoxazol-3-yl)sulfamoyl)benzoate | LCMS-D: $R_t$ 2.78 min, m/z 401.0 [M + H]$^+$; $^1$H NMR (400 MHz, DMSO-$d_6$) δ 8.09 (d, J = 2.0 Hz, 1H), 7.88 (d, J = 8.4 Hz, 1H), 7.74-7.65 (m, 3H), 7.48 (d, J = 7.6 Hz, 1H), 3.64 (s, 3H). | | FD | Added 0.67 eq. KHMDS, stirred at 0° C. for 1 h before adding 0.67 eq. sulfonyl chloride. Column chromatography (Pet. ether/EtOAc = 1/1) |
| 116 | 5-Ethyl-2-methoxy-N-(4-methoxybenzo[d]isoxazol-3-yl)benzenesulfonamide | LCMS-D: $R_t$ 2.56 min, m/z 363.1 [M + H]$^+$; $^1$H NMR (400 MHz, DMSO-$d_6$) δ 9.96 (s, 1H), 7.66 (d, J = 1.6 Hz, 1H), 7.57 (t, J = 8.0 Hz, 1H), 7.48-7.46 (m, 1H), 7.12-7.11 (m, 2H), 6.84 (d, J = 8.0 Hz, 1H), 3.87 (s, 3H), 3.75 (s, 3H), 2.64 (q, J = 7.6 Hz, 2H), 1.17 (t, J = 7.6 Hz, 3H). | 5-Ethyl-2-methoxybenzene-sulfonyl chloride I112 | FA | Added 2 eq. LiHMDS at −78° C. and stirred at 0° C. for 1 h before adding 2 eq. sulfonyl chloride. Column chromatography (DCM/MeOH = 30/1) |
| 117 | N-(4-Chlorobenzo[d]isoxazol-3-yl)-2,3,4-trifluorobenzenesulfonamide | LCMS-D: $R_t$ 2.59 min, m/z 363.0 [M + H]$^+$; $^1$H NMR (400 MHz, DMSO-$d_6$) δ 7.74-7.69 (m, 1H), 7.54-7.40 (m, 3H), 7.31 (d, J = 7.0 Hz, 1H). | | FA | Added 1 eq. LiHMDS at −78° C. and stirred at 0° C. for 1 h before adding 1 eq. sulfonyl chloride. Column chromatography (DCM/MeOH = 100/1 to 30/1) |
| 118 | N-(4-Chlorobenzo[d]isoxazol-3-yl)-3-methylquinoline-8-sulfonamide | LCMS-D: $R_t$ 2.62 min, m/z 374.1 [M + H]$^+$; $^1$H NMR (400 MHz, DMSO-$d_6$) δ 8.81 (d, J = 2.4 Hz, 1H), 8.34-8.25 (m, 3H), 7.76-7.61 (m, 3H), 7.43 (d, J = 8.8 Hz, 1H), 2.50 (s, 3H). | | FA | Added 1.5 eq. LiHMDS at −78° C. and stirred at 0° C. for 1 h before adding 1.5 eq. sulfonyl chloride. Column chromatography (DCM/MeOH = 20/1) |

TABLE F-continued

| | Name and structure | Analytical | Intermediates (if applicable) | Method | Notes |
|---|---|---|---|---|---|
| 119 | 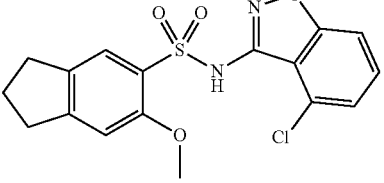<br>N-(4-Chlorobenzo[c]isoxazol-3-yl)-6-methoxy-2,3-dihydro-1H-indene-5-sulfonamide | LCMS-D: R$_t$ 2.69 min, m/z 379.0 [M + H]$^+$; $^1$H NMR (400 MHz, DMSO-d$_6$) δ 10.4 (s, 1H), 7.75-7.63 (m, 2H), 7.58 (s, 1H), 7.47 (d, J = 7.2 Hz, 1H), 7.11 (s, 1H), 3.69 (s, 3H), 2.93 (t, J = 7.2 Hz, 2H), 2.84 (t, J = 7.2 Hz, 2H), 2.07-2.00 (m, 2H). | 6-Methoxy-2,3-dihydro-1H-indene-5-sulfonyl chloride I108 | FD | Added 0.67 eq. KHMDS, stirred at 0° C. for 1 h before adding 0.67 eq. sulfonyl chloride. Column chromatography (Pet. ether/ EtOAc = 1/1) |
| 120 | 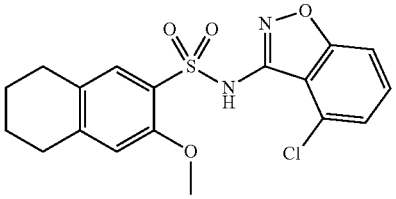 [SMILES: COc1cc2c(cc1S(=O)(=O)Nc1noc3cccc(Cl)c13)CCCC2]<br>N-(4-Chlorobenzo[c]isoxazol-3-yl)-3-methoxy-5,6,7,8-tetrahydronaphthalene-2-sulfonamide | LCMS-D: R$_t$ 2.86 min, m/z 393.1 [M + H]$^+$; $^1$H NMR (400 MHz, DMSO-d$_6$) δ 10.4 (s, 1H), 7.73-7.64 (m, 2H), 7.48 (d, J = 7.6 Hz, 1H), 7.45 (s, 1H), 6.91 (s, 1H), 3.67 (s, 3H), 2.78 (m, 2H), 2.67 (m, 2H), 1.72 (m, 4H). | 3-Methoxy-5,6,7,8-tetrahydronaph-thalene-2-sulfonyl chloride I109 | FA | Added 1 eq. LiHMDS at −78° C. and stirred at 0° C. for 1 h before adding 1 eq. sulfonyl chloride. Column chromatography (Pet. ether/ EtOAc = 50/1 to 2/1) |
| 121 | 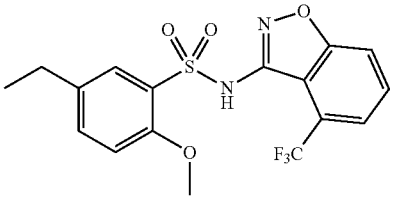 [SMILES: CCc1ccc(OC)c(S(=O)(=O)Nc2noc3cccc(C(F)(F)F)c23)c1]<br>5-Ethyl-2-methoxy-N-(4-(trifluoromethyl)benzo[d]isoxazol-3-yl)benzenesulfonamide | LCMS-D: R$_t$ 2.74 min, m/z 401.1 [M + H]$^+$; $^1$H NMR (400 MHz, DMSO-d$_6$) δ 10.3 (s, 1H), 8.14 (t, J = 6.4 Hz, 1H), 7.91-7.88 (m, 2H), 7.55 (d, J = 2.4 Hz, 1H), 7.51 (dd, J = 8.8, 2.4 Hz, 1H), 7.20 (d, J = 8.4 Hz, 1H), 3.82 (s, 3H), 2.63 (q, J = 7.6 Hz, 2H), 1.17 (t, J = 7.6 Hz, 3H). | 5-Ethyl-2-methoxybenzene-sulfonyl chloride I112 4-(Trifluoromethyl) benzo[d]isoxazol-3-amine I42 | FA | Added 2 eq. LiHMDS at −78° C. and stirred at 0° C. for 1 h before adding 2 eq. sulfonyl chloride. Column chromatography (DCM/ MeOH = 20/1) |
| 122 | 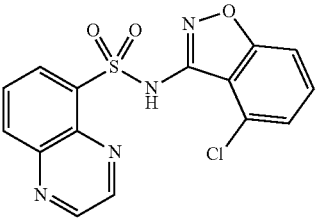 [SMILES: O=S(=O)(Nc1noc2cccc(Cl)c12)c1cccc2nccnc12]<br>N-(4-Chlorobenzo[c]isoxazol-3-yl)quinoxaline-5-sulfonamide | LCMS-D: R$_t$ 2.30 min, m/z 361.0 [M + H]$^+$; $^1$H NMR (400 MHz, DMSO-d$_6$) δ 11.0 (s, 1H), 9.09 (d, J = 1.4 Hz, 1H), 9.08(d, J = 1.4 Hz, 1H), 8.47-8.43 (m, 2H), 8.05 (t, J = 8.0 Hz, 1H), 7.72-7.62 (m, 2H), 7.42 (d, J = 7.8 Hz, 1H). | | FA | 2 eq. LiHMDS used. Purification: dissolved in 2 M aq. NaOH, washed with EtOAc, then acidified to pH 2 and extracted with DCM |

TABLE F-continued

| | Name and structure | Analytical | Intermediates (if applicable) | Method | Notes |
|---|---|---|---|---|---|
| 123 | 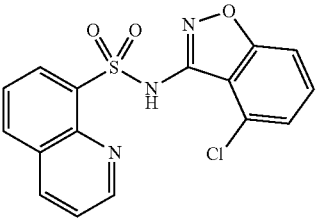<br>N-(4-chlorobenzo[d]isoxazol-3-yl)quinoline-8-sulfonamide | LCMS-D: $R_t$ 2.41 min, m/z 360.0 [M + H]$^+$; $^1$H NMR (400 MHz, DMSO-$d_6$) δ 8.93 (dd, J = 4.3, 1.8 Hz, 1H), 8.58 (dd, J = 8.4, 1.8 Hz, 1H), 8.40-8.35 (m, 2H), 7.79 (t, J = 7.8 Hz, 1H), 7.73-7.60 (m, 3H), 7.41 (d, J = 7.4 Hz, 1H). | | FA | 2 eq. LiHMDS used. Purification: dissolved in 2 M aq NaOH, washed with EtOAc, then acidified to pH 2 and extracted with DCM |
| 124 | 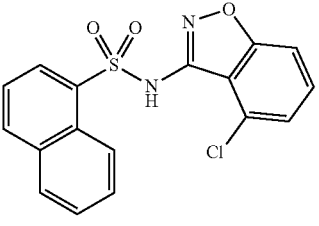 [SMILES: O=S(=O)(Nc1noc2cccc(Cl)c12)c1cccc2ccccc12]<br>N-(4-Chlorobenzo[d]isoxazol-3-yl)naphthalene-1-sulfonamide | LCMS-D: $R_t$ 2.60 min, m/z 359.0 [M + H]$^+$; $^1$H NMR (400 MHz, DMSO-$d_6$) δ 8.73 (t, J = 8.4 Hz, 1H), 8.31-8.24 (m, 2H), 8.14 (d, J = 7.8 Hz, 1H), 7.74-7.63 (m, 5H), 7.46 (d, J = 7.2 Hz, 1H). | | FA | 2 eq. LiHMDS used. Column chromatography (Pet. ether/EtOAc = 50/1 to 2/1) |
| 125 | 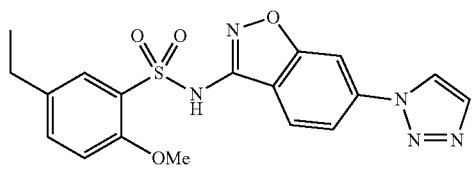 [SMILES: CCc1ccc(OC)c(S(=O)(=O)Nc2noc3cc(-n4ccnn4)ccc23)c1]<br>N-(6-(1H-1,2,3-Triazol-1-yl)benzo[d]isoxazol-3-yl)-5-ethyl-2-methoxybenzenesulfonamide | LCMS-D: $R_t$ 2.48 min, m/z 400.1 [M + H]$^+$; $^1$H NMR (400 MHz, DMSO-$d_6$) δ 11.9 (s, 1H), 8.96 (s, 1H), 8.26-8.23 (m, 2H), 8.04-8.01 (m, 2H), 7.73 (d, J = 2.0 Hz, 1H), 7.49 (dd, J = 8.4, 2.0 Hz, 1H), 7.11 (d, J = 8.4 Hz, 1H), 3.73 (s, 3H), 2.65 (q, J = 8.0 Hz, 2H), 1.23 (t, J = 8.0 Hz, 3H). | 5-Ethyl-2-methoxybenzenesulfonyl chloride I112 6-(1H-1,2,3-Triazol-1-yl)benzo[d]isoxazol-3-amine I36 | FB | Column chromatography (DCM/MeOH = 100/0 to 50/1) |
| 126 | 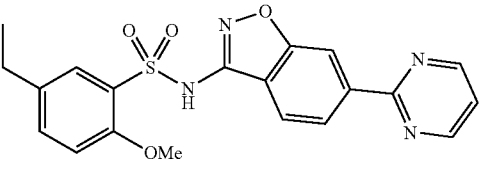 [SMILES: CCc1ccc(OC)c(S(=O)(=O)Nc2noc3cc(-c4ncccn4)ccc23)c1]<br>5-Ethyl-2-methoxy-N-(6-(pyrimidin-2-yl)benzo[d]isoxazol-3-yl)benzenesulfonamide | LCMS-D: $R_t$ 2.65 min, m/z 411.1 [M + H]$^+$; $^1$H NMR (400 MHz, DMSO-$d_6$) δ 11.8 (s, 1H), 8.98 (d, J = 4.8 Hz, 2H), 8.43 (d, J = 8.4 Hz, 1H), 8.48 (s, 1H), 8.20 (d, J = 8.4 Hz, 1H), 7.73 (d, J = 2.0 Hz, 1H), 7.55 (t, J = 4.8 Hz, 1H), 7.48 (dd, J = 8.4, 2.0 Hz, 1H), 7.11 (d, J = 8.8 Hz, 1H), 3.72 (s, 3H), 2.65 (q, J = 7.2 H, 2H), 1.17 (t, J = 7.2 Hz, 3H). | 5-Ethyl-2-methoxybenzenesulfonyl chloride I112 6-(Pyrimidin-2-yl)benzo[d]isoxazol-3-amine I39 | FB | Prep. TLC (DCM/MeOH = 50/1) |

TABLE F-continued

| | Name and structure | Analytical | Intermediates (if applicable) | Method | Notes |
|---|---|---|---|---|---|
| 127 | <br>5-Bromo-N-(4-chlorobenzo[d]isoxazol-3-yl)-2,3-dihydrobenzofuran-7-sulfonamide | LCMS-D: $R_t$ 2.66 min, m/z 428.9 [M + H]$^+$; $^1$H NMR (400 MHz, DMSO-$d_6$) δ 11.2 (s, 1H), 7.75-7.65 (m, 3H), 7.58 (d, J = 2.0 Hz, 1H), 7.48 (d, J = 7.2 Hz, 1H), 4.57 (t, J = 8.8 Hz, 2H), 3.26 (t, J = 8.8 Hz, 2H). | 5-Bromo-2,3-dihydrobenzo-furan-7-sulfonyl chloride I95 | FA | Added LiHMDS at −78° C. and stirred at 0° C. for 1 h before adding sulfonyl chloride. Column chromatography (Pet. ether/EtOAc = 5/1) |
| 128 | 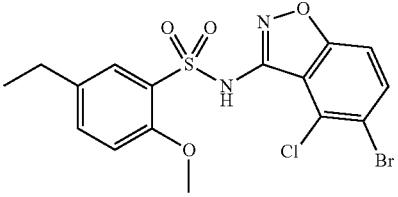 [SMILES: CCc1ccc(OC)c(S(=O)(=O)Nc2noc3ccc(Br)c(Cl)c23)c1]<br>N-(5-Bromo-4-chlorobenzo[d]isoxazol-3-yl)-5-ethyl-2-methoxybenzenesulfonamide | LCMS-E: $R_t$ 5.81 min, m/z 444.7 [M + H]$^+$; $^1$H NMR (400 MHz, DMSO-$d_6$) δ 10.7 (s, 1H), 8.02 (d, J = 8.8 Hz, 1H), 7.74 (d, J = 8.8 Hz, 1H), 7.60 (d, J = 2.4 Hz, 1H), 7.50-7.48 (m, 1H), 7.16 (d, J = 8.4 Hz, 1H), 3.66 (s, 3H), 2.63 (q, J = 7.6 Hz, 2H), 1.17 (t, J = 7.6 Hz, 3H). | 5-Ethyl-2-methoxybenzene-sulfonyl chloride I112 5-Bromo-4-chlorobenzo[d]isoxazol-3-amine I44 | FD | Added 1 eq. KHMDS, stirred at −78° C. for 30 min before adding 2 eq. sulfonyl chloride. Column chromatography (Pet. ether/EtOAc = 50/1 to 2/1) |
| 129 | <br>N-(4-Bromobenzo[d]isoxazol-3-yl)-5-ethyl-2-methoxybenzenesulfonamide | LCMS-D: $R_t$ 2.69 min, m/z 410.9 [M + H]$^+$; $^1$H NMR (400 MHz, DMSO-$d_6$) δ 10.4 (s, 1H), 7.78 (d, J = 8.0 Hz, 1H), 7.65-7.56 (m, 3H), 7.49 (dd, J = 8.4, 2.4 Hz, 1H), 7.15 (d, J = 8.4 Hz, 1H), 3.68 (s, 3H), 2.60 (q, J = 7.6 Hz, 2H), 1.16 (t, J = 7.6 Hz, 3H). | 5-Ethyl-2-methoxybenzene-sulfonyl chloride I112 4-Bromobenzo[d]isoxazol-3-amine I41 | FA | 1.5 eq. LiHMDS used. Column chromatography (Pet. ether/EtOAc = 2/1 to 1/1) |
| 130 | 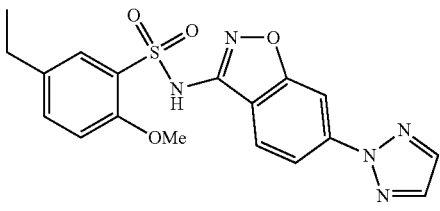 [SMILES: CCc1ccc(OC)c(S(=O)(=O)Nc2noc3cc(-n4nccn4)ccc23)c1]<br>N-(6-(2H-1,2,3-Triazol-2-yl)benzo[d]isoxazol-3-yl)-5-ethyl-2-methoxybenzenesulfonamide | LCMS-D: $R_t$ 2.77 min, m/z 400.1 [M + H]$^+$; $^1$H NMR (400 MHz, DMSO-$d_6$) δ 11.9 (s, 1H), 8.24-8.17 (m, 3H), 8.12-8.10 (m, 2H), 7.70 (s, 1H), 7.48 (d, J = 8.4 Hz, 1H), 7.11 (d, J = 8.4 Hz, 1H), 3.76 (s, 3H), 2.65 (q, J = 7.6 Hz, 2H), 1.17 (t, J = 7.6 Hz, 3H). | 5-Ethyl-2-methoxybenzene-sulfonyl chloride I112 6-(2H-1,2,3-Triazol-2-yl)benzo[d]isoxazol-3-amine I72 | FB | 3 eq. sulfonyl chloride used. Prep. TLC (DCM/MeOH = 50/1) |
| 131 | 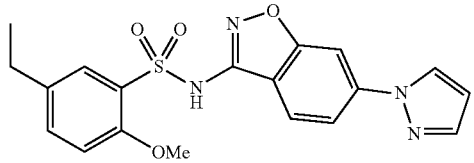 [SMILES: CCc1ccc(OC)c(S(=O)(=O)Nc2noc3cc(-n4cccn4)ccc23)c1]<br>N-(6-(1H-Pyrazol-1-yl)benzo[d]isoxazol-3-yl)-5-ethyl-2-methoxybenzenesulfonamide | LCMS-D: $R_t$ 2.61 min, m/z 399.1 [M + H]$^+$; $^1$H NMR (400 MHz, DMSO-$d_6$) δ 11.8 (s, 1H), 8.66 (d, J = 2.4 Hz, 1H), 8.15 (d, J = 8.4 Hz, 1H), 8.07 (d, J = 2.0 Hz, 1H), 7.97 (dd, J = 8.8, 2.0 Hz, 1H), 7.83 (d, J = 1.2 Hz, 1H), 7.72 (d, J = 2.0 Hz, 1H), 7.48 (dd, J = | 5-Ethyl-2-methoxybenzene-sulfonyl chloride I112 6-(1H-Pyrazol-1-yl)benzo[d]isoxazol-3-amine I70 | FB | 3 eq. sulfonyl chloride used. Column chromatography (DCM/MeOH = 50/1) |

TABLE F-continued

| | Name and structure | Analytical | Intermediates (if applicable) | Method | Notes |
|---|---|---|---|---|---|
| | | 8.4, 2.0 Hz, 1H), 7.11 (d, J = 8.4 Hz, 1H), 6.62 (d, J = 1.2 Hz, 1H), 3.73 (s, 3H), 2.65 (q, J = 7.6 Hz, 2H), 1.18 (t, J = 7.6 Hz, 3H). | | | |
| 132 | 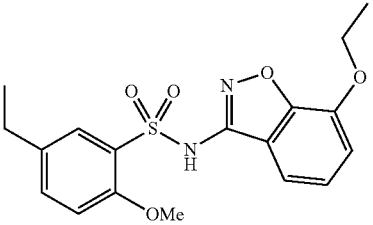 [SMILES: CCOc1cccc2c(NS(=O)(=O)c3cc(CC)ccc3OC)noc12]<br>N-(7-Ethoxybenzo[d]isoxazol-3-yl)-5-ethyl-2-methoxybenzenesulfonamide | LCMS-D: R$_t$ 2.67 min, m/z 377.1 [M + H]$^+$; $^1$H NMR (400 MHz, DMSO-d$_6$) δ 11.6 (s, 1H), 7.69 (d, J = 2.0 Hz, 1H), 7.57 (d, J = 7.6 Hz, 1H), 7.46 (dd, J = 8.8, 2.0 Hz, 1H), 7.26 (d, J = 8.0 Hz, 1H), 7.15 (d, J = 8.0 Hz, 1H), 7.08 (d, J = 8.4 Hz, 1H), 4.21 (q, J = 6.8 Hz, 2H), 3.72 (s, 3H), 3.62 (q, J = 7.6 Hz, 2H), 1.36 (t, J = 6.8 Hz, 3H), 1.16 (t, J = 7.6 Hz, 3H). | 5-Ethyl-2-methoxybenzenesulfonyl chloride I112 7-Ethoxybenzo [d]isoxazol-3-amine I26 | FB | Column chromatography (Pet. ether/ EtOAc = 5/1) |
| 133 | 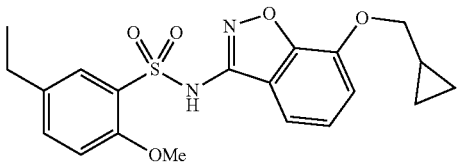 [SMILES: CCc1ccc(OC)c(S(=O)(=O)Nc2noc3c(OCC4CC4)cccc23)c1]<br>N-(7-(Cyclopropylmethoxy) benzo[d]isoxazol-3-yl)-5-ethyl-2-methoxybenzenesulfonamide | LCMS-D: R$_t$ 2.87 min, m/z 403.1 [M + H]$^+$; $^1$H NMR (400 MHz, DMSO-d$_6$) δ 11.6 (s, 1H), 7.69 (d, J = 1.6 Hz, 1H), 7.56 (d, J = 8.0 Hz, 1H), 7.46 (d, J = 8.0 Hz, 1H), 7.24 (t, J = 8.0 Hz, 1H), 7.14 (d, J = 7.6 Hz, 1H), 7.09 (d, J = 8.4 Hz, 1H), 3.99 (d, J = 7.2 Hz, 2H), 3.72 (s, 3H), 2.63 (q, J = 7.6 Hz, 2H), 1.30 (m, 1H), 1.16 (t, J = 7.6 H, 3H), 0.59-0.54 (m, 2H), 0.35-0.30 (m, 2H). | 5-Ethyl-2-methoxybenzenesulfonyl chloride I112 7-(Cyclopropyl-methoxy)benzo [d]isoxazol-3-amine I28 | FB | Column chromatography (DCM/ MeOH = 200/1) |
| 134 | 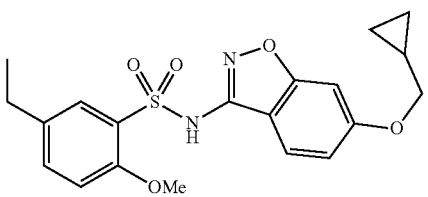 [SMILES: CCc1ccc(OC)c(S(=O)(=O)Nc2noc3cc(OCC4CC4)ccc23)c1]<br>N-(6-(Cyclopropylmethoxy) benzo[d]isoxazol-3-yl)-5-ethyl-2-methoxybenzenesulfonamide | LCMS-D: R$_t$ 2.89 min, m/z 403.1 [M + H]$^+$; $^1$H NMR (400 MHz, DMSO-d$_6$) δ 11.5 (s, 1H), 7.87 (d, J = 8.8 Hz, 1H), 7.68 (d, J = 2.4 Hz, 1H), 7.46 (dd, J = 8.4, 2.0 Hz, 1H), 7.09-7.07 (m, 2H), 6.96 (dd, J = 8.8, 2.0 Hz, 1H), 3.88 (d, J = 6.8 Hz, 2H), 3.73 (s, 3H), 2.63 (q, J = 7.6 Hz, 2H), 1.30 (m, 1H), 1.16 (t, J = 7.6 Hz, 3H), 0.60-0.55 (m, 2H), 0.25-0.22 (m, 2H). | 5-Ethyl-2-methoxybenzenesulfonyl chloride I112 6-(Cyclopropyl methoxy)benzo [d]isoxazol-3-amine I33 | FB | Purified by prep. HPLC |

TABLE F-continued

| | Name and structure | Analytical | Intermediates (if applicable) | Method | Notes |
|---|---|---|---|---|---|
| 135 | 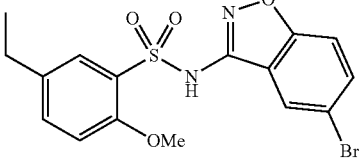<br>N-(5-Bromobenzo[d]isoxazol-3-yl)-5-ethyl-2-methoxybenzenesulfonamide | LCMS-D: R$_t$ 2.83 min, m/z 410.9 [M + H]$^+$; $^1$H NMR (400 MHz, DMSO-d$_6$) δ 11.8 (s, 1H), 8.25 (s, 1H), 8.78 (d, J = 8.8 Hz, 1H), 7.71 (s, 1H), 7.62 (d, J = 8.8 Hz, 1H), 7.48 (d, J = 8.0 Hz, 1H), 7.11 (d, J = 8.4 Hz, 1H), 3.72 (s, 3H), 3.64 (q, J = 7.2 Hz, 2H), 1.17 (t, J = 7.2 Hz, 3H). | 5-Ethyl-2-methoxybenzene-sulfonyl chloride I112 5-Bromobenzo[d]isoxazol-3-amine I40 | FA | 2 eq. LiHMDS and 2 eq. sulfonyl chloride used. Prep. TLC (Pet. ether/EtOAc = 2/1) |
| 136 | 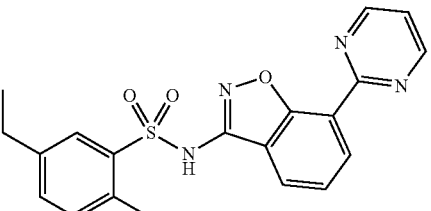<br>5-Ethyl-2-methoxy-N-(7-(pyrimidin-2-yl)benzo[d]isoxazol-3-yl)benzenesulfonamide | LCMS-D: R$_t$ 2.52 min, m/z 411.1 [M + H]$^+$; $^1$H NMR (400 MHz, methanol-d$_4$/CDCl$_3$) δ 8.87 (d, J = 4.8 Hz, 2H), 8.51 (d, J = 7.6 Hz, 1H), 8.15-8.13 (m, 1H), 7.76 (d, J = 2.4 Hz, 1H), 7.49 (t, J = 8.0 Hz, 1H), 7.37-7.33 (m, 2H), 6.95 (d, J = 8.8 Hz, 1H), 3.81 (s, 3H), 2.61 (q, J = 7.6 Hz, 2H), 1.18 (t, J = 7.6 Hz, 3H). | 5-Ethyl-2-methoxybenzene-sulfonyl chloride I112 7-(Pyrimidin-2-yl)benzo[d]isoxazol-3-amine I68 | FB | Prep. TLC (Pet. ether/EtOAc = 1/1) |
| 137 | 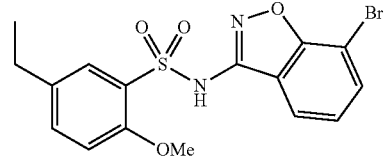 [SMILES: CCc1ccc(OC)c(S(=O)(=O)Nc2noc3c(Br)cccc23)c1]<br>N-(7-Bromobenzo[d]isoxazol-3-yl)-5-ethyl-2-methoxybenzenesulfonamide | LCMS-D: R$_t$ 2.85 min, m/z 411.0 [M + H]$^+$; $^1$H NMR (400 MHz, DMSO-d$_6$) δ 11.9 (s, 1H), 8.08 (d, J = 8.0 Hz, 1H), 7.89 (d, J = 7.2 Hz, 1H), 7.71 (d, J = 2.0 Hz, 1H), 7.48 (d, J = 8.4 Hz, 1H), 7.34 (d, J = 7.6 Hz, 1H), 7.10 J = 8.4 Hz, 1H), 3.71 (s, 3H), 2.64 (q, J = 7.6 Hz, 2H), 1.17 (t, J = 7.6 Hz, 3H). | 5-Ethyl-2-methoxybenzene-sulfonyl chloride I112 7-Bromobenzo[d]isoxazol-3-amine I66 | FB | 3 eq. sulfonyl chloride used. Prep. TLC (Pet. ether/EtOAc = 5/1) |
| 138 | 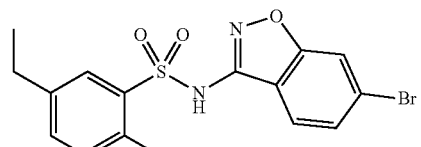<br>N-(6-Bromobenzo[d]isoxazol-3-yl)-5-ethyl-2-methoxybenzenesulfonamide | LCMS-D: R$_t$ 2.93 min, m/z 411.0 [M + H]$^+$; $^1$H NMR (400 MHz, DMSO-d$_6$) δ 11.8 (s, 1H), 8.08-7.99 (m, 2H), 7.70 (d, J = 2.0 Hz, 1H), 7.58 (dd, J = 8.8, 1.6 Hz, 1H), 7.48 (dd, J = 8.8, 2.0 Hz, 1H), 7.10 (d, J = 8.4 Hz, 1H), 3.71 (s, 3H), 2.64 (q, J = 7.6 Hz, 2H), 1.17 (t, J = 7.6 Hz, 3H). | 5-Ethyl-2-methoxybenzene-sulfonyl chloride I112 6-Bromobenzo[d]isoxazol-3-amine I75 | FB | 1.8 eq. sulfonyl chloride used. Column chromatography (Pet. ether/EtOAc = 100/0 to 5/1) |

TABLE F-continued

| | Name and structure | Analytical | Intermediates (if applicable) | Method | Notes |
|---|---|---|---|---|---|
| 139 | 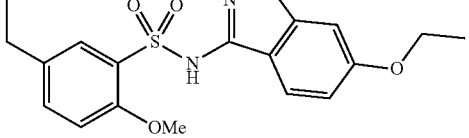<br>N-(6-Ethoxybenzo[d]isoxazol-3-yl)-5-ethyl-2-methoxybenzenesulfonamide | LCMS-D: R$_t$ 2.76 min, m/z 377.1 [M + H]$^+$; $^1$H NMR (400 MHz, DMSO-d$_6$) δ 11.5 (s, 1H), 7.88 (d, J = 8.8 Hz, 1H), 7.66 (d, J = 2.0 Hz, 1H), 7.47-7.44 (m, 1H), 7.11-7.08 (m, 1H), 6.94 (dd, J = 8.8, 2.0 Hz, 1H), 4.11 (q, J = 7.2 Hz, 2H), 3.73 (s, 3H), 2.63 (q, J = 7.6 Hz, 2H), 1.36 (t, J = 7.2 Hz, 3H), 1.17 (t, J = 7.6 Hz, 3H). | 5-Ethyl-2-methoxybenzene-sulfonyl chloride I112 6-Ethoxy benzo[d]isoxazol-3-amine I32 | FB | Column chromatography (Pet. ether/ EtOAc = 100/0 to 5/1) |
| 140 | 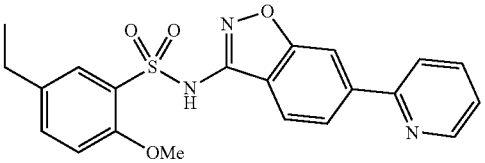<br>5-Ethyl-2-methoxy-N-(6-(pyridin-2-yl)benzo[d]isoxazol-3-yl)benzenesulfonamide | LCMS-D: R$_t$ 2.63 min, m/z 410.1 [M + H]$^+$; $^1$H NMR (400 MHz, DMSO-d$_6$) δ 11.8 (s, 1H), 8.74-8.69 (m, 1H), 8.26 (s, 1H), 8.18-8.09 (m, 3H), 7.98-7.90 (m, 1H), 7.72 (d, J = 2.3 Hz, 1H), 7.50-7.39 (m, 2H), 7.13-7.06 (m, 1H), 3.73 (s, 3H), 2.61 (q, J = 7.6 Hz, 2H), 1.15 (t, J = 7.6 Hz, 3H). | 5-Ethyl-2-methoxybenzene-sulfonyl chloride I112 6-(Pyridin-2-yl)benzo[d] isoxazol-3-amine I74 | FB | Column chromatography (DCM/ MeOH = 100/0 to 100/1) |
| 141 | 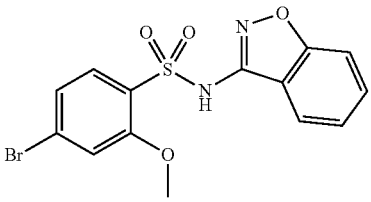 [SMILES: COc1cc(Br)ccc1S(=O)(=O)Nc1noc2ccccc12]<br>N-(benzo[d]isoxazol-3-yl)-4-bromo-2-methoxybenzenesulfonamide | LCMS-D: R$_t$ 2.58 min, m/z 382.9 [M + H]$^+$; | 4-Bromo-2-methoxybenzene-sulfonyl chloride I110 | FB | 1.2 eq. sulfonyl chloride used. Column chromatography (Pet. ether/ EtOAc = 5/1 to 2/1) |
| 142 | 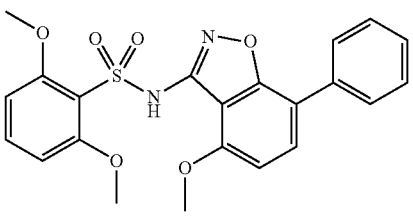 [SMILES: COc1cccc(OC)c1S(=O)(=O)Nc1noc2c(-c3ccccc3)ccc(OC)c12]<br>2,6-Dimethoxy-N-(4-methoxy-7-phenylbenzo[d]isoxazol-3-yl)benzenesulfonamide | LCMS-C: R$_t$ 2.39 min, m/z 441.0 [M + H]$^+$; $^1$H NMR (400 MHz, DMSO-d$_6$) δ 9.62 (s, 1H), 7.90-7.69 (m, 3H), 7.59-7.32 (m, 4H), 6.97 (d, J = 8.4 Hz, 1H), 6.86-6.73 (m, 2H), 3.98 (s, 3H), 3.79 (s, 6H). | 2,6-Dimethoxy benzenesulfonyl chloride I111 4-Methoxy-7-phenylbenzo[d] isoxazol-3-amine I80 | FA | 4 eq. LiHMDS used, stirred 2 h before adding sulfonyl chloride. Prep. TLC (DCM/ MeOH = 100/1) |

TABLE F-continued

| | Name and structure | Analytical | Intermediates (if applicable) | Method | Notes |
|---|---|---|---|---|---|
| 143 | 2,6-Dimethoxy-N-(4-methoxy-7-(1-methyl-1H-pyrazol-4-yl)benzo[d]isoxazol-3-yl)benzenesulfonamide | LCMS-C: $R_t$ 1.89 min, m/z 445.0 [M + H]$^+$; $^1$H NMR (400 MHz, DMSO-$d_6$) δ 9.58 (s, 1H), 8.22 (s, 1H), 7.96 (s, 1H), 7.80 (d, J = 8.2 Hz, 1H), 7.50 (t, J = 8.5 Hz, 1H), 6.88 (d, J = 8.3 Hz, 1H), 6.78 (d, J = 8.5 Hz, 2H), 3.95 (s, 3H), 3.88 (s, 3H), 3.79 (s, 6H). | 2,6-Dimethoxy benzenesulfonyl chloride I111 4-Methoxy-7-(1-methyl-1H-pyrazol-4-yl)benzo[d]isoxazol-3-amine I82 | FA | 4 eq. LiHMDS used, stirred 2 h before adding sulfonyl chloride. Prep. TLC (DCM/MeOH = 30/1) |
| 144 | 2,6-Dimethoxy-N-(4-methoxy-6-(oxazol-2-yl)benzo[d]isoxazol-3-yl)benzenesulfonamide | LCMS-C: $R_t$ 1.81 min, m/z 431.9 [M + H]$^+$; $^1$H NMR (400 MHz, DMSO-$d_6$) δ 9.81 (s, 1H), 8.33 (d, J = 0.9 Hz, 1H), 7.73 (d, J = 0.9 Hz, 1H), 7.51 (t, J = 8.5 Hz, 1H), 7.48 (d, J = 0.8 Hz, 1H), 7.38 (d, J = 1.0 Hz, 1H), 6.79 (d, J = 8.5 Hz, 2H), 4.01 (s, 3H), 3.78 (s, 6H). | 2,6-Dimethoxy benzenesulfonyl chloride I111 4-Methoxy-6-(oxazol-2-yl)benzo[d]isoxazol-3-amine I86 | FA | Stirred 2 h before adding sulfonyl chloride. Prep. TLC (DCM/MeOH = 75/1) |
| 145 | N-(5-Chloro-4-methoxy-6-(methoxymethyl)benzo[d]isoxazol-3-yl)-2,6-dimethoxybenzenesulfonamide | LCMS-C: $R_t$ 2.27 min, m/z 442.9 [M + H]$^+$; $^1$H NMR (400 MHz, DMSO-$d_6$) δ 10.4 (s, 1H), 7.56-7.49 (m, 2H), 6.80 (d, J = 8.5 Hz, 2H), 4.58 (s, 2H), 3.93 (s, 3H), 3.78 (s, 6H), 3.41 (s, 3H). | 2,6-Dimethoxy benzenesulfonyl chloride I111 5-Chloro-4-methoxy-6-(methoxymethyl)benzo[d]isoxazol-3-amine I83 | FA | 1.5 eq. LiHMDS used, stirred 2 h before adding 2 eq. sulfonyl chloride. Prep. TLC (DCM/MeOH = 100/1) |
| 146 | 2,6-Dimethoxy-N-(4-methoxy-6-(pyridin-2-yl)benzo[d]isoxazol-3-yl)benzenesulfonamide | LCMS-C: $R_t$ 1.89 min, m/z 442.0 [M + H]$^+$; $^1$H NMR (400 MHz, DMSO-$d_6$) δ 9.67 (s, 1H), 8.75-8.68 (m, 1H), 8.15 (d, J = 8.0 Hz, 1H), 7.98-7.90 (m, 1H), 7.86 (s, 1H), 7.59 (s 1H), 7.51 (t, J = 8.5 Hz, 1H), 7.47-7.41 (m, 1H), 6.79 (d, J = 8.6 Hz, 2H), 4.02 (s, 3H), 3.79 (s, 6H). | 2,6-Dimethoxy benzenesulfonyl chloride I111 4-Methoxy-6-(pyridin-2-yl)benzo[d]isoxazol-3-amine I77 | FA | 4 eq. LiHMDS used and stirred 1 h before adding sulfonyl chloride. Prep. TLC (DCM/MeOH = 50/1) |

TABLE F-continued

| Name and structure | Analytical | Intermediates (if applicable) | Method | Notes |
|---|---|---|---|---|
| 147 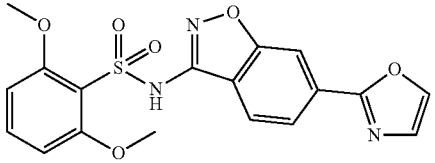 [SMILES: COc1cccc(OC)c1S(=O)(=O)Nc1noc2cc(-c3ncco3)ccc12] 2,6-Dimethoxy-N-(6-(oxazol-2-yl)benzo[d]isoxazol-3-yl)benzenesulfonamide | LCMS-D: R$_t$ 2.31 min, m/z 401.8 [M + H]$^+$; $^1$H NMR (400 MHz, DMSO-d$_6$) δ 11.6 (s, 1H), 8.32 (s, 1H), 8.19-8.18 (m, 1H), 8.07 (s, 1H), 7.96 (d, J = 8.4 Hz, 1H), 7.45-7.40 (m, 2H), 6.73 (d, J = 8.4 Hz, 2H), 3.71 (s, 6H). | 2,6-Dimethoxy benzenesulfonyl chloride I111 6-(Oxazol-2-yl)benzo[d]isoxazol-3-amine I90 | FB | Prep. TLC (Pet. ether/ EtOAc = 1/1) |

Example 148: N-(benzo[d]isoxazol-3-yl)-2,4-dimethoxybenzenesulfonamide 148

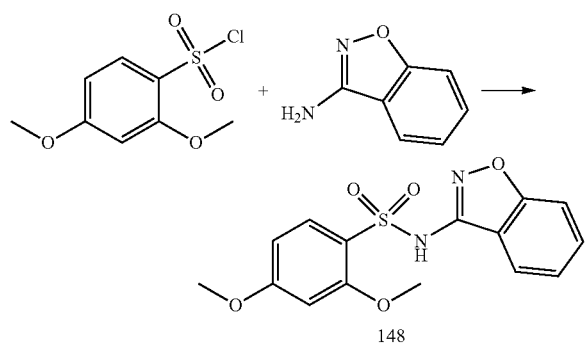

148

A solution of 2,4-dimethoxybenzenesulfonyl chloride (0.18 g, 0.75 mmol) and benzo[d]isoxazol-3-amine (0.10 g, 0.75 mmol) in pyridine (1 mL) was irradiated in the microwave at 110° C. for 2 hours. The resultant mixture was loaded onto silica gel and the product purified twice by column chromatography (4 g SiO$_2$ cartridge, 0-45% EtOAc in petroleum benzine 40-60° C. then 4 g SiO$_2$ cartridge, 0-35% EtOAc in petroleum benzine 40-60° C.) to yield two batches (78 mg and 5 mg) of the title compound (total mass 83 mg, 33% yield) as white solids. $^1$H NMR (400 MHz, CDCl$_3$) δ 8.11 (d, J=8.05 Hz, 1H), 7.79 (s, 1H), 7.70 (d, J=8.81 Hz, 1H), 7.57-7.50 (m, 1H), 7.47-7.40 (m, 1H), 7.37-7.29 (m, 1H), 6.50 (d, J=2.27 Hz, 1H), 6.42 (dd, J=2.25, 8.81 Hz, 1H), 3.98 (s, 3H), 3.81 (s, 3H). LCMS-B: rt 3.20 min, m/z=356.8 [M+Na]$^+$, 334.8 [M+H]$^+$.

Example 149: N-(benzo[d]isoxazol-3-yl)-2,6-dimethoxybenzenesulfonamide 149

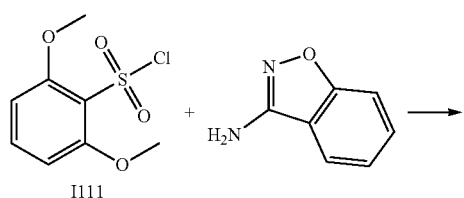

I111

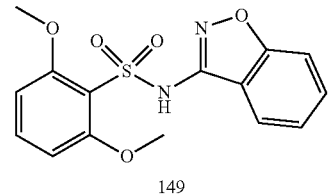

149

A solution of 2,6-dimethoxybenzene-1-sulfonyl chloride I111 (0.088 g, 0.37 mmol) and benzo[d]isoxazol-3-amine (0.050 g, 0.37 mmol) in pyridine (1 mL) was irradiated in the microwave at 110° C. for 2 hours, then at 120° C. for 2 hours. The reaction mixture was loaded onto silica and purified by column chromatography (12 g SiO$_2$ cartridge, 0-35% EtOAc in petroleum benzine 40-60° C.) to give the title compound (3.9 mg, 3.1% yield) as a white solid. $^1$H NMR (400 MHz, CDCl$_3$) δ 8.30 (s, 1H), 8.17 (dt, J=1.04, 8.15 Hz, 1H), 7.55-7.47 (m, 1H), 7.47-7.34 (m, 2H), 7.34-7.28 (m, 1H), 6.60 (d, J=8.52 Hz, 2H), 3.91 (s, 6H). LCMS-B: rt 3.13 min, m/z=334.8 [M+H]$^+$.

Example 150: N-(5-chlorobenzo[d]isoxazol-3-yl)-5-ethyl-2-methoxybenzenesulfonamide 150

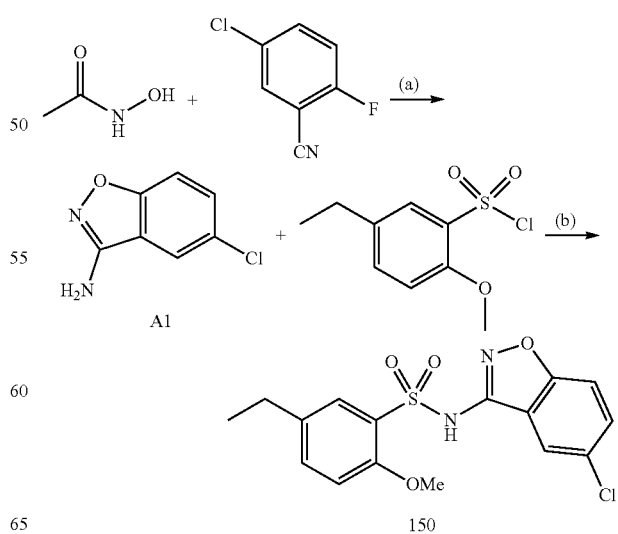

150 a) 5-Chlorobenzo[d]isoxazol-3-amine A1

Potassium tert-butoxide (793 mg, 7.07 mmol) was added to a suspension of acetohydroxamic acid (531 mg, 7.07 mmol) in DMF (10 mL) and stirred at room temperature for 30 minutes. 5-Chloro-2-fluorobenzonitrile (1.00 g, 6.43 mmol) was added and the reaction heated to 50° C. for 1 hour. Upon cooling, the reaction mixture was diluted with an aqueous saturated solution of NaCl (15 mL), the aqueous layer was extracted with EtOAc (3×100 mL), the organics were combined, dried (Na$_2$SO$_4$), filtered and the volatiles were removed in vacuo. The residue was loaded onto silica gel and the product purified by column chromatography (Biotage Isolera, 40 g SiO$_2$ cartridge, 0-40% EtOAc in petroleum benzine 40-60° C.) to yield the title compound as a white solid (507 mg, 47%). $^1$H NMR (400 MHz, DMSO-d$_6$) δ=7.94 (dd, J=2.1, 0.6, 1H), 7.59-7.48 (m, 1H), 6.51 (s, 1H).

b) N-(5-chlorobenzo[d]isoxazol-3-yl)-5-ethyl-2-methoxybenzenesulfonamide 150

A suspension of 5-ethyl-2-methoxybenzene-1-sulfonyl chloride (150 mg, 0.639 mmol) and 5-chlorobenzo[d]isoxazol-3-amine A1 (108 mg, 0.639 mmol) in pyridine (1.5 mL) was irradiated in the microwave at 110° C. for 2 hours. A 10 M aqueous solution of KOH (1 mL) was added and the resultant mixture was stirred for 4 hours at room temperature. The reaction mixture was loaded onto silica gel and the product purified by column chromatography (0-100% EtOAc in petroleum benzine 40-60° C.) to yield the title compound as a white solid (53 mg, 23%). $^1$H NMR (400 MHz, DMSO-d$_6$) δ=8.11 (t, J=1.4, 1H), 7.71 (d, J=2.3, 1H), 7.68 (d, J=1.4, 2H), 7.48 (dd, J=8.5, 2.3, 1H), 7.10 (d, J=8.6, 1H), 3.72 (s, 3H), 2.62 (q, J=7.6, 2H), 1.16 (t, J=7.6, 3H). LCMS-A: rt 6.637 min; m/z 367.0 [M+H]$^+$.

Example 151: N-(4-chlorobenzo[d]isoxazol-3-yl) benzenesulfonamide 151

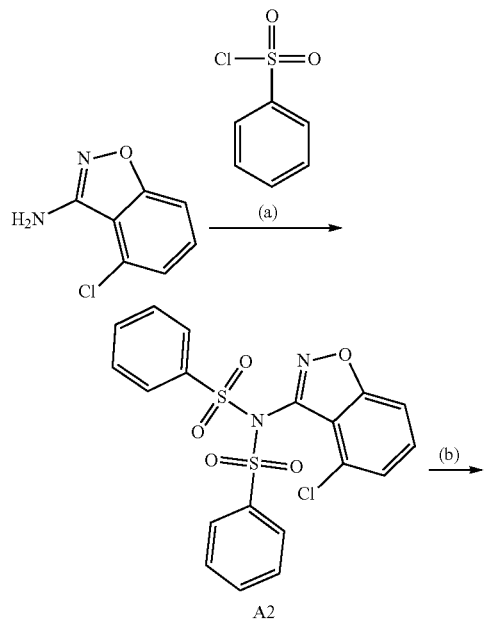

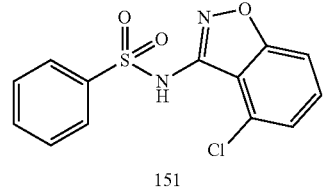

151 a) N-(4-chlorobenzo[d]isoxazol-3-yl)-N-(phenylsulfonyl)benzenesulfonamide A2

A solution of 4-chlorobenzo[d]isoxazol-3-amine (50 mg, 0.298 mmol) and benzenesulfonyl chloride (2 eq., 0.595 mmol) in pyridine (1.5 mL) was irradiated in the microwave for 2 hours at 100° C. Upon cooling, the reaction mixture was loaded onto silica gel and purified using silica gel column chromatography (Biotage Isolera, 24 g SiO$_2$ cartridge, 0-100% EtOAc in petroleum benzine 40-60° C.) to yield the title compound. $^1$H NMR (400 MHz, DMSO-d$_6$) δ=7.97 (d, J=8.6, 1H), 7.90-7.77 (m, 6H), 7.71-7.64 (m, 7H), 7.57 (d, J=7.7, 1H).

b) N-(4-chlorobenzo[d]isoxazol-3-yl)benzenesulfonamide 151

A suspension of N-(4-chlorobenzo[d]isoxazol-3-yl)-N-(phenylsulfonyl)benzenesulfonamide A2 (50 mg, 0.11 mmol) in THF (10 mL) and 10M KOH aqueous solution (1 mL) was stirred at room temperature for 16 hours. The reaction mixture was diluted with water (25 mL) and the aqueous layer extracted with EtOAc (3×50 mL), the combined organics were washed with brine (25 mL) dried (Na$_2$SO$_4$), filtered and concentrated under reduced pressure. The resulting gum was dissolved in a minimum amount of acetone before petroleum benzine 40-60° C. (50 mL) was added and the precipitate was filtered and air dried to give the title compound as a tan solid (10 mg, 29%). $^1$H NMR (400 MHz, DMSO-d$_6$) δ=7.89-7.80 (m, 2H), 7.41-7.30 (m, 4H), 7.26 (dd, J=8.3, 0.8, 1H), 7.10 (dd, J=7.5, 0.8, 1H). LCMS-A: rt 6.334 min, m/z 307.0 [M−H]$^-$.

Example 152: 5-Ethyl-N-(7-fluorobenzo[d]isoxazol-3-yl)-2-methoxybenzenesulfonamide 152

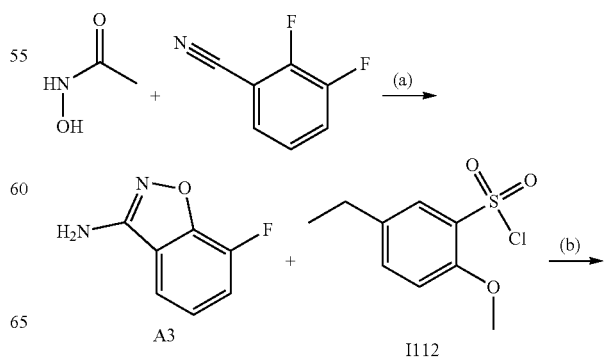

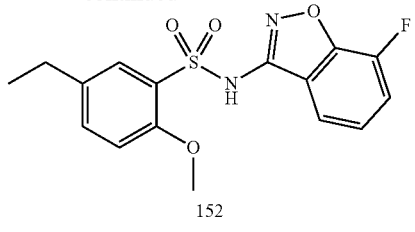

152

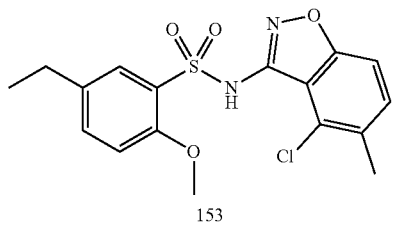

153 a) 7-Fluorobenzo[d]isoxazol-3-amine A3

Potassium tert-butoxide (887 mg, 7.91 mmol) was added to a suspension of acetohydroxamic acid (594 mg, 7.91 mmol) in DMF (10 mL) and the reaction was stirred at room temperature for 30 minutes. 2,3-Difluorobenzonitrile (1.00 g, 7.19 mmol) was added and the reaction was heated to 50° C. for 1 hour. Upon cooling, the reaction mixture was diluted with an aqueous saturated solution of NaCl (15 mL), the aqueous layer was extracted with EtOAc (3×100 mL) the organics were combined, dried (Na$_2$SO$_4$) and filtered and the volatiles were removed in vacuo. The resulting gum was loaded onto silica gel and purified by column chromatography (Biotage Isolera, 24 g SiO$_2$ cartridge, 0-100% EtOAc in petroleum benzine 40-60° C.) to yield the title compound as a white solid (303 mg, 27%). $^1$H NMR (400 MHz, CDCl$_3$) δ=7.33 (dd, J=7.6, 1.3, 1H), 7.30-7.26 (m, 1H), 7.26-7.19 (m, 1H), 4.45 (s, 2H). LCMS-B: rt 3.371 min, m/z 153.2 [M+H]$^+$.

b) 5-Ethyl-N-(7-fluorobenzo[d]isoxazol-3-yl)-2-methoxybenzenesulfonamide 152

A solution of 7-fluorobenzo[d]isoxazol-3-amine A3 (100 mg, 0.657 mmol) and 2-methoxy-5-ethylsulfonyl chloride I112 (154 mg, 0.657 mmol) in pyridine (2 mL) was irradiated in the microwave for 2 hours at 100° C. Upon cooling, the reaction mixture was loaded onto silica gel and purified by column chromatography (Biotage Isolera, 24 g SiO$_2$ cartridge, 0-100% EtOAc in petroleum benzine 40-60° C.) to yield the title compound as a white solid (127 mg, 55%). $^1$H NMR (400 MHz, DMSO-d$_6$) δ=7.91 (dd, J=8.1, 0.8, 1H), 7.73 (d, J=2.3, 1H), 7.57 (dd, J=11.9, 8.0, 1H), 7.48 (dd, J=8.5, 2.3, 1H), 7.38 (td, J=8.0, 4.1, 1H), 7.10 (d, J=8.6, 1H), 3.73 (s, 3H), 2.63 (q, J=7.6, 2H), 1.16 (t, J=7.6, 3H). LCMS-A: rt 6.429 min, m/z 351.1 [M+H]$^+$.

Example 153: N-(4-Chloro-5-methylbenzo[d]isoxazol-3-yl)-5-ethyl-2-methoxybenzenesulfonamide 153

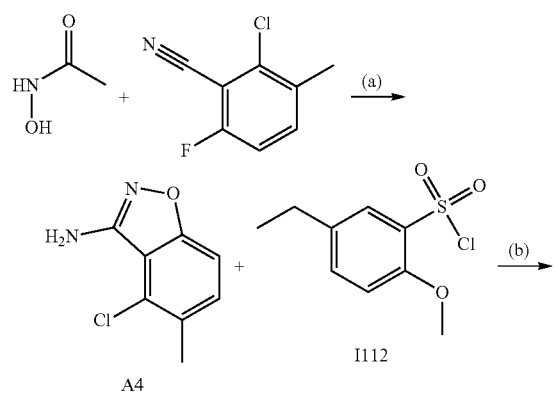

a) 4-Chloro-5-methylbenzo[d]isoxazol-3-amine A4

Potassium tert-butoxide (728 mg, 6.49 mmol) was added to a suspension of acetohydroxamic acid (487 mg, 6.49 mmol) in DMF (10 mL) and stirred at room temperature for 30 minutes. 2-Chloro-6-fluoro-3-methylbenzonitrile (1.00 g, 5.90 mmol) was added and the reaction heated to 50° C. for 1 hour. Upon cooling, the reaction mixture was diluted with an aqueous saturated solution of NaCl (15 mL), the aqueous layer was extracted with EtOAc (3×100 mL), the organics were combined, dried (Na$_2$SO$_4$), filtered and the volatiles were removed in vacuo. The resultant solid was sonicated in acetone (10 mL) before petroleum benzine 40-60° C. (50 mL) was added, the precipitate was collected by filtration and air dried to yield the product as a white solid (524 mg, 49%). $^1$H NMR (400 MHz, DMSO-d$_6$) δ=7.51 (d, J=8.5, 1H), 7.38 (d, J=8.5, 1H), 6.15 (s, 2H), 2.38 (s, 3H). LCMS-B: rt 3.562 min, m/z 183.1 [M+H]$^+$.

b) N-(4-Chloro-5-methylbenzo[d]isoxazol-3-yl)-5-ethyl-2-methoxybenzenesulfonamide 153

A solution of 4-chloro-5-methylbenzo[d]isoxazol-3-amine A4 (100 mg, 0.548 mmol) and 2-methoxy-5-ethylsulfonyl chloride I112 (129 mg, 0.548 mmol) in pyridine (2 mL) was irradiated in the microwave for 2 hours at 100° C. Upon cooling, the reaction mixture was added to water, the precipitate was removed by filtration and the filtrate was loaded onto silica gel and purified by column chromatography (Biotage Isolera, 24 g SiO$_2$ cartridge, 0-100% EtOAc in petroleum benzine 40-60° C.) to give the title compound as a white solid (33 mg, 16%). $^1$H NMR (400 MHz, DMSO-d$_6$) δ=10.48 (s, 1H), 7.69-7.57 (m, 3H), 7.48 (dd, J=8.5, 2.3, 1H), 7.15 (d, J=8.5, 1H), 3.68 (s, 3H), 2.60 (q, J=7.5, 2H), 2.42 (s, 3H), 1.15 (t, J=7.6, 3H). LCMS-A: rt 6.665 min, m/z 381.1 [M+H]$^+$.

Example 154: N-(4-chlorobenzo[d]isoxazol-3-yl)-5-ethyl-2-methoxybenzenesulfonamide 154

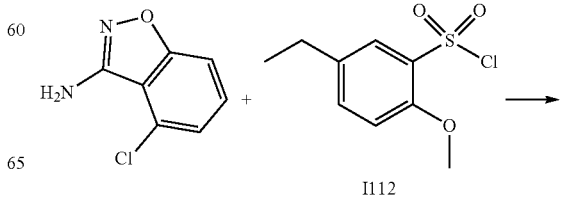

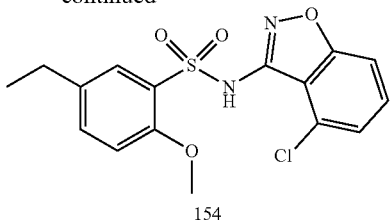

154

A mixture of 5-ethyl-2-methoxybenzenesulfonyl chloride I112 (0.414 g, 1.77 mmol) and 4-chlorobenzo[d]isoxazol-3-amine (0.225 g, 1.34 mmol) in pyridine (2.0 mL) was stirred at 30° C. for 40 hours under a nitrogen atmosphere. The reaction was concentrated, then sonicated for 2 hours with aqueous HCl (5%) and the resulting precipitate collected. The precipitate was purified using silica gel column chromatography (0-100% ethyl acetate/petroleum benzine 40-60° C.) to give the title compound as two fractions (A and B) with a combined yield of 0.060 g, 12% yield.

Fraction A: Yield 0.038 g. $^1$H NMR (400 MHz, acetone-$d_6$) δ 8.88 (br s, 1H), 7.75 (d, J=2.3 Hz, 1H), 7.66 (dd, J=8.5, 7.6 Hz, 1H), 7.57 (dd, J=8.5, 0.6 Hz, 1H), 7.49 (dd, J=8.5, 2.3 Hz, 1H), 7.42 (dd, J=7.6, 0.6 Hz, 1H), 7.14 (d, J=8.5 Hz, 1H), 3.91 (s, 3H), 2.66 (q, J=7.6 Hz, 2H), 1.21 (t, J=7.6 Hz, 3H). LCMS-B: rt 3.766 min; m/z 367.1/369.1 [M+H]$^+$.

Fraction B: Yield 0.021 g. $^1$H NMR (400 MHz, acetone-$d_6$) δ 8.88 (br s, 1H), 7.75 (d, J=2.3 Hz, 1H), 7.65 (dd, J=8.5, 7.6 Hz, 1H), 7.59-7.55 (m, 1H), 7.49 (dd, J=8.5, 2.3 Hz, 1H), 7.44-7.40 (m, 1H), 7.14 (d, J=8.5 Hz, 1H), 3.90 (s, 3H), 2.66 (q, J=7.6 Hz, 2H), 1.21 (t, J=7.6 Hz, 3H). LCMS-B: rt 3.755 min; m/z 367.1/369.1 [M+H]$^+$ Example 155: N-(4-chlorobenzo[d]isoxazol-3-yl)-2-methoxybenzenesulfonamide 155

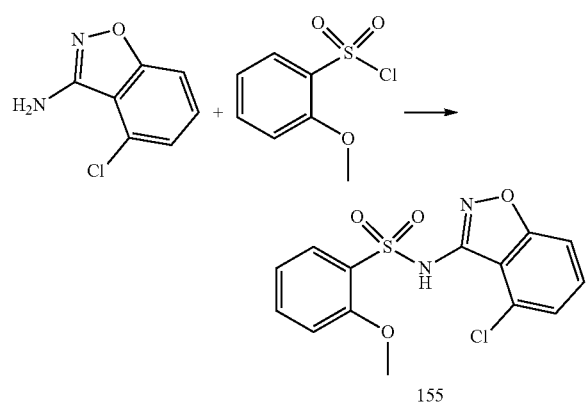

155

A mixture of 4-chlorobenzo[d]isoxazol-3-amine (0.034 g, 0.200 mmol) and 2-methoxybenzenesulfonyl chloride (0.092 g, 0.450 mmol) in pyridine (1.0 mL) and triethylamine (0.1 mL) was stirred at room temperature for 16 hours. The reaction was concentrated and diluted with 5% aqueous HCl (1 mL) and sonicated for a minimum of 30 minutes. The resulting precipitate was collected by filtration and purified using preparative mass-directed HPLC to give the title compound. $^1$H NMR (400 MHz, acetone-$d_6$) δ 7.94-7.91 (dd, J=7.8, 1.7 Hz, 1H), 7.69-7.63 (m, 2H), 7.60-7.57 (dd, J=8.5, 0.7 Hz, 1H), 7.44-7.42 (dd, J=7.6, 0.7 Hz, 1H), 7.25-7.22 (m, 1H), 7.16-7.11 (m, 1H), 3.94-3.94 (s, 3H). HPLC-MS: rt 6.02 min; m/z 339.16/341.18 [M+H]$^+$.

Example 156: N-(4-fluorobenzo[d]isoxazol-3-yl)-2-methoxybenzenesulfonamide

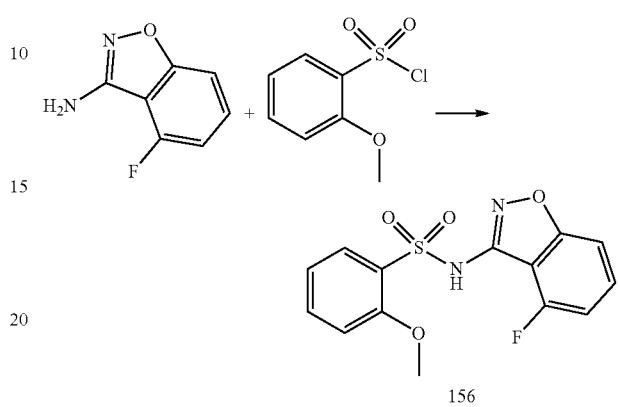

156

A mixture of 4-fluorobenzo[d]isoxazol-3-amine (0.032 g, 0.21 mmol) and 2-methoxybenzenesulfonyl chloride (0.109 g, 0.529 mmol) in pyridine (1.0 mL) and triethylamine (0.1 mL) was stirred at room temperature for 16 hours. The reaction was concentrated and diluted with 5% aqueous HCl (1 mL) and sonicated for a minimum of 30 minutes. The resulting precipitate was collected by filtration and purified using preparative mass-directed HPLC to give the title compound. $^1$H NMR (400 MHz, acetone-$d_6$) δ 9.73-9.45 (br s, 1H), 7.92-7.88 (dd, J=7.9, 1.7 Hz, 1H), 7.70-7.61 (m, 2H), 7.44-7.40 (d, J=8.5 Hz, 1H), 7.25-7.21 (d, J=8.3 Hz, 1H), 7.13-7.07 (m, 2H), 3.95-3.91 (s, 3H). HPLC-MS: rt 5.72 min; m/z 323.16 [M+H]$^+$.

Example 157: N-(6-bromobenzo[d]isoxazol-3-yl)-2-methoxybenzenesulfonamide 157

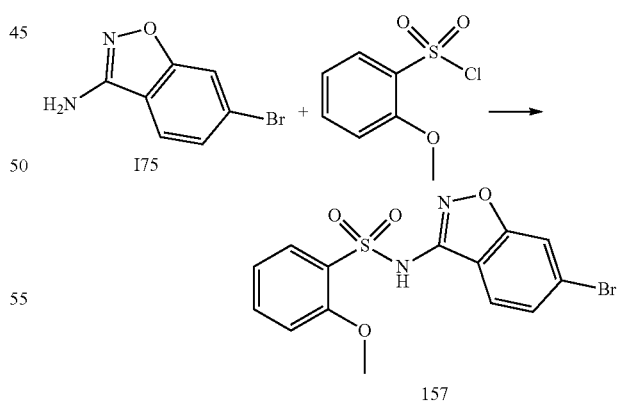

157

A mixture of 6-bromobenzo[d]isoxazol-3-amine I75 (0.039 g, 0.180 mmol) and 2-methoxybenzenesulfonyl chloride (0.101 g, 0.490 mmol) in pyridine (1.0 mL) and triethylamine (0.1 mL) was stirred at room temperature for 16 hours. The reaction was concentrated and diluted with 5% aqueous HCl (1 mL) and sonicated for a minimum of 30 minutes. The resulting precipitate was collected by filtration and purified using preparative mass-directed HPLC to give the title compound. ¹H NMR (400 MHz, acetone-d₆) δ 8.06-8.02 (dd, J=8.6, 0.5 Hz, 1H), 7.90-7.87 (dd, J=7.9, 1.7 Hz, 1H), 7.85-7.83 (dd, J=1.6, 0.5 Hz, 1H), 7.64-7.59 (ddd, J=8.4, 7.4, 1.8 Hz, 1H), 7.58-7.54 (dd, J=8.6, 1.6 Hz, 1H), 7.21-7.18 (dd, J=8.4, 0.8 Hz, 1H), 7.10-7.05 (m, 1H), 3.88-3.85 (s, 3H). HPLC-MS: rt 6.32 min; m/z 383.1/385.2 [M+H]⁺.

Example 158: N-(6-chlorobenzo[d]isoxazol-3-yl)-2-methoxybenzenesulfonamide 158

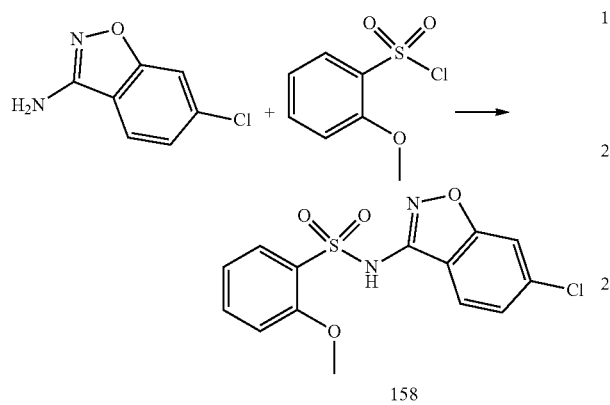

158

A mixture of 6-chlorobenzo[d]isoxazol-3-amine (0.033 g, 0.200 mmol) and 2-methoxybenzenesulfonyl chloride (0.095 g, 0.460 mmol) were stirred in pyridine (1.0 mL) and triethylamine (0.1 mL) at room temperature for 16 hours. The reaction was concentrated and diluted with 5% aqueous HCl (1 mL) and sonicated for a minimum of 30 min. The resulting precipitate was collected by filtration and purified using mass directed preparative HPLC to give the title compound. ¹H NMR (400 MHz, acetone-d₆) δ8.12-8.07 (dd, J=8.6, 0.5 Hz, 1H), 7.91-7.87 (dd, J=7.9, 1.7 Hz, 1H), 7.68-7.65 (dd, J=1.7, 0.5 Hz, 1H), 7.64-7.58 (ddd, J=8.4, 7.4, 1.8 Hz, 1H), 7.44-7.39 (dd, J=8.6, 1.7 Hz, 1H), 7.21-7.17 (m, 1H), 7.10-7.05 (m, 1H), 3.88-3.86 (s, 3H). HPLC-MS: rt 6.26 min; m/z 339.16/341.18 [M+H]⁺.

Example 159: N-(4-chlorobenzo[d]isoxazol-3-yl)isoquinoline-8-sulfonamide 159

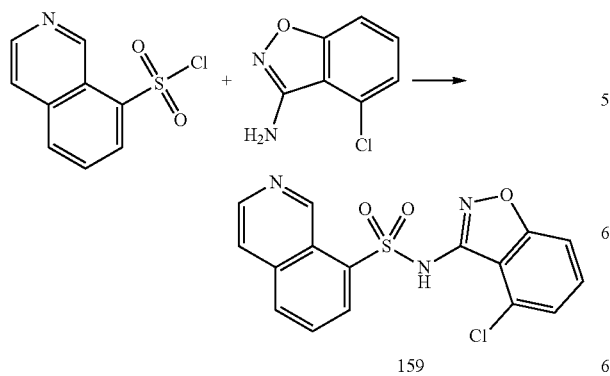

159

A solution of 4-chlorobenzo[d]isoxazol-3-amine (0.050 g, 0.30 mmol) in anhydrous THF (2 mL) was cooled to −78° C. under a nitrogen atmosphere. A solution of lithium bis(trimethylsilyl)amide (1.0 M in THF, 0.59 mL, 0.59 mmol) was cautiously added before the mixture was stirred at 0° C. for 1 hour. The mixture was cooled to −78° C., a solution of 8-isoquinolinesulfonyl chloride (0.068 g, 0.30 mmol) in anhydrous THF (1 mL) was added and the mixture was allowed to warm to room temperature. After stirring for 3 hours, TLC indicated only the presence of starting material. The mixture was cooled to −78° C., sodium hydride (60% dispersion in mineral oil, 0.059 g, 1.5 mmol) was added and the mixture was returned to room temperature and stirred overnight. Water (10 mL) was added and the pH was adjusted to ~3 with aq. HCl (2 M). The aqueous phase was extracted with DCM (3×20 mL), the organics were combined, dried (MgSO₄) and the solvent removed in vacuo. The solid residue was purified by column chromatography (Biotage Isolera, 12 g SiO₂ cartridge, 0-100% EtOAc in petroleum benzine 40-60° C., then 0-40% MeOH in EtOAc) to give the title compound as a white solid (0.026 g, 24%). ¹H NMR (400 MHz, DMSO-d₆) δ 10.31 (s, 1H), 8.53 (d, J=5.8 Hz, 1H), 8.28-8.21 (m, 1H), 8.09 (d, J=8.2 Hz, 1H), 7.92 (d, J=5.7 Hz, 1H), 7.89-7.82 (m, 1H), 7.39 (t, J=7.9 Hz, 1H), 7.31 (d, J=8.3 Hz, 1H), 7.17 (d, J=7.5 Hz, 1H). LCMS-A: rt 5.43 min; m/z 360.1 [M+H]⁺.

Example 160: N-(7-iodo-4-methoxy-6-(methoxymethyl)benzo[d]isoxazol-3-yl)-2,6-dimethoxybenzenesulfonamide 160

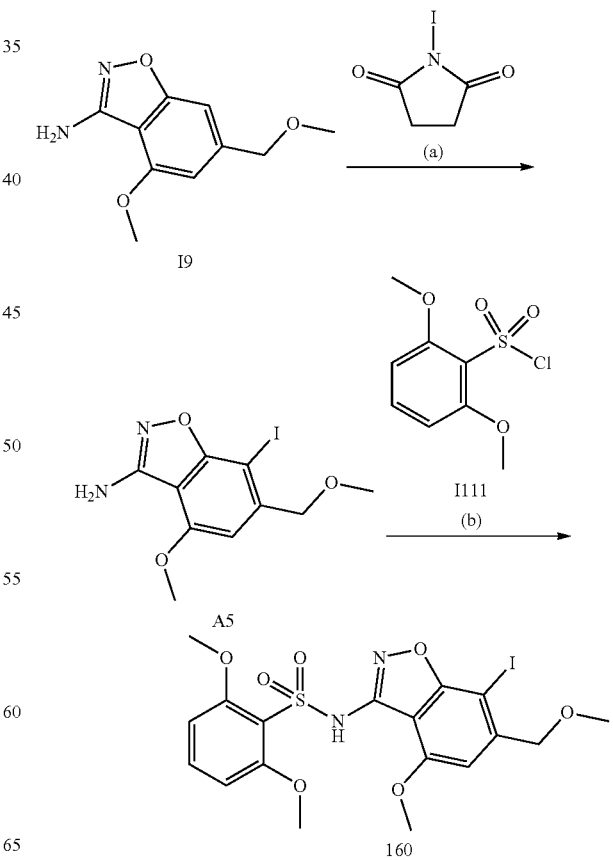

160 a) 7-iodo-4-methoxy-6-(methoxymethyl)benzo[d]isoxazol-3-amine A5

A portion of 4-methoxy-6-(methoxymethyl)benzo[d]isoxazol-3-amine I9 (0.121 g, 0.581 mmol) was dissolved in N,N-dimethylformamide (2 mL) and then N-iodosuccinimide (0.131 g, 0.581 mmol) was added. Upon completion of addition, the reaction mixture was heated at 50° C. for 2 h. At the conclusion of this period, the reaction mixture was poured over ice and then diluted with EtOAc (15 mL). The resulting mixture was washed with $H_2O$ (3×8 mL) and brine (8 mL), dried over $Na_2SO_4$ and filtered. The volatiles were removed under reduced pressure and the residue purified twice by column chromatography (12 g $SiO_2$ cartridge, 0-35% EtOAc in petroleum benzine 40-60° C. then 12 g $SiO_2$ cartridge, 0-25% EtOAc in petroleum benzine 40-60° C.) to give the title compound (0.038 g, 20% yield) as an off-white solid. $^1$H NMR (400 MHz, $CDCl_3$) δ 6.78 (s, 1H), 4.73 (s, 2H), 4.54 (s, 2H), 3.96 (s, 3H), 3.50 (s, 3H). LCMS-A: rt 3.26 min. m/z 334.7 [M+H]$^+$.

b) N-(7-iodo-4-methoxy-6-(methoxymethyl)benzo[d]isoxazol-3-yl)-2,6-dimethoxybenzenesulfonamide 160

A solution of 7-iodo-4-methoxy-6-(methoxymethyl)benzo[d]isoxazol-3-amine A5 (0.024 g, 0.099 mmol) and 2,6-dimethoxybenzenesulfonyl chloride I111 (0.023 g, 0.099 mmol) in pyridine (0.5 mL) was irradiated in the microwave at 110° C. for 2 h. The reaction mixture was cooled to room temperature and wet-loaded onto a silica cartridge. The residue was purified by column chromatography (12 g $SiO_2$ cartridge, 0-70% EtOAc in petroleum benzine 40-60° C.) to give the title compound (0.032 g, 53% yield) as a white solid. $^1$H NMR (400 MHz, $CDCl_3$) δ 7.38 (t, J=8.5 Hz, 1H), 6.86 (s, 1H), 6.58 (d, J=8.5 Hz, 2H), 4.52 (s, 2H), 4.04 (s, 3H), 3.88 (s, 6H), 3.51 (s, 3H). LCMS-A: rt 5.86 min, m/z 534.6 [M+H]$^+$.

Example 161: N-(7-chloro-4-methoxy-6-(methoxymethyl)benzo[d]isoxazol-3-yl)-2,6-dimethoxybenzenesulfonamide 161

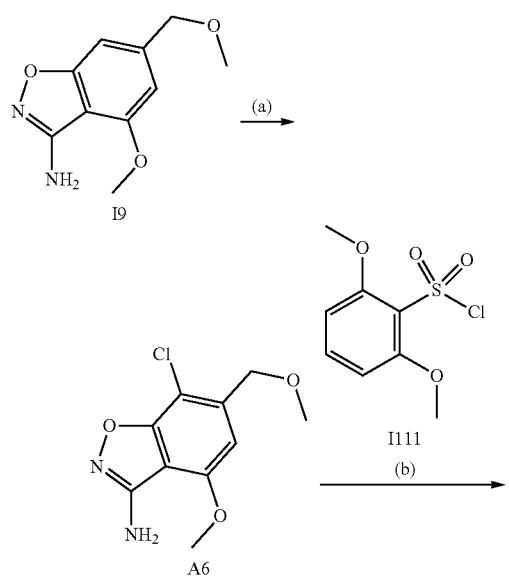

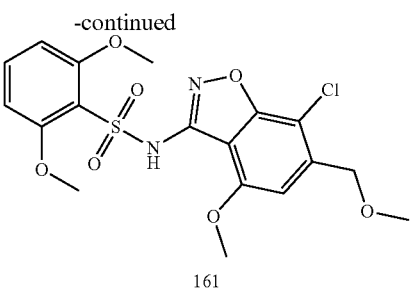

a) 7-Chloro-4-methoxy-6-(methoxymethyl)benzo[d]isoxazol-3-amine A6

4-Methoxy-6-(methoxymethyl)benzo[d]isoxazol-3-amine I9 (0.150 g, 0.720 mmol) was dissolved in N,N-dimethylformamide (2 mL) and then N-chlorosuccinimide (96 mg, 0.72 mmol) was added. Upon completion of addition, the reaction mixture was heated at 50° C. for 2 hours. At the conclusion of this period, the reaction mixture was poured over ice and then diluted with EtOAc (15 mL). The resulting mixture was washed with $H_2O$ (3×8 mL) and brine (8 mL), dried over $Na_2SO_4$ and filtered. The volatiles were removed under reduced pressure and the residue purified by column chromatography (12 g $SiO_2$ cartridge, 0-40% EtOAc in petroleum benzine 40-60° C.) to give the title compound (0.0240 g, 14% yield) as a white solid. $^1$H NMR (400 MHz, $CDCl_3$) δ 6.77 (s, 1H), 4.63 (d, J=0.6 Hz, 2H), 3.97 (s, 3H), 3.49 (s, 3H).

b) N-(7-chloro-4-methoxy-6-(methoxymethyl)benzo[d]isoxazol-3-yl)-2,6-dimethoxybenzene-sulfonamide 161

A solution of 7-chloro-4-methoxy-6-(methoxymethyl)benzo[d]isoxazol-3-amine A6 (0.024 g, 0.099 mmol) and 2,6-dimethoxybenzenesulfonyl chloride I111 (0.023 g, 0.099 mmol) in pyridine (0.5 mL) was irradiated in the microwave at 110° C. for 2 hours. The reaction mixture was cooled to room temperature and wet-loaded onto a silica cartridge. The residue was purified by column chromatography (12 g $SiO_2$ cartridge, 0-100% EtOAc in petroleum benzine 40-60° C.) to give the title compound (0.0094 g, 21% yield) as a white solid. $^1$H NMR (400 MHz, $CDCl_3$) δ 8.20 (s, 1H), 7.39 (t, J=8.5 Hz, 1H), 6.85 (s, 1H), 6.59 (d, J=8.5 Hz, 2H), 4.61 (d, J=0.6 Hz, 2H), 4.04 (s, 3H), 3.88 (s, 6H), 3.49 (s, 3H). LCMS-F: rt 6.39 min, m/z 442.8 [M+H]$^+$.

Example 162: 5-methoxy-N-(4-methoxy-6-(methoxymethyl)benzo[d]isoxazol-3-yl)quinoline-8-sulfonamide 162

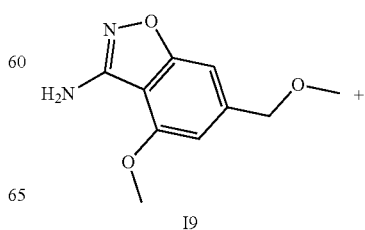

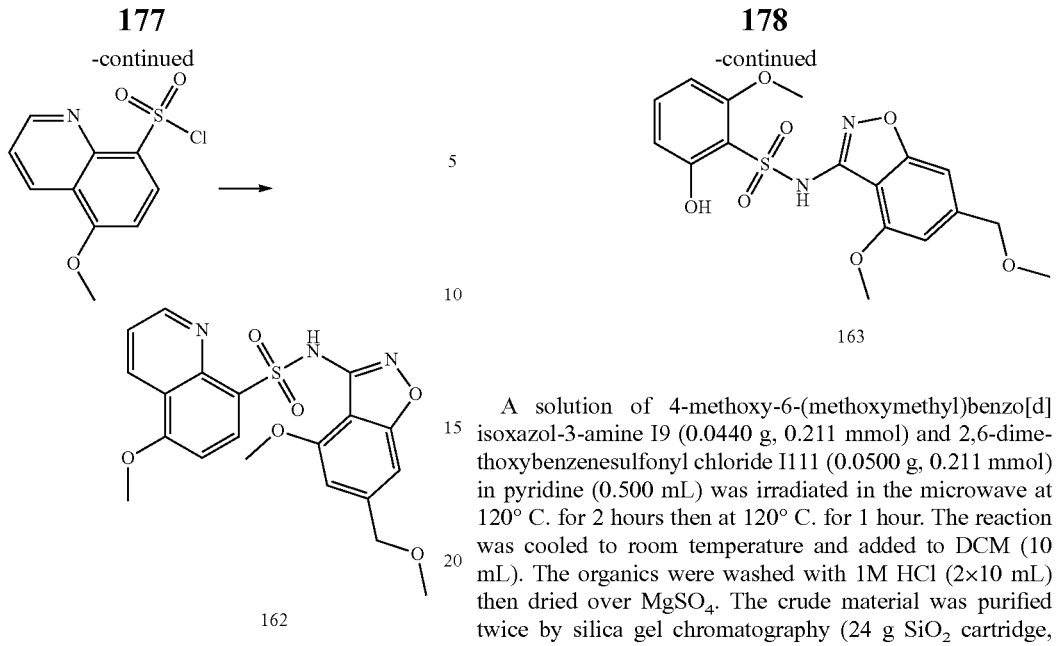

A solution of 4-methoxy-6-(methoxymethyl)benzo[d]isoxazol-3-amine I9 (0.0500 g, 0.240 mmol) and 5-methoxyquinoline-8-sulfonyl chloride (0.0619 g, 0.240 mmol) in pyridine (0.500 mL) was irradiated in the microwave at 110° C. for 2 hours. The reaction was cooled to room temperature and added to DCM (10 mL). The organic layer was washed with 0.5 M HCl (10 mL) and the layers separated by phase separation cartridge. The collected organic layers was dried in vacuo and the residue purified by column chromatography (12 g SiO$_2$ cartridge, 0-80% EtOAc in petroleum benzine 40-60° C.) to give the title compound (0.0110 g, 11% yield) as an off-white solid. $^1$H NMR (400 MHz, CDCl$_3$) δ 8.98 (dd, J=4.3, 1.8 Hz, 1H), 8.64-8.53 (m, 2H), 7.45 (dd, J=8.5, 4.3 Hz, 1H), 6.91 (d, J=8.4 Hz, 1H), 6.87 (d, J=0.9 Hz, 1H), 6.54 (s, 1H), 4.44 (s, 2H), 4.05 (s, 3H), 4.03 (s, 3H), 3.36 (s, 3H). LCMS-B: rt 3.49 min, m/z=429.8 [M+H]$^+$.

Example 163: 2-hydroxy-6-methoxy-N-(4-methoxy-6-(methoxymethyl)benzo[d]isoxazol-3-yl)benzenesulfonamide 163

A solution of 4-methoxy-6-(methoxymethyl)benzo[d]isoxazol-3-amine I9 (0.0440 g, 0.211 mmol) and 2,6-dimethoxybenzenesulfonyl chloride I111 (0.0500 g, 0.211 mmol) in pyridine (0.500 mL) was irradiated in the microwave at 120° C. for 2 hours then at 120° C. for 1 hour. The reaction was cooled to room temperature and added to DCM (10 mL). The organics were washed with 1M HCl (2×10 mL) then dried over MgSO$_4$. The crude material was purified twice by silica gel chromatography (24 g SiO$_2$ cartridge, 0-85% EtOAc in petroleum benzine 40-60° C. then 12 g SiO$_2$ cartridge, 0-75% EtOAc in petroleum benzine 40-60° C.) to give the title compound (1.5 mg). $^1$H NMR (400 MHz, CDCl$_3$) δ 9.62 (s, 1H), 8.14 (s, 1H), 7.33 (t, J=8.4 Hz, 1H), 6.99 (q, J=0.9 Hz, 1H), 6.70-6.61 (m, 2H), 6.37 (dd, J=8.3, 1.0 Hz, 1H), 4.51 (s, 1H), 4.03 (s, 3H), 3.87 (s, 3H), 3.42 (s, 3H). LCMS-A: rt 3.54 min, m/z 394.8 [M+H]$^{30}$ Example 164: 6-methoxy-N-(6-(methoxymethyl)-5-methylbenzo[d]isoxazol-3-yl)pyridine-3-sulfonamide 164

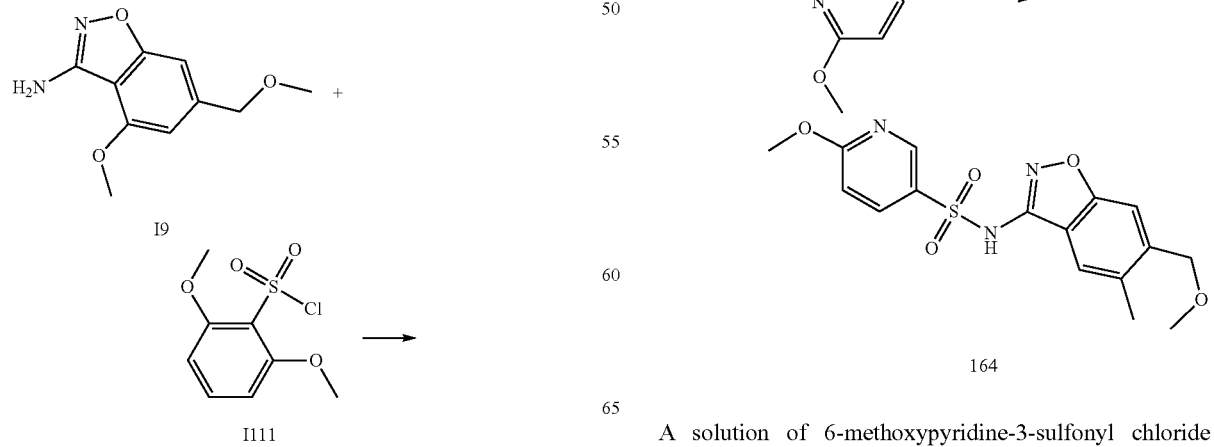

A solution of 6-methoxypyridine-3-sulfonyl chloride (0.0540 g, 0.260 mmol) and 6-(methoxymethyl)-5-methylbenzo[d]isoxazol-3-amine I4 (0.050 g, 0.26 mmol) in pyridine (0.500 mL) was irradiated in the microwave at 120° C. for 2 hours. The reaction was cooled to room temperature then taken up in DCM and washed (×2) with 1M HCl. The organic layer was dried in vacuo then wet-loaded onto silica gel and the product purified by column chromatography (24 g SiO$_2$ cartridge, 0-80% EtOAc in petroleum benzine 40-60° C.) to give the title compound (15.6 mg, 17% yield) as a colourless oil. $^1$H NMR (400 MHz, CDCl$_3$) δ 8.63 (dd, J=0.71, 2.62 Hz, 1H), 7.99-7.89 (m, 2H), 7.72 (s, 1H), 7.55 (s, 1H), 6.75 (dd, J=0.71, 8.94 Hz, 1H), 4.54 (s, 2H), 3.95 (s, 3H), 3.50 (s, 3H), 2.39 (s, 3H). LCMS-F: rt 6.39 min, m/z 348.1 [M+H]$^+$.

Example 165: N-(6-(methoxymethyl)-5-methyl-benzo[d]isoxazol-3-yl)pyridine-3-sulfonamide 165

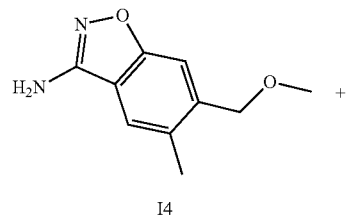

I4

A solution of pyridine-3-sulfonyl chloride (0.0462 g, 0.260 mmol) and 6-(methoxymethyl)-5-methylbenzo[d]isoxazol-3-amine I4 (0.050 g, 0.26 mmol) in pyridine (0.500 mL) was irradiated in the microwave at 120° C. for 2 hours. The reaction was cooled to room temperature then wet-loaded onto silica gel and the product purified by column chromatography (24 g SiO$_2$ cartridge, 0-80% EtOAc in petroleum benzine 40-60° C.) to give the title compound (0.0220 g, 25% yield) as a yellow solid. $^1$H NMR (400 MHz, CDCl$_3$) δ 9.09 (s, 1H), 8.83 (s, 1H), 8.18 (d, J=8.09 Hz, 1H), 7.70 (s, 1H), 7.57 (s, 1H), 7.46 (s, 1H), 4.54 (s, 2H), 3.50 (s, 3H), 2.40 (s, 3H). LCMS-F: rt 6.12 min m/z 334.1 [M+H]$^+$, 332.0 [M–H]$^–$.

Example 166: 2,4-dimethoxy-N-(6-(methoxymethyl)-5-methylbenzo[d]isoxazol-3-yl)benzenesulfonamide 166

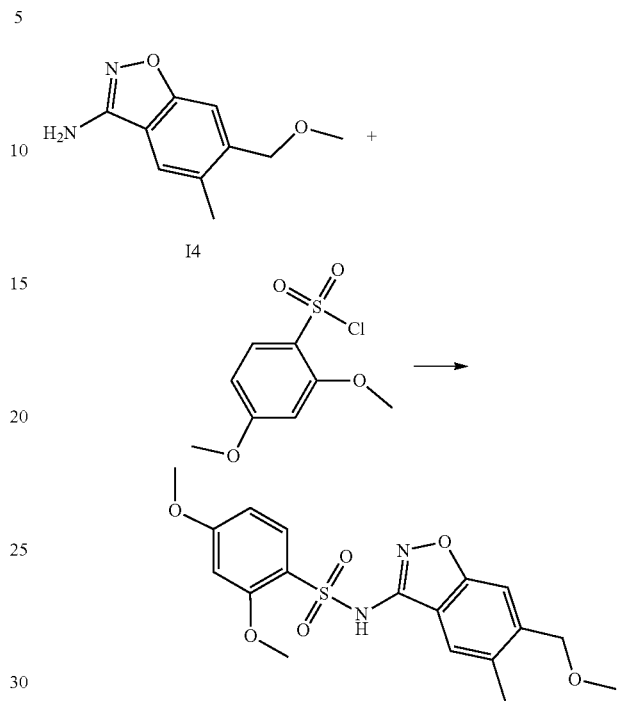

A solution of 2,4-dimethoxybenzenesulfonyl chloride (0.052 g, 0.22 mmol) and 6-(methoxymethyl)-5-methylbenzo[d]isoxazol-3-amine I4 (0.042 g, 0.22 mmol) in pyridine (0.500 mL) was irradiated in the microwave at 110° C. for 2 hours. The resulting mixture was loaded onto silica gel and the product purified by column chromatography (4 g SiO$_2$ cartridge, 0-45% EtOAc in petroleum benzine 40-60° C.) to yield the title compound (0.0413 g, 48% yield) as a white solid. $^1$H NMR (400 MHz, CDCl$_3$) δ 7.96 (s, 1H), 7.83 (s, 1H), 7.71 (d, J=8.33 Hz, 1H), 7.47 (s, 1H), 6.48 (d, J=1.82 Hz, 1H), 6.42 (d, J=8.36 Hz, 1H), 4.50 (s, 2H), 3.95 (s, 3H), 3.80 (s, 3H), 3.47 (s, 3H), 2.37 (s, 3H). LCMS-A: rt 5.78 min. m/z=392.8 [M+H]$^+$, 414.7 [M+Na]$^+$.

Example 167: N-(6-(hydroxymethyl)benzo[d]isoxazol-3-yl)-2,4-dimethoxybenzenesulfonamide 167

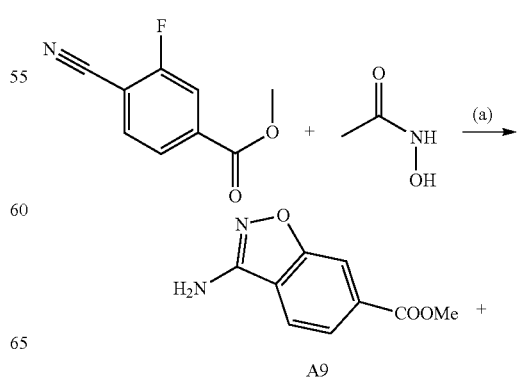

A9

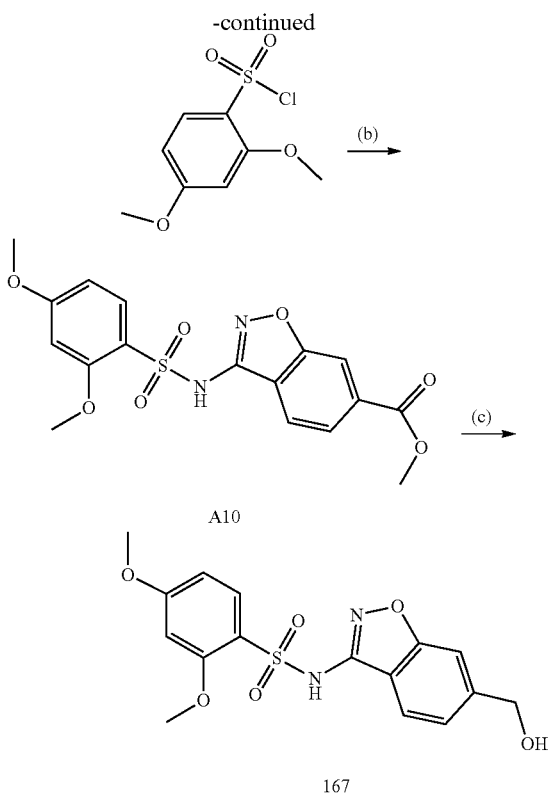

a) Methyl 3-aminobenzo[d]isoxazole-6-carboxylate A9

To a solution of ethanehydroxamic acid (0.629 g, 8.37 mmol) in DMF (5 mL) was added potassium 2-methylpropan-2-olate (0.94 g, 8.4 mmol) and the reaction was stirred for 30 minutes. Methyl 4-cyano-3-fluorobenzoate (1.0 g, 5.6 mmol) was added followed by DMF (2 mL) and the reaction was stirred for a further 2 hours at room temperature. The reaction was diluted with ethyl acetate (50 mL) and water (50 mL), the aqueous layer was extracted with ethyl acetate and the combined organic layers were washed with water, dried, filtered and concentrated. The crude material was purified by silica gel chromatography (12 g SiO$_2$ cartridge, 0-50% EtOAc in petroleum benzine 40-60° C.) to give the title compound (0.55 g, 51% yield) as a white solid. $^1$H NMR (400 MHz, CDCl$_3$) δ 8.12 (d, J=1.02 Hz, 1H), 7.96 (dd, J=1.24, 8.29 Hz, 1H), 7.59 (dd, J=0.77, 8.25 Hz, 1H), 3.98 (s, 3H). LCMS: rt 2.97 min, m/z 193.0 [M+H]$^+$.

b) Methyl 3-((2,4-dimethoxyphenyl)sulfonamido)benzo[d]isoxazole-6-carboxylate A10

A solution of 2,4-dimethoxybenzene-1-sulfonyl chloride (0.67 g, 2.8 mmol) and methyl 3-aminobenzo[d]isoxazole-6-carboxylate A9 (0.55 g, 2.8 mmol) in pyridine (4 mL) was irradiated in the microwave at 130° C. for 3 hours. The reaction was cooled to room temperature then diluted with DCM (40 mL). The organics were washed with 1M HCl (40 mL) and the aqueous layer back-extracted with DCM (2×40 mL). The combined organic layers were dried in vacuo and the residue purified twice by column chromatography (24 g SiO$_2$ cartridge, 0-35% EtOAc in petroleum benzine 40-60° C.) to give two batches of the title compound (0.369 g, impure and 0.0310 g, 2.8% yield, >95% purity) as white solids. $^1$H NMR (400 MHz, methanol-d$_4$) δ 8.13-8.06 (m, 2H), 7.97 (dd, J=1.25, 8.47 Hz, 1H), 7.86-7.80 (m, 1H), 6.58 (dq, J=2.29, 4.60 Hz, 2H), 3.95 (s, 3H), 3.83 (s, 3H), 3.79 (s, 3H). LCMS: rt 3.26 min, m/z 392.8 [M+H]$^+$, 415.8 [M+Na]$^+$.

c) N-(6-(hydroxymethyl)benzo[d]isoxazol-3-yl)-2,4-dimethoxybenzenesulfonamide 167

To a suspension of lithium aluminium hydride powder (0.0758 g, 2.00 mmol) in anhydrous THF (4 mL) under nitrogen was added a solution of methyl 3-((2,4-dimethoxyphenyl)sulfonamido)benzo[d]isoxazole-6-carboxylate A10 (impure, 0.392 g, 0.500 mmol) in THF (8 mL). The mixture was stirred overnight at room temperature. The reaction was quenched under nitrogen by the dropwise addition of wet THF followed by 1 mL of water. After the evolution of gas ceased, a solution of 0.5 M aqueous HCl was added and the aqueous layer extracted with ethyl acetate (3×20 mL). The combined organic layers were washed with water, brine, dried over MgSO$_4$ and the solvent removed in vacuo. The crude residue was purified by column chromatography (24 g SiO$_2$ cartridge, 0-100% EtOAc in petroleum benzine 40-60° C.) to give the title compound (0.191 g, 100% yield) as a white solid. $^1$H NMR (400 MHz, CDCl) δ8.08 (dd, J=0.78, 8.30 Hz, 1H), 7.77 (s, 1H), 7.69 (d, J=8.82 Hz, 1H), 7.47 (t, J=1.03 Hz, 1H), 7.30 (dd, J=1.34, 8.29 Hz, 1H), 6.49 (d, J=2.26 Hz, 1H), 6.42 (dd, J=2.30, 8.79 Hz, 1H), 4.84 (s, 2H), 3.98 (s, 3H), 3.80 (s, 3H). LCMS-B: rt 3.02 min. m/z 364.8 [M+H]$^+$, 386.8 [M+Na]$^+$.

Example 168: 3-((5-methoxyquinoline)-8-sulfonamido)-5-methylbenzo[d]isoxazole-6-carboxamide 168

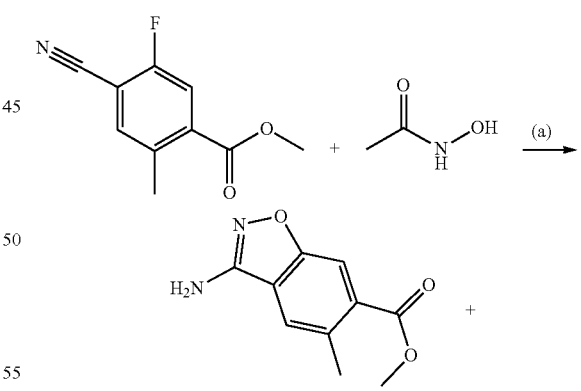

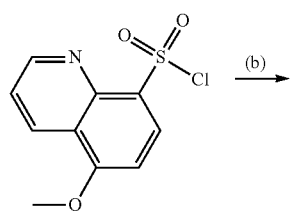

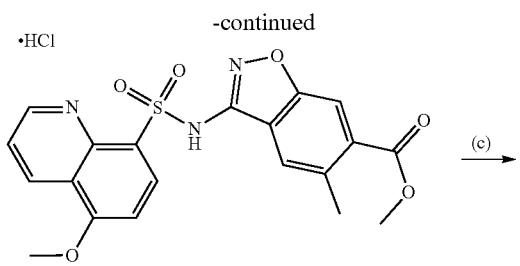

168 a) Methyl 3-amino-5-methylbenzo[d]isoxazole-6-carboxylate A11

To a solution of ethanehydroxamic acid (0.126 g, 1.69 mmol) in DMF (2 mL) was added potassium 2-methylpropan-2-olate (0.19 g, 1.7 mmol) and the reaction was stirred for 30 minutes. Methyl 4-cyano-5-fluoro-2-methylbenzoate (0.22 g, 1.1 mmol) was added followed by DMF (3 mL) and the reaction was stirred for a further 2 hours at 40° C. The reaction was diluted with ethyl acetate (50 mL) and water (50 mL). The aqueous layer was extracted with ethyl acetate and the combined organic layers were washed with water, dried, filtered and concentrated. The crude material was purified by silica gel chromatography (12 g SiO$_2$ cartridge, 0-50% EtOAc in petroleum benzine 40-60° C.) to give the title compound (0.11 g, 48% yield) as a white solid. $^1$H NMR (400 MHz, methanol-d$_4$) δ 7.85 (s, 1H), 7.64 (t, J=0.79 Hz, 1H), 3.92 (s, 3H), 2.62 (d, J=0.85 Hz, 3H). LCMS: rt 3.02 min, m/z 207.0 [M+H]$^+$.

b) Methyl 3-((5-methoxyquinoline)-8-sulfonamido)-5-methylbenzo[d]isoxazole-6-carboxylate hydrochloride salt A12

A solution of 5-methoxyquinoline-8-sulfonyl chloride (0.12 g, 0.48 mmol) and methyl 3-amino-5-methylbenzo[d]isoxazole-6-carboxylate A11 (0.10 g, 0.48 mmol) in pyridine (3 mL) was irradiated in the microwave at 110° C. for 2 hours. The reaction was irradiated in the microwave at 110° C. for a further 1.5 hours. The resultant mixture was loaded onto silica gel and the product purified by column chromatography (4 g SiO$_2$ cartridge, 0-45% EtOAc in petroleum benzine 40-60° C.). The product was purified further by solid phase extraction (1 g, Si-amine, 3 void volumes of MeOH followed by 4 void volumes of methanolic HCl). The acidic elutes were collected and dried in vacuo to give the title compound (17.7 mg, 7.9% yield) as a pale yellow solid. $^1$H NMR (400 MHz, methanol-d$_4$) δ 9.40-9.33 (m, 2H), 8.77 (d, J=8.66 Hz, 1H), 8.14-8.05 (m, 1H), 7.91 (s, 1H), 7.80-7.73 (m, 1H), 7.47 (d, J=8.73 Hz, 1H), 4.23 (s, 3H), 3.91 (s, 3H), 2.62 (s, 3H). LCMS: rt 3.35 min, m/z 427.8 [M+H]$^+$.

c) 3-((5-Methoxyquinoline)-8-sulfonamido)-5-methylbenzo[d]isoxazole-6-carboxamide 168

To a 15 mL heavy walled pressure tube equipped with magnetic stir bar under nitrogen was added methyl 3-((5-methoxyquinoline)-8-sulfonamido)-5-methylbenzo[d]isoxazole-6-carboxylate hydrochloride salt A12 (15.0 mg, 0.0323 mmol), ammonia solution (2.0 M in methanol, 0.50 mL, 1.0 mmol) and calcium dichloride (3.59 mg, 0.0323 mmol). The reaction vessel was sealed and heated at 80° C. for 3 days. The solvent was removed under a stream of air and ammonia solution (7.0 M in methanol, 0.50 mL, 3.5 mmol) and calcium dichloride (3.6 mg, 0.032 mmol) were added. The reaction vessel was sealed and heated at 80° C. for 24 hours. The reaction was cooled to room temperature and the solvent removed in vacuo. The compound was purified by column chromatography (4 g SiO$_2$ cartridge, 0-100% EtOAc in petroleum benzine 40-60° C.) to give the title compound (0.00180 g, 13% yield) as a white solid. $^1$H NMR (400 MHz, methanol-d$_4$) δ 9.01 (dd, J=1.78, 4.24 Hz, 1H), 8.65 (dd, J=1.78, 8.52 Hz, 1H), 8.43 (d, J=8.47 Hz, 1H), 7.73 (d, J=12.46 Hz, 2H), 7.57 (dd, J=4.28, 8.54 Hz, 1H), 7.08 (d, J=8.50 Hz, 1H), 4.09 (s, 3H), 2.57 (s, 3H). LCMS-B: rt 3.15 min, m/z 413.8 [M+H]$^+$.

Example 169: N-(6-cyano-5-methylbenzo[d]isoxazol-3-yl)-2,4-dimethoxybenzenesulfonamide 169

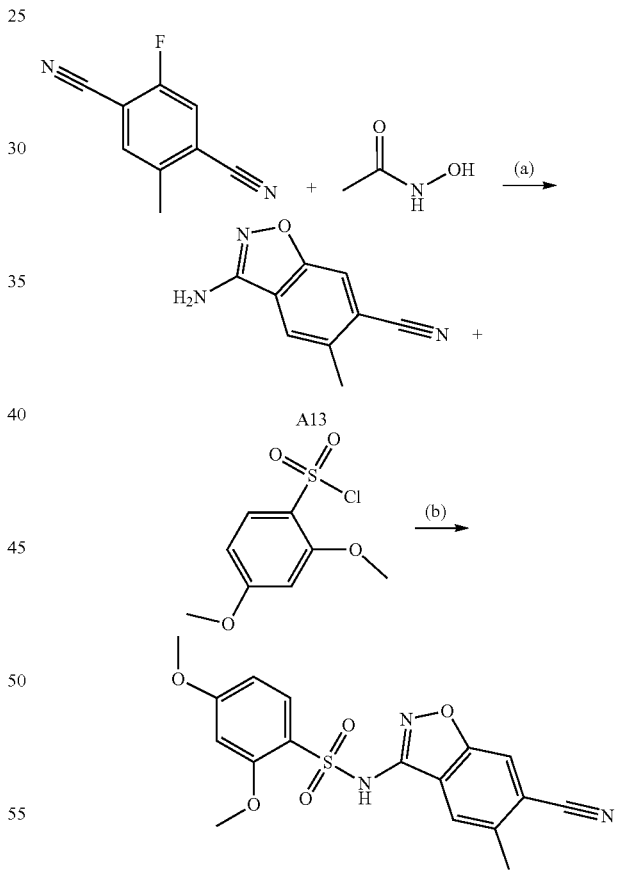

169 a) 3-Amino-5-methylbenzo[d]isoxazole-6-carbonitrile A13

To a solution of ethanehydroxamic acid (0.176 g, 2.34 mmol) in DMF (5 mL) was added potassium 2-methylpropan-2-olate (0.26 g, 2.3 mmol) and the reaction was stirred for 30 minutes. 2-Fluoro-5-methyl-terephthalonitrile (0.25 g, 1.6 mmol) was added followed by DMF (3 mL) and the reaction was stirred overnight at room temperature. The reaction was diluted with ethyl acetate (50 mL) and water (50 mL), the aqueous layer was extracted with ethyl acetate and the combined organic layers were washed with water, dried, filtered and concentrated. The crude material was purified by silica gel chromatography (12 g SiO₂ cartridge, 0-50% EtOAc in petroleum benzine 40-60° C.) to give the title compound (0.16 g, 59% yield) as an off-white solid. $^1$H NMR (400 MHz, CDCl₃) δ 7.72 (s, 1H), 7.47 (t, J=0.86 Hz, 1H), 2.65 (d, J=0.86 Hz, 3H). LCMS-B: rt 2.90 min, m/z 174.0 [M+H]⁺.

b) N-(6-cyano-5-methylbenzo[d]isoxazol-3-yl)-2,4-dimethoxybenzenesulfonamide 169

A solution of 2,4-dimethoxybenzene-1-sulfonyl chloride (0.22 g, 0.92 mmol) and 3-amino-5-methyl-1,2-benzoxazole-6-carbonitrile A13 (0.16 g, 0.92 mmol) in pyridine (2.5 mL) was irradiated in the microwave at 130° C. for 2 hours. The reaction sat at room temperature for 50 minutes, then irradiated in the microwave at 130° C. for a further 2 hours. The reaction was cooled to room temperature then diluted with DCM (40 mL). The organics were washed with 1M HCl (40 mL) and the aqueous layer back extracted twice with DCM (2×40 mL). The combined organic layers were dried in vacuo and the residue loaded onto silica gel and the product purified by column chromatography (24 g SiO₂ cartridge, 0-45% EtOAc in petroleum benzine 40-60° C.) to give a yellow solid. The solid was dissolved in warm MeOH and DCM and purified by solid phase extraction (1 g Si-amine, 3 void volumes of MeOH followed by 3 void volumes of ~1.25 M methanolic ammonia). The acidic elute was dried in vacuo to give a white solid. The solid was taken up in MeOH and the MeOH removed in vacuo (repeated×3). The residue was repurified by column chromatography (24 g SiO₂ cartridge, 45% EtOAc in petroleum benzine 40-60° C.) to give two batches of the title compound (22 and 78 mg, total mass 100 mg, 29% yield) as off white solids. $^1$H NMR (400 MHz, CDCl₃) δ 8.09 (s, 1H), 7.82 (s, 1H), 7.72 (s, 1H), 7.66 (d, J=8.80 Hz, 1H), 6.52 (d, J=2.25 Hz, 1H), 6.44 (dd, J=2.24, 8.85 Hz, 1H), 3.98 (s, 3H), 3.82 (s, 3H), 2.67 (s, 3H). LCMS-B: rt 3.30 min, m/z=373.8 [M+H]⁺, 371.9 [M−H]⁻.

Example 170: 2,4-dimethoxy-N-(5-methylbenzo[d]isoxazol-3-yl)benzenesulfonamide 170

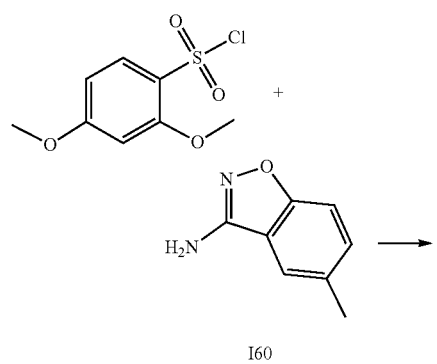

I60

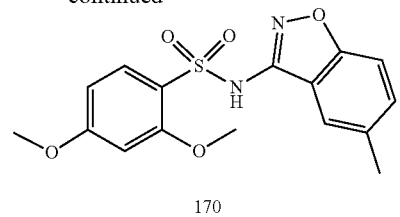

170

A solution of 2,4-dimethoxybenzene-1-sulfonyl chloride (0.0799 g, 0.337 mmol) and 5-methylbenzo[d]isoxazol-3-amine I60 (0.050 g, 0.34 mmol) in pyridine (1 mL) was irradiated in the microwave at 110° C. for 2 hours. The resultant mixture was loaded onto silica gel and the product purified by column chromatography (12 g SiO₂ cartridge, 0-45% EtOAc in petroleum benzine 40-60° C.) to yield the title compound (55.0 mg, 42% yield) as a white solid. $^1$H NMR (400 MHz, CDCl₃) δ 7.86-7.82 (m, 1H), 7.72 (d, J=8.81 Hz, 1H), 7.37-7.28 (m, 2H), 6.49 (d, J=2.26 Hz, 1H), 6.43 (dd, J=2.29, 8.82 Hz, 1H), 3.96 (s, 3H), 3.80 (s, 3H), 2.47 (s, 3H). LCMS-A: rt 5.66 min, m/z 348.8 [M+H]⁺, 347.1 [M−H]⁻.

Example 171: N-(6-bromo-5-methylbenzo[d]isoxazol-3-yl)-2,4-dimethoxybenzenesulfonamide 171

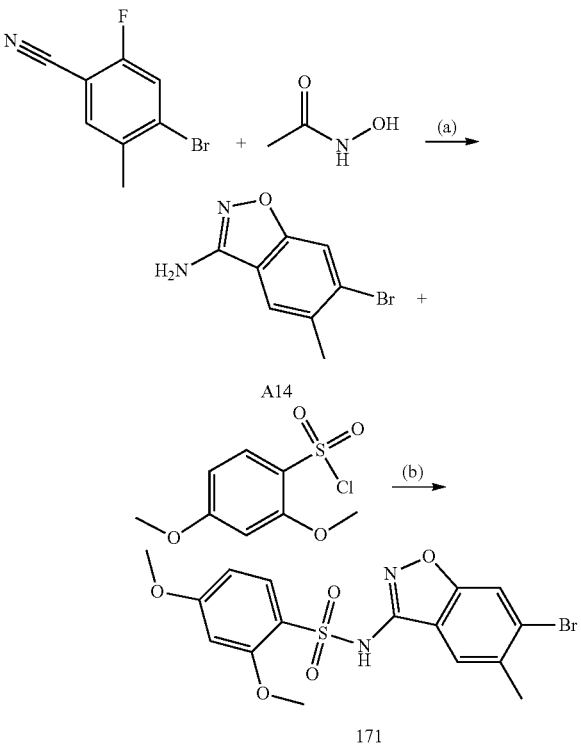

a) 6-Bromo-5-methylbenzo[d]isoxazol-3-amine A14

To a solution of ethanehydroxamic acid (0.263 g, 3.50 mmol) in N,N-dimethylformamide (5 mL) was added t-BuOK (393 mg, 3.50 mmol) and the reaction was stirred for 30 minutes. 4-Bromo-2-fluoro-5-methylbenzonitrile (0.50 g, 2.3 mmol) was added to the reaction which was stirred for a further 2 hours at room temperature. The reaction was diluted with ethyl acetate (50 mL) and water (50 mL), the aqueous layer was extracted with ethyl acetate and the combined organic layers were washed with water, dried, filtered and concentrated. The crude material was purified by silica gel chromatography (12 g SiO$_2$ cartridge, 0-50% EtOAc in petroleum benzine 40-60° C.) to give the title compound (0.30 g, 56% yield) as a white solid. $^1$H NMR (400 MHz, CDCl$_3$) δ 7.68 (s, 1H), 7.37 (s, 1H), 4.35 (br s, 2H), 2.49 (s, 3H). LCMS-B: rt 3.18 min. m/z 229.8 [M+H]$^+$.

b) N-(6-bromo-5-methylbenzo[d]isoxazol-3-yl)-2,4-dimethoxybenzenesulfonamide 171

A solution of 2,4-dimethoxybenzenesulfonyl chloride (0.052 g, 0.22 mmol) and 6-bromo-5-methylbenzo[d]isoxazol-3-amine A14 (0.050 g, 0.22 mmol) in pyridine (1 mL) was irradiated twice in the microwave at 110° C. for 2 hours, then at 130° C. for 2 hours. The resultant mixture was loaded onto silica gel and the product purified by column chromatography (4 g SiO$_2$ cartridge, 0-45% EtOAc in petroleum benzine 40-60° C.) to give the title compound (102 mg, quantitative yield) as a white solid. $^1$H NMR (400 MHz, CDCl$_3$) δ 7.98-7.94 (m, 1H), 7.70-7.65 (m, 2H), 6.50 (d, J=2.24 Hz, 1H), 6.43 (dd, J=2.26, 8.82 Hz, 1H), 3.97 (s, 3H), 3.81 (s, 3H), 2.51 (d, J=0.87 Hz, 4H). LCMS-A: rt 6.08 min, m/z 426.9 [M+H]$^+$.

Example 172: N-(6-(Ethoxymethyl)-4-methoxybenzo[d]isoxazol-3-yl)-2,6-dimethoxybenzenesulfonamide 172

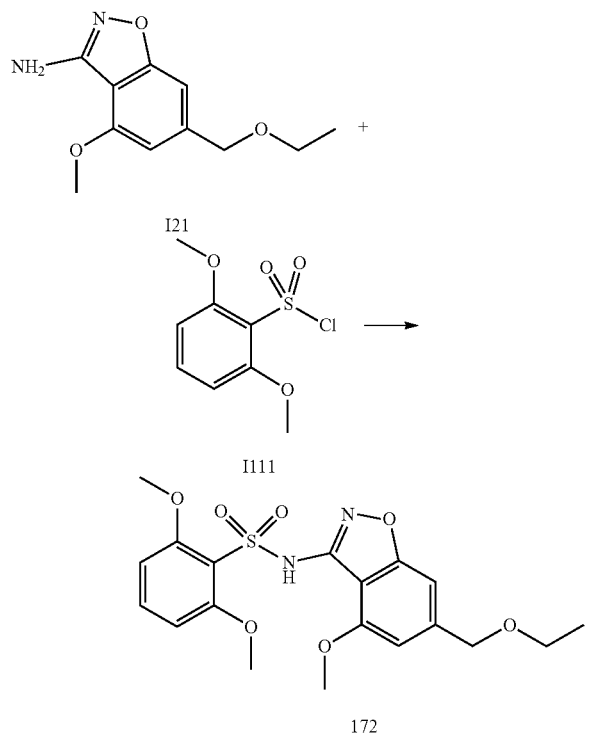

To a solution of 6-(ethoxymethyl)-4-methoxybenzo[d]isoxazol-3-amine I21 (250 mg, 1.13 mmol) in anhydrous THF (25 mL) at −78° C. under N$_2$ was added LiHMDS (1 M solution in THF, 4.5 mL, 4.5 mmol) dropwise and the mixture was stirred at −78° C. for 2 h. A solution of 2,6-dimethoxybenzenesulfonyl chloride I111 (400 mg, 1.69 mmol) in anhydrous THF (2 mL) was then added dropwise and the mixture was allowed to warm to RT and stirred overnight. The mixture was acidified to pH 4-5 with 2 M aqueous HCl and extracted with EtOAc. The combined organic extracts were washed with water, brine, dried over anhydrous Na$_2$SO$_4$, filtered and concentrated under reduced pressure. The residue was purified by prep. TLC (DCM/MeOH=100/1) to give the title compound (170 mg, 96% purity) as a white solid. Further purification by prep. HPLC gave the title compound (60 mg, 100% purity, 13% yield). LCMS-C: R$_t$ 2.08 min; m/z 423.0 [M+H]$^+$; $^1$H NMR (400 MHz, DMSO-d$_6$) δ 9.53 (s, 1H), 7.51 (t, J=8.4 Hz, 1H), 7.09 (s, 1H), 6.78-6.76 (m, 3H), 4.55 (s, 2H), 3.91 (s, 3H), 3.77 (s, 6H), 3.54 (q, J=6.8 Hz, 2H), 1.19 (t, J=6.8 Hz, 3H).

Example 173: 2,6-Dimethoxy-N-(4-methoxy-6-(methoxymethyl)benzo[d]isoxazol-3-yl)benzenesulfonamide 173

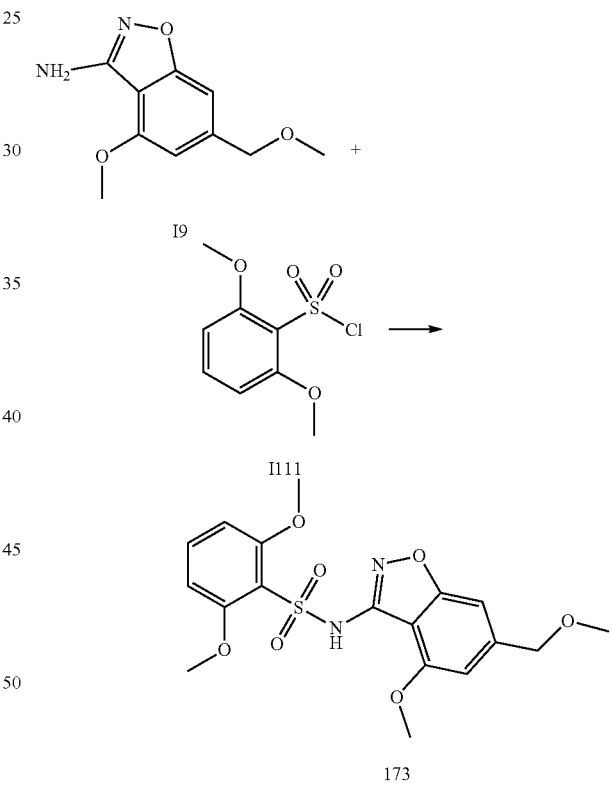

To a solution of 4-methoxy-6-(methoxymethyl)benzo[d]isoxazol-3-amine I9 (3.0 g, 14.4 mmol) in anhydrous THF (200 mL) at −78° C. under N$_2$ was added LiHMDS (1 M solution in THF, 43.2 mL, 43.2 mmol) dropwise and the mixture was stirred at −78° C. for 2 h. A solution of 2,6-dimethoxybenzenesulfonyl chloride I111 (5.1 g, 21.6 mmol) in anhydrous THF (10 mL) was then added dropwise and the mixture was allowed to warm to RT and stirred overnight. The mixture was acidified to pH 4-5 with 2 M aqueous HCl and extracted with EtOAc. The combined organic extracts were washed with water, brine, dried over anhydrous Na$_2$SO$_4$, filtered and concentrated under reduced pressure. The reaction was repeated using 4-methoxy-6-(methoxymethyl)benzo[d]isoxazol-3-amine I9 (2.0 g, 9.6 mmol) in 150 mL of THF and the two batches were combined and purified by column chromatography (Pet. ether/EtOAc=8/1 to 2/1) to give the title compound (4.1 g, 42%) as a white solid. LCMS-C: $R_t$ 1.96 min; m/z 409.0 [M+H]$^+$; $^1$H NMR (400 MHz, DMSO-d$_6$) δ 9.58 (s, 1H), 7.52 (t, J=8.4 Hz, 1H), 7.09 (s, 1H), 6.78 (d, J=8.4 Hz, 2H), 6.76 (s, 1H), 4.51 (s, 2H), 3.91 (s, 3H), 3.77 (s, 6H), 3.33 (s, 3H).

Example 174: 2,6-Dimethoxy-N-(4-methoxy-6-phenylbenzo[d]isoxazol-3-yl)benzenesulfonamide 174

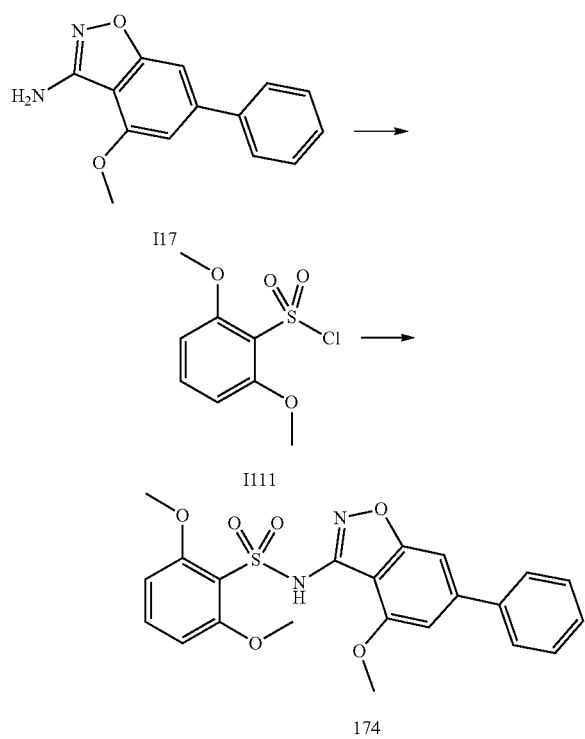

To a solution of 4-methoxy-6-phenylbenzo[d]isoxazol-3-amine I17 (2.5 g, 10.4 mmol) in anhydrous THF (60 mL) at −78° C. under N$_2$ was added LiHMDS (1 M solution in THF, 31.0 mL, 31.0 mmol) dropwise and the mixture was stirred at −78° C. for 2 h. A solution of 2,6-dimethoxybenzenesulfonyl chloride I111 (3.7 g, 15.6 mmol) in anhydrous THF (20 mL) was then added dropwise and the mixture was allowed to warm to 0° C. and stirred overnight. Water was added and the mixture was washed with EtOAc (50 mL×2). The aqueous layer was acidified to pH 3 with 1 M aqueous HCl and extracted with EtOAc (50 mL×3). The combined organic extracts were washed with brine, dried over anhydrous Na$_2$SO$_4$, filtered and concentrated under reduced pressure. The residue was purified by column chromatography (DCM/MeOH=300/1) and further purified by column chromatography (DCM/MeOH=200/1) to give the title compound (1.5 g, 33%) as a white solid. $^1$H NMR (400 MHz, DMSO-d$_6$) δ 9.61 (s, 1H), 7.80 (d, J=7.2 Hz, 2H), 7.50-7.44 (m, 5H), 7.09 (s, 1H), 6.80 (d, J=8.8 Hz, 2H), 4.02 (s, 3H), 3.79 (s, 6H); LCMS-C: $R_t$ 2.46 min; m/z 441.0 [M+H]$^+$.

Example 175: 3-Chloro-2,6-dimethoxy-N-(4-methoxy-6-(methoxymethyl)benzo[d]isoxazol-3-yl)benzenesulfonamide 175

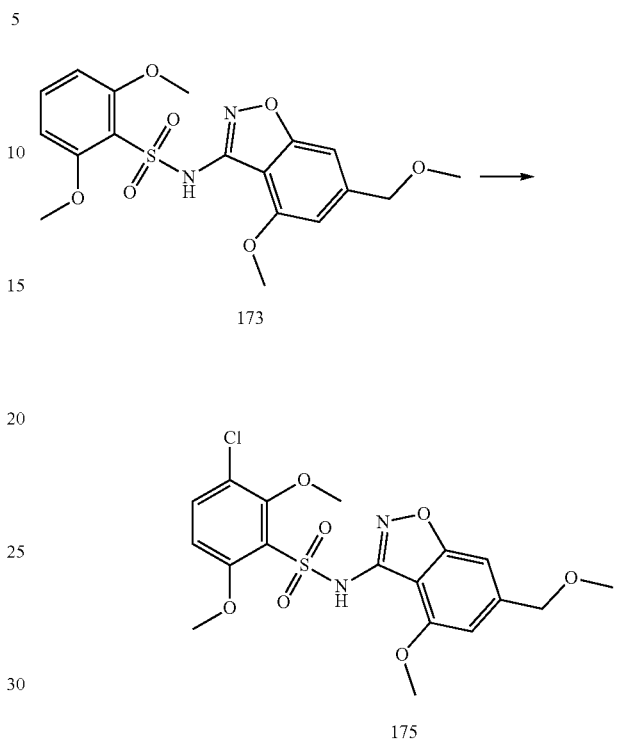

To a solution of 2,6-dimethoxy-N-(4-methoxy-6-(methoxymethyl)benzo[d]isoxazol-3-yl)benzenesulfonamide 173 (50 mg, 0.123 mmol) in DMF (10 mL) was added NCS (14 mg, 0.123 mmol) and the mixture was heated at 50° C. for 2 h. The mixture was then diluted with EtOAc (150 mL) and washed with water, brine, dried over anhydrous Na$_2$SO$_4$, filtered and concentrated under reduced pressure. The residue was purified by prep-TLC (DCM/MeOH=120/1) to give the title compound (15 mg, 27%) as a white solid. LCMS-C: $R_t$ 2.21 min; m/z 441.0 [M+H]$^+$. $^1$H NMR (400 MHz, methanol-d$_4$) δ 7.56 (d, J=9.1 Hz, 1H), 7.01 (s, 1H), 6.91 (d, J=9.1 Hz, 1H), 6.76 (s, 1H), 4.55 (s, 2H), 3.99 (s, 6H), 3.76 (s, 3H), 3.41 (s, 3H).

Example 176: 2,6-Dimethoxy-N-(4-methoxy-6-(2-methoxyphenyl)benzo[d]isoxazol-3-yl)benzenesulfonamide 176

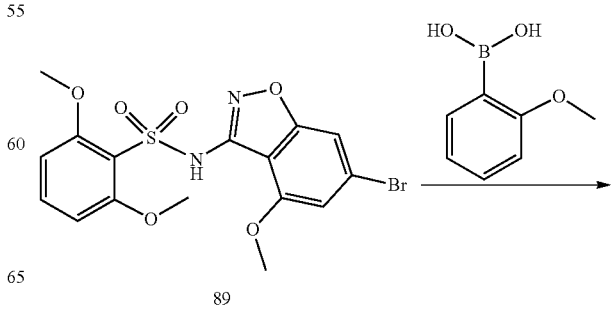

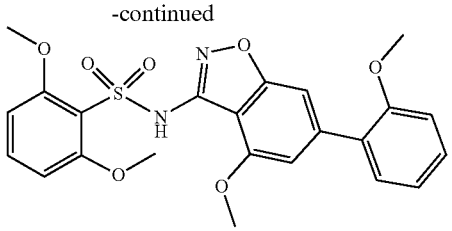

176

A mixture of N-(6-bromo-4-methoxybenzo[d]isoxazol-3-yl)-2,6-dimethoxybenzenesulfonamide 89 (30 mg, 0.068 mmol), (2-methoxyphenyl)boronic acid (21 mg, 0.135 mmol), Pd(PPh$_3$)$_4$ (9 mg, 0.007 mmol) and Na$_2$CO$_3$ (22 mg, 0.203 mmol) in 1,4-dioxane (4 mL) and water (1 mL) was heated at 100° C. under N$_2$ overnight. The mixture was diluted with water and extracted with EtOAc. The combined organic extracts were washed with brine, dried over anhydrous Na$_2$SO$_4$, filtered and concentrated under reduced pressure. The residue was purified by prep. TLC (Pet. ether/EtOAc=½) to give the title compound (10 mg, 31%) as a white solid. LCMS-C: R$_t$ 2.36 min, m/z 471.0 [M+H]$^+$. $^1$H NMR (400 MHz, DMSO-d$_6$) δ 9.60 (s, 1H), 7.51 (t, J=8.5 Hz, 1H), 7.44-7.37 (m, 2H), 7.22 (s, 1H), 7.16 (d, J=8.8 Hz, 1H), 7.05 (t, J=7.4 Hz, 1H), 6.90 (s, 1H), 6.79 (d, J=8.6 Hz, 2H), 3.94 (s, 3H), 3.81 (s, 6H), 3.79 (s, 3H).

Example 177: 2,6-Dimethoxy-N-(4-methoxy-6-(3-methoxyphenyl)benzo[d]isoxazol-3-yl)benzenesulfonamide 177

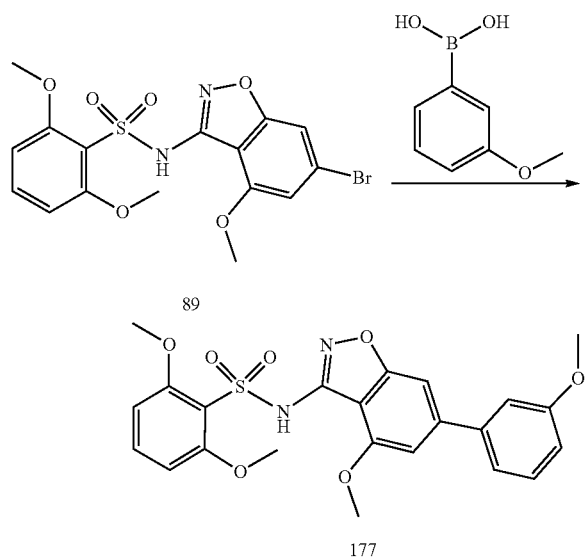

A mixture of N-(6-bromo-4-methoxybenzo[d]isoxazol-3-yl)-2,6-dimethoxybenzenesulfonamide 89 (50 mg, 0.113 mmol), (3-methoxyphenyl)boronic acid (35 mg, 0.226 mmol), Pd(PPh$_3$)$_4$ (14 mg, 0.011 mmol) and Na$_2$CO$_3$ (36 mg, 0.339 mmol) in 1,4-dioxane (8 mL) and water (2 mL) was heated at 100° C. under N$_2$ overnight. The mixture was allowed to cool to RT, adjusted to pH 4-5 then diluted with water and extracted with EtOAc. The combined organic extracts were washed with brine, dried over anhydrous Na$_2$SO$_4$, filtered and concentrated under reduced pressure. The residue was purified by prep. TLC (DCM/MeOH=50/1) to give the title compound (8 mg, 15%) as a white solid. LCMS-C: R$_t$ 2.35 min; m/z 471.0 [M+H]$^+$. $^1$H NMR (400 MHz, DMSO-d$_6$) δ 9.63 (s, 1H), 7.51 (t, J=8.5 Hz, 1H), 7.46 (d, J=1.0 Hz, 1H), 7.41 (t, J=7.9 Hz, 1H), 7.37-7.29 (m, 2H), 7.07 (s, 1H), 7.03-6.98 (m, 1H), 6.79 (d, J=8.5 Hz, 2H), 4.02 (s, 3H), 3.84 (s, 3H), 3.79 (s, 6H).

Example 178: 5-Ethyl-2-methoxy-N-(7-phenylbenzo[d]isoxazol-3-yl)benzenesulfonamide 178

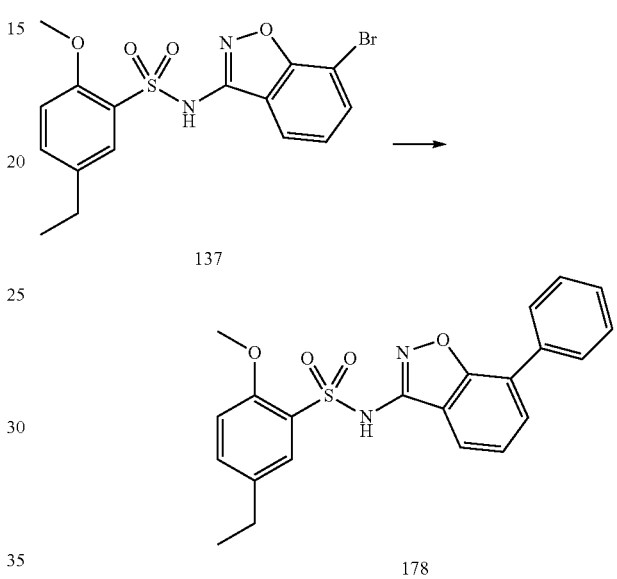

A suspension of N-(7-bromobenzo[d]isoxazol-3-yl)-5-ethyl-2-methoxybenzenesulfonamide 137 (100 mg, 0.24 mmol), phenylboronic acid (60 mg, 0.48 mmol), Pd(dppf)Cl$_2$ (18 mg, 0.024 mmol) and K$_3$PO$_4$·3H$_2$O (260 mg, 0.97 mmol) in toluene (5 mL), isopropanol (2 mL) and water (5 mL) was heated at 100° C. under N$_2$ for 2 h. The mixture was allowed to cool to RT, diluted with EtOAc and washed with water (25 mL×3). The organic layer was dried over anhydrous Na$_2$SO$_4$, filtered and concentrated under reduced pressure. The residue was purified by preparative TLC (Pet. ether/EtOAc=2/1) to give the title compound (55 mg, 55%) as a white solid. LCMS-D: R$_t$ 3.06 min; m/z 409.1 [M+H]$^+$. $^1$H NMR (400 MHz, DMSO-d$_6$) δ 11.8 (s, 1H), 8.08-8.02 (m, 1H), 7.89-7.78 (m, 3H), 7.72 (d, J=2.3 Hz, 1H), 7.55-7.40 (m, 5H), 7.13-7.08 (m, 1H), 3.75 (s, 3H), 2.61 (q, J=7.5 Hz, 2H), 1.15 (t, J=7.5 Hz, 3H).

Example 179: 5-Ethyl-2-methoxy-N-(6-phenylbenzo[d]isoxazol-3-yl)benzenesulfonamide 179

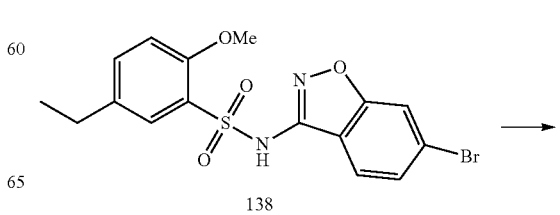

138

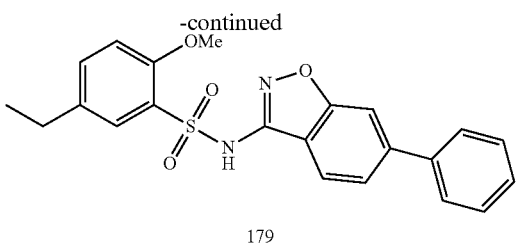

179

A mixture of N-(6-bromobenzo[d]isoxazol-3-yl)-5-ethyl-2-methoxybenzenesulfonamide 138 (120 mg, 0.3 mmol), Pd(dppf)Cl₂ (45 mg, 0.06 mmol), phenylboronic acid (150 mg, 1.2 mmol) and K₃PO₄.3H₂O (399 mg, 1.5 mmol) in water (10 mL), toluene (10 mL) and isopropanol (5 mL) was heated at 85° C. under N₂ for 4 h. The mixture was allowed to cool to RT, diluted with water (200 mL) and extracted with diethyl ether (200 mL×3). The combined organic extracts were washed with water, brine, dried over anhydrous Na₂SO₄, filtered and concentrated under reduced pressure. The residue was purified by column chromatography (Pet. ether/EtOAc=100/1 to 5/1) to give the title compound (60 mg, 50%) as a white solid. LCMS-D: R$_t$ 3.10 min; m/z 409.1 [M+H]⁺. ¹H NMR (400 MHz, DMSO-d₆) δ 11.7 (s, 1H), 8.14-8.08 (m, 1H), 7.87 (s, 1H), 7.79-7.74 (m, 2H), 7.73-7.67 (m, 2H), 7.54-7.39 (m, 4H), 7.12-7.07 (m, 1H), 3.74 (s, 3H), 2.61 (q, J=7.5 Hz, 2H), 1.15 (t, J=7.6 Hz, 3H).

Example 180: N-(4-Chlorobenzo[d]isoxazol-3-yl)-2,3-dihydrobenzofuran-7-sulfonamide 180

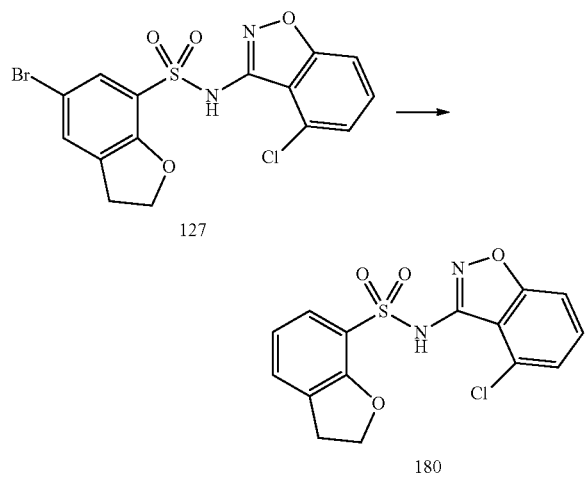

To a solution of 5-bromo-N-(4-chlorobenzo[d]isoxazol-3-yl)-2,3-dihydrobenzofuran-7-sulfonamide 127 (100 mg, 0.23 mmol) in THF (10 mL) was added 10% Pd/C (20 mg) and KOAc (20 mg, 0.28 mmol) and the mixture was stirred at 40° C. under a H₂ atmosphere for 2 h then at RT overnight. The mixture was filtered and the filtrate was concentrated under reduced pressure. The residue was purified by prep. TLC (DCM/MeOH=30/1) to give the title compound (22 mg 27%) as a light yellow solid. LCMS-D: R$_t$ 2.32 min; m/z 351.0 [M+H]⁺. ¹H NMR (400 MHz, DMSO-d₆) δ 10.9 (s, 1H), 7.76-7.62 (m, 2H), 7.53-7.43 (m, 3H), 6.96 (t, J=7.7 Hz, 1H), 4.50 (t, J=8.8 Hz, 2H), 3.22 (t, J=8.8 Hz, 2H).

Example 181: N-(4-Chlorobenzo[d]isoxazol-3-yl)-5-ethyl-2,3-dihydrobenzofuran-7-sulfonamide 181

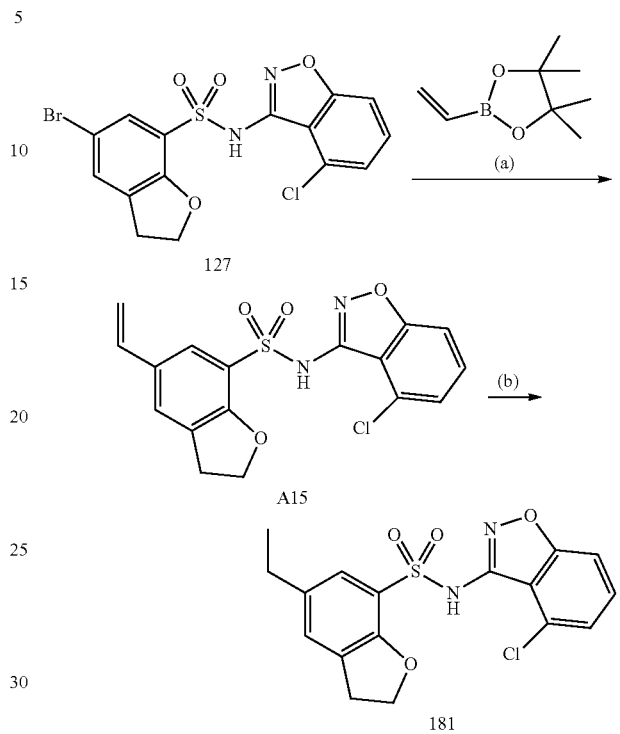

a) N-(4-Chlorobenzo[d]isoxazol-3-yl)-5-vinyl-2,3-dihydrobenzofuran-7-sulfonamide A15

To a solution of 5-bromo-N-(4-chlorobenzo[d]isoxazol-3-yl)-2,3-dihydrobenzofuran-7-sulfonamide 127 (200 mg, 0.47 mmol) in 1,4-dioxane (20 mL), EtOH (10 mL) and H₂O (10 mL) was added K₂CO₃ (206 mg, 1.86 mmol), 4,4,5,5-tetramethyl-2-vinyl-1,3,2-dioxaborolane (140 mg, 0.93 mmol) and Pd(PPh₃)₄ (54 mg, 0.047 mmol) and the mixture was heated at 90° C. under a N₂ atmosphere overnight. The solvents were removed under reduced pressure and the residue was partitioned between DCM (50 mL), water (45 mL) and 2 M aq. HCl (5 mL). The layers were separated and the organic layer was washed with brine, dried over anhydrous Na₂SO₄, filtered and concentrated under reduced pressure. The residue was purified by silica gel column chromatography (Pet. ether/EtOAc=3/1) to give the title compound (120 mg 70%) as a yellow solid. LCMS-D: R$_t$ 0.40 min; m/z 377.0 [M+H]⁺.

b) N-(4-chlorobenzo[d]isoxazol-3-yl)-5-ethyl-2,3-dihydrobenzofuran-7-sulfonamide 181

To a solution of N-(4-chlorobenzo[d]isoxazol-3-yl)-5-vinyl-2,3-dihydrobenzofuran-7-sulfonamide A15 (120 mg, 0.32 mmol) in MeOH (15 mL) was added 10% Pd/C (24 mg) and the mixture was stirred at RT under a H₂ atmosphere overnight. The mixture was filtered and the filtrate was concentrated under reduced pressure. The residue was purified by prep. TLC (DCM/MeOH=30/1) to give the title compound (33 mg, 27%) as a white solid. LCMS-D: R$_t$ 2.59 min; m/z 379.1 [M+H]⁺. ¹H NMR (400 MHz, DMSO-d₆) δ 10.8 (s, 1H), 7.75-7.70 (m, 1H), 7.69-7.63 (m, 1H), 7.47-

7.43 (m, 1H), 7.37 (s, 1H), 7.29 (s, 1H), 4.46 (t, J=8.7 Hz, 2H), 3.18 (t, J=8.7 Hz, 2H), 2.56 (q, J=7.6 Hz, 2H), 1.13 (t, J=7.6 Hz, 3H).

Example 182: N-(Benzo[d]isoxazol-3-yl)-4-ethyl-2-methoxybenzenesulfonamide 182

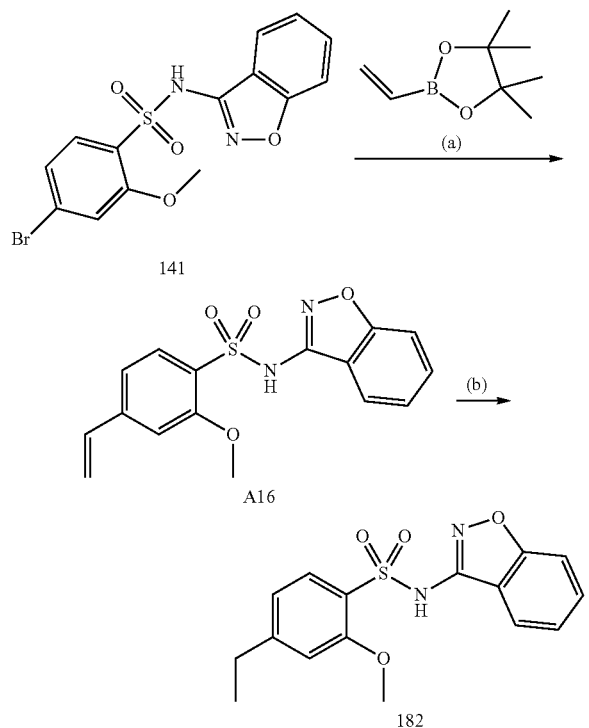

a) N-(Benzo[d]isoxazol-3-yl)-2-methoxy-4-vinyl-benzenesulfonamide A16

To a solution of N-(benzo[d]isoxazol-3-yl)-4-bromo-2-methoxybenzenesulfonamide 141 (200 mg, 0.52 mmol) in toluene (16 mL), water (8 mL) and isopropanol (8 mL) was added K$_2$CO$_3$ (288 mg, 2.09 mmol), 4,4,5,5-tetramethyl-2-vinyl-1,3,2-dioxaborolane (160 mg, 1.04 mmol) and Pd(PPh$_3$)$_4$ (60 mg, 0.052 mmol) and the mixture was heated at 90° C. under a N$_2$ atmosphere for 2 h. The mixture was diluted with water (50 mL) and 2 M aq. HCl (20 mL) and extracted with EtOAc (80 mL×2). The combined organic extracts were washed with brine, dried over anhydrous Na$_2$SO$_4$, filtered and concentrated under reduced pressure. The residue was purified by silica gel chromatography (Pet. ether/EtOAc=5/1) to give the title compound (150 mg, 76%) as a light yellow solid. LCMS-D: R$_t$ 2.47 min; m/z 331.0 [M+H]$^+$, 353.0 [M+Na]$^+$.

b) N-(Benzo[d]isoxazol-3-yl)-4-ethyl-2-methoxy-benzenesulfonamide 182

To a solution of N-(benzo[d]isoxazol-3-yl)-2-methoxy-4-vinylbenzenesulfonamide A16 (80 mg, 0.24 mmol) in MeOH (10 mL) was added 10% Pd/C (16 mg) and the mixture was stirred at 25° C. overnight under a H$_2$ atmosphere. The mixture was filtered and the filtrate was concentrated under reduced pressure. The residue was purified by prep. TLC (Pet. ether/EtOAc=5/1) to give the title compound (20 mg, 25%) as a light yellow solid. LCMS-D: R$_t$ 2.55 min; m/z 333.1 [M+H]$^+$. $^1$H NMR (400 MHz, DMSO-d$_6$) δ 11.7 (s, 1H), 8.07 (d, J=8.0 Hz, 1H), 7.79 (d, J=8.0 Hz, 1H), 7.66-7.55 (m, 2H), 7.44-7.31 (m, 1H), 7.01 (s, 1H), 6.96 (d, J=8.4 Hz, 1H), 3.76 (s, 3H), 2.63 (q, J=7.6 Hz, 2H), 1.17 (t, J=7.6 Hz, 3H).

Example 183: N-(Benzo[d]isoxazol-3-yl)-3-methoxy-[1,1-biphenyl]-4-sulfonamide 183

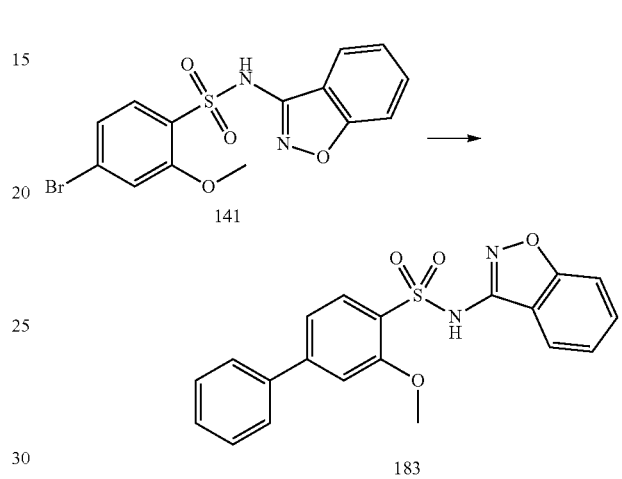

To a solution of N-(benzo[d]isoxazol-3-yl)-4-bromo-2-methoxybenzenesulfonamide 141 (100 mg, 0.26 mmol) in toluene (7 mL), water (7 mL) and isopropanol (2.5 mL) was added K$_2$CO$_3$ (144 mg, 10 mmol), phenylboronic acid (64 mg, 0.52 mmol) and Pd(PPh$_3$)$_4$ (30 mg, 0.026 mmol) and the mixture was heated at 90° C. under a N$_2$ atmosphere for 2 h. The mixture was diluted with water (50 mL) and 2 M aq. HCl (10 mL) and extracted with EtOAc (70 mL×2). The combined organic extracts were washed with brine, dried over anhydrous Na$_2$SO$_4$, filtered and concentrated under reduced pressure. The residue was purified by silica gel chromatography (Pet. ether/EtOAc=100/1 to 5/1) to give the title compound (55 mg, 46%) as a light yellow solid. LCMS-D: R$_t$ 2.79 min; m/z 381.0 [M+H]$^+$. $^1$H NMR (400 MHz, DMSO-d$_6$) δ 11.9 (s, 1H), 8.10 (d, J=8.0 Hz, 1H), 7.98 (d, J=8.0 Hz, 1H), 7.79-7.72 (m, 2H), 7.66-7.58 (m, 2H), 7.54-7.35 (m, 6H), 3.89 (s, 3H).

Example 184: 3-(5-Ethyl-2-methoxyphenylsulfonamido)-N-methylbenzo[d]isoxazole-7-carboxamide 184

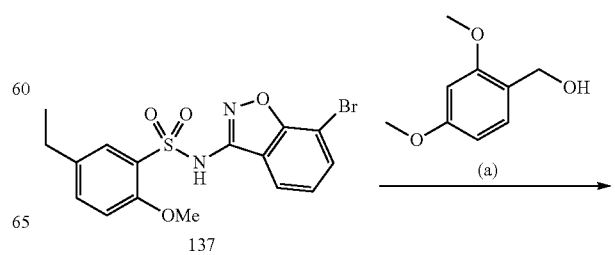

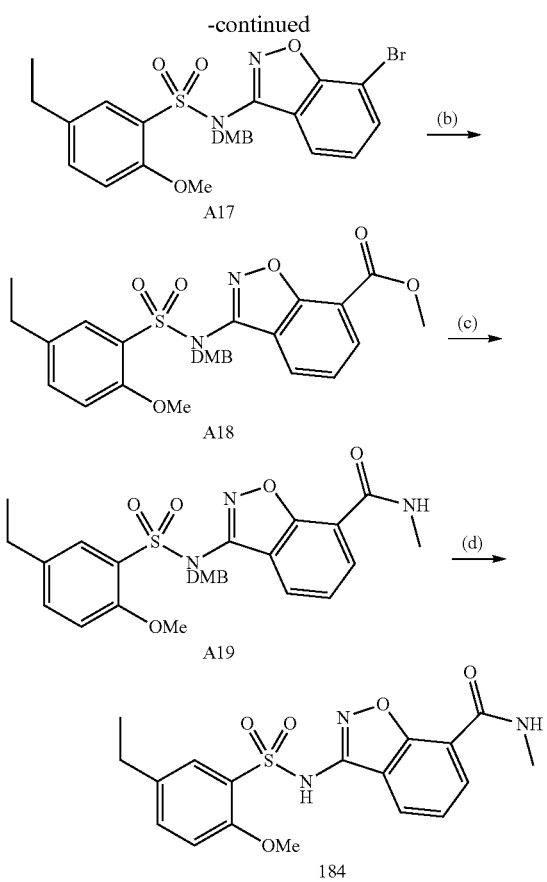

a) N-(7-Bromobenzo[d]isoxazol-3-yl)-N-((2,4-dimethoxybenzyl)oxy)-5-ethyl-2-methoxybenzenesulfonamide A17

To a solution of N-(7-bromobenzo[d]isoxazol-3-yl)-5-ethyl-2-methoxybenzenesulfonamide 137 (2.3 g, 5.5 mmol), (2,4-dimethoxyphenyl)methanol (1.4 g, 8.4 mmol) and PPh$_3$ (3.6 g, 14.2 mmol) in THF (400 mL) at 0° C. under N$_2$ was added DIAD (3.3 g, 16.4 mmol) and the mixture was stirred at RT over the weekend. The mixture was concentrated under reduced pressure and the residue was purified by silica gel chromatography (Pet. ether/EtOAc=5/1) to give the title compound (1.0 g, 32%) as a light blue solid. LCMS-D: R$_t$ 3.35 min; m/z 583.1/585.1 [M+Na]$^+$.

b) Methyl 3-(N-((2,4-dimethoxybenzyl)oxy)-5-ethyl-2-methoxyphenylsulfonamido) benzo[d]isoxazole-7-carboxylate A18

To a solution of N-(7-bromobenzo[d]isoxazol-3-yl)-N-((2,4-dimethoxybenzyl)oxy)-5-ethyl-2-methoxybenzenesulfonamide A17 (250 mg, 1.34 mmol) in MeOH (5 mL) and DMF (45 mL) was added Et$_3$N (675 mg, 6.68 mmol) and Pd(dppf)Cl$_2$ (98 mg, 0.13 mmol) and the mixture was heated at 80° C. under a CO atmosphere overnight. The solvent was removed under reduced pressure and the residue was diluted with EtOAc (50 mL), washed with water (50 mL×3), brine, dried over anhydrous Na$_2$SO$_4$, filtered and concentrated under reduced pressure. The residue was purified by silica gel chromatography (Pet. ether/EtOAc=4/1) to give the title compound (210 mg, 31%) as a white solid. LCMS-D: R$_t$ 3.10 min; m/z 541.2 [M+H]$^+$.

c) 3-(N-((2,4-Dimethoxybenzyl)oxy)-5-ethyl-2-methoxyphenylsulfonamido)-N-methylbenzo[d]isoxazole-7-carboxamide A19

A mixture of methyl 3-(N-((2,4-dimethoxybenzyl)oxy)-5-ethyl-2-methoxyphenylsulfonamido) benzo[d]isoxazole-7-carboxylate A18 (20 mg, 0.037 mmol) and CH$_3$NH$_2$ (33% solution in EtOH, 4 mL) was heated at 100° C. in a sealed tube for 30 min. The solvent was removed under reduced pressure to give the title compound (20 mg, 100%), which was used in the next step without further purification. LCMS-D: R$_t$ 2.86 min; m/z 540.2 [M+H]$^+$.

d) 3-(5-Ethyl-2-methoxyphenylsulfonamido)-N-methylbenzo[d]isoxazole-7-carboxamide I84

A mixture of 3-(N-((2,4-dimethoxybenzyl)oxy)-5-ethyl-2-methoxyphenyl sulfonamido)-N-methylbenzo[d]isoxazole-7-carboxamide A19 (40 mg, 0.07 mmol) and TFA (2 mL) was stirred at RT for 3 h, then concentrated under reduced pressure. The residue was purified by preparative TLC to give the title compound (18 mg, 64%) as a white solid. LCMS-D: R$_t$ 2.35 min; m/z 390.1 [M+H]$^+$. $^1$H NMR (400 MHz, DMSO-d$_6$) δ 11.9 (s, 1H), 8.31-8.11 (m, 2H), 8.00-7.90 (m, 1H), 7.72 (s, 1H), 7.52-7.41 (m, 2H), 7.14-7.04 (m, 1H), 3.73 (s, 3H), 2.81 (s, 3H), 2.62 (q, J=8.0, 7.6 Hz, 2H), 1.15 (t, J=7.9 Hz, 3H).

Example 185: 3-(5-Ethyl-2-methoxyphenylsulfonamido)-N,N-dimethylbenzo[d]isoxazole-7-carboxamide I85

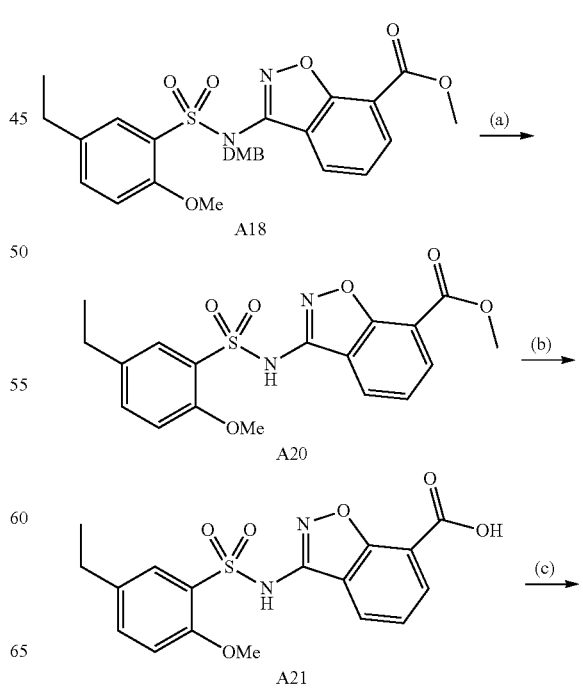

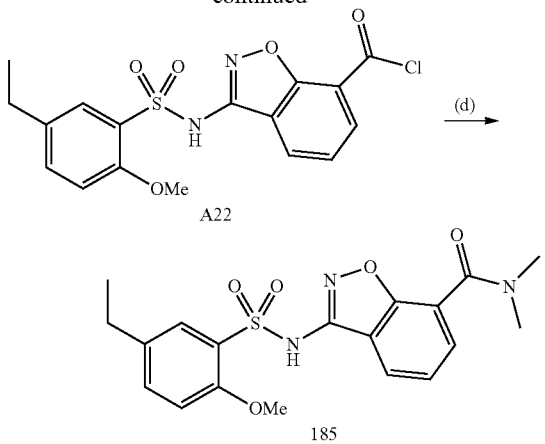

a) Methyl 3-(5-ethyl-2-methoxyphenylsulfonamido)benzo[d]isoxazole-7-carboxylate A20

A mixture of methyl 3-(N-((2,4-dimethoxybenzyl)oxy)-5-ethyl-2-methoxyphenylsulfonamido) benzo[d]isoxazole-7-carboxylate A18 (150 mg, 0.28 mmol) and TFA (5 mL) was stirred at RT for 3 h then concentrated under reduced pressure. The residue was purified by silica gel chromatography (Pet. ether/EtOAc=3/1) to give the title compound (80 mg, 74%) as a white solid. LCMS-D: $R_t$ 2.63 min; m/z 391.1 [M+H]$^+$, 413.1 [M+Na]$^+$. $^1$H NMR (400 MHz, DMSO-d$_6$) δ 11.9 (s, 1H), 8.39-8.32 (m, 1H), 8.19-8.12 (m, 1H), 7.72 (d, J=2.2 Hz, 1H), 7.56-7.44 (m, 2H), 7.12-7.05 (m, 1H), 3.89 (s, 3H), 3.71 (s, 3H), 2.62 (q, J=7.5 Hz, 2H), 1.16 (t, J=7.6 Hz, 3H).

b) 3-((5-Ethyl-2-methoxyphenyl)sulfonamido)benzo[d]isoxazole-7-carboxylic acid A21

To a suspension of methyl 3-(5-ethyl-2-methoxyphenylsulfonamido) benzo[d]isoxazole-7-carboxylate A20 (200 mg, 0.5 mmol) in MeOH (10 mL) and THF (10 mL) was added 2 M aq. NaOH (1.28 mL) and the mixture was stirred at RT overnight. The solvent was removed under reduced pressure and the residue was diluted with water and adjusted to pH 2-3. The resulting precipitate was collected by filtration to give the title compound (144 mg, 75%) as an off-white solid. LCMS-D: $R_t$ 2.43 min; m/z 377.1 [M+H]$^+$. $^1$H NMR (400 MHz, DMSO-d$_6$) δ 13.5 (s, 1H), 11.8 (s, 1H), 8.35-8.29 (m, 1H), 8.15-8.09 (m, 1H), 7.72 (d, J=2.3 Hz, 1H), 7.53-7.44 (m, 2H), 7.12-7.05 (m, 1H), 3.71 (s, 3H), 2.62 (q, J=7.6 Hz, 2H), 1.16 (t, J=7.6 Hz, 3H).

c) 3-(5-Ethyl-2-methoxyphenylsulfonamido)benzo[d]isoxazole-7-carbonyl chloride A22

A mixture of 3-((5-ethyl-2-methoxyphenyl)sulfonamido)benzo[d]isoxazole-7-carboxylic acid A21 (30 mg, 0.08 mmol) and SOCl$_2$ (5 mL) was heated at 85° C. under a N$_2$ atmosphere for 3 h, then concentrated under reduced pressure to give the title compound (31 mg, 100%), which was used directly in the next step without further purification.

d) 3-(5-Ethyl-2-methoxyphenylsulfonamido)-N,N-dimethylbenzo[d]isoxazole-7-carboxamide I85

To a solution of 3-(5-ethyl-2-methoxyphenylsulfonamido)benzo[d]isoxazole-7-carbonyl chloride A22 (31 mg, 0.08 mmol) in THF (1 mL) was added dimethylamine (40% solution in water, 2 mL) dropwise and the mixture was stirred at RT for 1 h. The mixture concentrated under reduced pressure and the residue was diluted with water, adjusted to pH 2-3 and extracted with DCM (30 mL×3). The combined organic extracts were washed with brine, dried over anhydrous Na$_2$SO$_4$, filtered and concentrated under reduced pressure. The residue was purified by prep. TLC to give the title compound (18 mg, 56%) as a white solid. LCMS-D: $R_t$ 2.36 min; m/z 404.1 [M+H]$^+$. $^1$H NMR (400 MHz, DMSO-d$_6$) δ 11.9 (s, 1H), 8.21-8.06 (m, 1H), 7.78-7.56 (m, 2H), 7.45 (s, 2H), 7.17-6.97 (m, 1H), 3.71 (s, 3H), 3.01 (s, 3H), 2.80 (s, 3H), 2.61 (m, 2H), 1.15 (m, 3H).

Example 186: 5-Ethyl-N-(7-(hydroxymethyl)benzo[d]isoxazol-3-yl)-2-methoxybenzenesulfonamide 186

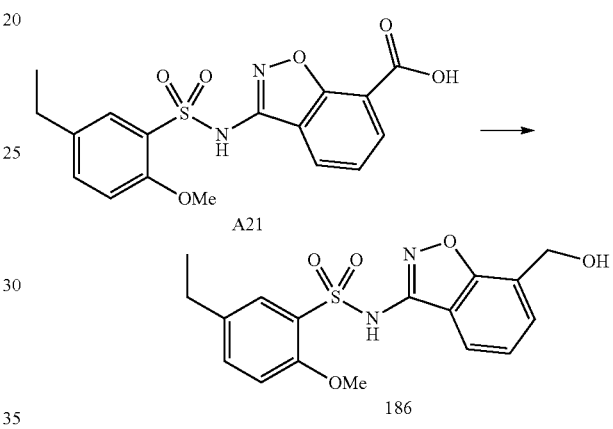

A mixture of 3-(5-ethyl-2-methoxyphenylsulfonamido)benzo[d]isoxazole-7-carboxylic acid A21 (30 mg, 0.08 mmol) and BH$_3$-THF (1 M solution in THF, 3 mL, 3 mmol) was stirred at RT under a N$_2$ atmosphere for 5 h. The reaction was quenched with water and most of the THF was removed under reduced pressure. The residue was adjusted to pH 2-3 and extracted with DCM (15 mL×3). The combined organic extracts were dried over anhydrous Na$_2$SO$_4$, filtered and concentrated under reduced pressure. The residue was purified by a silica gel chromatography (DCM/MeOH=30/1) to give the title compound (20 mg, 71%) as a light red solid. LCMS-D: $R_t$ 2.35 min; m/z 363.1 [M+H]$^+$. $^1$H NMR (400 MHz, DMSO-d$_6$) δ 11.7 (s, 1H), 7.96-7.89 (m, 1H), 7.70 (d, J=2.3 Hz, 1H), 7.61-7.55 (m, 1H), 7.46 (dd, J=8.5, 2.3 Hz, 1H), 7.34 (t, J=7.6 Hz, 1H), 7.12-7.05 (m, 1H), 5.39 (t, J=5.7 Hz, 1H), 4.70 (d, J=5.4 Hz, 2H), 3.73 (s, 3H), 2.61 (q, J=7.2 Hz, 2H), 1.16 (t, J=7.6 Hz, 3H).

Example 187: 5-Ethyl-2-methoxy-N-(7-methylbenzo[d]isoxazol-3-yl)benzenesulfonamide 187

201

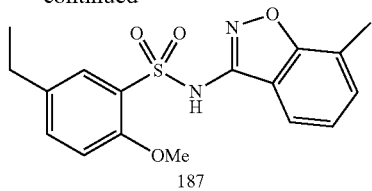

187

To a suspension of N-(7-bromobenzo[d]isoxazol-3-yl)-5-ethyl-2-methoxybenzenesulfonamide 137 (150 mg, 0.36 mmol) in 1,4-dioxane (18 mL) and water (4.5 mL) was added $K_2CO_3$ (150 mg, 1.09 mmol), methylboronic acid (45 mg, 0.73 mmol) and Pd(dppf)Cl$_2$ (27 mg, 0.036 mmol) and the mixture was heated at 90° C. under a $N_2$ atmosphere for 4 h. The mixture was concentrated under reduced pressure and the residue was partitioned between EtOAc (50 mL), water (40 mL) and 1 M aq. HCl (15 mL). The layers were separated and the organic layer was washed with 0.5 M aq. HCl (40 mL×2), brine, dried over anhydrous $Na_2SO_4$, filtered and concentrated under reduced pressure. The residue was purified by preparative HPLC to give the title compound (20 mg, 16%) as a white solid. LCMS-D: $R_t$ 2.25 min; m/z 347.1 [M+H]$^+$, 369.1 [M+Na]$^+$. $^1$H NMR (400 MHz, DMSO-d$_6$) δ 11.7 (s, 1H), 7.89-7.82 (m, 1H), 7.70 (d, J=2.3 Hz, 1H), 7.50-7.38 (m, 2H), 7.25 (t, J=7.6 Hz, 1H), 7.12-7.04 (m, 1H), 3.73 (s, 3H), 2.60 (q, J=7.6 Hz, 2H), 2.39 (s, 3H), 1.15 (t, J=7.6 Hz, 3H).

Example 188: 5-Ethyl-N-(7-ethylbenzo[d]isoxazol-3-yl)-2-methoxybenzenesulfonamide 188

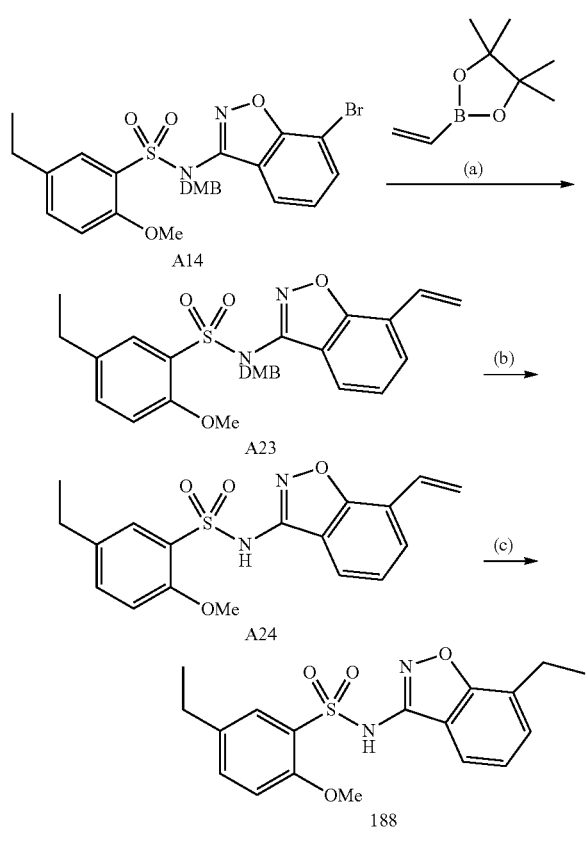

202 a) N-((2,4-dimethoxybenzyl)oxy)-5-ethyl-2-methoxy-N-(7-vinylbenzo[d]isoxazol-3-yl)benzenesulfonamide A23

To a suspension of N-(7-bromobenzo[d]isoxazol-3-yl)-N-((2,4-dimethoxybenzyl)oxy)-5-ethyl-2-methoxybenzenesulfonamide A17 (200 mg, 0.36 mmol) in 1,4-dioxane (15 mL) and water (3 mL) was added 4,4,5,5-tetramethyl-2-vinyl-1,3,2-dioxaborolane (110 mg, 0.71 mmol), $K_2CO_3$ (148 mg, 1.07 mmol) and Pd(dppf)Cl$_2$ (26 mg, 0.036 mmol) and the mixture was heated at 90° C. under a $N_2$ atmosphere for 4 h. The mixture was concentrated under reduced pressure and the residue was diluted with EtOAc (30 mL) and washed with water (25 mL×3). The organic layer was dried over anhydrous $Na_2SO_4$, filtered and concentrated under reduced pressure. The residue was purified by a silica gel chromatography (Pet. ether/EtOAc=2/1) to give the title compound (95 mg, 52%) as a white solid. LCMS-D: $R_t$ 3.28 min; m/z 509.0 [M+H]$^+$.

b) 5-Ethyl-2-methoxy-N-(7-vinylbenzo[d]isoxazol-3-yl)benzenesulfonamide A24

A mixture of N-((2,4-dimethoxybenzyl)oxy)-5-ethyl-2-methoxy-N-(7-vinylbenzo[d]isoxazol-3-yl)benzenesulfonamide A23 (95 mg, 0.18 mmol) and TFA (4 mL) was stirred at RT for 3 h then concentrated under reduced pressure. The residue was purified by a silica gel chromatography (Pet. ether/EtOAc=2/1) to give the title compound (40 mg, 61%) as a white solid. LCMS-D: $R_t$ 2.78 min; m/z 359.1 [M+H]$^{30}$ c) 5-Ethyl-N-(7-ethylbenzo[d]isoxazol-3-yl)-2-methoxybenzenesulfonamide 188

To a solution of 5-ethyl-2-methoxy-N-(7-vinylbenzo[d]isoxazol-3-yl)benzenesulfonamide A24 (35 mg, 0.098 mmol) in EtOAc (5 mL) was added 10% Pd/C (7 mg) and the mixture was stirred at RT under a $H_2$ atmosphere overnight. The mixture was filtered, the filtrate was concentrated and the residue was purified by silica gel chromatography (Pet. ether/EtOAc=4/1) to give the title compound (30 mg, 85%) as a white solid. LCMS-D: $R_t$ 2.83 min; m/z 361.1 [M+H]$^+$. $^1$H NMR (400 MHz, DMSO-d$_6$) δ 11.7 (s, 1H), 7.90-7.83 (m, 1H), 7.70 (d, J=2.3 Hz, 1H), 7.50-7.40 (m, 2H), 7.28 (t, J=7.6 Hz, 1H), 7.12-7.05 (m, 1H), 3.73 (s, 3H), 2.80 (q, J=7.5 Hz, 2H), 2.61 (q, J=7.6 Hz, 2H), 1.22 (t, J=7.5 Hz, 3H), 1.15 (t, J=7.6 Hz, 3H).

Example 189: N-(7-Cyclopropylbenzo[d]isoxazol-3-yl)-5-ethyl-2-methoxybenzenesulfonamide 189

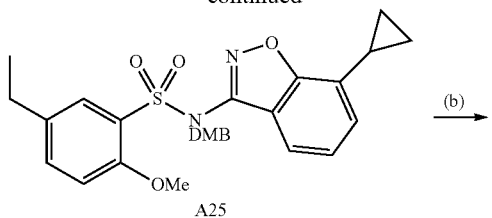

A25

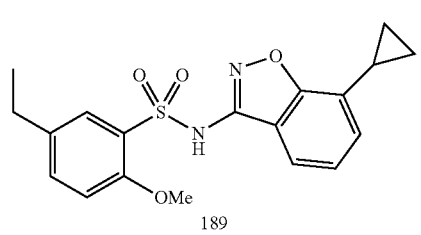

189 a) N-(7-Cyclopropylbenzo[d]isoxazol-3-yl)-N-((2,4-dimethoxybenzyl)oxy)-5-ethyl-2-methoxybenzenesulfonamide A25

To a suspension of N-(7-bromobenzo[d]isoxazol-3-yl)-N-((2,4-diethylbenzyl)oxy)-5-ethyl-2-methoxybenzenesulfonamide A17 (200 mg, 0.36 mmol) in 1,4-dioxane (15 mL) and H$_2$O (3 mL) was added cyclopropylboronic acid (61 mg, 0.71 mmol), K$_2$CO$_3$ (148 mg, 1.07 mmol) and Pd(dppf)Cl$_2$ (26 mg, 0.036 mmol) and the mixture was heated at 90° C. under a N$_2$ atmosphere for 4 h. The mixture was concentrated under reduced pressure and the residue was diluted with EtOAc (30 mL) and washed with water (25 mL×3). The organic layer was dried over anhydrous Na$_2$SO$_4$, filtered and concentrated under reduced pressure. The residue was purified by silica gel chromatography (Pet. ether/EtOAc=3/1) to give the title compound (140 mg, 75%) as a white solid. LCMS-D: R$_t$ 3.34 min; m/z 523.2 [M+H]$^+$.

b) N-(7-Cyclopropylbenzo[d]isoxazol-3-yl)-5-ethyl-2-methoxybenzenesulfonamide 189

A mixture of N-(7-cyclopropylbenzo[d]isoxazol-3-yl)-N-((2,4-dimethoxybenzyl)oxy)-5-ethyl-2-methoxybenzenesulfonamide A25 (140 mg, 0.27 mmol) and TFA (6 mL) was stirred at RT for 3 h then concentrated under reduced pressure. The residue was purified by silica gel chromatography (Pet. ether/EtOAc=2/1) to give the title compound (80 mg, 81%) as a white solid. LCMS-D: R$_t$ 2.86 min; m/z 373.1 [M+H]$^+$. $^1$H NMR (400 MHz, DMSO-d$_6$) δ 11.7 (s, 1H), 7.81 (dd, J=7.0, 2.1 Hz, 1H), 7.70 (d, J=2.3 Hz, 1H), 7.50-7.43 (m, 1H), 7.27-7.19 (m, 2H), 7.12-7.06 (m, 1H), 3.73 (s, 3H), 2.61 (q, J=7.6 Hz, 2H), 2.17-2.10 (m, 1H), 1.15 (t, J=7.5 Hz, 3H), 1.04-0.97 (m, 2H), 0.90-0.84 (m, 2H).

Example 190: N-(7-Cyclohexylbenzo[d]isoxazol-3-yl)-5-ethyl-2-methoxybenzenesulfonamide 190

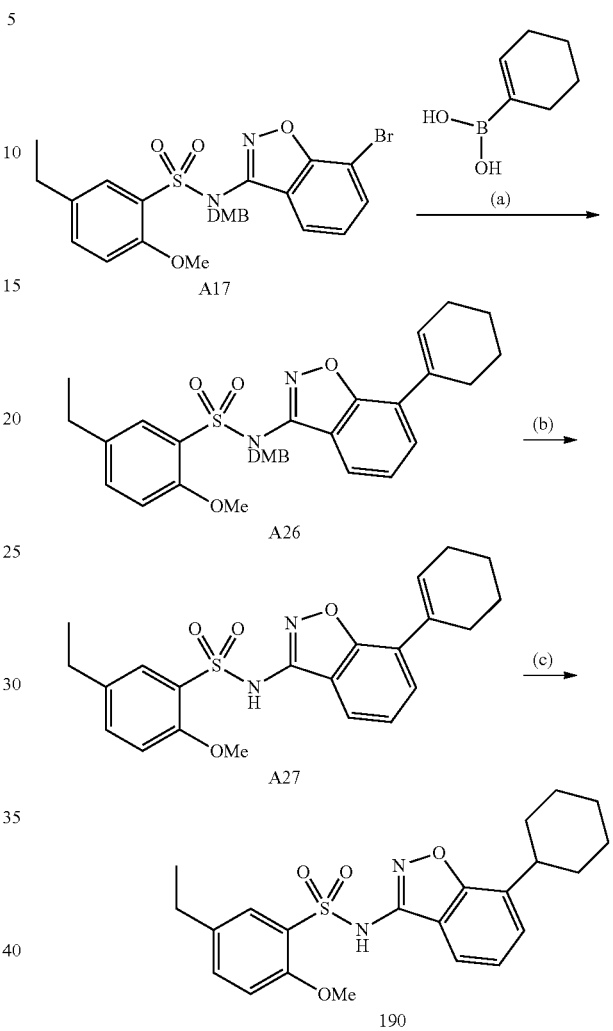

a) N-(7-(cyclohex-1-en-1-yl)benzo[d]isoxazol-3-yl)-N-(2,4-dimethoxybenzyl)-5-ethyl-2-methoxybenzenesulfonamide A26

To a suspension of N-(7-bromobenzo[d]isoxazol-3-yl)-N-(2,4-dimethoxybenzyl)-5-ethyl-2-methoxybenzenesulfonamide A17 (200 mg, 0.36 mmol) in 1,4-dioxane (15 mL) and water (3 mL) was added cyclohex-1-en-1-ylboronic acid (90 mg, 0.71 mmol), Pd(dppf)Cl$_2$ (26 mg, 0.036 mmol) and K$_2$CO$_3$ (148 mg, 1.07 mmol) and the mixture was heated at 90° C. under N$_2$ for 4 h. The mixture was concentrated under reduced pressure and the residue was diluted with EtOAc (30 mL) and washed with water (25 mL×3). The organic layer was dried over anhydrous Na$_2$SO$_4$, filtered and concentrated under reduced pressure. The residue was purified by column chromatography (Pet. ether/EtOAc=3/1) to give the title compound (150 mg, 75%) as a white solid, which was used directly in the next step.

b) N-(7-(Cyclohex-1-en-1-yl)benzo[d]isoxazol-3-yl)-5-ethyl-2-methoxybenzenesulfonamide A27

A mixture of N-(7-(cyclohex-1-en-1-yl)benzo[d]isoxazol-3-yl)-N-(2,4-dimethoxybenzyl)-5-ethyl-2-methoxybenzenesulfonamide A26 (150 mg, 0.26 mmol) and TFA (7 mL) was stirred at RT for 3 h then concentrated under reduced pressure. The residue was purified by silica gel chromatography (Pet. ether/EtOAc=2/1) to give the title compound (65 mg, 60%) as a white solid. LCMS-D: $R_t$ 3.64 min; m/z 413 [M+H]$^+$.

c) N-(7-Cyclohexylbenzo[d]isoxazol-3-yl)-5-ethyl-2-methoxybenzenesulfonamide 190

A mixture of N-(7-(cyclohex-1-en-1-yl)benzo[d]isoxazol-3-yl)-5-ethyl-2-methoxybenzenesulfonamide A27 (65 mg, 0.15 mmol) and 10% Pd/C (13 mg) in EtOAc (10 mL) was stirred at RT under a H$_2$ atmosphere for 3 h. The mixture was filtered and the filtrate was concentrated under reduced pressure to give the title compound (40 mg, 61%) as a white solid. LCMS-D: $R_t$ 3.34 min; m/z 415.2 [M+H]$^+$. 1H NMR (400 MHz, DMSO-d$_6$) δ 11.7 (s, 1H), 7.87-7.82 (m, 1H), 7.70 (d, J=2.3 Hz, 1H), 7.49-7.41 (m, 2H), 7.28 (t, J=7.6 Hz, 1H), 7.12-7.06 (m, 1H), 3.72 (s, 3H), 2.62 (q, J=7.6 Hz, 2H), 1.85-1.75 (m, 4H), 1.75-1.67 (m, 1H), 1.61-1.48 (m, 2H), 1.44-1.20 (m, 4H), 1.15 (t, J=7.6 Hz, 3H).

Example 191: 5-Ethyl-2-methoxy-N-(7-(1-methyl-1H-pyrazol-4-yl)benzo[d]isoxazol-3-yl)benzenesulfonamide 191

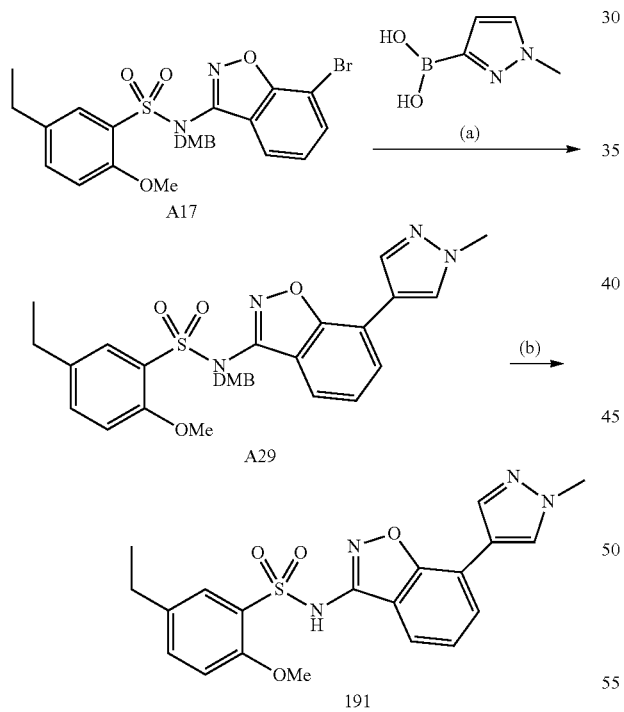

a) N-((2,4-Dimethoxybenzyl)oxy)-5-ethyl-2-methoxy-N-(7-(1-methyl-1H-pyrazol-4-yl)benzo[d]isoxazol-3-yl)benzenesulfonamide A29

To a mixture of N-(7-bromobenzo[d]isoxazol-3-yl)-N-((2,4-dimethoxybenzyl)oxy)-5-ethyl-2-methoxybenzenesulfonamide A17 (150 mg, 0.27 mmol) in 1,4-dioxane (15 mL) and H$_2$O (3 mL) was added K$_2$CO$_3$ (110 mg, 0.80 mmol), (1-methyl-1H-pyrazol-4-yl)boronic acid (67 mg, 0.33 mmol) and Pd(dppf)Cl$_2$ (20 mg, 0.027 mmol) and the mixture was heated at 90° C. under a N$_2$ atmosphere overnight. The mixture was diluted with 0.5 M aq. HCl (30 mL) and the organic solvent was mostly removed under reduced pressure. The remaining aqueous mixture was extracted with DCM (40 mL×3) and the combined organic extracts were dried over anhydrous Na$_2$SO$_4$, filtered and concentrated under reduced pressure. The residue was purified by silica gel chromatography (DCM/MeOH=100/1) to give the title compound (80 mg, 53%) as a light yellow solid, which was used directly in the next step.

b) 5-Ethyl-2-methoxy-N-(7-(1-methyl-1H-pyrazol-4-yl)benzo[d]isoxazol-3-yl)benzenesulfonamide 191

A mixture of N-((2,4-dimethoxybenzyl)oxy)-5-ethyl-2-methoxy-N-(7-(1-methyl-1H-pyrazol-4-yl)benzo[d]isoxazol-3-yl)benzenesulfonamide A29 (80 mg, 0.14 mmol) and TFA (3 mL) was stirred at RT for 3 h then concentrated under reduced pressure. The residue was purified by silica gel chromatography (DCM/MeOH=80/1) to give the title compound (50 mg, 86%) as a light yellow solid. LCMS-D: $R_t$ 2.59 min; m/z 413.1 [M+H]$^+$. $^1$H NMR (400 MHz, DMSO-d$_6$) δ 11.8 (s, 1H), 8.34 (s, 1H), 8.06 (s, 1H), 7.91-7.84 (m, 2H), 7.72 (d, J=2.3 Hz, 1H), 7.50-7.43 (m, 1H), 7.41-7.32 (m, 1H), 7.13-7.06 (m, 1H), 3.90 (s, 3H), 3.74 (s, 3H), 2.62 (q, J=7.6 Hz, 2H), 1.16 (t, J=7.5 Hz, 3H).

Example 192: 5-Ethyl-2-methoxy-N-(7-(pyrimidin-5-yl)benzo[d]isoxazol-3-yl)benzenesulfonamide 192

To a suspension of N-(7-bromobenzo[d]isoxazol-3-yl)-5-ethyl-2-methoxybenzenesulfonamide 137 (200 mg, 0.49 mmol) in toluene (16 mL), water (8 mL) and isopropanol (8 mL) was added pyrimidin-5-ylboronic acid (181 mg, 1.46 mmol), K$_3$PO$_4$ (518 mg, 1.95 mmol) and Pd(dppf)Cl$_2$ (36 mg, 0.049 mmol) and the mixture was heated at 90° C. under a N$_2$ atmosphere overnight. The mixture was adjusted to pH 5-6 and extracted with EtOAc (20 mL×3). The combined organic extracts were dried over anhydrous Na$_2$SO$_4$, filtered and concentrated under reduced pressure. The residue was purified by silica gel chromatography (DCM/MeOH=40/1) to give the title compound (18 mg, 9%) as a brown solid. LCMS-D: $R_t$ 2.49 min; m/z 411.1 [M+H]$^+$. $^1$H NMR (400 MHz, DMSO-d$_6$) δ 11.9 (s, 1H), 9.34-9.18 (m, 2H), 8.17 (d, J=8.1 Hz, 1H), 8.06 (d, J=7.4 Hz, 1H), 7.73 (s, 1H), 7.62-7.42 (m, 3H), 7.17-7.06 (m, 1H), 3.75 (s, 3H), 2.62 (q, J=7.6 Hz, 2H), 1.16 (t, J=7.6 Hz, 3H).

Example 193: 5-Ethyl-2-methoxy-N-(6-methylbenzo[d]isoxazol-3-yl)benzenesulfonamide 193

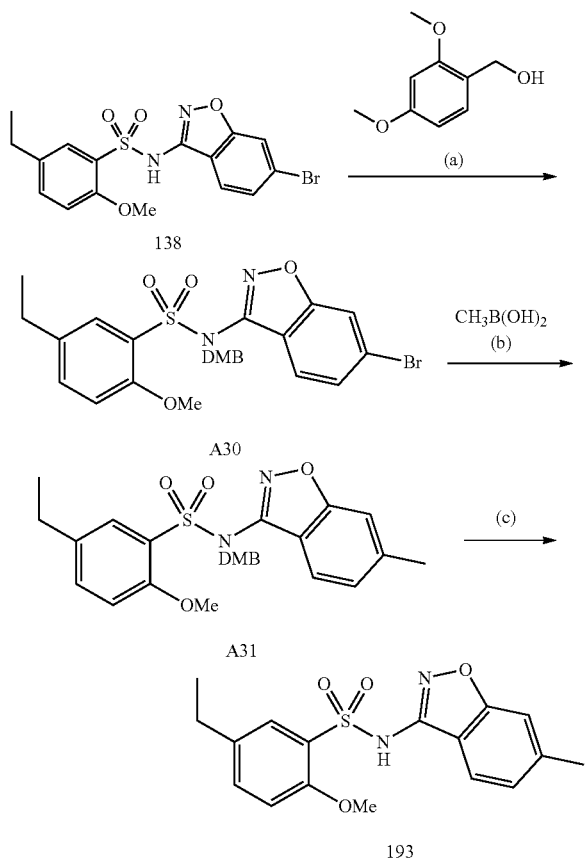

a) N-(6-Bromobenzo[d]isoxazol-3-yl)-N-(2,4-dimethoxybenzyl)-5-ethyl-2-methoxybenzenesulfonamide A30

To a solution of N-(6-bromobenzo[d]isoxazol-3-yl)-5-ethyl-2-methoxybenzenesulfonamide 138 (4.1 g, 10.0 mmol), (2,4-dimethoxyphenyl)methanol (2.5 g, 15.0 mmol) and PPh₃ (6.6 g, 25.0 mmol) in THF (100 mL) at 0° C. under N₂ was added DIAD (4.0 g, 20.0 mmol) and the mixture was stirred at RT overnight. The mixture was concentrated under reduced pressure and the residue was purified by silica gel chromatography (Pet. ether/EtOAc=50/1 to 5/1) to give the title compound (4.0 g, 71%) as a white solid, which was used directly in the next step.

b) N-(2,4-Dimethoxybenzyl)-5-ethyl-2-methoxy-N-(6-methylbenzo[d]isoxazol-3-yl)benzenesulfonamide A31

A mixture of N-(6-bromobenzo[d]isoxazol-3-yl)-N-(2,4-dimethoxybenzyl)-5-ethyl-2-methoxybenzenesulfonamide A30 (120 mg, 0.214 mmol), CH₃B(OH)₂ (64 mg, 1.07 mmol), Pd(dppf)Cl₂ (31 mg, 0.428 mmol) and K₂CO₃ (148 mg, 1.07 mmol) in 1,4-dioxane (10 mL) and water (2 mL) was heated at 90° C. under N₂ overnight. The solvent was removed under reduced pressure and the residue was purified by column chromatography (Pet. ether/EtOAc=50/1 to 5/1) to give the title compound (72 mg, 68%) as a white solid, which was used directly in the next step.

c) 5-Ethyl-2-methoxy-N-(6-methylbenzo[d]isoxazol-3-yl)benzenesulfonamide 193

A mixture of N-(2,4-dimethoxybenzyl)-5-ethyl-2-methoxy-N-(6-methylbenzo[d]isoxazol-3-yl)benzenesulfonamide A31 (72 mg, 0.145 mmol) and TFA (3 mL) was stirred at RT for 3 h then concentrated under reduced pressure. The residue was purified by column chromatography (Pet. ether/EtOAc=50/1 to 3/1) to give the title compound (45 mg, 90%) as a white solid. LCMS-D: R$_t$ 2.76 min; m/z 347.1 [M+H]⁺. ¹H NMR (400 MHz, DMSO-d₆) δ 11.6 (s, 1H), 7.94-7.87 (m, 1H), 7.68 (d, J=2.3 Hz, 1H), 7.49-7.42 (m, 1H), 7.39 (s, 1H), 7.23-7.16 (m, 1H), 7.13-7.05 (m, 1H), 3.72 (s, 3H), 2.60 (q, J=7.5 Hz, 2H), 2.43 (s, 3H), 1.14 (t, J=7.5 Hz, 3H).

Example 194: 5-Ethyl-N-(6-ethylbenzo[d]isoxazol-3-yl)-2-methoxybenzenesulfonamide 194

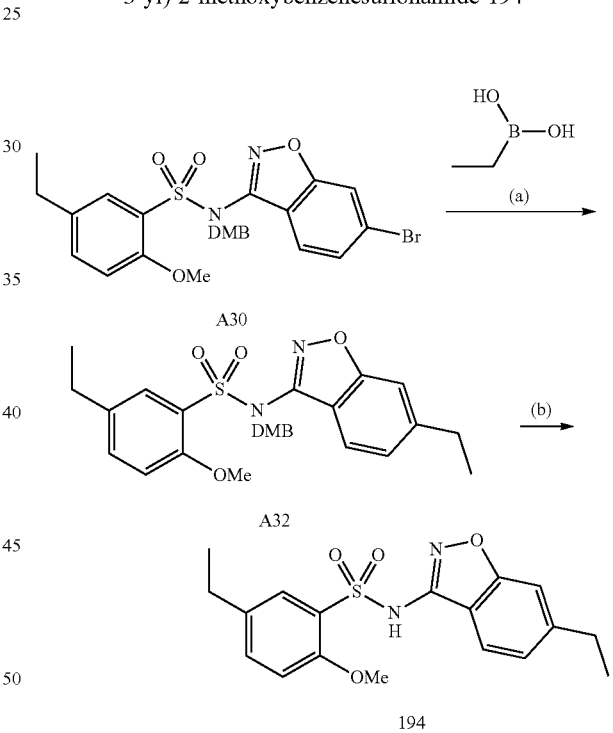

a) N-(2,4-Dimethoxybenzyl)-5-ethyl-N-(6-ethylbenzo[d]isoxazol-3-yl)-2-methoxybenzenesulfonamide A32

A mixture of N-(6-bromobenzo[d]isoxazol-3-yl)-N-(2,4-dimethoxybenzyl)-5-ethyl-2-methoxybenzenesulfonamide A30 (200 mg, 0.356 mmol), ethylboronic acid (132 mg, 1.78 mmol), Pd(dppf)Cl₂ (52 mg, 0.071 mmol) and K₂CO₃ (246 mg, 1.78 mmol) in 1,4-dioxane (20 mL) and water (4 mL) was heated at 90° C. under N₂ overnight. The solvent was removed under reduced pressure and the residue was partitioned between DCM (200 mL) and water (50 mL). The layers were separated and the organic layer was washed with water, brine, dried over anhydrous Na$_2$SO$_4$, filtered and concentrated under reduced pressure. The residue was purified by column chromatography (Pet. ether/EtOAc=100/1 to 5/1) to give the title compound (120 mg, 67%) as a white solid, which was used directly in the next step.

b) 5-Ethyl-N-(6-ethylbenzo[d]isoxazol-3-yl)-2-methoxybenzenesulfonamide 194

A mixture of N-(2,4-dimethoxybenzyl)-5-ethyl-N-(6-ethylbenzo[d]isoxazol-3-yl)-2-methoxybenzenesulfonamide A32 (120 mg, 0.24 mmol) and TFA (5 mL) was stirred at RT overnight then concentrated under reduced pressure. The residue was purified by column chromatography (Pet. ether/EtOAc=50/1 to 3/1) to give the title compound (80 mg, 94%) as a white solid. LCMS-D: R$_t$ 2.84 min; m/z 361.1 [M+H]$^+$. $^1$H NMR (400 MHz, DMSO-d$_6$) δ 11.6 (s, 1H), 7.97-7.90 (m, 1H), 7.69 (d, J=2.3 Hz, 1H), 7.49-7.37 (m, 2H), 7.26-7.19 (m, 1H), 7.11-7.04 (m, 1H), 3.72 (s, 3H), 2.73 (q, J=7.6 Hz, 2H), 2.60 (q, J=7.6 Hz, 2H), 1.20 (t, J=7.6 Hz, 3H), 1.14 (t, J=7.6 Hz, 3H).

Example 195: N-(6-Cyclopropylbenzo[d]isoxazol-3-yl)-5-ethyl-2-methoxybenzenesulfonamide 195

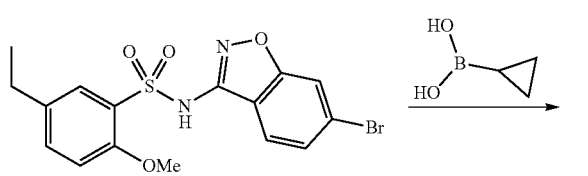

138

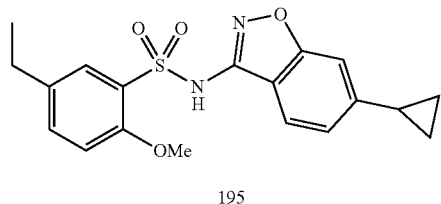

195

A mixture of N-(6-bromobenzo[d]isoxazol-3-yl)-5-ethyl-2-methoxybenzenesulfonamide 138 (206 mg, 0.5 mmol), cyclopropylboronic acid (215 mg, 2.5 mmol), Pd(dppf)Cl$_2$ (73 mg, 0.1 mmol) and K$_2$CO$_3$ (345 mg, 2.5 mmol) in 1,4-dioxane (20 mL) and water (4 mL) was heated at 90° C. under N$_2$ overnight. The solvent was removed under reduced pressure and the residue was purified by column chromatography (Pet. ether/EtOAc=50/1 to 3/1) to give the title compound (80 mg, 43%) as a white solid. LCMS-D: R$_t$ 2.86 min; m/z 373.1 [M+H]$^+$. $^1$H NMR (400 MHz, DMSO-d$_6$) δ 11.6 (s, 1H), 7.91-7.85 (m, 1H), 7.68 (d, J=2.3 Hz, 1H), 7.48-7.42 (m, 1H), 7.27 (s, 1H), 7.12-7.04 (m, 2H), 3.72 (s, 3H), 2.60 (q, J=7.6 Hz, 2H), 2.10-2.00 (m, 1H), 1.14 (t, J=7.5 Hz, 3H), 1.07-0.99 (m, 2H), 0.83-0.75 (m, 2H).

Example 196: 5-Ethyl-2-methoxy-N-(6-(1-methyl-1H-pyrazol-4-yl)benzo[d]isoxazol-3-yl)benzenesulfonamide 196

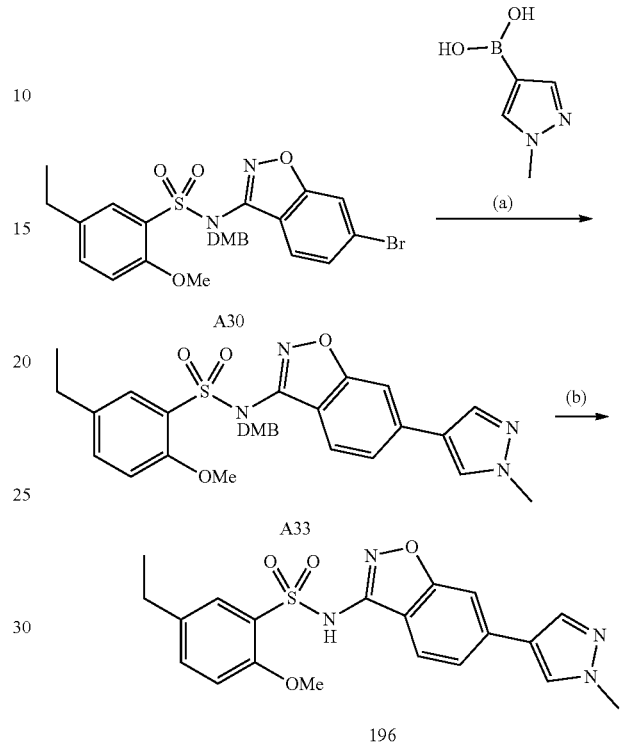

a) N-(2,4-Dimethoxybenzyl)-5-ethyl-2-methoxy-N-(6-(1-methyl-1H-pyrazol-4-yl)benzo[d]isoxazol-3-yl)benzenesulfonamide A33

A mixture of N-(6-bromobenzo[d]isoxazol-3-yl)-N-(2,4-dimethoxybenzyl)-5-ethyl-2-methoxybenzenesulfonamide A30 (120 mg, 0.214 mmol), (1-methyl-1H-pyrazol-4-yl) boronic acid (54 mg, 0.428 mmol), Pd(dppf)Cl$_2$ (31 mg, 0.043 mmol) and K$_2$CO$_3$ (148 mg, 1.07 mmol) in 1,4-dioxane (10 mL) and water (2 mL) was heated at 90° C. under N$_2$ overnight. The solvent was removed under reduced pressure and the residue was partitioned between DCM (150 mL) and water (50 mL). The layers were separated and the organic layer was washed with water, brine, dried over anhydrous Na$_2$SO$_4$, filtered and concentrated under reduced pressure. The residue was purified by column chromatography (Pet. ether/EtOAc=50/1 to 5/1) to give the title compound (90 mg, 75%) as a brown solid. LCMS-D: R$_t$ 3.05 min; m/z 563.0 [M+H]$^+$.

b) 5-Ethyl-2-methoxy-N-(6-(1-methyl-1H-pyrazol-4-yl)benzo[d]isoxazol-3-yl)benzenesulfonamide 196

A mixture of N-(2,4-dimethoxybenzyl)-5-ethyl-2-methoxy-N-(6-(1-methyl-1H-pyrazol-4-yl) benzo[d]isoxazol-3-yl)benzenesulfonamide A33 (90 mg, 0.16 mmol) and TFA (5 mL) was stirred at RT overnight then concentrated under reduced pressure. The residue was purified by column chromatography (Pet. ether/EtOAc=50/1 to 5/1) to give the title compound (30 mg, 46%) as a brown solid. LCMS-D: R$_t$ 2.57 min; m/z 413.2 [M+H]$^+$. $^1$H NMR (400 MHz, DMSO-d$_6$) δ 11.6 (s, 1H), 8.29 (s, 1H), 8.06-7.95 (m, 2H), 7.78 (s, 1H), 7.70 (d, J=2.3 Hz, 1H), 7.64-7.56 (m, 1H), 7.50-7.42 (m, 1H), 7.13-7.05 (m, 1H), 3.87 (s, 3H), 3.71 (s, 3H), 2.61 (q, J=7.6 Hz, 2H), 1.15 (t, J=7.5 Hz, 3H).

Example 197: 5-Ethyl-2-methoxy-N-(6-(pyrimidin-5-yl)benzo[d]isoxazol-3-yl)benzenesulfonamide 197

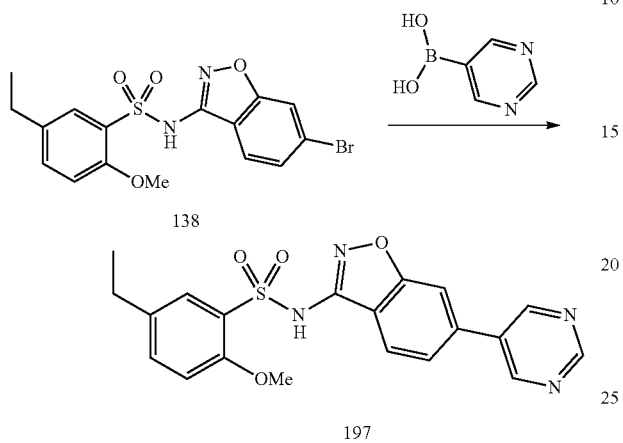

A mixture of N-(6-bromobenzo[d]isoxazol-3-yl)-5-ethyl-2-methoxybenzenesulfonamide 138 (100 mg, 0.24 mmol), pyrimidin-5-ylboronic acid (45 mg, 0.36 mmol), Pd(PPh$_3$)$_4$ (28 mg, 0.024 mmol) and K$_2$CO$_3$ (166 mg, 1.2 mmol) in toluene (8 mL), water (8 mL) and isopropanol (2 mL) was heated at 90° C. under N$_2$ for 4 h. 2 M aq. NaOH (15 mL) was added and the mixture was stirred at RT for 20 min. The mixture was washed with EtOAc (20 mL×2) then adjusted to pH 2 with conc. HCl and extracted with DCM (50 mL×2). The combined organic extracts were washed with water, brine, dried over anhydrous Na$_2$SO$_4$, filtered and concentrated under reduced pressure. The residue was purified by silica gel chromatography (DCM/MeOH=30/1) to give the title compound (15 mg, 15%) as a white solid. LCMS-D: R$_t$ 2.97 min; m/z 411.0 [M+H]$^+$. $^1$H NMR (400 MHz, DMSO-d$_6$) δ 11.8 (s, 1H), 9.24 (s, 3H), 8.21-8.15 (m, 1H), 8.11 (s, 1H), 7.85-7.78 (m, 1H), 7.72 (d, J=2.3 Hz, 1H), 7.49-7.42 (m, 1H), 7.13-7.05 (m, 1H), 3.73 (s, 3H), 2.61 (q, J=7.6 Hz, 2H), 1.15 (t, J=7.6 Hz, 3H).

Example 198: 5-Ethyl-2-methoxy-N-(4-methylbenzo[d]isoxazol-3-yl)benzenesulfonamide 198

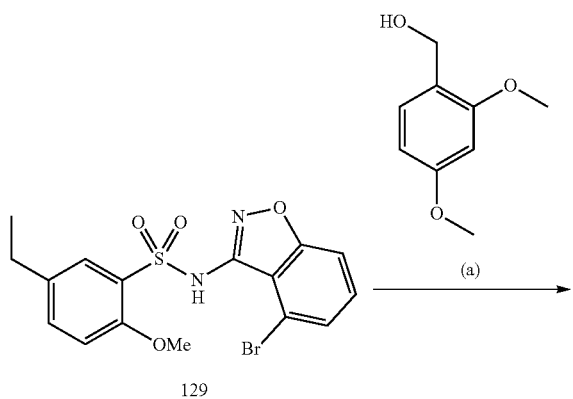

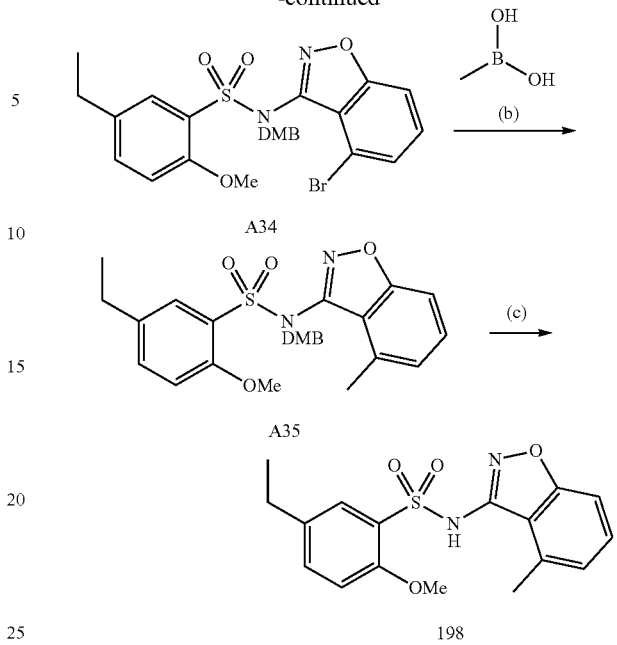

a) N-(4-Bromobenzo[d]isoxazol-3-yl)-N-((2,4-dimethoxybenzyl)oxy)-5-ethyl-2-methoxybenzenesulfonamide A34

To a solution of N-(4-bromobenzo[d]isoxazol-3-yl)-5-ethyl-2-methoxybenzenesulfonamide 129 (2.1 g, 5.1 mmol), (2,4-dimethoxyphenyl)methanol (1.3 g, 7.7 mmol) and PPh$_3$ (3.35 g, 12.8 mmol) in THF (200 mL) at 0° C. under N$_2$ was added DIAD (3.1 g, 15.3 mmol) and the mixture was stirred at 0° C. for 1 h then allowed to warm to RT and stirred overnight. The mixture was concentrated under reduced pressure and the residue was purified by column chromatography (Pet. ether/EtOAc=5/1) to give the title compound (1.2 g, 42%) as a white solid. LCMS-D: R$_t$ 3.40 min; m/z 583.0 [M+H]$^+$.

b) N((2,4-Dimethoxybenzyl)oxy)-5-ethyl-2-methoxy-N-(4-methylbenzo[d]isoxazol-3-yl)benzenesulfonamide A35

A mixture of N-(4-bromobenzo[d]isoxazol-3-yl)-N-((2,4-dimethoxybenzyl)oxy)-5-ethyl-2-methoxybenzenesulfonamide A34 (200 mg, 0.36 mmol), methylboronic acid (43 mg, 0.71 mmol), K$_2$CO$_3$ (148 mg, 1.07 mmol) and Pd(dppf)Cl$_2$ (26 mg, 0.036 mmol) in 1,4-dioxane (15 mL) and water (3 mL) was heated at 90° C. under N$_2$ for 4 h. The mixture was adjusted to pH 2-3 and most of the solvent was removed under reduced pressure. The residue was diluted with water (10 mL) and extracted with DCM (25 mL×3). The combined organic layers were dried over anhydrous Na$_2$SO$_4$, filtered and concentrated under reduced pressure. The residue was purified by column chromatography (Pet. ether/EA=5/1) to give the title compound (125 mg, 71%) as a white solid, which was used directly in the next step.

c) 5-Ethyl-2-methoxy-N-(4-methylbenzo[d]isoxazol-3-yl)benzenesulfonamide 198

A mixture of N-((2,4-dimethoxybenzyl)oxy)-5-ethyl-2-methoxy-N-(4-methyl benzo[d]isoxazol-3-yl)benzenesulfonamide A35 (125 mg, 0.26 mmol) and TFA (3 mL) was stirred at RT under for 3 h then diluted with DCM (100 mL), washed with water, dried over anhydrous Na$_2$SO$_4$, filtered and concentrated under reduced pressure. The residue was purified by column chromatography (Pet. ether/EtOAc=3/1) to give the title compound (85 mg, 92%) as a white solid. LCMS-D: R$_t$ 2.69 min m/z 347.1 [M+H]$^+$. $^1$H NMR (400 MHz, DMSO-d$_6$) δ 10.6 (s, 1H), 7.58-7.56 (m, 1H), 7.52-7.46 (m, 3H), 7.18-7.14 (m, 2H), 3.73 (s, 3H), 2.62-2.56 (m, 5H), 1.14 (t, J=7.6 Hz, 3H)

Example 199: 5-Ethyl-N-(4-ethylbenzo[d]isoxazol-3-yl)-2-methoxybenzenesulfonamide 199

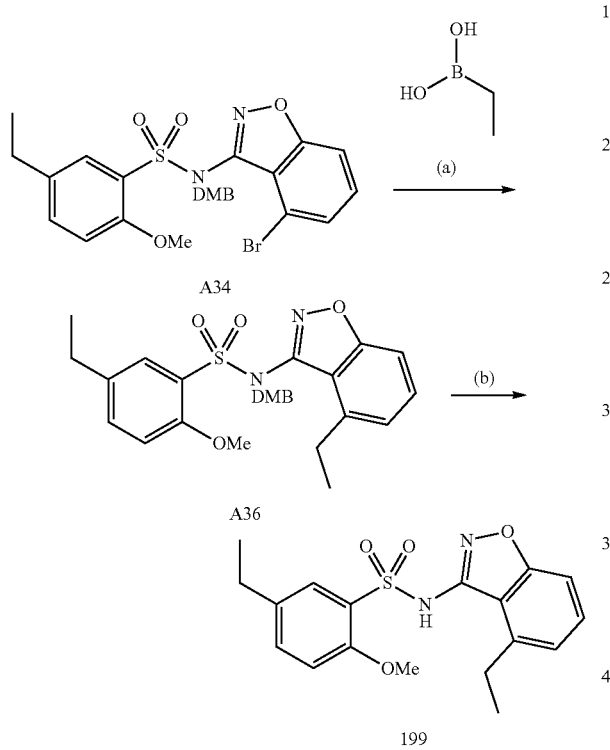

a) N-(2,4-Dimethoxybenzyl)-5-ethyl-N-(4-ethyl-benzo[d]isoxazol-3-yl)-2-methoxybenzenesulfonamide A36

A mixture of N-(4-bromobenzo[d]isoxazol-3-yl)-N-((2,4-dimethoxybenzyl)oxy)-5-ethyl-2-methoxybenzenesulfonamide A34 (200 mg, 0.36 mmol), ethylboronic acid (53 mg, 0.71 mmol), K$_2$CO$_3$ (148 mg, 1.07 mmol) and Pd(dppf)Cl$_2$ (26 mg, 0.036 mmol) in 1,4-dioxane (15 mL) and H$_2$O (3 mL) was heated at 90° C. under N$_2$ for 4 h. The mixture was adjusted to pH 2-3 and most of the solvent was removed under reduced pressure. The residue was diluted with water (15 mL) and extracted with DCM (20 mL×3). The combined organic layers were dried over anhydrous Na$_2$SO$_4$, filtered and concentrated under reduced pressure. The residue was purified by column chromatography (Pet. ether/EtOAc=5/1) to give the title compound (120 mg, 66%) as a white solid, which was used directly in the next step.

b) 5-Ethyl-N-(4-ethylbenzo[d]isoxazol-3-yl)-2-methoxybenzenesulfonamide 199

A mixture of N-(2,4-dimethoxybenzyl)-5-ethyl-N-(4-ethylbenzo[d]isoxazol-3-yl)-2-methoxybenzenesulfonamide A36 (120 mg, 0.23 mmol) and TFA (3 mL) was stirred at room temperature under N$_2$ for 3 h then diluted with DCM (100 mL), washed with water, dried over anhydrous Na$_2$SO$_4$, filtered and concentrated under reduced pressure. The residue was purified by column chromatography (Pet. ether/EtOAc=3/1) to give the title compound (75 mg, 89%) as a white solid. LCMS-D: R$_t$ 2.80 min 361.1 [M+H]$^+$. $^1$H NMR (400 MHz, DMSO-d$_6$) δ 10.5 (s, 1H), 7.60-7.49 (m, 4H), 7.22-7.18 (m, 2H), 3.81 (s, 3H), 8.09 (q, J=7.6 Hz, 2H), 2.59 (q, J=7.6 Hz, 2H), 1.25 (t, J=7.6 Hz, 3H), 1.14 (t, J=7.6 Hz, 3H).

Example 200: N-(4-Cyclopropylbenzo[d]isoxazol-3-yl)-5-ethyl-2-methoxybenzenesulfonamide 200

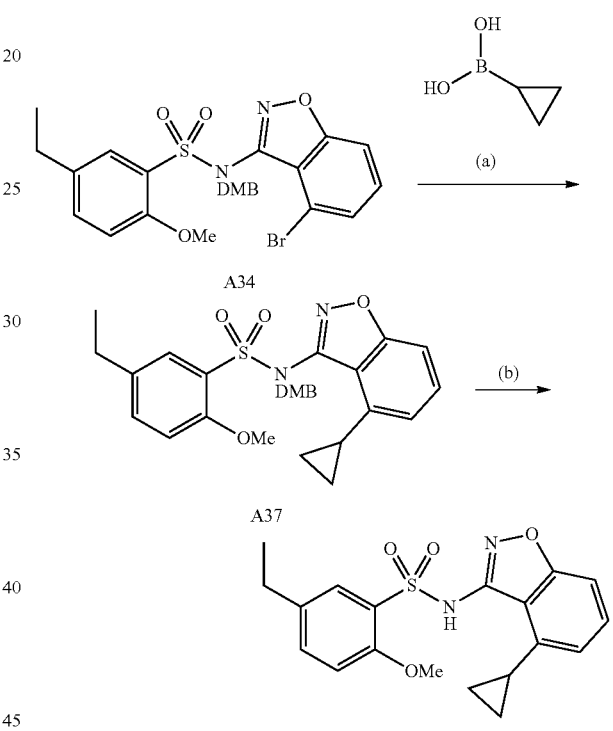

a) N-(4-Cyclopropylbenzo[d]isoxazol-3-yl)-N-(2,4-dimethoxybenzyl)-5-ethyl-2-methoxybenzenesulfonamide A37

A mixture of N-(4-bromobenzo[d]isoxazol-3-yl)-N-((2,4-dimethoxybenzyl)oxy)-5-ethyl-2-methoxybenzenesulfonamide A34 (200 mg, 0.36 mmol), cyclopropylboronic acid (61 mg, 0.71 mmol), K$_2$CO$_3$ (148 mg, 1.07 mmol) and Pd(dppf)Cl$_2$ (26 mg, 0.036 mmol) in 1,4-dioxane (15 mL) and H$_2$O (3 mL) was heated at 90° C. under N$_2$ for 4 h. The mixture was adjusted to pH 2-3 and most of the solvent was removed under reduced pressure. The residue was diluted with water (15 mL) and extracted with DCM (20 mL×3). The combined organic extracts were dried over anhydrous Na$_2$SO$_4$, filtered and concentrated under reduced pressure. The residue was purified by column chromatography (Pet. ether/EtOAc=5/1) to give the title compound (120 mg, 66%) as a yellow solid, which was used directly in the next step.

b) N-(4-Cyclopropylbenzo[d]isoxazol-3-yl)-5-ethyl-2-methoxybenzenesulfonamide 200

A mixture of N-(4-cyclopropylbenzo[d]isoxazol-3-yl)-N-(2,4-dimethoxybenzyl)-5-ethyl-2-methoxybenzenesulfonamide A37 (130 mg, 0.25 mmol) and TFA (3 mL) was stirred at RT under $N_2$ for 3 h then concentrated under reduced pressure. The residue was purified by column chromatography (Pet. ether/EtOAc=3/1) to give the title compound (85 mg, 92%) as a yellow solid. LCMS-D: $R_t$ 2.81 min, 373.1 [M+H]$^+$. $^1$H NMR (400 MHz, DMSO-$d_6$) δ 10.6 (s, 1H), 7.58-7.57 (d, J=2.0 Hz, 1H), 7.53-7.42 (m, 3H), 7.18-7.16 (m, 1H), 6.86-6.84 (m, 1H), 3.74 (s, 3H), 2.72 (m, 1H), 2.60 (q, J=7.6 Hz, 2H), 1.14 (t, J=7.6 Hz, 3H), 1.02-0.98 (m, 2H), 0.82-0.78 (m, 2H).

Example 201: N-(4-cyclohexylbenzo[d]isoxazol-3-yl)-5-ethyl-2-methoxybenzenesulfonamide 201

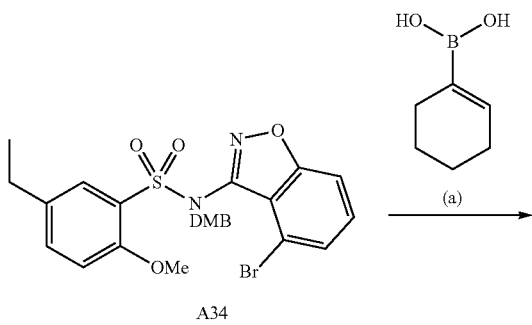

A34

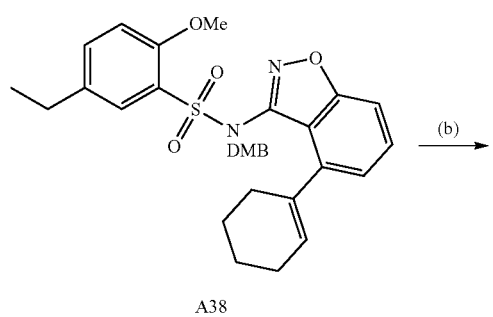

A38

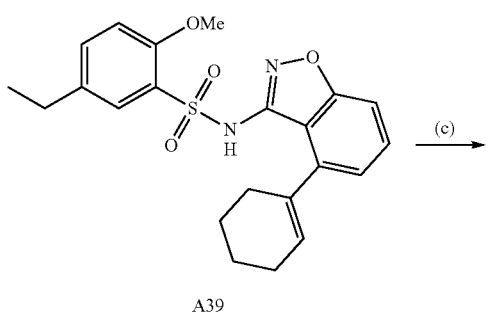

A39

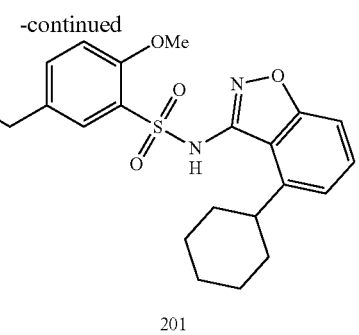

201 a) N-(4-(Cyclohex-1-en-1-yl)benzo[d]isoxazol-3-yl)-N-(2,4-dimethoxybenzyl)-5-ethyl-2-methoxybenzenesulfonamide A38

A mixture of N-(4-bromobenzo[d]isoxazol-3-yl)-N-((2,4-dimethoxybenzyl)oxy)-5-ethyl-2-methoxybenzenesulfonamide A34 (200 mg, 0.36 mmol), cyclohex-1-en-1-ylboronic acid (90 mg, 0.71 mmol), $K_2CO_3$ (148 mg, 1.07 mmol) and Pd(dppf)Cl$_2$ (26 mg, 0.036 mmol) in 1,4-dioxane (15 mL) and H$_2$O (3 mL) was heated at 90° C. under $N_2$ for 4 h. Most of the solvent was removed under reduced pressure, the residue was diluted with water (30 mL), adjusted to pH 1-2 and extracted with DCM (35 mL×3). The combined organic extracts were dried over anhydrous Na$_2$SO$_4$, filtered and concentrated under reduced pressure. The residue was purified by column chromatography (DCM/MeOH=100/1) to give the title compound (150 mg, 75%) as a white solid, which was used directly in the next step.

b) N-(4-(Cyclohex-1-en-1-yl)benzo[d]isoxazol-3-yl)-5-ethyl-2-methoxybenzenesulfonamide A39

A mixture of N-(4-(cyclohex-1-en-1-yl)benzo[d]isoxazol-3-yl)-N-(2,4-dimethoxybenzyl)-5-ethyl-2-methoxybenzenesulfonamide A38 (150 mg, 0.27 mmol) and TFA (3 mL) was stirred at RT under $N_2$ for 3 h then concentrated under reduced pressure. The residue was purified by column chromatography (Pet. ether/EtOAc=2/1) to give the title compound (80 mg, 73%) as a white solid, which was used directly in the next step.

c) N-(4-Cyclohexylbenzo[d]isoxazol-3-yl)-5-ethyl-2-methoxybenzenesulfonamide 201

A mixture of N-(4-(cyclohex-1-en-1-yl)benzo[d]isoxazol-3-yl)-5-ethyl-2-methoxy benzenesulfonamide A39 (80 mg, 0.19 mmol) and 10% Pd/C (16 mg) in EtOAc (10 mL) was stirred at RT under a $H_2$ atmosphere for 3 h. The mixture was filtered and the filtrate was concentrated under reduced pressure to give the title compound (75 mg, 94%) as a white solid. LCMS-D: $R_t$ 3.24 min, 415.2 [M+H]$^+$. $^1$H NMR (400 MHz, DMSO-$d_6$) δ 10.5 (s, 1H), 7.58-7.48 (m, 4H), 7.26 (d, J=7.2 Hz, 1H), 7.19 (d, J=8.8 Hz, 1H), 3.80 (s, 3H), 3.62-3.56 (m, 1H), 2.59 (q, J=7.6 Hz, 2H), 1.91-1.71 (m, 5H), 1.45-1.23 (m, 5H), 1.15 (t, J=7.6 Hz, 3H).

Example 202: 5-Ethyl-2-methoxy-N-(4-(1-methyl-1H-pyrazol-4-yl)benzo[d]isoxazol-3-yl)benzenesulfonamide 202

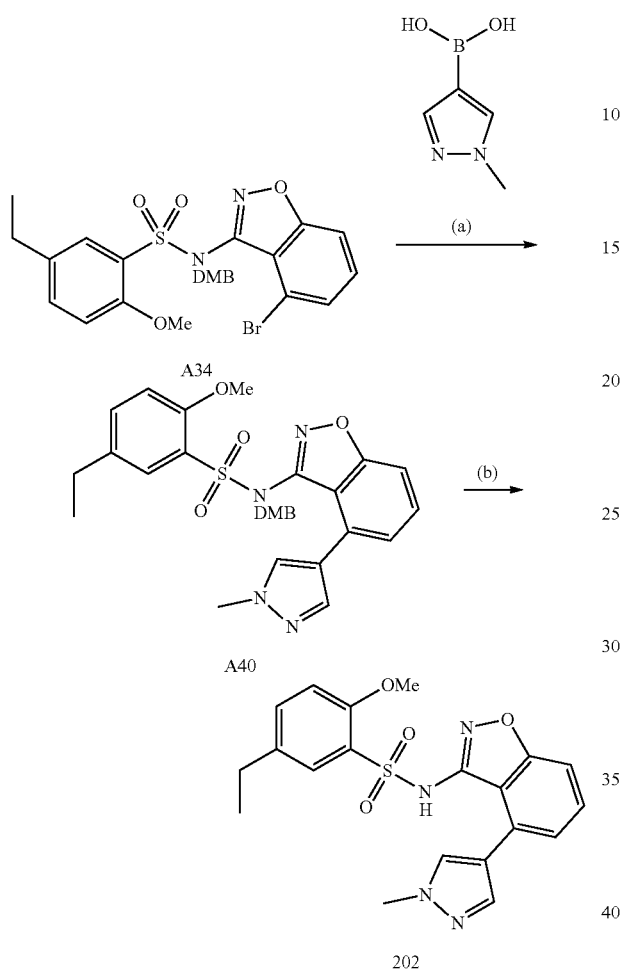

a) N-(2,4-Dimethoxybenzyl)-5-ethyl-2-methoxy-N-(4-(1-methyl-1H-pyrazol-4-yl)benzo[d]isoxazol-3-yl)benzenesulfonamide A40

A mixture of N-(4-bromobenzo[d]isoxazol-3-yl)-N-((2,4-dimethoxybenzyl)oxy)-5-ethyl-2-methoxybenzenesulfonamide A34 (200 mg, 0.36 mmol), (1-methyl-1H-pyrazol-4-yl)boronic acid (90 mg, 0.71 mmol), $K_2CO_3$ (148 mg, 1.07 mmol) and Pd(dppf)$Cl_2$ (26 mg, 0.036 mmol) in 1,4-dioxane (15 mL) and $H_2O$ (3 mL) was heated at 90° C. under $N_2$ for 4 h. Most of the solvent was removed under reduced pressure, the residue was diluted with water (30 mL), adjusted to pH 1-2 and extracted with DCM (35 mL×3). The combined organic extracts were dried over anhydrous $Na_2SO_4$, filtered and concentrated under reduced pressure. The residue was purified by column chromatography (DCM/MeOH=100/1) to give the title compound (105 mg, 53%) as a yellow solid, which was used directly in the next step.

b) 5-Ethyl-2-methoxy-N-(4-(1-methyl-1H-pyrazol-4-yl)benzo[d]isoxazol-3-yl)benzenesulfonamide 202

A mixture of N-(2,4-dimethoxybenzyl)-5-ethyl-2-methoxy-N-(4-(1-methyl-1H-pyrazol-4-yl) benzo[d]isoxazol-3-yl)benzenesulfonamide A40 (105 mg, 0.19 mmol) and TFA (2 mL) was stirred at RT under $N_2$ for 3 h then concentrated under reduced pressure. The residue was purified by column chromatography (DCM/MeOH=80/1) to give the title compound (60 mg, 79%) as a yellow solid. LCMS-D: $R_t$ 2.587 min, m/z 413.1 [M+H]$^+$. $^1$H NMR (400 MHz, DMSO-$d_6$) δ 10.2 (s, 1H), 8.12 (s, 1H), 7.90 (s, 1H), 7.66-7.45 (m, 4H), 7.39 (d, J=7.2 Hz, 1H), 7.13 (d, J=8.4 Hz, 1H), 3.88 (s, 3H), 3.75 (s, 3H), 2.58 (q, J=7.6 Hz, 2H), 1.15 (t, J=7.6 Hz, 3H).

Example 203: 5-Ethyl-2-methoxy-N-(4-(pyrimidin-5-yl)benzo[d]isoxazol-3-yl)benzenesulfonamide 203

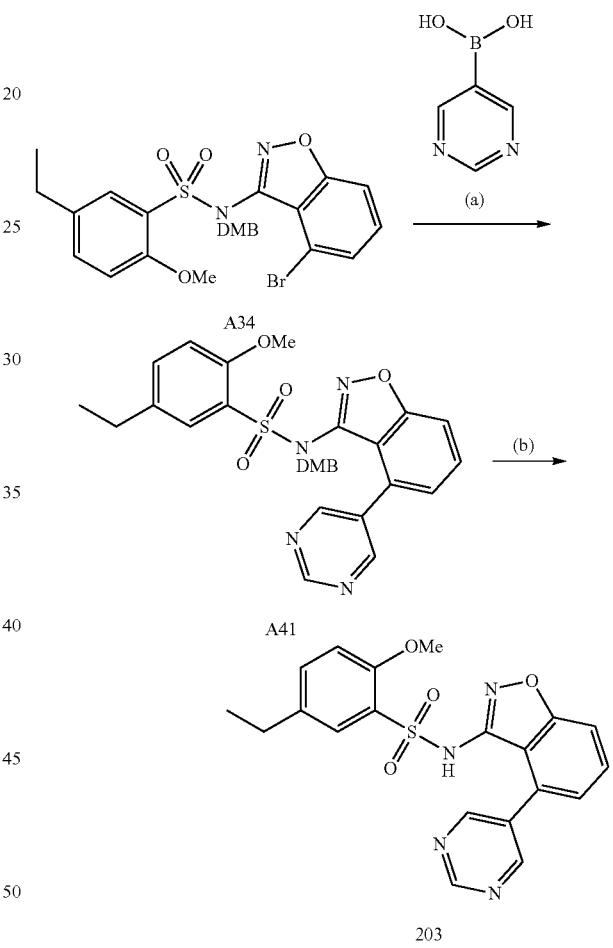

a) N-(2,4-Dimethoxybenzyl)-5-ethyl-2-methoxy-N-(4-(pyrimidin-5-yl)benzo[d]isoxazol-3-yl)benzenesulfonamide A41

A mixture of N-(4-bromobenzo[d]isoxazol-3-yl)-N-((2,4-dimethoxybenzyl)oxy)-5-ethyl-2-methoxybenzenesulfonamide A34 (200 mg, 0.36 mmol), pyrimidin-5-ylboronic acid (43 mg, 0.71 mmol), $K_2CO_3$ (148 mg, 1.07 mmol) and Pd(dppf)$Cl_2$ (26 mg, 0.036 mmol) in 1,4-dioxane (15 mL) and $H_2O$ (3 mL) was heated at 90° C. under $N_2$ for 4 h. Most of the solvent was removed under reduced pressure, the residue was diluted with water (30 mL), adjusted to pH 1-2 and extracted with DCM (35 mL×3). The combined organic extracts were dried over anhydrous Na₂SO₄, filtered and concentrated under reduced pressure. The residue was purified by column chromatography (DCM/MeOH=60/1) to give the title compound (95 mg, 47%) as a yellow solid, which was used directly in the next step.

b) 5-Ethyl-2-methoxy-N-(4-(pyrimidin-5-yl)benzo[d]isoxazol-3-yl)benzenesulfonamide 203

A mixture of N-(2,4-dimethoxybenzyl)-5-ethyl-2-methoxy-N-(4-(pyrimidin-5-yl) benzo[d]isoxazol-3-yl)benzenesulfonamide A41 (95 mg, 0.17 mmol) and TFA (2 mL) was stirred at RT under N₂ for 3 h then concentrated under reduced pressure. The residue was purified by column chromatography (DCM/MeOH=40/1) to give the title compound (45 mg, 65%) as a red solid. LCMS-D: $R_t$ 2.50 min, m/z 411.1 [M+H]⁺. ¹H NMR (400 MHz, DMSO-d₆) δ 10.5 (s, 1H), 9.24 (s, 1H), 8.97 (s, 2H), 7.86-7.79 (m, 2H), 7.53-7.38 (m, 3H), 7.13-7.11 (m, 1H), 3.75 (s, 3H), 2.55 (t, J=7.6 Hz, 2H), 1.11 (t, J=7.6 Hz, 3H).

Example 204: N-(5-Ethylbenzo[d]isoxazol-3-yl)-3-methoxy-5,6,7,8-tetrahydronaphthalene-2-sulfonamide 204

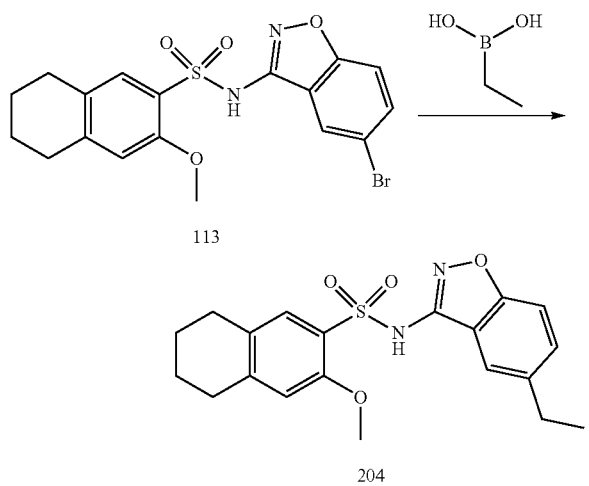

A mixture of N-(5-bromobenzo[d]isoxazol-3-yl)-3-methoxy-5,6,7,8-tetrahydronaphthalene-2-sulfonamide 113 (219 mg, 0.5 mmol), ethylboronic acid (185 mg, 2.5 mmol), Pd(dppf)Cl₂ (73 mg, 0.1 mmol) and K₂CO₃ (345 mg, 2.5 mmol) in 1,4-dioxane (20 mL) and water (20 mL) was heated at 90° C. under N₂ overnight. The mixture was then adjusted to pH 1 and most of the solvent was removed under reduced pressure. The residue was diluted with water (50 mL) and extracted with DCM (100 mL). The organic extract was washed with water, brine, dried over anhydrous Na₂SO₄, filtered and concentrated under reduced pressure. The residue was purified by silica gel chromatography (Pet. ether/EtOAc=10/1 to 2/1) followed by preparative TLC (Pet. ether/EtOAc=1/1) to give the title compound (52 mg, 27%) as a white solid. LCMS-D: $R_t$ 3.06 min, m/z 387.1 [M+H]⁺. ¹H NMR (400 MHz, DMSO-d₆) δ11.4 (s, 1H), 7.83 (s, 1H), 7.54 (s, 1H), 7.51-7.43 (m, 2H), 6.84 (s, 1H), 3.71 (s, 3H), 2.77-2.65 (m, 6H), 1.75-1.66 (m, 4H), 1.24 (t, J=7.6 Hz, 3H).

Example 205: N-(5-Cyclopropylbenzo[d]isoxazol-3-yl)-3-methoxy-5,6,7,8-tetrahydronaphthalene-2-sulfonamide 205

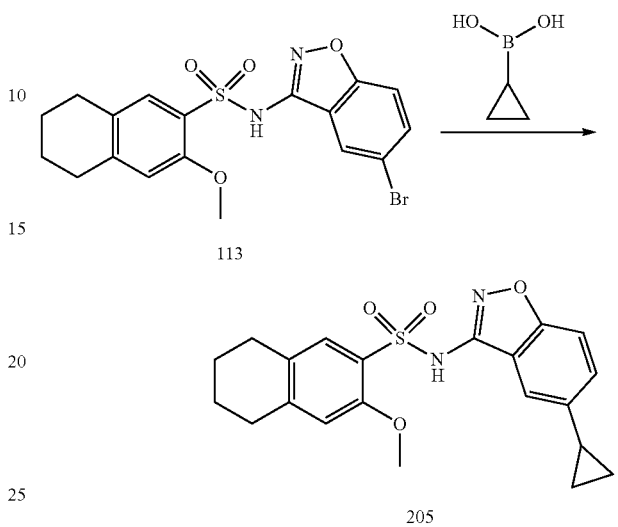

A mixture of N-(5-bromobenzo[d]isoxazol-3-yl)-3-methoxy-5,6,7,8-tetrahydronaphthalene-2-sulfonamide 113 (219 mg, 0.5 mmol), cyclopropylboronic acid (215 mg, 2.5 mmol), Pd(dppf)Cl₂ (73 mg, 0.1 mmol) and K₂CO₃ (345 mg, 2.5 mmol) in 1,4-dioxane (20 mL) and water (4 mL) was heated at 90° C. under N₂ overnight. The mixture was then adjusted to pH 1 with conc. HCl and most of the solvent was removed under reduced pressure. The residue was diluted with water (30 mL) and extracted with DCM (100 mL). The organic extract was washed with water, brine, dried over anhydrous Na₂SO₄, filtered and concentrated under reduced pressure. The residue was purified by silica gel chromatography (Pet. ether/EtOAc=10/1 to 2/1) followed by preparative TLC (Pet. ether/EtOAc=1/1) to give the title compound (50 mg, 25%) as a white solid. LCMS-D: $R_t$ 3.07 min, m/z 399.1 [M+H]⁺. ¹H NMR (400 MHz, DMSO-d₆) δ 11.4 (s, 1H), 7.68 (s, 1H), 7.54 (s, 1H), 7.47-7.43 (m, 1H), 7.40-7.35 (m, 1H), 6.84 (s, 1H), 3.71 (s, 3H), 2.77-2.65 (m, 4H), 2.08-2.00 (m, 1H), 1.74-1.66 (m, 4H), 1.04-0.96 (m, 2H), 0.68-0.61 (m, 2H).

Example 206: N-(4-Chloro-5-ethylbenzo[d]isoxazol-3-yl)-5-ethyl-2-methoxybenzenesulfonamide 206

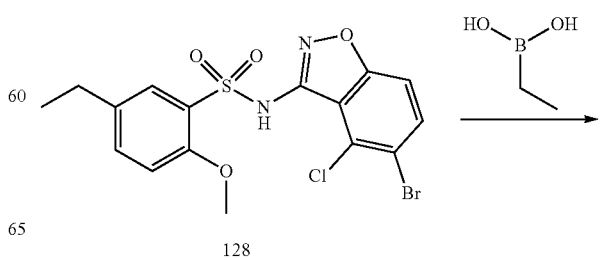

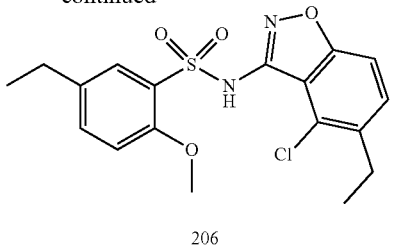

206

A mixture of N-(5-bromo-4-chlorobenzo[d]isoxazol-3-yl)-5-ethyl-2-methoxy benzenesulfonamide 128 (200 mg, 0.449 mmol), ethylboronic acid (166 mg, 2.244 mmol), Pd(dppf)Cl$_2$ (66 mg, 0.09 mmol) and K$_2$CO$_3$ (310 mg, 2.244 mmol) in 1,4-dioxane (20 mL) and water (4 mL) was heated at 90° C. under N$_2$ overnight. The mixture was then adjusted to pH 2 with 1 M aq. HCl and most of the solvent was removed under reduced pressure. The residue was diluted with water and extracted with DCM. The organic extract was washed with water, brine, dried over anhydrous Na$_2$SO$_4$, filtered and concentrated under reduced pressure. The residue was purified by silica gel chromatography (Pet. ether/EtOAc=50/1 to 2/1) followed by preparative TLC (DCM/MeOH=10/1) to give the title compound (15 mg, 9%) as a white solid. LCMS-D: R$_t$ 2.89 min, m/z 395.1 [M+H]$^+$. $^1$H NMR (400 MHz, DMSO-d$_6$) δ 10.4 (s, 1H), 7.64 (s, 2H), 7.61-7.57 (m, 1H), 7.49-7.44 (m, 1H), 7.15-7.10 (m, 1H), 3.66 (s, 3H), 2.80 (q, J=7.6 Hz, 2H), 2.60 (q, J=7.6 Hz, 2H), 1.21-1.11 (m, 6H).

Example 207: N-(4-Chloro-5-cyclopropylbenzo[d]isoxazol-3-yl)-5-ethyl-2-methoxybenzenesulfonamide 207

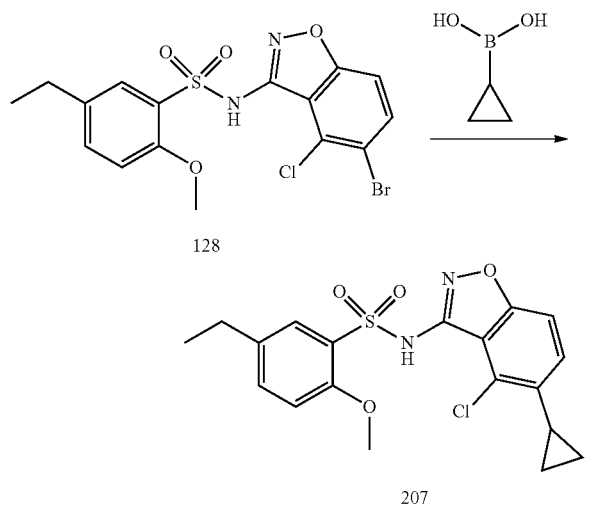

A mixture of N-(5-bromo-4-chlorobenzo[d]isoxazol-3-yl)-5-ethyl-2-methoxy benzenesulfonamide 128 (200 mg, 0.449 mmol), cyclopropylboronic acid (193 mg, 2.244 mmol), Pd(dppf)Cl$_2$ (66 mg, 0.09 mmol) and K$_2$CO$_3$ (310 mg, 2.244 mmol) in 1,4-dioxane (20 mL) and water (4 mL) was heated at 90° C. under N$_2$ overnight. The mixture was then adjusted to pH 2 with 1 M aq. HCl and most of the solvent was removed under reduced pressure. The residue was diluted with water and extracted with DCM. The organic extract was washed with water, brine, dried over anhydrous Na$_2$SO$_4$, filtered and concentrated under reduced pressure. The residue was purified by silica gel chromatography (Pet. ether/EtOAc=50/1 to 3/1) followed by preparative TLC (DCM/MeOH=100/1) to give the title compound (20 mg, 11%) as a white solid. LCMS-D: R$_t$ 2.91 min, m/z 407.1 [M+H]$^+$. $^1$H NMR (400 MHz, DMSO-d$_6$) δ 10.4 (s, 1H), 7.64-7.56 (m, 2H), 7.52-7.44 (m, 1H), 7.34-7.27 (m, 1H), 7.17-7.11 (m, 1H), 3.67 (s, 3H), 2.60 (q, J=7.6 Hz, 2H), 2.27-2.17 (m, 1H), 1.15 (t, J=7.6 Hz, 3H), 1.08-1.00 (m, 2H), 0.78-0.70 (m, 2H).

Example 208: N-(5-Cyclopropyl-4-methoxybenzo[d]isoxazol-3-yl)-5-ethyl-2-methoxybenzenesulfonamide 208

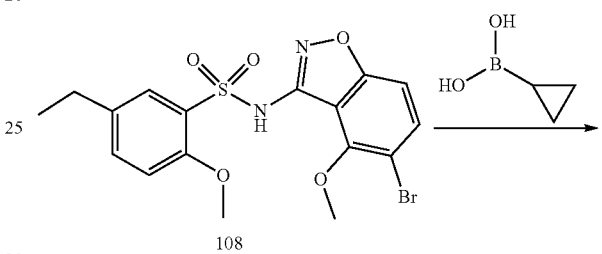

108

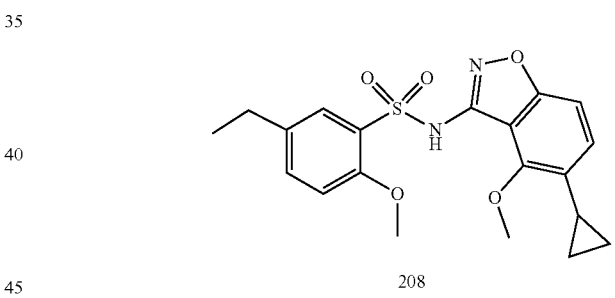

208

A mixture of N-(5-bromo-4-methoxybenzo[d]isoxazol-3-yl)-5-ethyl-2-methoxy benzenesulfonamide 108 (100 mg, 0.227 mmol), cyclopropylboronic acid (97 mg, 1.133 mmol), Pd(dppf)Cl$_2$ (33 mg, 0.046 mmol) and K$_2$CO$_3$ (156 mg, 1.133 mmol) in 1,4-dioxane (20 mL) and water (4 mL) was heated at 90° C. under N$_2$ overnight. The mixture was then adjusted to pH 2 with 1 M aq. HCl and most of the solvent was removed under reduced pressure. The residue was diluted with water and extracted with DCM. The organic extract was washed with water, brine, dried over anhydrous Na$_2$SO$_4$, filtered and concentrated under reduced pressure. The residue was purified by silica gel chromatography (Pet. ether/EtOAc=50/1 to 3/1) followed by preparative TLC (DCM/MeOH=100/1) to give the title compound (30 mg, 33%) as a white solid. LCMS-D: R$_t$ 2.87 min; m/z 403.1 [M+H]$^+$. $^1$H NMR (400 MHz, DMSO-d$_6$) δ 10.4 (s, 1H), 7.63 (d, J=2.3 Hz, 1H), 7.50-7.45 (m, 1H), 7.32-7.26 (m, 1H), 7.19-7.12 (m, 2H), 3.92 (s, 3H), 3.81 (s, 3H), 2.61 (q, J=7.6 Hz, 2H), 2.22-2.15 (m, 1H), 1.15 (t, J=7.5 Hz, 3H), 1.03-0.94 (m, 2H), 0.76-0.64 (m, 2H).

Examples 209, 210 and 211

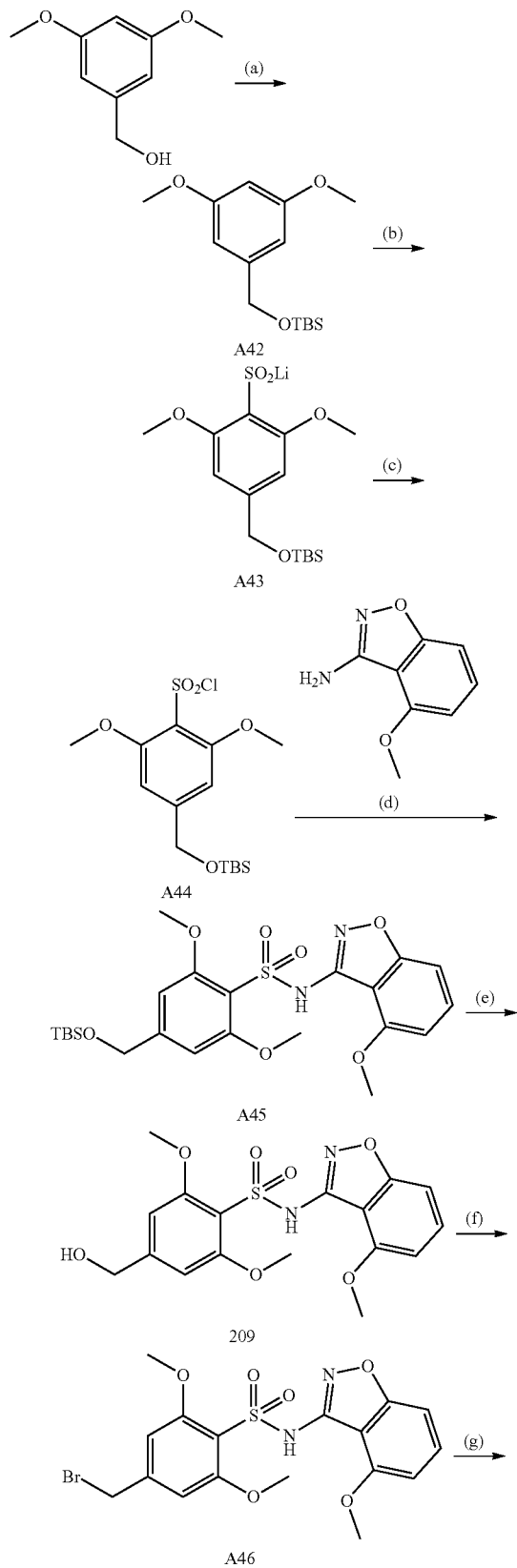

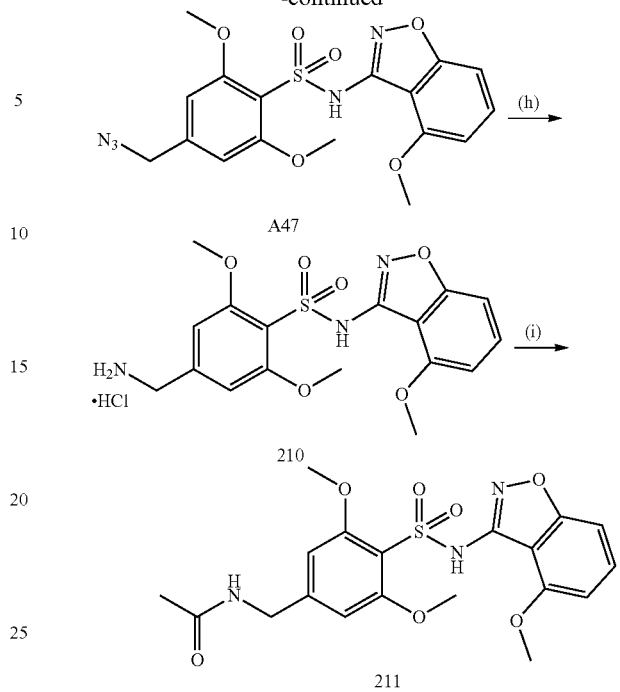

a) tert-Butyl((3,5-dimethoxybenzyl)oxy)dimethylsilane A42

To a solution of (3,5-dimethoxyphenyl)methanol (10 g, 0.059 mol) and imidazole (6.07 g, 0.089 mol) in DMF (100 mL) at RT was added TBSCl (9.86 g, 0.065 mol) and the mixture was stirred overnight. Water was added and the mixture was extracted with EtOAc. The organic extract was washed with water, concentrated under reduced pressure and the residue was purified by column chromatography (Pet. ether/EtOAc=20/1 to 10/1) to give the title compound (13 g, 77%) as a colorless oil, which was used directly in the next step.

b) Lithium 4-(((tert-butyldimethylsilyl)oxy)methyl)-2,6-dimethoxybenzenesulfinate A43

To a solution of tert-butyl((3,5-dimethoxybenzyl)oxy) dimethylsilane A42 (5 g, 0.018 mol) and TMEDA (2.26 g, 0.020 mol) in n-hexane (100 mL) at −70° C. was added n-BuLi (2.5 M solution in hexanes, 7.8 mL, 0.020 mol) and the mixture was stirred at 0° C. for 1 h. The mixture was then re-cooled to −60° C. and bubbled with SO$_2$ gas for 30 min. The resulting precipitate was collected by filtration and washed with n-hexane to give the title compound (6.2 g, 100%), which was used directly in the next step.

c) 4-(((tert-Butyldimethylsilyl)oxy)methyl)-2,6-dimethoxybenzenesulfonyl chloride A44

To a mixture of lithium 4-(((tert-butyldimethylsilyl)oxy) methyl)-2,6-dimethoxy benzenesulfinate A43 (6.2 g, 0.018 mol) in n-hexane (100 mL) at 0° C. was added SO$_2$Cl$_2$ (2.39 g, 0.018 mol) and the mixture was stirred at 0° C. for 1 h. The solids were collected by filtration, washed with n-hexane then dissolved in EtOAc and washed with water. The organic layer was concentrated under reduced pressure and the residue was purified by column chromatography (Pet. ether/EtOAc=20/1 to 5/1) to give the title compound (2.4 g, 36%) as a yellow solid, which was used directly in the next step.

d) 4-(((tert-Butyldimethylsilyl)oxy)methyl)-2,6-dimethoxy-N-(4-methoxybenzo[d]isoxazol-3-yl)benzenesulfonamide A45

To a solution of 4-methoxybenzo[d]isoxazol-3-amine (819 mg, 4.99 mmol) in THF (20 mL) at −78° C. was added LiHMDS (1 M solution in THF, 5.98 mL, 5.98 mmol) and the mixture was stirred at 0° C. for 30 min, then cooled to −60° C. A solution of 4-(((tert-butyldimethylsilyl)oxy)methyl)-2,6-dimethoxybenzenesulfonyl chloride A44 (1.9 g, 4.99 mmol) in THF (20 mL) was added and the mixture was stirred at RT overnight. The mixture was adjusted to pH 5 with 1 M aq. HCl and extracted with EtOAc. The organic extract was concentrated under reduced pressure and the residue was purified by column chromatography (Pet. ether/EtOAc=100/1 to 20/1) to give the title compound (170 mg, 7%) as a yellow solid. LCMS-D: $R_t$ 3.33 min, m/z 509.0 $[M+H]^+$.

e) 4-(Hydroxymethyl)-2,6-dimethoxy-N-(4-methoxybenzo[d]isoxazol-3-yl)benzenesulfonamide 209

To a solution of 4-(((tert-butyldimethylsilyl)oxy)methyl)-2,6-dimethoxy-N-(4-methoxybenzo[d]isoxazol-3-yl)benzenesulfonamide A45 (170 mg, 0.334 mmol) in THF (10 mL) was added TBAF (175 mg, 0.668 mmol) and the mixture was stirred at RT for 3 h. The reaction was quenched with 1 M aq. HCl and the mixture was extracted with EtOAc. The organic extract was concentrated under reduced pressure and the residue was purified by preparative TLC (DCM/MeOH=100/1 to 50/1) to give the title compound (30 mg, 23%) as a white solid. LCMS-D: $R_t$ 1.93 min, m/z 394.9 $[M+H]^+$. $^1$H NMR (400 MHz, DMSO-$d_6$) δ 9.40 (s, 1H), 7.55 (t, J=8.2 Hz, 1H), 7.18-7.12 (m, 1H), 6.89-6.82 (m, 1H), 6.72 (s, 2H), 5.39 (t, J=5.8 Hz, 1H), 4.49 (d, J=5.8 Hz, 2H), 3.95 (s, 3H), 3.77 (s, 6H).

f) 4-(Bromomethyl)-2,6-dimethoxy-N-(4-methoxybenzo[d]isoxazol-3-yl)benzenesulfonamide A46

A solution of 4-(hydroxymethyl)-2,6-dimethoxy-N-(4-methoxybenzo[d]isoxazol-3-yl) benzenesulfonamide 209 (1.0 g, 2.53 mmol), CBr$_4$ (2.52 g, 7.60 mmol) and PPh$_3$ (1.99 g, 7.60 mmol) in DCM (20 mL) was stirred at RT overnight. The mixture was concentrated under reduced pressure and the residue was purified by column chromatography (DCM/MeOH=50/1 to 10:1) to give the title compound (600 mg, 52%) as a yellow solid, which was used directly in the next step.

g) 4-(Azidomethyl)-2,6-dimethoxy-N-(4-methoxybenzo[d]isoxazol-3-yl)benzenesulfonamide A47

A solution of 4-(bromomethyl)-2,6-dimethoxy-N-(4-methoxybenzo[d]isoxazol-3-yl) benzenesulfonamide A46 (200 mg, 0.44 mmol) and NaN$_3$ (85 mg, 1.31 mmol) in DMF (5 mL) was heated at 50° C. for 3 h. The mixture was poured into water and the precipitate was collected by filtration. The filter cake was washed with water and dried to give the title compound (100 mg, 54%) as gray solid. LCMS-D: $R_t$ 2.45 min, m/z 420.1 $[M+H]^+$.

h) 4-(Aminomethyl)-2,6-dimethoxy-N-(4-methoxybenzo[d]isoxazol-3-yl)benzenesulfonamide hydrochloride 210

A solution of 4-(azidomethyl)-2,6-dimethoxy-N-(4-methoxybenzo[d]isoxazol-3-yl) benzenesulfonamide A47 (300 mg, 0.716 mmol) and PPh$_3$ (207 mg, 0.788 mmol) in THF (8 mL) and EtOH (6 mL) was stirred at RT for 3 h. Water (2 mL) and concentrated HCl (2 mL) were added and the mixture was heated at 55° C. for 3 h. Most of the organic solvents were removed under reduced pressure and the aqueous residue was washed with DCM. The aqueous phase was concentrated under reduced pressure to give the title compound (150 mg, 53%) as a yellow solid. LCMS-D: $R_t$ 0.38 min, m/z 394.1 $[M+H]^+$. $^1$H NMR (400 MHz, methanol-$d_4$) δ 7.54 (t, J=8.2 Hz, 1H), 7.06-7.01 (m, 1H), 6.87 (s, 2H), 6.86-6.82 (m, 1H), 4.12 (s, 2H), 4.07 (s, 3H), 3.89 (s, 6H).

i) N-(3,5-Dimethoxy-4-(N-(4-methoxybenzo[d]isoxazol-3-yl)sulfamoyl)benzyl)acetamide 211

A mixture of 4-(aminomethyl)-2,6-dimethoxy-N-(4-methoxybenzo[d]isoxazol-3-yl) benzenesulfonamide hydrochloride 210 (130 mg, 0.33 mmol), NaHCO$_3$ (83 mg, 0.99 mmol) and acetic anhydride (101 mg, 0.99 mmol) in THF (5 mL) was stirred at RT for 3 h then concentrated under reduced pressure. The residue was purified by preparative TLC to give the title compound (50 mg, 34%) as a yellow solid. LCMS-D: $R_t$ 1.93 min, m/z 436.1 $[M+H]^+$. $^1$H NMR (400 MHz, DMSO-$d_6$) δ 9.47 (s, 1H), 8.36 (t, J=5.8 Hz, 1H), 7.55 (m, 1H), 7.18-7.12 (m, 1H), 6.89-6.81 (m, 1H), 6.66 (s, 2H), 4.24 (d, J=5.9 Hz, 2H), 3.94 (s, 3H), 3.76 (s, 6H), 1.88 (s, 3H).

Example 212: 2-Fluoro-6-methoxy-N-(4-methoxybenzo[d]isoxazol-3-yl)benzenesulfonamide 212

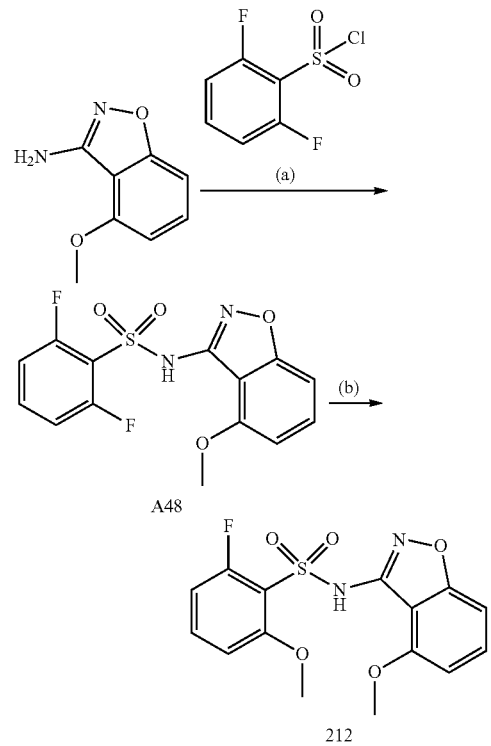

a) 2,6-Difluoro-N-(4-methoxybenzo[d]isoxazol-3-yl)benzenesulfonamide A48

To a solution of 4-methoxybenzo[d]isoxazol-3-amine (4.0 g, 24.0 mmol) in THF (200 mL) at −78° C. under nitrogen was added LiHMDS (1 M solution in THF, 31.2 mL, 31.2 mmol) dropwise and the mixture was stirred at −78° C. for 3 h. A solution of 2,6-difluorophenylsulfonyl chloride (10.2 g, 48 mmol) in THF (20 mL) was then added dropwise and the mixture was allowed to warm slowly to RT and stirred overnight. Water was added and the mixture was extracted with EtOAc (200 mL×3). The combined organic extracts were washed with water, brine, dried over anhydrous $Na_2SO_4$, filtered and concentrated under reduced pressure. The residue was purified by column chromatography (Pet. ether/EtOAc=6/1 to 2/1) to give the title compound (2.9 g, 35%) as a white solid. LCMS-D: $R_t$ 1.94 min, m/z 341.1 $[M+H]^+$.

b) 2-Fluoro-6-methoxy-N-(4-methoxybenzo[d]isoxazol-3-yl)benzenesulfonamide 212

A mixture of 2,6-difluoro-N-(4-methoxybenzo[d]isoxazol-3-yl)benzenesulfonamide A48 (450 mg, 1.32 mmol) and NaOMe (428 mg, 7.92 mmol) in MeOH (6 mL) was heated at 120° C. overnight then allowed to cool to RT and filtered. The filtrate was concentrated under reduced pressure and the residue was purified by preparative TLC (DCM/MeOH=50/1) to give the title compound (100 mg, 21%) as a white solid. LCMS-D: $R_t$ 2.22 min, m/z 353.0 $[M+H]^+$. $^1$H NMR (400 MHz, DMSO-$d_6$) δ 10.6 (s, 1H), 7.62 (m, 1H), 7.56 (t, J=8.3 Hz, 1H), 7.18 (d, J=8.4 Hz, 1H), 7.04 (d, J=8.5 Hz, 1H), 7.00-6.92 (m, 1H), 6.84 (d, J=8.0 Hz, 1H), 3.85 (s, 3H), 3.80 (s, 3H).

Example 213: 2-Hydroxy-6-methoxy-N-(4-methoxybenzo[d]isoxazol-3-yl)benzenesulfonamide 213

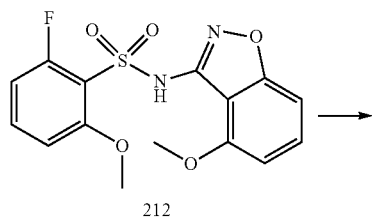

212

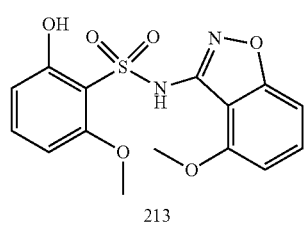

213

A mixture of 2-fluoro-6-methoxy-N-(4-methoxybenzo[d]isoxazol-3-yl)benzenesulfonamide 212 (20 mg, 0.06 mmol), (6-methoxypyridin-3-yl)methanol (50.1 mg, 0.36 mmol) and t-BuOK (20.2 mg, 0.18 mmol) in NMP (1 mL) was heated at 120° C. for 16 h. LCMS analysis indicated that only the F hydrolysis product had formed. The mixture was adjusted to pH<4 with aq. HCl, diluted with water and extracted with EtOAc. The organic extract was washed with water, brine, dried over anhydrous $Na_2SO_4$, filtered and concentrated under reduced pressure. The procedure was repeated with another batch of 2-fluoro-6-methoxy-N-(4-methoxybenzo[d]isoxazol-3-yl)benzenesulfonamide 212 (52 mg, 0.15 mmol), the two crude products were combined and purified by prep. TLC (EtOAc/Pet. ether=1/13 then DCM/MeOH=50/1 to 100/1) to give the title compound (135 mg, 19%) as a white solid. LCMS-D: $R_t$ 2.39 min; m/z 350.9 $[M+H]^+$. $^1$H NMR (400 MHz, DMSO-$d_6$) δ 10.2 (s, 1H), 7.57 (t, J=8.4 Hz, 1H), 7.41 (t, J=8.4 Hz, 1H), 7.16 (d, J=8.4 Hz, 1H), 6.84 (d, J=8.0 Hz, 1H), 6.60-6.56 (m, 2H), 3.91 (s, 3H), 3.75 (s, 3H).

Example 214: 2-Methoxy-N-(4-methoxybenzo[d]isoxazol-3-yl)-6-(methylamino)benzenesulfonamide 214

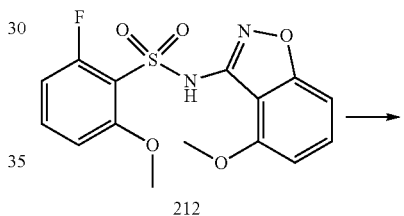

212

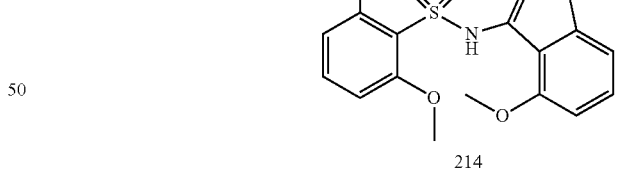

214

A solution of 2-fluoro-6-methoxy-N-(4-methoxybenzo[d]isoxazol-3-yl)benzenesulfonamide 212 (30 mg, 0.085 mmol), methylamine HCl (23 mg, 0.34 mmol) and $Et_3N$ (52 mg, 0.51 mmol) in ethanol (3 mL) was heated at 120° C. in a sealed tube overnight. The mixture was concentrated under reduced pressure and the residue was purified by prep. TLC (DCM) to give the title compound (4 mg, 13%) as a yellow solid. LCMS-D: $R_t$ 2.49 min; m/z 364.0 $[M+H]^+$. $^1$H NMR (400 MHz, DMSO-$d_6$) δ 7.56 (t, J=8.0 Hz, 1H), 7.30 (t, J=8.0 Hz, 1H), 7.14 (d, J=8.0 Hz, 1H), 6.84 (d, J=8.0 Hz, 1H), 6.33 (d, J=8.0 Hz, 1H), 6.24 (d, J=8.0 Hz, 1H), 3.94 (s, 3H), 3.70 (s, 3H), 2.79 (s, 3H).

Example 215: 2-(Cyclopropylmethoxy)-6-methoxy-N-(4-methoxybenzo[d]isoxazol-3-yl)benzenesulfonamide 215

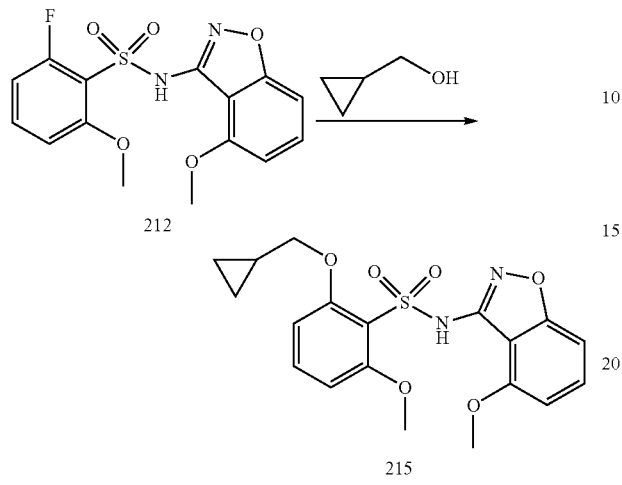

Example 216: 2-Methoxy-N-(4-methoxybenzo[d]isoxazol-3-yl)-6-((2-methoxypyridin-4-yl)methoxy)benzenesulfonamide 216

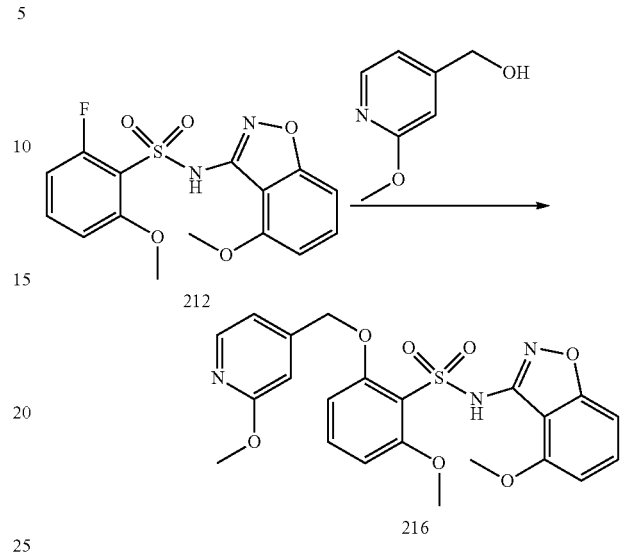

To a solution of 2-fluoro-6-methoxy-N-(4-methoxybenzo[d]isoxazol-3-yl)benzenesulfonamide 212 (30 mg, 0.08 mmol) in THF (4 mL) was added t-BuOK (27 mg, 0.24 mmol) followed by cyclopropylmethanol (17 mg, 0.24 mmol) and the mixture was heated at 50° C. overnight. The mixture was diluted with water and extracted with EtOAc (20 mL×3). The combined organic extracts were washed with brine, dried over anhydrous $Na_2SO_4$, filtered and concentrated under reduced pressure. The residue was purified by prep. TLC (Pet. ether/EtOAc=1/1) to give the title compound (4.4 mg, 13%) as a grey solid. LCMS-D: $R_t$ 2.54 min, m/z 405.1 [M+H]$^+$. $^1$H NMR (400 MHz, DMSO-$d_6$) δ 9.33 (s, 1H), 7.57 (t, J=8.0 Hz, 1H), 7.48 (t, J=8.0 Hz, 1H), 7.15 (d, J=8.4 Hz, 1H), 6.85 (d, J=8.0 Hz, 1H), 6.77-6.75 (m, 2H), 3.91 (s, 3H), 3.89 (d, J=6.8 Hz, 2H), 3.77 (s, 3H), 0.86-0.83 (m, 1H), 0.43-0.24 (m, 4H).

To a solution of 2-fluoro-6-methoxy-N-(4-methoxybenzo[d]isoxazol-3-yl)benzenesulfonamide 212 (30 mg, 0.08 mmol) in NMP (3 mL) was added t-BuOK (48 mg, 0.43 mmol) followed by (2-methoxypyridin-4-yl)methanol (118 mg, 0.85 mmol) and the mixture was stirred at RT for 6 h. The mixture was diluted with water, adjusted to pH 5-6 with 1 M aq. HCl and extracted with EtOAc (20 mL×3). The combined organic extracts were washed with brine, dried over anhydrous $Na_2SO_4$, filtered and concentrated under reduced pressure. The residue was purified by prep. TLC (DCM/MeOH=40/1) to give the title compound (5 mg, 12%) as a yellow solid. LCMS-D: $R_t$ 2.43 min, m/z 472.0 [M+H]$^+$. $^1$H NMR (400 MHz, DMSO-$d_6$) δ 9.65 (s, 1H), 8.07 (d, J=5.2 Hz, 1H), 7.51-7.39 (m, 2H), 7.07-6.98 (m, 3H), 6.79-6.75 (m, 3H), 5.22 (s, 2H), 3.84 (s, 3H), 3.83 (s, 3H), 3.81 (s, 3H).

Examples 217-222 (Table G)

TABLE G

The following examples were synthesised according to the methods described for 215 or 216. Varitaions of conditions have been noted in the table.

| | R-OH | Name and structure | Analytical | Method | Note |
|---|---|---|---|---|---|
| 217 | Isopropanol | 2-Isopropoxy-6-methoxy-N-(4-methoxybenzo[d]isoxazol-3-yl)benzenesulfonamide | LCMS-C: $R_t$ 2.18 min, m/z 393.0 [M + H]$^+$; $^1$H NMR (400 MHz, DMSO-$d_6$) δ 9.13 (s, 1H), 7.58 (t, J = 8.0 Hz, 1H), 7.49 (t, J = 8.0 Hz, 1H), 7.17 (d, J = 8.0 Hz, 1H), 6.87 (d, J = 8.0 Hz, 1H), 6.79-6.75 (m, 2H), 4.75-4.65 (m, 1H), 3.95 (s, 3H), 3.80 (s, 3H), 1.17 (d, J = 6.0 Hz, 6H). | As for Example 216 | 120° C., 16 h; Ratio of fluoride/base/R-OH 1:3:3 |

TABLE G-continued

The following examples were synthesised according to the methods described for 215 or 216. Varitaions of conditions have been noted in the table.

| | R-OH | Name and structure | Analytical | Method | Note |
|---|---|---|---|---|---|
| 218 | Ethanol | 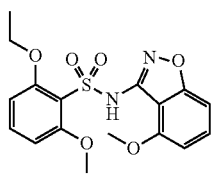 [SMILES: CCOc1cccc(OC)c1S(=O)(=O)Nc1noc2cccc(OC)c12]<br>2-Ethoxy-6-methoxy-N-(4-methoxybenzo[d]isoxazol-3-yl)benzenesulfonamide | LCMS-C: $R_t$ 2.03 min, m/z 379.0 [M + H]$^+$; $^1$H NMR (400 MHz, DMSO-$d_6$) δ 9.13 (s, 1H), 7.58(t, J = 8.0 Hz, 1H), 7.50 (t, J = 8.0 Hz, 1H), 7.17 (d, J = 8.0 Hz, 1H), 6.86 (d, J = 8.0 Hz, 1H), 6.78 (d, J = 8.0 Hz, 2H), 4.01 (q, J = 7.2 Hz, 2H), 3.94 (s, 3H), 3.76 (s, 3H), 1.12 (t, J = 7.2 Hz, 3H). | As for Example 216 | 120° C., 16 h; Ratio of fluoride/base/R-OH 1:3:3 |
| 219 | H$_2$N-C(=O)-CH$_2$-OH | 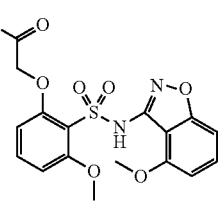<br>2-(3-Methoxy-2-(N-(4-methoxybenzo[d]isoxazol-3-yl)sulfamoyl)phenoxy)acetamide | LCMS-D: $R_t$ 0.31 min, m/z 408.0 [M + H]$^+$; $^1$H NMR (400 MHz, DMSO-$d_6$) δ 10.0 (s, 1H), 7.61-7.45 (m, 4H), 7.15 (d, J = 8.4 Hz, 1H), 7.83-6.74 (m, 3H), 4.51 (s, 2H), 3.83 (s, 3H), 3.77 (s, 3H). | As for Example 216 | 120° C., 16 h; Ratio of fluoride/base/R-OH 1:6:10; Eluent: DCM/MeOH = 80/1 |
| 220 | TBSO-CH$_2$CH$_2$-OH | 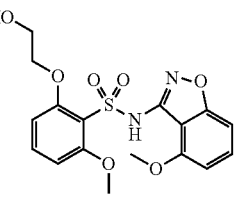<br>2-(2-Hydroxyethoxy)-6-methoxy-N-(4-methoxybenzo[d]isoxazol-3-yl)benzenesulfonamide | LCMS-D: $R_t$ 2.11 min, m/z 395.0 [M + H]$^+$; $^1$H NMR (400 MHz, DMSO-$d_6$) δ 9.70 (s, 1H), 7.57-7.48 (m, 2H), 7.15 (d, J = 8.4 Hz, 1H), 6.84-6.80 (m, 3H), 5.10 (br s, 1H), 4.06 (t, J = 5.0 Hz, 2H), 3.90 (s, 3H), 3.80 (s, 3H), 3.63 (t, J = 5.0 Hz, 2H). | As for Example 216 | RT o/n then 80° C., 16 h; ratio of fluoride/base/R-OH 1:6:10; Eluent: DCM/MeOH = 60/1 |
| 221 | (1-methyl-1H-pyrazol-4-yl)methanol | 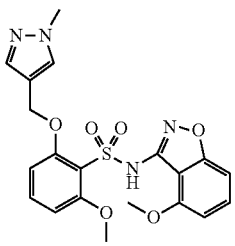 [SMILES: COc1cccc(OCc2cnn(C)c2)c1S(=O)(=O)Nc1noc2cccc(OC)c12]<br>2-Methoxy-N-(4-methoxybenzo[d]isoxazol-3-yl)-6-((1-methyl-1H-pyrazol-4-yl)methoxy)benzenesulfonamide | LCMS-D: $R_t$ 2.25 min, m/z 445.0 [M + H]$^+$; $^1$H NMR (400 MHz, DMSO-$d_6$) δ 7.62 (s, 1H) 7.54 (t, J = 8.4 Hz, 1H), 7.46 (t, J = 8.4 Hz, 1H), 7.40 (s, 1H), 7.12 (d, J = 8.4 Hz, 1H), 6.86 (d, J = 8.4 Hz, 1H), 6.81 (d, J = 8.0 Hz, 1H), 6.76 (d, J = 8.4 Hz, 1H), 5.04 (s, 2H), 3.86 (s, 3H), 3.75 (s, 3H), 3.73 (s, 3H). | As for Example 215 | 50° C., 16 h; Ratio of fluoride/base/R-OH 1:3:3 |

TABLE G-continued

The following examples were synthesised according to the methods described for 215 or 216. Varitaions of conditions have been noted in the table.

| R-OH | Name and structure | Analytical | Method | Note |
|---|---|---|---|---|
| 222 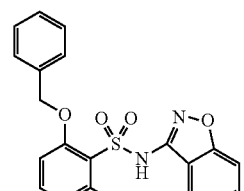 | 2-(Benzyloxy)-6-methoxy-N-(4-methoxybenzo[d]isoxazol-3-yl)benzenesulfonamide | LCMS-D: $R_t$ 2.67 min, m/z 441.1 [M + H]+; $^1$H NMR (400 MHz, DMSO-$d_6$) δ 7.51-7.43 (m, 4H), 7.36-7.30 (m, 3H), 7.05 (d, J = 8.4 Hz, 1H), 6.79-6.72 (m, 3H), 5.25 (s, 2H), 3.89 (s, 3H), 3.75 (s, 3H). | As for Example 215 | 50° C., 16 h; Ratio of fluoride/base/R-OH 1:3:3 |

Example 223: 2,6-Dimethoxy-N-(4-nitrobenzo[d]isoxazol-3-yl)benzenesulfonamide 223

Example 224: N-(4-Aminobenzo[d]isoxazol-3-yl)-2,6-dimethoxybenzenesulfonamide 224

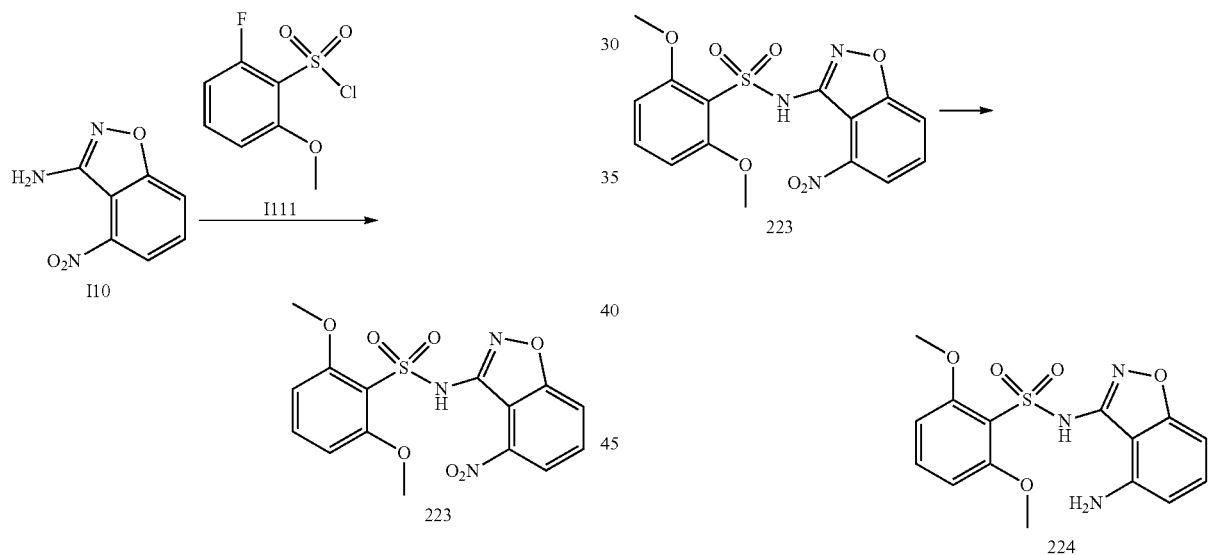

To a solution of 4-nitrobenzo[d]isoxazol-3-amine I10 (478 mg, 2.63 mmol) in THF (9 mL) at −78° C. under nitrogen was added LiHMDS (1 M solution in THF, 5.30 mL, 5.30 mmol) and the mixture was stirred at −78° C. for 3 h. 2,6-Dimethoxysufonyl chloride I111 (1.25 g, 5.27 mmol) was then added and the mixture was allowed to warm to RT and stirred overnight. The reaction was quenched with water and the mixture was extracted with EtOAc (80 mL×3). The combined organic extracts were washed with water (100 mL×3), brine (50 mL×3), dried over anhydrous $Na_2SO_4$, filtered and concentrated under reduced pressure. The residue was purified by column chromatography (DCM/MeOH=1/0 to 50/1) to give the title compound (108 mg, 11%) as a yellow solid. LCMS-D: $R_t$ 2.23 min; m/z 380.1 [M+H]+. $^1$H NMR (400 MHz, DMSO-$d_6$) δ 10.2 (s, 1H), 8.19 (d, J=8.4 Hz, 2H), 7.92 (t, J=8.4 Hz, 1H), 7.79 (d, J=8.4 Hz, 1H), 6.79 (d, J=8.4 Hz, 2H), 3.71 (s, 6H).

To a solution of 2,6-dimethoxy-N-(4-nitrobenzo[d]isoxazol-3-yl)benzenesulfonamide 223 (70.0 mg, 0.18 mmol) in EtOAc (30 mL) was added 10% Pd/C (40.0 mg) and the mixture was stirred at RT overnight under a hydrogen atmosphere. The catalyst was removed by filtration, rinsed with EtOAc and the filtrate was concentrated under reduced pressure. The procedure was repeated on an additional batch of 2,6-dimethoxy-N-(4-nitrobenzo[d]isoxazol-3-yl)benzenesulfonamide 223 (30 mg, 0.079 mmol) and the crude products were combined and purified twice by prep. TLC (DCM/MeOH=50/1) and twice by prep. HPLC to give the title compound (2.5 mg, 3%) as a white solid. LCMS-D: $R_t$ 2.25 min; m/z 350.1 [M+H]+. $^1$H NMR (400 MHz, FDMSO-$d_6$) δ 7.52 (t, J=8.4 Hz, 1H), 7.25 (t, J=8.0 Hz, 1H), 6.80 (d, J=8.4 Hz, 2H), 6.66 (d, J=8.0 Hz, 1H), 6.43 (d, J=8.0 Hz, 1H), 3.78 (s, 6H).

Example 225: N-(5-((1H-Pyrazol-1-yl)methyl)benzo[d]isoxazol-3-yl)-5-ethyl-2-methoxybenzenesulfonamide 225

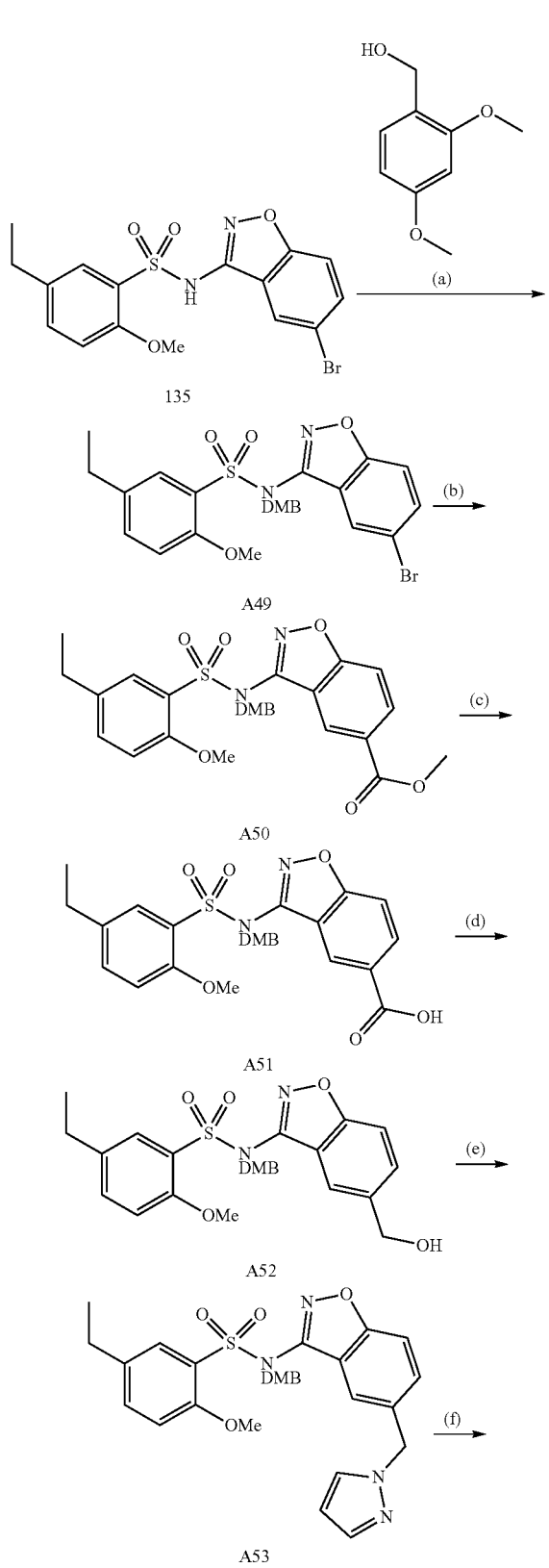

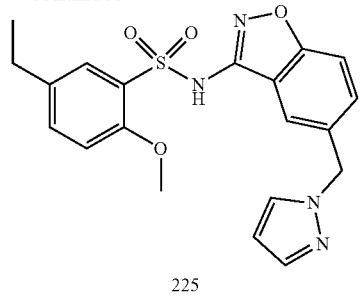 [SMILES: CCc1ccc(OC)c(S(=O)(=O)Nc2noc3ccc(Cn4cccn4)cc23)c1 ; "225"]

a) N-(5-Bromobenzo[d]isoxazol-3-yl)-N-(2,4-dimethoxybenzyl)-5-ethyl-2-methoxybenzenesulfonamide A49

To a solution of N-(5-bromobenzo[d]isoxazol-3-yl)-5-ethyl-2-methoxybenzenesulfonamide 135 (8.2 g, 19.9 mmol), (2,4-dimethoxyphenyl)methanol (5.03 g, 29.9 mmol) and PPh$_3$ (13.1 g, 49.9 mmol) in THF (400 mL) at 0° C. under nitrogen was added DIAD (8.06 g, 39.9 mmol) slowly dropwise and the mixture was stirred at RT overnight. The solvent was removed under reduced pressure and the residue was purified by column chromatography (Pet. ether/EtOAc=100/1 to 5/1) to give the title compound (4.7 g, 42%) as a white solid. LCMS-D: R$_t$ 3.39 min. m/z 583.1 [M+Na]$^+$ b) Methyl 3-((N-(2,4-dimethoxybenzyl)-5-ethyl-2-methoxyphenyl)sulfonamido)benzo[d]isoxazole-5-carboxylate A50

A mixture of N-(5-bromobenzo[d]isoxazol-3-yl)-N-(2,4-dimethoxybenzyl)-5-ethyl-2-methoxybenzenesulfonamide A49 (1.5 g, 2.67 mmol), Et$_3$N (10 mL) and Pd(dppf)Cl$_2$ (732 mg, 1 mmol) in MeOH (150 mL) was heated at 120° C. under a carbon monoxide atmosphere (20 bar) for 7 h. The reaction was repeated with 1.7 g N-(5-bromobenzo[d]isoxazol-3-yl)-N-(2,4-dimethoxybenzyl)-5-ethyl-2-methoxybenzenesulfonamide A49 and 1.5 g N-(5-bromobenzo[d]isoxazol-3-yl)-N-(2,4-dimethoxybenzyl)-5-ethyl-2-methoxybenzenesulfonamide A49 and the mixtures were combined and concentrated under reduced pressure. The residue was purified by column chromatography (Pet. ether/EtOAc=100/1 to 3/1) to give the title compound (2.2 g, 49%) as a white solid. LCMS-D: R$_t$ 3.17 min, m/z 563.1 [M+Na]$^+$ c) 3-((N-(2,4-Dimethoxybenzyl)-5-ethyl-2-methoxyphenyl)sulfonamido)benzo[d]isoxazole-5-carboxylic acid A51

To a solution of methyl 3-((N-(2,4-dimethoxybenzyl)-5-ethyl-2-methoxyphenyl) sulfonamido)benzo[d]isoxazole-5-carboxylate A50 (2.2 g, 4.07 mmol) in methanol (30 mL) was added 3 M aq. NaOH (20 mL) and the mixture was stirred at RT overnight. The mixture was adjusted to pH 1 with aq. HCl and the solvent was removed under reduced pressure. The residue was diluted with water (100 mL) and extracted with DCM (200 mL). The organic extract was washed with water, brine, dried over anhydrous Na$_2$SO$_4$, filtered and concentrated under reduced pressure to give the title compound (1.9 g, 89%) as a light yellow solid. LCMS-D: R$_t$ 2.99 min, m/z 549.1 [M+Na]$^+$.

d) N-(2,4-Dimethoxybenzyl)-5-ethyl-N-(5-(hydroxymethyl)benzo[d]isoxazol-3-yl)-2-methoxybenzenesulfonamide A52

To a solution of 3-((N-(2,4-dimethoxybenzyl)-5-ethyl-2-methoxyphenyl)sulfonamido) benzo[d]isoxazole-5-carboxylic acid (800 mg, 1.52 mmol) A51 in THF (5 mL) at 0° C. under nitrogen was added BH$_3$-THF (1 M solution in THF, 10 mL, 10 mmol) slowly dropwise and the mixture was allowed to warm to RT and stirred for 2 h. The mixture was cooled to 0° C. and the reaction was quenched by slow addition of methanol (20 mL). The solvent was removed under reduced pressure and the residue was diluted with water and extracted with DCM (200 mL). The organic extract was washed with water, brine, dried over anhydrous Na$_2$SO$_4$, filtered and concentrated under reduced pressure. The residue was purified by column chromatography (DCM/MeOH=100/0 to 40/1) to give the title compound (700 mg, 90%) as a white solid. LCMS-D: R$_t$ 2.99 min, m/z 513.1 [M+H]$^+$.

e) N-(5-((1H-Pyrazol-1-yl)methyl)benzo[d]isoxazol-3-yl)-N-(2,4-dimethoxybenzyl)-5-ethyl-2-methoxybenzenesulfonamide A53

To a solution of N-(2,4-dimethoxybenzyl)-5-ethyl-N-(5-(hydroxymethyl) benzo[d]isoxazol-3-yl)-2-methoxybenzenesulfonamide A52 (200 mg, 0.39 mmol) and Et$_3$N (197 mg, 1.95 mmol) in DCM (10 mL) at 0° C. under nitrogen was added methanesulfonyl chloride (89 mg, 0.78 mmol) and the mixture was stirred at RT for 1.5 h then used in next step directly without workup and isolation. To a solution of pyrazole (133 mg, 1.95 mmol) in DMF (20 mL) at 0° C. under nitrogen was added t-BuOK (219 mg, 1.95 mmol) portion-wise and the mixture was stirred at RT for 1.5 h. The reaction mixture containing (3-((N-(2,4-dimethoxybenzyl)-5-ethyl-2-methoxyphenyl)sulfonamido) benzo[d]isoxazol-5-yl)methyl methanesulfonate (assumed 0.39 mmol) was then added slowly and the resulting mixture was stirred at RT for 30 min. The mixture was diluted with water and extracted with EtOAc. The organic extract was washed with water (×3), brine, dried over anhydrous Na$_2$SO$_4$, filtered and concentrated under reduced pressure. The residue was purified by column chromatography (DCM/MeOH=40/1) to give the title compound (60 mg, 27%) as a white solid. LCMS-D: R$_t$ 3.01 min. m/z 563.2 [M+H]$^+$.

f) N-(5-((1H-Pyrazol-1-yl)methyl)benzo[d]isoxazol-3-yl)-5-ethyl-2-methoxybenzenesulfonamide 225

A mixture of N-(5-((1H-pyrazol-1-yl)methyl)benzo[d]isoxazol-3-yl)-N-(2,4-dimethoxybenzyl)-5-ethyl-2-methoxybenzenesulfonamide A53 (60 mg, 0.107 mmol) and TFA (5 mL) was stirred at RT for 3 h then concentrated under reduced pressure. The residue was purified by column chromatography (DCM/MeOH=20/1) to give the title compound (30 mg, 68%) as a white solid. LCMS-D: R$_t$ 6.03 min, m/z 412.5 [M+H]$^+$. $^1$H NMR (400 MHz, DMSO-d$_6$) δ 11.9 (s, 1H), 7.89 (s, 1H), 7.85 (d, J=2.0 Hz, 1H), 7.68 (d, J=2.0 Hz, 1H), 7.58-7.49 (m, 3H), 7.46 (dd, J=8.4, 2.0 Hz, 1H), 7.08 (d, J=8.8 Hz, 1H), 6.31 (t, J=2.0 Hz, 1H), 5.54 (s, 2H), 3.68 (s, 3H), 2.63 (q, J=7.6 Hz, 2H), 1.16 (t, J=7.6 Hz, 3H).

Example 226: N-(5-(Aminomethyl)benzo[d]isoxazol-3-yl)-5-ethyl-2-methoxybenzenesulfonamide trifluoroacetate 226

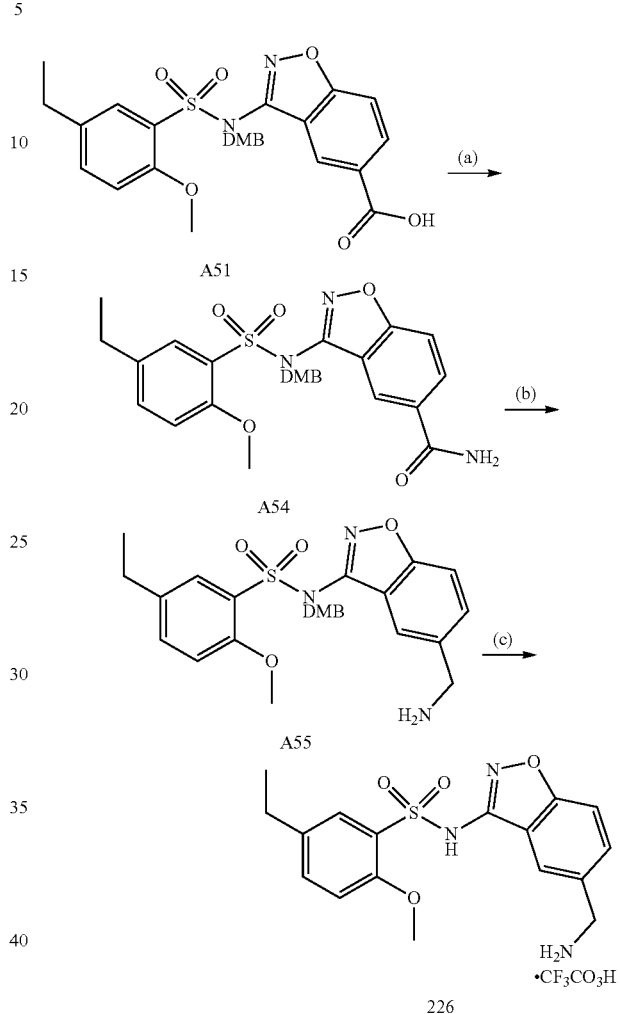

a) 3-((N-(2,4-dimethoxybenzyl)-5-ethyl-2-methoxyphenyl)sulfonamido)benzo[d]isoxazole-5-carboxamide A54

A mixture of 3-((N-(2,4-dimethoxybenzyl)-5-ethyl-2-methoxyphenyl)sulfonamido) benzo[d]isoxazole-5-carboxylic acid A51 (600 mg, 1.14 mmol) and thionyl chloride (5 mL) was heated at 85° C. for 1.5 h then concentrated under reduced pressure. The residue was dissolved in in DCM (3 mL) and added dropwise to conc. NH$_4$OH (10 mL) at 0° C. and the mixture was stirred at RT for 30 min. Most of the solvent was removed under reduced pressure and the residue was diluted with water (20 mL). The resulting precipitate was collected by filtration, washed twice with water and dried to give the title compound (400 mg, 67%) as a light-yellow solid. LCMS-D: R$_t$ 2.86 min, m/z 526.2 [M+H]$^+$.

b) N-(5-(Aminomethyl)benzo[d]isoxazol-3-yl)-N-(2,4-dimethoxybenzyl)-5-ethyl-2-methoxybenzenesulfonamide A55

A mixture of 3-((N-(2,4-dimethoxybenzyl)-5-ethyl-2-methoxyphenyl) sulfonamido)benzo[d]isoxazole-5-carboxamide A54 (400 mg, 0.76 mmol) and BH₃-THF (1 M solution in THF, 20 mL) was heated at 75° C. under nitrogen overnight. The mixture was then cooled to 0° C. and the reaction was quenched by slow addition of methanol (10 mL). The solvent was removed under reduced pressure and the residue was diluted with water and extracted with DCM (100 mL). The organic extract was washed with water, brine, dried over anhydrous Na₂SO₄, filtered and concentrated under reduced pressure. The residue was purified by column chromatography (DCM/MeOH=100/1 to 10/1) to give the title compound (150 mg, 39%) as a light-yellow solid, which was used directly in the next step.

c) N-(5-(Aminomethyl)benzo[d]isoxazol-3-yl)-5-ethyl-2-methoxybenzenesulfonamide trifluoroacetate 226

A mixture of N-(5-(aminomethyl)benzo[d]isoxazol-3-yl)-N-(2,4-dimethoxybenzyl)-5-ethyl-2-methoxybenzenesulfonamide A55 (50 mg, 0.098 mmol) and TFA (5 mL) was stirred at RT for 3 h then concentrated under reduced pressure. The residue was purified by prep. TLC (DCM/MeOH=10/1) to give the title compound (30 mg, 86%) as a white solid. LCMS-D: R_t 1.93 min, m/z 362.1[M+H]⁺. ¹H NMR (400 MHz, DMSO-d₆) δ11.8 (br s, 1H), 8.53 (br s, 3H), 8.11 (s, 1H), 7.83 (d, J=8.4 Hz, 1H), 7.70-7.68 (m, 2H), 7.48 (d, J=8.0 Hz, 1H), 7.12 (d, J=8.8 Hz, 1H), 4.13 (s, 2H), 3.71 (s, 3H), 2.64 (q, J=7.6 Hz, 2H), 1.17 (t, J=7.6 Hz, 3H).

Example 227: Methyl ((3-((5-ethyl-2-methoxyphenyl)sulfonamido)benzo[d]isoxazol-5-yl)methyl) carbamate 227

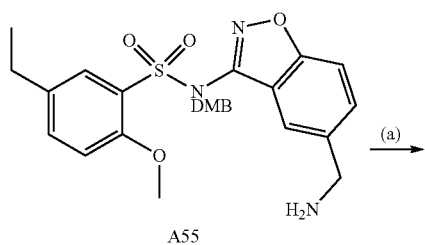

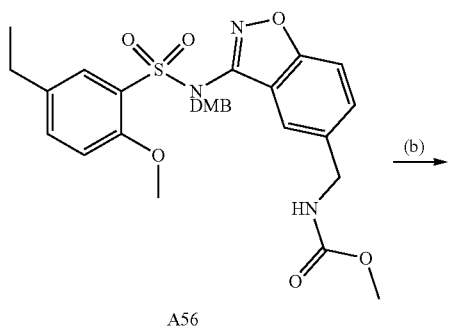

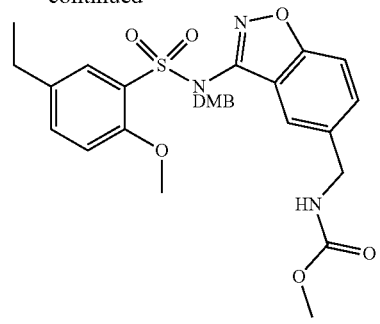

a) Methyl ((3-((N-(2,4-dimethoxybenzyl)-5-ethyl-2-methoxyphenyl)sulfonamido)benzo[d]isoxazol-5-yl)methyl) carbamate A56

To a solution of N-(5-(aminomethyl)benzo[d]isoxazol-3-yl)-N-(2,4-dimethoxybenzyl)-5-ethyl-2-methoxybenzenesulfonamide A55 (70 mg, 0.137 mmol) and Et₃N (69 mg, 0.685 mmol) in DCM (20 mL) at 0° C. was added methyl chloroformate (39 mg, 0.411 mmol) dropwise and the mixture was stirred at RT for 20 min. The solvent was removed under reduced pressure and the residue was diluted with water and extracted with DCM. The organic extract was washed with water, brine, dried over anhydrous Na₂SO₄, filtered and concentrated under reduced pressure. The residue was purified by column chromatography (DCM/MeOH=100/0 to 40/1) to give the title compound (30 mg, 43%) as a white solid, which was used directly in the next step.

b) Methyl ((3-((5-ethyl-2-methoxyphenyl)sulfonamido)benzo[d]isoxazol-5-yl)methyl) carbamate 227

A mixture of methyl ((3-((N-(2,4-dimethoxybenzyl)-5-ethyl-2-methoxyphenyl)sulfonamido) benzo[d]isoxazol-5-yl)methyl)carbamate A56 (30 mg, 0.0558 mmol) and TFA (3 mL) was stirred at RT for 3 h then concentrated under reduced pressure. The residue was purified by column chromatography (DCM/MeOH=40/1) to give the title compound (15 mg, 64%) as a white solid. LCMS-D: R_t 2.45 min, m/z 420.1 [M+H]⁺. ¹H NMR (400 MHz, DMSO-d₆) δ 11.7 (s, 1H), 7.91 (s, 1H), 7.79 (t, J=5.6 Hz, 1H), 7.69 (d, J=2.0 Hz, 1H), 7.55-7.43 (m, 3H), 7.09 (d, J=8.4 Hz, 1H), 4.29 (d, J=6.0 Hz, 2H), 3.73 (s, 3H), 3.58 (s, 3H), 2.63 (q, J=7.6 Hz, 2H), 1.16 (t, J=7.6 Hz, 3H).

Example 228: N-((3-((5-Ethyl-2-methoxyphenyl)sulfonamido)benzo[d]isoxazol-5-yl)methyl)acetamide 228

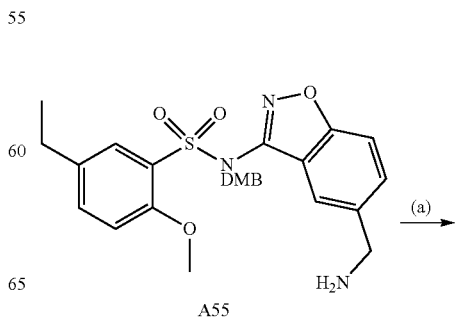

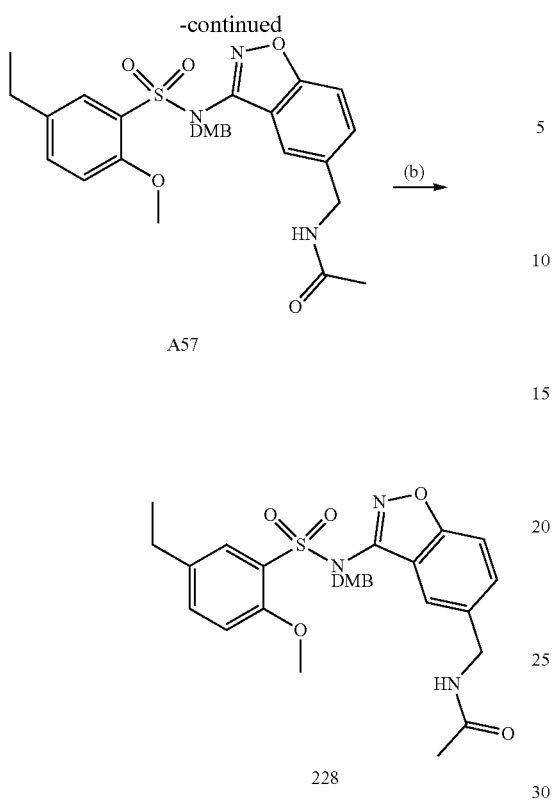

a) N-((3-((N-(2,4-dimethoxybenzyl)-5-ethyl-2-methoxyphenyl)sulfonamido)benzo[d]isoxazol-5-yl)methyl)acetamide A57

To a solution of N-(5-(aminomethyl)benzo[d]isoxazol-3-yl)-N-(2,4-dimethoxybenzyl)-5-ethyl-2-methoxybenzenesulfonamide A55 (100 mg, 0.195 mmol) and Et₃N (98 mg, 0.975 mmol) in DCM (10 mL) at 0° C. under nitrogen was added acetyl chloride (31 mg, 0.391 mmol) and the mixture was stirred at RT for 30 min. The mixture was diluted with water and extracted with DCM. The organic extract was washed with water, brine, dried over anhydrous Na₂SO₄, filtered and concentrated under reduced pressure. The residue was purified by prep. TLC (DCM/MeOH=30/1) to give the title compound (60 mg, 56%) as a white solid, which was used directly in the next step.

b) N-((3-((5-Ethyl-2-methoxyphenyl)sulfonamido)benzo[d]isoxazol-5-yl)methyl)acetamide 228

A mixture of N-((3-((N-(2,4-dimethoxybenzyl)-5-ethyl-2-methoxyphenyl)sulfonamido) benzo[d]isoxazol-5-yl)methyl)acetamide A57 (60 mg, 0.108 mmol) and TFA (5 mL) was stirred at RT for 3 h then concentrated under reduced pressure. The residue was purified by column chromatography (DCM/MeOH=40/1) to give the title compound (30 mg, 68%) as a white solid. LCMS-D: R$_t$ 2.35 min, m/z 404.1 [M+H]⁺. ¹H NMR (400 MHz, DMSO-d₆) δ 11.7 (br s, 1H), 8.55 (br s, 1H), 7.85 (s, 1H), 7.69 (s, 1H), 7.47-7.39 (m, 3H), 7.06 (d, J=7.2 Hz, 1H), 4.33 (d, J=3.6 Hz, 2H), 3.72 (s, 3H), 2.60 (q, J=6.8 Hz, 2H), 1.91 (s, 3H), 1.17 (t, J=6.8 Hz, 3H).

Example 229: 5-Ethyl-N-(5-(hydroxymethyl)benzo[d]isoxazol-3-yl)-2-methoxybenzenesulfonamide 229

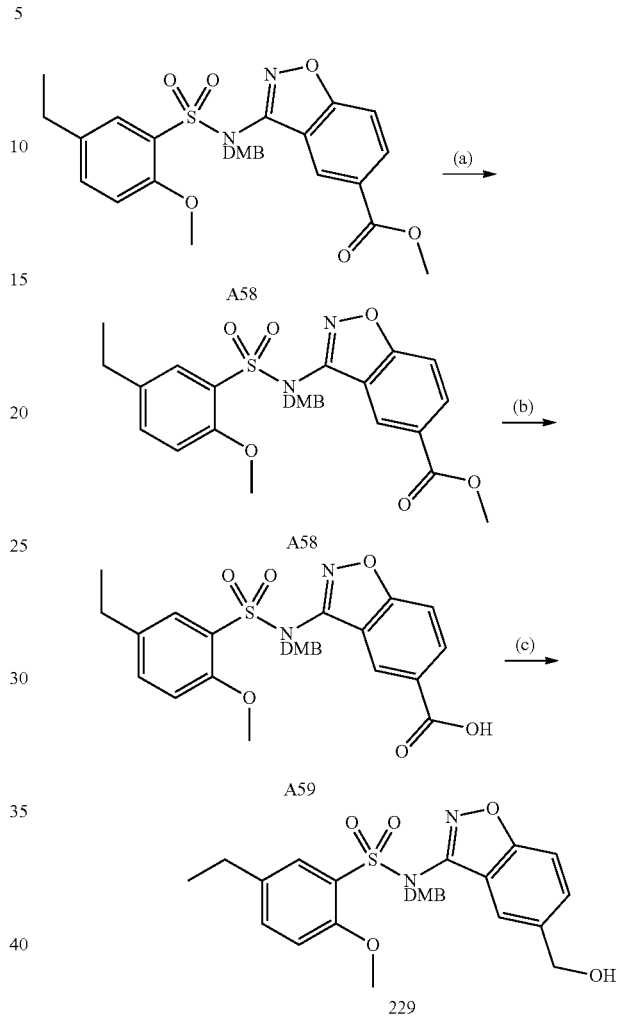

a) Methyl 3-((5-ethyl-2-methoxyphenyl)sulfonamido)benzo[d]isoxazole-5-carboxylate A58

A mixture of methyl 3-((N-(2,4-dimethoxybenzyl)-5-ethyl-2-methoxyphenyl)sulfonamido) benzo[d]isoxazole-5-carboxylate A50 (435 mg, 0.8 mmol) and TFA (9 mL) was stirred at RT for 3 h then concentrated under reduced pressure. The residue was purified by column chromatography (Pet. ether/EtOAc=2/1) to give the title compound (200 mg, 89%) as a light yellow solid. LCMS-D: R$_t$ 2.69 min, m/z 391.1 [M+H]⁺. ¹H NMR (400 MHz, DMSO-d₆) δ 11.9 (br s, 1H), 8.82 (s, 1H), 8.18 (dd, J=9.2, 1.6 Hz, 1H), 7.72-7.70 (m, 2H), 7.48 (dd, J=8.8, 2.0 Hz, 1H), 7.10 (d, J=8.8 Hz, 1H), 3.90 (s, 3H), 3.71 (s, 3H), 2.64 (q, J=7.6 Hz, 2H), 1.16 (t, J=7.6 Hz, 3H).

b) 3-((5-ethyl-2-methoxyphenyl)sulfonamido)benzo[d]isoxazole-5-carboxylic acid A59

To a solution of methyl 3-((5-ethyl-2-methoxyphenyl)sulfonamido)benzo[d]isoxazole-5-carboxylate A58 (220 mg, 0.56 mmol) in THF/MeOH (10 mL/10 mL) was added 2 M aq. NaOH (1.4 mL, 2.8 mmol) and the mixture was stirred at RT overnight. The solvent was removed under reduced pressure and the residue was dissolved in water (10 mL) and the solution was adjusted to pH 2-3. The resulting precipitate was collected by filtration to give the title compound (180 mg, 85%) as a light yellow solid. LCMS-D: $R_t$ 2.51 min, m/z 377.2 [M+H]$^+$. $^1$H NMR (400 MHz, DMSO-d$_6$) δ 13.2 (s, 1H), 11.86 (s, 1H), 8.78 (s, 1H), 8.16 (dd, J=8.8, 1.2 Hz, 1H), 7.71-7.66 (m, 2H), 7.47 (dd, J=8.4, 1.6 Hz, 1H), 7.10 (d, J=8.4 Hz, 1H), 3.70 (s, 3H), 2.63 (q, J=7.6 Hz, 2H), 1.16 (t, J=7.6 Hz, 3H).

c) 5-Ethyl-N-(5-(hydroxymethyl)benzo[d]isoxazol-3-yl)-2-methoxybenzenesulfonamide 229

A mixture of 3-((5-ethyl-2-methoxyphenyl)sulfonamido)benzo[d]isoxazole-5-carboxylic acid A59 (50 mg, 0.13 mmol) and BH$_3$-THF (1 M solution in THF, 5 mL, 5 mmol) was stirred at RT for 5 h under nitrogen. The reaction was quenched with water (10 mL) and most of the THF was removed under reduced pressure. The aqueous residue was adjusted to pH 2-3 and extracted with DCM (15 mL×3). The combined organic layers were dried over anhydrous Na$_2$SO$_4$, filtered and concentrated under reduced pressure. The residue was purified by column chromatography (DCM/MeOH=30/1) to give the title compound (30 mg, 62%) as a light yellow solid. LCMS-D: $R_t$ 2.46 min, m/z 363.1 [M+H]$^+$. $^1$H NMR (400 MHz, DMSO-d$_6$) δ 11.6 (s, 1H), 7.98 (s, 1H), 7.69 (d, J=2.0 Hz, 1H), 7.53 (s, 2H), 7.46 (dd, J=8.4, 2.0 Hz, 1H), 7.10 (d, J=8.4 Hz, 1H), 5.35 (t, J=5.6 Hz, 1H), 4.59 (d, J=5.6 Hz, 2H), 3.72 (s, 3H), 2.63 (q, J=7.6 Hz, 2H), 1.16 (t, J=7.6 Hz, 3H).

Example 230: 3-((5-Ethyl-2-methoxyphenyl)sulfonamido)-N-methylbenzo[d]isoxazole-5-carboxamide 230

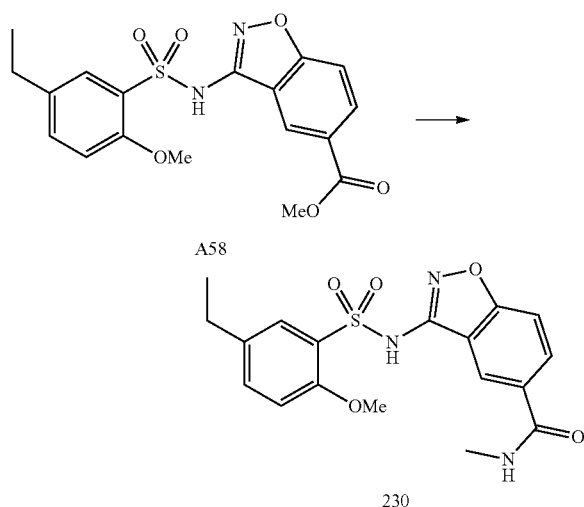

A mixture of methyl 3-((5-ethyl-2-methoxyphenyl)sulfonamido)benzo[d]isoxazole-5-carboxylate A58 (50 mg, 0.13 mmol) and methylamine (33% solution in EtOH, 5 mL) was heated at 90° C. for 80 min in a sealed tube. The solvent was removed under reduced pressure and the residue was purified by prep. TLC to give the desired product (18 mg, 36%) as a light yellow solid. LCMS-D: $R_t$ 2.39 min, m/z 390.2 [M+H]$^+$. $^1$H NMR (400 MHz, DMSO-d$_6$) δ 11.8 (s, 1H), 8.53-8.51 (m, 2H), 8.03 (d, J=8.8 Hz, 1H), 7.69 (d, J=2.0 Hz, 1H), 7.62 (d, J=8.8 Hz, 1H), 7.42 (d, J=8.0 Hz, 1H), 7.06 (d, J=8.4 Hz, 1H), 3.69 (s, 3H), 2.81 (d, J=4.4 Hz, 3H), 2.62 (q, J=7.6 Hz, 2H), 1.16 (t, J=7.6 Hz, 3H).

Example 231: 3-((5-Ethyl-2-methoxyphenyl)sulfonamido)-N,N-dimethylbenzo[d]isoxazole-5-carboxamide 231

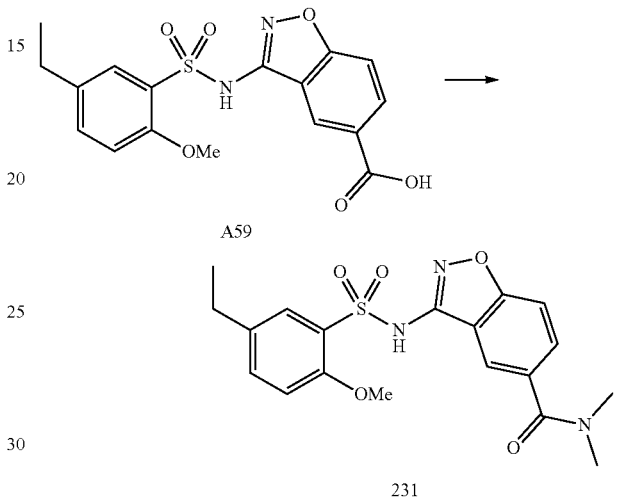

A solution of 3-((5-ethyl-2-methoxyphenyl)sulfonamido)benzo[d]isoxazole-5-carboxylic acid A59 (70 mg, 0.19 mmol) in thionyl chloride (10 mL) was heated at 85° C. for 3 h under nitrogen. The mixture was then concentrated under reduced pressure to give 3-((5-ethyl-2-methoxyphenyl)sulfonamido)benzo[d]isoxazole-5-carbonyl chloride, which was dissolved in THF (2.5 mL) and treated with dimethylamine (40% solution in water, 5 mL). The mixture was stirred at RT overnight. Most of the THF was removed under reduced pressure and the aqueous residue was adjusted to pH 2-3. The precipitate was collected by filtration to give the title compound (60 mg, 80%) as a light-yellow solid. LCMS-D: $R_t$ 2.40 min, m/z 404.2 [M+H]$^+$. $^1$H NMR (400 MHz, DMSO-d$_6$) δ 8.13 (s, 1H), 7.71-7.63 (m, 3H), 7.48 (dd, J=8.8, 2.0 Hz, 1H), 7.10 (d, J=8.8 Hz, 1H), 3.70 (s, 3H), 3.01 (s, 3H), 2.96 (s, 3H), 2.63 (q, J=7.6 Hz, 2H), 1.16 (t, J=7.6 Hz, 3H).

Example 232: 3-((5-Ethyl-2-methoxyphenyl)sulfonamido)benzo[d]isoxazole-5-carboxamide 232

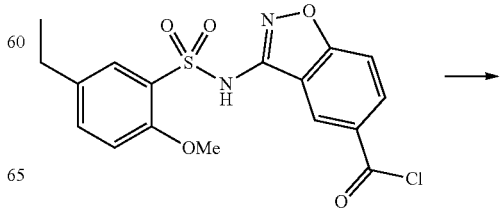

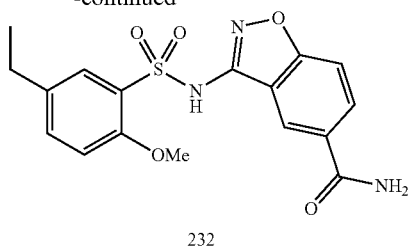

232

To a solution of 3-((5-ethyl-2-methoxyphenyl)sulfonamido)benzo[d]isoxazole-5-carbonyl chloride (63 mg, 0.16 mmol), prepared according to the procedure described for 3-((5-ethyl-2-methoxyphenyl)sulfonamido)-N,N-dimethylbenzo[d]isoxazole-5-carboxamide 231, in THF (2.5 mL) was added conc. NH₄OH (5 mL) and the mixture was stirred at RT over a weekend. Most of the THF was removed under reduced pressure and the aqueous residue was adjusted to pH 2-3. The resulting precipitate was collected by filtration to give the title compound (37 mg, 62%) as a light-yellow solid. LCMS-D: R$_t$ 2.33 min, m/z 376.1 [M+H]⁺. ¹H NMR (400 MHz, DMSO-d₆) δ 11.8 (s, 1H), 8.49 (s, 1H), 8.04 (d, J=7.6 Hz, 2H), 7.69 (d, J=2.4 Hz, 1H), 7.54 (d, J=8.4 Hz, 2H), 7.36 (d, J=6.8 Hz, 1H), 7.02 (d, J=8.4 Hz, 1H), 3.68 (s, 3H), 2.61 (q, J=7.6 Hz, 2H), 1.16 (t, J=7.6 Hz, 3H).

Example 233: N-(5-Cyanobenzo[d]isoxazol-3-yl)-5-ethyl-2-methoxybenzenesulfonamide 233

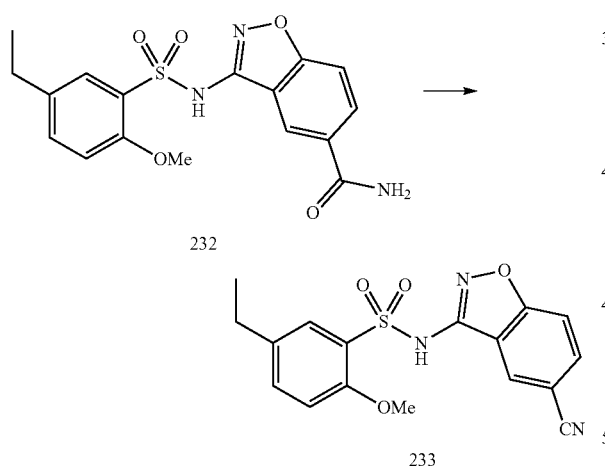

A solution of 3-((5-ethyl-2-methoxyphenyl)sulfonamido)benzo[d]isoxazole-5-carboxamide 232 (22 mg, 0.058 mmol) in POCl₃ was heated at 110° C. overnight under nitrogen. The reaction was quenched with ice-water (25 mL) and the mixture was extracted with DCM (35 mL×2). The combined organic extracts were washed with water (50 mL×3), dried over anhydrous Na₂SO₄, filtered and concentrated under reduced pressure to give the title compound (19.8 mg, 90%) as a light-yellow solid. LCMS-D: R$_t$ 2.61 min, m/z 358.1 [M+H]⁺. ¹H NMR (400 MHz, DMSO-d₆) δ 12.0 (s, 1H), 8.54 (s, 1H), 8.07 (d, J=8.8, 1.2 Hz, 1H), 7.86 (d, J=8.8 Hz, 1H), 7.73 (d, J=2.0 Hz, 1H), 7.49 (dd, J=8.4, 1.6 Hz, 1H), 7.11 (d, J=8.4 Hz, 1H), 3.70 (s, 3H), 2.65 (q, J=7.6 Hz, 2H), 1.17 (t, J=7.6 Hz, 3H).

Example 234: 5-Ethyl-2-methoxy-N-(5-methylbenzo[d]isoxazol-3-yl)benzenesulfonamide 234

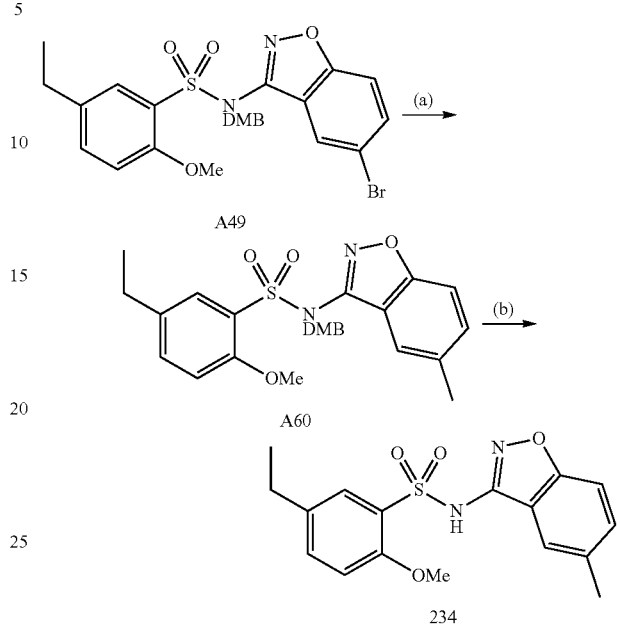

a) N-(2,4-Dimethoxybenzyl)-5-ethyl-2-methoxy-N-(5-methylbenzo[d]isoxazol-3-yl)benzenesulfonamide A60

A mixture of N-(5-bromobenzo[d]isoxazol-3-yl)-N-(2,4-dimethoxybenzyl)-5-ethyl-2-methoxybenzenesulfonamide A49 (112 mg, 0.2 mmol), methyl boronic acid (60 mg, 1 mmol), Pd(dppf)Cl₂ (29 mg, 0.04 mmol) and K₂CO₃ (138 mg, 1 mmol) in 1,4-dioxane (10 mL) and water (2 mL) was heated at 90° C. under nitrogen overnight. The solvent was removed under reduced pressure and the residue was diluted with water (30 mL) and extracted with EtOAc (100 mL). The organic extract was washed with water, brine, dried over anhydrous Na₂SO₄, filtered and concentrated under reduced pressure. The residue was purified by prep. TLC (Pet. ether/EtOAc=3/1) to give the title compound (60 mg, 61%) as a white solid. LCMS-D: R$_t$ 2.72 min, m/z 347.2[M-DMB]⁺.

b) 5-Ethyl-2-methoxy-N-(5-methylbenzo[d]isoxazol-3-yl)benzenesulfonamide 234

A mixture of N-(2,4-dimethoxybenzyl)-5-ethyl-2-methoxy-N-(5-methylbenzo[d]isoxazol-3-yl) benzenesulfonamide A60 (60 mg, 0.12 mmol) and TFA (5 mL) was stirred at RT for 4 h then concentrated under reduced pressure. The residue was purified by prep. TLC (Pet. ether/EtOAc=2/1) to give the title compound (30 mg, 71%) as a white solid. LCMS-D: R$_t$ 2.72 min, m/z 347.2 [M+H]⁺. ¹H NMR (400 MHz, DMSO-d₆) δ 7.78 (s, 1H), 7.69 (d, J=2.0 Hz, 1H), 7.49-7.44 (m, 3H), 7.10 (d, J=8.4 Hz, 1H), 3.72 (s, 3H), 2.61 (q, J=7.6 Hz, 2H), 2.40 (s, 3H), 1.16 (t, J=7.6 Hz, 3H).

Examples 235-238 (Table H)

TABLE H

The following targets were prepared according to the procedure described for 5-ethyl-2-methoxy-N-(5-methylbenzo[d]isoxazol-3-yl)benzenesulfonamide 234

| Example | Starting materials | Name and structure | LCMS | ¹H NMR |
|---|---|---|---|---|
| 235 | HO-B(OH)-ethyl | 5-Ethyl-N-(5-ethylbenzo[d]isoxazol-3-yl)-2-methoxybenzenesulfonamide | LCMS-D: $R_t$ 2.84 min, m/z 361.1 [M + H]⁺ | ¹H NMR (400 MHz, DMSO-$d_6$) δ 11.6 (s, 1H), 7.83 (s, 1H), 7.69 (s, 1H), 7.51-7.44 (m, 3H), 7.10 (d, J = 8.4 Hz, 1H), 3.74 (s, 3H), 2.74 (q, J = 7.6 Hz, 2H), 2.63 (q, J = 7.6 Hz, 2H), 1.24 (t, J = 7.6 Hz, 3H), 1.16 (t, J = 7.6 Hz, 3H). |
| 236 | HO-B(OH)-cyclopropyl | N-(5-Cyclopropylbenzo[d]isoxazol-3-yl)-5-ethyl-2-methoxybenzenesulfonamide | LCMS-D: $R_t$ 2.87 min, m/z 373.1 [M + H]⁺ | ¹H NMR (400 MHz, DMSO-$d_6$) δ 11.5 (s, 1H), 7.70 (d, J = 2.8 Hz, 1H), 7.69 (s, 1H), 7.47 (d, J = 8.8 Hz, 2H), 7.38-7.36 (m, 1H), 7.10 (d, J = 8.8 Hz, 1H), 3.74 (s, 3H), 2.63 (q, J = 7.6 Hz, 2H), 2.06-2.01 (m, 1H), 1.17 (t, J = 7.6 Hz, 3H), 1.02-0.96 (m, 2H), 0.68-0.64 (m, 2H). |
| 237 | HO-B(OH)-(1-methylpyrazol-4-yl) | 5-Ethyl-2-methoxy-N-(5-(1-methyl-1H-pyrazol-4-yl)benzo[d]isoxazol-3-yl)benzenesulfonamide | LCMS-D: $R_t$ 2.57 min, m/z 413.1 [M + H]⁺ | ¹H NMR (400 MHz, DMSO-$d_6$) δ 11.6 (s, 1H), 8.17 (s, 1H), 8.10 (s, 1H), 7.82-7.80 (m, 2H), 7.72 (d, J = 1.6 Hz, 1H), 7.60 (d, J = 8.8 Hz, 1H), 7.47 (dd, J = 8.4, 1.6 Hz, 1H), 7.11 (d, J = 8.8 Hz, 1H), 3.90 (s, 3H), 3.75 (s, 3H), 2.64 (q, J = 7.6 Hz, 2H), 1.16 (t, J = 7.6 Hz, 3H). |
| 238 | HO-B(OH)-pyrimidin-5-yl | 5-Ethyl-2-methoxy-N-(5-(pyrimidin-5-yl)benzo[d]isoxazol-3-yl)benzenesulfonamide | LCMS-D: $R_t$ 2.52 min, m/z 442.9 [M + H]⁺ | ¹H NMR (400 MHz, DMSO-$d_6$) δ 11.8 (s, 1H), 9.24 (s, 1H), 9.14 (s, 2H), 8.44 (s, 1H), 8.09 (d, J = 8.8 Hz, 1H), 7.80-7.74 (m, 2H), 7.48 (d, J = 7.6 Hz, 1H), 7.12 (d, J = 8.8 Hz, 1H), 3.74 (s, 3H), 2.65 (q, J = 7.6 Hz, 2H), 1.17 (t, J = 7.6 Hz, 3H). |

Examples 239-242 (Table I)

Method IA:

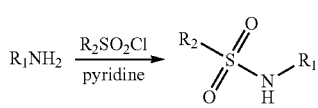

To a solution of the amine (0.2 mmol, 1.0 eq.) in pyridine (2 mL) was added the sulfonyl chloride (1.5 eq.) and the mixture was heated at 120° C. under microwave irradiation for 2 h. The mixture was partitioned between water and EtOAc, the layers were separated and the organic layer was washed with brine, dried over Na₂SO₄, filtered and concentrated under reduced pressure. The residue was purified by prep. TLC to give the title compound. Variations to above conditions have been noted in Table I.

TABLE I

The following examples were synthesised according to the method IA.
Variations of conditions have been noted in the table.

| Ex | Name and structure | Analytical | Intermediates (if applicable) | Method | Notes |
|---|---|---|---|---|---|
| 239 | 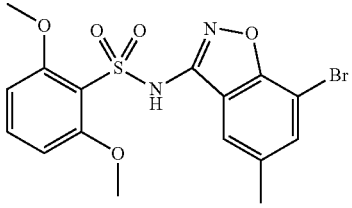 [SMILES: COc1cccc(OC)c1S(=O)(=O)Nc1noc2c(Br)cc(C)cc12]<br>N-(7-Bromo-5-methylbenzo[d]isoxazol-3-yl)-2,6-dimethoxybenzenesulfonamide | LCMS-C: $R_t$ 2.45 min; m/z 427.0, 429.0 [M + H]$^+$; $^1$H NMR (400 MHz, DMSO-$d_6$) δ 11.5 (s, 1H), 7.85 (s, 1H), 7.73 (s, 1H), 7.48 (t, J = 8.4 Hz, 1H), 6.75 (d, J = 8.4 Hz, 2H), 3.74 (s, 6H), 2.40 (s, 3H). | 2,6-Dimethoxy benzenesulfonyl chloride I111<br>7-Bromo-5-methylbenzo[d]isoxazol-3-amine I132 | IA | 0.2 eq. DMAP used. Organic layer washed with 0.1 M aq. HCl in workup. Prep. TLC (DCM/MeOH, 20/1) |
| 240 | 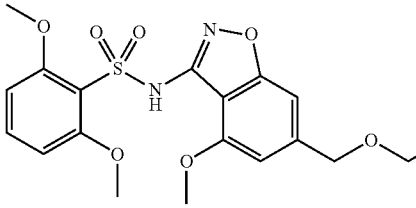<br>2,6-Dimethoxy-N-(4-methoxy-6-((2,2,2-trifluoroethoxy)methyl)benzo[d]isoxazol-3-yl)benzenesulfonamide | LCMS-C: $R_t$ 2.33 min; m/z 476.9 [M + H]$^+$; $^1$H NMR (400 MHz, DMSO-$d_6$) δ 9.59 (br s, 1H), 7.49 (s, 1H), 7.18-7.06 (m, 1H), 6.86-6.62 (m, 3H), 4.75 (s, 2H), 4.15-4.11 (m, 2H), 3.91 (s, 3H), 3.76 (s, 6H). | 2,6-Dimethoxy benzenesulfonyl chloride I111<br>4-Methoxy-6-((2,2,2-trifluoroethoxy)methyl)benzo[d]isoxazol-3-amine I118 | IA | 1 mL pyridine used. Prep. TLC (Pet. ether/EtOAc = 1/1) |
| 241 | 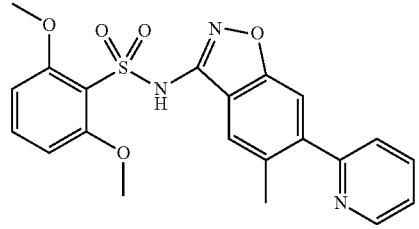 [SMILES: COc1cccc(OC)c1S(=O)(=O)Nc1noc2cc(-c3ccccn3)c(C)cc12]<br>2,6-Dimethoxy-N-(5-methyl-6-(pyridin-2-yl)benzo[d]isoxazol-3-yl)benzenesulfonamide | LCMS-D: $R_t$ 3.32 min; m/z 426.0 [M + H]$^+$; $^1$H NMR (400 MHz, DMSO-$d_6$) δ 11.4 (br s, 1H), 8.68 (d, J = 3.6 Hz, 1H), 7.96-7.90 (m, 2H), 7.59-7.43 (m, 4H), 6.76 (d, J = 8.4 Hz, 2H), 3.76 (s, 6H), 2.34 (s, 3H). | 2,6-Dimethoxy benzenesulfonyl chloride I111<br>5-Methyl-6-(pyridin-2-yl)benzo[d]isoxazol-3-amine I127 | IA | 5 mL pyridine used; 0.1 eq. DMAP used. Prep. TLC (Pet. ether/EtOAc = 1/1) |
| 242 | <br>N-(6-(Difluoromethoxy)-4-methoxybenzo[d]isoxazol-3-yl)-2,6-dimethoxybenzenesulfonamide | LCMS-C $R_t$ 2.13 min; m/z 430.9 [M + H]$^+$; $^1$H NMR (400 MHz, DMSO-$d_6$) δ 9.73 (br s, 1H), 7.52 (t, J = 8.4 Hz, 1H), 7.40 (t, J = 73.2 Hz, 1H), 7.04 (d, J = 1.6 Hz, 1H), 6.78 (d, J = 8.4 Hz, 2H), 6.69 (d, J = 1.6 Hz, 1H), 3.91 (s, 3H), 3.76 (s, 6H). | 2,6-Dimethoxy benzenesulfonyl chloride I111<br>6-(Difluoromethoxy)-4-methoxybenzo[d]isoxazol-3-amine I121 | IA | Heated for 1 h. Adjusted aqueous phase to pH 5 with 1 M aq. HCl in workup. Prep. TLC (DCM/MeOH = 50/1) |

Example 243: N-(6-(3-Cyanophenyl)-4-methoxy-benzo[d]isoxazol-3-yl)-2,6-dimethoxybenzenesulfonamide 243

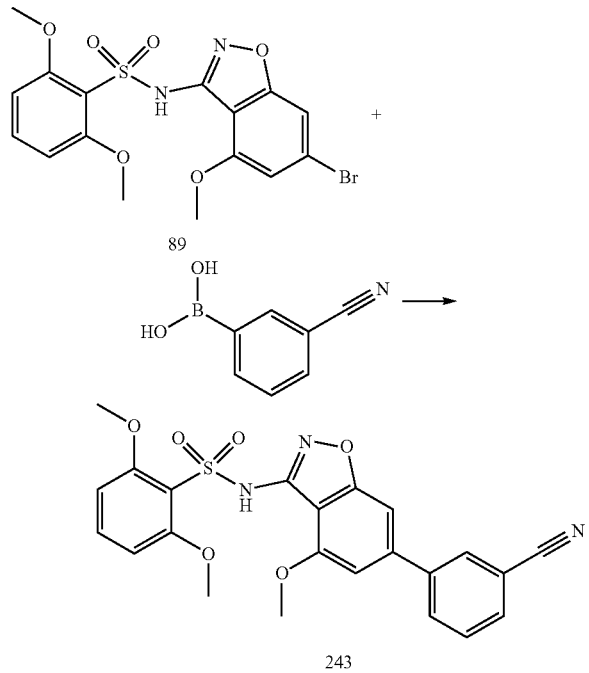

243

To a solution of N-(6-bromo-4-methoxybenzo[d]isoxazol-3-yl)-2,6-dimethoxybenzenesulfonamide 89 (50 mg, 0.113 mmol) in 1,4-dioxane (8 mL) and water (2 mL) was added (3-cyanophenyl)boronic acid (34 mg, 0.226 mmol), Na$_2$CO$_3$ (36 mg, 0.339 mmol) and Pd(PPh$_3$)$_4$ (14 mg, 0.011 mmol) and the mixture was heated at reflux under a N$_2$ atmosphere overnight. The mixture was adjusted to pH 4-5 with 1 M aqueous HCl and extracted with EtOAc. The combined organic extracts were washed with water, brine, dried over Na$_2$SO$_4$, filtered and concentrated under reduced pressure. The residue was purified by prep. TLC (DCM/MeOH=100/1) to give the title compound (24 mg, 46%) as a white solid. LCMS-C: R$_t$ 2.44 min, m/z 466.0 [M+H]$^+$. $^1$H NMR (400 MHz, DMSO-d$_6$) δ 9.70 (s, 1H), 8.34 (s, 1H), 8.16 (d, J=7.5 Hz, 1H), 7.90 (d, J=7.7 Hz, 1H), 7.70 (t, J=7.8 Hz, 1H), 7.57 (s, 1H), 7.51 (t, J=8.4 Hz, 1H), 7.19 (s, 1H), 6.79 (d, J=8.5 Hz, 2H), 4.03 (s, 3H), 3.78 (s, 6H).

Example 244: 2,6-Dimethoxy-N-(4-methoxy-6-methylbenzo[d]isoxazol-3-yl)benzenesulfonamide 244

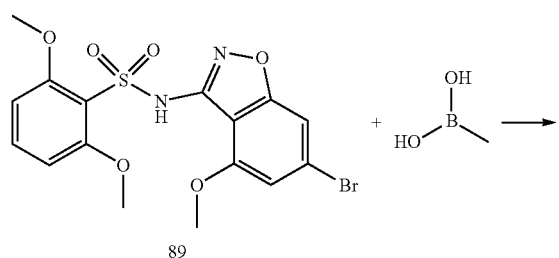

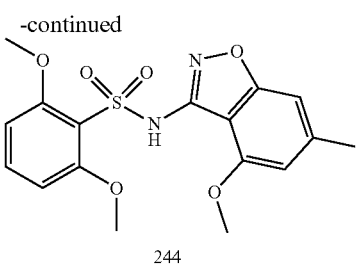

244

To a solution of N-(6-bromo-4-methoxybenzo[d]isoxazol-3-yl)-2,6-dimethoxybenzenesulfonamide 89 (50 mg, 0.113 mmol) in 1,4-dioxane (8 mL) and water (2 mL) was added methylboronic acid (14 mg, 0.226 mmol), Na$_2$CO$_3$ (36 mg, 0.339 mmol) and Pd(PPh$_3$)$_4$ (14 mg, 0.011 mmol) and the mixture was heated at reflux under a N$_2$ atmosphere overnight. The mixture was adjusted to pH 4-5 with 1 M aqueous HCl and extracted with EtOAc. The combined organic extracts were washed with water, brine, dried over Na$_2$SO$_4$, filtered and concentrated under reduced pressure. The residue was purified by prep. HPLC to give the title compound (8 mg, 19%) as a white solid. LCMS-C: R$_t$ 2.18 min, m/z 379.0 [M+H]$^+$. $^1$H NMR (400 MHz, DMSO-d$_6$) δ 9.45 (s, 1H), 7.49 (t, J=8.5 Hz, 1H), 6.97 (s, 1H), 6.77 (d, J=8.5 Hz, 2H), 6.70 (s, 1H), 3.91 (s, 3H), 3.77 (s, 6H), 2.42 (s, 3H).

Example 245: 2,6-Dimethoxy-N-(4-methoxy-6-(pyridin-4-yl)benzo[d]isoxazol-3-yl)benzenesulfonamide 245

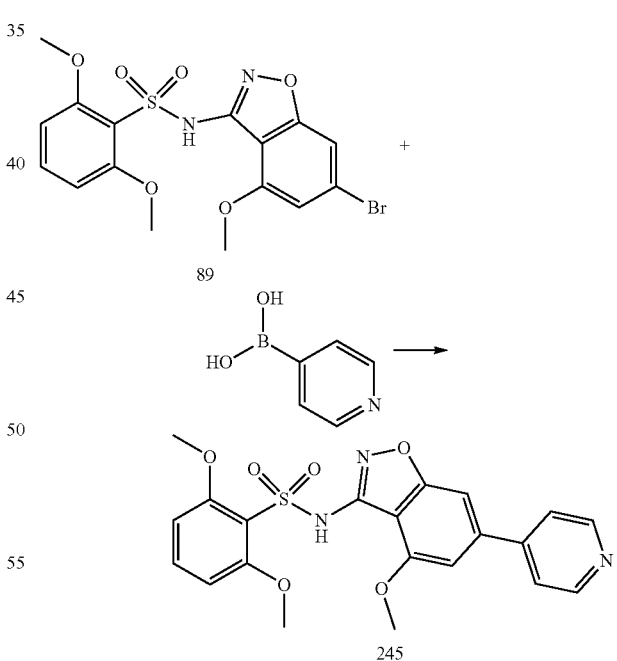

245

To a solution of N-(6-bromo-4-methoxybenzo[d]isoxazol-3-yl)-2,6-dimethoxybenzenesulfonamide 89 (50 mg, 0.113 mmol) in 1,4-dioxane (8 mL) and water (2 mL) was added pyridin-4-ylboronic acid (28 mg, 0.226 mmol), Na$_2$CO$_3$ (36 mg, 0.339 mmol) and Pd(PPh$_3$)$_4$ (14 mg, 0.011 mmol) and the mixture was heated at reflux under a N$_2$ atmosphere overnight. The mixture was adjusted to pH 4-5

Example 246: 2,6-Dimethoxy-N-(4-methoxy-6-(pyridin-3-yl)benzo[d]isoxazol-3-yl)benzenesulfonamide 246

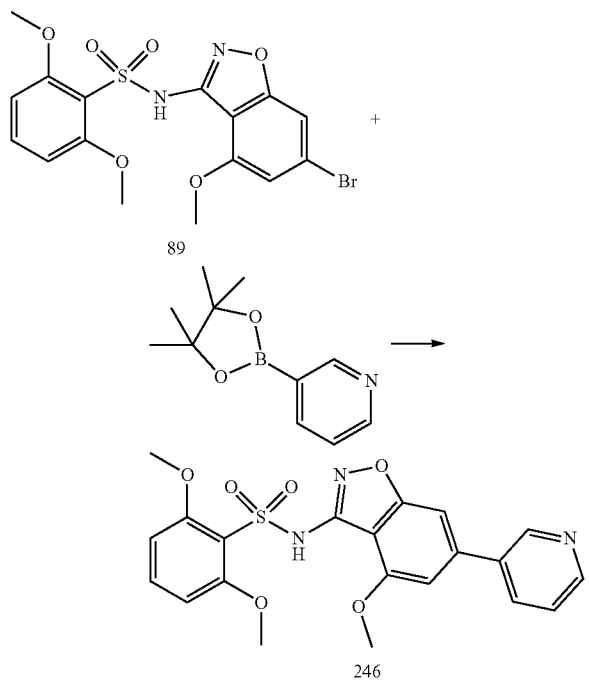

To a solution of N-(6-bromo-4-methoxybenzo[d]isoxazol-3-yl)-2,6-dimethoxybenzenesulfonamide 89 (50 mg, 0.113 mmol) in 1,4-dioxane (8 mL) and water (2 mL) was added 3-(4,4,5,5-tetramethyl-1,3,2-dioxaborolan-2-yl)pyridine (47 mg, 0.226 mmol), Na$_2$CO$_3$ (36 mg, 0.339 mmol) and Pd(PPh$_3$)$_4$ (14 mg, 0.011 mmol) and the mixture was heated at reflux under a N$_2$ atmosphere overnight. The mixture was adjusted to pH 4-5 with 1 M aqueous HCl and extracted with EtOAc. The combined organic extracts were washed with water, brine, dried over Na$_2$SO$_4$, filtered and concentrated under reduced pressure. The residue was purified by prep. TLC (DCM/MeOH=30/1) to give the title compound (9 mg, 18%) as a white solid. LCMS-C: R$_t$ 0.77 min, m/z 442.0 [M+H]$^+$. $^1$H NMR (400 MHz, DMSO-d$_6$) δ 9.67 (s, 1H), 9.02 (d, J=2.5 Hz, 1H), 8.63 (dd, J=4.8, 1.6 Hz, 1H), 8.21 (dt, J=8.0, 2.0 Hz, 1H), 7.56 (s, 1H), 7.54-7.48 (m, 2H), 7.17 (s, 1H), 6.79 (d, J=8.5 Hz, 2H), 4.03 (s, 3H), 3.79 (s, 6H).

Example 247: 2,6-Dimethoxy-N-(4-methoxy-6-(6-methoxypyridin-3-yl)benzo[d]isoxazol-3-yl)benzenesulfonamide 247

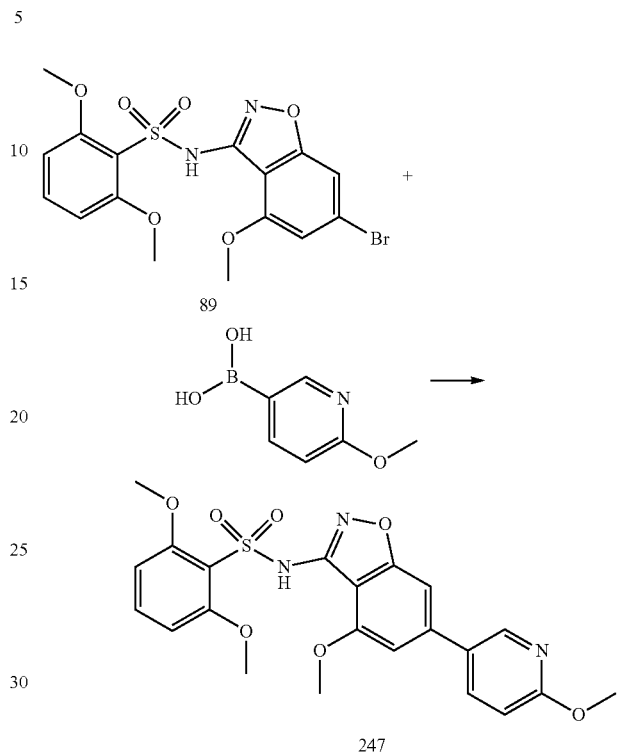

To a solution of N-(6-bromo-4-methoxybenzo[d]isoxazol-3-yl)-2,6-dimethoxybenzenesulfonamide 89 (50 mg, 0.113 mmol) in 1,4-dioxane (8 mL) and water (2 mL) was added (6-methoxypyridin-3-yl)boronic acid (35 mg, 0.226 mmol), Na$_2$CO$_3$ (36 mg, 0.339 mmol) and Pd(PPh$_3$)$_4$ (14 mg, 0.011 mmol) and the mixture was heated at reflux under a N$_2$ atmosphere overnight. The mixture was adjusted to pH 4-5 with 1 M aqueous HCl and extracted with EtOAc. The combined organic extracts were washed with water, brine, dried over Na$_2$SO$_4$, filtered and concentrated under reduced pressure. The residue was purified by prep. TLC (DCM/MeOH=60/1) to give the title compound (45 mg, 85%) as a white solid. LCMS-C: R$_t$ 2.33 min, m/z 472.0 [M+H]$^+$. $^1$H NMR (400 MHz, DMSO-d$_6$) δ 9.61 (s, 1H), 8.63 (d, J=2.6 Hz, 1H), 8.15 (dd, J=8.7, 2.6 Hz, 1H), 7.51 (t, J=8.5 Hz, 1H), 7.47 (s, 1H), 7.10 (s, 1H), 6.94 (d, J=8.6 Hz, 1H), 6.79 (d, J=8.5 Hz, 2H), 4.02 (s, 3H), 3.91 (s, 3H), 3.79 (s, 6H).

Example 248: 2,6-Dimethoxy-N-(4-methoxy-6-(3-methoxy-5-methylphenyl)benzo[d]isoxazol-3-yl)benzenesulfonamide 248

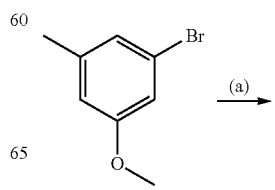

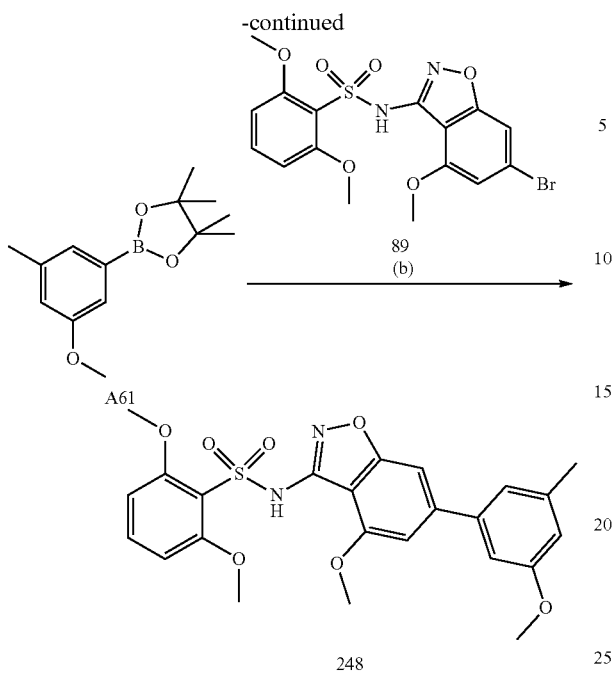

248 a) 2-(3-Methoxy-5-methylphenyl)-4,4,5,5-tetramethyl-1,3,2-dioxaborolane A61

A mixture of 1-bromo-3-methoxy-5-methylbenzene (500 mg, 2.49 mmol), 4,4,4',4',5,5,5',5'-octamethyl-2,2'-bi(1,3,2-dioxaborolane) (1.9 g, 7.49 mmol), potassium acetate (977 mg, 9.96 mmol) and Pd(dppf)Cl₂ (196 mg, 0.25 mmol) in 1,4-dioxane (20 mL) was heated at reflux under N₂ for 3 h. The mixture was diluted with EtOAc (300 mL), washed with water (50 mL×3) and the organic layer was dried over Na₂SO₄, filtered, concentrated under reduced pressure. The residue was purified by column chromatography (Pet. ether/EtOAc=20/1) to give the title compound (300 mg, 49%) as a white solid. ¹H NMR (400 MHz, DMSO-d₆) δ 7.08 (s, 1H), 6.94 (d, J=2.6 Hz, 1H), 6.87 (s, 1H), 3.73 (s, 3H), 2.30-2.25 (m, 3H), 1.28 (s, 12H).

b) 2,6-Dimethoxy-N-(4-methoxy-6-(3-methoxy-5-methylphenyl)benzo[d]isoxazol-3-yl)benzenesulfonamide 248

To a solution of N-(6-bromo-4-methoxybenzo[d]isoxazol-3-yl)-2,6-dimethoxybenzenesulfonamide 89 (50 mg, 0.11 mmol) in 1,4-dioxane (8 mL) and water (2 mL) was added 2-(3-methoxy-5-methylphenyl)-4,4,5,5-tetramethyl-1,3,2-dioxaborolane A61 (55 mg, 0.22 mmol), K₂CO₃ (61 mg, 0.44 mmol) and Pd(PPh₃)₄ (13 mg, 0.011 mmol) and the mixture was heated at reflux under a N₂ atmosphere overnight. The mixture was adjusted to pH 4-5 with 1 M aqueous HCl and extracted with EtOAc. The combined organic extracts were washed with water, brine, dried over Na₂SO₄, filtered and concentrated under reduced pressure. The residue was purified by prep. HPLC to give the title compound (4.3 mg, 8%) as a white solid. LCMS-C: R_t 2.56 min, m/z 485.3 [M+H]⁺. ¹H NMR (400 MHz, DMSO-d₆) δ 9.62 (s, 1H), 7.51 (t, J=8.5 Hz, 1H), 7.43 (s, 1H), 7.18 (s, 1H), 7.10 (s, 1H), 7.05 (s, 1H), 6.83 (s, 1H), 6.79 (d, J=8.5 Hz, 2H), 4.02 (s, 3H), 3.81 (s, 3H), 3.79 (s, 6H), 2.36 (s, 3H).

Example 249: 2,6-Dimethoxy-N-(4-methoxy-6-(2-methoxypyridin-4-yl)benzo[d]isoxazol-3-yl)benzenesulfonamide 249

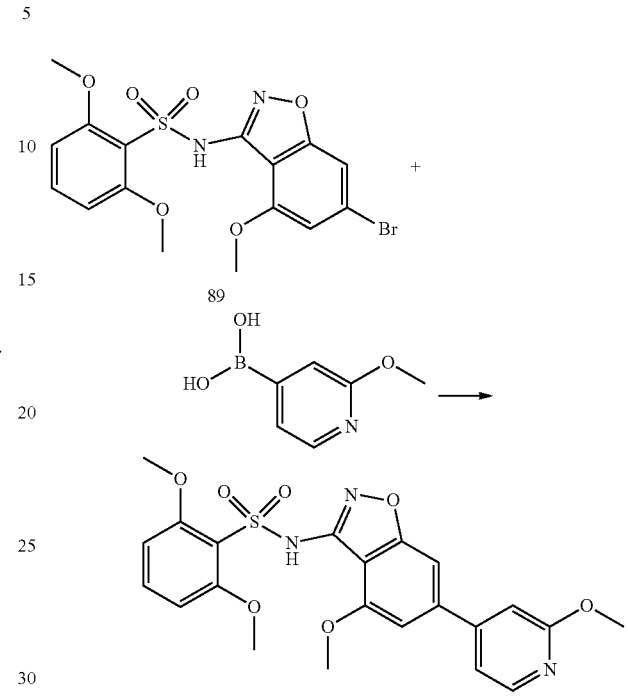

249

To a solution of N-(6-bromo-4-methoxybenzo[d]isoxazol-3-yl)-2,6-dimethoxybenzenesulfonamide 89 (50 mg, 0.11 mmol) in 1,4-dioxane (4 mL) and water (1 mL) was added (2-methoxypyridin-4-yl)boronic acid (33 mg, 0.22 mmol), Na₂CO₃ (35 mg, 0.33 mmol) and Pd(PPh₃)₄ (13 mg, 0.011 mmol) and the mixture was heated at reflux under a N₂ atmosphere overnight. The mixture was poured into water and extracted with DCM. The combined organic extracts were dried over Na₂SO₄, filtered and concentrated under reduced pressure. The residue was purified by prep. HPLC to give the title compound (5 mg, 10%) as a white solid. LCMS-C: R_t 2.29 min, m/z 472.0 [M+H]⁺. ¹H NMR (400 MHz, DMSO-d₆) δ 9.71 (br s, 1H), 8.26 (d, J=5.4 Hz, 1H), 7.59 (s, 1H), 7.50 (t, J=8.5 Hz, 1H), 7.42 (dd, J=5.4, 1.6 Hz, 1H), 7.25 (s, 1H), 7.16 (s, 1H), 6.78 (d, J=8.5 Hz, 2H), 4.02 (s, 3H), 3.90 (s, 3H), 3.78 (s, 6H).

Example 250: 2,6-Dimethoxy-N-(4-methoxy-6-(5-methoxypyridin-3-yl)benzo[d]isoxazol-3-yl)benzenesulfonamide 250

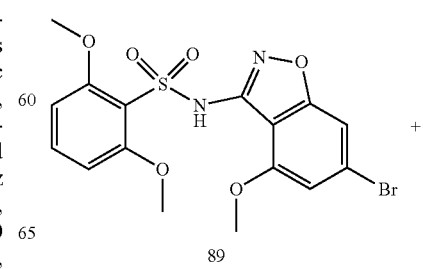

89

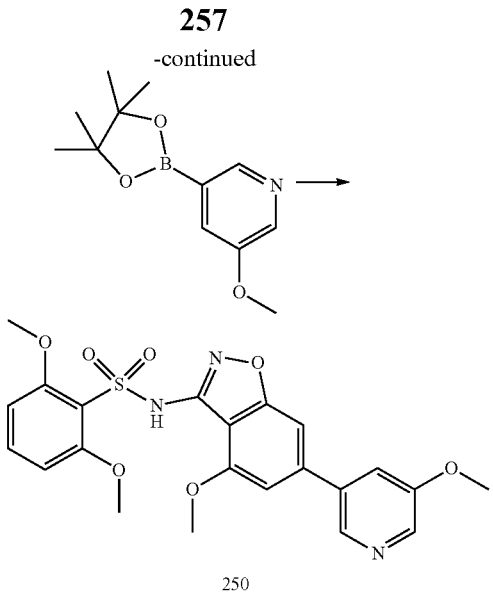

250

To a solution of N-(6-bromo-4-methoxybenzo[d]isoxazol-3-yl)-2,6-dimethoxybenzenesulfonamide 89 (50 mg, 0.11 mmol) in 1,4-dioxane (4 mL) and water (1 mL) was added 3-methoxy-5-(4,4,5,5-tetramethyl-1,3,2-dioxaborolan-2-yl)pyridine (52 mg, 0.22 mmol), Na$_2$CO$_3$ (35 mg, 0.33 mmol) and Pd(PPh$_3$)$_4$ (13 mg, 0.011 mmol) and the mixture was heated at reflux under a N$_2$ atmosphere overnight. The mixture was poured into water and extracted with DCM. The combined organic extracts were dried over Na$_2$SO$_4$, filtered and concentrated under reduced pressure. The residue was purified by prep. HPLC to give the title compound (5 mg, 10%) as a white solid. LCMS-C: R$_t$ 2.25 min, m/z 472.0 [M+H]$^+$. $^1$H NMR (400 MHz, DMSO-d$_6$) δ 9.67 (s, 1H), 8.63 (s, 1H), 8.38 (d, J=2.7 Hz, 1H), 7.81-7.79 (m, 1H), 7.59 (s, 1H), 7.51 (t, J=8.5 Hz, 1H), 7.18 (s, 1H), 6.79 (d, J=8.5 Hz, 2H), 4.04 (s, 3H), 3.94 (s, 3H), 3.79 (s, 6H).

Example 251: N-(6-(3-Cyano-5-methoxyphenyl)-4-methoxybenzo[d]isoxazol-3-yl)-2,6-dimethoxybenzenesulfonamide 251

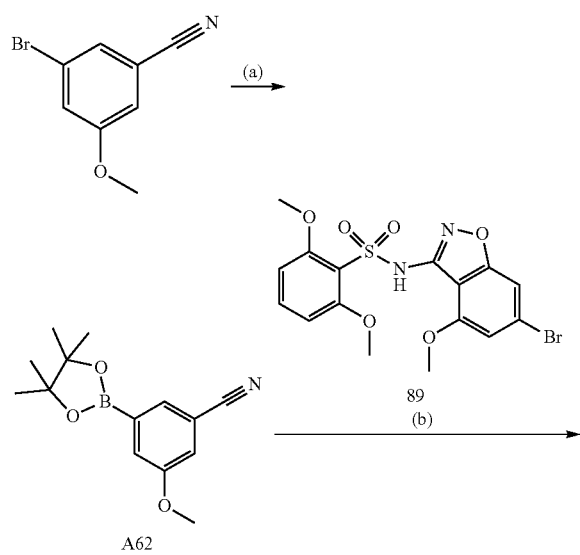

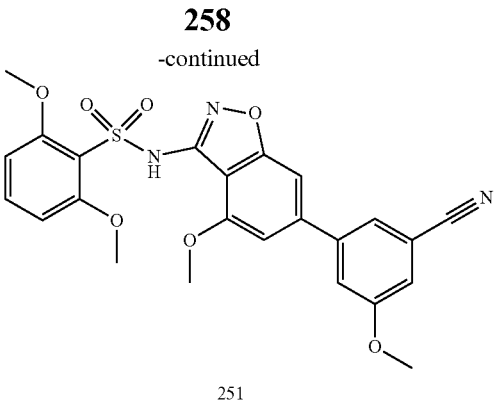

251 a) 3-Methoxy-5-(4,4,5,5-tetramethyl-1,3,2-dioxaborolan-2-yl)benzonitrile A62

A mixture of 3-bromo-5-methoxybenzonitrile (500 mg, 2.35 mmol), 4,4,4',4',5,5,5',5'-octamethyl-2,2'-bi(1,3,2-dioxaborolane) (1.8 g, 7.07 mmol), potassium acetate (923 mg, 9.4 mmol) and Pd(dppf)Cl$_2$.DCM (196 mg 0.24 mmol) was heated at reflux under N$_2$ for 4 h. Water was added and the mixture was extracted with EtOAc (20 mL×3). The combined organic extracts were washed with brine, dried over Na$_2$SO$_4$, filtered and concentrated under reduced pressure. The residue was purified by prep. TLC (EtOAc/Pet. ether=⅕) to give the title compound (600 mg, 98%) as a yellow oil. LCMS-C: R$_t$ 2.66 min; m/z 260.0 [M+H]$^+$.

b) N-(6-(3-Cyano-5-methoxyphenyl)-4-methoxybenzo[d]isoxazol-3-yl)-2,6-dimethoxybenzenesulfonamide 251

To a solution of N-(6-bromo-4-methoxybenzo[d]isoxazol-3-yl)-2,6-dimethoxybenzenesulfonamide 89 (415 mg, 0.94 mmol) in 1,4-dioxane (80 mL) and water (20 mL) was added 3-methoxy-5-(4,4,5,5-tetramethyl-1,3,2-dioxaborolan-2-yl)benzonitrile A62 (500 mg, 2.82 mmol), Na$_2$CO$_3$ (399 mg, 3.77 mmol) and Pd(PPh$_3$)$_4$ (116 mg, 0.1 mmol) and the mixture was heated at reflux under a N$_2$ atmosphere overnight. The mixture was diluted with water and extracted with EtOAc. The combined organic extracts were dried over Na$_2$SO$_4$, filtered and concentrated under reduced pressure. The residue was purified by prep. TLC (DCM/MeOH=30/1) to give the title compound (40 mg, 8.6%) as a white solid. LCMS-C: R$_t$ 2.48 min, m/z 495.9 [M+H]$^+$. $^1$H NMR (400 MHz, DMSO-d$_6$) δ 9.69 (br s, 1H), 7.89 (s, 1H), 7.67 (s, 1H), 7.57 (m, 1H), 7.49 (s, 2H), 7.15 (s, 1H), 6.77 (d, J=8.5 Hz, 2H), 4.02 (s, 3H), 3.90 (s, 3H), 3.77 (s, 6H).

Example 252: 2,6-Dimethoxy-N-(5-methyl-7-phenylbenzo[d]isoxazol-3-yl)benzenesulfonamide 252

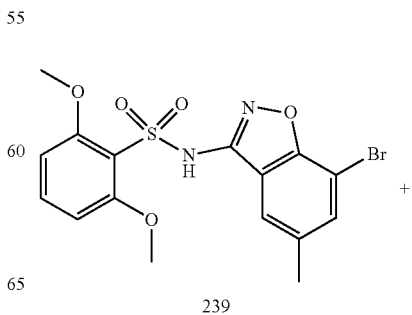

239

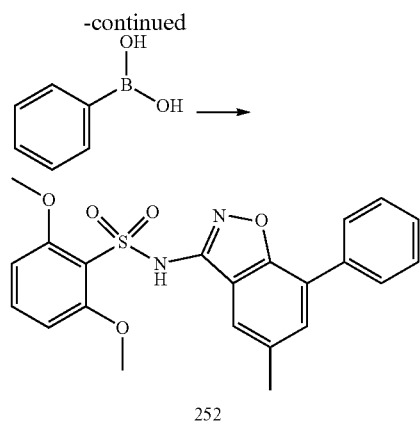

252

To a solution of N-(7-bromo-5-methylbenzo[d]isoxazol-3-yl)-2,6-dimethoxybenzenesulfonamide 239 (50 mg, 0.117 mmol) in 1,4-dioxane (8 mL) and water (2 mL) was added phenylboronic acid (22 mg, 0.176 mmol), $Na_2CO_3$ (50 mg, 0.468 mmol) and $Pd(PPh_3)_4$ (14 mg, 0.012 mmol) and the mixture was heated at reflux under a $N_2$ atmosphere overnight. The mixture was diluted with water and extracted with EtOAc (30 mL×3). The combined organic extracts were washed with brine, dried over $Na_2SO_4$, filtered and concentrated under reduced pressure. The residue was purified by prep. TLC (Pet. ether/EtOAc=3/1) to give the title compound (40 mg, 80%) as a white solid. LCMS-C: $R_t$ 2.49 min; m/z 425.0 $[M+H]^+$. $^1H$ NMR (400 MHz, DMSO-$d_6$) δ 7.87-7.80 (m, 2H), 7.67-7.55 (m, 2H), 7.48 (t, J=7.7 Hz, 2H), 7.42-7.32 (m, 2H), 6.69 (d, J=8.4 Hz, 2H), 3.70 (s, 6H), 2.45 (s, 3H).

Assays
Protein Preparation
KAT5
Molecular Biology:

A codon optimized DNA sequence (for expression in *Escherichia coli*) encoding amino acid residues 2 to 461 (Uniprot Q92993-2) of human KAT5 isoform was synthesised by GenScript USA Inc (Piscataway, N.J., USA). This was ligated into a modified pET43a *E. coli* expression vector designed to encode an N-terminal hexahistidine tag followed by a tobacco etch virus protease (TEV) cleavage site and by the KAT5 sequence. The resulting protein sequence is listed below.

```
                                         (SEQ ID NO: 1)
MGHHHHHHGTENLYFQGSAEVGEIIEGCRLPVLRRNQDNEDEWPLAEILS

VKDISGRKLFYVHYIDFNKRLDEWVTHERLDLKKIQFPKKEAKTPTKNGL

PGSRPGSPEREVKRKVEVVSPATPVPSETAPASVFPQNGAARRAVAAQPG

RKRKSNCLGTDEDSQDSSDGIPSAPRMTGSLVSDRSHDDIVTRMKNIECI

ELGRHRLKPWYFSPYPQELTTLPVLYLCEFCLKYGRSLKCLQRHLTKCDL

RHPPGNEIYRKGTISFFEIDGRKNKSYSQNLCLLAKCFLDHKTLYYDTDP

FLFYVMTEYDCKGFHIVGYFSKEKESTEDYNVACILTLPPYQRRGYGKLL

IEFSYELSKVEGKTGTPEKPLSDLGLLSYRSYWSQTILEILMGLKSESGE

RPQITINEISEITSIKKEDVISTLQYLNLINYYKGQYILTLSEDIVDGHE

RAMLKRLLRIDSKCLHFTPKDWSKRGKWAS*
```

Protein Expression:

To produce recombinant KAT5 protein, expression plasmid was transformed into *E. coli* BL21 DE3 strain and grown with shaking at 37° C. in 1 L volumes of Terrific broth (TB) supplemented with 100 μg/mL Ampicillin and 50 μM zinc until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification:

Protein purification was initiated by thawing the cell pellet (25 g wet weight) in Lysis buffer (50 mM Hepes pH 7.4, 500 mM NaCl, 5 mM imidazole, 5% [v/v]glycerol, 0.1% [w/v] CHAPS, 2 mM 2-mercaptoethanol, 3 mM $MgCl_2$, 0.5 mg/mL lysozyme, benzonase endonuclease [EMD Millipore], 1 mM PMSF, complete protease inhibitor tablets EDTA-free [Roche]) using a ratio of 6 mL of buffer per 1 g of cells. Cells were further lysed by sonication using a Misonix Liquid Processor (6×30 second pulses, amplitude 60 [70 watts]) and then centrifuged at 48,000×g at 4° C. Supernatant (cell lysate) was mixed with 20 mL of Q-Sepharose FF resin (GE Healthcare) pre-equilibrated with Q buffer (20 mM Hepes pH 7.4, 1 M NaCl). The unbound fraction from Q-Sepharose FF was then incubated with 5 mL of cOmplete His-Tag Purification Resin (Roche), pre-equilibrated with IMAC Wash Buffer (20 mM hepes pH 7.4, 500 mM NaCl, 35 mM imidazole). The resin was washed with IMAC Wash Buffer, and bound KAT5 eluted with IMAC Elution buffer (20 mM hepes pH 7.4, 500 mM NaCl, 300 mM imidazole). IMAC-eluted protein was immediately desalted into Storage buffer (50 mM Na citrate pH 6.5, 500 mM NaCl, 5% [v/v] glycerol) using 2×HiPrep 26/10 desalting columns (GE Healthcare) in series. Desalted protein was further purified by passing through a HiLoad 26/60 Superdex 75 column pre-equilibrated in Storage buffer. Finally, KAT5 protein was concentrated to 1.5 mg/mL using Amicon Ultra centrifugal filter unit (Utra-15 MWCO 10 kDa), flash-frozen in liquid nitrogen and stored in −70° C. freezer.

KAT6A
Molecular Biology:

The DNA sequence encoding amino acid residues 507 to 778 (Uniprot Q92794-1) of human KAT6A was amplified by PCR and was ligated into a modified pET *E. coli* expression vector designed to encode a NusA solubility tag followed by a hexahistidine tag and a tobacco etch virus protease (TEV) cleavage site and by the KAT6A sequence. The resulting protein sequence is listed below.

```
                                         (SEQ ID NO: 2)
MNKEILAVVEAVSNEKALPREKIFEALESALATATKKKYEQEIDVRVQID

RKSGDFDTFRRWLVVDEVTQPTKEITLEAARYEDESLNLGDYVEDQIESV

TFDRITTQTAKQVIVQKVREAERAMVVDQFREHEGEIITGVVKKVNRDNI

SLDLGNNAEAVILREDMLPRENFRPGDRVRGVLYSVRPEARGAQLFVTRS

KPEMLIELFRIEVPEIGEEVIEIKAAARDPGSRAKIAVKTNDKRIDPVGA

CVGMRGARVQAVSTELGGERIDIVLWDDNPAQFVINAMAPADVASIVVDE

DKHTMDIAVEAGNLAQAIGRNGQNVRLASQLSGWELNVMTVDDLQAKHQA

EAHAAIDTFTKYLDIDEDFATVLVEEGFSTLEELAYVPMKELLEIEGLDE

PTVEALRERAKNALATIAQAQEESLGDNKPADDLLNLEGVDRDLAFKLAA
```

-continued

```
RGVCTLEDLAEQGIDDLADIEGLTDEKAGALIMAARNICWFGDEATSGSG

HHHHHHSAGENLYFQGAMGRCPSVIEFGKYEIHTWYSSPYPQEYSRLPKL

YLCEFCLKYMKSRTILQQHMKKCGWFHPPVNEIYRKNNISVFEVDGNVST

IYCQNLCLLAKLFLDHKTLYYDVEPFLFYVLTQNDVKGCHLVGYFSKEKH

CQQKYNVSCIMILPQYQRKGYGRFLIDFSYLLSKREGQAGSPEKPLSDLG

RLSYMAYWKSVILECLYHQNDKQISIKKLSKLTGICPQDITSTLHHLRML

DFRSDQFVIIRREKLIQDHMAKLQLNLRPVDVDPECLRWTP
```

Protein Expression:

To produce recombinant KAT6A protein, expression plasmid was transformed into E. coli BL21 DE3 strain and grown with shaking at 37° C. in 1 L volumes of Terrific broth (TB) supplemented with 100 μg/mL Ampicillin until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification:

Protein purification was initiated by thawing the cell pellet (40 g wet weight) in Lysis buffer (25 mM Tris-HCl pH 7.8, 500 mM NaCl, 5 mM DTT, 0.01% [v/v] Triton-X 100, 5% [v/v] glycerol, 2 mM MgCl$_2$, 10 mM Imidazole, 0.5 mg/mL lysozyme, benzonase endonuclease [EMD Millipore], 1 mM PMSF, complete protease inhibitor tablets EDTA-free [Roche]) using a ratio of 5 mL of buffer per 1 g of cells. Cells were further lysed by 3 passes (at 15000 psi) through an ice cooled Avestin C5 cell crusher and then centrifuged at 48,000×g at 4° C. Supernatant (cell lysate) was filtered through a 5 μm filter and applied onto 5 mL HiTrap IMAC Sepharose FF column (GE Healthcare) pre-equilibrated with IMAC wash buffer (25 mM Tris-HCl pH 7.8, 500 mM NaCl, 5 mM DTT, 0.01% [v/v] Triton-X 100, 5% [v/v] glycerol, 20 mM Imidazole) using a Profinia Affinity chromatography purification system (Bio-Rad). The IMAC column was then washed with IMAC Wash buffer and bound KAT6A protein eluted with IMAC Elution buffer (25 mM Tris-HCl pH 7.8, 500 mM NaCl, 5% [v/v] glycerol, 5 mM DTT, 250 mM Imidazole). IMAC-eluted protein was further purified by passing through a HiLoad 26/60 Superdex 200 column pre-equilibrated in Storage buffer (25 mM Tris-HCl pH 7.8, 500 mM NaCl, 5 mM DTT, 5% [v/v] glycerol). Finally, KAT6A protein was concentrated to ≤1 mg/mL using Amicon Ultra centrifugal filter unit (Utra-15 MWCO 10 kDa), flash-frozen in liquid nitrogen and stored in −70° C. freezer.

KAT6B was obtained from SignalChem, catalog ID: K315-381BG

KAT7

Molecular Biology:

A codon optimized DNA sequence encoding amino acid residues 325 to 611 (Uniprot O95251-1) of human KAT7 was synthesised by GenScript USA Inc (Piscataway, N.J., USA). This was ligated into a modified pET43a E. coli expression vector designed to encode an N-terminal hexa-histidine tag followed by a tobacco etch virus protease (TEV) cleavage site and by the KAT7 sequence. The resulting protein sequence is listed below.

(SEQ ID NO: 3)
```
MGHHHHHHGTENLYFQGSRLQGQITEGSNMIKTIAFGRYELDTWYHSPYP

EEYARLGRLYMCEFCLKYMKSQTILRRHMAKCVWKHPPGDEIYRKGSISV

FEVDGKKNKIYCQNLCLLAKLFLDHKTLYYDVEPFLFYVMTEADNTGCHL

IGYFSKEKNSFLNYNVSCILTMPQYMRQGYGKMLIDFSYLLSKVEEKVGS

PERPLSDLGLISYRSYWKEVLLRYLHNFQGKEISIKEISQETAVNPVDIV

STLQALQMLKYWKGKHLVLKRQDLIDEWIAKEAKRSNSNKTMDPSCLKWT

PPKGTAS
```

Protein Expression:

To produce recombinant KAT7 protein, expression plasmid was transformed into E. coli BL21 DE3 RIL strain and grown with shaking at 37° C. in 1 L volumes of Terrific broth (TB) supplemented with 100 μg/mL Ampicillin and 50 μM zinc until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification:

Protein purification was initiated by thawing the cell pellet (10 g wet weight) in Lysis buffer (50 mM Hepes pH 7.5, 300 mM NaCl, 5 mM DTT, 5 mM Imidazole, 0.05% [v/v] Brij 35, 10% [v/v] glycerol, 3 mM MgCl$_2$, 0.5 mg/mL lysozyme, benzonase endonuclease [EMD Millipore], 1 mM PMSF, complete protease inhibitor tablets EDTA-free [Roche]) using a ratio of 10 mL of buffer per 1 g of cells. Cells were further lysed by sonication using a Misonix Liquid Processor (6×30 second pulses, amplitude 60 [70 watts]) and then centrifuged at 48,000×g at 4° C. Supernatant (cell lysate) was incubated with 1 mL of cOmplete His-Tag Purification Resin (Roche), pre-equilibrated with IMAC Wash Buffer 1 (25 mM Hepes pH 7.5, 800 mM NaCl, 5 mM imidazole, 10% [v/v] glycerol, 5 mM DTT, 0.01% [v/v] Brij 35, 50 mM arginine, 50 mM glutamic acid). The resin was sequentially washed with IMAC Wash buffer 1 and IMAC Wash buffer 2 (25 mM hepes pH 7.5, 300 mM NaCl, 20 mM imidazole, 10% [v/v] glycerol, 5 mM DTT, 0.01% [v/v] Brij 35, 50 mM arginine, 50 mM glutamic acid). Bound KAT7 protein was eluted with IMAC Elution buffer (25 mM hepes pH 7.5, 200 mM NaCl, 500 mM imidazole, 10% [v/v] glycerol, 5 mM DTT 0.01% [v/v] Brij 35, 50 mM arginine, 50 mM glutamic acid). The eluting protein was collected directly into 4 volumes of Desalt Buffer (50 mM Na citrate pH 6.5, 200 mM NaCl, 0.01% [v/v] Brij 35, 10% [v/v] glycerol, 5 mM DTT) to bring the final imidazole concentration to 100 mM. IMAC-eluted protein was immediately desalted into Desalt buffer using 2× HiPrep 26/10 desalting columns (GE Healthcare) in series. Desalted protein was further purified by passing through a HiLoad 26/60 Superdex 75 column pre-equilibrated in Storage Buffer (50 mM Na citrate pH 6.5, 200 mM NaCl, 10% [v/v] glycerol, 5 mM DTT). Finally, KAT7 protein was concentrated to 3.5 mg/mL using Amicon Ultra centrifugal filter unit (Utra-15 MWCO 10 kDa), flash-frozen in liquid nitrogen and stored in −70° C. freezer.

KAT8

Molecular Biology:

A codon optimized DNA sequence (for expression in E. coli) encoding amino acid residues 177 to 447 (Uniprot Q9H7Z6-1) of human KAT8 was synthesised by Thermo Fisher Scientific GENEART GmbH (Regensberg, Germany). This was ligated into pPROEX Hta E. coli expression vector designed to encode an N-terminal hexahistidine tag followed by a tobacco etch virus protease (TEV) cleavage site and by the KAT8 sequence. The resulting protein sequence is listed below.

(SEQ ID NO: 4)
MSYYHHHHHHDYDIPTTENLYFQGAKYVDKIHIGNYEIDAWYFSPFPEDY

GKQPKLWLCEYCLKYMKYEKSYRFHLGQCQWRQPPGKEIYRKSNISVYEV

DGKDHKIYCQNLCLLAKLFLDHKTLYFDVEPFVFYILTEVDRQGAHIVGY

FSKEKESPDGNNVACILTLPPYQRRGYGKFLIAFSYELSKLESTVGSPEK

PLSDLGKLSYRSYWSWVLLEILRDFRGTLSIKDLSQMTSITQNDIISTLQ

SLNMVKYWKGQHVICVTPKLVEEHLKSAQYKKPPITVDSVCLKWAP*

Protein Expression:

To produce recombinant KAT8 protein, expression plasmid was transformed into E. coli BL21 DE3 strain and grown with shaking at 37° C. in 1 L volumes of Terrific broth (TB) supplemented with 100 μg/mL Ampicillin until an OD600 of 0.8 was reached. Cultures were transferred to 18° C. and protein expression induced by the addition of Isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −20° C.

Protein Purification:

Protein purification was initiated by thawing the cell pellet (34 g wet weight) in Lysis buffer (20 mM Hepes pH 7.5, 500 mM NaCl, 5 mM Imidazole, 5% [v/v]glycerol, 0.01% [v/v] Triton-X 100, 5 mM 2-mercaptoethanol, 2 mM $MgCl_2$, 0.5 mg/mL lysozyme, benzonase endonuclease [EMD Millipore], 1 mM PMSF, complete protease inhibitor tablets EDTA-free [Roche]) using a ratio of 3 mL of buffer per 1 g of cells. Cells were further lysed by 3 passes (at 15000 psi) through an ice cooled Avestin C5 cell crusher and then centrifuged at 48,000×g at 4° C. Supernatant (cell lysate) was filtered through a 0.2 μm filter and applied onto 5 mL HiTrap IMAC Sepharose FF column (GE Healthcare) pre-equilibrated with IMAC wash buffer 1 (20 mM Hepes pH 7.5, 500 mM NaCl, 0.5 mM TCEP, 5 mM Imidazole) using a Profinia Affinity chromatography purification system (Bio-Rad). The IMAC column was then sequentially washed with IMAC Wash buffer 1 and IMAC Wash buffer 2 (20 mM Hepes pH 7.5, 500 mM NaCl, 0.5 mM TCEP, 10 mM Imidazole) and bound KAT8 protein eluted with IMAC Elution buffer (20 mM Hepes pH 7.5, 500 mM NaCl, 0.5 mM TCEP, 500 mM Imidazole). IMAC-eluted protein was further purified by passing through a HiLoad 26/60 Superdex 200 column pre-equilibrated in Storage buffer (20 mM Hepes pH 7.5, 500 mM NaCl, 1 mM TCEP). Finally, KAT8 protein was concentrated to 0.2 mg/mL using Amicon Ultra centrifugal filter unit (Utra-15 MWCO 10 kDa), flash-frozen in liquid nitrogen and stored in −70° C. freezer.

Acetyltransferase Biochemical Assay

To determine the inhibition of KAT enzymatic activity by test compounds, assay reactions were conducted in a volume of 8 μL in 384-well low volume assay plates. The reactions were performed in assay buffer (100 mM Tris-HCl, pH 7.8, 15 mM NaCl, 1 mM EDTA, 0.01% Tween-20, 1 mM Dithiothreitol, and 0.01% m/v chicken egg white albumin). Reactions were set up with 1 μM Acetyl coenzyme A, 100 nM of full-length recombinant histone labelled by limited biotinylation (KAT6A, KAT6B, KAT7: H3.1, KAT5, KAT8: H4), 10/5/8/40/20 nM of KAT5/KAT6A/KAT6B/KAT7/KAT8 enzyme respectively, and an acetyl-lysine specific antibody (H3.1: Cell Signaling Technology, H4: Abcam). 11-point dilution series of the test compounds were prepared in DMSO; a volume of 100 nL was transferred using a pin tool into assay plates containing substrates, before adding enzyme to start the reaction. Positive (no compound, DMSO only) and negative (AcCoA omitted) control reactions were included on the same plates and received the same amount of DMSO as the compound treated wells. After adding all reagents, the plates were sealed with adhesive seals and incubated for 90 min at room temperature. An additional 4 μL of assay buffer containing AlphaScreen® Protein A acceptor beads and Streptavidin donor beads (PerkinElmer, Waltham, Mass.) to a final concentration of 8 μg/mL was then added. After incubation for 2 hours the plates were read using an EnVision 2103 multi label plate reader (PerkinElmer) in HTS AlphaScreen® mode. $IC_{50}$ values were obtained from the raw readings by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, E is the upper asymptote, C is the $IC_{50}$ value, and D is the slope.

The results are shown in tables 1 to 5 below:

TABLE 1

(TIP60-KAT5)

| Example | IC50 (μM) |
|---|---|
| 1 | >125.000 |
| 2 | >125.000 |
| 3 | =65.106 |
| 4 | =35.221 |
| 5 | =114.325 |
| 6 | =94.934 |
| 7 | >125.000 |
| 8 | >125.000 |
| 9 | =40.976 |
| 10 | =93.664 |
| 11 | >125.000 |
| 12 | >125.000 |
| 13 | =119.896 |
| 14 | >125.000 |
| 15 | =7.294 |
| 16 | =30.179 |
| 17 | =27.659 |
| 18 | =118.055 |
| 19 | =64.983 |
| 20 | =81.458 |
| 21 | >125.000 |
| 22 | =38.877 |
| 23 | =72.865 |
| 24 | >125.000 |
| 25 | =120.445 |
| 26 | >125.000 |
| 27 | >125.000 |
| 28 | >125.000 |
| 29 | >125.000 |
| 30 | >125.000 |
| 31 | >125.000 |
| 32 | =56.003 |
| 33 | =90.452 |
| 34 | >125.000 |
| 35 | =33.836 |
| 36 | =38.979 |
| 37 | >125.000 |
| 38 | =80.086 |
| 39 | >125.000 |
| 40 | =121.024 |

TABLE 1-continued

| (TIP60-KAT5) | |
|---|---|
| Example | IC50 (μM) |
| 41 | =65.079 |
| 42 | =11.568 |
| 43 | =23.002 |
| 44 | =60.208 |
| 45 | =34.341 |
| 46 | >125.000 |
| 47 | =123.081 |
| 48 | =92.895 |
| 49 | =74.577 |
| 50 | >125.000 |
| 51 | =87.660 |
| 52 | >125.000 |
| 53 | >125.000 |
| 54 | >125.000 |
| 55 | >125.000 |
| 56 | >125.000 |
| 57 | >125.000 |
| 58 | >125.000 |
| 59 | >125.000 |
| 60 | >125.000 |
| 61 | =85.401 |
| 62 | >125.000 |
| 63 | >125.000 |
| 64 | >125.000 |
| 65 | >125.000 |
| 66 | =123.371 |
| 67 | =114.876 |
| 68 | >125.000 |
| 69 | =124.236 |
| 70 | =36.766 |
| 71 | =28.431 |
| 72 | >125.000 |
| 73 | =2.161 |
| 74 | =8.132 |
| 75 | =33.535 |
| 76 | =2.578 |
| 77 | =51.770 |
| 78 | >125.000 |
| 79 | =17.451 |
| 80 | =10.913 |
| 81 | =31.488 |
| 82 | =8.247 |
| 83 | =17.898 |
| 84 | =50.464 |
| 85 | =28.466 |
| 86 | =97.635 |
| 88 | >125.000 |
| 89 | =5.785 |
| 90 | =90.684 |
| 91 | =2.183 |
| 92 | =1.387 |
| 93 | =53.063 |
| 94 | =124.242 |
| 95 | =13.967 |
| 96 | =28.640 |
| 97 | =6.181 |
| 98 | =31.286 |
| 99 | =9.699 |
| 100 | =51.711 |
| 101 | =98.204 |
| 102 | =9.330 |
| 103 | =69.326 |
| 104 | =28.112 |
| 105 | >125.000 |
| 106 | =14.254 |
| 107 | =74.084 |
| 108 | =41.946 |
| 109 | =69.262 |
| 110 | >125.000 |
| 111 | =26.608 |
| 112 | =16.494 |
| 113 | =4.836 |
| 114 | =59.355 |
| 115 | =23.660 |
| 116 | =10.463 |
| 117 | >125.000 |
| 118 | =37.082 |
| 119 | =8.726 |
| 120 | =5.781 |
| 121 | =29.010 |
| 122 | =58.591 |
| 123 | =59.355 |
| 124 | =27.879 |
| 125 | >125.000 |
| 126 | =51.346 |
| 127 | =49.699 |
| 128 | =6.301 |
| 129 | =18.536 |
| 130 | >125.000 |
| 131 | =69.740 |
| 132 | =53.030 |
| 133 | =45.717 |
| 134 | =51.523 |
| 135 | =4.788 |
| 136 | >125.000 |
| 137 | =14.209 |
| 138 | =5.115 |
| 139 | =34.292 |
| 140 | =47.841 |
| 141 | >125.000 |
| 142 | =32.183 |
| 143 | >125.000 |
| 144 | =11.487 |
| 145 | =20.967 |
| 146 | =21.951 |
| 147 | >125.000 |
| 148 | >125.000 |
| 149 | >125.000 |
| 150 | =50.012 |
| 151 | >125.000 |
| 152 | =38.945 |
| 153 | =4.055 |
| 154 | =25.313 |
| 155 | =0.672 |
| 156 | >125.000 |
| 157 | >125.000 |
| 158 | >125.000 |
| 159 | >125.000 |
| 160 | =46.217 |
| 161 | >125.000 |
| 162 | =13.954 |
| 163 | >125.000 |
| 164 | >125.000 |
| 165 | >125.000 |
| 166 | =3.093 |
| 167 | =32.157 |
| 168 | =3.415 |
| 169 | =63.197 |
| 170 | =4.826 |
| 171 | =4.374 |
| 172 | =9.070 |
| 173 | =4.050 |
| 174 | =1.833 |
| 175 | =43.215 |
| 176 | =5.670 |
| 177 | =7.082 |
| 178 | =7.535 |
| 179 | =32.129 |
| 180 | =25.476 |
| 181 | =23.827 |
| 182 | =65.635 |
| 183 | =33.231 |
| 184 | >125.000 |
| 185 | >125.000 |
| 186 | =84.702 |
| 187 | =65.279 |
| 188 | =69.912 |
| 189 | =31.983 |
| 190 | =19.884 |
| 191 | =68.651 |
| 192 | =29.888 |
| 193 | =53.125 |

TABLE 1-continued

(TIP60-KAT5)

| Example | IC50 (μM) |
|---|---|
| 194 | =37.844 |
| 195 | =16.708 |
| 196 | =95.399 |
| 197 | >125.000 |
| 198 | =73.654 |
| 199 | =14.892 |
| 200 | =4.733 |
| 201 | =21.848 |
| 202 | =110.730 |
| 203 | =74.251 |
| 204 | =4.565 |
| 205 | =3.729 |
| 206 | =6.361 |
| 207 | =4.605 |
| 208 | =28.461 |
| 209 | =28.674 |
| 210 | >125.000 |
| 211 | =7.931 |
| 212 | =9.302 |
| 213 | >125.000 |
| 214 | >125.000 |
| 215 | >125.000 |
| 216 | =123.671 |
| 217 | >125.000 |
| 218 | >125.000 |
| 219 | >125.000 |
| 220 | >125.000 |
| 221 | >125.000 |
| 222 | =26.758 |
| 223 | >125.000 |
| 224 | >125.000 |
| 225 | >125.000 |
| 226 | =80.348 |
| 227 | >125.000 |
| 228 | =124.363 |
| 229 | >125.000 |
| 230 | >125.000 |
| 231 | >125.000 |
| 232 | >125.000 |
| 233 | >125.000 |
| 234 | =10.877 |
| 235 | =9.044 |
| 236 | =10.055 |
| 237 | >125.000 |
| 238 | >125.000 |
| 239 | =17.373 |
| 240 | =122.168 |
| 241 | =26.350 |
| 242 | =27.314 |
| 243 | =18.076 |
| 244 | =30.172 |
| 245 | =57.554 |
| 246 | =27.066 |
| 247 | =96.592 |
| 248 | =9.331 |
| 249 | =69.187 |
| 250 | =12.220 |
| 251 | =46.983 |
| 252 | =101.708 |

TABLE 2

(MOZ-KAT6A)

| Example | IC50 (μM) |
|---|---|
| 1 | =91.387 |
| 2 | =94.607 |
| 3 | =23.759 |
| 4 | =6.223 |
| 5 | =31.283 |
| 6 | =30.156 |
| 7 | =62.687 |

TABLE 2-continued

(MOZ-KAT6A)

| Example | IC50 (μM) |
|---|---|
| 8 | =113.061 |
| 9 | =26.816 |
| 10 | =17.503 |
| 11 | >125.000 |
| 12 | >125.000 |
| 13 | =63.854 |
| 14 | =45.004 |
| 15 | =1.907 |
| 16 | =15.105 |
| 17 | =11.820 |
| 18 | =74.876 |
| 19 | =32.241 |
| 20 | =29.373 |
| 21 | =24.799 |
| 22 | =5.206 |
| 23 | =21.776 |
| 24 | >125.000 |
| 25 | =33.179 |
| 26 | =60.096 |
| 27 | =71.527 |
| 28 | =117.346 |
| 29 | >125.000 |
| 30 | =89.484 |
| 31 | =36.075 |
| 32 | =31.124 |
| 33 | =6.847 |
| 34 | >125.000 |
| 35 | =4.632 |
| 36 | =17.653 |
| 37 | =24.848 |
| 38 | =27.525 |
| 39 | =38.220 |
| 40 | =2.128 |
| 41 | =4.274 |
| 42 | =5.947 |
| 43 | =5.971 |
| 44 | =10.569 |
| 45 | =2.085 |
| 46 | =36.202 |
| 47 | =12.863 |
| 48 | =7.410 |
| 49 | =8.133 |
| 50 | =123.076 |
| 51 | =15.032 |
| 52 | =85.314 |
| 53 | =90.683 |
| 54 | =63.015 |
| 55 | =103.246 |
| 56 | =72.793 |
| 57 | =56.212 |
| 58 | =28.364 |
| 59 | =49.410 |
| 60 | =116.146 |
| 61 | =51.918 |
| 62 | =43.709 |
| 63 | =2.558 |
| 64 | =26.746 |
| 65 | =27.934 |
| 66 | =14.554 |
| 67 | =22.711 |
| 68 | =85.089 |
| 69 | =42.890 |
| 70 | =31.339 |
| 71 | =11.578 |
| 72 | =46.210 |
| 73 | =4.547 |
| 74 | =3.914 |
| 75 | =23.533 |
| 76 | =0.688 |
| 77 | =10.814 |
| 78 | =93.778 |
| 79 | =13.890 |
| 80 | =3.473 |
| 81 | =43.616 |
| 82 | =6.128 |
| 83 | =13.571 |

TABLE 2-continued (MOZ-KAT6A)

| Example | IC50 (μM) |
|---|---|
| 84 | =18.678 |
| 85 | =3.866 |
| 86 | =5.890 |
| 88 | =41.205 |
| 89 | =0.285 |
| 90 | =4.779 |
| 91 | =0.009 |
| 92 | =0.006 |
| 93 | =0.181 |
| 94 | =6.105 |
| 95 | =0.430 |
| 96 | =1.203 |
| 97 | =0.061 |
| 98 | =5.602 |
| 99 | =2.099 |
| 100 | =0.972 |
| 101 | =3.798 |
| 102 | =0.143 |
| 103 | =0.810 |
| 104 | =0.786 |
| 105 | =2.903 |
| 106 | =0.782 |
| 107 | =14.870 |
| 108 | =3.089 |
| 109 | =1.207 |
| 110 | =7.890 |
| 111 | =0.842 |
| 112 | =1.463 |
| 113 | =0.775 |
| 114 | =29.278 |
| 115 | =28.986 |
| 116 | =0.560 |
| 117 | =85.409 |
| 118 | =10.003 |
| 119 | =0.570 |
| 120 | =0.310 |
| 121 | =1.236 |
| 122 | =24.400 |
| 123 | =26.864 |
| 124 | =11.011 |
| 125 | =24.458 |
| 126 | =10.472 |
| 127 | =9.165 |
| 128 | =0.250 |
| 129 | =0.772 |
| 130 | =2.956 |
| 131 | =3.106 |
| 132 | =7.454 |
| 133 | =4.449 |
| 134 | =6.449 |
| 135 | =0.563 |
| 136 | =34.274 |
| 137 | =8.579 |
| 138 | =2.892 |
| 139 | =2.144 |
| 140 | =2.256 |
| 141 | =39.557 |
| 142 | =3.296 |
| 143 | =32.391 |
| 144 | =0.261 |
| 145 | =0.127 |
| 146 | =0.153 |
| 147 | =93.597 |
| 148 | =23.965 |
| 149 | =5.272 |
| 150 | =4.966 |
| 151 | =27.867 |
| 152 | =6.276 |
| 153 | =0.437 |
| 154 | =0.516 |
| 155 | =2.116 |
| 156 | =1.535 |
| 157 | =23.036 |
| 158 | =62.560 |
| 159 | =66.556 |
| 160 | =1.048 |
| 161 | =1.871 |
| 162 | =0.147 |
| 163 | =0.884 |
| 164 | =27.173 |
| 165 | =99.899 |
| 166 | =0.123 |
| 167 | =8.666 |
| 168 | =10.006 |
| 169 | =24.793 |
| 170 | =1.504 |
| 171 | =1.876 |
| 172 | =0.037 |
| 173 | =0.015 |
| 174 | =0.013 |
| 175 | =0.441 |
| 176 | =0.030 |
| 177 | =0.127 |
| 178 | =1.440 |
| 179 | =2.864 |
| 180 | =9.437 |
| 181 | =1.058 |
| 182 | =15.217 |
| 183 | =5.601 |
| 184 | >125.000 |
| 185 | =104.789 |
| 186 | =25.161 |
| 187 | =5.664 |
| 188 | =9.228 |
| 189 | =4.347 |
| 190 | =9.733 |
| 191 | =12.582 |
| 192 | =9.394 |
| 193 | =1.950 |
| 194 | =1.507 |
| 195 | =1.322 |
| 196 | =13.919 |
| 197 | =20.970 |
| 198 | =2.818 |
| 199 | =0.709 |
| 200 | =0.364 |
| 201 | =1.482 |
| 202 | =18.907 |
| 203 | =22.648 |
| 204 | =0.400 |
| 205 | =0.115 |
| 206 | =0.302 |
| 207 | =0.104 |
| 208 | =1.629 |
| 209 | =2.029 |
| 210 | =8.532 |
| 211 | =2.128 |
| 212 | =2.117 |
| 213 | =8.280 |
| 214 | =36.431 |
| 215 | =4.469 |
| 216 | =0.625 |
| 217 | =10.237 |
| 218 | =6.594 |
| 219 | =33.313 |
| 220 | =3.497 |
| 221 | =37.464 |
| 222 | =0.655 |
| 223 | =25.496 |
| 224 | =50.368 |
| 225 | =3.625 |
| 226 | =10.774 |
| 227 | =41.520 |
| 228 | =75.246 |
| 229 | =85.020 |
| 230 | =48.075 |
| 231 | =58.983 |
| 232 | =46.464 |
| 233 | =9.950 |
| 234 | =0.381 |
| 235 | =0.395 |
| 236 | =0.318 |

TABLE 2-continued

(MOZ-KAT6A)

| Example | IC50 (μM) |
|---|---|
| 237 | =4.950 |
| 238 | =12.039 |
| 239 | =2.132 |
| 240 | =1.828 |
| 241 | =0.157 |
| 242 | =3.232 |
| 243 | =0.654 |
| 244 | =2.126 |
| 245 | =3.901 |
| 246 | =0.676 |
| 247 | =3.476 |
| 248 | =0.139 |
| 249 | =1.271 |
| 250 | =0.423 |
| 251 | =1.156 |
| 252 | =4.160 |

TABLE 3

(HBO-KAT7)

| Example | IC50 (μM) |
|---|---|
| 1 | =53.948 |
| 2 | =15.521 |
| 3 | =23.243 |
| 4 | =5.168 |
| 5 | =6.011 |
| 6 | =6.277 |
| 7 | =14.175 |
| 8 | >125.000 |
| 9 | =8.418 |
| 10 | =54.053 |
| 11 | =60.488 |
| 12 | =49.922 |
| 13 | =63.834 |
| 14 | =15.174 |
| 15 | =1.456 |
| 16 | =9.635 |
| 17 | =14.575 |
| 18 | =34.064 |
| 19 | =36.094 |
| 20 | =41.258 |
| 21 | =25.506 |
| 22 | =6.300 |
| 23 | =23.893 |
| 24 | =33.854 |
| 25 | =41.948 |
| 26 | =34.465 |
| 27 | =32.121 |
| 28 | =54.786 |
| 29 | =94.098 |
| 30 | =11.481 |
| 31 | =53.590 |
| 32 | =14.923 |
| 33 | =11.409 |
| 34 | =31.493 |
| 35 | =8.748 |
| 36 | =26.267 |
| 37 | =114.461 |
| 38 | =6.698 |
| 39 | =10.116 |
| 40 | =19.929 |
| 41 | =11.845 |
| 42 | =8.384 |
| 43 | =12.914 |
| 44 | =10.794 |
| 45 | =6.833 |
| 46 | =74.439 |
| 47 | =29.419 |
| 48 | =54.767 |
| 49 | =77.831 |
| 50 | >125.000 |

TABLE 3-continued

(HBO-KAT7)

| Example | IC50 (μM) |
|---|---|
| 51 | =28.277 |
| 52 | >125.000 |
| 53 | >125.000 |
| 54 | >125.000 |
| 55 | >125.000 |
| 56 | >125.000 |
| 57 | >125.000 |
| 58 | =16.607 |
| 59 | >125.000 |
| 60 | >125.000 |
| 61 | >125.000 |
| 62 | =70.618 |
| 63 | =60.060 |
| 64 | =105.707 |
| 65 | =59.720 |
| 66 | =113.991 |
| 67 | >125.000 |
| 68 | >125.000 |
| 69 | =94.149 |
| 70 | =32.029 |
| 71 | =21.593 |
| 72 | =11.413 |
| 73 | =0.508 |
| 74 | =1.665 |
| 75 | =5.748 |
| 76 | =0.937 |
| 77 | =12.022 |
| 78 | >125.000 |
| 79 | =4.059 |
| 80 | =1.129 |
| 81 | =6.726 |
| 82 | =1.496 |
| 83 | =3.792 |
| 84 | =20.038 |
| 85 | =1.769 |
| 86 | =1.981 |
| 88 | =7.509 |
| 89 | =0.168 |
| 90 | =18.889 |
| 91 | =0.079 |
| 92 | =0.060 |
| 93 | =2.799 |
| 94 | =16.059 |
| 95 | =0.754 |
| 96 | =4.265 |
| 97 | =0.444 |
| 98 | =3.411 |
| 99 | =5.739 |
| 100 | =2.240 |
| 101 | =32.782 |
| 102 | =0.568 |
| 103 | =5.928 |
| 104 | =3.132 |
| 105 | =63.160 |
| 106 | =3.977 |
| 107 | =11.732 |
| 108 | =2.038 |
| 109 | =4.067 |
| 110 | =17.497 |
| 111 | =4.536 |
| 112 | =3.014 |
| 113 | =0.914 |
| 114 | =41.609 |
| 115 | =95.520 |
| 116 | =1.435 |
| 117 | >125.000 |
| 118 | =0.852 |
| 119 | =1.146 |
| 120 | =0.503 |
| 121 | =5.211 |
| 122 | =4.122 |
| 123 | =4.198 |
| 124 | =13.017 |
| 125 | =85.834 |
| 126 | =28.884 |
| 127 | =9.487 |

TABLE 3-continued

(HBO-KAT7)

| Example | IC50 (μM) |
|---|---|
| 128 | =0.618 |
| 129 | =1.318 |
| 130 | =21.712 |
| 131 | =23.780 |
| 132 | =11.785 |
| 133 | =5.342 |
| 134 | =27.644 |
| 135 | =1.426 |
| 136 | =28.316 |
| 137 | =6.558 |
| 138 | =3.683 |
| 139 | =10.043 |
| 140 | =9.895 |
| 141 | =24.336 |
| 142 | =1.165 |
| 143 | =7.883 |
| 144 | =0.286 |
| 145 | =0.259 |
| 146 | =0.511 |
| 147 | >125.000 |
| 148 | =36.783 |
| 149 | =9.432 |
| 150 | =8.039 |
| 151 | =25.571 |
| 152 | =9.866 |
| 153 | =0.507 |
| 154 | =3.128 |
| 155 | =0.248 |
| 156 | =1.975 |
| 157 | =15.514 |
| 158 | =44.862 |
| 159 | =37.620 |
| 160 | =1.577 |
| 161 | =2.506 |
| 162 | =0.969 |
| 163 | =13.103 |
| 164 | =61.638 |
| 165 | =30.654 |
| 166 | =0.328 |
| 167 | =6.854 |
| 168 | =36.401 |
| 169 | =8.646 |
| 170 | =0.982 |
| 171 | =0.292 |
| 172 | =0.426 |
| 173 | =0.169 |
| 174 | =0.031 |
| 175 | =5.949 |
| 176 | =0.138 |
| 177 | =0.021 |
| 178 | =0.482 |
| 179 | =13.481 |
| 180 | =1.759 |
| 181 | =5.137 |
| 182 | =15.608 |
| 183 | =4.480 |
| 184 | =30.983 |
| 185 | =60.714 |
| 186 | =47.092 |
| 187 | =21.961 |
| 188 | =40.080 |
| 189 | =8.016 |
| 190 | =18.459 |
| 191 | =1.576 |
| 192 | =24.230 |
| 193 | =15.518 |
| 194 | =6.872 |
| 195 | =4.963 |
| 196 | =23.280 |
| 197 | =45.687 |
| 198 | =6.951 |
| 199 | =0.632 |
| 200 | =0.678 |
| 201 | =0.773 |
| 202 | =54.375 |
| 203 | =23.360 |
| 204 | =3.045 |
| 205 | =0.936 |
| 206 | =0.626 |
| 207 | =0.257 |
| 208 | =4.654 |
| 209 | =1.054 |
| 210 | =6.539 |
| 211 | =0.917 |
| 212 | =1.048 |
| 213 | =20.519 |
| 214 | >125.000 |
| 215 | =16.630 |
| 216 | =3.106 |
| 217 | =18.406 |
| 218 | =6.444 |
| 219 | =60.688 |
| 220 | =11.008 |
| 221 | =63.721 |
| 222 | =1.422 |
| 223 | =43.526 |
| 224 | >125.000 |
| 225 | =31.135 |
| 226 | =37.985 |
| 227 | =63.139 |
| 228 | >125.000 |
| 229 | =115.218 |
| 230 | =109.417 |
| 231 | >125.000 |
| 232 | >125.000 |
| 233 | =17.872 |
| 234 | =3.739 |
| 235 | =0.820 |
| 236 | =1.070 |
| 237 | =18.016 |
| 238 | =94.180 |
| 239 | =3.003 |
| 240 | =10.198 |
| 241 | =2.510 |
| 242 | =1.785 |
| 243 | =0.720 |
| 244 | =1.113 |
| 245 | =2.761 |
| 246 | =0.478 |
| 247 | =5.897 |
| 248 | =0.375 |
| 249 | =0.889 |
| 250 | =0.050 |
| 251 | =0.473 |
| 252 | =1.303 |

TABLE 4

(MOF-KAT8)

| Example | IC50 (μM) |
|---|---|
| 11 | =35.565 |
| 18 | =63.474 |
| 19 | =40.985 |
| 20 | =61.440 |
| 21 | =39.655 |
| 26 | =29.480 |
| 73 | =3.459 |
| 81 | =9.425 |
| 93 | =96.545 |
| 94 | =60.943 |
| 95 | =6.447 |
| 96 | =53.767 |
| 100 | =62.604 |
| 102 | =11.485 |
| 107 | =42.081 |
| 109 | =9.122 |
| 111 | =3.221 |

TABLE 4-continued (MOF-KAT8)

| Example | IC50 (μM) |
|---|---|
| 132 | =15.285 |
| 151 | =34.717 |
| 154 | =2.570 |
| 161 | =117.753 |
| 162 | =10.649 |
| 163 | >125.000 |
| 164 | >125.000 |
| 165 | >125.000 |
| 166 | =2.920 |
| 168 | =6.458 |
| 170 | =9.666 |
| 173 | =3.522 |
| 178 | =0.770 |
| 204 | =3.063 |
| 205 | =3.441 |
| 211 | =29.532 |
| 214 | >125.000 |
| 216 | =11.172 |
| 219 | =69.922 |
| 221 | =27.895 |
| 223 | =42.389 |
| 224 | =112.662 |
| 236 | =3.682 |

TABLE 5

(QKF-KAT6B)

| Example | IC50 (μM) |
|---|---|
| 73 | =4.047 |
| 91 | =0.037 |
| 92 | =0.053 |
| 95 | =1.640 |
| 96 | =3.395 |
| 97 | =0.049 |
| 102 | =0.282 |
| 116 | =1.616 |
| 143 | =50.697 |
| 144 | =0.057 |
| 146 | =0.291 |
| 147 | >125.000 |
| 162 | =0.180 |
| 166 | =0.227 |
| 172 | =0.042 |
| 173 | =0.040 |
| 174 | =0.018 |
| 175 | =0.821 |
| 176 | =0.121 |
| 177 | =0.092 |
| 178 | =2.455 |
| 207 | =1.454 |

Histone H3 Lysine 23 Acetylation Biomarker Assay

Compounds were tested for their ability to inhibit acetylation of the histone H3K23 marker in the following assay:

The cell line U2OS was seeded at a density of 9,000 cells per well in 96 well optical quality tissue culture plates in RPMI medium and 10% foetal bovine serum, and allowed to adhere for 24 hours under standard culture conditions (37 degree Celsius, 5% CO2). At the end of this period the medium was aspirated. Compound dilutions prepared in DMSO were added to medium, with negative control wells reserved for treatment with DMSO only and 100% inhibition positive controls receiving a potent inhibitor compound (e.g. cas 2055397-28-7, benzoic acid, 3-fluoro-5-(2-pyridinyl)-, 2-[(2-fluorophenyl)sulfonyl]hydrazide) (Baell, J., Nguyen, H. N., Leaver, D. J., Cleary, B. L., Lagiakos, H. R., Sheikh, B. N., Thomas. T. J., Aryl sulfonohydrazides, WO2016198507A1, 2016) at 10 μM concentration and 200 μL transferred to the cells. After incubation for 24 hours, the cells were fixed with 3.7% formaldehyde in PBS for 20 minutes at room temperature, washed (5×5 minutes) with phosphate buffer saline containing 0.1% Tween 20 and blocked with Odyssey blocking buffer (LI-COR, Lincoln, Nebr.) containing 0.1% TritonX100. Anti-H3K23ac specific antibody (Abcam ab177275) in Odyssey blocking buffer containing 0.1% Tween 20 was added and incubated for 16 hours at 4 degree Celsius. After washing (as above), a secondary antibody labelled with Alexa647 dye (LifeTechnologies) and Hoechst 33342 (1 μg/mL, SigmaAldrich) were added for 1 hour incubation. Plates were washed as previously and read on a PerkinElmer Phenix high content imaging platform. Using a Columbus image analysis pipeline, individual nuclei were located by Hoechst 33342 stain and the acetylation level was calculated from the Alexa647-related intensity in the same area. The resulting mean intensity per cell was directly converted to percent inhibition relative to controls on the same plate and the data fitted against a four-parameter logistic model to determine the 50% inhibitory concentration (IC50).

The results are shown in table 6 below:

TABLE 6

| Example | IC50 (μM) |
|---|---|
| 73 | >10.000 |
| 86 | =1.579 |
| 91 | =0.182 |
| 92 | =0.013 |
| 95 | >10.000 |
| 96 | >10.000 |
| 97 | =0.045 |
| 116 | =3.455 |
| 144 | =0.128 |
| 145 | =0.098 |
| 146 | =0.045 |
| 147 | >10.000 |
| 155 | >10.000 |
| 162 | =0.144 |
| 166 | =0.398 |
| 172 | =0.014 |
| 173 | =0.020 |
| 174 | =0.017 |
| 176 | =0.685 |
| 177 | =1.486 |
| 178 | >10.000 |
| 191 | >10.000 |
| 242 | =0.672 |
| 250 | =3.713 |

Histone H3 Lysine 14 Acetylation Biomarker Assay

Compounds were tested for their ability to inhibit acetylation of the histone H3 Lysine 14 marker in the following assay:

The cell line U2OS was seeded at a density of 3,000 cells per well in 384-well optical quality tissue culture plates in RPMI medium supplemented with 10% foetal bovine serum and 10 mM Hepes. The cells were allowed to adhere for 24 hours under standard culture conditions (37 degree Celsius, 5% CO2). At the end of this period the cells were washed with serum free medium. Compound dilutions prepared in DMSO were added to the serum free medium, with negative control wells reserved for treatment with DMSO only and 100% inhibition positive controls receiving a potent inhibitor compound (e.g. (Z)-4-fluoro-N-((3-hydroxyphenyl)sulfonyl)-5-methyl-[1,1ᴇ biphenyl]-3-carbohydrazonic acid) at 10 μM concentration. After incubation for 24 hours, the cells were fixed with 4% formaldehyde in PBS for 15 minutes at room temperature, washed with phosphate buffer saline and blocked with blocking buffer containing 0.2%

TritonX100 and 2% BSA. Anti-H3K14ac specific antibody (Cell Signalling Technologies) in blocking buffer was added and incubated overnight at 4 degree Celsius. After washing, a secondary antibody labelled with AlexaFluor 488 dye (ThermoFisher) and Hoechst 33342 (1 µg/mL, Life Technologies) were added for 2 hours incubation at room temperature. Plates were washed and read on a PerkinElmer Opera HCS high content imaging platform. Using a Columbus image analysis pipeline, individual nuclei were located by Hoechst 33342 stain and the acetylation level was calculated from the AlexaFluor 488-related intensity in the same area. The resulting mean intensity per cell was converted to percent inhibition relative to controls on the same plate and the data fitted against a four-parameter logistic model to determine the 50% inhibitory concentration (IC50).

The results are shown in table 7 below:

TABLE 7

| Example | IC50 (µM) |
| --- | --- |
| 73 | =12.451 |
| 74 | =31.675 |
| 75 | >40.000 |
| 80 | =11.511 |
| 82 | =12.600 |
| 89 | =3.957 |
| 91 | =0.874 |
| 92 | =0.703 |
| 95 | =9.089 |
| 97 | =1.093 |
| 102 | =3.686 |
| 144 | =2.954 |
| 145 | =3.383 |
| 146 | =2.304 |
| 147 | >40.000 |
| 155 | =26.130 |
| 162 | =1.527 |
| 163 | =20.356 |
| 166 | =3.686 |
| 171 | =2.574 |
| 172 | =1.453 |
| 173 | =0.533 |
| 174 | =0.068 |
| 176 | =1.071 |
| 177 | =0.135 |
| 178 | =3.068 |
| 191 | =17.835 |
| 211 | >40.000 |
| 212 | =10.347 |
| 218 | >40.000 |
| 236 | >40.000 |
| 250 | =3.482 |
| 252 | =24.719 |

H2A.Z Lysine 7 Acetylation Biomarker Assay

Compounds were tested for their ability to inhibit the histone H2A.Z Lysine 7 acetylation marker in the following assay:

The cell line U2OS was seeded at a density of 3,000 cells per well in 384-well optical quality tissue culture plates in RPMI medium supplemented with 10% foetal bovine serum and 10 mM Hepes. The cells were allowed to adhere for 24 hours under standard culture conditions (37 degree Celsius, 5% $CO_2$). At the end of this period the cells were washed with serum free medium. Compound dilutions prepared in DMSO were added to the serum free medium, with negative control wells reserved for treatment with DMSO only and 100% inhibition positive controls receiving a potent inhibitor compound enantiomer 1 of 7-iodo-N-(2-(oxazol-2-yl)-2-phenylethyl)-2H-benzo[e][1,2,4]thiadiazine-3-carboxamide 1,1-dioxide, which is compound 146 of co-pending application GB1713962.7, filed on 31 Aug. 2018, at 30 µM concentration. After incubation for 24 hours, the cells were fixed with 4% formaldehyde in PBS for 15 minutes at room temperature, washed with phosphate buffer saline and blocked with blocking buffer containing 0.2% TritonX100 and 2% BSA. Anti-H2A.ZK7ac specific antibody (Abcam) in blocking buffer was added and incubated overnight at 4 degree Celsius. After washing, a secondary antibody labelled with AlexaFluor 488 dye (ThermoFisher) and Hoechst 33342 (1 µg/mL, Life Technologies) were added for 2 hours incubation at room temperature. Plates were washed and read on a PerkinElmer Opera HCS high content imaging platform. Using a Columbus image analysis pipeline, individual nuclei were located by Hoechst 33342 stain and the acetylation level was calculated from the AlexaFluor 488-related intensity in the same area. The resulting mean intensity per cell was converted to percent inhibition relative to controls on the same plate and the data fitted against a four-parameter logistic model to determine the 50% inhibitory concentration ($IC_{50}$).

The results are shown in table 8 below:

TABLE 8

| Example | IC50 (µM) |
| --- | --- |
| 73 | =36.725 |
| 89 | =19.816 |
| 91 | =8.022 |
| 92 | =4.619 |
| 95 | >40.000 |
| 97 | =27.988 |
| 102 | >40.000 |
| 144 | =18.752 |
| 145 | >40.000 |
| 146 | =15.065 |
| 147 | >40.000 |
| 155 | >40.000 |
| 162 | =29.540 |
| 166 | =33.304 |
| 168 | >40.000 |
| 172 | =29.159 |
| 173 | =26.225 |
| 174 | =1.544 |
| 176 | =7.612 |
| 177 | =1.088 |
| 178 | =5.589 |
| 191 | >40.000 |
| 234 | >40.000 |
| 236 | >40.000 |
| 250 | =13.197 |
| 252 | >40.000 |

STATEMENTS OF INVENTION

1. A compound of formula (I), or a pharmaceutically acceptable salt thereof, for use in a method of therapy:

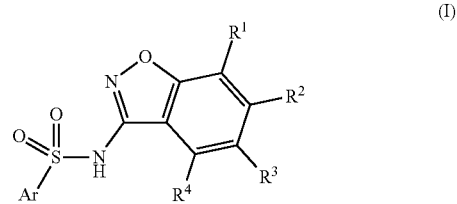

(I)

wherein $R^1$, $R^2$, $R^3$ and $R^4$ are independently selected from:
  (i) H;
  (ii) $C_{1-3}$ alkyl, optionally substituted by:
    hydroxy,
    $C_{1-2}$ alkoxy, optionally substituted by one or more fluoro groups,
    $NH_2$,
    phenyl,
    $C_{5-6}$ heteroaryl,
    $C_{1-4}$ alkyl carbamoyl,
    acylamido, or
    one or more fluoro groups;
  (iii) $C_{1-3}$ alkoxy, optionally substituted by $C_{3-6}$ cycloalkyl or by one or more fluoro groups;
  (iv) $C_{3-6}$ cycloalkyl;
  (v) halo;
  (vi) $COR^C$, where $R^C$ is selected from $NR^{N1}R^{N2}$, where $R^{N1}$ and $R^{N2}$ are independently selected from H and methyl;
  (vii) cyano, $NH_2$, or $NO_2$; and
  (viii) phenyl or $C_{5-6}$ heteroaryl, optionally substituted by methyl, cyano, hydroxy or methoxy;
Ar is a phenyl, napthyl or $C_{5-10}$ heteroaryl group, which groups are optionally substituted by one or more groups selected from:
  (i) $C_{1-4}$ alkyl, optionally substituted by hydroxy, $C_{1-2}$ alkoxy, $NH_2$, $C_{1-4}$alkyl carbamoyl, or by one or more fluoro groups;
  (ii) $C_{3-6}$ cycloalkyl;
  (iii) hydroxy; cyano; $NR^{N3}R^{N4}$, where $R^{N3}$ and $R^{N4}$ are independently selected from H and methyl; or acylamido;
  (iv) halo;
  (v) $C_{1-3}$ alkoxy, optionally substituted by hydroxy, $C(O)NH_2$, $C_{3-6}$ cycloalkyl, phenyl, $C_{5-6}$ heteroaryl, or by one or more fluoro groups;
  (vi) phenoxy, optionally substituted by fluoro;
  (vii) phenyl or $C_{5-6}$ heteroaryl;
  (viii) $SF_5$ or $SO_2CH_3$;
  (ix) —$(CH_2)_n$—Y—, where Y is O or $CH_2$, and n is 2 or 3; or
  (x) $C_{1-4}$ alkyl ester.

2. A compound for use according to statement 1, wherein at least one of $R^1$, $R^2$, $R^3$ and $R^4$ is H.

3. A compound for use according to either statement 1 or statement 2, wherein one of $R^1$, $R^2$, $R^3$ and $R^4$ are H.

4. A compound for use according to either statement 1 or statement 2, wherein two of $R^1$, $R^2$, $R^3$ and $R^4$ are H.

5. A compound for use according to either statement 1 or statement 2, wherein three of $R^1$, $R^2$, $R^3$ and $R^4$ are H.

6. A compound for use according to either statement 1 or statement 2, wherein at least one of $R^1$, $R^2$, $R^3$ and $R^4$ is not H.

7. A compound for use according to any one of statements 1 to 6, wherein at least one of $R^1$, $R^2$, $R^3$ and $R^4$ is $C_{1-3}$ alkyl, optionally substituted by:
  hydroxy,
  $C_{1-2}$ alkoxy, optionally substituted by one or more fluoro groups,
  $NH_2$,
  phenyl,
  $C_{5-6}$ heteroaryl,
  $C_{1-4}$ alkyl carbamoyl,
  acylamido, or
  one or more fluoro groups.

8. A compound for use according to statement 7, wherein the $C_{1-3}$ alkyl group is unsubstituted.

9. A compound for use according to statement 7, wherein the $C_{1-3}$ alkyl group is perfluorinated.

10. A compound for use according to statement 7, wherein the $C_{1-3}$ alkyl group is substituted, by a group selected from:
  (i) hydroxy;
  (ii) $C_{1-2}$ alkoxy;
  (iii) $NH_2$;
  (iv) phenyl;
  (v) $C_{5-6}$ heteroaryl;
  (vi) $C_{1-4}$ alkyl carbamoyl; and
  (vii) acylamido.

11. A compound for use according to any one of statements 1 to 10, wherein at least one of $R^1$, $R^2$, $R^3$ and $R^4$ is $C_{1-3}$ alkoxy, optionally substituted by $C_{3-6}$ cycloalkyl or by one of more fluoro groups.

12. A compound for use according to statement 11, wherein the $C_{1-3}$ alkoxy group is unsubstituted.

13. A compound for use according to statement 11, wherein the $C_{1-3}$ alkoxy group is perfluorinated.

14. A compound for use according to statement 11, wherein the $C_{1-3}$ alkoxy group is substituted by $C_{3-6}$ cycloalkyl.

15. A compound for use according to any one of statements 1 to 14, wherein at least one of $R^1$, $R^2$, $R^3$ and $R^4$ is $C_{3-6}$ cycloalkyl.

16. A compound for use according to statement 15, wherein the $C_{3-6}$ cycloalkyl group is cyclopropyl.

17. A compound for use according to any one of statements 1 to 16, wherein at least one of $R^1$, $R^2$, $R^3$ and $R^4$ is halo.

18. A compound for use according to any one of statements 1 to 17, wherein at least one of $R^1$, $R^2$, $R^3$ and $R^4$ is $COR^C$, where $R^C$ is selected from $NR^{N1}R^{N2}$, where $R^{N1}$ and $R^{N2}$ are independently selected from H and methyl.

19. A compound for use according to any one of statements 1 to 18, wherein at least one of $R^1$, $R^2$, $R^3$ and $R^4$ is selected from cyano, $NH_2$ and $NO_2$.

20. A compound for use according to statement 19, wherein at least one of $R^1$, $R^2$, $R^3$ and $R^4$ is cyano.

21. A compound for use according to statement 19, wherein at least one of $R^1$, $R^2$, $R^3$ and $R^4$ is $NH_2$.

22. A compound for use according to statement 19, wherein at least one of $R^1$, $R^2$, $R^3$ and $R^4$ is $NO_2$.

23. A compound for use according to any one of statements 1 to 22, wherein at least one of $R^1$, $R^2$, $R^3$ and $R^4$ is phenyl or $C_{5-6}$ heteroaryl, optionally substituted by methyl, cyano, hydroxy or methoxy.

24. A compound for use according to statement 23, wherein at least one of $R^1$, $R^2$, $R^3$ and $R^4$ is phenyl, optionally substituted by methyl or methoxy.

25. A compound for use according to statement 23, wherein at least one of $R^1$, $R^2$, $R^3$ and $R^4$ is $C_{5-6}$ heteroaryl, optionally substituted by one or more methyl groups.

26. A compound for use according to statement 1, wherein $R^4$ is methoxy, $R^2$ is $CH_2OCH_3$ or $CH_2OCH_2CH_3$ and $R^1$ and $R^3$ are H.

27. A compound for use according to statement 1, wherein $R^4$ is methoxy, $R^2$ is phenyl, optionally substituted by methyl or methoxy, and $R^1$ and $R^3$ are H.

28. A compound for use according to statement 1, wherein $R^4$ is methoxy, $R^2$ is $C_{5-6}$ heteroaryl, optionally substituted by methyl.

29. A compound for use according to statement 1, wherein $R^4$ is methoxy, $R^2$ is C heteroaryl, optionally substituted by methyl.

30. A compound for use according to statement 1, wherein $R^4$ is methoxy and $R^1$, $R^2$ and $R^3$ are H.

31. A compound for use according to statement 1, wherein $R^4$ is chloro, $R^2$ is $C_{1-3}$ alkyl or bromo, and $R^1$ and $R^3$ are H.

32. A compound for use according to statement 1, wherein $R^4$ is chloro and $R^1$, $R^2$ and $R^4$ are H.

33. A compound for use according to statement 1, wherein $R^3$ is $C_{1-3}$ alkyl and $R^1$, $R^2$ and $R^4$ are H.

34. A compound for use according to any one of statements 1 to 33, wherein Ar is phenyl, which may be unsubstituted or substituted.

35. A compound for use according to any one of statements 1 to 33, wherein Ar is napthyl, which may be unsubstituted or substituted.

36. A compound for use according to any one of statements 1 to 33, wherein Ar is substituted phenyl.

37. A compound for use according to any one of statements 1 to 33, wherein Ar is a $C_{5-10}$ heteroaryl group, which may be unsubstituted or substituted.

38. A compound for use according to statement 37, wherein the $C_{5-10}$ heteroaryl group is selected from: quinolinyl, benzothiazolyl, quinoxalinyl, benzooxadiazolyl, benzothiadiazolyl, benzofuran and benzotriazolyl.

39. A compound for use according to statement 37, wherein the $C_{5-10}$ heteroaryl group is quinolinyl or benzothiazolyl.

40. A compound for use according to any one of statements 1 to 33, wherein Ar is the group:

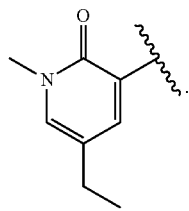 [SMILES: *c1cc(CC)cn(C)c1=O]

41. A compound for use according to any one of statements 33 to 39, wherein Ar is substituted by $C_{1-4}$ alkyl, optionally substituted by hydroxy, $C_{1-2}$ alkoxy, $NH_2$, $C_{1-4}$ alkyl carbamoyl, or by one or more fluoro groups.

42. A compound for use according to statement 41, wherein the $C_{1-4}$ alkyl group is unsubstituted.

43. A compound for use according to statement 41, wherein the $C_{1-4}$ alkyl group is perfluorinated.

44. A compound for use according to statement 41, wherein the $C_{1-4}$ alkyl group is substituted, by a group selected from:
   (i) hydroxy;
   (ii) $C_{1-2}$ alkoxy;
   (iii) $NH_2$; and
   (iv) $C_{1-4}$ alkyl carbamoyl.

45. A compound for use according to any one of statements 33 to 39, wherein Ar is substituted by $C_{3-6}$ cycloalkyl.

46. A compound for use according to statement 45, wherein the $C_{3-6}$ cycloalkyl group is cyclohexyl.

47. A compound for use according to any one of statements 33 to 39, wherein Ar is substituted by hydroxy; cyano; $NR^{N3}R^{N4}$, where $R^{N3}$ and $R^{N4}$ are independently selected from H and methyl; or acylamido.

48. A compound for use according to statement 47, wherein the substituent is hydroxy.

49. A compound for use according to statement 47, wherein the substituent is cyano.

50. A compound for use according to statement 47, wherein the substituent is $NR^{N3}R^{N4}$, where $R^{N3}$ and $R^{N4}$ are independently selected from H and methyl.

51. A compound for use according to statement 47, wherein the substituent acylamido.

52. A compound for use according to any one of statements 33 to 39, wherein Ar is substituted by halo.

53. A compound for use according to any one of statements 33 to 39, wherein Ar is substituted by $C_{1-3}$ alkoxy, optionally substituted by hydroxy, $C(O)NH_2$, $C_{3-6}$ cycloalkyl, phenyl, $C_{5-6}$ heteroaryl, or by one of more fluoro groups.

54. A compound for use according to statement 53, wherein the $C_{1-3}$ alkoxy group is unsubstituted.

55. A compound for use according to statement 53, wherein the $C_{1-3}$ alkoxy group is perfluorinated.

56. A compound for use according to statement 53, wherein the $C_{1-3}$ alkoxy group is substituted by hydroxy.

57. A compound for use according to statement 53, wherein the $C_{1-3}$ alkoxy group is substituted by $C(O)NH_2$.

58. A compound for use according to statement 53, wherein the $C_{1-3}$ alkoxy group is substituted by $C_{3-6}$ cycloalkyl.

59. A compound for use according to statement 53, wherein the $C_{1-3}$ alkoxy group is substituted by phenyl.

60. A compound for use according to statement 53, wherein the $C_{1-3}$ alkoxy group is substituted by $C_{5-6}$ heteroaryl.

61. A compound for use according to any one of statements 33 to 39, wherein Ar is substituted by phenoxy, optionally substituted by fluoro.

62. A compound for use according to statement 61, wherein Ar is substituted by phenoxy.

63. A compound for use according to statement 61, wherein Ar is substituted by $OC_6H_4F$.

64. A compound for use according to any one of statements 33 to 39, wherein Ar is substituted by phenyl or $C_{5-6}$ heteroaryl.

65. A compound for use according to statement 64, wherein Ar is substituted by phenyl.

66. A compound for use according to statement 64, wherein Ar is substituted by $C_{5-6}$ heteroaryl.

67. A compound for use according to any one of statements 33 to 39, wherein Ar is substituted by $SF_5$ or $SO_2CH_3$.

68. A compound for use according to statement 67, wherein Ar is substituted by $SF_5$.

69. A compound for use according to statement 67, wherein Ar is substituted by $SO_2CH_3$.

70. A compound for use according to any one of statements 33 to 39, wherein Ar is substituted by —$(CH_2)_n$—Y—, where Y is O or $CH_2$, and n is 2 or 3.

71. A compound for use according to statement 70, where Ar is phenyl.

72. A compound for use according to any one of statements 33 to 39, wherein Ar is substituted by $C_{1-4}$ alkyl ester.

73. A compound for use according to statement 72, where Ar is substituted by $C(O)OCH_3$.

74. A compound for use according to statement 72, where Ar is substituted by $C(O)OC(CH_3)_3$.

75. A compound for use according to any one of statements 1 to 33 and 41 to 74, wherein Ar is represented by the formula (Ar-1):

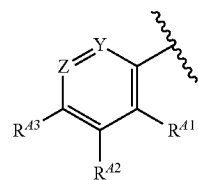

(Ar-1)

where Y is either N or C—$R^{44}$, and Z is either N or C—$R^{45}$; and $R^{A1}$, $R^{A2}$, $R^{A3}$, $R^{A4}$ (if present) and $R^{A5}$ (if present) are independently selected from H and the optional substituents for Ar.

76. A compound for use according to statement 75, wherein $R^{A2}$ is ethyl.

77. A compound for use according to statement 75, wherein $R^{A3}$ is selected from cycloalkyl; phenoxy; phenyl; $C_{5-6}$ heteroaryl; $SF_5$; and $SO_2CH_3$.

78. A compound for use according to any one of statements 1 to 33, wherein Ar is 5-ethyl-2-methoxyphenyl.

79. A compound for use according to any one of statements 1 to 33, wherein Ar is 5-$CF_3$-2-methoxyphenyl.

80. A compound for use according to any one of statements 1 to 33, wherein Ar is 2,6-dimethoxyphenyl.

81. A compound for use according to statement 1, with the proviso that when:
   $R^1$, $R^2$, $R^3$ and $R^4$ are H,
   Ar is not 4-aminophenyl.

82. A pharmaceutical composition comprising a compound as defined in any one of statements 1 to 81 and a pharmaceutically acceptable excipient.

83. A method of treatment of cancer, comprising administering to a patient in need of treatment, a compound as defined in any one of statements 1 to 81 or a pharmaceutical composition according to statement 82.

84. A method according to statement 83, wherein the compound is administered simultaneously or sequentially with radiotherapy and/or chemotherapy.

85. The use of a compound as defined in any one of statements 1 to 81 in the manufacture of a medicament for treating cancer.

86. A compound as defined in any one of statements 1 to 81 or a pharmaceutical composition according to statement 82 for use in the treatment of cancer.

87. A compound or pharmaceutical composition according to statement 86, wherein the treatment is for simultaneous or sequential administration with radiotherapy and/or chemotherapy.

88. A compound as defined in any one of statements 1 to 81 or a pharmaceutical salt thereof.

89. A compound according to statement 88, wherein at least one of $R^1$, $R^2$, $R^3$ and $R^4$ is not H.

90. A compound according to statement 89, wherein $R^3$ is not $CF_3$.

91. A compound according to statement 89, wherein $R^3$ is not substituted $C_{1-3}$ alkyl.

92. A compound according to statement 89, wherein $R^3$ is ethyl or propyl.

93. A compound according to statement 89, wherein $R^3$ is not $C_{1-3}$ alkyl, optionally substituted by hydroxy, $C_{1-2}$ alkoxy, $NH_2$, phenyl, $C_{5-6}$ heteroaryl, $C_{1-4}$alkyl carbamoyl, acylamido or by one or more fluoro groups.

94. A compound according to statement 88, wherein $R^4$ is methoxy.

95. A compound according to statement 88, wherein $R^4$ is Cl, and $R^1$, $R^2$ and $R^3$ are H.

96. A compound according to statement 88, wherein $R^4$ is Cl, and $R^2$ is $C_{1-3}$ alkyl or bromo, and $R^1$ and $R^3$ are H.

97. A compound according to statement 88, wherein $R^3$ is $C_{1-3}$ alkyl and $R^1$, $R^2$ and $R^4$ are H.

98. A compound according to statement 88, with the proviso that when:
   $R^1$, $R^2$ and $R^3$ are H, and $R^4$ is methoxy,
   Ar is not unsubstituted napthyl.

99. A compound according to statement 88, with the proviso that when:
   $R^1$, $R^2$, $R^3$ and $R^4$ are H,
   Ar is not 2,4,6-trimethylphenyl.

100. A compound according to statement 88, with the proviso that when:
   $R^1$, $R^2$ and $R^4$ are H, and $R^3$ is $CF_3$,
   Ar is not 2-(difluromethoxy)phenyl.

101. A compound according to statement 88, with the proviso that when:
   $R^1$, $R^2$, $R^3$ and $R^4$ are H,
   Ar is not 4-fluoro-3-methyl-phenyl.

102. A compound for use according to statement 88, with the proviso that when:
   $R^1$, $R^2$, $R^3$ and $R^4$ are H,
   Ar is not 4-aminophenyl.

103. A method of synthesis of a compound as defined in any one of statements 88 to 102.

104. A compound for use according to statement 1, wherein:
   $R^1$, $R^2$, $R^3$ and $R^4$ are independently selected from:
   (i) H;
   (ii) $C_{1-3}$ alkyl, optionally substituted by: hydroxy, $C_{1-2}$ alkoxy, $NH_2$, phenyl, $C_{5-6}$ heteroaryl, $C_{1-4}$ alkyl carbamoyl, acylamido, or one or more fluoro groups;
   (iii) $C_{1-3}$ alkoxy, optionally substituted by $C_{3-6}$ cycloalkyl or by one of more fluoro groups;
   (iv) $C_{3-6}$ cycloalkyl;
   (v) halo;
   (vi) $COR^C$, where $R^C$ is selected from $NR^{N1}R^{N2}$, where $R^{N1}$ and $R^{N2}$ are independently selected from H and methyl;
   (vii) cyano, $NH_2$, $NO_2$;
   (viii) phenyl or $C_{5-6}$ heteroaryl, optionally substituted by methyl, hydroxy or methoxy;
   Ar is a phenyl, napthyl, or $C_{5-10}$ heteroaryl group, which groups are optionally substituted by one or more groups selected from:
   (i) $C_{1-4}$ alkyl, optionally substituted by hydroxy, $C_{1-2}$ alkoxy, $NH_2$, $C_{1-4}$alkyl carbamoyl, or by one or more fluoro groups;
   (ii) $C_{3-6}$ cycloalkyl;
   (iii) hydroxy; cyano; $NR^{N3}R^{N4}$, where $R^{N3}$ and $R^{N4}$ are independently selected from H and methyl; acylamido;
   (iv) halo;
   (v) $C_{1-3}$ alkoxy, optionally substituted by hydroxy, C(O)$NH_2$, $C_{3-6}$ cycloalkyl, phenyl, $C_{5-6}$ heteroaryl, or by one of more fluoro groups;
   (vi) phenoxy, optionally substituted by fluoro;
   (vii) phenyl, $C_{5-6}$ heteroaryl
   (viii) $SF_5$, $SO_2CH_3$;
   (ix) —$(CH_2)_n$—Y—, where Y is O or $CH_2$, and n is 2 or 3;

105. A compound for use according to statement 104, wherein at least one of $R^1$, $R^2$, $R^3$ and $R^4$ is not H.

106. A compound for use according to either statement 104 or 105, wherein at least one of $R^1$, $R^2$, $R^3$ and $R^4$ is $C_{1-3}$ alkyl, optionally substituted by: hydroxy, $C_{1-2}$ alkoxy, $NH_2$, phenyl, $C_{5-6}$ heteroaryl, $C_{1-4}$ alkyl carbamoyl, acylamido, or one or more fluoro groups.

107. A compound for use according to any one of statements 104 to 106, wherein at least one of $R^1$, $R^2$, $R^3$ and $R^4$ is $C_{1-3}$ alkoxy, optionally substituted by $C_{3-6}$ cycloalkyl or by one of more fluoro groups.

108. A compound for use according to any one of statements 104 to 107, wherein at least one of $R^1$, $R^2$, $R^3$ and $R^4$ is $C_{3-6}$ cycloalkyl.

109. A compound for use according to any one of statements 104 to 108, wherein at least one of $R^1$, $R^2$, $R^3$ and $R^4$ is halo.

110. A compound for use according to any one of statements 104 to 109, wherein at least one of $R^1$, $R^2$, $R^3$ and $R^4$ is COR$^C$, where R$^C$ is selected from NR$^{N1}$R$^{N2}$, where R$^{N1}$ and R$^{N2}$ are independently selected from H and methyl.

111. A compound for use according to any one of statements 104 to 110, wherein at least one of R$^1$, R$^2$, R$^3$ and R$^4$ is selected from cyano, NH$_2$ and NO$_2$.

112. A compound for use according to any one of statements 104 to 111, wherein at least one of R$^1$, R$^2$, R$^3$ and R$^4$ is phenyl or C$_{5-6}$ heteroaryl, optionally substituted by methyl, hydroxy or methoxy.

113. A compound for use according to statement 104, wherein:
(a) R$^4$ is methoxy, R$^2$ is CH$_2$OCH$_3$ or CH2OCH$_2$CH$_3$ and R$^1$ and R$^3$ are H;
(b) R$^4$ is methoxy, R$^2$ is phenyl, optionally substituted by methyl or methoxy, and R$^1$ and R$^3$ are H;
(c) R$^4$ is methoxy, R$^2$ is C$_{5-6}$ heteroaryl, optionally substituted by methyl;
(d) R$^4$ is methoxy and R$^1$, R$^2$ and R$^3$ are H;
(e) R$^4$ is chloro, R$^2$ is C$_{1-3}$ alkyl or bromo, and R$^1$ and R$^3$ are H;
(f) R$^4$ is chloro and R$^1$, R$^2$ and R$^4$ are H; or
(g) R$^3$ is C$_{1-3}$ alkyl and R$^1$, R$^2$ and R$^4$ are H.

114. A compound for use according to any one of statements 104 to 113, wherein Ar is:
(a) phenyl, which may be unsubstituted or substituted;
(b) napthyl, which may be unsubstituted or substituted; or
(c) a C$_{5-10}$ heteroaryl group, which may be unsubstituted or substituted.

115. A compound for use according to statement 114, wherein Ar is substituted by C$_{1-4}$ alkyl, optionally substituted by hydroxy, C$_{1-2}$ alkoxy, NH$_2$, C$_{1-4}$alkyl carbamoyl, or by one or more fluoro groups.

116. A compound for use according to statement 114, wherein Ar is substituted by C$_{3-6}$ cycloalkyl.

117. A compound for use according to statement 114, wherein Ar is substituted by hydroxy; cyano; NR$^{N3}$R$^{N4}$, where R$^{N3}$ and R$^{N4}$ are independently selected from H and methyl; or acylamido.

118. A compound for use according to statement 114, wherein Ar is substituted by halo.

119. A compound for use according to statement 114, wherein Ar is substituted by C$_{1-3}$ alkoxy, optionally substituted by hydroxy, C(O)NH$_2$, C$_{3-6}$ cycloalkyl, phenyl, C$_{5-6}$ heteroaryl, or by one of more fluoro groups.

120. A compound for use according to statement 114, wherein Ar is substituted by phenoxy, optionally substituted by fluoro.

121. A compound for use according to statement 114, wherein Ar is substituted by phenyl or C$_{5-6}$ heteroaryl.

122. A compound for use according to statement 114, wherein Ar is substituted by SF$_5$ or SO$_2$CH$_3$.

123. A compound for use according to statement 114, wherein Ar is substituted by —(CH$_2$)$_n$—Y—, where Y is O or CH$_2$, and n is 2 or 3.

124. A compound for use according to any one of statements 104 to 113, wherein Ar is represented by the formula (Ar-1):

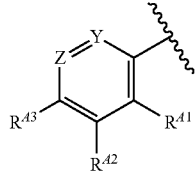

(Ar-1)

where Y is either N or C—R$^{A4}$, and Z is either N or C—R$^{A5}$; and

R$^{A1}$, R$^{A2}$, R$^{A3}$, R$^{A4}$ (if present) and R$^{A5}$ (if present) are independently selected from H and the optional substituents for Ar.

125. A compound for use according to statement 124, wherein:
(a) R$^{A2}$ is ethyl; or
(b) R$^{A3}$ is selected from cycloalkyl; phenoxy; phenyl; C$_{5-6}$ heteroaryl; SF$_5$; and SO$_2$CH$_3$.

126. A compound for use according to any one of statements 104 to 113, wherein Ar is:
(a) 5-ethyl-2-methoxyphenyl;
(b) 5-CF$_3$-2-methoxyphenyl; or
(c) 2,6-dimethoxyphenyl.

127. A compound as defined in any one of statements 104 to 126 or a pharmaceutical salt thereof.

128. A compound according to statement 127, wherein:
(a) at least one of R$^1$, R$^2$, R$^3$ and R$^4$ is not H;
(b) R$^3$ is not CF$_3$;
(c) R$^3$ is not substituted C$_{1-3}$ alkyl;
(d) R$^3$ is ethyl or propyl;
(e) R$^3$ is not C$_{1-3}$ alkyl, optionally substituted by hydroxy, C$_{1-2}$ alkoxy, NH$_2$, phenyl, C$_{5-6}$ heteroaryl, C$_{1-4}$ alkyl carbamoyl, acylamido or by one or more fluoro groups;
(f) R$^4$ is methoxy;
(g) R$^4$ is Cl, and R$^1$, R$^2$ and R$^3$ are H;
(h) R$^4$ is Cl, and R$^2$ is C$_{1-3}$ alkyl or bromo, and R$^1$ and R$^3$ are H; or
(i) R$^3$ is C$_{1-3}$ alkyl and R$^1$, R$^2$ and R$^4$ are H.

REFERENCES

Aggarwal and Calvi, *Nature,* 2004, 430, 372-376 doi: 10.1038/nature02694

Avvakumov et al., *Oncogene,* 2007, 26, 5395-5407 doi: 10.1038/sj.onc.1210608

Berge et al., *J. Pharm. Sci.,* 1977, 66, 1-19 doi:10.1002/jps.2600660104

Borrow et al., *Nat. Genet.,* 1996, 14, 33-41 doi:10.1038/ng0996-33

Dekker et al., *Drug, Discov. Today,* 2014, 19, 654-660 doi:10.1016/j.drudis.2013.11.012

Doyon et al., *Mol. Cell.,* 2006, 21, 51-64 doi:10.1016/j.molcel.2005.12.007

Dhuban et al., *Sci. Immunol.,* 2017, 2, 9297 doi:10.1126/sciimmunol.aai9297

Duong et al., *Cancer Res.,* 2013, 73, 5556-5568 doi: 10.1158/0008-5472.CAN-13-0013

Ghizzoni et al., *Eur. J. Med. Chem.,* 2012, 47, 337-344 doi:10.1016/j.ejmech.2011.11.001

Gil et al., *J. Proteomics,* 2017, 150, 297-309 doi:10.1016/j.jprot.2016.10.003

Gobert, M. et al., *Cancer Research,* 2009, 69, 2000-2009 doi:10.1158/0008-5472.CAN-08-2360

Holbert et al., *J. Biol. Chem.,* 2007, 282, 36603-36613 doi:10.1074/jbc.M705812200

Iizuka et al., *Mol. Cell. Biol.,* 2006, 26, 1098-1108 doi: 10.1128/MCB.26.3.1098-1108.2006

Iizuka et al., *Cancer Sci.,* 2013, 104, 1647-1655 doi: 10.1111/cas.12303

Jeong, et al., *Blood Res* 2016 51(3), 152-154 doi:10.5045/br.2016.51.3.152

Joshi, et al., *Immunity* 2015, 43, 579-590 doi:10.1016/j.immuni.2015.08.006

Li, B. et al., *PNAS,* 2007, 104, 4571-4576 doi:10.1073/pnas.0700298104

Melero, et al. *Nature Reviews Cancer*, 2015, 15, 457-472 doi:10.1038/nrc3973

Merson et al., *J. Neurosci.*, 2006, 26, 11359-11370 doi:10.1523/JNEUROSCI.2247-06.2006

Miller, A. M. et al. *J. Immunol.*, 2006, 177, 7398-7405 doi:10.4049/jimmunol.177.10.7398

Persa, E. et al. *Cancer Letters*, 2015 368(2), 252-261 doi:10.1016/j.canlet.2015.03.003

Sheikh et al., *Blood*, 2015, 125(12), 1910-21 doi:10.1182/blood-2014-08-594655

Shi et al, *Nature Biotech*, 2015, 33, 661-667 doi:10.1038/nbt.3235

Su et al., *Int. J. Mol. Sci.*, 2016, 17, 1-18 doi:10.3390/ijms17101594

Stern et al., *Crit. Rev. Oncol. Hematol.*, 2005, 54, 11-29 doi:10.1016/j.critrevonc.2004.10.011

Thomas et al., *Development*, 2000, 127, 2537-2548 PMID:10821753

Tao, H. et al., *Lung Cancer*, 2012, 75, 95-101 doi:10.1016/j.lungcan.2011.06.002

Turner-Ivey et al., *Neoplasia*, 2014, 16(8): 644-655 doi:10.1016/j.neo.2014.07.007

Valerio et al., *Cancer Research*, 2017, 77(7), 1753-62 doi:10.1158/0008-5472.CAN-16-2374

Vizmanos et al., *Genes Chromosomes Cancer*, 2003, 36(4), 402-405 doi:10.1002/gcc.10174

Voss et al., *BioEssays*, 2009, 31(10), 1050-1061 doi:10.1002/bies.200900051

Wang, L., et al. *EBioMedicine*, 2016, 13, 99-112 doi:10.1016/j.ebiom.2016.10.018

Wang, X. et al., *Oncogene*, 2017, 36, 3048-3058 doi:10.1038/onc.2016.458

Xiao, Y. et al., *Cell reports*, 2014, 7, 1471-1480 doi:10.1016/j.celrep.2014.04.021

Yan, M. et al., *Breast Cancer Research*, 2011, 13, R47 doi:10.1186/bcr2869

Zack et al., *Nature Genetics* 2013 45, 1134-1140 doi:10.1038/ng.2760

Zhang et al., *Mini. Rev. Med. Chem.*, 2017, 17, 1-8 doi:10.2174/1389557516666160923125031

---

The invention claimed is:

1. A compound of formula (I), or a pharmaceutically acceptable salt thereof:

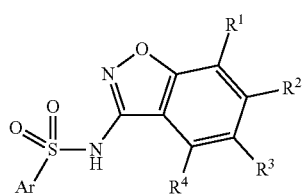

wherein:
R¹, R², R³ and R⁴ are independently selected from the group consisting of:
(i) H;
(ii) $C_{1-3}$ alkyl, optionally substituted by:
hydroxy,
$C_{1-2}$ alkoxy,
$NH_2$,
phenyl,
$C_{5-6}$ heteroaryl,
$C_{1-4}$ alkyl carbamoyl, or
acylamido;
(iii) $C_{1-3}$ alkoxy, optionally substituted by $C_{3-6}$ cycloalkyl or by one or more fluoro groups;
(iv) $C_{3-6}$ cycloalkyl;
(v) halo;
(vi) $COR^C$, where $R^C$ is selected from $NR^{N1}R^{N2}$, where $R^{N1}$ and $R^{N2}$ are independently selected from H and methyl;
(vii) cyano, $NH_2$, or $NO_2$; and
(viii) phenyl or $C_{5-6}$ heteroaryl, optionally substituted by methyl, hydroxy or methoxy; and
Ar is a phenyl, optionally substituted by one or more groups selected from the group consisting of:
(i) $C_{1-4}$ alkyl, optionally substituted by hydroxy, $C_{1-2}$ alkoxy, $NH_2$, $C_{1-4}$ alkyl carbamoyl, or by one or more fluoro groups;
(ii) $C_{3-6}$ cycloalkyl;
(iii) hydroxy; cyano; $NR^{N3}R^{N4}$, where $R^{N3}$ and $R^{N4}$ are independently selected from H and methyl; or acylamido;
(iv) halo;
(v) $C_{1-3}$ alkoxy, optionally substituted by hydroxy, $C(O)NH_2$, $C_{3-6}$ cycloalkyl, phenyl, $C_{5-6}$ heteroaryl, or by one or more fluoro groups;
(vi) phenoxy, optionally substituted by fluoro;
(vii) phenyl or $C_{5-6}$ heteroaryl; and
(viii) $SF_5$ or $SO_2CH_3$;
and wherein at least one of R¹, R², R³ and R⁴ is not H.

2. The compound or salt of claim 1, wherein at least one of R¹, R², R³ and R⁴ is $C_{1-3}$ alkyl, optionally substituted by:
hydroxy,
$C_{1-2}$ alkoxy,
$NH_2$,
phenyl,
$C_{5-6}$ heteroaryl,
$C_{1-4}$ alkyl carbamoyl, or
acylamido.

3. The compound or salt of claim 1, wherein at least one of R¹, R², R³ and R⁴ is $C_{1-3}$ alkoxy, optionally substituted by $C_{3-6}$ cycloalkyl or one of or more fluoro groups.

4. The compound or salt of claim 1, wherein at least one of R¹, R², R³ and R⁴ is $C_{3-6}$ cycloalkyl.

5. The compound or salt of claim 1, wherein at least one of R¹, R², R³ and R⁴ is halo.

6. The compound or salt of claim 1, wherein at least one of R¹, R², R³ and R⁴ is $COR^C$, where $R^C$ is selected from $NR^{N1}R^{N2}$, where $R^{N1}$ and $R^{N2}$ are independently selected from H and methyl.

7. The compound or salt of claim 1, wherein at least one of R¹, R², R³ and R⁴ is cyano, $NH_2$ or $NO_2$.

8. The compound or salt of claim 1, wherein at least one of R¹, R², R³ and R⁴ is phenyl or $C_{5-6}$ heteroaryl, optionally substituted by methyl, cyano, hydroxy or methoxy.

9. The compound or salt of claim 1, wherein:
(a) $R^4$ is methoxy, $R^2$ is $CH_2OCH_3$ or $CH_2OCH_2CH_3$, and $R^1$ and $R^3$ are H;
(b) $R^4$ is methoxy, $R^2$ is phenyl, optionally substituted by methyl or methoxy, and $R^1$ and $R^3$ are H;
(c) $R^4$ is methoxy, $R^2$ is $C_{5-6}$ heteroaryl, optionally substituted by methyl;
(d) $R^4$ is methoxy and $R^1$, $R^2$ and $R^3$ are H;
(e) $R^4$ is chloro, $R^2$ is $C_{1-3}$ alkyl or bromo, and $R^1$ and $R^3$ are H;
(f) $R^4$ is chloro and $R^1$, $R^2$ and $R^4$ are H; or
(g) $R^3$ is $C_{1-3}$ alkyl and $R^1$, $R^2$ and $R^4$ are H.

10. The compound or salt of claim 1, wherein:
(a) Ar is substituted by $C_{1-4}$ alkyl, optionally substituted by hydroxy, $C_{1-2}$ alkoxy, $NH_2$, $C_{1-4}$ alkyl carbamoyl, or one or more fluoro groups;
(b) Ar is substituted by $C_{3-6}$ cycloalkyl;
(c) Ar is substituted by hydroxy; cyano; $NR^{N3}R^{N4}$, where $R^{N3}$ and $R^{N4}$ are independently selected from H and methyl; or acylamido; or
(d) Ar is substituted by halo.

11. The compound or salt of claim 1, wherein Ar is substituted by $C_{1-3}$ alkoxy, optionally substituted by hydroxy, $C(O)NH_2$, $C_{3-6}$ cycloalkyl, phenyl, $C_{5-6}$ heteroaryl, or one or more fluoro groups.

12. The compound or salt of claim 1, wherein:
(a) Ar is substituted by phenoxy, optionally substituted by fluoro;
(b) Ar is substituted by phenyl or $C_{5-6}$ heteroaryl; or
(c) Ar is substituted by $SF_5$ or $SO_2CH_3$.

13. The compound or salt of claim 1, wherein Ar is:
(a) 5-ethyl-2-methoxyphenyl;
(b) 5-$CF_3$-2-methoxyphenyl; or
(c) 2,6-dimethoxyphenyl.

14. The compound or salt of claim 1, wherein two of $R^1$, $R^2$, $R^3$ and $R^4$ are H.

* * * * *